US009885023B2

(12) United States Patent
Bohlmann et al.

(10) Patent No.: US 9,885,023 B2
(45) Date of Patent: Feb. 6, 2018

(54) CYTOCHROME P450 AND CYTOCHROME P450 REDUCTASE POLYPEPTIDES, ENCODING NUCLEIC ACID MOLECULES AND USES THEREOF

(71) Applicants: THE UNIVERSITY OF BRITISH COLUMBIA, Vancouver (CA); THE UNIVERSITY OF WESTERN AUSTRALIA, Nedlands (AU)

(72) Inventors: Carl Joerg Bohlmann, Vancouver (CA); Maria Luisa Diaz Chavez, Vancouver (CA); Jessie Moniodis, Perth (AU)

(73) Assignees: University of British Columbia, Vancouver (CA); The University of Western Australia, Nedlands (AU)

( * ) Notice: Subject to any disclaimer, the term of this patent is extended or adjusted under 35 U.S.C. 154(b) by 0 days.

(21) Appl. No.: 14/440,122

(22) PCT Filed: Oct. 31, 2013

(86) PCT No.: PCT/CA2013/050828
§ 371 (c)(1),
(2) Date: May 1, 2015

(87) PCT Pub. No.: WO2014/067007
PCT Pub. Date: May 8, 2014

(65) Prior Publication Data
US 2016/0108374 A1 Apr. 21, 2016

Related U.S. Application Data

(60) Provisional application No. 61/956,086, filed on May 31, 2013, provisional application No. 61/796,129, filed on Nov. 1, 2012.

(51) Int. Cl.
| | |
|---|---|
| *C12N 15/53* | (2006.01) |
| *C12N 9/02* | (2006.01) |
| *C12P 5/00* | (2006.01) |
| *C11B 9/00* | (2006.01) |
| *C12P 7/02* | (2006.01) |
| *C12P 15/00* | (2006.01) |

(52) U.S. Cl.
CPC .............. *C12N 9/0042* (2013.01); *C11B 9/00* (2013.01); *C12N 9/0071* (2013.01); *C12P 5/007* (2013.01); *C12P 7/02* (2013.01); *C12P 15/00* (2013.01); *C12Y 106/02004* (2013.01); *C12Y 114/00* (2013.01)

(58) Field of Classification Search
None
See application file for complete search history.

(56) References Cited

U.S. PATENT DOCUMENTS

| | | |
|---|---|---|
| 5,605,793 A | 2/1997 | Stemmer |
| 5,811,238 A | 9/1998 | Stemmer et al. |
| 5,824,774 A | 10/1998 | Chappell et al. |
| 5,830,721 A | 11/1998 | Stemmer et al. |
| 5,834,252 A | 11/1998 | Stemmer et al. |
| 5,837,458 A | 11/1998 | Minshull et al. |
| 6,072,045 A | 6/2000 | Chappell et al. |
| 6,531,303 B1 | 3/2003 | Millis et al. |
| 6,689,593 B2 | 2/2004 | Millis et al. |
| 7,186,891 B1 | 3/2007 | Chappell et al. |
| 7,838,279 B2 | 11/2010 | Millis et al. |
| 7,842,497 B2 | 11/2010 | Millis et al. |
| 7,906,710 B2 | 3/2011 | Karunanandaa et al. |
| 8,106,260 B2 | 1/2012 | Chappell et al. |
| 2004/0249219 A1 | 12/2004 | Saucy |
| 2009/0123984 A1 | 5/2009 | Chappell et al. |
| 2011/0081703 A1 | 4/2011 | Chappell et al. |
| 2011/0189717 A1 | 8/2011 | Ajikumar et al. |

FOREIGN PATENT DOCUMENTS

| | | |
|---|---|---|
| WO | WO97/07205 | 2/1997 |
| WO | WO 2008/034648 A1 | 3/2008 |
| WO | WO2011/000026 | 1/2011 |

OTHER PUBLICATIONS

GenBank: ACF17649 (Aug. 2009).*
The International Preliminary Report on Patentability for International Application No. PCT/CA2013/050828 dated Feb. 11, 2015, pp. 1-9.
The International Search Report for International Application No. PCT/CA2013/050828 dated Jan. 8, 2014, pp. 1-6.
Davies et al., "Differential screening indicates a dramatic change in mRNA profiles during grape berry ripening. Cloning and characterization of cDNAs encoding putative cell wall and stress response proteins." Plant Physiol. (122 (3):803-12 (Mar. 2000).
Jones et al., "Sandalwood fragrance biosynthesis involves sesquiterpene synthases of both the terpene synthase (TPS)-a and TPS-b subfamilies, including santalene synthases." J Biol Chem. 286(20):17445-54 (May 2011, Epub Mar. 24, 2011).
Baudry et al., Class-dependent sequence alignment strategy improves the structural and functional modeling of P450s Prot Eng Design & Selection 19(8):345-53 (Jun. 2006).

(Continued)

*Primary Examiner* — Rebecca Prouty
(74) *Attorney, Agent, or Firm* — McDonnell Boehnen Hulbert & Berghoff LLP

(57) ABSTRACT

Provided are cytochrome P450 polypeptides, including cytochrome P450 santalene oxidase polypeptides, cytochrome P450 bergamotene oxidase polypeptides and cytochrome P450 reductase polypeptides. Also provided are nucleic acid molecules encoding the cytochrome P450 polypeptides. Cells containing the nucleic acids and/or the polypeptides are provided as are methods for producing terpenes, such as santalols and bergamotols, by culturing the cells.

28 Claims, 27 Drawing Sheets

(56) References Cited

OTHER PUBLICATIONS

Dym & Eisenberg, "Sequence-structure analysis of FAD-containing proteins." Protein Science 10(9):1712-28 (Sep. 2001).
Hubbard et al. "NADPH-cytochrome P450 oxidoreductase. Structural basis for hydride and electron transfer." J Biol Chem 276(31):29163-70 (Aug. 2001).
Louerat-Orieu et al., "Differential redox and electron-transfer properties of purified yeast, plant and human NADPH-cytochrome P-450 reductases highly modulate cytochrome P-450 activities." Eur J Biochem 258(3):1040-49 (Dec. 1998).
Mizutani and Ohta "Two isoforms of NADPH:cytochrome P450 reductase in Arabidopsis thaliana, Gene structure, heterologous expression in insect cells, and differential regulation." Plant Physiology 116(1):357-67 (Jan. 1998).
Nelson et al, "Comparative genomics of rice and Arabidopsis. Analysis of 727 cytochrome P450 genes and pseudogenes from a monocot and a dicot." Plant Physiol. 135(2):756-72 (Jun. 2004).
Ro et al., "Cloning, functional expression, and subcellular localization of multiple NADPH-cytochrome P450 reductases from hybrid poplar." Plant Physiology 130(4):1837-51 (Dec. 2002).
Ro et al., "Loblolly pine abietadienol/abietadienal oxidase PtAO (CYP720B1) is a multifunctional, multisubstrate cytochrome P450 monooxygenase." Proc Natl Acad Sci USA 102(22):8060-65 (May 2005).
Sirim et al., "Prediction and analysis of the modular structure of cytochrome P450 monooxygenases." BMC Structural Biology 10:34, 12 pages (Oct. 2010).
Stemmer et al.,"DNA shuffling by random fragmentation and reassembly: in vitro recombination for molecular evolution." Proc Natl Acad Sci USA 91(22):10747-51 (Oct. 1994).
Wang et al., "Three-dimensional structure of NADPH-cytochrome P450 reductase: Prototype for FMN- and FAD-,conntaining enzymes." Proc Natl Acad Sci USA 94(16):8411-16 (Aug. 1997).
Werck-Reichhart and Feyereisen, "Cytochromes P450: a success story." Genome Biology 1(6):Reviews 3003, 9 pages (Dec. 2000).
Yamazaki et al., "Importance of the proline-rich region following signal-anchor sequence in the formation of correct conformation of microsomal cytochrome P-450s." J Biochem 114(5):652-57 (Nov. 1993).
Beier and Young, "Characterization of a regulatory region upstream of the ADR2 locus of S. cerevisiae." Nature 300 (5894):724-28 (Dec. 1982).
Chapple, "Molecular-Genetic Analysis of Plant Cytochrome P450-Dependent Monooxygenases" Annu. Rev. Plant Physiol. Plant Mol. Biol. 49:311-343 (Jun. 1998).
Collu et al., "Geraniol 10-hydroxylase, a cytochrome P450 enzyme involved in terpenoid indole alkaloid biosynthesis." FEBS Lett 508(2):215-20 (Nov. 2001).
Cullin and Pompon "Synthesis of functional mouse cytochromes P-450 P1 and chimeric P-450 P3-1 in the yeast Saccharomyces cerevisiae." Gene 65(2):203-217 (May 1988).
Daramwar et al., "Preparative separation of α- and β-santalenes and (Z)-α- and (Z)-β-santalols using silver nitrate-impregnated silica gel medium pressure liquid chromatography and analysis of sandalwood oil." Analyst 137 (19):4564-4570 (Oct. 2012).
Gietz et al. "Improved method for high efficiency transformation of intact yeast cells." Nucleic Acids Res 20(6):1425 (Mar. 1992).
Groves et al., 1995 in Cytochrome P450: Structure, Mechanism, and Biochemistry (Ed: Ortiz de Montellano) Plenum Press, New York, N.Y., pp. 3-48.
Guengerich et al. "Measurement of cytochrome P450 and NADPH-cytochrome P450 reductase." Nat Protoc 4 (9):1245-51 (Aug. 2009).
Hamann and Moller "Improved cloning and expression of cytochrome P450s and cytochrome P450 reductase in yeast." Protein Expr Purif 56(1):121-127 (Nov. 2007).
Hamdane et al. "Structure and function of an NADPH-cytochrome P450 oxidoreductase in an open conformation capable of reducing cytochrome P450." J Biol Chem 284(17):11374-84 (Apr. 2009).
Mizutani et al. "Purification and Characterization of a Cytochrome P450 (trans-Cinnamic Acid 4-Hydroxylase) from Etiolated Mung Bean Seedlings") Plant and Cell Physiology 34(3):481-88 (Apr. 1993).
Omura and Sato, "The Carbon Monoxide-Binding Pigment of Liver Microsomes. I. Evidence for Its Hemoprotein Nature" J Biol Chem 239:2370-78 (Jul. 1964).
Pompon et al., "Genetically engineered yeast cells and their applications. " Toxicol Left 82-83:815-22 (Dec. 1995).
Pompon et al. "Yeast expression of animal and plant P450s in optimized redox environments." Methods Enzymol 272:51-64 (1996).
Ro et al. "Functional characterization and subcellular localization of poplar (Populus trichocarpa x Populus deltoides) ainnamate 4-hydroxylase." Plant Physiology 126(1):317-29 (May 2001).
Ro et al. "Induction of multiple pleiotropic drug resistance genes in yeast engineered to produce an increased level of anti-malarial drug precursor, artemisinic acid." BMC Biotechnology 8:83 (Nov. 2008).
Russell et al. "Nucleotide sequence of the yeast alcohol dehydrogenase II gene." J. Biol. Chem. 258(4):2674-82 (Feb. 1983).
Sciarrone et al. "Application of a multidimensional gas chromatography system with simultaneous mass spectrometric and flame ionization detection to the analysis of sandalwood oil." J Chromatogr A 1218(1):137-42 (Jan. 2011).
Shen et al. "Structural analysis of the FMN binding domain of NADPH-cytochrome P-450 oxidoreductase by site-directed mutagenesis." J Biol Chem 264(13):7584-89 (May 1989).
Szczesna-Skorupa et al., "Deletion of a conserved tetrapeptide, PPGP, in P450 2C2 results in loss of enzymatic activity without a change in its cellular location." Arch Biochem Biophys 304(1):170-75 (Jul. 1993).
Valder et al., "Western Australian sandalwood oil—New constituents of Santalum spicatum (R. Br.) A. DC. (Santalaceae)." J Essent Oil Res. 15:178-86 (2003).
Xia et al. "Conformational changes of NADPH-cytochrome P450 oxidoreductase are essential for catalysis and cofactor binding." J Biol Chem 286(18):16246-60 (May 2011).
Jones et al., "Isolation of cDNAs and functional characterisation of two multi-product terpene synthase enzymes from sandalwood, Santalum album L", Archives of Biochemistry and Biophysics, 477(1):121-130 (Sep. 2008).
Nguyen et al., "De novo synthesis of high-value plant sesquiterpenoids in yeast", Methods in Enzymology 517:261-78 (2012).

\* cited by examiner

```
CYP76-G5  (SEQ ID NO:6)    MDFLSFILFVLFAWALVRALPTLSRGSKAAGGRLPPGPVPLPVVGNLLKLGSKPHKSLAE  60
CYP76-G12 (SEQ ID NO:9)    MDFLSCILFVLFAWALVRALPTLSRGSKAAGGRLPPGPVPLPVVGNLLKLGSKPHKSLAE  60
CYP76-G11 (SEQ ID NO:8)    MDFLSCILSVLFAWALVRALPTLSRGSKAAGGRLPPGPVPLPVVGNLLKLGSKPHKSLAE  60
CYP76-G10 (SEQ ID NO:7)    MDFLSCILFVLFAWALVRALPTLSRGSKAASGRLPPGPVPWPVVGNLLKLGNKPHKSLAE  60
                           *****  **  *******************  ***************** ********

CYP76-G5  (SEQ ID NO:6)    LAKSYGPIMCLKLGHIITTIVISTPTVAKEVLQKQDVAFCNRTIPDAVRAHRHDLHSMVWL 120
CYP76-G12 (SEQ ID NO:9)    LAKSYGPIMCLKLGHIITTIVISTPTVAKEVLQKQDVAFCNRTIPDAVRAHRHDLHSMVWL 120
CYP76-G11 (SEQ ID NO:8)    LAKSYGPIMCLKLGHIITTIVISTPTVAKEVLQKQDVAFCNRTIPDAVRAHRHDLHSMVWL 120
CYP76-G10 (SEQ ID NO:7)    LAKSYGPIMCLKLGHMTTIVISTPTVAKEVLQKQDVAFSNRTTPDAVRAHGHDLYSMAWL  120
                           *************** * ******************** *** ******* *** * **

CYP76-G5  (SEQ ID NO:6)    PVSTRWRTLRKISNSHIFSSQRLDENHHLRRRKLDELLARVAESSLVGAVVDIGAVAFLT  180
CYP76-G12 (SEQ ID NO:9)    PVSTRWRTLRKISNSHIFSSQRLDENHHLRRRKLDELLTRVAESSLVGAVVDIGAVAFLT  180
CYP76-G11 (SEQ ID NO:8)    PVSTRWRTLRKISNSHIFSSQRLDENHHLRRRKLDELLTRVAESSLVGAVVDIGAVAFLT  180
CYP76-G10 (SEQ ID NO:7)    PVSTRWRTLRKISNSHIFTSQRLDENHHLRRRKLDELLARVAESSLVGAVVDMGAVAFLT  180
                           ****************** ******************* ************ *******

CYP76-G5  (SEQ ID NO:6)    SLNLLSNTVFSKDLVEPGLGAVQEMEEVVWGITEEAGRPNLVDYFPVLRRLDPQGTRRRM 240
CYP76-G12 (SEQ ID NO:9)    SLNLLSNTVFSKDLVEPGLGAVQEMEEVVWGITEEAGRPNLVDYFPVLRRLDPQGTRRRM 240
CYP76-G11 (SEQ ID NO:8)    SLNLLSNTVFSKDLVEPGLGAVQEMEEVVWGITEEAGRPNLVDYFPVLRRLDPQGTRRRM 240
CYP76-G10 (SEQ ID NO:7)    SLNLLSNTVFSKDLVEPGLGAVQETKEVVWGMMEEAGRPNLVDYFPVLRRLDPQGIRRRM 240
                           ************************ ******  ******************** ****

CYP76-G5  (SEQ ID NO:6)    MGYFGKMFEVFGDIIDERLELRKQQSDGDSPAATTNDVLDVLLNIIEDAEIEEKPNRTDV 300
CYP76-G12 (SEQ ID NO:9)    MGYFGKMFEVFGDIIDERLELRKQQSDGDSPAATTNDVLDVLLNIIEDAEIEEKPNRTDV 300
CYP76-G11 (SEQ ID NO:8)    MGYFGKMLEVFGDIIDERLEWRKQQSDGDSPAGTTNDVLDVLLNIIEDAEIEEKPNRTDV 300
CYP76-G10 (SEQ ID NO:7)    TGYFGKMLEVFGDIIDERLEWRKQQSDGDSPAGTTNDVLDVLLNIIEDAEIEEKPNRTDV 300
                            ****** ************ *********** *************************
```

FIGURE 2A

| | | |
|---|---|---|
| CYP76-G5 (SEQ ID NO:6) | EHFIVDLFVAGSDTTSSTVEWAMTELLRKPETLERARSELHETIGPKNLVQEADMPRLPY | 360 |
| CYP76-G12 (SEQ ID NO:9) | EHFIVDLFVAGSDTTSSTVEWAMTELLRKPETLERARSELHETIGPKNLVQEADMPRLPY | 360 |
| CYP76-G11 (SEQ ID NO:8) | EHFLLDLFAAGSDTTSSTVEWAMTELLRKPETLERARSELHETIGPENLVQEADLPRLPY | 360 |
| CYP76-G10 (SEQ ID NO:7) | EHFLLDLFAAGSDTTSSTVEWAMTELLRKPETLERARSELHETIGPENLVQEADLPRLPY | 360 |
| | *::.*********************************:***.:*** | |
| CYP76-G5 (SEQ ID NO:6) | LQAVVKETFRLHPPVPLLLPRTAEKDAELCGFTVPAGAQIMVNAWAIGRDPGTWEDPESF | 420 |
| CYP76-G12 (SEQ ID NO:9) | LQAVVKETFRLHPPVPLLLPRTAEKDAELCGFTVPAGAQIMVNAWAIGRDPGTWEDPESF | 420 |
| CYP76-G11 (SEQ ID NO:8) | LQAVVKETFRLHPPVPLLLPRTAEKDAELCGFTVPAGAQIMVNAWAIGRDPGTWEDPESF | 420 |
| CYP76-G10 (SEQ ID NO:7) | LQAVVKETFRLHPPVPLLLPRTAEKDAELCGFTVPAGAQIMVNAWAIGRDPGTWEDPESF | 420 |
| | ************************************************************ | |
| CYP76-G5 (SEQ ID NO:6) | LPERFLGSDVDVKGRSFELIPFGGGRRICPGLPLAIRMVHLMLGSLIHGFRWKVFDDGMG | 480 |
| CYP76-G12 (SEQ ID NO:9) | LPERFLGSDVDVKGRSFELIPFGGGRRICPGLPLAIRMVHLMLGSLIHGFRWKVDDDGMG | 480 |
| CYP76-G11 (SEQ ID NO:8) | LPERFLGSDVDVKGRSFELIPFGGGRRICPGLPLAIRMVHLMLGSLIHGFRWKVDDDGMG | 480 |
| CYP76-G10 (SEQ ID NO:7) | LPERFLGSDVDVKGRSFELIPFGGGRRICPGLPLAIRMVHLMLGSLIHGFRWKVDDDGMG | 480 |
| | ********************************************************* ***** | |
| CYP76-G5 (SEQ ID NO:6) | SPETAMDMDEKFGITLQKAKSLCAVPIRG | 509 |
| CYP76-G12 (SEQ ID NO:9) | SPETAMDMDEKFGITLQKAKPLCAVPIRG | 509 |
| CYP76-G11 (SEQ ID NO:8) | SPETAMDMDEKFGITLQKAKPLCAVPIRG | 509 |
| CYP76-G10 (SEQ ID NO:7) | SPETAMDMDEKFGITLQKAKPLCAVPIRG | 509 |
| | ******************.****** | |

FIGURE 2B

```
SaCPR2 (SEQ ID NO:13)   -MQLSSVKLIPLDLMTAIFNGG-----GSPAGS------GEALSMLLENREVVALTTSL     48
CPR    (SEQ ID NO:46)   MSSSSSSTSMIDLMAAIIKGEPVIVSDPANASAYESVAAELSSMLIENRQFAMIVTTSI     60
SaCPR1 (SEQ ID NO:12)   -MSS---SSELWKSIGSALGVSPP---------------PAWAEEWAAVIVTTSA       36
CPR    (SEQ ID NO:58)   -MTSALYASDLFKQLKSIMGTDS---------------------LSDDVLVIATTSL    36
                                   :              .             ***

SaCPR2 (SEQ ID NO:13)   AVLIGCVFAYLWRFSSSQKAVAAAKGVEVARKPVIGKESEAAEVDDGKKKVTIFFGTQTG  108
CPR    (SEQ ID NO:46)   AVLIGCIVMLVWRRSGS----GNSKRVEPLKPLVIKPREE--EIDDGRKKVTIFFGTQTG  114
SaCPR1 (SEQ ID NO:12)   ALIVG-FVMFMWRRS-GEKS-KELRPVVALKAAPIEAEEDDGEVDSGKTKVTVFFGTQTG   93
CPR    (SEQ ID NO:58)   ALVAG-FVVLLNKKTTADRS-GELKPLMIPKSLMAKDEDDLDLGSGKTRVSIFFGTQTG    94
                       *::::  *::: :::  :.      :: ::   :     : :..*::*:*::******

SaCPR2 (SEQ ID NO:13)   TAEGFAKALVEEAKARYEKAIFKLVDLDDYAAEDDEYEEKLKKEKFALFFLATYGDGEPT  168
CPR    (SEQ ID NO:46)   TAEGFAKALGEEAKARYEKTRFKIVDLDDYAADDEYEEKLKKEDVAFFFLATYGDGEPT  174
SaCPR1 (SEQ ID NO:12)   TAEGFAKALAEEIKARYEKAVVKVVDLDDYAADDDQYGEKLKNETLTFFMVATYGDGEPT  153
CPR    (SEQ ID NO:58)   TAEGFAKALSEEIKARYEKAAVKVIDLDDYAADDDQYEEKLKKETLAFFCVATYGDGEPT  154
                       *********  * *******  *::********:*::* ****:* ::*  .*******

SaCPR2 (SEQ ID NO:13)   DNAARFYKWFTEENESGEWLQKLQFGVFGLGNRQYEHFNKVAKVVDEILAEQGGKRLVPV  228
CPR    (SEQ ID NO:46)   DNAARFYKWFTEGNDRGEWLKNLKYGVFGLGNRQYEHFNKVAKVVDDILVEQGAQRLVQV  234
SaCPR1 (SEQ ID NO:12)   DNAARFYKWFTEEKEREAWLQQLTYGIFGLGNRQYEHFNKIAKVLDEQLTEQGAKRLIQV  213
CPR    (SEQ ID NO:58)   DNAARFSKWFTEENERDIKLQQLAYGVFALGNRQYEHFNKIGIVLDEELCKKGAKRLIEV  214
                       ******.*****.  .. : : *.*:*.************:  ::*:   : **:**: *

SaCPR2 (SEQ ID NO:13)   GLGDDDQCIEDDFTAWRELVWPELDKLLLDED-DATVSTPYTASVPEYRVVFHDSPDD-Y  286
CPR    (SEQ ID NO:46)   GLGDDDQCIEDDFTAWREALWPELDTILREEG-DTAVATPYTAAVLEYRVSIHDSEDAKF  293
SaCPR1 (SEQ ID NO:12)   GLGDDDQSIEDDFSAWRELLWPELDQLLRGDDGANSVSTPYTAAVPEYRVVIHDPTITSS  273
CPR    (SEQ ID NO:58)   GLGDDDQSIEDDFNAWKESLWSELDKLLKDED-DKSVATPYTAVIPEYRVVTHDPRFTTQ  273
                       *******.*****.**:*.:*.***.::  :  ::: :****.::****  **   :
```

FIGURE 3A

```
SaCPR2 (SEQ ID NO:13)  LQKNSSNANGHSMHDAQHPCRANVAVRRELHSPLSDRSCTHLEFDIAGTGLAYETGDHVG  346
CPR    (SEQ ID NO:46)  NDITLANGNGYTVFDAQHPYKANVAVKRELHTPESDRSCIHLEFDIAGSGLTMKLGDHVG  353
SaCPR1 (SEQ ID NO:12)  EDKSLATANGAALFDIHHPCRVKVAVQRELHKADSDRSCIHLEFDISGTGLMYETGDHVG  333
CPR    (SEQ ID NO:58)  KSMESNVANGNTTIDIHHPCRVDVAVQKELHTHESDRSCIHLEFDISRTGITYETGDHVG  333
                            *  *   *   ***  * ********   **:***  * *** :**

SaCPR2 (SEQ ID NO:13)  VCCENLPEVVEEAERVLGLSPGIYFSIHADKEDGTPLGSSLPPLFP-PCTLRTALTQHAD  405
CPR    (SEQ ID NO:46)  VLCDNLSETVDEALRLLDMSPDTYFSLHAEKEDGTPISSSLPPPFP-PCNLRTALTRYAC  412
SaCPR1 (SEQ ID NO:12)  VYAENCVETVEEAGKLLGQPLDLLFSVHTDKDGTSLESSLPPPFPGPCTLRTALFQYAD  393
CPR    (SEQ ID NO:58)  VYAENHVEIVEEAGKLLGHSLDLVFSIHADKEDGSPLESAVPPPFPGPCTLGTGLARYAD  393
                      *  :* **:** .::*:  : .::*.: * :: ** : .::  **   * *

SaCPR2 (SEQ ID NO:13)  LLSFPKKAALLALAAHASDPSEADRLKYLASPAGKDEYAQWVVASQRSLLEVMAEFPSAK  465
CPR    (SEQ ID NO:46)  LLSSPKKSALVALAAHASDPTEAERLKHLASPAGKDEYSKWVVESQRSLLEVMAEFPSAK  472
SaCPR1 (SEQ ID NO:12)  LLNPPRKAALVALAAHAVEPSEADRLKFLSSPQGKDEYAKWVVGSQRSLLEVMAEFPSIK  453
CPR    (SEQ ID NO:58)  LLNPPRKSALVALAAYATEPSEAEKLKHLTSPDGKDEYSQWIVASQRSLLEVMAAFPSAK  453
                      **.  :*:**:****    .*.::**:*:.* ***** :*:*.*********.***.*

SaCPR2 (SEQ ID NO:13)  PPLGVLFAAVAPRLQPRFYSISSSPKIAPSRIHVTCALVYDKTPTGRIHKGVCSTWMKNA  525
CPR    (SEQ ID NO:46)  PPLGVFAGVAPRLQPRFYSISSSPKIAETRIHVTCALVYEKMPTGRIHKGVCSTWMKNA  532
SaCPR1 (SEQ ID NO:12)  VPLGVFAAVAPRLQPRYYSISSSPRFSSDRVHVTCALVYGPSPTGRIHRGVCSTWMKNA  513
CPR    (SEQ ID NO:58)  PPLGVFAAIAPRLQPRYYSISSCQDWAPSRVHVTSALVYGPTPTGRIHKGVCSTWMKNA  513
                       ****:*. *****:*****.    .*:***.****   .*****:***********

SaCPR2 (SEQ ID NO:13)  MPREESHDCSWA-PIFVRQSNFKLPSNTSVPVIMIGPGTGLAPFRGFLQERLALKEAGVE  584
CPR    (SEQ ID NO:46)  VPYEKSEKLFLGRPIFVRQSNFKLPSDSKVPIIMIGPGTGLAPFRGFLQERLALVESGVE  592
SaCPR1 (SEQ ID NO:12)  VPLEESRECSWA-PIFIRTSNFKLPANPSTPVIMVGPGTGLAPFRGFLQERMALLEGSAQ  572
CPR    (SEQ ID NO:58)  VPAEKSHECSGA-PIFIRASNFKLPSNPSTPIVMVGPGTGLAPFRGFLQERMALKEDGEE  572
                       *  .*.   .  ***:* *******:   *::*:************:** *
```

FIGURE 3B

```
SaCPR2 (SEQ ID NO:13)  LGPAILFFGCRNRKMDYIYEDELAHFVEAGALSELIVAFSREGPAKQYVQHKMMEKASEI 644
CPR    (SEQ ID NO:46)  LGPSVLFFGCRNRRMDFIYEEELQRFVESGALAELSVAFSREGPTKEYVQHKMMDKASDI 652
SaCPR1 (SEQ ID NO:12)  LGPALLFFGCRNRRMDFIYEDELNNFVEQGVISELIVAFSRDGPTKEYVQHKMMDKAAYI 632
CPR    (SEQ ID NO:58)  LGSSLLFFGCRNRQMDFIYEDELNNFVDQGVISELIMAFSREGAQKEYVQHKMMEKAAQV 632
                       **.: :.******:***:****:**  **. *::*: :*** ..*:*:******:*: :

SaCPR2 (SEQ ID NO:13)  WNMISDGGYVVVCGDAKGMAKDVHRALHTIVHEQGSLDNSKTESMVKNLQMNGRYLRDVW 704
CPR    (SEQ ID NO:46)  WNMISQGAYLYVCGDAKGMARDVHRSLHTIAQEQGSMDSTKAEGFVKNLQTSGRYLRDVW 712
SaCPR1 (SEQ ID NO:12)  WSLISQGAYLYVCGDAKGMARDVHRTLHTLVQQQESVDSSKAESIVKKLQMDGRYLRDVW 692
CPR    (SEQ ID NO:58)  WDLIKEEGYLYVCGDAKGMARDVHRTLHTIVQEQEGVSSSEAEAIVKKLQTEGRYLRDVW 692
                       *.:*.  ** .:***********:*****:***:  ::: .:: :.:*:**:  ********
```

FIGURE 3C

| CYP76-G5 (SEQ ID NO:7) | MDFLSFILFVLFAWALVRALPTLSRGSKAAGGRLPPGPVPLPVVGNLLLKLGSKPHKSLAE | 60 |
| CYP76-G10 (SEQ ID NO:6) | MDFLSCILFVLFAWALVRALPTLSRGSKAASGRLPPGPVPWPVVGNLLLKLGNKPHKSLAE | 60 |
| P450BM-3 (SEQ ID NO:66) | ------------------------TIKEMPQPKTFGELKN------LPLLN-----TDKPVQALMK | 31 |
| | : * . . . * . * . ** . ::* . : | |
| | | |
| CYP76-G5 (SEQ ID NO:7) | LAKSYGPIMCLKLIGHITTIVISTPTVAKEVLQKQDVAFCNRTIPDAVRAHRHDLHSMVWL | 120 |
| CYP76-G10 (SEQ ID NO:6) | LAKSYGPIMCLKLIGHMTTIVISTPTVAKEVLQKQDVAFSNRTTPDAVRAHGHDLYSMAWL | 120 |
| P450BM-3 (SEQ ID NO:66) | IADELGEIFKFEAPGRVTRYLSSQRLIKEACDESRFDKNLSQALKFVRDFAGDGLFTSWT | 91 |
| | :*: : :*: .* . : :**.: : .: *. **.* * | |
| | | |
| CYP76-G5 (SEQ ID NO:7) | PVSTRWRTLRKISNSHIFSSQRLDENHHLRRKLDELLARVAESSLVGAVVDIGAVAFLT | 180 |
| CYP76-G10 (SEQ ID NO:6) | PVSTRWRTLRKISNSHIFTSQRLDENHHLRRKLDELLARVAESSLVGAVVDMGAVAFLT | 180 |
| P450BM-3 (SEQ ID NO:66) | HEKN-WKKAHNILLPSFS--QQAMKGYHAMMVDIAVQLVQKWERLNADEHIEVPEDMTRL | 148 |
| | . .* : . . *.: . : .: . ::: | |
| | | |
| CYP76-G5 (SEQ ID NO:7) | SLNLLSNTVFSKDLVEPGLGAVQEMEEVVWNGITEEAGRPNLVDYFPVLRRLDPQG-TRRR | 239 |
| CYP76-G10 (SEQ ID NO:6) | SLNLLSNTVFSKDLVEPGLGAVQETKEVVWNGMMEEAGRPNLVDYFPVLRRLDPQG-IRRR | 239 |
| P450BM-3 (SEQ ID NO:66) | TLDTIGLCGFNYRFNSFYRDQPHPFITSMVRALDEAMN------KLQRANPDDPAYDE | 200 |
| | :*: . . . . . : . * . | |
| | | |
| CYP76-G5 (SEQ ID NO:7) | MMGYFGKMFEVFGDIIDERLELRKQQSDGDSPAATTNDVLDVLLNIIEDAEIEEKPNRTD | 299 |
| CYP76-G10 (SEQ ID NO:6) | MTGYFGKMLEVFGDIIDERLEWRKQQSDGDSPAGTTNDVLDVLLNIIEDAEIEEKPNRTD | 299 |
| P450BM-3 (SEQ ID NO:66) | NKRQFQEDIKVMNDLVDKIIADRKASGE------QSDDLLTHMLNG-KDPETGEPLDDEN | 253 |
| | : : :*. . ::::*** .:** * .. | |
| | | |
| CYP76-G5 (SEQ ID NO:7) | VEHFIVDLFVAGSDTTSSTVEWAMTELLRKPETLERARSELHETIGPKNLVQEADMPRLP | 359 |
| CYP76-G10 (SEQ ID NO:6) | VEHFIVDLFAAGSDTTSSTVEWAMTELLRKPETLERARSELHETIGPENLVQEADLPRLP | 359 |
| P450BM-3 (SEQ ID NO:66) | IRYQIITFLIAGHETTSGLLSFALYFLVKNPHVLQKAAEEAARVLVDP-VPSYKQVKQLK | 312 |
| | :: .: :***. : .. *: ..::* :* .: .: | |

FIGURE 5A

```
CYP76-G5  (SEQ ID NO:7)   YLQAVVKETFRLHPPVPLLLPRTAEKDAELCGFTVPAGAQIMVNAWAIGRDPGTW-EDPE 418
CYP76-G10 (SEQ ID NO:6)   YLQAVVKETFRLHPPVPLLLPRTAEKDAELCGFTVPAGAQIMVNAWAIGRDPGTW-EDPE 418
P450BM-3  (SEQ ID NO:66)  YVGMVLNEALRLWPTAPAFSLYAKEDTVLGGEYPLEKGDELMVLIPQLHRDKTIWGDDVE 372
                          *:  :*::*:::**  *  *    : ..  *     .  : :  ::*  ..  * :**

CYP76-G5  (SEQ ID NO:7)   SFLPERFLGSDVDVKGRSFELIPFGGGRRICPGLPLAIRMVHLMLGSLIHGFRWKVEDDG 478
CYP76-G10 (SEQ ID NO:6)   SFLPERFLGSDVDVKGRSFELIPFGGGRRICPGLPLAIRMVHLMLGSLIHGFRWKVDDDG 478
P450BM-3  (SEQ ID NO:66)  EFRPERFENPSAIP---QHAFKPFGNGQRACIGQQFALHEATLVLGMMLKHFDFEDHTNY 429
                           * ****     .    :.*  ***.*: ***  :** ** :* *  :: * :: ..

CYP76-G5  (SEQ ID NO:7)   MGSPETAMDMDEKFGITLQKAK--SLCAVPIRG---------- 509
CYP76-G10 (SEQ ID NO:6)   MGSPETAMDMDEKFGITLQKAK--PLCAVPIRG---------- 509
P450BM-3  (SEQ ID NO:66)  ELDIKETLTLKPEGFVVKAKSKKIPLGGIPSPSTEQSAKKVR  471
                            : :*  : :* *.: :.*:*  .* .:*   .
```

FIGURE 5B

| | | |
|---|---|---|
| CYP76F39v1 | (SEQ ID NO:7) | MDFLSCILFVLFAWALVRALPTLSRGSKAASGRLPPGPVPWPVVGNLLKLGNKPHKSLAE 60 |
| CYP76F39v2 | (SEQ ID NO:74) | MDFLSCILSVLFAWALVRALRKLSRGSKAASGRLPPGPVPWPVVGNLLKLGNKPHKSLAE 60 |
| CYP76F40 | (SEQ ID NO:75) | MDFLSCILSVLFAWALVRALRKLSRGSKAASGRLPPGPVPWPVVGNLLKLGNKPHKSLAE 60 |
| CYP76F41 | (SEQ ID NO:76) | MDFLSCILFVLFAWALVHALRTLSRGSKAAGGRLPPGPVPLPVVGNLLKLGNKPHKSLAE 60 |
| CYP76F42 | (SEQ ID NO:77) | MDFLSCILSVLFAWALVRALPTLSRGSKAAGGRLPPGPVPLPVVGNLLKLGNKPHKSLAE 60 |
| CYP76F37v1 | (SEQ ID NO:8) | MDFLSCILFVLFAWALVRALPTLSRGSKAAGGRLPPGPVPLPVVGNLLKLGSKPHKSLAA 60 |
| CYP76F37v2 | (SEQ ID NO:73) | MDFLSCILFVLFAWALVRALPTLSRGSKAAGGRLPPGPVPLPVVGNLLKLGSKPHKSLAE 60 |
| CYP76F38v2 | (SEQ ID NO:9) | MDFLSCILFVLFAWALVRALPTLSRGSKAAGGRLPPGPVPLPVVGNLLKLGSKPHKSLAE 60 |
| CYP76F38v1 | (SEQ ID NO:6) | MDFLSFILFVLFAWALVRALPTLSRGSKAAGGRLPPGPVPLPVVGNLLKLGSKPHKSLAE 60 |
| CYP76F43 | (SEQ ID NO:78) | MDFLSCILFVLFAWALVRALPTLSRGSKAAGGRLPPGPVPLPVVGNLLKLGSKPHKSLAE 60 |
| | | ***   ***  . ***********.*********** |

← a →

| | | |
|---|---|---|
| CYP76F39v1 | (SEQ ID NO:7) | LAKSYGPIMCLKLGHMTTIVISTPTVAKEVLQKQDVAFSNRTTPDAVRAHGHDLYSMAWL 120 |
| CYP76F39v2 | (SEQ ID NO:74) | LAKSYGPIMCLKLGHMTTIVISTPTVAKEVLQKQDVAFSNRTIPDAVRAYGHDLYSMAWL 120 |
| CYP76F40 | (SEQ ID NO:75) | LAKSYGPIMCLKLGHMTTIVISTPTVAKEVLQKQDVAFSNRTTPDAVRAHGHDLYSMAWL 120 |
| CYP76F41 | (SEQ ID NO:76) | LAKSYGPIMCLKLGHITTIVISTPTVAKEVLQKQDVAFSNRTTPDAVRAHGHDLYSMAWL 120 |
| CYP76F42 | (SEQ ID NO:77) | LAKSYGPIMCLKLGHMTTIVISSPTVAKEVLQKQDVAFCNRTTPDAVRAHGHDLYSMAWL 120 |
| CYP76F37v1 | (SEQ ID NO:8) | LAKSYDPIMCLKLGHITTIVISTPTVAKEVLQKQDVAFCNRTIPDAVRAHRHDLHSMVWL 120 |
| CYP76F37v2 | (SEQ ID NO:73) | LAKSYGPIMCLKLGHITTIVISTPTVAKEVLQKQDVAFCNRTIPDAVRAHRHDLHSMVWL 120 |
| CYP76F38v2 | (SEQ ID NO:9) | LAKSYGPIMCLKLGHITTIVISTPTVAKEVLQKQDVAFCNRTIPDAVRAHRHDLHSMVWL 120 |
| CYP76F38v1 | (SEQ ID NO:6) | LAKSYGPIMCLKLGHITTIVISTPTVAKEVLQKQDVAFCNRTIPDAVRAHRHDLHSMVWL 120 |
| CYP76F43 | (SEQ ID NO:78) | LAKSYGPIMCLKLGHITTIVISTPTVAKEVLQKQDVAFCNRTIPDAVRAHRHDLYSMAWL 120 |
| | | *** ****:**:*********** *:****:.* *  |

SRS1

| | | |
|---|---|---|
| CYP76F39v1 | (SEQ ID NO:7) | PVSTRWRTLRKISNSHIFTSQRLDENHHLRRRKLDELLARVAESSLVGAVVDMGAVAFLT 180 |
| CYP76F39v2 | (SEQ ID NO:74) | PVSTRWRTLRKISNSHIFTSQRLDENHHLRRRKLDELLARVAESSLVGAVVDMGAVAFLT 180 |
| CYP76F40 | (SEQ ID NO:75) | PVSTRWRTLRKISNSHIFTSQRLDENHHLRRRKLDELLARVAESSLVGAVVDMGAVAFLT 180 |
| CYP76F41 | (SEQ ID NO:76) | PVSTRWRTLRKISNSHIFTSQRLDENHHLRRRKLDELLARVAESSLVGAVVDMGAVAFLT 180 |
| CYP76F42 | (SEQ ID NO:77) | PVSTRWRTLRKISNSHIFSSQRLDENHHLRRQKLDELLARVAESSLVGAVVDIGAVAFVT 180 |
| CYP76F37v1 | (SEQ ID NO:8) | PVSTRWRTLRKISNSHIFSSQRLDENHHLRRRKLDELLTRVAESSLVGAVVDIGAVAFLT 180 |
| CYP76F37v2 | (SEQ ID NO:73) | PVSTRWRTLRKISNSHIFSSQRLDENHHLRRRKLDELLTRVAESSLVGAVVDIGAVAFLT 180 |
| CYP76F38v2 | (SEQ ID NO:9) | PVSTRWRTLRKISNSHIFSSQRLDENHHLRRRKLDELLTRVAESSLVGAVVDIGAVAFLT 180 |
| CYP76F38v1 | (SEQ ID NO:6) | PVSTRWRTLRKISNSHIFSSQRLDENHHLRRRKLDELLTRVAESSLVGAVVDIGAVAFLT 180 |
| CYP76F43 | (SEQ ID NO:78) | PVSTRWRTLRKISNSHIFSSQRLDENHHLRRQKLDELLARVAESSLVGAAVDIGAVAFVT 180 |
| | | **************** :******* ***.****::*****:* |

FIGURE 21A

```
                                                                                   SRS2
CYP76F39v1 (SEQ ID NO:7)  SLNLLSNTVFSKDLVEPGLGAVQE TKEVVWGMMEEAGRPNLVDYFPVLRRLDPQGIRRRM 240
CYP76F39v2 (SEQ ID NO:74) SLNLLSNTVFSKDLVEPGLGAVQE TKEVVWGMMEEAGRPNLVDYFPVLRRLDPQGIRRRM 240
CYP76F40   (SEQ ID NO:75) SLNLLSNTVFSKDLVEPGLGAVQE TKEVVWGMMEEAGRPNLVDYFPVLRRLDPQGIRRRM 240
CYP76F41   (SEQ ID NO:76) SLNLLSNTVFSKDLVEPGLGAVQE MEEVVWGITEEAGRPNLVDYFPVLRRLDPQGTRRRM 240
CYP76F42   (SEQ ID NO:77) SLNLLSNTVFSKDLVEPGLGAVQE MEEVVWGITEEAGRPNLVDYFPVLRRLDPQGTRRRM 240
CYP76F37v1 (SEQ ID NO:8)  SLNLLSNTVFSKDLVEPGLGAVQE MEEVVWGITEEAGRPNLVDYFPVLRRLDPQGIRRRM 240
CYP76F37v2 (SEQ ID NO:73) SLNLLSNTVFSKDLVEPGLGAVQE MEEVVWGITEEAGRPNLVDYFPVLRRLDPQGTRRRM 240
CYP76F38v2 (SEQ ID NO:9)  SLNLLSNTVFSKDLVEPGLGAVQE MEEVVWGITEEAGRPNLVDYFPVLRRLDPQGTRRRM 240
CYP76F38v1 (SEQ ID NO:6)  SLNLLSNTVFSKDLVEPGLGAVQE MEEVVWGITEEAGRPNLVDYFPVLRRLDPQGTRRRM 240
CYP76F43   (SEQ ID NO:78) SLNLLSNTVFSKDLVEPGLGAVQE MKEVVWGIMEEAGRPNLVDYFPVLRRLDPQGIRRRM 240
                          *************************  : ***  :**.**************.**:****

SRS3
CYP76F39v1 (SEQ ID NO:7)  TGYFGKMLEVFGDIIDERLEWRKQQSDGDSPAGTTNDVLDVLLNIIEDAEIEEKPNRTDV 300
CYP76F39v2 (SEQ ID NO:74) TGYFGKMLEVFGDIIDERLEWRKQQSDGDSPAGTTNDVLDVLLNIIEDAEIEEKPNRTDV 300
CYP76F40   (SEQ ID NO:75) TGYFGKMLEVFGDIIDERLELRKQQSDGDSPAGTTNDVLDVLLNIIEDAEIEEKPNRTDV 300
CYP76F41   (SEQ ID NO:76) MGYFGKMFEVFGDIIDERLELRKQQSDGDSPAATTNDVLDVLLNIIEDAEIEEKPNRTDV 300
CYP76F42   (SEQ ID NO:77) MGYFGKMFEVFGDIIDERLELRKQQSDGDSPAATTNDVLDVLLNIIEDAEIEEKPNRTDV 300
CYP76F37v1 (SEQ ID NO:8)  MGYFGKMFEVFGDIIDERLEWRKQQSDGDSPAGTTNDVLDVLLNIIEDAEIEEKPNRTDV 300
CYP76F37v2 (SEQ ID NO:73) MGYFGKMFEVFGDIIDERLELRKQQSDGDSPAATTNDVLDVLLNIIEDAEIEEKPNRTDV 300
CYP76F38v2 (SEQ ID NO:9)  MGYFGKMFEVFGDIIDERLELRKQQSDGDSPAATTNDVLDVLLNIIEDAEIEEKPNRTDV 300
CYP76F38v1 (SEQ ID NO:6)  MGYFGKMFEVFGDIIDERLELRKQQSDGDSPAATTNDVLDVLLNIIEDAEIEEKPNRTDV 300
CYP76F43   (SEQ ID NO:78) TGNFGKMLEVFGDIIDERLEWRKQQSDGDSPAGTTNDVLDVLLNIIEDAEIEEKPNRTDV 300
                          * .****:************ ***********.********************

SRS4
                          ←——→
                           b
CYP76F39v1 (SEQ ID NO:7)  EHFLLIDLFAAGSDTTSSTVEWAMTELLRKPETLERARSELHETIGPENLVQEADLPRLPY 360
CYP76F39v2 (SEQ ID NO:74) EHFLLIDLFAAGSDTTSSTVEWAMTELLRKPETLERARSELHETIGPENLVQEADLPRLPY 360
CYP76F40   (SEQ ID NO:75) EHFIVDLFVAGSDTTSSTVEWAMTELLRKPETLERARSELHETIGPKNLVQEADMPRLPY 360
CYP76F41   (SEQ ID NO:76) EHFIVDLFVAGSDTTSSTVEWAMTELLRKPETLERARSELHETIGPKNLVQEADMPRLPY 360
CYP76F42   (SEQ ID NO:77) EHFIVDLFVAGSDTTSSTVEWAMTELLRKPETLERARSELHETIGPKNLVQEADMPRLPY 360
CYP76F37v1 (SEQ ID NO:8)  EHFLLIDLFAAGSDTTSSTVEWAMTELLRKPETLERARSELHETIGPENLVQEADLPRLPY 360
CYP76F37v2 (SEQ ID NO:73) EHFIVDLFVAGSDTTSSTVEWAMTELLRKPETLERARSELHETIGPENLVQEADMPRLPY 360
CYP76F38v2 (SEQ ID NO:9)  EHFIVDLFVAGSDTTSSTVEWAMTELLRKPETLERARSELHETIGPENLVQEADLPRLPY 360
CYP76F38v1 (SEQ ID NO:6)  EHFIVDLFVAGSDTTSSTVEWAMTELLRKPETLERARSELHETIGPENLVQEADLPRLPY 360
CYP76F43   (SEQ ID NO:78) EHLLLIDLFVAGSDTTSSTVEWAMTELLRKPETLERARSELHETIGPKNLVQEADMPRLPY 360
                          **  :: ** .************************************:*******:*****
```

FIGURE 21B

| | | |
|---|---|---|
| CYP76F39v1 | (SEQ ID NO:7) | LQAVVKETFRLHPPVPLLLPRTAEKDAELCGFTVPAGAQIMVNAWAIGRDPGTWEDPESF 420 |
| CYP76F39v2 | (SEQ ID NO:74) | LQAVVKETFRLHPPVPLLLPRTAEKDAELCGFTVPAGAQIMVNAWAIGRDPGTWEDPESF 420 |
| CYP76F40 | (SEQ ID NO:75) | LQAVVKETFRLHPPVPLLLPRTAEKDAELCGFTVPAGAQIMVNAWAIGRDPGTWEDPESF 420 |
| CYP76F41 | (SEQ ID NO:76) | LQAVVKETFRLHPPVPLLLPRTAEKDAELCGFTVPAGAQIMVNAWAIGRDPGTWEDPESF 420 |
| CYP76F42 | (SEQ ID NO:77) | LQAVVKETFRLHPPVPLLLPRTAEKDAELCGFTVPAGAQIMVNAWAIGRDPGTWEDPESF 420 |
| CYP76F37v1 | (SEQ ID NO:8) | LQAVVKETFRLHPPVPLLLPRTAEKDAELCGFTVPAGAQIMVNAWAIGRDPGTWEDPESF 420 |
| CYP76F37v2 | (SEQ ID NO:73) | LQAVVKETFRLHPPVPLLLPRTAEKDAELCGFTVPAGAQIMVNAWAIGRDPGTWEDPESF 420 |
| CYP76F38v2 | (SEQ ID NO:9) | LQAVVKETFRLHPPVPLLLPRTAEKDAELCGFTVPAGAQIMVNAWAIGRDPGTWEDPESF 420 |
| CYP76F38v1 | (SEQ ID NO:6) | LQAVVKETFRLHPPVPLLLPRTAEKDAELCGFTVPAGAQIMVNAWAIGRDPGTWEDPESF 420 |
| CYP76F43 | (SEQ ID NO:78) | LQAVVKETFRLHPPVPLLLPRTAEKDAELCGFTVPAGAQIMVNAWAIGRDPGTWEDPESF 420 |
| | | ************************************************************ |
| CYP76F39v1 | (SEQ ID NO:7) | LPERFLGSDVDVKGRSFELIPFGGGRRICPGLPLAIRMVHLMLGSLIHGFRWKVDDDGMG 480 |
| CYP76F39v2 | (SEQ ID NO:74) | LPERFLGSDVDVKGRSFELIPFGGGRRICPGLPLAIRMVHLMLGSLIHGFRWKVDDDGMG 480 |
| CYP76F40 | (SEQ ID NO:75) | LPERFLGSDVDVKGRSFELIPFGGGRRICPGLPLAIRMVHLMLGSLIHGFRWKVDDDGMG 480 |
| CYP76F41 | (SEQ ID NO:76) | LPERFLGSDVDVKGRSFELIPFGGGRRICPGLPLAIRMVHLMLGSLIHGFRWKVADDGMG 480 |
| CYP76F42 | (SEQ ID NO:77) | LPERFLGSDVDVKGRSFELIPFGGGRRICPGLPLAIRMVHLMLGSLIHGFRWKVADDGMG 480 |
| CYP76F37v1 | (SEQ ID NO:8) | LPERFLGSDVDVKGRSFELIPFGGGRRICPGLPLAIRMVHLMLGSLIHGFRWKVADDGMG 480 |
| CYP76F37v2 | (SEQ ID NO:73) | LPERFLGSDVDVKGRSFELIPFGGGRRICPGLPLAIRMVHLMLGSLIHGFRWKVDDDGMG 480 |
| CYP76F38v2 | (SEQ ID NO:9) | LPERFLGSDVDVKGRSFELIPFGGGRRICPGLPLAIRMVHLMLGSLIHGFRWKVDDDGMG 480 |
| CYP76F38v1 | (SEQ ID NO:6) | LPERFLGSDVDVKGRSFELIPFGGGRRICPGLPLAIRMVHLMLGSLIHGFRWKVFDDGMG 480 |
| CYP76F43 | (SEQ ID NO:78) | LPERFLGSDVDVKGRSFELIPFGGGRRICPGLPLAIRMVHLMLGSLIHGFRWKVFDDGMG 480 |
| | | ***************************************************** *** *** |
| CYP76F39v1 | (SEQ ID NO:7) | SPETAMDMDEKFGITLQKAKPLCAVPIRG 509 |
| CYP76F39v2 | (SEQ ID NO:74) | SPETAMDMDEKFGITLQKAKPLCAVPIRG 509 |
| CYP76F40 | (SEQ ID NO:75) | SPETAMDMDEKFGITLQKAKSLCAVPIRG 509 |
| CYP76F41 | (SEQ ID NO:76) | SPETAMDMDEKFGITLQKAKSLCAVPIRG 509 |
| CYP76F42 | (SEQ ID NO:77) | SPETAMDMDEKFGITLQKAKSLCAVPIRG 509 |
| CYP76F37v1 | (SEQ ID NO:8) | SPETAMDMDEKFGITLQKAKPLCAVPIRG 509 |
| CYP76F37v2 | (SEQ ID NO:73) | SPETAMDMDEKFGITLQKAKPLCAVPIRG 509 |
| CYP76F38v2 | (SEQ ID NO:9) | SPETAMDMDEKFGITLQKAKPLCAVPIRG 509 |
| CYP76F38v1 | (SEQ ID NO:6) | SPETAMDMDEKFGITLQKAKSLCAVPIRG 509 |
| CYP76F43 | (SEQ ID NO:78) | SPETAMDMDEKFGITLQKAKSLCAVPIRG 509 |
| | | ******************.***** |

FIGURE 21C

CYTOCHROME P450 AND CYTOCHROME P450 REDUCTASE POLYPEPTIDES, ENCODING NUCLEIC ACID MOLECULES AND USES THEREOF

RELATED APPLICATIONS

Benefit of priority is claimed to U.S. Provisional Application Ser. No. 61/796,129, filed Nov. 1, 2012, entitled "CYTOCHROME P450 AND CYTOCHROME P450 REDUCTASE POLYPEPTIDES, ENCODING NUCLEIC ACID MOLECULES AND USES THEREOF" and to U.S. Provisional Application Ser. No. 61/956,086, filed May 31, 2013, entitled "CYTOCHROME P450 AND CYTOCHROME P450 REDUCTASE POLYPEPTIDES, ENCODING NUCLEIC ACID MOLECULES AND USES THEREOF." The subject matter of each of the above-noted applications is incorporated by reference in its entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file is 301 kilobytes in size, and titled 229SEQPC1.txt.

FIELD OF THE INVENTION

Provided are cytochrome P450 santalene oxidases, cytochrome P450 bergamotene oxidases and cytochrome P450 reductases, nucleic acid molecules encoding the P450 santalene oxidases, cytochrome P450 bergamotene oxidases and cytochrome P450 reductases, and methods for producing products whose synthesis includes reactions catalyzed by the cytochrome P450 santalene and bergamotene oxidases. Included among the products are santalols and bergamotols and precursors and derivatives thereof.

BACKGROUND

Sandalwood (*Santalum album*) is a slow-growing hemiparasitic tropical tree of great economic value found growing in southern India, Sri Lanka, eastern Indonesia and northern Australia. The timber is highly sought after for its fine grain, high density and excellent carving properties. Sandalwood heartwood has a unique fragrance imparted by the resins and essential oils, including santalols, santalenes and other sesquiterpenoids, in the heartwood. In general, *Santalum album* heartwood contains up to 6% dry weight sesquiterpene oils. Sandalwood oil predominantly contains the sesquiterpene alcohols α-santalol, β-santalol, Z-α-transbergamotol and epi-β-santalol, and additionally includes α-santalene, β-santalene, α-bergamotene, epi-β-santalene, β-bisabolene, α-curcumene, β-curcumene and γ-curcumene. Sandalwood oil has a soft, sweet-woody and animal-balsamic odor that is imparted from the terpenoid β-santalol and is highly valued. Sandalwood oil has been obtained by distillation of the heartwood of *Santalum* species and is used as a perfume ingredient, in incenses and traditional medicine and in pesticides.

Centuries of over-exploitation has led to the demise of sandalwood in natural stands. Large plantations are being established throughout northern Australia to satisfy demand and conserve remaining reserves. In addition, there is great variation in the amount of heartwood oil produced, even under near-identical growing conditions, due to genetic and environmental factors, such as climate and local conditions. Generally, the price and availability of plant natural extracts depend upon the abundance, oil yield and geographical origins of the plants.

Although chemical approaches to generate santalols and the other sesquiterpenoids in sandalwood oil have been attempted, the highly complex structures of these compounds have rendered economically viable synthetic processes for their preparation in large quantities unattainable. Thus, there is a need for efficient, cost-effective syntheses of santalols and other sesquiterpenoids that impart the highly sought after sandalwood fragrance for use in the fragrance industry.

Thus, among the objects herein, is the provision of methods for the production of santalols and other sesquiterpenoids and the resulting products of the methods.

SUMMARY

Provided herein are nucleic acid molecules encoding cytochrome P450 polypeptides or catalytically active fragments thereof and the encoded polypeptides, and host cells containing such nucleic acid molecules or encoded polypeptides. For example, the encoded cytochrome P450 polypeptide or catalytically active fragment or portion thereof exhibits at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity to SEQ ID NO:50, such as at least 90% sequence identity to SEQ ID NO:50. Also provided are nucleic acid molecules encoding cytochrome P450 reductase polypeptides or catalytically active fragments thereof and the encoded polypeptides, and host cells containing such nucleic acid molecules or encoded polypeptides. For example, the encoded cytochrome reductase polypeptide or catalytically active fragment thereof exhibits at least 80%, 85%, 86%, 87%, 88%, 89%, 90%, 91%, 92%, 93%, 94%, 95%, 96%, 97%, 98% or 99% sequence identity to a cytochrome P450 reductase polypeptide set forth in SEQ ID NO:12 or 13, such as at least 90% sequence identity to a cytochrome P450 reductase polypeptide set forth in SEQ ID NO:12 or 13. Any of the nucleic acid molecules provided herein can be cDNA or can be an isolated or purified nucleic acid molecule. Among the nucleic acid molecules and polypeptides provided herein are a set of CYP450s that exhibit santalene/bergamotene oxidase activity, which provide for, among other things, metabolic engineering of sandalwood oil biosynthesis, improvement of sandalwood plantations, and conservation of native sandalwood forests.

In particular, among the host cells provided herein are host cells that are engineered to contain heterologous nucleic acid encoding any of the cytochrome P450 polypeptides provided herein, whereby the host cells are capable of producing one or more of α-santalol from α-santalene, β-santalol from β-santalene, epi-β-santalol from epi-β-santalene and α-trans-bergamotol from α-trans-bergamotene, such as one or more of (E)-α-santalol, (Z)-α-santalol, (E)-β-santalol, (Z)-β-santalol, (E)-epi-β-santalol, (Z)-epi-β-santalol, (Z)-α-trans-bergamotol or (E)-α-trans-bergamotol. For example, the host cells are also engineered to also contain a santalene synthase as described herein to produce a santalene and/or bergamotene terpene substrate of the encoded cytochrome P450 polypeptide. The host cells also can be engineered to also contain heterologous nucleic acid encoding a cytochrome P450 reductase, such as any provided herein. The host cells is a prokaryotic cell or an eukaryotic cell, such as a bacteria, yeast, insect, plant or mammalian cell. For example, the host cell is a *Saccharomyces* genus cell, a *Pichia* genus cell or an *Escherichia coli* cell. In particular examples herein, the host cell is a *Saccharomyces cerevisiae* cell. The host cell produces or is modified to produce or overexpress an acyclic pyrophosphate terpene precursor, such as farnesyl diphosphate.

For example, provided herein are isolated *Santalum album* cytochrome P450 polypeptides or catalytically active fragments thereof, including cytochrome P450 santalene oxidases or catalytically active fragments thereof and cytochrome P450 bergamotene oxidases or catalytically active fragments thereof. Also provided herein are nucleic acid molecules encoding the cytochrome P450 santalene oxidases and cytochrome P450 bergamotene oxidases or catalytically active fragments thereof. Also provided are modified forms thereof.

Also provided are nucleic acid molecules encoding cytochrome P450 reductase polypeptides, including modified cytochrome P450 reductase polypeptides. Provided herein are isolated *Santalum album* cytochrome P450 reductase polypeptides, and host cells containing the polypeptides, where the polypeptides are heterologous to the host cell. Provided are nucleic acid molecules encoding a fusion protein containing a cytochrome P450 enzyme and a second moiety such as a synthase or catalytically active portion thereof.

Also provided are nucleic acid molecules encoding fusion proteins containing a *Santalum album* santalene synthase and/or a cytochrome P450 santalene oxidase or bergamotene oxidase and/or a cytochrome P450 reductase, or catalytically active fragments of any of the enzymes. Exemplary of the nucleic acid molecules encoding fusion proteins are nucleic acid molecules encoding a fusion protein containing: a santalene synthase and a cytochrome P450 santalene oxidase; a santalene synthase and a bergamotene oxidase; a cytochrome P450 santalene oxidase and a cytochrome P450 reductase; and a cytochrome P450 bergamotene oxidase and a cytochrome P450 reductase or catalytically active fragments of any the preceding enzymes. The encoded proteins and host cells containing the nucleic acids and/or the proteins are provided.

Also provided herein are methods for producing any of the encoded cytochrome P450 polypeptides or catalytically active fragments thereof, including methods for producing a cytochrome P450 reductase polypeptide. Also provided herein are methods for production of a santalol, bergamotol and/or mixtures thereof by contacting the cytochrome P450 santalene oxidases and/or cytochrome P450 bergamotene oxidases with a substrate therefor from which these products are produced. The methods can be performed in vitro with isolated reagents or partially isolated reagents or in vivo in a host cell that encodes the enzymes, and optionally a synthase and/or other substrate.

For example, provided herein are isolated *Santalum album* cytochrome P450 santalene oxidases or catalytically active fragments thereof. The provided isolated *Santalum album* cytochrome P450 santalene oxidases catalyze the hydroxylation or monooxygenation of santalene and/or bergamotene. In one example, the provided isolated *Santalum album* cytochrome P450 santalene oxidases catalyze the formation of a santalol from a santalene and/or a bergamotol from a bergamotene. For example, the isolated *Santalum album* cytochrome P450 santalene oxidases catalyze the formation of α-santalol from α-santalene, β-santalol from β-santalene, epi-β-santalol from epi-β-santalene and/or Z-α-trans-bergamotol from α-trans-bergamotene. For example, the isolated *Santalum album* cytochrome P450 santalene oxidases catalyze the formation of (E)-α-santalol, (Z)-α-santalol, (E)-β-santalol, (Z)-β-santalol, (E)-epi-β-santalol, (Z)-epi-β-santalol, (Z)-α-trans-bergamotol or (E)-α-trans-bergamotol. Also provided herein are isolated cytochrome P450 santalene oxidases that are members of the CYP76 family.

Provided herein are isolated nucleic acid molecules encoding a *Santalum album* cytochrome P450 santalene oxidase polypeptide or a catalytically active fragment thereof. For example, provided herein are isolated nucleic acid molecules (and host cells containing the nucleic acid molecules, which are heterologous to the host cells) encoding a cytochrome P450 santalene oxidase polypeptide having a sequence of amino acids set forth in SEQ ID NO:7, 74, 75, 76 or 77; or a cytochrome P450 santalene oxidase polypeptide having a sequence of amino acids that has at least 96% sequence identity to a cytochrome P450 santalene oxidase whose sequence is set forth in SEQ ID NO:7, 74, 75, 76 or 77. In another example provided herein are isolated nucleic acid molecules encoding a cytochrome P450 santalene oxidase polypeptide having a sequence of amino acids that has at least 50% sequence identity to a cytochrome P450 santalene oxidase polypeptide set forth in SEQ ID NO:7, 74, 75, 76 or 77. The cytochrome P450 santalene oxidase polypeptide catalyzes the hydroxylation or monooxygenation of santalene and/or bergamotene. For example, the encoded cytochrome P450 santalene oxidase polypeptide exhibits at least 55%, 60%, 65%, 70%, 75%, 80%, 85%, 86%, 87%, 88%, 89%, 90%, 91%, 92%, 93%, 94%, 95%, 96%, 97%, 98% or 99% amino acid sequence identity to a sequence of amino acids set forth in SEQ ID NO:7, 74, 75, 76 or 77.

Also provided herein are isolated nucleic acid molecules encoding a cytochrome P450 santalene oxidase or a catalytically active fragment thereof selected from among nucleic acid molecules having a sequence of nucleic acids set forth in SEQ ID NO:3, 68, 69, 70 or 71; a sequence of nucleic acids having at least 98% sequence identity to a sequence of nucleic acids set forth in SEQ ID NO:3, 68, 69, 70 or 71; and degenerates thereof. In a particular example, the isolated nucleic acid molecule has the sequence of nucleotides set forth SEQ ID NO:3, 68, 69, 70 or 71. In some examples, the isolated nucleic acid molecules encode a cytochrome P450 santalene oxidase polypeptide having a sequence of amino acids set forth in SEQ ID NO:7, 74, 75, 76 or 77. The provided isolated nucleic acid molecules encode cytochrome P450 santalene oxidase polypeptides that catalyze the formation of a santalol, such as a α-santalol, β-santalol or epi-β-santalol, from a santalene, such as a α-santalene, β-santalene or epi-β-santalene, and/or catalyze the hydroxylation or monooxygenation of santalene. In some examples, the encoded cytochrome P450 santalene oxidase polypeptide catalyzes the formation of Z-α-trans-bergamotol from α-trans-bergamotene. Also provided herein are cytochrome P450 santalene oxidase polypeptides encoded by any of the isolated nucleic acid molecules provided herein.

For example, provided herein are isolated *Santalum album* cytochrome P450 bergamotene oxidases or catalytically active fragments thereof. The provided isolated *Santalum album* cytochrome P450 bergamotene oxidases or catalytically active fragments thereof catalyze the hydroxylation or monooxygenation of bergamotene and/or catalyze the formation of a bergamotol from a bergamotene. For example, the isolated *Santalum album* cytochrome P450 bergamotene oxidases catalyze the formation of Z-α-transbergamotol or (E)-α-trans-bergamotol from α-trans-bergamotene. In some examples, the isolated *Santalum album* cytochrome P450 bergamotene oxidases do not catalyze the hydroxylation of a santalene. In other examples, the isolated *Santalum album* cytochrome P450 bergamotene oxidases catalyze the hydroxylation of a santalene. Also provided herein are isolated *Santalum album* cytochrome P450 bergamotene oxidases that are members of the CYP76 family.

Provided herein are isolated nucleic acid molecules encoding a *Santalum album* cytochrome P450 bergamotene oxidase polypeptide or a catalytically active fragment thereof. For example, provided herein are isolated nucleic acid molecules encoding a cytochrome P450 bergamotene oxidase polypeptide having a sequence of amino acids set forth in SEQ ID NO:6, 8, 9 or 73; or a cytochrome P450 bergamotene oxidase polypeptide having a sequence of amino acids that has at least 96% sequence identity to a cytochrome P450 polypeptide set forth in SEQ ID NO:6, 8, 9 or 73. In another example, provided herein are isolated nucleic acid molecules encoding a cytochrome P450 bergamotene oxidase polypeptide having a sequence of amino acids that has at least 50% sequence identity to a cytochrome P450 bergamotene oxidase polypeptide set forth in SEQ ID NO:6, 8, 9 or 73. The cytochrome P450 bergamotene oxidase polypeptide catalyzes the hydroxylation or monooxygenation of bergamotene. For example, the encoded cytochrome P450 bergamotene oxidase polypeptide exhibits at least 55%, 60%, 65%, 70%, 75%, 80%, 85%, 86%, 87%, 88%, 89%, 90%, 91%, 92%, 93%, 94%, 95%, 96%, 97%, 98% or 99% amino acid sequence identity to a sequence of amino acids set forth in SEQ ID NO:6, 8, 9 or 73.

Also provided herein are isolated nucleic acid molecules encoding a cytochrome P450 bergamotene oxidase polypeptide or a catalytically active fragment thereof having a sequence of nucleic acids set forth in any of SEQ ID NOS:2, 4, 5 or 67; a sequence of nucleic acids having at least 98% sequence identity to a sequence of nucleic acids set forth in any of SEQ ID NOS: 2, 4, 5 or 67; and degenerates thereof. In a particular example, the isolated nucleic acid molecule has sequence of nucleic acids set forth in SEQ ID NO:2, 4, 5 or 67. In some examples, the isolated nucleic acid molecule encodes a cytochrome P450 bergamotene oxidase polypeptide having a sequence of amino acids set forth in SEQ ID NO:6, 8, 9 or 73. The provided isolated nucleic acid molecules encode a cytochrome P450 bergamotene oxidase polypeptide that catalyzes the formation of a bergamotol, such as Z-α-trans-bergamotol, from a bergamotene, such as α-trans-bergamotene, and/or catalyzes the hydroxylation or monooxygenation of bergamotene, such as α-trans-bergamotene. In some examples, the encoded cytochrome P450 bergamotene oxidase does not catalyze the hydroxylation of a santalene. Also provided herein are cytochrome P450 bergamotene oxidase polypeptides encoded by any of the isolated nucleic acid molecules provided herein.

Also provided herein are isolated nucleic acid molecules encoding a *Santalum album* cytochrome P450 polypeptide or catalytically active fragments thereof having a sequence of nucleic acids set forth in SEQ ID NO:1 or 72; a sequence of nucleic acids having at least 99% sequence identity to a sequence of nucleic acids set forth in SEQ ID NO:1 or 72; and degenerates thereof. Also provided herein are isolated nucleic acid molecules encoding a cytochrome P450 polypeptide having a sequence of amino acids set forth in SEQ ID NO:50 or 78; or having a sequence of amino acids having at least 99% sequence identity to the sequence of amino acids set forth in SEQ ID NO:50 or 78. Also provided herein are *Santalum album* cytochrome P450 polypeptides encoded by any of the isolated nucleic acid molecules provided herein.

Also provided herein are nucleic acid molecules encoding a cytochrome P450 polypeptide or catalytically active fragments thereof having one or more heterologous domains or portions thereof from one or more cytochrome P450s. The domain is selected from among helix A, β strand 1-1, β strand 1-2, helix B, β strand 1-5, helix B', helix C, helix D, β strand 3-1, helix E, helix F, helix G, helix H, β strand 5-1, β strand 5-2, helix I, helix J, helix J', helix K, β strand 1-4, β strand 2-1, β strand 2-2, β strand 1-3, Heme domain, helix L, β strand 3-3, β strand 4-1, β strand 4-2 and β strand 3-2. In some examples, the heterologous domain or a contiguous portion thereof replaces all or a contiguous portion of the corresponding native domain of the cytochrome P450 polypeptide not containing the heterologous domain. For example, the encoded modified cytochrome P450 polypeptide contains all of a heterologous domain of a different cytochrome P450. In other examples, the encoded modified cytochrome P450 polypeptide has at least 50%, 60%, 70%, 80%, 90%, or 95% of contiguous amino acids of a heterologous domain from one or more different cytochrome P450s.

Provided herein are isolated *Santalum album* cytochrome P450 reductases or catalytically active fragments thereof. For example, provided herein are isolated *Santalum album* cytochrome P450 reductases that catalyze the transfer of two electrons from NADPH to an electron acceptor, that is a cytochrome P450, heme oxygenase, cytochrome $b_5$ or squalene epoxidase. In particular examples, the electron acceptor is a cytochrome P450.

Also provided herein are isolated nucleic acid molecules encoding a *Santalum album* cytochrome P450 reductase polypeptide or catalytically active fragments thereof. For example, provided herein are isolated nucleic acid molecules encoding a cytochrome P450 reductase polypeptide having a sequence of amino acids set forth in SEQ ID NO:12 or 13; or encoding a cytochrome P450 reductase polypeptide having a sequence of amino acids that has at least 80% sequence identity to a cytochrome P450 reductase polypeptide set forth in SEQ ID NO:12 or 13. In another example, provided herein is an isolated nucleic acid molecule encoding a cytochrome P450 reductase polypeptide that exhibits at least 85%, 86%, 87%, 88%, 89%, 90%, 91%, 92%, 93%, 94%, 95%, 96%, 97%, 98% or 99% amino acid sequence identity to a sequence of amino acids set forth in SEQ ID NO:12 or 13.

Also provided herein are isolated nucleic acid molecule having a sequence of nucleic acids set forth in SEQ ID NO:10 or 11; a sequence of nucleic acids having at least 95% sequence identity to a sequence of nucleic acids set forth in SEQ ID NO:10 or 11; and degenerates thereof. For example, provided herein is are isolated nucleic acid molecules having a sequence of nucleic acids set forth in SEQ ID NO:10 or 11. In some examples, the isolated nucleic acid molecules of encode cytochrome P405 reductase polypeptides having a sequence of amino acids that has at least 95% sequence identity to a cytochrome P450 reductase polypeptide set forth in SEQ ID NO:12 or 13. In a particular example, the isolated nucleic acid molecule encodes a cytochrome P450 reductase polypeptide having a sequence of amino acids set forth in SEQ ID NO:12 or 13. The provided nucleic acid molecules encode a cytochrome P450 reductase polypeptides catalyze the transfer of two electrons from NADPH to an electron acceptor, such as a cytochrome P450, heme oxygenase, cytochrome $b_5$ or squalene epoxidase. In a particular example, the electron acceptor is a cytochrome P450. Also provided herein are cytochrome P450 reductase polypeptides encoded by the nucleic acid molecules.

Also provided herein are nucleic acid molecule encoding a modified *Santalum album* cytochrome P450 reductase polypeptide or catalytically active fragments thereof. For example, provided here are nucleic acid molecules encoding modified cytochrome P450 reductase polypeptides that contain at least one amino acid replacement, addition or deletion compared to the cytochrome P450 reductase polypeptide not containing the modification. In some examples, the encoded modified cytochrome P450 reductase polypeptide is N- or C-terminally truncated. For example, provide herein are nucleic acid molecules encoding a modified cytochrome P450 reductase polypeptide that is N-terminally truncated. For example, the nucleic acid molecule encodes a modified cytochrome P450 reductase polypeptide that has a sequence of amino acids set forth in SEQ ID NO:14 or 15; or has a sequence of amino acids that is at least 80%, 85%, 86%, 87%, 88%, 89%, 90%, 91%, 92%, 93%, 94%, 95%, 96%, 97%, 98%, 99% identical to SEQ ID NO:14 or 15. Also provided herein are nucleic acid molecules having a sequence of nucleic acids set forth in SEQ ID NO:63 or 64; a sequence of nucleic acids having at least 95% sequence identity to a sequence of nucleic acids set forth in SEQ ID NO:63 or 64; and degenerates thereof. The provided nucleic acid molecules encode a cytochrome P450 reductase polypeptides catalyze the transfer of two electrons from NADPH to an electron acceptor, such as a cytochrome P450, heme oxygenase, cytochrome $b_5$ or squalene epoxidase. In a particular example, the electron acceptor is a cytochrome P450. Also provided herein are cytochrome P450 reductase polypeptides encoded by the nucleic acid molecules.

Provided herein are nucleic acid molecules encoding a fusion protein containing a *Santalum album* santalene synthase or a catalytically active fragment thereof and/or a cytochrome P450 santalene oxidase or bergamotene oxidase or a catalytically active fragment thereof and/or a cytochrome P450 reductase or a catalytically active fragment thereof.

Provided herein are nucleic acid molecules encoding a fusion protein containing santalene synthase and a cytochrome P450 santalene oxidase or a catalytically active fragment thereof. The full-length santalene synthase is encoded by a sequence of nucleotides set forth in any of SEQ ID NOS:58-60 and the cytochrome P450 santalene oxidase is encoded b any nucleic acid molecule provided herein that encodes a cytochrome P450 santalene oxidase. In another example, provided herein are nucleic acid molecules encoding a santalene synthase and a cytochrome P450 santalene oxidase. The santalene synthase has a sequence of amino acids set forth in any of SEQ ID NOS: 17, 52 and 53, and the cytochrome P450 santalene oxidase has a sequence of amino acids set forth in any of SEQ ID NOS:7, 73, 74, 75 and 76.

Provided herein are nucleic acid molecules encoding a fusion protein containing santalene synthase and a cytochrome P450 bergamotene oxidase or a catalytically active fragment thereof. The santalene synthase has a sequence of nucleotides set forth in any of SEQ ID NOS: 58-60 and the cytochrome P450 bergamotene oxidase is any nucleic acid molecule provided herein that encodes a cytochrome P450 bergamotene oxidase. In another example, provided herein are nucleic acid molecules encoding a santalene synthase and a cytochrome P450 bergamotene oxidase. The santalene synthase has a sequence of amino acids set forth in any of SEQ ID NOS: 17, 52 and 53 and the cytochrome P450 bergamotene oxidase has a sequence of amino acids set forth in any of SEQ ID NOS:6, 8, 9 and 73.

Provided herein are nucleic acid molecules encoding a fusion protein containing a cytochrome P450 or a catalytically active fragment thereof and a cytochrome P450 reductase or a catalytically active fragment thereof, where the cytochrome P450 is any nucleic acid molecule provided herein that encodes a cytochrome P450 oxidase and the cytochrome P450 reductase is any nucleic acid molecule provided herein that encodes a cytochrome P450 reductase. For example, provided herein are nucleic acid molecules encoding a cytochrome P450 that has a sequence of amino acids set forth in any of SEQ ID NOS:6-9 and 73-78 and a cytochrome P450 reductase that has a sequence of amino acids set forth in any of SEQ ID NOS:12-15.

In some examples, in the nucleic acid molecules provided herein encoding a fusion protein, the santalene synthase and/or cytochrome P450 santalene oxidase or bergamotene oxidase and/or cytochrome P450 reductase are linked directly. In other examples, in the nucleic acid molecules provided herein encoding a fusion protein, the santalene synthase and/or cytochrome P450 santalene oxidase or bergamotene oxidase and/or cytochrome P450 reductase are linked via a linker.

Also provided herein are vectors containing any nucleic acid molecule provided herein, including nucleic acid molecules encoding cytochrome P450s, such as santalene oxidases and bergamotene oxidases, cytochrome P450 reductases, modified cytochrome P450 reductases and fusion proteins. In some examples, the vector is a prokaryotic vector, a viral vector, or an eukaryotic vector. For example, the vector is a yeast vector. Also provided herein are cells containing any vector provided herein. Also provided herein are cells containing any nucleic acid molecule provided herein, including nucleic acid molecules encoding cytochrome P450s, such as santalene oxidases and bergamotene oxidases, cytochrome P450 reductases, modified cytochrome P450 reductases and fusion proteins. In some examples, the cell is a prokaryotic cell or an eukaryotic cell. In other examples, the cells is selected from among a bacteria, yeast, insect, plant or mammalian cell. In an example, the cell is a yeast cell. Included among yeast cells is a *Saccharomyces* genus cell and a *Pichia* genus cell. For example, the cell is a *Saccharomyces cerevisiae* cell. In another example, the cell is an *Escherichia coli* cell. Thus, provided are of recombinant cells, including yeast cells, for production of santalols and bergamotol.

The cells can include nucleic acid encoding a synthase, such as santalene synthase, such as a *Santalum album* synthase, to catalyze production of a substrate for the P450 enzymes provided herein.

Also provided herein are cells that express a cytochrome P450 santalene oxidase polypeptide, a cytochrome P450 bergamotene oxidase polypeptide, a cytochrome P450 reductase polypeptide and/or a fusion protein containing a *Santalum album* santalene synthase and/or a cytochrome P450 santalene oxidase or bergamotene synthase and/or a cytochrome P450 reductase. Also provided herein are transgenic plants containing any vector provided herein. In some examples, the transgenic plant is a tobacco plant.

Provided herein are methods for producing a cytochrome P450 polypeptide, by: introducing a nucleic acid molecule provided herein that encodes a cytochrome P450 polypeptide or any vector provided herein that encodes a cytochrome P450 polypeptide into a cell; culturing the cell under conditions suitable for expression of the cytochrome P450 polypeptide encoded by the nucleic acid or vector; and, optionally isolating the cytochrome P450 polypeptide.

Provided herein are methods for producing a cytochrome P450 reductase polypeptide, by: introducing a nucleic acid molecule provided herein that encodes a cytochrome P450 reductase polypeptide or any vector provided herein that encodes a cytochrome P450 reductase polypeptide into a cell; culturing the cell under conditions suitable for expression of the cytochrome P450 reductase polypeptide encoded by the nucleic acid or vector; and, optionally isolating the cytochrome P450 reductase polypeptide.

Provided herein are methods for production of a santalol, bergamotol and/or mixtures thereof, by: (a) contacting a santalene and/or bergamotene with a cytochrome P450 santalene oxidase or bergamotene oxidase under conditions suitable for the formation of a santalol, bergamotol and/or mixtures thereof; and (b) optionally isolating the santalol, bergamotol and/or mixtures thereof. In some examples, step (a) is effected in vitro or in vivo. For example, step (a) is effected in vivo in a cell transformed with a nucleic acid molecule or vector encoding a cytochrome P450 santalene oxidase or bergamotene oxidase polypeptide, whereby the cytochrome P450 santalene oxidase or bergamotene oxidase polypeptide encoded by the nucleic acid molecule or vector is expressed; and the cytochrome P450 santalene oxidase or bergamotene oxidase polypeptide catalyzes the formation of santalol and/or bergamotol from santalene and/or bergamotene.

Provided herein is a host cell containing a nucleic acid molecule encoding a cytochrome P450 or cytochrome P450 polypeptide provided herein. The nucleic acid molecule and cytochrome P450 polypeptide is heterologous to the cell. In some examples, the host cell further contains nucleic acid encoding a synthase that produces a terpene substrate of a cytochrome P450. In some examples, the synthase is heterologous to the host cell. In particular examples, the terpene synthase is a santalene synthase, such as a terpene synthase that catalyzes the formation of santalene and/or bergamotene. For example, the terpene synthase has a sequence of amino acids set forth in any of SEQ ID NOS:17, 52 and 53 or a sequence of amino acids that is at least 80%, 85%, 86%, 87%, 88%, 89%, 90%, 91%, 92%, 93%, 94%, 95%, 96%, 97%, 98%, 99% identical to any of SEQ ID NOS:17, 52 and 53. In some examples, the host cell is a prokaryotic cell or an eukaryotic cell that is selected from among a bacteria, yeast, insect, plant or mammalian cell. In a particular example, the host cell is a yeast cell that is a *Saccharomyces* genus cell or a *Pichia* genus cell. For example, the host cell is a *Saccharomyces cerevisiae* cell. In other examples, the host cell is an *Escherichia coli* cell. In some examples, the host cell produces an acyclic pyrophosphate terpene precursor, such as farnesyl diphosphate. In particular examples, the host cell produces farnesyl diphosphate natively or is modified to produce more farnesyl diphosphate compared to an unmodified cell. Also provided herein is a method for production of a santalol, bergamotol and/or mixtures thereof, said method including the steps of culturing any of the host cell provided herein under conditions suitable for the formation of a santalol, bergamotol and/or mixtures thereof; and optionally isolating the santalol, bergamotol and/or mixtures thereof.

Provided herein are methods for production of a santalol, bergamotol and/or mixtures thereof, by: (a) contacting an acyclic pyrophosphate terpene precursor with a santalene synthase under conditions suitable for the formation of a santalene and/or bergamotene; (b) contacting the resulting santalene and/or bergamotene with a cytochrome P450 santalene oxidase or bergamotene oxidase under conditions suitable for the formation of a santalol, bergamotol and/or mixture thereof to produce a santalol, bergamotol or mixture thereof; and (c) optionally isolating the santalene and bergamotene produced in step (a) or the santalol, bergamotol, and/or mixtures thereof produced in step (b). In some examples, step (a) and/or step (b) is/are performed in vitro or in vivo. For example, step (a) is performed in vivo in a cell transformed with a nucleic acid molecule encoding a santalene synthase, whereby the santalene synthase encoded by the nucleic acid molecule is expressed; and the santalene synthase catalyzes the formation of santalene and bergamotene from the acyclic pyrophosphate terpene precursor; and/or step (b) is effected in vivo in a cell transformed with a nucleic acid molecule or vector encoding a cytochrome P450 santalene oxidase or bergamotene oxidase polypeptide, whereby the cytochrome P450 santalene oxidase or bergamotene oxidase polypeptide encoded by the nucleic acid molecule or vector is expressed; and the cytochrome P450 santalene oxidase or bergamotene oxidase polypeptide catalyzes the formation of santalol and/or bergamotol from santalene and/or bergamotene. In such examples, the acyclic pyrophosphate terpene precursor can be a farnesyl pyrophosphate. In In any of the methods provided herein, the call can be a prokaryotic cell or an eukaryotic cell that is selected from among a bacteria, yeast, insect, plant or mammalian cell. In some examples, the cell is a yeast cell that is a *Saccharomyces* genus cell or a *Pichia* genus cell, such as a *Saccharomyces cerevisiae* cell. In some examples, the cell is modified to produce more FPP compared to an unmodified cell. In some examples of the methods, the cell is modified to produce a santalene synthase. For example, the cell is modified to produce a santalene synthase that has a sequence of amino acids set forth in SEQ ID NO:17, 52 or 53 or a synthase having at least 80%, 85%, 90%, 95% sequence identity therewith.

In some examples of the methods provided herein the santalene or bergamotene is an α-santalene, β-santalene, epi-β-santalene or α-trans-bergamotene. In some examples, the santalol or bergamotol is an α-santalol, β-santalol, epi-β-santalol or α-trans-bergamotol. In some examples, the santalol or bergamotol is an (E)-α-santalol, (Z)-α-santalol, (E)-β-santalol, (Z)-β-santalol, (E)-epi-β-santalol, (Z)-epi-β-santalol, (Z)-α-trans-bergamotol or (E)-α-trans-bergamotol. In further examples of the provided methods, the santalene, bergamotene, santalol, bergamotol or mixtures thereof are isolated by extraction with an organic solvent and/or column chromatography.

In some examples of the provided methods, santalene and/or bergamotene is contacted with a cytochrome P450 santalene oxidase that is: a cytochrome P450 santalene oxidase polypeptide provided herein; a cytochrome P450 santalene oxidase polypeptide provided herein encoded by any nucleic acid molecule provided herein; a nucleic acid molecule provided herein that encodes a cytochrome P450 santalene oxidase; or a vector provided herein that encodes a cytochrome P450 santalene oxidase, whereby santalol and/or bergamotol are produced.

In some examples of the provided methods, bergamotene is contacted with a cytochrome P450 bergamotene oxidase that is: a cytochrome P450 bergamotene oxidase polypeptide provided herein; a cytochrome P450 bergamotene oxidase polypeptide provided herein encoded by any nucleic acid molecule provided herein; a nucleic acid molecule provided herein that encodes a cytochrome P450 bergamotene oxidase; or a vector provided herein that encodes a cytochrome P450 bergamotene oxidase, whereby bergamotol is produced.

Also provided herein are methods for production of a santalol, bergamotol and/or mixtures thereof. Each of steps (a) and (b) can be effected simultaneously or sequentially. In one example, steps (a) and (b) are effected simultaneously with a nucleic acid molecule encoding a fusion polypeptide containing a santalene synthase and a cytochrome P450 santalene oxidase or bergamotene oxidase; or a fusion polypeptide containing a santalene synthase and a cytochrome P450 santalene oxidase or bergamotene oxidase. In particular examples, santalene and/or bergamotene is contacted with a nucleic acid molecule provided herein that encodes a fusion polypeptide; or a fusion polypeptide encoded by a nucleic acid molecule provided herein.

BRIEF DESCRIPTION OF THE FIGURES

FIGS. 2A-2B depict the alignment of the santalene oxidase set forth in SEQ ID NO:7 with the bergamotene oxidases set forth in SEQ ID NOS:6, 8 and 9. A "*" means that the aligned residues are identical, a ":" means that aligned residues are not identical, but are similar and contain conservative amino acids residues at the aligned position, and a "." means that the aligned residues are similar and contain semi-conservative amino acid residues at the aligned position.

FIGS. 3A-3C depict the alignment of *Santalum album* cytochrome P450 reductases set forth in SEQ ID NOS:12 and 13 with *Arabidopsis thaliana* cytochrome P450 reductases set forth in SEQ ID NOS:46 and 58. A "*" means that the aligned residues are identical, a ":" means that aligned residues are not identical, but are similar and contain conservative amino acids residues at the aligned position, and a "." means that the aligned residues are similar and contain semi-conservative amino acid residues at the aligned position.

FIGS. 5A-5B depict the alignment of the santalene oxidase set forth in SEQ ID NO:7 and the bergamotene oxidase set forth in SEQ ID NO:6 with cytochrome P450BM-3 set forth in SEQ ID NO:66. A "*" means that the aligned residues are identical, a ":" means that aligned residues are not identical, but are similar and contain conservative amino acids residues at the aligned position, and a "." means that the aligned residues are similar and contain semi-conservative amino acid residues at the aligned position.

FIG. 15B depicts the GC-MS analysis (extracted ion chromatograms) of authentic *S. album* oil. FIG. 15C depicts the GC-MS analysis (extracted ion chromatograms) from control assays performed with microsomes isolated from yeast cells transformed with an empty vector. The peaks are identified in Table 12.

FIGS. 20A-20C depict product profiles in assays with SaCYP76F39v1 (SaCYP76-G10) using α-santalene (FIG. 20A), α-exo-bergamotene (FIG. 20B), or epi-β-santalene and β-santalene (FIG. 20C) as the substrates. FIGS. 20D-20F depict product profiles in assays with SaCYP76F37v1 (SaCYP76-G11) using α-santalene (FIG. 20D), α-exo-bergamotene (FIG. 20E), or epi-β-santalene and β-santalene (FIG. 20F) as the substrates. FIG. 20G depicts the extracted ion chromatogram for authentic *Santalum album* oil. The peaks are identified in Table 12.

FIGS. 21A-21C depict the alignment of the *S. album* cytochrome P450s set forth in SEQ ID NOS:6-9 and 73-78. Horizontal arrows indicate the proline region (a), oxygen binding motif (b) and heme binding motif (c). Boxes indicate the substrate recognition sites (SRS) regions originally described by Gotoh (1992) *J Biol Chem* 267:83-90. A "*" means that the aligned residues are identical, a ":" means that aligned residues are not identical, but are similar and contain conservative amino acids residues at the aligned position, and a "." means that the aligned residues are similar and contain semi-conservative amino acid residues at the aligned position.

DETAILED DESCRIPTION

Figure 1:
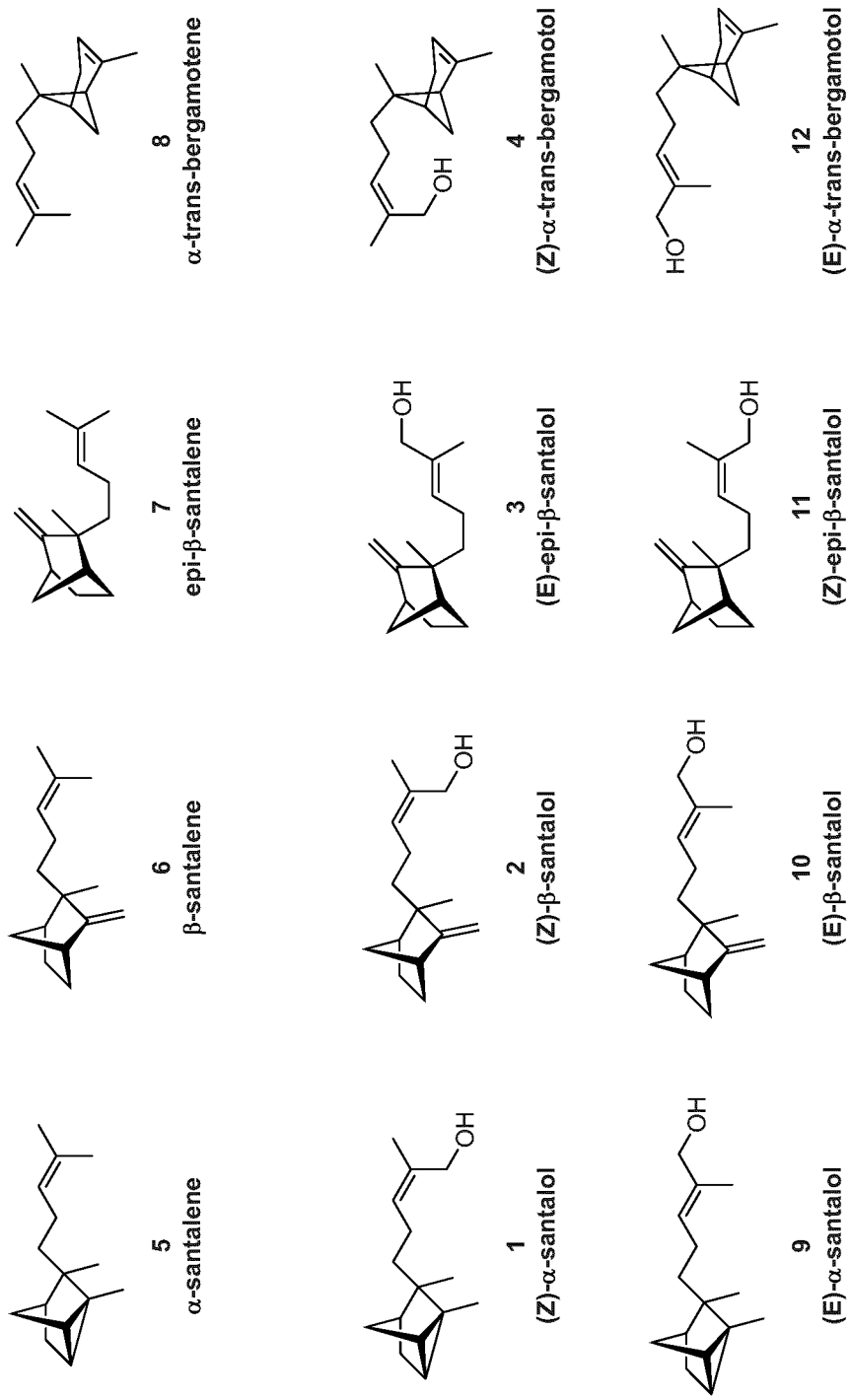
FIG. 1 depicts the chemical structures of (Z)-α-santalol (1), (E)-α-santalol (9), (Z)-β-santalol (2), (E)-β-santalol (10), (E)-epi-βp-santalol (3), (Z)-epi-β-santalol (11), (Z)-α-trans-bergamotol (4), (E)-α-trans-bergamotol (12), α-santalene (5), β-santalene (6), epi-β-santalene (7) and α-trans-bergamotene (8).

| Outline |
|---|
| A. Definitions |
| B. Overview |
|     1. Biosynthesis of Terpenoids |
|         a. Santalols |
|         b. Bergamotols |
|     2. Cytochrome P450 Enzymes |
|         a. Structure |
|         b. Activity |
|     3. Cytochrome P450 Reductases |
|         a. Structure |
|         b. Activity |
| C. Cytochrome P450 polypeptides and encoding nucleic acid molecules |
|     1. Cytochrome P450 santalene oxidase polypeptides |
|         Modified cytochrome P450 santalene oxidase polypeptides |
|     2. Cytochrome P450 bergamotene oxidase polypeptides |
|         Modified cytochrome P450 bergamotene oxidase polypeptides |
|     3. Additional modifications |
|         a. Truncated polypeptides |
|         b. Polypeptides with altered activities or properties |
|         c. Domain swaps |
|         d. Fusion proteins |
| D. Cytochrome P450 reductase polypeptides and encoding nucleic acid molecules |
|     1. Cytochrome P450 reductase polypeptides |
|     2. Modified cytochrome P450 reductase polypeptides |
|     3. Additional modifications |
|         a. Truncated polypeptides |
|         b. Polypeptides with altered activities or properties |
|         c. Domain swaps |
|         d. Fusion proteins |
| E. Methods for producing modified cytochrome P450 and cytochrome P450 reductase polypeptides and encoding nucleic acid molecules |
| F. Expression of cytochrome P450 and cytochrome P450 reductase polypeptides and encoding nucleic acid molecules |
|     1. Isolation of nucleic acid encoding Santalum album cytochrome P450 and cytochrome P450 reductase polypeptides |
|     2. Generation of modified nucleic acids |
|     3. Vectors and Cells |
|     4. Expression systems |
|         a. Prokaryotic cells |
|         b. Yeast cells |

Outline -continued c. Plants and plant cells
d. Insects and insect cells
e. Mammalian cells
f. Exemplary host cells
5. Purification
6. Fusion proteins
G. Methods for producing terpenoids and methods for detecting such products and the activity of the cytochrome P450 and cytochrome P450 reductase polypeptides
1. Synthesis of Santalols and Bergamotols
a. Oxidation of Santalenes and Bergamotenes
b. Conversion of acyclic pyrophosphate terpene precursors
2. Methods for production
a. Exemplary cells
b. Culture of cells
c. Isolation and assays for detection and identification
3. Production of sandalwood oil
4. Assays for detecting enzymatic activity of cytochrome P450 and cytochrome P450 reductase polypeptides
a. Methods for determining the activity of cytochrome P450 polypeptides
b. Methods for determining the activity of cytochrome P450 reductase polypeptides
H. Examples

A. Definitions

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, an acyclic pyrophosphate terpene precursor is any acyclic pyrophosphate compound that is a precursor to the production of at least one terpene, including, but not limited to, farnesyl-pyrophosphate (FPP), geranyl-pyrophosphate (GPP) and geranylgeranyl-pyrophosphate (GGPP). Acyclic pyrophosphate terpene precursors are thus substrates for terpene synthases.

As used herein, a terpene is an unsaturated hydrocarbon based on the isoprene unit ($C_5H_8$), and having a general formula $C_{5x}H_{8x}$, such as $C_{10}H_{16}$. Reference to a terpene includes acyclic, monocyclic and polycyclic terpenes. Terpenes include, but are not limited to, monoterpenes, which contain 10 carbon atoms; sesquiterpenes, which contain 15 carbon atoms; diterpenes, which contain 20 carbon atoms, and triterpenes, which contain 30 carbon atoms. Reference to a terpene also includes stereoisomers of the terpene.

As used herein, a terpenoid is a chemically modified terpene. In one example, a terpenoid is a terpene that has been chemically modified by addition of a hydroxyl group, such as a santalol or bergamotol. Reference to a terpenoid includes acyclic, monocyclic and polycyclic terpenoids, including monoterpenoids, sesquiterpenoids and diterpenoids. Reference to a terpenoid also includes stereoisomers of the terpenoid.

As used herein, a terpene synthase is a polypeptide capable of catalyzing the formation of one or more terpenes from a pyrophosphate terpene precursor. In some examples, a terpene synthase catalyzes the formation of one or more terpenes from an acyclic pyrophosphate terpene precursor, for example, FPP, GPP or GGPP, including, but not limited to, santalene synthase. In other examples, a terpene synthase catalyzes the formation of one or more terpenes from an acyclic pyrophosphate terpene precursor, including, but not limited to, santalene synthase.

As used herein, "cytochrome P450," "cytochrome P450 oxidase," "cytochrome P450 polypeptide," "cytochrome P450 oxidase polypeptide" or "CYP" is a polypeptide capable of catalyzing the monooxygenation of any terpene precursor, including monoterpenes, sesquiterpenes and diterpenes. A cytochrome P450 can catalyze the monooxygenation of a terpene or a mixture of terpenes, resulting in the production one or more terpenoids.

For purposes herein, cytochrome P450 oxidases provided herein are enzymes with cytochrome P450 oxidase activity and have greater than or greater than about or 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity, when aligned with the cytochrome P450 oxidase sequence set forth in SEQ ID NO:50. Reference to a cytochrome P450 oxidase includes any cytochrome P450 oxidase polypeptide including, but not limited to, a recombinantly produced polypeptide, synthetically produced polypeptide and a cytochrome P450 oxidase polypeptide extracted or isolated from cells or plant matter, including, but not limited to, heartwood of a sandalwood tree. Exemplary of cytochrome P450 oxidase polypeptides include those isolated from *Santalum album*. Reference to a cytochrome P450 oxidase includes cytochrome P450 oxidase from any genus or species, and included allelic or species variants, variants encoded by splice variants, and other variants thereof, including polypeptides that have at least or at least about 50%, 55%, 60%, 65%, 70%, 75%, 80%, 85%, 90%, 95%, 96%, 97%, 98%, 99% or more sequence identity to the cytochrome P450 oxidase set forth in SEQ ID NO:50 when aligned therewith. Cytochrome P450 oxidase also includes catalytically active fragments thereof that retain cytochrome P450 oxidase activity.

As used herein, "cytochrome P450 santalene oxidase" or "cytochrome P450 santalene oxidase polypeptide" is a polypeptide capable of catalyzing the formation of a santalol from a santalene, for example, capable of catalyzing the monooxygenation or hydroxylation of a santalene. A cytochrome P450 santalene oxidase polypeptide can produce one or a mixture of santalols from one or a mixture of santalenes. A cytochrome P450 santalene oxidase polypeptide is also capable of catalyzing the formation of a bergamotol from a bergamotene. For example, a cytochrome P450 santalene oxidase catalyzes the formation of α-santalol from α-santalene, β-santalol from β-santalene, epi-β-santalol from epi-β-santalene and/or Z-α-trans-bergamotol or E-α-trans-bergamotol from α-trans-bergamotene.

For purposes herein, cytochrome P450 santalene oxidases provided herein are enzymes with cytochrome P450 santalene oxidase activity and have greater than or greater than about or 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity, when aligned with the cytochrome P450 santalene oxidase sequence set forth in SEQ ID NO:7, 74, 75, 76 or 77. Reference to a cytochrome P450 santalene oxidase includes any cytochrome P450 santalene oxidase polypeptide including, but not limited to, a recombinantly produced polypeptide, synthetically produced polypeptide and a cytochrome P450 santalene oxidase polypeptide extracted or isolated from cells or plant matter, including, but not limited to, heartwood of a sandalwood tree. Exemplary of cytochrome P450 santalene oxidase polypeptides include those isolated from Santalum album. Reference to a cytochrome P450 santalene oxidase includes cytochrome P450 santalene oxidase from any genus or species, and included allelic or species variants, variants encoded by splice variants, and other variants thereof, including polypeptides that have at least or at least about 50%, 55%, 60%, 65%, 70%, 75%, 80%, 85%, 90%, 95%, 96%, 97%, 98%, 99% or more sequence identity to the cytochrome P450 santalene oxidase set forth in SEQ ID NO:7, 74, 75, 76 or 77 when aligned therewith. Cytochrome P450 santalene oxidase also includes catalytically active fragments thereof that retain cytochrome P450 santalene oxidase activity.

As used herein, "cytochrome P450 santalene oxidase activity" or "santalene oxidase activity" refers to the ability to catalyze the formation of one or more santalols from one or more santalenes. That is, cytochrome P450 santalene oxidases catalyze the monooxygenation or hydroxylation of santalenes. Cytochrome P450 santalene oxidases also catalyze the hydroxylation of bergamotene. For example, cytochrome P450 santalene oxidases catalyze the formation of α-santalol from α-santalene, β-santalol from β-santalene, epi-β-santalol from epi-β-santalene and/or Z-α-trans-bergamotol from α-trans-bergamotene. Methods to assess santalol or bergamotol formation from a reaction of a santalene or bergamotene are well known in the art and described herein. The production of a santalol or bergamotol can be assessed by methods such as, for example, gas chromatography-mass spectrometry (GC-MS) (see Examples below). A cytochrome P450 exhibits cytochrome P450 santalene oxidase activity or the ability to catalyze the formation of santalols or bergamotol from santalenes and bergamotene if the amount of santalols and bergamotol produced from the reaction is at least or at least about 0.5%, 1%, 5%, 10%, 20%, 30%, 40%, 50%, 60%, 70%, 80%, 90% or more of the total amount of terpenoids produced in the reaction.

As used herein, "cytochrome P450 bergamotene oxidase" or "cytochrome P450 bergamotene oxidase polypeptide" is a polypeptide capable of catalyzing the monooxygenation or hydroxylation of a bergamotene. For example, a cytochrome P450 bergamotene oxidase catalyzes the formation of Z-α-trans-bergamotol or E-α-trans-bergamotol from α-trans-bergamotene.

For purposes herein, cytochrome P450 bergamotene oxidases provided herein are enzymes with cytochrome P450 bergamotene oxidase activity and have greater than or greater than about or 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity, when aligned with the cytochrome P450 bergamotene oxidase sequence set forth in SEQ ID NO:6, 8, 9 or 73. Reference to a cytochrome P450 bergamotene oxidase includes any cytochrome P450 bergamotene oxidase polypeptide including, but not limited to, a recombinantly produced polypeptide, synthetically produced polypeptide and a cytochrome P450 bergamotene oxidase polypeptide extracted or isolated from cells or plant matter, including, but not limited to, heartwood of a sandalwood tree. Exemplary of cytochrome P450 bergamotene oxidase polypeptides include those isolated from Santalum album. Reference to a cytochrome P450 bergamotene oxidase includes cytochrome P450 bergamotene oxidase from any genus or species, and included allelic or species variants, variants encoded by splice variants, and other variants thereof, including polypeptides that have at least or at least about 50%, 55%, 60%, 65%, 70%, 75%, 80%, 85%, 90%, 95%, 96%, 97%, 98%, 99% or more sequence identity to the cytochrome P450 bergamotene oxidase set forth in SEQ ID NO: 6, 8, 9 or 73 when aligned therewith. Cytochrome P450 bergamotene oxidase also includes catalytically active fragments thereof that retain cytochrome P450 bergamotene oxidase activity.

As used herein, "cytochrome P450 bergamotene oxidase activity" or "bergamotene oxidase activity" refers to the ability catalyze the formation of bergamotols from bergamotenes That is, cytochrome P450 bergamotene oxidases catalyze the monooxygenation or hydroxylation of bergamotene. For example, cytochrome P450 bergamotene oxidases catalyze the formation of Z-α-trans-bergamotol from α-trans-bergamotene. Methods to assess bergamotol formation from a reaction of a bergamotene are well known in the art and described herein. The production of a bergamotol can be assessed by methods such as, for example, gas chromatography-mass spectrometry (GC-MS) (see Examples below). A cytochrome P450 exhibits cytochrome P450 bergamotene oxidase activity or the ability to catalyze the formation of bergamotol from bergamotene if the amount of bergamotol produced from the reaction is at least or at least about 0.5%, 1%, 5%, 10%, 20%, 30%, 40%, 50%, 60%, 70%, 80%, 90% or more of the total amount of terpenoids produced in the reaction.

As used herein, α-santalol is a sesquiterpenoid having the following structure or isomers or stereoisomers thereof:

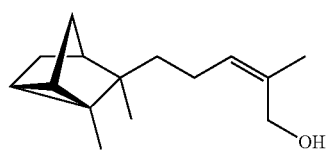

As used herein, β-santalol is a sesquiterpenoid having the following structure or isomers or stereoisomers thereof:

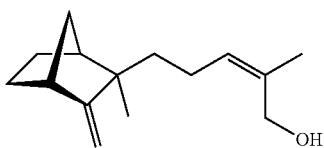

As used herein, epi-β-santalol is a sesquiterpenoid having the following structure or isomers or stereoisomers thereof:

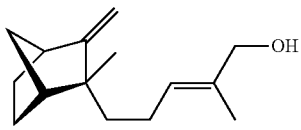

As used herein, Z-α-trans-bergamotol or Z-α-exo-bergamotol is a sesquiterpenoid having the following structure or isomers or stereoisomers thereof:

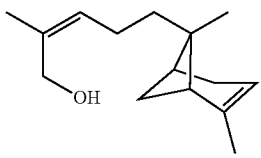 [SMILES: CC1=CCC2CC1C2(C)CC/C=C(/C)CO]

As used herein, E-α-trans-bergamotol or E-α-exo-bergamotol is a sesquiterpenoid having the following structure or isomers or stereoisomers thereof:

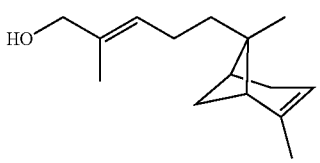 [SMILES: CC1=CCC2CC1C2(C)CC/C=C(\C)CO]

As used herein, α-santalene is a sesquiterpene having the following structure or isomers or stereoisomers thereof:

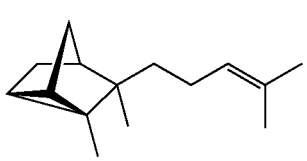

As used herein, β-santalene is a sesquiterpene having the following structure or isomers or stereoisomers thereof:

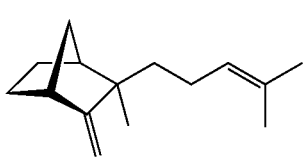

As used herein, epi-β-santalene is a sesquiterpene having the following structure or isomers or stereoisomers thereof:

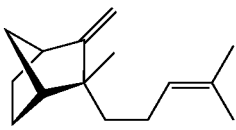

As used herein, α-trans-bergamotene or α-exo-bergamotene is a sesquiterpene having the following structure or isomers or stereoisomers thereof:

As used herein, "cytochrome P450 reductase" or "CPR" is a polypeptide capable of catalyzing the transfer of two electrons from NADPH to an electron acceptor, such as a cytochrome P450. For purposes herein, cytochrome P450 reductases provided herein are enzymes with cytochrome P450 reductase activity and have greater than or greater than about or 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity, when aligned with the cytochrome P450 reductase sequence set forth in SEQ ID NO:12 or 13. Reference to a cytochrome P450 reductase includes any cytochrome P450 reductase polypeptide including, but not limited to, a recombinantly produced polypeptide, synthetically produced polypeptide and a cytochrome P450 reductase polypeptide extracted or isolated from cells or plant matter, including, but not limited to, heartwood of a sandalwood tree. Exemplary of cytochrome P450 reductase polypeptides include those isolated from *Santalum album*. Reference to a cytochrome P450 reductase includes a cytochrome P450 reductase from any genus or species, and included allelic or species variants, variants encoded by splice variants, and other variants thereof, including polypeptides that have at least or at least about 50%, 55%, 60%, 65%, 70%, 75%, 80%, 85%, 90%, 95%, 96%, 97%, 98%, 99% or more sequence identity to the cytochrome P450 reductase set forth in SEQ ID NO:12 or 13 when aligned therewith. Cytochrome P450 reductase also includes catalytically active fragments thereof that retain cytochrome P450 reductase activity.

As used herein, "cytochrome P450 reductase activity" refers to the ability to catalyze the transfer of two electrons from NADPH to an electron acceptor, such as a cytochrome P450. Methods to assess cytochrome P450 reductase activity are well known in the art and described herein. For example, cytochrome P450 reductase activity can be determined by reduction of an artificial electron receptor, such as cytochrome c.

As used herein, "wild type" or "native" with reference to a cytochrome P450 or cytochrome P450 reductase refers to a cytochrome P450 polypeptide or cytochrome P450 reductase polypeptide encoded by a native or naturally occurring cytochrome P450 gene or cytochrome P450 reductase gene, including allelic variants, that are present in an organism, including a plant, in nature. Reference to wild type cytochrome P450 or cytochrome P450 reductase without reference to a species is intended to encompass any species of a wild type cytochrome P450 or cytochrome P450 reductase.

As used herein, species variants refer to variants in polypeptides among different species, including different sandalwood species, such Santalum album, Santalum australocaledonicum, Santalum spicatum and Santalum murrayanum. Generally, species variants share at least or at least about 40%, 50%, 60%, 70%, 75%, 80%, 85%, 90%, 91%, 92%, 93%, 94%, 95%, 96%, 97%, 98% or more sequence identity. Corresponding residues between and among species variants can be determined by comparing, generally one-by-one to the same reference sequence, and aligning each sequence with the reference sequence to maximize the number of matching nucleotides or amino acid residues. The position of interest is then given the number assigned in the reference nucleic acid molecule or polypeptide. Alignment can be effected manually or by eye, particularly, where sequence identity is greater than 80%. To determine sequence identity among a plurality of variants, alignments are effected one-by-one against the same reference polypeptide.

As used herein, an allelic variant or allelic variation references any of two or more alternative forms of a gene occupying the same chromosomal locus. Allelic variation arises naturally through mutation, and can result in phenotypic polymorphism within populations. Gene mutations can be silent (no change in the encoded polypeptide) or can encode polypeptides having altered amino acid sequence. The term "allelic variant" also is used herein to denote a protein encoded by an allelic variant of a gene. Typically the reference form of the gene encodes a wild type form and/or predominant form of a polypeptide from a population or single reference member of a species. Typically, allelic variants, which include variants between and among species typically, have at least 80%, 90% or greater amino acid identity with a wild type and/or predominant form from the same species; the degree of identity depends upon the gene and whether comparison is interspecies or intraspecies. Generally, intraspecies allelic variants have at least about 80%, 85%, 90% or 95% identity or greater with a wild type and/or predominant form, including 96%, 97%, 98%, 99% or greater identity with a wild type and/or predominant form of a polypeptide. Reference to an allelic variant herein generally refers to variations n proteins among members of the same species.

As used herein, a splice variant refers to a variant produced by differential processing of a primary transcript of genomic DNA that results in more than one type of mRNA.

As used herein, a "modified cytochrome P450" or "modified cytochrome P450 polypeptide" or "modified CYP" refers to a cytochrome P450 polypeptide that has one or more amino acid differences compared to an unmodified or wild type cytochrome P450 polypeptide. The one or more amino acid differences can be amino acid mutations such as one or more amino acid replacements (substitutions), insertions or deletions, or can be insertions or deletions or replacements of entire domains or portions thereof, and any combination thereof. Modification can be effected by any mutational protocol, including gene shuffling methods. Typically, a modified cytochrome P450 polypeptide has one or more modifications in primary sequence compared to an unmodified cytochrome P450 polypeptide. For example, a modified cytochrome P450 polypeptide provided herein can have at least 1, 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120, 125, 130, 135 or more amino acid differences compared to an unmodified cytochrome P450 polypeptide. Typically, the modified cytochrome P450 polypeptide will have 1, 2, 3, 4, 5, 6, 7, 8, 9, 10, 11, 12, 13, 14 or 15 amino acid replacements, but can include more, particularly when domains or portions thereof are swapped. Any modification is contemplated as long as the resulting polypeptide has at least one cytochrome P450 activity associated with the wild type cytochrome P450, such as, for example, catalytic activity, monooxygenase activity, and/or the ability to catalyze the formation of a terpenoid from a terpene. Generally, the resulting cytochrome P450 polypeptide will have at least 50% sequence identity with the wild type cytochrome P450 polypeptide provided herein.

As used herein, a "modified cytochrome P450 santalene oxidase" or "modified cytochrome P450 santalene oxidase polypeptide" refers to a cytochrome P450 santalene oxidase polypeptide that has one or more amino acid differences compared to an unmodified or wild type cytochrome P450 santalene oxidase polypeptide. The one or more amino acid differences can be amino acid mutations such as one or more amino acid replacements (substitutions), insertions or deletions, or can be insertions or deletions or replacements of entire domains or portions thereof, and any combination thereof. Modification can be effected by any mutational protocol, including gene shuffling methods. Typically, a modified cytochrome P450 santalene oxidase polypeptide has one or more modifications in primary sequence compared to an unmodified cytochrome P450 santalene oxidase polypeptide. For example, a modified cytochrome P450 santalene oxidase polypeptide provided herein can have at least 1, 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120, 125, 130, 135 or more amino acid differences compared to an unmodified cytochrome P450 santalene oxidase polypeptide. Typically, the modified cytochrome P450 santalene oxidase polypeptide will have 1, 2, 3, 4, 5, 6, 7, 8, 9, 10, 11, 12, 13, 14 or 15 amino acid replacements, but can include more, particularly when domains or portions thereof are swapped. Any modification is contemplated as long as the resulting polypeptide has at least one cytochrome P450 santalene oxidase activity associated with the wild type cytochrome P450 santalene oxidase, such as, for example, catalytic activity, the ability to catalyze the formation of santalols or bergamotols from santalenes or bergamotenes. Generally, the resulting cytochrome P450 polypeptide santalene oxidase will have at least 50% sequence identity with the wild type cytochrome P450 santalene oxidase polypeptide provided herein.

As used herein, a "modified cytochrome P450 bergamotene oxidase" or "modified cytochrome P450 bergamotene oxidase polypeptide" refers to a cytochrome P450 bergamotene oxidase polypeptide that has one or more amino acid differences compared to an unmodified or wild type cytochrome P450 bergamotene oxidase polypeptide. The one or more amino acid differences can be amino acid mutations such as one or more amino acid replacements (substitutions), insertions or deletions, or can be insertions or deletions or replacements of entire domains or portions thereof, and any combination thereof. Modification can be effected by any mutational protocol, including gene shuffling methods. Typically, a modified cytochrome P450 bergamotene oxidase polypeptide has one or more modifications in primary sequence compared to an unmodified cytochrome P450 bergamotene oxidase polypeptide. For example, a modified cytochrome P450 bergamotene oxidase polypeptide provided herein can have at least 1, 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120, 125, 130, 135 or more amino acid differences compared to an unmodified cytochrome P450 polypeptide. Typically, the modified cytochrome P450 bergamotene oxidase polypeptide will have 1, 2, 3, 4, 5, 6, 7, 8, 9, 10, 11, 12, 13, 14 or 15 amino acid replacements, but can include more, particularly when domains or portions thereof are swapped. Any modification is contemplated as long as the resulting polypeptide has at least one cytochrome P450 bergamotene oxidase activity associated with the wild type cytochrome P450 bergamotene oxidase polypeptide, such as, for example, catalytic activity, the ability to catalyze the formation of bergamotols from bergamotenes. Generally, the resulting cytochrome P450 polypeptide bergamotene oxidase will have at least 50% sequence identity with the wild type cytochrome P450 bergamotene oxidase polypeptide provided herein.

As used herein, a "modified cytochrome P450 reductase" or "modified CPR" refers to a cytochrome P450 polypeptide that has one or more amino acid differences compared to an unmodified or wild type cytochrome P450 reductase polypeptide. The one or more amino acid differences can be amino acid mutations such as one or more amino acid replacements (substitutions), insertions or deletions, or can be insertions or deletions or replacements of entire domains or portions thereof, and any combination thereof. Modification can be effected by any mutational protocol, including gene shuffling methods. Typically, a modified cytochrome P450 reductase polypeptide has one or more modifications in primary sequence compared to an unmodified cytochrome P450 reductase polypeptide. For example, a modified cytochrome P450 reductase polypeptide provided herein can have at least 1, 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120, 125, 130, 135 or more amino acid differences compared to an unmodified cytochrome P450 reductase polypeptide. Typically, the modified cytochrome P450 reductase polypeptide will have 1, 2, 3, 4, 5, 6, 7, 8, 9, 10, 11, 12, 13, 14 or 15 amino acid replacements, but can include more, particularly when domains or portions thereof are swapped. Any modification is contemplated as long as the resulting polypeptide has at least one cytochrome P450 reductase activity associated with the wild type cytochrome P450 reductase, such as, for example, catalytic activity, the ability to transfer two electrons to an electron receptor, such as a cytochrome P450. Generally, the resulting cytochrome P450 reductase polypeptide will have at least 50% sequence identity with the wild type cytochrome P450 reductase polypeptide provided herein.

As used herein, corresponding residues refers to residues that occur at aligned loci. Related or variant polypeptides are aligned by any method known to those of skill in the art. Such methods typically maximize matches, and include methods such as manual alignments and those produced by the numerous alignment programs available (for example, BLASTP) and others known to those of skill in the art. By aligning the sequences of polypeptides, one skilled in the art can identify corresponding residues, using conserved and identical amino acid residues as guides. Corresponding positions also can be based on structural alignments, for example by using computer simulated alignments of protein structure. For example, corresponding residues between a cytochrome P450 santalene oxidase synthase and cytochrome P450 bergamotene oxidase synthase are shown in FIGS. 2A-2B and 21A-21C and corresponding residues between *Arabidopsis thaliana* cytochrome P450 reductases and *Santalum album* cytochrome P450 reductases are shown in FIG. 3A-3C.

As used herein, domain or region (typically a sequence of at least three or more, generally 5 or 7 or more amino acids) refers to a portion of a molecule, such as a protein or the encoding nucleic acids, that is structurally and/or functionally distinct from other portions of the molecule and is identifiable. A protein can have one, or more than one, distinct domains. For example, a domain can be identified, defined or distinguished by homology of the sequence therein to related family members, such as other terpene synthases. A domain can be a linear sequence of amino acids or a non-linear sequence of amino acids. Many polypeptides contain a plurality of domains. Such domains are known, and can be identified by, those of skill in the art. For exemplification herein, definitions are provided, but it is understood that it is well within the skill in the art to recognize particular domains by name. If needed, appropriate software can be employed to identify domains. For example, as discussed above, corresponding domains in different cytochrome P450s or cytochrome P450 reductases can be identified by sequence alignments, such as using tools and algorithms well known in the art (for example, BLASTP).

As used herein, a functional domain refers to those portions of a polypeptide that is recognized by virtue of a functional activity, such as catalytic activity. A functional domain can be distinguished by its function, such as by catalytic activity, or an ability to interact with a biomolecule, such as substrate binding or metal binding. In some examples, a domain independently can exhibit a biological function or property such that the domain independently or fused to another molecule can perform an activity, such as, for example catalytic activity or substrate binding.

As used herein, a structural domain refers to those portions of a polypeptide chain that can form an independently folded structure within a protein made up of one or more structural motifs.

As used herein, "heterologous" with respect to an amino acid or nucleic acid sequence refers to portions of a sequence that is not present in a native polypeptide or encoded by a polynucleotide. For example, a portion of amino acids of a polypeptide, such as a domain or region or portion thereof, for a cytochrome P450 santalene oxidase synthase is heterologous thereto if such amino acids is not present in a native or wild type cytochrome P450 santalene oxidase synthase (e.g. as set forth in SEQ ID NO:7), or encoded by the polynucleotide encoding therefor. Polypeptides containing such heterologous amino acids or polynucleotides encoding therefor are referred to as "chimeric polypeptides" or "chimeric polynucleotides," respectively. As used herein, the phrase "a property of the modified cytochrome P450 is improved compared to the first cytochrome P450" refers to a desirable change in a property of a modified cytochrome P450 compared to a cytochrome P450 that does not contain the modification(s). Typically, the property or properties are improved such that the amount of a desired terpenoid produced from the reaction of a terpene substrate with the modified cytochrome P450 synthase is increased compared to the amount of the desired terpenoid produced from the reaction of a substrate with a cytochrome P450 synthase that is not so modified. Exemplary properties that can be improved in a modified cytochrome P450 synthase include, for example, terpenoid production, catalytic activity, product distribution, substrate specificity, regioselectivity and stereoselectivity. One or more of the properties can be assessed using methods well known in the art to determine whether the property had been improved (i.e. has been altered to be more desirable for the production of a desired terpenoid or terpenoids).

As used herein, terpenoid production (also referred to as terpenoid yield) refers to the amount (in weight or weight/volume) of terpenoid produced from the reaction of a terpene with a cytochrome P450. Reference to total terpenoid production refers to the total amount of all terpenoids produced from the reaction, while reference to particular terpenoid production refers to the amount of a particular terpenoid (e.g. β-santalol and α-santalol), produced from the reaction.

As used herein, an improved terpenoid production refers to an increase in the total amount of terpenoid (i e improved total terpenoid production) or an increase in the particular amount of terpenoid resulting from the reaction of a terpene with a modified cytochrome P450 compared to the amount produced from the reaction of the same terpene with a cytochrome P450 that is not so modified. The amount of terpenoid (total or particular) produced from the reaction of a terpene with a cytochrome P450 can be increased by at least or at least about 1%, 3%, 5%, 10%, 15%, 20%, 30%, 40%, 50%, 60%, 70%, 80%, 90%, 100% or more compared to the amount of terpenoid produced from the reaction of the same terpene under the same conditions with a cytochrome P450 that is not so modified.

As used herein, substrate specificity refers to the preference of a cytochrome P450 for one target substrate over another, such as one terpene (e.g. β-santalene, α-santalene, epi-β-santalene or α-trans-bergamotene) over another. Substrate specificity can be assessed using methods well known in the art, such as those that calculate $k_{cat}/K_m$. For example, the substrate specificity can be assessed by comparing the relative $K_{cat}/K_m$, which is a measure of catalytic efficiency, of the enzyme against various substrates (e.g. β-santalene, α-santalene, epi-β-santalene or α-trans-bergamotene).

As used herein, altered substrate specificity refers to a change in substrate specificity of a modified cytochrome P450 polypeptide (such as a modified cytochrome P450 santalene oxidase polypeptide or cytochrome P450 bergamotene oxidase polypeptide) compared to a cytochrome P450 that is not so modified (such as, for example, a wild type cytochrome P450 santalene oxidase or cytochrome P450 bergamotene oxidase). The specificity (e.g. $k_{cat}/K_m$) of a modified cytochrome P450 polypeptide for a substrate, such as β-santalene, α-santalene, epi-β-santalene or α-trans-bergamotene, can be altered by at least or at least about 10%, 15%, 20%, 30%, 40%, 50%, 60%, 70%, 80%, 90%, 100% or more compared to the specificity of a starting cytochrome P450 for the same substrate.

As used herein, "improved substrate specificity" refers to a change or alteration in the substrate specificity to a more desired specificity. For example, an improved substrate specificity can include an increase in substrate specificity of a modified cytochrome P450 polypeptide for a desired substrate, such as β-santalene, α-santalene, epi-β-santalene or α-trans-bergamotene. The specificity (e.g. $k_{cat}/K_m$) of a modified cytochrome P450 polypeptide for a substrate, such as β-santalene, α-santalene, epi-β-santalene or α-trans-bergamotene, can be increased by at least or at least about 1%, 5%, 10%, 15%, 20%, 30%, 40%, 50%, 60%, 70%, 80%, 90%, 100% or more compared to the specificity of a cytochrome P450 that is not so modified. As used herein, "product distribution" refers to the relative amounts of different terpenoids produced from the reaction between a terpene, such as β-santalene, and a cytochrome P450, including the cytochrome P450 polypeptides provided herein. The amount of a produced terpenoid can be depicted as a percentage of the total products produced by the cytochrome P450. For example, the product distribution resulting from reaction of β-santalene with a cytochrome P450 santalene oxidase can be 90% (weight/volume) β-santalol and 10% (weight/volume) other compounds. Methods for assessing the type and amount of a terpenoid in a solution are well known in the art and described herein, and include, for example, gas chromatography-mass spectrometry (GC-MS) (see Examples below).

As used herein, an altered product distribution refers to a change in the relative amount of individual terpenoids produced from the reaction between a terpene, such as β-santalene, and a cytochrome P450, such as cytochrome P450 santalene oxidase. Typically, the change is assessed by determining the relative amount of individual terpenoids produced from the terpene using a first cytochrome P450 (e.g. wild type cytochrome P450) and then comparing it to the relative amount of individual terpenoids produced using a second cytochrome P450 (e.g. a modified cytochrome P450). An altered product distribution is considered to occur if the relative amount of any one or more terpenoids is increased or decreased by at least or by at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more.

As used herein, an improved product distribution refers to a change in the product distribution to one that is more desirable, i.e. contains more desirable relative amounts of terpenoids. For example, an improved product distribution can contain an increased amount of a desired terpenoid and/or a decreased amount of a terpenoid that is not so desired. The amount of desired terpenoid in an improved production distribution can be increased by at least or by at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more. The amount of a terpenoid that is not desired in an improved production distribution can be decreased by at least or by at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more.

As used herein, nucleic acids or nucleic acid molecules include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, heterologous nucleic acid is nucleic acid that is not normally produced in vivo by the cell in which it is expressed or that is produced by the cell but is at a different locus or expressed differently or that mediates or encodes mediators that alter expression of endogenous nucleic acid, such as DNA, by affecting transcription, translation, or other regulatable biochemical processes. Heterologous nucleic acid is generally not endogenous to the cell into which it is introduced, but has been obtained from another cell or prepared synthetically. Heterologous nucleic acid can be endogenous, but is nucleic acid that is expressed from a different locus or altered in its expression. Generally, although not necessarily, such nucleic acid encodes RNA and proteins that are not normally produced by the cell or in the same way in the cell in which it is expressed. Heterologous nucleic acid, such as DNA, also can be referred to as foreign nucleic acid, such as DNA. Thus, heterologous nucleic acid or foreign nucleic acid includes a nucleic acid molecule not present in the exact orientation or position as the counterpart nucleic acid molecule, such as DNA, is found in a genome. It also can refer to a nucleic acid molecule from another organism or species (i.e., exogenous).

Any nucleic acid, such as DNA, that one of skill in the art would recognize or consider as heterologous or foreign to the cell in which the nucleic acid is expressed is herein encompassed by heterologous nucleic acid; heterologous nucleic acid includes exogenously added nucleic acid that also is expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acid, such as DNA, that encodes other types of proteins, such as antibodies. Antibodies that are encoded by heterologous nucleic acid can be secreted or expressed on the surface of the cell in which the heterologous nucleic acid has been introduced.

As used herein, a peptide refers to a polypeptide that is from 2 to 40 amino acids in length.

As used herein, the amino acids that occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids in which the α-carbon has a side chain).

In keeping with standard polypeptide nomenclature described in *J. Biol. Chem.*, 243: 3557-3559 (1968), and adopted 37 C.F.R. §§1.821-1.822, abbreviations for the amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

All amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§1.821-1.822, and incorporated herein by reference. Furthermore, a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound containing an amino group and a carboxylic acid group that is not one of the naturally-occurring amino acids listed in Table 1. Non-naturally occurring amino acids thus include, for example, amino acids or analogs of amino acids other than the 20 naturally-occurring amino acids and include, but are not limited to, the D-isostereomers of amino acids. Exemplary non-natural amino acids are known to those of skill in the art and can be included in a modified cytochrome P450 polypeptide or cytochrome P450 reductase polypeptide provided herein.

As used herein, modification is in reference to modification of the primary sequence of amino acids of a polypeptide or a sequence of nucleotides in a nucleic acid molecule and includes deletions, insertions, and replacements and rearrangements of amino acids and nucleotides. For purposes herein, amino acid replacements (or substitutions), deletions and/or insertions, can be made in any of the cytochrome P450s or cytochrome P450 reductases provided herein. Modifications can be made by making conservative amino acid replacements and also non-conservative amino acid substitutions as well as by insertions, domain swaps and other such changes in primary sequence. For example, amino acid replacements that desirably or advantageously alter properties of the cytochrome P450 or cytochrome P450 reductase can be made. For example, amino acid replacements can be made to the cytochrome P450 santalene oxidase such that the resulting modified cytochrome P450 santalene oxidase can produce more β-santalol from a mixture of santalenes and bergamotenes compared to an unmodified cytochrome P450 santalene oxidase. For example, amino acid replacements can be made to the cytochrome P450 bergamotene oxidase such that the resulting cytochrome P450 bergamotene oxidase can produce more bergamotol from a mixture of santalenes and bergamotenes compared to an unmodified cytochrome P450 bergamotene oxidase. Modifications also can include post-translational modifications or other changes to the molecule that can occur due to conjugation or linkage, directly or indirectly, to another moiety, but when such modifications are contemplated they are referred to as post-translational modifications or conjugates or other such term as appropriate. Methods of modifying a polypeptide are routine to those of skill in the art, and can be performed by standard methods, such as site directed mutations, amplification methods, and gene shuffling methods.

As used herein, amino acid replacements or substitutions contemplated include, but are not limited to, conservative substitutions, including, but not limited to, those set forth in Table 2. Suitable conservative substitutions of amino acids are known to those of skill in the art and can be made generally without altering the conformation or activity of the polypeptide. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. co., p. 224). Conservative amino acid substitutions are made, for example, in accordance with those set forth in Table 2 as follows:

TABLE 2

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu; Met |

Other conservative substitutions also are contemplated and can be determined empirically or in accord with known conservative substitutions.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, "primary sequence" refers to the sequence of amino acid residues in a polypeptide.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

As used herein, "at a position corresponding to" or recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. For purposes herein, alignment of a cytochrome P450 santalene oxidase sequence is to the amino acid sequence set forth in SEQ ID NO:7. For purposes herein, alignment of a cytochrome P450 bergamotene oxidase sequence is to the amino acid sequence set forth in any of SEQ ID NOS:6, 8 or 9, and in particular SEQ ID NO:6. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carillo et al. (1988) *SIAM J Applied Math* 48:1073). FIGS. 2A-2B, 3A-3C, 5A-5B and 21A-21C exemplify exemplary alignments and identification of exemplary corresponding residues for replacement.

As used herein, "sequence identity" refers to the number of identical or similar amino acids or nucleotide bases in a comparison between a test and a reference polypeptide or polynucleotide. Sequence identity can be determined by sequence alignment of nucleic acid or protein sequences to identify regions of similarity or identity. For purposes herein, sequence identity is generally determined by alignment to identify identical residues. The alignment can be local or global. Matches, mismatches and gaps can be identified between compared sequences. Gaps are null amino acids or nucleotides inserted between the residues of aligned sequences so that identical or similar characters are aligned. Generally, there can be internal and terminal gaps. Sequence identity can be determined by taking into account gaps as the number of identical residues/length of the shortest sequence×100. When using gap penalties, sequence identity can be determined with no penalty for end gaps (e.g. terminal gaps are not penalized). Alternatively, sequence identity can be determined without taking into account gaps as the number of identical positions/length of the total aligned sequence×100.

As used herein, a "global alignment" is an alignment that aligns two sequences from beginning to end, aligning each letter in each sequence only once. An alignment is produced, regardless of whether or not there is similarity or identity between the sequences. For example, 50% sequence identity based on "global alignment" means that in an alignment of the full sequence of two compared sequences each of 100 nucleotides in length, 50% of the residues are the same. It is understood that global alignment also can be used in determining sequence identity even when the length of the aligned sequences is not the same. The differences in the terminal ends of the sequences will be taken into account in determining sequence identity, unless the "no penalty for end gaps" is selected. Generally, a global alignment is used on sequences that share significant similarity over most of their length. Exemplary algorithms for performing global alignment include the Needleman-Wunsch algorithm (Needleman et al. (1970) *J. Mol. Biol.* 48: 443). Exemplary programs for performing global alignment are publicly available and include the Global Sequence Alignment Tool available at the National Center for Biotechnology Information (NCBI) website (ncbi.nlm.nih.gov/), and the program available at deepc2.psi.iastate.edu/aat/align/align.html.

As used herein, a "local alignment" is an alignment that aligns two sequence, but only aligns those portions of the sequences that share similarity or identity. Hence, a local alignment determines if sub-segments of one sequence are present in another sequence. If there is no similarity, no alignment will be returned. Local alignment algorithms include BLAST or Smith-Waterman algorithm (*Adv. Appl. Math.* 2:482 (1981)). For example, 50% sequence identity based on "local alignment" means that in an alignment of the full sequence of two compared sequences of any length, a region of similarity or identity of 100 nucleotides in length has 50% of the residues that are the same in the region of similarity or identity.

For purposes herein, sequence identity can be determined by standard alignment algorithm programs used with default gap penalties established by each supplier or manually. Default parameters for the GAP program can include: (1) a unary comparison matrix (containing a value of 1 for identities and 0 for non identities) and the weighted comparison matrix of Gribskov et al. (1986) *Nucl. Acids Res.* 14:6745, as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps. Whether any two nucleic acid molecules have nucleotide sequences or any two polypeptides have amino acid sequences that are at least 80%, 85%, 90%, 95%, 96%, 97%, 98% or 99% "identical," or other similar variations reciting a percent identity, can be determined using known computer algorithms based on local or global alignment (see e.g., wikipedia.org/wiki/Sequence_alignment_software, providing links to dozens of known and publicly available alignment databases and programs). Generally, for purposes herein sequence identity is determined using computer algorithms based on global alignment, such as the Needleman-Wunsch Global Sequence Alignment tool available from NCBI/BLAST (blast.ncbi.nlm.nih.gov/Blast.cgi?CMD=Web&Page_TYPE=BlastHome); LAlign (William Pearson implementing the Huang and Miller algorithm (*Adv. Appl. Math.* (1991) 12:337-357)); and program from Xiaoqui Huang available at deepc2.psi.iastate.edu/aat/align/align.html. Generally, when comparing nucleotide sequences herein, an alignment with penalty for end gaps is used. Local alignment also can be used when the sequences being compared are substantially the same length.

As used herein, the term "identity" represents a comparison between a test and a reference polypeptide or polynucleotide. In one non-limiting example, "at least 90% identical to" refers to percent identities from 90 to 100% relative to the reference polypeptides. Identity at a level of 90% or more is indicative of the fact that, assuming for exemplification purposes a test and reference polypeptide length of 100 amino acids are compared, no more than 10% (i.e., 10 out of 100) of amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences also can be due to deletions or truncations of amino acid residues. Differences are defined as nucleic acid or amino acid substitutions, insertions or deletions. Depending on the length of the compared sequences, at the level of homologies or identities above about 85-90%, the result reasonably independent of the program and gap parameters set; such high levels of identity can be assessed readily, often without relying on software.

As used herein, the terms "substantially identical" or "similar" varies with the context as understood by those skilled in the relevant art, but that those of skill can assess such.

As used herein, an aligned sequence refers to the use of homology (similarity and/or identity) to align corresponding positions in a sequence of nucleotides or amino acids. Typically, two or more sequences that are related by about or 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, isolated or purified polypeptide or protein or biologically-active portion thereof is substantially free of cellular material or other contaminating proteins from the cell of tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as proteolytic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

As used herein, substantially free of cellular material includes preparations of cytochrome P450s, cytochrome P450 reductases, terpenes or terpenoid products in which the cytochrome P450, cytochrome P450 reductase, terpene or terpenoid product is separated from cellular components of the cells from which it is isolated or produced. In one embodiment, the term substantially free of cellular material includes preparations of cytochrome P450s, cytochrome P450 reductases, terpenes or terpenoid products having less that about or less than 30%, 20%, 10%, 5% or less (by dry weight) of non-cytochrome P450s, cytochrome P450 reductases, terpenes or terpenoid products, including cell culture medium. When the cytochrome P450 or cytochrome P450 reductase is recombinantly produced, it also is substantially free of culture medium, i.e., culture medium represents less than about or at 20%, 10% or 5% of the volume of the cytochrome P450 or cytochrome P450 reductase preparation.

As used herein, the term substantially free of chemical precursors or other chemicals includes preparations of cytochrome P450 or cytochrome P450 reductase proteins in which the protein is separated from chemical precursors or other chemicals that are involved in the synthesis of the protein. The term includes preparations of cytochrome P450 or cytochrome P450 reductase proteins having less than about or less than 30% (by dry weight), 20%, 10%, 5% or less of chemical precursors or non-synthase chemicals or components.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant methods by using recombinant DNA methods refers to the use of the well known methods of molecular biology for expressing proteins encoded by cloned DNA.

As used herein, vector (or plasmid) refers to discrete DNA elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as bacterial artificial chromosomes, yeast artificial chromosomes and mammalian artificial chromosomes. Selection and use of such vehicles are well known to those of skill in the art.

As used herein, expression refers to the process by which nucleic acid is transcribed into mRNA and translated into peptides, polypeptides, or proteins. If the nucleic acid is derived from genomic DNA, expression can, if an appropriate eukaryotic host cell or organism is selected, include processing, such as splicing of the mRNA.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells. Viral vectors include, but are not limited to, adenoviral vectors, retroviral vectors and vaccinia virus vectors. As used herein, operably or operatively linked when referring to DNA segments means that the segments are arranged so that they function in concert for their intended purposes, e.g., transcription initiates downstream of the promoter and upstream of any transcribed sequences. The promoter is usually the domain to which the transcriptional machinery binds to initiate transcription and proceeds through the coding segment to the terminator.

As used herein, a "chimeric protein" or "fusion protein" refers to a polypeptide operatively-linked to a different polypeptide. For example, a polypeptide encoded by a nucleic acid sequence containing a coding sequence from one nucleic acid molecule and the coding sequence from another nucleic acid molecule in which the coding sequences are in the same reading frame such that when the fusion construct is transcribed and translated in a host cell, the protein is produced containing the two proteins. The two molecules can be adjacent in the construct or separated by a linker polypeptide that contains, 1, 2, 3, or more, but typically fewer than 10, 9, 8, 7, or 6 amino acids. The protein product encoded by a fusion construct is referred to as a fusion polypeptide. A chimeric or fusion protein provided herein can include one or more santalene synthase polypeptides, or a portion thereof, and/or one or more cytochrome P450 polypeptides, or a portion thereof, and/or one or more cytochrome P450 reductase polypeptides and/or one or more other polypeptides, for any one or more of a transcriptional/translational control signals, signal sequences, a tag for localization, a tag for purification, a protein for identification, part of a domain of an immunoglobulin G, and/or a targeting agent. A chimeric cytochrome P450 polypeptide or cytochrome P450 reductase polypeptide also includes those having their endogenous domains or regions of the polypeptide exchanged with another polypeptide. These chimeric or fusion proteins include those produced by recombinant means as fusion proteins, those produced by chemical means, such as by chemical coupling, through, for example, coupling to sulfhydryl groups, and those produced by any other method whereby at least one polypeptide (i.e. cytochrome P450 or cytochrome P450 reductase), or a portion thereof, is linked, directly or indirectly via linker(s) to another polypeptide.

As used herein, the term assessing or determining includes quantitative and qualitative determination in the sense of obtaining an absolute value for the activity of a product, and also of obtaining an index, ratio, percentage, visual or other value indicative of the level of the activity. Assessment can be direct or indirect.

As used herein, recitation that a polypeptide "consists essentially" of a recited sequence of amino acids means that only the recited portion, or a fragment thereof, of the full-length polypeptide is present. The polypeptide can optionally, and generally will, include additional amino acids from another source or can be inserted into another polypeptide As used herein, the singular forms "a", "an" and "the" include plural referents unless the context clearly dictates otherwise. Thus, for example, reference to polypeptide, comprising "an amino acid replacement" includes polypeptides with one or a plurality of amino acid replacements.

As used herein, ranges and amounts can be expressed as "about" a particular value or range. About also includes the exact amount. Hence "about 5%" means "about 5%" and also "5%."

As used herein, "optional" or "optionally" means that the subsequently described event or circumstance does or does not occur, and that the description includes instances where the event or circumstance occurs and instances where it does not. For example, an optional step of isolating a terpene means that the terpene is isolated or is not isolated, or, an optional stop of isolating a terpenoid means that the terpenoid is isolated or is not isolated.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description is divided into the subsections that follow.

B. Overview

Provided herein are cytochrome P450 enzymes from *Santalum album*, and variants and modified forms thereof, for production of santalols and other sesquiterpenoids. Such cytochrome P450s catalyze the biosynthetic production of santalols or bergamotols from santalenes and bergamotenes, both of which can be generated biosynthetically from farnesyl pyrophosphate by the enzyme santalene synthase (see, WO 2011/000026 and Jones et al. (2011) *J Biol Chem* 286:17445-17454. Also provided herein are cytochrome P450 reductases from *Santalum album*, and variants and modified forms thereof. Also provided herein are methods of making santalols and other sesquiterpenoids from farnesyl diphosphate and/or santalenes and bergamotene. The provided cytochrome P450 enzymes provide for production of these valuable products, including santalols and bergamotols, in commercially useful quantities and in a cost effective and energy efficient manner.

1. Biosynthesis of Terpenoids

Terpenes are a large and diverse class of organic compounds that are produced by a variety of plants from acyclic pyrophosphate isoprene precursors such as geranyl pyrophosphate (GPP), farnesyl pyrophosphate (FPP), and geranylgeranyl pyrophosphate (GGPP). Terpenes are named based on the number of isoprene ($C_5H_8$) units they contain. For example, monoterpenes are derived from GPP and contain 10 carbons, sesquiterpenes are derived from FPP and contain 15 carbons and diterpenes are derived from GGPP and contain 20 carbons. Terpenes that have been chemically modified are referred to as terpenoids or isoprenoids. Terpenes and terpenoids are the primary constituents of essential oils of plants and are widely used as flavor additives for food, fragrances in perfumery and in traditional and alternative medicine.

Santalols and bergamotol are sesquiterpenoids that occur in plants, including the heartwood of *Santalum* species, including *Santalum album* (Indian Sandalwood, White Sandalwood, Chandana), *Santalum austrocaledonicum* (Australian Sandalwood) and *Santalum spicatum*. Bergamotol can additionally be found in plants such as orchids. Santalols and bergamotol are the oxidation products of santalenes and bergamotene, respectively. In *S. album*, about 90% of the essential oil is composed of the sesquiterpene alcohols (Z)-α-, (Z)-β-, and (Z)-epi-β-santalol and (Z)-α-exo-bergamotol. The α- and β-santalols are the most important contributors to sandalwood oil fragrance. (Z)-α-Santalol and (Z)-β-santalol are the major components of authentic *S. album* oil.

The P450 enzymes provided herein can be employed to produce the sesquiterpene alcohols important for the sandalwood oil fragrance. Santalenes and bergamotene are synthesized biosynthetically from the acyclic pyrophosphate precursor FPP by the terpene synthase santalene synthase (see WO 2011/000026 and Jones et al. (2011) J Biol Chem 286:17445-17454). Santalene synthase is known to produce a mixture of santalenes (i.e. α-, β-, epi-β-santalene and α-exo-bergamotene). Exemplary of santalene synthases are *Santalum album* santalene synthase (SaSSY) set forth in SEQ ID NO:16 and encoding the amino acid sequence set forth in SEQ ID NO:17; *Santalum austrocaledonicum* santalene synthase (SauSSY, Genbank Accession Nos. HQ343277 or AD087001) set forth in SEQ ID NO:59 and encoding the sequence of amino acids set forth in SEQ ID NO:52; or *Santalum spicatum* santalene synthase (SspiSSy, Genbank Accession No. HQ343278 or AD087002) set forth in SEQ ID NO: 60 and encoding the sequence of amino acids set forth in SEQ ID NO:53.

The cytochrome P450 oxidase polypeptides provided herein are found to catalyze the formation of one or more of an α-santalol from α-santalene, β-santalol from β-santalene, epi-β-santalol from epi-β-santalene and/or α-trans-bergamotol from α-trans-bergamotene. Hydroxylation or monooxygenation of terpene substrates by the cytochrome P450 oxidase is generally performed in the presence of a cytochrome reductase. For example, *Santalum album* cytochrome reductases (SaCPR) provided herein are included in biosynthesis to supply electrons from NADPH to the cytochrome P450. Thus, the pathways for biosynthesis of santalols and bergamotols, including components of sandalwood oil, can be metabolically engineered in host cells by transforming nucleic acid encoding a cytochrome P450 oxidase and cytochrome P450 reductase provided herein in combination with a nucleic acid molecule encoding a santalene synthase.

a. Santalols

In particular, santalols responsible for the fragrance of sandalwood oil include α-santalols (1 and 9), β-santalols (2 and 10) and epi-β-santalols (3 and 11) (see FIG. 1). (Z)-α-Santalol (Z-α-santalol; (Z)-5-(1R,2S,6S)-2,3-dimethyltricyclol[2.2.1.0$^{2,6}$]heptan-3-yl)-2-methylpent-2-en-1-ol; 1) and (E)-α-Santalol ((E)-5-((1R,2s,6S)-2,3-dimethyltricyclo[2.2.1.02,6]heptan-3-yl)-2-methylpent-2-en-1-ol; 9) are synthesized biosynthetically by oxidation of the sesquiterpene α-santalene 5 (see FIG. 1). (Z)-β-Santalol (Z-ββ-santalol; (Z)-2-methyl-5-[(1S,2R,4R)-2-methyl-3-methylene-bicyclo[2.2.1]heptan-2-yl]pent-2-en-1-ol; 2) and (E)-β-Santalol ((E)-2-methyl-5-((1S,2R,4R)-2-methyl-3-methylenebicyclo[2.2.1]heptan-2-yl)pent-2-en-1-ol; 10) are synthesized biosynthetically by oxidation of the sesquiterpene β-santalene 6 (see FIG. 1). (E)-epi-β-Santalol ((E)-2-methyl-5-[(1R,2R,4S)-2-methyl-3-methylenebicyclo[2.2.1]heptan-2-yl)pent-2-en-1-ol; 3) and (Z)-epi-β-Santalol ((Z)-2-methyl-5-((1R,2R,4S)-2-methyl-3-methylenebicyclo[2.2.1]heptan-2-yl)pent-2-en-1-ol; 11) are synthesized biosynthetically by oxidation of the sesquiterpene epi-β-santalene 7 (see FIG. 1).

1

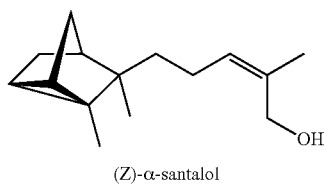

(Z)-α-santalol

2

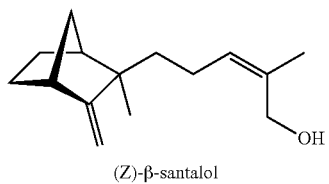

(Z)-β-santalol

3

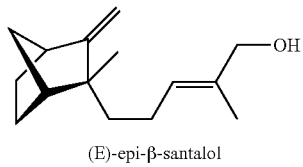

(E)-epi-β-santalol

9

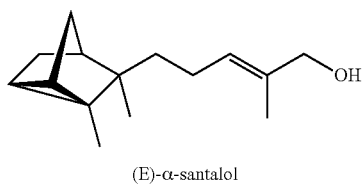

(E)-α-santalol

10

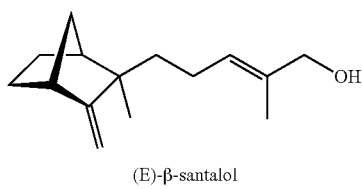

(E)-β-santalol

11

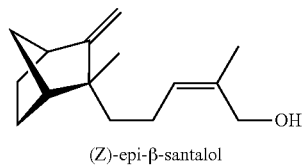

(Z)-epi-β-santalol b. Bergamotol (Z)-α-trans-Bergamotol ((Z)-α-exo-bergamotol; cis-α-trans-bergamotol; (2Z)-5-[(1S,5S,6R)-2,6-dimethylbicyclo[3.3.1]hept-2-en-6-yl]-2-methyl-2-penten-1-ol; 4) and (E)-α-trans-Bergamotol ((E)-α-exo-bergamotol; (E)-5-((1S,5S,6R)-2,6-dimethylbicyclo[3.1.1]hept-2-en-6-yl)-2-methylpent-2-en-1-ol; 12) are sesquiterpenoids found in sandalwood oil that are synthesized biosynthetically by oxidation of the sesquiterpene α-trans-bergamotene 8 (see FIG. 1).

4

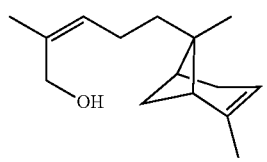

(Z)-α-bergamotol

12

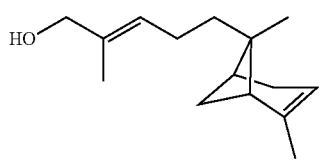

(E)-α-trans-bergamotol

2. Cytochrome P450 Enzymes

Cytochromes P450 (CYPs) are a superfamily of hemoproteins, or heme-thiolate proteins, that catalyze the singular insertions of oxygen into a diverse range of hydrophobic substrates, often with high regio- and stereoselectivity. Cytochrome P450s are ubiquitous proteins that participate in metabolizing a wide range of compounds. As such, P450s are widespread in nature and are involved in processes such as detoxifying xenobiotics, catabolism of unusual carbon sources and biosynthesis of secondary metabolites. CYPs are noted for their broad substrate specificities and use of oxygen without the need for phosphorylation of adenosine diphosphate (ADP). They can mediate monooxygenations, hydroxylations at nitrogen and sulfur heteroatoms, epoxidations, dehalogenations, deaminations and dealkylations. Particular reactions catalyzed by CYPs include demethylation, hydroxylation, epoxidation, N-oxidation, sulfooxidation, N-, S-, and O-dealkylations, desulfation, deamination, and reduction of azo, nitro, and N-oxide groups.

Typically, cytochrome P450s are monooxygenases, incorporating one oxygen atom into a substrate. In general, monooxygenations require one or two additional proteins to transfer electrons from NAD(P)H to the heme iron and CYPs are placed in groups or classes based on their electron transfer partner. Class I CYPs, common in bacterial and eukaryotic mitochondrial P450 systems, use a FAD-containing reductase and an iron-sulfer redoxin or ferrodoxin. The FAD-containing reductase transfers electrons from NAD (P)H to the ferrodoxin which in turn reduces the CYP. Class II cytochrome P450s are the most common CYPs in eukaryotes and plants, and also include microsomal and bacterial P450 systems. Class II CYPs use a NADPH:Cytochrome P450 reductase (or cytochrome P450 reductase) to transfer electrons from NAD(P)H to a cytochrome P450. Numerous other classes exist that exploit other electron transfer chains.

Cytochrome P450s are named using a systematic nomenclature that includes the root symbol CYP followed by number designating the family, a letter designating the subfamily and a number representing the individual gene, for example, CYP76-G5. Families share greater than 40% amino acid sequence identity and subfamilies share greater than 55% amino acid sequence identity.

Plant cytochrome P450 gene families are very large. For example, total genome sequence examination reveals at least 272 predicted cytochrome P450 genes in *Arabidopsis* and at least 455 unique cytochrome P450 genes in rice (see, e.g., Nelson et al. (2004) *Plant Physiol.* 135(2):756-772). Plant CYPs can be localized to the endoplasmic reticulum (ER) and to chloroplasts. In plants, CYPs include a wide range of hydroxylases, epoxidases, peroxidases and oxygenases that largely are based upon Class II monooxygenations. Plant p450s participate in biochemical pathways that include, for example, the synthesis of plant products such as phenylpropanoids, alkaloids, terpenoids, lipids, cyanogenic glycosides, and glucosinolates (see, e.g., Chapple (1998) *Annu. Rev. Plant Physiol. Plant Mol. Biol.* 49:311-343).

a. Structure

While sequence conservation among cytochrome P450s is relatively low, their general topography and structural fold are highly conserved. There are only 3 absolutely conserved residues among all CYPs, namely the glutamic acid and arginine of the ExxR motif (SEQ ID NO:54) and the heme-binding cysteine. Conserved structural nodules are important for structure and function, and variable regions involved in substrate recognition dictate individual properties (see, e.g., Werck-Reichhart and Feyereisen (2000) *Genome Biology* 1(6)3000.1-3000.9, Sirim et al. (2010) *BMC Structural Biology* 10:34 and Baudry et al. (2006) *Prot Eng Design & Selection* 19:343-353).

Cytochrome P450s typically contain α helices, designated A through L, and β-pleated sheets, designated 1 through 5, contained within a β domain that is associated with substrate recognition and composed predominately of β sheets and an α domain that contains the catalytic center and is predominantly α helices. The structural regions are as follows, from N-terminus to C-terminus: helix A, β strand 1-1, β strand 1-2, helix B, β strand 1-5, helix B', helix C, helix C', helix D, β strand 3-1, helix E, helix F, helix G, helix H, β strand 5-1, β strand 5-2, helix I, helix J, helix J', helix K, β strand 1-4, β strand 2-1, β strand 2-2, β strand 1-3, helix K', helix K", Heme domain, helix L, β strand 3-3, β strand 4-1, β strand 4-2 and β strand 3-2 (see, e.g., Werck-Reichhart and Feyereisen (2000) *Genome Biology* 1(6)3000.1-3000.9).

Cytochrome P450s are anchored to the endoplasmic reticulum (ER) or chloroplast in plants via a transmembrane helix near the N-terminus of the protein (Chapple (1998) *Annu Rev Plant Physiol Plant Mol Biol* 49:311-343). The transmembrane helix is typically followed by hinge region containing a series of basic amino acid residues and a proline-rich region containing the consensus sequence (P/I)PGPx(G/P)xP (SEQ ID NO:55). This hinge region allows for optimal orientation of the enzyme in relation to the membrane. Deletion of the proline hinge region resulted in complete loss of activity (Szczesna-Skorupa et al. (1993) *Arch Biochem Biophys* 304:170-175) and mutation of proline residues to alanine disrupted structure so as to eliminate heme incorporation (Yamazaki et al. (1993) *J Biochem* 114:652-657).

The conserved CYP core region is composed of a coil termed the 'meander', a four-helix bundle (helices D, E, I and L), helices J and K and two sets of β-sheets (Werck-Reichhart and Feyereisen (2000) *Genome Biology* 1(6) 3000.1-3000.9). The core region contains the heme-binding loop containing the P450 consensus sequence GRRxCP(A/G) (SEQ ID NO:56) located on the proximal face of the heme just before helix L, with an absolutely conserved cysteine that serves as the 5th ligand for the heme iron. The active site for catalysis is the iron-protoporphryin IX (heme) with the thiolate of the conserved cysteine residue as the fifth ligand; the final coordination site is left to bind and activate molecular oxygen (Groves et al., 1995 In Cytochrome P450: Structure, Mechanism, and Biochemistry (Ed: Ortiz de Montellano) Plenum Press, New York, N.Y., pp. 3-48). The core region also contains the central part of helix I containing the threonine-containing binding pocket for the oxygen molecule required in catalysis having a consensus sequence (A/G)Gx(D/E)T(T/S) (SEQ ID NO:57) which also corresponds to the proton-transfer groove. Finally, the core region contains the absolutely conserved ExxR motif (SEQ ID NO:54) in helix K on the proximal side of heme (see, e.g., Werck-Reichhart and Feyereisen (2000) *Genome Biology* 1(6)3000.1-3000.9). The proximal face of the enzyme is involved in redox partner recognition and electron transfer to active site. Protons flow into active site channel from distal face. The substrate access channel is located in close contact with the membrane between the F-G loop, A helix and β strands 1-1 and 1-2.

Cytochrome P450 substrate recognitions sites (SRS) are diverse and include SRS1, the loop region between B and C helices; SRS2, the C-terminal end of the F helix; SRS3, part of the FG loop and N-terminal end of the G helix; SRS4, helix I containing SRS4 extending over the pyrrole ring B in the active site; SRS5, the loop between the K helix and strand 4 of β-sheet 1; and SRS6, the β turn in β-sheet 4.

b. Function

Cytochrome P450s catalyze regiospecific and stereospecific oxidation of non-activated hydrocarbons at physiological temperatures. Cytochrome P450s activate molecular oxygen using an iron-heme center and use a redox electron shuttle to support the oxidation reaction. The general reaction for hydroxylation by the cytochrome P450 system is,

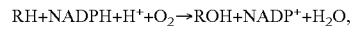

$$RH + NADPH + H^+ + O_2 \rightarrow ROH + NADP^+ + H_2O,$$

where R represents a substrate compound. As noted, typically, cytochrome P450s are monooxygenases, catalyzing the insertion of one of the atoms of molecular oxygen into a substrate, with the second oxygen being reduced to water. Catalysis involves 1) substrate binding; 2) one-electron reduction of the complex to a ferrous state; 3) binding of molecular oxygen to give the superoxide complex; and 4) a second reduction leading to a short lived activated oxygen species. The activated oxygen attacks the substrate resulting, typically, in monooxygenation of the substrate. Other reactions catalyzed by CYPs include dealkylation, dehydration, dehydrogenation, isomerization, dimerization, carbon-carbon bond cleavage and reduction.

3. Cytochrome P450 Reductase

Cytochrome P450 reductases (NADPH:cytochrome P450 reductase; NADPH-cytochrome P450 oxidoreductase; NADPH:ferrihemoprotein oxidoreductase; NADPH:P450 oxidoreductase; CPR; CYPOR; EC 1.6.2.4) are multidomain enzymes of the diflavin reductase family required for electron transfer from NAD(P)H to cytochrome P450s, heme oxygenases, cytochrome $b_5$ and squalene epoxidases (Louerat-Orieu et al (1998) *Eur J Biochem* 258:1040-1049). Plants are known to contain multiple isoforms of cytochrome P450 reductases (see, Ro et al. (2002) *Plant Physiology* 130:1837-1851; Mizutani and Ohta (1998) *Plant Physiology* 116:357-367). Generally, at least one CPR is constitutively expressed and the other CPRs are enhanced by environmental stresses such as UV light and pathogen infection. In addition, plant cytochrome P450 reductases can be localized to the ER or to the chloroplast, with the location determined by the corresponding partner cytochrome P450 enzyme.

a. Structure

Cytochrome P450 reductases share amino acid sequence homology (about 30% up to about 90%) among different species, including as bacteria, yeast, fungi, plants, fish, insects and mammals (Louerat-Orieu et al (1998) *Eur J Biochem* 258:1040-1049). Cytochrome P450 reductases contain two functional domains, a hydrophobic N-terminal single α-helical membrane anchoring domain (amino acids 1-95 of SEQ ID NO:12) and a hydrophilic C-terminal catalytic domain (amino acids 96-704 of SEQ ID NO:12) (Wang et al. (1997) *Proc Natl Acad Sci USA* 94:8111-8416). The N-terminal domain contains a hydrophobic membrane anchoring domain (amino acids 40-60 of SEQ ID NO:12) that anchors the protein to a membrane, for example, to the ER or chloroplast in plants, thus ensuring the CPR and the CYP are spatially related to allow for electron transfer. The N-terminal domain is not necessary for activity, as the C-terminal soluble domain alone is capable transferring electrons to cytochrome c or other electron acceptors. The C-terminal soluble domain contains two structural domains, a N-terminal flavin mononucleotide (FMN) domain (amino acids of 101-244 SEQ ID NO:12) and a C-terminal flavin adenine dinucleotide (FAD) domain (amino acids 301-704 of SEQ ID NO:12) (Dym and Eisenberg (2001) *Protein Science* 10:1712-1728). The FMN domain is homologous to flavodoxin that allows for binding to flavin cofactor FMN. The FAD domain that contains binding domains for flavin cofactor FAD and for NADPH, and additionally contains residues necessary for catalytic activity. The FMN and FAD domains are joined by a connecting domain (amino acids 245-300 of SEQ ID NO:12) that is responsible for the relative orientation of the FMN and FAD domains ensuring proper alignment of the two flavin cofactors necessary for efficient electron transfer.

The N-terminal FMN domain has an antiparallel β-structure while the C-terminal NAD(P) subdomain has the typology typical of pyridine dinucleotide-binding folds. The FMN domain contains a five-stranded β-sheet flanked by five α-helices, with the FMN positioned at the C-terminal side of the β-sheet. The core of the FAD binding domain is an anti-parallel flattened β-barrel and the NADP(H) binding domain is a parallel five-stranded β-sheet flanked by α-helices. The connecting domain is composed mainly of α-helices. The structural regions are as follows, from N-terminus to C-terminus: α-helix A; β-strand 1; α-helix B; β-strand 2; α-helix C; β-strand 3; α-helix D; β-strand 4; α-helix E; β-strand 5; α-helix F; β-strand 6; β-strand 7; β-strand 8, β-strand 9; β-strand 10; α-helix G; β-strand 11; β-strand 12; β-strand 12'; α-helix H; α-helix I; α-helix J; α-helix K; α-helix M; β-strand 13; β-strand 14; β-strand 15; α-helix N; β-strand 16; β-strand 16'; β-strand 17; α-helix O; β-strand 18; α-helix P; β-strand 10; α-helix Q; α-helix R; β-strand 20; α-helix S; α-helix T; and β-strand 21.

Cytochrome P450 reductases contain conserved cofactor and substrate binding domains, including FMN-, FAD-, NADPH-binding regions and cytochrome c- and cytochrome P450-binding sites. The P450 and cytochrome c binding sites contains amino acids 232-240 of SEQ ID NO12. The FMN domain contains binding regions for the FMN pyrophosphate (amino acids 98-119 of SEQ ID NO:12) and the FMN isoalloxazine ring (amino acids 161-214 of SEQ ID NO:12). The FAD domain contains binding regions for the FAD pyrophosphate (amino acids 317-353 of SEQ ID NO:12) and the FAD isoalloxazine ring (amino acids 482-505 of SEQ ID NO:12). The FAD binding pocket includes amino acids 344, 482, 484, 485, 500-502, 516-519 and 704 of SEQ ID NO:12 and the FAD binding motif includes amino acids 482, 484 and 485 of SEQ ID NO:12. The FAD domain also contains binding regions for the NADPH ribose and pyrophosphate (amino acids 555-576 of SEQ ID NO:12) and the NADPH nicotinamide (amino acids 651-668 of SEQ ID NO:12). The NADPH binding pocket includes amino acid residues 324, 502, 204, 560, 561, 595, 595, 624, 625, 630, 632 634, 659, 663 and 666 of SEQ ID NO:12. Amino acid residues Ser485, Cys657, Asp702 and Trp704 of SEQ ID NO:12 are the catalytic residues involved in hydride transfer (Hubbard et al. (2001) *J Biol Chem* 276:29163-29170). Amino acid residues 516, 519 and 522 of SEQ ID NO:12 are involved in the phosphate binding motif (Dym and Eisenberg (2001) *Protein Science* 10:1712-1728). The βαβ structure motif is formed from amino acid residues 557, 560-563 and 565 of SEQ ID NO:12 (Dym and Eisenberg (2001) *Protein Science* 10:1712-1728).

b. Function

Cytochrome P450 reductases shuttle two electrons from NAD(P)H to cytochrome P450 through the flavin cofactors FAD and FMN. FAD receives a hydride anion from the two electron donor NAD(P)H and passes the electrons one at a time to FMN. FMN then donates the electrons to the cytochrome P450. Cytochrome P450 uses the electrons, as described above, for the hydroxylation of various substrates.

C. Cytochrome P450 Polypeptides And Nucleic Acid Molecules Encoding The Cytochrome P450 Polypeptides Provided herein are cytochrome P450 polypeptides, including cytochrome P450 santalene oxidase polypeptides and cytochrome P450 bergamotene oxidase polypeptides. Also provided herein are nucleic acid molecules that encode any of the cytochrome P450 polypeptides provided herein. The cytochrome P450 santalene oxidase polypeptides provided herein catalyze the formation of α-santalol, β-santalol or epi-β-santalol from α-santalene, β-santalene or epi-β-santalene, respectively, including, the production of β-santalol from β-santalene. The cytochrome P450 santalene oxidase polypeptides provided herein are also capable of catalyzing the formation of α-trans-bergamotol from α-trans-bergamotene. In some examples, the nucleic acid molecules that encode the cytochrome P450 santalene oxidase polypeptides are those that are the same as or substantially the same as those that are isolated from the sandalwood tree *Santalum album*. In other example, the nucleic acid molecules and encoded cytochrome P450 santalene oxidase polypeptides are variants of those isolated from the sandalwood tree *Santalum album*. The cytochrome P450 bergamotene oxidase polypeptides provided herein catalyze the formation of α-trans-bergamotol from α-trans-bergamotene. In some examples, the nucleic acid molecules that encode the cytochrome P450 bergamotene oxidase polypeptides are those that are the same as those that are isolated from the sandalwood tree *Santalum album*. In other examples, the nucleic acid molecules and encoded cytochrome P450 bergamotene oxidase polypeptides are variants of those isolated from the sandalwood tree *Santalum album*.

Also provided herein are modified cytochrome P450 polypeptides and nucleic acid molecules that encode any of the modified cytochrome P450 polypeptides provided herein. The modifications can be made in any region of a cytochrome P450 polypeptide, including a cytochrome P450 santalene oxidase polypeptide or cytochrome P450 bergamotene oxidase polypeptide, provided the resulting modified cytochrome P450 polypeptide retains at least retains the catalytic activity of the unmodified cytochrome P450 polypeptide. For example, modifications can be made to a cytochrome P450 santalene oxidase polypeptide provided the resulting modified cytochrome P450 santalene oxidase polypeptide retains cytochrome P450 santalene oxidase activity (i.e., the ability to catalyze the hydroxylation of a santalene, namely α-santalene, β-santalene or epi-β-santalene). In another example, modifications can be made to a cytochrome P450 bergamotene oxidase polypeptide provided the resulting modified cytochrome P450 bergamotene oxidase polypeptide retains cytochrome P450 bergamotene oxidase activity (i.e., the ability to catalyze the hydroxylation of a bergamotene, namely α-trans-bergamotene).

The modifications can include, but are not limited to, codon optimization of the nucleic acids and/or changes that results in a single amino acid modification in the encoded polypeptide, such as single or multiple amino acid replacements (substitutions), insertions or deletions, or multiple amino acid modifications, such as multiple amino acid replacements, insertions or deletions, including swaps of regions or domains of the polypeptide. In some examples, entire or partial domains or regions, such as any domain or region described herein below, are exchanged with corresponding domains or regions or portions thereof from another cytochrome P450 polypeptide. Exemplary of modifications are amino acid replacements, including single or multiple amino acid replacements. For example, modified cytochrome P450 polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the cytochrome P450 polypeptide not containing the modification.

Provided herein are cytochrome P450 polypeptides from the CYP76 family. Provided herein is a CYP76 cytochrome P450 polypeptide having a sequence of amino acids set forth in SEQ ID NO:50. Also provided herein are cytochrome P450 polypeptides that exhibit at least 60% amino acid sequence identity to a cytochrome P450 polypeptide set forth in SEQ ID NO:50. For example, the cytochrome P450 polypeptides provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a cytochrome P450 polypeptide set forth in SEQ ID NO:50, providing the resulting cytochrome P450 polypeptide at least retains cytochrome P450 monooxygenase activity (i.e., the ability to catalyze the hydroxylation or monooxygenation of a terpene). Also provided herein are modified cytochrome P450 polypeptides from the CYP76 family. In particular, modified cytochrome P450 polypeptides provided herein contain amino acid replacements or substitutions, additions or deletions, truncations or combinations thereof with reference to the cytochrome P450 polypeptide having a sequence of amino acids set forth in SEQ ID NO:50. It is within the level of one of skill in the art to make such modifications in cytochrome P450 polypeptides or any variant thereof and test each for cytochrome P450 activity described herein, such as monooxygenase activity.

Also provided herein are CYP76 nucleic acid molecules that have a sequence of amino acids set forth in SEQ ID NO:1, or degenerates thereof, that encode a cytochrome P450 polypeptide having a sequence of amino acids set forth in SEQ ID NO:50. The CYP76 nucleic acid molecule set forth in SEQ ID NO:1 can be used to design primers that are used to identify and/or clone additional CYP proteins. Also provided herein are nucleic acid molecules encoding a cytochrome P450 polypeptide having at least 85% sequence identity to a sequence of nucleotides set forth in SEQ ID NO:1. For example, the nucleic acid molecules provided herein can exhibit at least or about at least 85%, 86%, 87%, 88%, 89%, 90%, 91%, 92%, 93%, 94%, 95%, 96%, 97%, 98% or 99% or more sequence identity to a sequence of nucleotides set forth in SEQ ID NO:1, so long as the encoded cytochrome P450 polypeptide at least retains cytochrome P450 monooxygenase activity (i.e., the ability to catalyze the hydroxylation of a terpene). Also provided herein are degenerate sequences of the sequence set forth in SEQ ID NO:1 encoding a cytochrome P450 polypeptide having a sequence of amino acids set forth in SEQ ID NO:50. Percent identity can be determined by one skilled in the art using standard alignment programs.

Provided herein are cytochrome P450 SaCYP76F39v1 (CYP76-G10), SaCYP76F42 (CYP76-G13), SaCYP76F39v2 (CYP76-G15), SaCYP76F40 (CYP76-G16) and SaCYP76F41 (CYP76-G17) polypeptides. Provided herein are cytochrome P450 santalene oxidase polypeptides having a sequence of amino acids set forth in SEQ ID NO:7, 74, 75, 76 or 77. Also provided herein are cytochrome P450 santalene oxidase polypeptides that exhibit at least 60% amino acid sequence identity to a cytochrome P450 santalene oxidase polypeptide set forth in any of SEQ ID NOS:7, 74, 75, 76 or 77. For example, the cytochrome P450 santalene oxidase polypeptides provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a cytochrome P450 santalene oxidase polypeptide set forth in SEQ ID NO: 7, 73, 74, 75 or 76, providing the resulting cytochrome P450 santalene oxidase polypeptides at least retain cytochrome P450 santalene oxidase activity (i.e., the ability to catalyze the hydroxylation of a santalene, namely α-santalene, β-santalene or epi-β-santalene). Percent identity can be determined by one skilled in the art using standard alignment programs.

Provided herein are cytochrome P450 SaCYP76F38v1 (CYP76-G5), SaCYP76F37v1 (CYP76-G11), SaCYP76F38v2 (CYP76-G12) and SaCYP76F37v2 (CYP76-G14) polypeptides. Provided herein are cytochrome P450 bergamotene oxidase polypeptides having a sequence of amino acids set forth in SEQ ID NO:6, 8, 9 or 73. Also provided herein are cytochrome P450 bergamotene oxidase polypeptides that exhibit at least 60% amino acid sequence identity to a cytochrome P450 bergamotene oxidase polypeptide set forth in SEQ ID NO:6, 8, 9 or 73. For example, the cytochrome P450 bergamotene oxidase polypeptides provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a cytochrome P450 bergamotene oxidase polypeptide set forth in SEQ ID NO:6, 8, 9 or 73, providing the resulting cytochrome P450 bergamotene oxidase polypeptide at least retains cytochrome P450 bergamotene oxidase activity (i.e., the ability to catalyze the hydroxylation of a bergamotene). Percent identity can be determined by one skilled in the art using standard alignment programs.

Also provided herein is cytochrome P450 SaCYP76F43 (CYP76-G18) polypeptide. Provided herein is a cytochrome P450 polypeptide having a sequence of amino acids set forth in SEQ ID NO:78. Also provided herein are cytochrome P450 polypeptides that exhibit at least 60% amino acid sequence identity to a cytochrome P450 polypeptide set forth in SEQ ID NO:78. For example, the cytochrome P450 polypeptides provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a cytochrome P450 polypeptide set forth in SEQ ID NO:78, providing the resulting cytochrome P450 polypeptide at least retains cytochrome P450 monooxygenase activity (i.e., the ability to catalyze the hydroxylation or monooxygenation of a terpene). In particular, modified cytochrome P450 polypeptides provided herein contain amino acid replacements or substitutions, additions or deletions, truncations or combinations thereof with reference to the cytochrome P450 polypeptide having a sequence of amino acids set forth in SEQ ID NO:78. It is within the level of one of skill in the art to make such modifications in cytochrome P450 polypeptides or any variant thereof and test each for cytochrome P450 activity described herein, such as monooxygenase activity.

Also, in some examples, provided herein are catalytically active fragments of cytochrome P450 polypeptides. In some examples, the active fragments of the cytochrome P450 polypeptides, including the cytochrome P450 santalene oxidase or cytochrome P450 bergamotene oxidase polypeptides, are modified as described above. Such fragments retain one or more properties of a full-length cytochrome P450 polypeptide, including full-length santalene oxidase or cytochrome P450 bergamotene oxidase polypeptides. Typically, the active fragments exhibit cytochrome P450 santalene oxidase or cytochrome P450 bergamotene oxidase activity (i.e., catalyze the formation of santalols and bergamotols, respectively).

The cytochrome P450s provided herein, including the cytochrome P450 santalene oxidase or cytochrome P450 bergamotene oxidase polypeptides provided herein, can contain other modifications, for example, modifications not in the primary sequence of the polypeptide, including post-translational modifications. For example, modification described herein can be a cytochrome P450 santalene oxidase or cytochrome P450 bergamotene oxidase that is a fusion polypeptide or chimeric polypeptide, including hybrids of different cytochrome P450 santalene oxidase or cytochrome P450 bergamotene oxidase polypeptides or different cytochrome P450 monooxygenases (e.g. contain one or more domains or regions from another cytochrome P450 monooxygenases) and also synthetic cytochrome P450 santalene oxidase or cytochrome P450 bergamotene oxidase polypeptides prepared recombinantly or synthesized or constructed by other methods known in the art based upon the sequence of known polypeptides.

The cytochrome P450 santalene oxidase polypeptides or cytochrome P450 bergamotene oxidase polypeptides provided herein can be used to catalyze the production of santalols and bergamotols, respectively. Typically, the cytochrome P450 santalene oxidase polypeptides provided herein catalyze the formation of santalols from santalenes, e.g., they catalyze the hydroxylation of santalenes. In some examples, the cytochrome P450 santalene oxidases also catalyze the formation of bergamotols from bergamotenes. Typically the cytochrome P450 bergamotene oxidase polypeptides provided herein catalyze the formation of bergamotol from bergamotene, e.g., they catalyze the hydroxylation of bergamotene. Reactions can be performed in vivo, such as in a host cell into which the nucleic acid has been introduced. At least one of the polypeptides will be heterologous to the host. Reactions also can be performed in vitro by contacting with enzyme with the appropriate substrate under appropriate conditions.

Also provided herein are nucleic acid molecules encoding a santalene synthase and a cytochrome P450 santalene oxidase. Also provided herein are nucleic acid molecules encoding a santalene synthase and a cytochrome P450 bergamotene oxidase. In such examples, expression of the nucleic acid molecule in a suitable host, for example, a bacterial or yeast cell, results in expression of santalene synthase and the cytochrome P450 oxidase. Such cells can be used to produce the santalene synthases and the cytochrome P450 oxidases and/or to perform reactions in vivo to produce santalols and bergamotols. For example, santalols and bergamotols can be generated in a host cell from farnesyl diphosphate (FPP), particularly a yeast cell that overproduces the acyclic terpene precursor FPP. In some examples, a nucleic acid molecule encoding a farnesyl diphosphate synthase, such as a *Santalum album* farnesyl diphosphate synthase, can also be expressed in the suitable host, for example, a bacterial or yeast cell, resulting in over-expression of FPP.

Also provided herein are nucleic acid molecules encoding a santalene synthase, cytochrome P450 polypeptide and a cytochrome P450 reductase polypeptide. For example, provided herein are nucleic acid molecules encoding a santalene synthase, cytochrome P450 santalene oxidase polypeptide and a cytochrome P450 reductase polypeptide. In another example, provided herein are nucleic acid molecules encoding a santalene synthase, cytochrome P450 bergamotene oxidase polypeptide and a cytochrome P450 reductase polypeptide. The nucleic acid molecules can be in the same vector or plasmid or on different vectors or plasmids. In such examples, expression of the nucleic acid molecule in a suitable host, for example, a bacterial or yeast cell, results in expression of santalene synthase and the cytochrome P450 oxidase. Such cells can be used to produce the santalene synthases and the cytochrome P450 oxidases and/or to perform reactions in vivo to produce santalols and bergamotols. For example, santalols and bergamotols can be generated in a host cell from farnesyl diphosphate (FPP), particularly a yeast cell that overproduces the acyclic terpene precursor FPP.

1. Cytochrome P450 Santalene Oxidase Polypeptides

Provided herein are cytochrome P450 santalene oxidase polypeptides. Also provided herein are nucleic acid molecules that encode any of the cytochrome P450 santalene oxidase polypeptides provided herein. The cytochrome P450 santalene oxidase polypeptides provided herein catalyze the formation of catalyze the formation of terpenoids found in sandalwood oil, including α-santalols, β-santalols, epi-β-santalols and α-trans-bergamotols. The cytochrome P450 santalene oxidase polypeptides provided herein catalyze the formation of santalols from santalenes. In some examples, the cytochrome P450 santalene oxidase polypeptides provided herein also catalyze the formation of bergamotols from bergamotene. For example, the cytochrome P450 santalene oxidase polypeptides catalyze the formation of α-santalol from α-santalene, β-santalol from β-santalene and/or epi-β-santalol from epi-β-santalene (e.g., the cytochrome P450 santalene oxidase polypeptides catalyze the hydroxylation of α-santalene, β-santalene and/or epi-β-santalene). In a particular example, the cytochrome P450 santalene oxidase polypeptides catalyze the formation of (E)-α-santalol from α-santalene, (Z)-α-santalol from α-santalene, (E)-β-santalol from β-santalene, (Z)-β-santalol from β-santalene, (E)-epi-β-santalol from epi-β-santalene and/or (Z)-epi-β-santalol from epi-β-santalene. In some examples, the cytochrome P450 santalene oxidase polypeptides provided herein also catalyze the formation of (Z)-α-trans-bergamotol and/or (E)-α-trans-bergamotol from α-trans-bergamotene. In a particular example, the cytochrome P450 santalene oxidase polypeptides provided herein catalyze the formation of (E)-α-santalol, (Z)-α-santalol, (E)-β-santalol, (Z)-β-santalol, (E)-epi-β-santalol, (Z)-epi-β-santalol, (Z)-α-trans-bergamotol and/or (E)-α-trans-bergamotol. In particular, the cytochrome P450 santalene oxidase polypeptides produce (Z) and (E) stereoisomers of α- and β-santalol in ratios of approximately 1:5 and 1:4, respectively. The cytochrome P450 santalene oxidase polypeptides exhibit narrow substrate specificity, preferring α-santalene or β-santalene. In some examples, the cytochrome P450 santalene oxidase polypeptides also converted the substrate α-bisabolol.

Figures 15A, 15B, 15C:
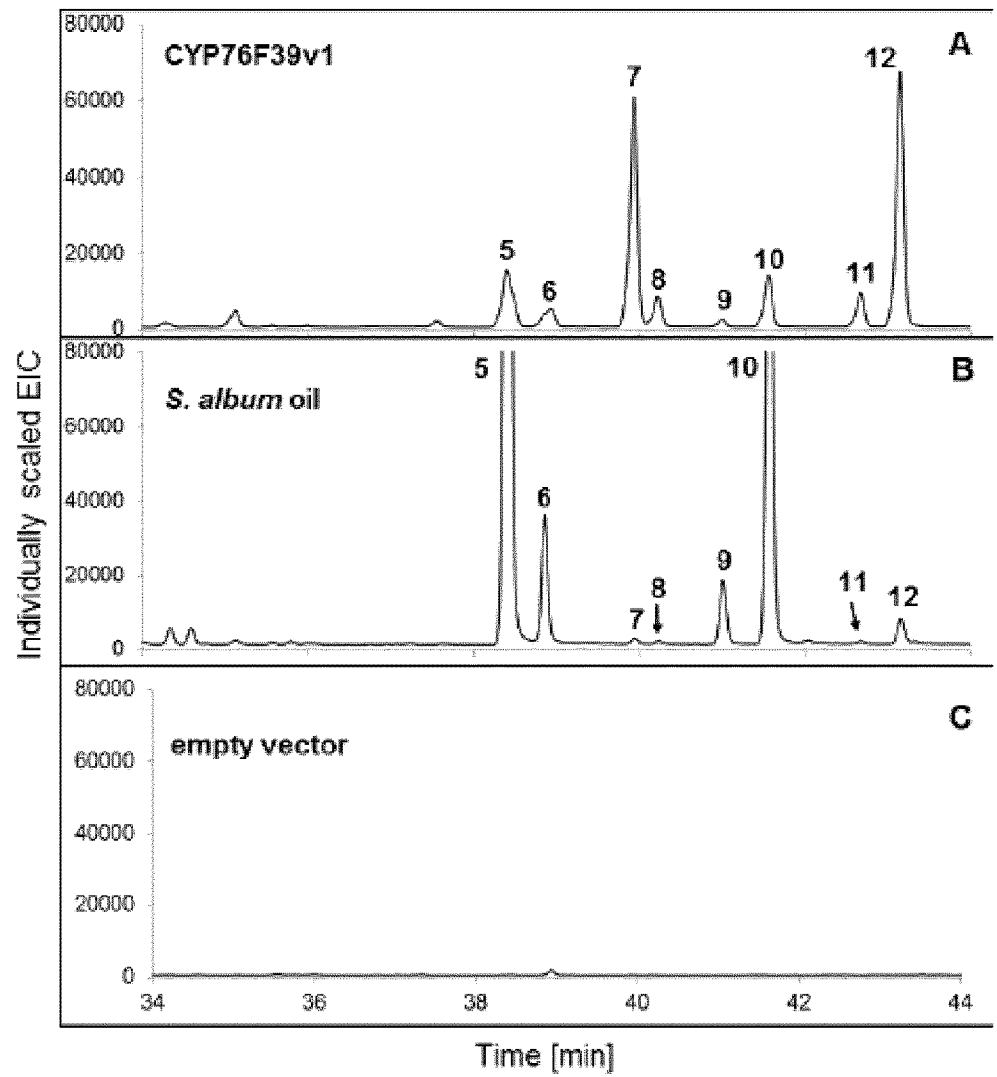
FIGS. 15A-15C depicts the GC-MS analysis (extracted ion chromatograms) of products formed in vitro with SaCYP76F39v1 (SaCYP76-G10) and a sesquiterpene mixture of α-, β- and epi-β-santalene and α-trans-bergamotene (FIG. 15A).

In some examples, the cytochrome P450 santalene oxidase polypeptides provided herein catalyze the formation of terpenoids found in sandalwood oil, including α-santalol, β-santalol, epi-β-santalol and α-trans-bergamotol, from the terpene reaction products of the acyclic precursor farnesyl pyrophosphate and a santalene synthase. For example, the cytochrome P450 santalene oxidase polypeptides provided herein catalyze the formation of (E)-α-santalol, (Z)-α-santalol, (E)-β-santalol, (Z)-β-santalol, (E)-epi-β-santalol, (Z)-epi-β-santalol, (Z)-α-trans-bergamotol and/or (E)-α-trans-bergamotol from the terpene reaction products of the acyclic precursor FPP and a santalene synthase, such as *Santalum album* santalene synthase (SaSSY; SEQ ID NO:16). The cytochrome P450 santalene oxidase polypeptides catalyze the formation of (E)-α-santalol, (Z)-α-santalol, (E)-β-santalol, (Z)-β-santalol, (E)-epi-β-santalol, (Z)-epi-β-santalol, (Z)-α-trans-bergamotol and/or (E)-α-trans-bergamotol in different ratios from those of authentic sandalwood oil (see Example 11 and FIGS. 15A and 15B). For example, the main products formed with SaCYP76F39v1 (SaCYP76-G10) were (E)-α-santalol and (E)-β-santalol while the main compounds of sandalwood oil are (Z)-α-santalol and (Z)-β-santalol (see FIGS. 15A and 15B).

For example, provided herein are cytochrome P450 santalene oxidase polypeptides that have a sequence of amino acids set forth in any of SEQ ID NOS:7, 74, 75, 76 and 77. Also provided herein are cytochrome P450 santalene oxidase polypeptides that exhibit at least 60% amino acid sequence identity to a cytochrome P450 santalene oxidase polypeptide having a sequence of amino acids set forth in any of SEQ ID NOS:7, 74, 75, 76 and 77. For example, the cytochrome P450 santalene oxidase polypeptides provided herein can exhibit at least at or about or 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% or more amino acid sequence identity to a cytochrome P450 santalene oxidase polypeptide set in any of SEQ ID NOS:7, 74, 75, 76 and 77, provided the cytochrome P450 santalene oxidase polypeptides exhibit cytochrome P450 santalene oxidase activity (i.e. catalyze the formation of santalols from santalenes and/or bergamotols from bergamotene). Percent identity can be determined by one skilled in the art using standard alignment programs.

Provided herein are cytochrome P450 santalene oxidases designated SaCYP76F39v1 (CYP76-G10), SaCYP76F39v2 (CYP76-G15), SaCYP76F40 (CYP76-G16), SaCYP76F41 (CYP76-G17) and SaCYP76F42 (CYP76-G13) that have a sequence of amino acids set forth in SEQ ID NOS:7, 74, 75, 76 and 77, respectively. Also provided herein are active fragments of cytochrome P450 santalene oxidase polypeptides having a sequence of amino acids set forth in any of SEQ ID NO:7, 74, 75, 76 and 77. Such fragments retain one or more properties of a cytochrome P450 santalene oxidase polypeptide. Typically, the active fragments exhibit cytochrome P450 santalene oxidase activity (i.e. the ability to catalyze the formation of santalols from santalenes).

Also provided herein are nucleic acid molecules that have a sequence of amino acids set forth in any of SEQ ID NOS:3, 68, 69, 70 and 71, or degenerates thereof, that encode a cytochrome P450 santalene oxidase polypeptide having a sequence of amino acids set forth in SEQ ID NOS:7, 74, 75, 76 and 77, respectively. Also provided herein are nucleic acid molecules encoding cytochrome P450 santalene oxidase polypeptides having at least 85% sequence identity to a sequence of nucleotides set forth in any of SEQ ID NOS:3, 68, 69, 70 and 71. For example, the nucleic acid molecules provided herein can exhibit at least or about at least 85%, 86%, 87%, 88%, 89%, 90%, 91%, 92%, 93%, 95%, 95%, 96%, 97%, 98% or 99% or more sequence identity to a sequence of nucleotides set forth in any of SEQ ID NOS:3, 68, 69, 70 and 71, so long as the encoded cytochrome P450 santalene oxidase polypeptides exhibits cytochrome P450 santalene oxidase activity (i.e. the ability to catalyze the formation of santalols from santalenes). Also provided herein are degenerate sequences of the sequence set forth in any of SEQ ID NOS:3, 68, 69, 70 and 71 encoding cytochrome P450 santalene oxidase polypeptides having a sequence of amino acids set forth in SEQ ID NO:7, 74, 75, 76 and 77, respectively. Percent identity can be determined by one skilled in the art using standard alignment programs.

In some examples, the nucleic acid molecules that encode the cytochrome P450 santalene oxidase polypeptides are isolated from the sandalwood tree *Santalum album*. In other examples, the nucleic acid molecules and encoded cytochrome P450 santalene oxidase polypeptides are variants of those isolated from the sandalwood tree *Santalum album*.

In a particular example, the SaCYP76F39v1 (CYP76-G10) polypeptide having a sequence of amino acids set forth in SEQ ID NO:7 catalyzed the formation of (E)-α-santalol, (Z)-α-santalol, (E)-β-santalol, (Z)-β-santalol, (E)-epi-β-santalol, (Z)-epi-β-santalol, (Z)-α-trans-bergamotol and (E)-α-trans-bergamotol in in vivo assays in yeast expressing a santalene synthase (see Example 10.B.2) and in in vitro assays with a mixture of α-santalene, α-trans-bergamotene, epi-β-santalene and β-santalene as the substrate (see Example 11.B.2.a.ii). In in vivo assays, (E)-β-santalol, (E)-α-santalol and (Z)-β-santalol were the major products (see FIG. 11A). In in vitro assays, (E)-β-santalol and (E)-α-santalol were the major products (see FIG. 15A). In yet other examples, in in vitro assays with either α-santalene, α-trans-bergamotene, or epi-β-santalene and β-santalene, the SaCYP76F39v1 (CYP76-G10) polypeptide catalyzed the formation of (Z)- and (E)-α-santalol, (Z)- and (E)-α-trans-bergamotol, and (Z)- and (E)-epi-β-santalol and (Z)- and (E)-β-santalol, respectively (see Example 11.C. and FIGS. 20A-20C). The kinetic properties of the SaCYP76F39v1

(CYP76-G10) polypeptide for α- and β-santalene as substrates are described in Example 12 below.

Figures 13A, 13B, 13C, 13D:
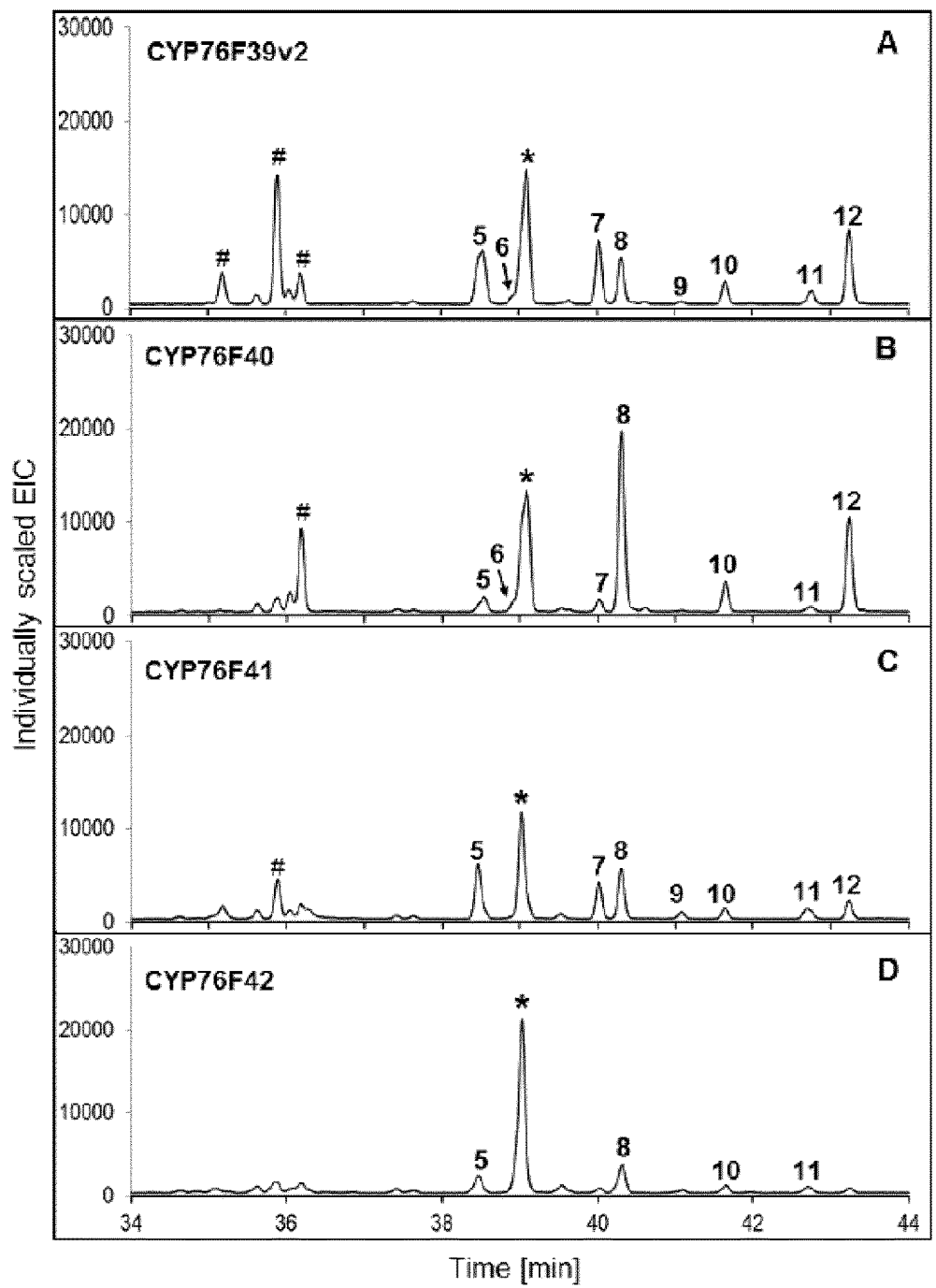
FIGS. 13A-13D depict the GC-MS analysis (extracted ion chromatograms) of compounds formed in vivo in yeast cells expressing SaSSy, SaCPR2 and SaCYP76F39v2 (SaCYP76-G15) (FIG. 13A), SaCYP76F40 (SaCYP76-G16) (FIG. 13B), SaCYP76F41 (SaCYP76-G17) (FIG. 13C), or SaCYP76F42 (SaCYP76-G13) (FIG. 13D). The peaks are identified in Table 12. Peaks marked with the symbol (*) correspond to farnesol which is produced in yeast cells without SaCYP76F. Peaks marked with the symbol (#) represent yeast in vivo modifications of santalols independent of SaCYP76F.
Figures 14A, 14B, 14C, 14D, 14E:
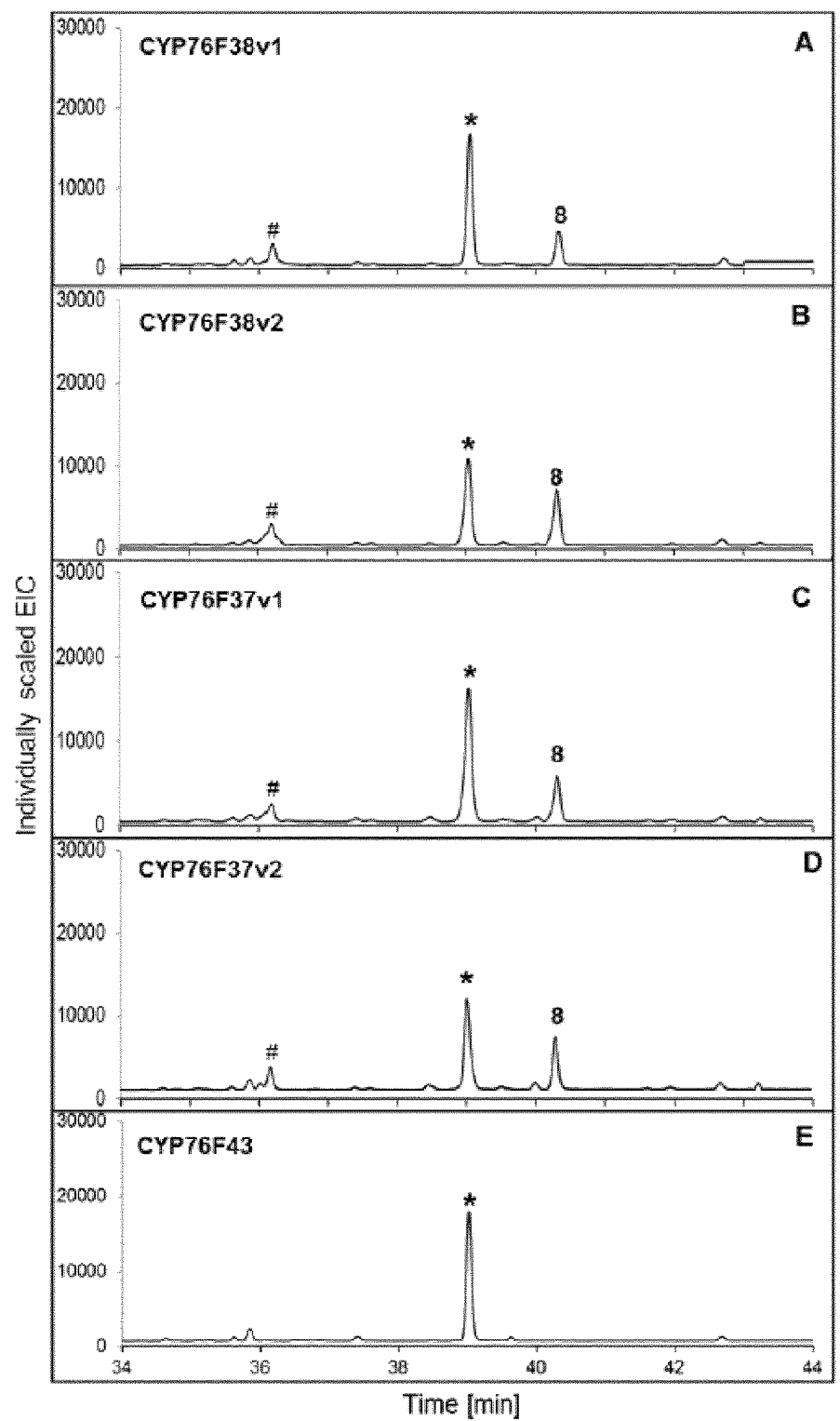
FIGS. 14A-14D depict the GC-MS analysis (extracted ion chromatograms) of compounds formed in vivo in yeast cells expressing SaSSy, SaCPR2 and SaCYP76F38v1 (SaCYP76-G5) (FIG. 14A), SaCYP76F38v2 (SaCYP76-G12) (FIG. 14B), SaCYP76F37v1 (SaCYP76-G11) (FIG. 14C), SaCYP76F37v2 (SaCYP76-G14) (FIG. 14D), or SaCYP76F43 (SaCYP76-G18) (FIG. 14E). The peaks are identified in Table 12. Peaks marked with the symbol (*) correspond to farnesol which is produced in yeast cells without SaCYP76F. Peaks marked with the symbol (#) represent yeast in vivo modifications of santalols independent of SaCYP76F.
Figures 16A, 16B, 16C, 16D, 16E:
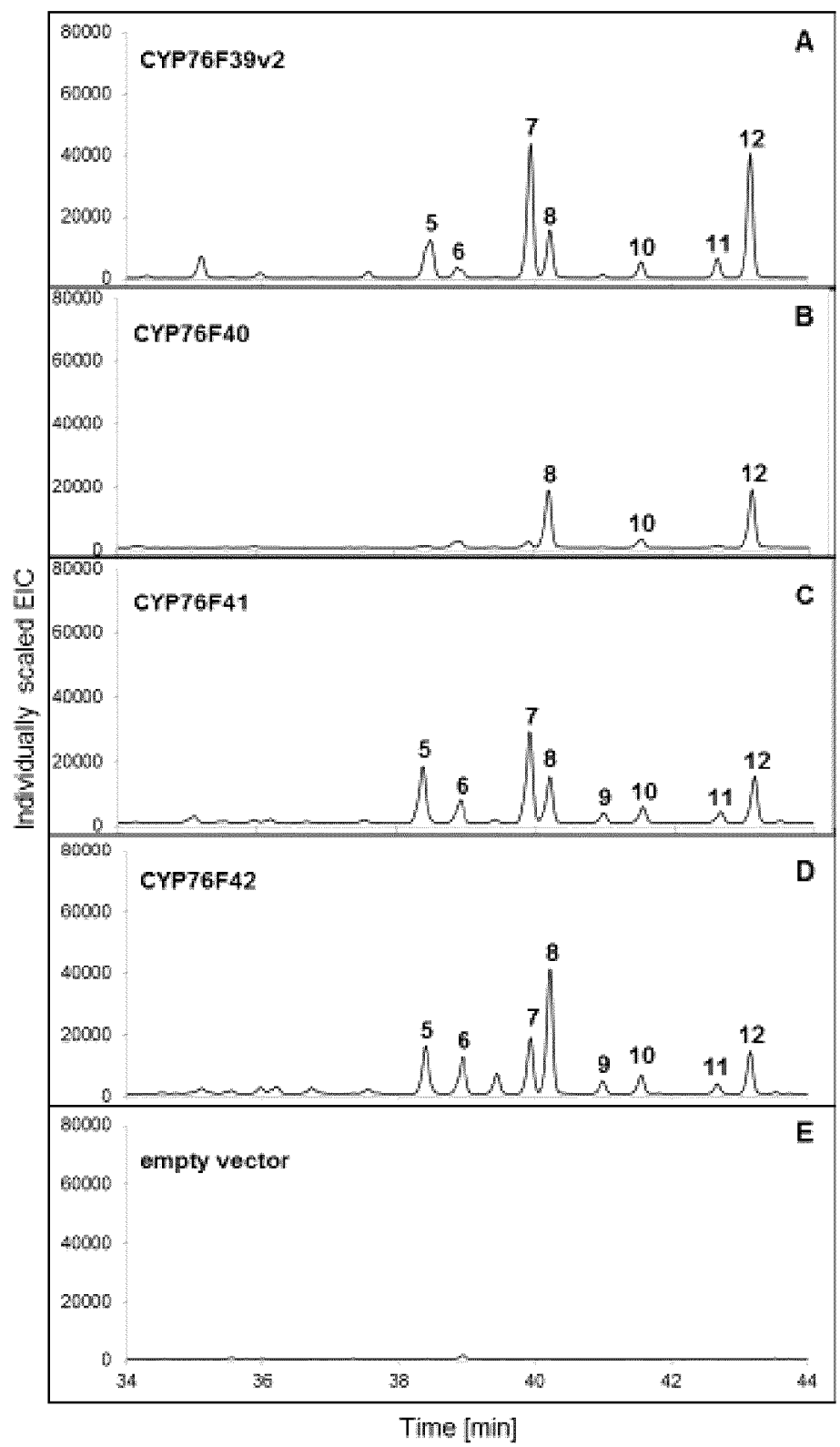
FIGS. 16A-16E depict the GC-MS analysis (extracted ion chromatograms) of products formed in vitro with a sesquiterpene mixture of α-, β- and epi-β-santalene and α-trans-bergamotene as the substrate and clade I SaCYP76F cDNAs SaCYP76F39v2 (SaCYP76-G15) (FIG. 16A); SaCYP76F40 (SaCYP76-G16) (FIG. 16B); SaCYP76F41 (SaCYP76-G17) (FIG. 16C); SaCYP76F42 (SaCYP76-G13) (FIG. 16D); or empty vector as control (FIG. 16E). The peaks are identified in Table 12.
Figures 17A, 17B, 17C, 17D, 17E:
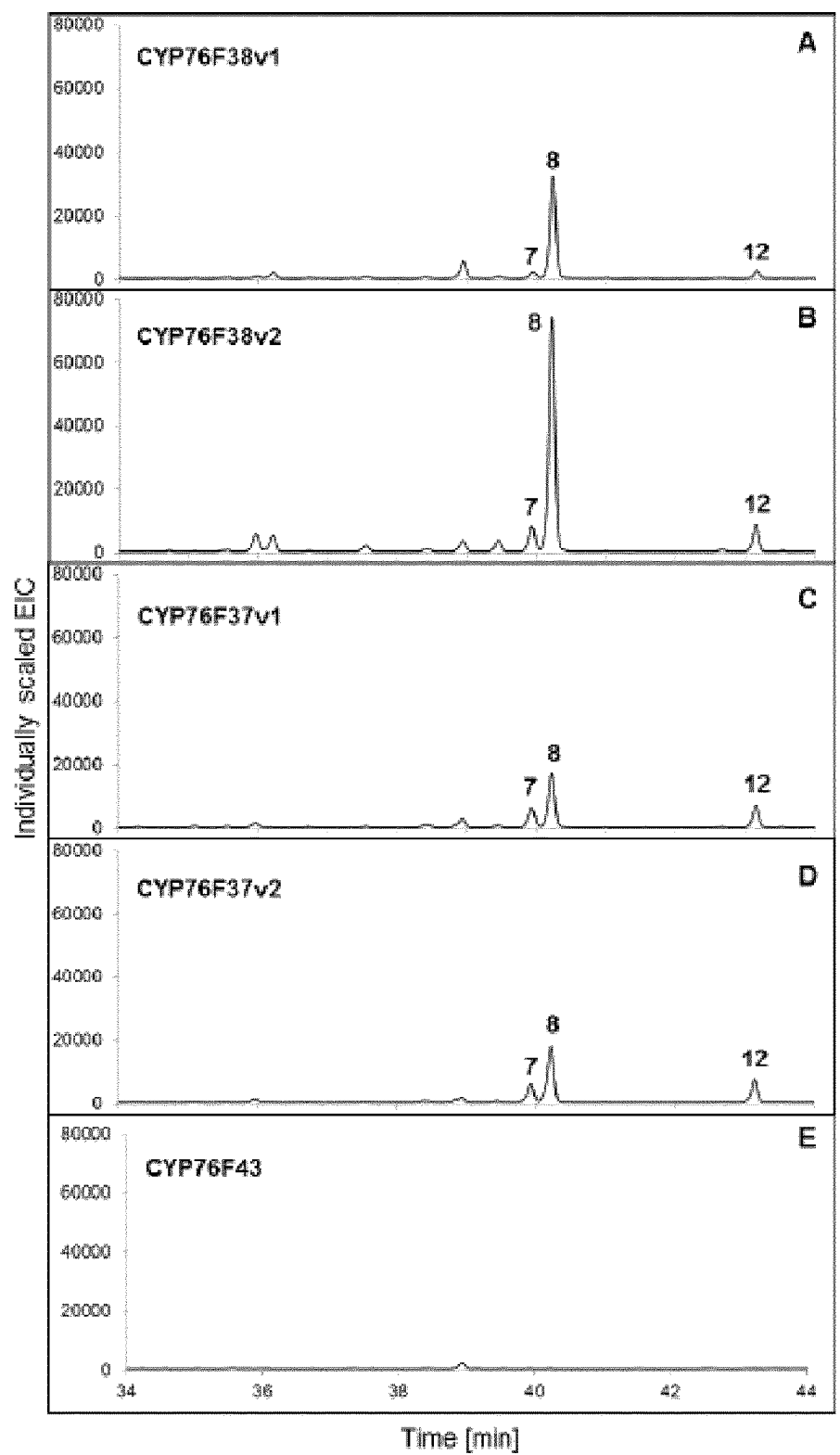
FIGS. 17A-17E depict the GC-MS analysis (extracted ion chromatograms) of products formed in vitro with a sesquiterpene mixture of α-, β- and epi-β-santalene and α-trans-bergamotene as the substrate and clade II SaCYP76F cDNAs SaCYP76F38v1 (SaCYP76-G5) (FIG. 17A); SaCYP76F38v2 (SaCYP76-G12) (FIG. 17B); SaCYP76F37v1 (SaCYP76-G11) (FIG. 17C); SaCYP76F37v2 (SaCYP76-G14) (FIG. 17D); or empty vector as control (FIG. 17E). The peaks are identified in Table 12.

In another example, the SaCYP76F39v2 (CYP76-G15) polypeptide having a sequence of amino acids set forth in SEQ ID NO:74 catalyzed the formation of (E)-α-santalol, (Z)-α-santalol, (E)-β-santalol, (Z)-β-santalol, (E)-epi-β-santalol, (Z)-epi-β-santalol, (Z)-α-trans-bergamotol and (E)-α-trans-bergamotol in in vivo assays in yeast expressing a santalene synthase (see Example 10.B.3 and FIG. 13A). In in vitro assays with a mixture of α-santalene, α-trans-bergamotene, epi-β-santalene and β-santalene as the substrate, the SaCYP76F39v2 (CYP76-G15) polypeptide catalyzed the formation of (E)-α-santalol, (Z)-α-santalol, (E)-β-santalol, (Z)-β-santalol, (E)-epi-β-santalol, (Z)-epi-β-santalol, (Z)-α-trans-bergamotol and (E)-α-trans-bergamotol (see Example 11.B.3.b and FIG. 16A) with (E)-α-santalol and (E)-β-santalol as the major products.

In another example, the SaCYP76F40 (CYP76-G16) polypeptide having a sequence of amino acids set forth in SEQ ID NO:75 catalyzed the formation of (E)-α-santalol, (Z)-α-santalol, (E)-β-santalol, (Z)-β-santalol, (E)-epi-β-santalol, (Z)-α-trans-bergamotol and (E)-α-trans-bergamotol in in vivo assays in yeast expressing a santalene synthase (see Example 10.B.3 and FIG. 13B). In in vitro assays with a mixture of α-santalene, α-trans-bergamotene, epi-β-santalene and β-santalene as the substrate, the SaCYP76F40 (CYP76-G16) polypeptide catalyzed the formation of (E)-α-santalol, (E)-β-santalol, (Z)-β-santalol, (Z)-α-trans-bergamotol and (E)-α-trans-bergamotol (see Example 11.B.3.b and FIG. 16B) with (E)-α-trans-bergamotol and (E)-β-santalol as the major products.

In another example, the SaCYP76F41 (CYP76-G17) polypeptide having a sequence of amino acids set forth in SEQ ID NO:76 catalyzed the formation of (E)-α-santalol, (Z)-α-santalol, (E)-β-santalol, (Z)-β-santalol, (E)-epi-β-santalol, (Z)-epi-β-santalol and (E)-α-trans-bergamotol in in vivo assays in yeast expressing a santalene synthase (see Example 10.B.3 and FIG. 13C). In in vitro assays with a mixture of α-santalene, α-trans-bergamotene, epi-β-santalene and β-santalene as the substrate, the SaCYP76F41 (CYP76-G17) polypeptide catalyzed the formation of (E)-α-santalol, (Z)-α-santalol, (E)-β-santalol, (Z)-β-santalol, (E)-epi-β-santalol, (Z)-epi-β-santalol, (Z)-α-trans-bergamotol and (E)-α-trans-bergamotol (see Example 11.B.3.b and FIG. 16C) with (E)-α-santalol as the major product.

In another example, the SaCYP76F42 (CYP76-G13) polypeptide having a sequence of amino acids set forth in SEQ ID NO:77 catalyzed the formation of (Z)-α-santalol, (Z)-β-santalol, (E)-epi-β-santalol and (E)-α-trans-bergamotol in in vivo assays in yeast expressing a santalene synthase (see Example 10.B.3 and FIG. 13D). In in vitro assays with a mixture of α-santalene, α-trans-bergamotene, epi-β-santalene and β-santalene as the substrate, the SaCYP76F42 (CYP76-G13) polypeptide catalyzed the formation of (E)-α-santalol, (Z)-α-santalol, (E)-β-santalol, (Z)-β-santalol, (E)-epi-β-santalol, (Z)-epi-β-santalol, (Z)-α-trans-bergamotol and (E)-α-trans-bergamotol (see Example 11.B.3.b and FIG. 16D) with (E)-α-trans-bergamotol as the major product.

Modified Cytochrome P450 Santalene Oxidase Polypeptides

Also provided herein are modified cytochrome P450 santalene oxidase polypeptides. The modifications, which typically are amino acid insertions, deletions and/or substitutions, can be effected in any region of a cytochrome P450 santalene oxidase polypeptide provided the resulting modified cytochrome P450 santalene oxidase polypeptides at least retain cytochrome P450 santalene oxidase activity. For example, modifications can be made in any region of a cytochrome P450 santalene oxidase provided the resulting modified cytochrome P450 santalene oxidase at least retains cytochrome P450 santalene oxidase activity (i.e., the ability to catalyze the formation of santalols from santalenes).

The modifications can be a single amino acid modification, such as single amino acid replacements (substitutions), insertions or deletions, or multiple amino acid modifications, such as multiple amino acid replacements, insertions or deletions. In some examples, entire or partial domains or regions, such as any domain or region described herein below, are exchanged with corresponding domains or regions or portions thereof from another cytochrome P450 polypeptide. Exemplary of modifications are amino acid replacements, including single or multiple amino acid replacements. For example, modified cytochrome P450 santalene oxidase polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the cytochrome P450 santalene oxidase polypeptide not containing the modification. For example, the modifications described herein can be in a cytochrome P450 santalene oxidase polypeptide having a sequence of amino acids set forth in any of SEQ ID NOS:7, 74, 75, 76 and 77 or any variant thereof, including any that have at least 60%, 65%, 70%, 75%, 80%, 85%, 90%, 91%, 92%, 93%, 94%, 95%, 96%, 97%, 98%, or 99% sequence identity to a cytochrome P450 santalene oxidase polypeptide set forth in any of SEQ ID NOS:7, 74, 75, 76 or 77. Based on this description, it is within the level of one of skill in the art to generate a cytochrome P450 santalene oxidase polypeptide containing any one or more of the described mutations, and test each for cytochrome P450 santalene oxidase activity described herein.

Also, in some examples, provided herein are modified active fragments of cytochrome P450 santalene oxidase polypeptides, that contain any of the modifications provided herein. Such fragments retain on or more properties of a cytochrome P450 santalene oxidase. Typically, the cytochrome P450 santalene oxidase polypeptides exhibit santalene oxidase (i.e., the ability to hydrolyze santalene and/or bergamotene).

Modifications in a cytochrome P450 santalene oxidase also can be made to a cytochrome P450 santalene oxidase polypeptide that also contains other modifications, including modifications of the primary sequence and modifications not in the primary sequence of the polypeptide. For example, modification described herein can be in a cytochrome P450 santalene oxidase polypeptide that is a fusion polypeptide or chimeric polypeptide, including hybrids of different cytochrome P450 santalene oxidase polypeptides with different cytochrome P450 polypeptides (e.g. contain one or more domains or regions from another cytochrome P450s) and also synthetic cytochrome P450 santalene oxidase polypeptides prepared recombinantly or synthesized or constructed by other methods known in the art based upon the sequence of known polypeptides.

In some examples, the modifications are amino acid replacements. In further examples, the modified cytochrome P450 santalene oxidase polypeptides provided herein contain one or more modifications in a domain. As described elsewhere herein, the modifications in a domain or structural domain can be by replacement of corresponding heterologous residues from another cytochrome P450 polypeptide.

To retain cytochrome P450 santalene oxidase activity, modifications typically are not made at those positions necessary for cytochrome P450 santalene oxidase activity, i.e., in the catalytic center or in conserved residues. For example, generally modifications are not made a position corresponding to Glu367, Arg370, Gly445, Arg446, Arg447, Ile448, Cys449, Pro450 or Gly451 with reference to a sequence of amino acids set forth in any of SEQ ID NOS:7, 74, 75, 76 or 77.

The modified cytochrome P450 santalene oxidase polypeptides can contain two or more modifications, including amino acid replacements or substitutions, insertions or deletions, truncations or combinations thereof. Generally, multiple modifications provided herein can be combined by one of skill in the art so long as the modified cytochrome P450 santalene oxidase polypeptide retains cytochrome P450 santalene oxidase activity.

Also provided herein are nucleic acid molecules that encode any of the modified cytochrome P450 santalene oxidase polypeptides provided herein. In particular examples, the nucleic acid sequence can be codon optimized, for example, to increase expression levels of the encoded sequence. The particular codon usage is dependent on the host organism in which the modified polypeptide is expressed. One of skill in the art is familiar with optimal codons for expression in bacteria or yeast, including for example *E. coli* or *Saccharomyces cerevisiae*. For example, codon usage information is available from the Codon Usage Database available at kazusa.or.jp.codon (see Richmond (2000) *Genome Biology*, 1:241 for a description of the database). See also, Forsburg (2004) *Yeast,* 10:1045-1047; Brown et al. (1991) *Nucleic Acids Research,* 19:4298; Sharp et al. (1988) *Nucleic Acids Research,* 12:8207-8211; Sharp et al. (1991) *Yeast,* 657-78. In examples herein, nucleic acid sequences provided herein are codon optimized based on codon usage in *Saccharomyces cerevisiae*.

The modified polypeptides and encoding nucleic acid molecules provided herein can be produced by standard recombinant DNA techniques known to one of skill in the art. Any method known in the art to effect mutation of any one or more amino acids in a target protein can be employed. Methods include standard site-directed or random mutagenesis of encoding nucleic acid molecules, or solid phase polypeptide synthesis methods. For example, as described herein, nucleic acid molecules encoding a cytochrome P450 santalene oxidase polypeptide can be subjected to mutagenesis, such as random mutagenesis of the encoding nucleic acid, by error-prone PCR, site-directed mutagenesis, overlap PCR, gene shuffling, or other recombinant methods. The nucleic acid encoding the polypeptides then can be introduced into a host cell to be expressed heterologously. Hence, also provided herein are nucleic acid molecules encoding any of the modified polypeptides provided herein. In some examples, the modified cytochrome P450 santalene oxidase polypeptides are produced synthetically, such as using solid phase or solutions phase peptide synthesis.

2. Cytochrome P450 Bergamotene Oxidase Polypeptides

Provided herein are cytochrome P450 bergamotene oxidase polypeptides. Also provided herein are nucleic acid molecules that encode any of the cytochrome P450 bergamotene oxidase polypeptides provided herein. The cytochrome P450 bergamotene oxidase polypeptides provided herein catalyze the formation of bergamotols from bergamotenes. Typically the cytochrome P450 bergamotene oxidase polypeptides catalyze the formation of (Z)-α-trans-bergamotol and (E)-α-trans-bergamotol from α-trans-bergamotene (e.g. the cytochrome P450 bergamotene oxidase polypeptides catalyze the hydroxylation of α-trans-bergamotene). In particular examples, the cytochrome P450 bergamotene oxidase polypeptides catalyze the formation of (E)-α-trans-bergamotol from α-trans-bergamotene. In some examples, the cytochrome P450 bergamotene oxidase polypeptides additionally catalyze the formation of minor amounts of (E)-α-santalol and (E)-β-santalol. The cytochrome P450 bergamotene oxidase polypeptides exhibit narrow substrate specificity, preferring α-santalene or β-santalene. In some examples, the cytochrome P450 bergamotene oxidase polypeptides also converted the substrate trans-nerolidol.

For example, provided herein are cytochrome P450 bergamotene oxidase polypeptides that have a sequence of amino acids set forth in any of SEQ ID NOS:6, 8, 9 and 73. Also provided herein are cytochrome P450 bergamotene oxidase polypeptides that exhibit at least 60% amino acid sequence identity to a cytochrome P450 bergamotene oxidase polypeptide having a sequence of amino acids set forth in any of SEQ ID NOS:6, 8, 9 and 73. For example, the cytochrome P450 bergamotene oxidase polypeptides provided herein can exhibit at least at or about or 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% or more amino acid sequence identity to a cytochrome P450 bergamotene oxidase polypeptide set forth in any of SEQ ID NOS:6, 8, 9 and 73, provided the cytochrome P450 bergamotene oxidase polypeptides exhibit cytochrome P450 bergamotene oxidase activity (i.e. catalyze the formation of bergamotols from bergamotenes). Percent identity can be determined by one skilled in the art using standard alignment programs.

Provided herein are cytochrome P450 bergamotene oxidases designated SaCYP76F38v1 (CYP76-G5), SaCYP76F37v1 (CYP76-G11), SaCYP76F38v2 (CYP76-G11) and SaCYP76F37v2 (CYP76-G14), that have a sequence of amino acids set forth in SEQ ID NOS: 6, 8, 9 and 73, respectively. Also provided herein are active fragments of cytochrome P450 bergamotene oxidase polypeptides having a sequence of amino acids set forth in any of SEQ ID NOS: 6, 8, 9 and 73. Such fragments retain one or more properties of a cytochrome P450 bergamotene oxidase polypeptide. Typically, the active fragments exhibit cytochrome P450 bergamotene oxidase activity (i.e. the ability to catalyze the hydroxylation of bergamotenes from bergamotols).

In particular examples, the cytochrome P450 bergamotene oxidases provided herein having a sequence of amino acids set forth in SEQ ID NOS: 6, 8, 9 and 73 catalyzed the formation of (E)-α-trans-bergamotol, (E)-α-santalol and (E)-β-santalol in in vitro assays with a mixture of α-santalene, α-trans-bergamotene, epi-β-santalene and β-santalene as the substrate. In such examples, (E)-α-trans-bergamotol was the major product, and (E)-α-santalol and (E)-β-santalol were minor products (see Example 11.B.3.b and FIGS. 17A-17D). In another example, in in vitro assays with either α-santalene, α-trans-bergamotene, or epi-β-santalene and β-santalene, the cytochrome P450 bergamotene oxidase provided herein having a sequence of amino acids set forth in SEQ ID NO:8 catalyzed the formation of (E)-α-santalol, (E)-α-trans-bergamotol or (E)-β-santalol, respectively (see Example 11.0 and FIGS. 20D-20F). In yet other examples, the cytochrome P450 bergamotene oxidases provided herein having a sequence of amino acids set forth in SEQ ID NOS: 6, 8, 9 and 73 catalyzed the formation of (E)-α-transbergamotol in in vivo assays in yeast that express santalene synthase (see Example 10.C.2 and FIGS. 14A-14D). The kinetic properties of the SaCYP76F37v1 (SaCYP76-G11) polypeptide for α- and β-santalene as substrates are described in Example 12 below.

Also provided herein are nucleic acid molecules that have a sequence of amino acids set forth in any of SEQ ID NOS:2, 4, 5 and 67, or degenerates thereof, that encode a cytochrome P450 bergamotene oxidase polypeptide having a sequence of amino acids set forth in SEQ ID NOS:6, 8, 9 and 73, respectively. Also provided herein are nucleic acid molecules encoding a cytochrome P450 bergamotene oxidase polypeptide having at least 85% sequence identity to a sequence of nucleotides set forth in any of SEQ ID NOS:2, 4, 5 and 67. For example, the nucleic acid molecules provided herein can exhibit at least or about at least 85%, 86%, 87%, 88%, 89%, 90%, 91%, 92%, 93%, 95%, 95%, 96%, 97%, 98% or 99% or more sequence identity to a sequence of nucleotides set forth in any of SEQ ID NOS:2, 4, 5 and 67, so long as the encoded cytochrome P450 bergamotene oxidase polypeptide exhibits cytochrome P450 bergamotene oxidase activity (i.e. the ability to catalyze the formation of bergamotols from bergamotene). Also provided herein are degenerate sequences of the sequence set forth in any of SEQ ID NOS:2, 4, 5 and 67 encoding a cytochrome P450 bergamotene oxidase polypeptide having a sequence of amino acids set forth in SEQ ID NO:6, 8, 9 and 73, respectively. Percent identity can be determined by one skilled in the art using standard alignment programs.

In some examples, the nucleic acid molecules that encode the cytochrome P450 bergamotene oxidase polypeptides are isolated from the sandalwood tree *Santalum album*. In other examples, the nucleic acid molecules and encoded cytochrome P450 bergamotene oxidase polypeptides are variants of those isolated from the sandalwood tree *Santalum album*.

Modified Cytochrome P450 Bergamotene Oxidase Polypeptides

Provided herein are modified cytochrome P450 bergamotene oxidase polypeptides. The modifications, which typically are amino acid insertions, deletions and/or substitutions, can be effected in any region of a cytochrome P450 bergamotene oxidase polypeptide provided the resulting modified cytochrome P450 bergamotene oxidase polypeptides at least retain cytochrome P450 bergamotene oxidase activity. For example, modifications can be made in any region of a cytochrome P450 bergamotene oxidase provided the resulting modified cytochrome P450 bergamotene oxidase at least retains cytochrome P450 bergamotene oxidase activity (i.e., the ability to catalyze the formation of a bergamotol from a bergamotene).

The modifications can be a single amino acid modification, such as single amino acid replacements (substitutions), insertions or deletions, or multiple amino acid modifications, such as multiple amino acid replacements, insertions or deletions. In some examples, entire or partial domains or regions, such as any domain or region described herein below, are exchanged with corresponding domains or regions or portions thereof from another cytochrome P450 bergamotene oxidase polypeptide. Exemplary of modifications are amino acid replacements, including single or multiple amino acid replacements. For example, modified cytochrome P450 bergamotene oxidase polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the cytochrome P450 polypeptide not containing the modification. For example, the modifications described herein can be in a cytochrome P450 bergamotene oxidase polypeptide having a sequence of amino acids set forth in any of SEQ ID NOS:6, 8, 9 or 73 or any variant thereof, including any that have at least 60%, 65%, 70%, 75%, 80%, 85%, 90%, 91%, 92%, 93%, 94%, 95%, 96%, 97%, 98%, or 99% sequence identity to a cytochrome P450 bergamotene oxidase polypeptide set forth in any of SEQ ID NOS:6, 8, 9 and 73. Based on this description, it is within the level of one of skill in the art to generate a cytochrome P450 bergamotene oxidase polypeptide containing any one or more of the described mutations, and test each for cytochrome P450 bergamotene oxidase activity described herein.

Also, in some examples, provided herein are modified active fragments of cytochrome P450 bergamotene oxidase polypeptides that contain any of the modifications provided herein. Such fragments retain on or more properties of a cytochrome P450 bergamotene oxidase. Typically, the modified cytochrome P450 bergamotene oxidase polypeptides exhibit bergamotene oxidase activity (i.e., the ability to hydrolyze bergamotene).

Modifications in a cytochrome P450 bergamotene oxidase polypeptide that also contains other modifications, including modifications of the primary sequence and modifications not in the primary sequence of the polypeptide. For example, modification described herein can be in a cytochrome P450 bergamotene oxidase polypeptide that is a fusion polypeptide or chimeric polypeptide, including hybrids of different cytochrome P450 bergamotene oxidase polypeptides with different cytochrome P450 polypeptides (e.g. contain one or more domains or regions from another cytochrome P450s) and also synthetic cytochrome P450 bergamotene oxidase polypeptides prepared recombinantly or synthesized or constructed by other methods known in the art based upon the sequence of known polypeptides.

In some examples, the modifications are amino acid replacements. In further examples, the modified cytochrome P450 bergamotene oxidase polypeptides provided herein contain one or more modifications in a domain. As described elsewhere herein, the modifications in a domain or structural domain can be by replacement of corresponding heterologous residues from another cytochrome P450 polypeptide.

To retain cytochrome P450 bergamotene oxidase activity, modifications typically are not made at those positions necessary for cytochrome P450 activity, i.e., in the catalytic center or in conserved residues. For example, generally modifications are not made a position corresponding to Glu367, Arg370, Gly445, Arg446, Arg447, Ile448, Cys449, Pro450 or Gly451 with reference to a sequence of amino acids set forth in SEQ ID NO:6, 8, 9 or 73.

The modified cytochrome P450 bergamotene oxidase polypeptides can contain two or more modifications, including amino acid replacements or substitutions, insertions or deletions, truncations or combinations thereof. Generally, multiple modifications provided herein can be combined by one of skill in the art so long as the modified cytochrome P450 bergamotene oxidase polypeptide retains cytochrome P450 bergamotene oxidase activity.

Also provided herein are nucleic acid molecules that encode any of the modified cytochrome P450 bergamotene oxidase polypeptides provided herein. In particular examples, the nucleic acid sequence can be codon optimized, for example, to increase expression levels of the encoded sequence. The particular codon usage is dependent on the host organism in which the modified polypeptide is expressed. One of skill in the art is familiar with optimal codons for expression in bacteria or yeast, including for example *E. coli* or *Saccharomyces cerevisiae*. For example, codon usage information is available from the Codon Usage Database available at kazusa.or.jp.codon (see Richmond (2000) *Genome Biology*, 1:241 for a description of the database). See also, Forsburg (2004) *Yeast*, 10:1045-1047; Brown et al. (1991) *Nucleic Acids Research*, 19:4298; Sharp et al. (1988) *Nucleic Acids Research*, 12:8207-8211; Sharp et al. (1991) *Yeast*, 657-78. In examples herein, nucleic acid sequences provided herein are codon optimized based on codon usage in *Saccharomyces cerevisiae*.

The modified polypeptides and encoding nucleic acid molecules provided herein can be produced by standard recombinant DNA techniques known to one of skill in the art. Any method known in the art to effect mutation of any one or more amino acids in a target protein can be employed. Methods include standard site-directed or random mutagenesis of encoding nucleic acid molecules, or solid phase polypeptide synthesis methods. For example, as described herein, nucleic acid molecules encoding a cytochrome P450 bergamotene oxidase polypeptide can be subjected to mutagenesis, such as random mutagenesis of the encoding nucleic acid, by error-prone PCR, site-directed mutagenesis, overlap PCR, gene shuffling, or other recombinant methods. The nucleic acid encoding the polypeptides then can be introduced into a host cell to be expressed heterologously. Hence, also provided herein are nucleic acid molecules encoding any of the modified polypeptides provided herein. In some examples, the modified cytochrome P450 bergamotene oxidase polypeptides are produced synthetically, such as using solid phase or solutions phase peptide synthesis.

3. Additional Modifications

Provided herein are cytochrome P450 polypeptides, including cytochrome P450 santalene oxidase and cytochrome P450 bergamotene oxidase polypeptides, that contain additional modifications. For example, modified cytochrome P450 polypeptides include, for example, truncated cytochrome P450 polypeptides, cytochrome P450 polypeptides having altered activities or properties, chimeric cytochrome P450 polypeptides, cytochrome P450 polypeptides containing domain swaps, cytochrome P450 fusion proteins, or cytochrome P450 polypeptides having any modification described elsewhere herein.

a. Truncated Polypeptides

Also provided herein are truncated cytochrome P450 polypeptides. The truncated cytochrome P450 polypeptides can be truncated at the N-terminus or C-terminus, so long as the truncated cytochrome P450 polypeptides retain the catalytic activity of a cytochrome P450, such as cytochrome P450 santalene oxidase or cytochrome P450 bergamotene oxidase activity. Typically, the truncated cytochrome P450 santalene oxidase polypeptides exhibit santalene oxidase activity (i.e., the ability to catalyze the hydroxylation of a santalene, namely α-santalene, β-santalene or epi-β-santalene). Typically, the truncated cytochrome P450 bergamotene oxidase polypeptides exhibit bergamotene oxidase activity (i.e., the ability to catalyze the hydroxylation of a bergamotene). In some examples, the cytochrome P450 polypeptides, including the cytochrome P450 santalene oxidase and cytochrome P450 bergamotene oxidase polypeptides, are truncated at the C-terminus. In other examples, the cytochrome P450 polypeptides, including the cytochrome P450 santalene oxidase and cytochrome P450 bergamotene oxidase polypeptides, are truncated at the N-terminus.

In some examples, the cytochrome P450 polypeptides, including the cytochrome P450 santalene oxidase and cytochrome P450 bergamotene oxidase polypeptides, are truncated at the N-terminus, C-terminus or both termini of a cytochrome P450 polypeptide provided herein, such as truncation of a sequence of amino acids set forth in any of SEQ ID NOS:6-9. In other examples, any of the modified cytochrome P450 polypeptides provided herein are truncated. The modified cytochrome P450 polypeptides can be truncated at their N-terminus, C-terminus, or both termini. For example, any cytochrome P450 polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the N-terminus, provided the cytochrome P450 polypeptide retains cytochrome P450 activity. In other examples, any cytochrome P450 polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the C-terminus, provided the cytochrome P450 polypeptide retains cytochrome P450 activity.

b. Polypeptides with Altered Activities or Properties

The modified cytochrome P450 polypeptides provided herein can also exhibit changes in activities and/or properties. The modified cytochrome P450 polypeptides can exhibit, for example, improved properties, such as increased catalytic activity, increased selectivity, increased substrate specificity, increased substrate binding, increased stability, and/or increased expression in a host cell, and altered properties, such as altered product distribution and altered substrate specificity. Such improved or altered activities can result in increased production of santalols and/or bergamotols.

In some examples, the modified cytochrome P450 polypeptides have altered substrate specificity. For example, the substrate specificity of a modified cytochrome P450 polypeptide can be altered by at least or at least about 10%, 15%, 20%, 30%, 40%, 50%, 60%, 70%, 80%, 90%, 100% or more compared to the unmodified cytochrome P450 polypeptide. For example, a modified cytochrome P450 santalene oxidase or cytochrome P450 bergamotene oxidase polypeptide can catalyze the monooxygenation of a terpene substrate that is not a santalene or bergamotene. In such examples, the modified cytochrome P450 polypeptides catalyze the formation of terpenoids other than santalols or bergamotols from any suitable terpene substrate. For example, the modified cytochrome P450 polypeptides can produce one or more different monoterpenoids, sesquiterpenoids or diterpenoids other than santalols and bergamotols.

In some examples, the modified cytochrome P450 polypeptides have an altered terpenoid product distribution. In some examples, altered product distribution results in an increased amount of a desired terpenoid product, and thus product distribution is improved compared to the product distribution of the unmodified cytochrome P450. In other examples, altered product distribution results in an decreased amount of a desired terpenoid product, and thus the product distribution of the modified cytochrome P450 is decreased compared to that of the unmodified cytochrome P450. In one example, the modified cytochrome P450 santalene oxidase produces a different ratio of terpenoid products compared to the unmodified cytochrome P450 santalene oxidase. For example, the amount of a terpenoid produced by the modified cytochrome P450 can be increased or decreased by at least or at least about or 0.5%, 1%, 2%, 3%, 4%, 5%, 6%, 7%, 8%, 9%, 10%, 15%, 20%, 25%, 30%, 35%, 40%, 50%, 60%, 70%, 80% or more compared to the amount of a different terpenoid produced by the unmodified cytochrome P450. For example, the amount of a terpenoid produced by the modified cytochrome P450 santalene oxidase, such as, for example, a β-santalol, can be increased by at least or at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more compared to the amount of a different terpenoid produced by the unmodified cytochrome P450 santalene oxidase, such as, for example, an α-santalol. In some examples, the modified cytochrome P450 santalene oxidases produce more β-santalol than any other terpenoid compound. In another example, the modified cytochrome P450 bergamotene oxidase produces a different ratio of terpenoid products compared to the unmodified cytochrome P450 bergamotene oxidase. For example, the amount of a terpenoid produced by the modified cytochrome P450 bergamotene oxidase, such as, for example, a α-trans-bergamotol, can be increased by at least or at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more compared to the amount of a different terpenoid produced by the unmodified cytochrome P450 bergamotene oxidase.

In some examples, the modified cytochrome P450 polypeptide exhibits a similar, increased and/or improved activity compared to the unmodified cytochrome P450 polypeptide. For example, a modified cytochrome P450 polypeptide exhibits increased terpenoid production compared to an unmodified cytochrome P450 polypeptide. The increased terpenoid production can be an increase in the total amount of terpenoids produced by the modified cytochrome P450 polypeptide or can be an increase in the amount of a particular terpenoid produced by the modified cytochrome P450 polypeptide. For example, the total terpenoid production of a modified cytochrome P450 polypeptide can be increased by at least or at least about 1%, 3%, 5%, 10%, 15%, 20%, 30%, 40%, 50%, 60%, 70%, 80%, 90%, 100% or more compared to an unmodified cytochrome P450 polypeptide. In some examples, the total terpenoid production of a modified cytochrome P450 polypeptide is at least or about 1.2-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold or more compared to an unmodified cytochrome P450 polypeptide. In another example, the production of a particular terpenoid by a modified cytochrome P450 polypeptide is increased by at least or at least about 1%, 3%, 5%, 10%, 15%, 20%, 30%, 40%, 50%, 60%, 70%, 80%, 90%, 100% or more compared to an unmodified cytochrome P450 polypeptide. In some examples, a modified cytochrome P450 polypeptide produces at least or about 1.2-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold or more of a particular terpenoid product compared to the unmodified cytochrome P450 polypeptide.

In some examples, the modified cytochrome P450 polypeptide exhibits improved substrate specificity compared to the unmodified cytochrome P450 polypeptide. Substrate specificity of the modified cytochrome P450 polypeptide can be increased by at least or at least about 1%, 5%, 10%, 15%, 20%, 30%, 40%, 50%, 60%, 70%, 80%, 90%, 100% or more compared to the substrate specificity of the unmodified cytochrome P450 polypeptide. For example, the modified cytochrome P450 polypeptide can exhibit increased substrate specificity for a terpene, such as a santalene, compared to a different terpene, such as a bergamotene. In such examples, increased specificity for a santalene results in increased production of santalols and decreased production of a bergamotol.

In some examples, the modified cytochrome P450 polypeptide, such as a modified cytochrome P450 santalene oxidase polypeptide, exhibits similar or increased or improved santalene oxidase activity compared to the unmodified cytochrome P450 santalene oxidase polypeptide. For example, the modified cytochrome P450 santalene oxidase polypeptide can exhibit increased specificity or selectivity for oxidation of α-santalene, β-santalene and/or epi-β-santalene compared to the unmodified cytochrome P450 santalene oxidase polypeptide. In some instances of such examples, the modified cytochrome P450 santalene oxidase selectively monooxygenates β-santalene compared to the unmodified cytochrome P450 santalene oxidase. In other examples, the modified cytochrome P450 santalene oxidase polypeptide exhibits reduced selectivity for oxidation of bergamotene compared to the unmodified cytochrome P450 santalene oxidase. For example, the modified cytochrome P450 santalene oxidase exhibits a decrease in activity towards oxidation of bergamotene of at least or at least about 10%, 15%, 20%, 30%, 40%, 50%, 60%, 70%, 80%, 90%, 100% or more compared to the unmodified cytochrome P450 santalene oxidase.

In some examples, the modified cytochrome P450 polypeptide, such as a modified cytochrome P450 bergamotene oxidase polypeptide, exhibits similar or increased or improved bergamotene oxidase activity compared to the unmodified cytochrome P450 bergamotene oxidase polypeptide. For example, the modified cytochrome P450 bergamotene oxidase polypeptide can exhibit increased specificity or selectivity for oxidation of α-trans-bergamotene compared to the unmodified cytochrome P450 bergamotene oxidase.

c. Domain Swaps

Provided herein are modified cytochrome P450 polypeptides that are chimeric polypeptides containing a swap (deletion and insertion) by deletion of amino acid residues of one of more domains or regions therein or portions thereof and insertion of a heterologous sequence of amino acids. In some examples, the heterologous sequence is a randomized sequence of amino acids. In other examples, the heterologous sequence is a contiguous sequence of amino acids for the corresponding domain or region or portion thereof from another cytochrome P450. The heterologous sequence that is replaced or inserted generally includes at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more amino acids. In examples where the heterologous sequence is from a corresponding domain or a portion thereof of another cytochrome P450, the heterologous sequence generally includes at least 50%, 60%, 70%, 80%, 90%, 95% or more contiguous amino acids of the corresponding domain or region or portion. In such an example, adjacent residues to the heterologous corresponding domain or region or portion thereof also can be included in a modified cytochrome P450 polypeptide provided herein.

In one example of swap mutants provided herein, at least one domain or region or portion thereof of a cytochrome P450 polypeptide is replaced with a contiguous sequence of amino acids for the corresponding domain or region or portions thereof from another cytochrome P450 polypeptide. In some examples, 2, 3, 4, 5, 6, 7, 8, 9, 10 or more domains or regions or portions thereof are replaced with a contiguous sequence of amino acids for the corresponding domain or region or portions thereof from another cytochrome P450 polypeptide.

Any domain or region or portion thereof of a cytochrome P450 polypeptide can be replaced with a heterologous sequence of amino acids, such as heterologous sequence from the corresponding domain or region from another cytochrome P450. A domain or region can be a structural domain or a functional domain. One of skill in the art is familiar with domains or regions in cytochrome P450s. Functional domains include, for example, the catalytic domain or a portion thereof. A structural domain can include all or a portion of helix A, β strand 1-1, β strand 1-2, helix B, β strand 1-5, helix B', helix C, helix C', helix D, β strand 3-1, helix E, helix F, helix G, helix H, β strand 5-1, β strand 5-2, helix I, helix J, helix J', helix K, β strand 1-4, β strand 2-1, β strand 2-2, β strand 1-3, helix K', helix K", Heme domain, helix L, β strand 3-3, β strand 4-1, β strand 4-2 and β strand 3-2. One of skill in the art is familiar with various cytochrome P450s and can identify corresponding domains or regions or portions of amino acids thereof.

Typically, the resulting modified cytochrome P450 polypeptides exhibit cytochrome P450 monooxygenase activity and the ability to produce santalols and/or bergamotols from santalenes and bergamotenes. For example, the modified cytochrome P450 santalene oxidase polypeptides exhibit 50% to 5000%, such as 50% to 120%, 100% to 500% or 110% to 250% of the santalol production from santalene compared to the cytochrome P450 santalene oxidase not containing the modification (e.g. the amino acid replacement or swap of amino acid residues of a domain or region) and/or compared to wild type cytochrome P450 santalene oxidase set forth in SEQ ID NO:7, 74, 75, 76 or 77. Typically, the modified cytochrome P450 santalene oxidase polypeptides exhibit increased santalol production from santalene compared to the cytochrome P450 santalene oxidase not containing the modification, such as compared to the cytochrome P450 santalene oxidase set forth in SEQ ID NO:7, 74, 75, 76 or 77. For example, the modified cytochrome P450 santalene oxidase polypeptides can produce santalols from santalenes in an amount that is at least or about 101%, 102%, 103%, 104%, 105%, 106%, 107%, 108%, 109%, 110%, 115%, 120%, 125%, 130%, 135%, 140%, 145%, 150%, 160%, 170%, 180%, 200%, 250%, 300%, 350%, 400%, 500%, 1500%, 2000%, 3000%, 4000%, 5000% of the amount of santalols produced from santalenes by wild type cytochrome P450 santalene oxidase synthase not containing the modification under the same conditions. For example, the santalol production is increased at least 1.2-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold or more.

In another example, the modified cytochrome P450 bergamotene oxidase polypeptides exhibit 50% to 5000%, such as 50% to 120%, 100% to 500% or 110% to 250% of the bergamotol production from bergamotene compared to the cytochrome P450 bergamotene oxidase not containing the modification (e.g. the amino acid replacement or swap of amino acid residues of a domain or region) and/or compared to wild type cytochrome P450 bergamotene oxidase set forth in SEQ ID NO:6, 8, 9 or 73. Typically, the modified cytochrome P450 bergamotene oxidase polypeptides exhibit increased bergamotol production from bergamotene compared to the cytochrome P450 bergamotene oxidase not containing the modification, such as compared to the cytochrome P450 bergamotene oxidase set forth in SEQ ID NO:6, 8, 9 or 73. For example, the modified cytochrome P450 bergamotene oxidase polypeptides can produce bergamotol from bergamotene in an amount that is at least or about 101%, 102%, 103%, 104%, 105%, 106%, 107%, 108%, 109%, 110%, 115%, 120%, 125%, 130%, 135%, 140%, 145%, 150%, 160%, 170%, 180%, 200%, 250%, 300%, 350%, 400%, 500%, 1500%, 2000%, 3000%, 4000%, 5000% of the amount of bergamotol produced from bergamotene by wild type cytochrome P450 bergamotene oxidase synthase not containing the modification under the same conditions. For example, the bergamotol production is increased at least 1.2-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold or more.

In particular examples herein, modified cytochrome P450 polypeptides provided herein are swap mutants whereby all or a portion of one or more structural domains is replaced with a corresponding structural domain of another cytochrome P450 polypeptide. Table 3 below identifies structural domains of cytochrome P450 santalene oxidase (SEQ ID NO:7) and cytochrome P450 bergamotene oxidase (SEQ ID NO:6) based on alignment of the cytochrome P450 polypeptides with cytochrome P450BM-3, a class II microsomal P450 (SEQ ID NO:66; Accession No. 2HPD; Ravichandran et al. (1993) *Science* 261:731-736; see also FIGS. 5A-5B). Hence, the corresponding domain can be identified in other cytochrome P450 polypeptides.

TABLE 3

| Structural Domains | | |
|---|---|---|
| structure | santalene oxidase (SEQ ID NO: 7) | bergamotene oxidase (SEQ ID NO: 6) |
| helix A | 54-65 | 54-65 |
| β strand 1-1 | 67-74 | 67-74 |
| β strand 1-2 | 75-82 | 75-82 |
| helix B | 83-91 | 83-91 |
| β strand 1-5 | 95-98 | 95-98 |
| helix B' | 101-108 | 101-108 |
| helix C | 124-133 | 124-133 |
| helix D | 149-164 | 149-164 |
| β strand 3-1 | 170-173 | 170-173 |
| helix E | 174-189 | 174-189 |
| helix F | 204-218 | 204-218 |
| helix G | 238-265 | 238-265 |
| helix H | 278-285 | 278-285 |
| β strand 5-1 | 287-290 | 287-290 |
| β strand 5-2 | 291-294 | 291-294 |
| helix I | 297-329 | 297-329 |
| helix J | 330-343 | 330-343 |
| helix J' | 351-358 | 351-358 |
| helix K | 359-371 | 359-371 |
| β strand 1-4 | 376-382 | 376-382 |
| β strand 2-1 | 383-389 | 383-389 |
| β strand 2-2 | 391-397 | 391-397 |
| β strand 1-3 | 398-402 | 398-402 |
| helix K' | 403-410 | 403-410 |
| Heme domain | 444-451 | 444-451 |
| helix L | 452-469 | 452-469 |
| β strand 3-3 | 470-474 | 470-474 |
| β strand 4-1 | 481-485 | 481-485 |
| β strand 4-2 | 487-491 | 487-491 |
| β strand 3-2 | 493-500 | 493-500 |

Any methods known in the art for generating chimeric polypeptides can be used to replace all or a contiguous portion of a domain or a cytochrome P450 with all or a contiguous portion of the corresponding domain of a second cytochrome P450 (see, U.S. Pat. Nos. 5,824,774, 6,072,045, 7,186,891 and 8,106,260, and U.S. Pat. Pub. No. 20110081703). Also, gene shuffling methods can be employed to generate chimeric polypeptides and/or polypeptides with domain or region swaps.

For example, corresponding domains or regions of any two cytochrome P450s can be exchanged using any suitable recombinant method known in the art, or by in vitro synthesis. Exemplary of recombinant methods is a two stage overlapping PCR method, such as described herein. In such methods, primers that introduce mutations at a plurality of codon positions in the nucleic acids encoding the targeted domain or portion thereof in the first cytochrome P450 can be employed. The mutations together form the heterologous region (i.e. the corresponding region from the second cytochrome P450). Alternatively, for example, randomized amino acids can be used to replace particular domains or regions. It is understood that primer errors, PCR errors and/or other errors in the cloning or recombinant methods can result in errors such that the resulting swapped or replaced region or domain does not exhibit an amino acid sequence that is identical to the corresponding region from the second cytochrome P450 reductase.

In an exemplary PCR-based method, the first stage PCR uses (i) a downstream primer that anneals downstream of the region that is being replaced with a mutagenic primer that includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene, and (ii) an upstream primer that anneals upstream of the region that is being replaced together with an opposite strand mutagenic primer that also includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene. If a replacement in which a domain or region of a first cytochrome P450 gene is replaced with the corresponding domain or region from a second cytochrome P450 is being performed, nucleotides in the mutagenic primers between the flanking regions from the first cytochrome P450 contain codons for the corresponding region of the second cytochrome P450. In instances where the amino acids in a domain or region are to be randomized, nucleotides of the mutagenic primers between the flanking regions from the first cytochrome P450 contains random nucleotides. An overlapping PCR is then performed to join the two fragments, using the upstream and downstream oligo. The resulting PCR product then can be cloned into any suitable vector for expression of the modified cytochrome P450.

Further, any of the modified cytochrome P450 polypeptides containing swap mutations herein can contain one or more further amino acid replacements as described herein above.

d. Additional Variants

Cytochrome P450 polypeptides provided herein can be modified by any method known to one of skill in the art for generating protein variants, including, but not limited to, DNA or gene shuffling, error prone PCR, overlap PCR or other recombinant methods. In one example, nucleic acid molecules encoding any cytochrome P450 polypeptide or variant cytochrome P450 polypeptide provided herein can be modified by gene shuffling. Gene shuffling involves one or more cycles of random fragmentation and reassembly of at least two nucleotide sequences, followed by screening to select nucleotide sequences encoding polypeptides with desired properties. The recombination can be performed in vitro (see Stemmer et al. (1994) *Proc Natl Acad Sci USA* 91:10747-10751; Stemmer et al. (1994) *Nature* 370:389-391; Cramieri et al. (1998) *Nature* 391:288-291; U.S. Pat. Nos. 5,605,793, 5,811,238, 5,830,721, 5,834,252 and 5,837,458) or in vivo (see, International Pat. Pub. No. WO199707205). The nucleic acid molecules encoding the polypeptides then can be introduced into a host cell to be expressed heterologously and tested for their cytochrome P450 activity by any method described in section G below.

e. Fusion or Chimeric Proteins

Nucleic acid molecules provided herein include fusion or chimeric nucleic acid molecules that contain a santalene synthase and a cytochrome P450 polypeptide. For example, provided herein are nucleic acid molecules encoding a fusion polypeptide that is capable of catalyzing the formation of a santalol, such as an α-santalol, β-santalol or epi-β-santalol, from FPP that contains any santalene synthase and cytochrome P450 santalene oxidase polypeptide provided herein. For example, provided herein are nucleic acid molecules encoding a fusion polypeptide that contains a santalene synthase set forth in any of SEQ ID NOS:17, 52 or 53 and a cytochrome P450 santalene oxidase polypeptide set forth in SEQ ID NO:7, 74, 75, 76 or 77. Also provided herein are fusion polypeptides containing a santalene synthase set forth in any of SEQ ID NOS: 17, 52 or 53 and a cytochrome P450 santalene oxidase polypeptide set forth in SEQ ID NO:7, 74, 75, 76 or 77. Also provided herein are nucleic acid molecules encoding a fusion polypeptide that is capable of catalyzing the formation of a bergamotol, such as an α-trans-bergamotol, from FPP that contains any santalene synthase and cytochrome P450 santalene bergamotene polypeptide provided herein. For example, provided herein are nucleic acid molecules encoding a fusion polypeptide that contains a santalene synthase set forth in any of SEQ ID NOS: 17, 52 or 53 and a cytochrome P450 bergamotene oxidase polypeptide set forth in any of SEQ ID NOS:6, 8, 9 or 73. Also provided herein are fusion polypeptides containing a santalene synthase set forth in any of SEQ ID NOS:17, 52 or 53 and a cytochrome P450 bergamotene oxidase polypeptide set forth in any of SEQ ID NOS:6, 8, 9 or 73. The fusion polypeptides can be linked directly or via a linker.

Nucleic acid molecules provided herein include fusion or chimeric nucleic acid molecules that contain a cytochrome P450 polypeptide and a cytochrome P450 reductase. For example, provided herein are nucleic acid molecules encoding a fusion polypeptide that contains a cytochrome P450 santalene oxidase polypeptide set forth in any of SEQ ID NOS:7, 74, 75, 76 or 77 and a cytochrome P450 reductase set forth in any of SEQ ID NOS:12-15. Also provided herein are fusion polypeptides containing a cytochrome P450 santalene oxidase polypeptide set forth in any of SEQ ID NOS:7, 74, 75, 76 or 77 and a cytochrome P450 reductase set forth in any of SEQ ID NOS:12-15. In another example, provided herein are nucleic acid molecules encoding a fusion polypeptide that contains a cytochrome P450 bergamotene oxidase polypeptide set forth in any of SEQ ID NOS:6, 8, 9 or 73 and a cytochrome P450 reductase set forth in any of SEQ ID NOS:12-15. Also provided herein are fusion polypeptides containing a cytochrome P450 bergamotene oxidase polypeptide set forth in any of SEQ ID NOS:6, 8, 9 or 73 and a cytochrome P450 reductase set forth in any of SEQ ID NOS:12-15. The fusion polypeptides can be linked directly or via a linker.

Nucleic acid molecules provided herein include fusion or chimeric nucleic acid molecules that contain a santalene synthase, cytochrome P450 polypeptide and a cytochrome P450 reductase. For example, provided herein are nucleic acid molecules encoding a fusion polypeptide that contains a santalene synthase set forth in any of SEQ ID NOS:17, 52 or 53, a cytochrome P450 santalene oxidase polypeptide set forth in any of SEQ ID NOS:7, 74, 75, 76 or 77 and a cytochrome P450 reductase set forth in any of SEQ ID NOS:12-15. Also provided herein are fusion polypeptides containing a santalene synthase set forth in any of SEQ ID NOS: 17, 52 or 53, a cytochrome P450 santalene oxidase polypeptide set forth in any of SEQ ID NOS:7, 74, 75, 76 or 77 and a cytochrome P450 reductase set forth in any of SEQ ID NOS:12-15. In another example, provided herein are nucleic acid molecules encoding a fusion polypeptide that contains a santalene synthase set forth in any of SEQ ID NOS:17, 52 or 53, a cytochrome P450 bergamotene oxidase polypeptide set forth in any of SEQ ID NOS:6, 8, 9 or 73 and a cytochrome P450 reductase set forth in any of SEQ ID NOS:12-15. Also provided herein are fusion polypeptides containing a santalene synthase set forth in any of SEQ ID NOS: 17, 52 or 53, a cytochrome P450 bergamotene oxidase polypeptide set forth in any of SEQ ID NOS:6, 8, 9 or 73 and a cytochrome P450 reductase set forth in any of SEQ ID NOS:12-15. The fusion polypeptides can be linked directly or via a linker.

In another example, provided herein is a nucleic acid molecule that encodes a santalene synthase, a cytochrome P450 and/or a cytochrome P450 reductase, such that, when expressed in a host cell, a bacterial or yeast host cell, a santalene synthase, a cytochrome P450 and/or a cytochrome P450 reductase are expressed. In one example, provided herein is a nucleic acid molecule that encodes a santalene synthase and a cytochrome P450 santalene oxidase. In another example, provided herein is a nucleic acid molecule that encodes a santalene synthase and a cytochrome P450 bergamotene oxidase. In yet another example, provided herein is a nucleic acid molecule that encodes a santalene synthase, a cytochrome P450 santalene oxidase and a cytochrome P450 reductase. In another example, provided herein is a nucleic acid molecule that encodes a santalene synthase, a cytochrome P450 bergamotene oxidase and a cytochrome P450 reductase. Further, when the host cell is capable of producing FPP, the encoded polypeptides catalyze the production of santalols and/or bergamotols.

Other examples of fusion proteins include, but are not limited to, fusions of a signal sequence, a tag such as for localization, e.g. a $his_6$ tag or a myc tag, or a tag for purification, for example, a GST fusion, GFP fusion or CBP fusion, and a sequence for directing protein secretion and/or membrane association.

D. Cytochrome P450 Reductase Polypeptides And Encoding Nucleic Acid Molecules

Provided herein are cytochrome P450 reductase polypeptides. Also provided herein are nucleic acid molecules that encode any of the cytochrome P450 reductase polypeptides provided herein. The cytochrome P450 reductase polypeptides provided herein transfer two electrons from NADPH to a cytochrome P450. In some examples, the nucleic acid molecules that encode the cytochrome P450 reductase polypeptides are those that are the same as those that are isolated from the sandalwood tree *Santalum album*. In other examples, the nucleic acid molecules and encoded cytochrome P450 reductase polypeptides are variants of those isolated from the sandalwood tree *Santalum album*.

Also provided herein are modified cytochrome P450 reductase polypeptides and nucleic acid molecules that encode any of the modified cytochrome P450 reductase polypeptides provided herein. The modifications can be made in any region of a cytochrome P450 reductase polypeptide provided the cytochrome P450 reductase polypeptide at least retains the CPR catalytic activity of the unmodified cytochrome P450 reductase polypeptide. For example, modifications can be made to a cytochrome P450 reductase polypeptide provided that the cytochrome P450 reductase polypeptide retains CPR activity (i.e., the ability to transfer two electrons from NADPH to a cytochrome P450).

The modifications can include codon optimization of the nucleic acids and/or changes that result in a single amino acid modification in the encoded polypeptide, such as single amino acid replacement (substitutions), insertions or deletions, or multiple amino acid modifications, such as multiple amino acid replacements, insertions or deletions, including swaps of domains or regions of the polypeptide. In some examples, entire or partial domains or regions, such as any domain or region described herein, are exchanged with corresponding domains or regions or portions thereof from another cytochrome P450 reductase polypeptide. Exemplary of modifications are amino acid replacements, including single or multiple amino acid replacements. For example, modified cytochrome P450 reductase polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the cytochrome P450 reductase polypeptide not containing the modification.

Provided herein are cytochrome P450 reductase polypeptides having a sequence of amino acids set forth in SEQ ID NO:12 or 13. Also provided herein are cytochrome P450 reductase polypeptides that exhibit at least 60% amino acid sequence identity to a cytochrome P450 reductase polypeptide set forth in SEQ ID NO:12 or 13. For example, the cytochrome P450 reductase polypeptides provided herein can exhibit at least at or at least about or 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a cytochrome P450 reductase polypeptide set forth in SEQ ID NO:12 or 13, provided that the resulting cytochrome P450 reductase polypeptide at least retains CPR activity (i.e., the ability to transfer two electrons from NADPH to a cytochrome P450). Percent identity can be determined by one skilled in the art using standard alignment programs.

Also, in some examples, provided herein are catalytically active fragments of cytochrome P450 reductase polypeptides. In some examples, the active fragments of cytochrome P450 reductase polypeptides are modified as described above. Such fragments retain one or more properties of a full-length cytochrome P450 reductase polypeptide. Typically, the active fragments exhibit CPR activity (i.e., the ability to transfer two electrons from NADPH to a cytochrome P450).

The cytochrome P450 reductase polypeptides provided herein can contain other modifications, for example, modifications not in the primary sequence of the polypeptide, including post-translational modifications. For example, modification described herein can be a cytochrome P450 reductase polypeptide that is a fusion polypeptide or chimeric polypeptide, including hybrids of different cytochrome P450 reductase polypeptides (e.g. contain one or more domains or regions from another cytochrome P450 reductase polypeptide) and also synthetic cytochrome P450 reductase polypeptides prepared recombinantly or synthesized or constructed by other methods known in the art based upon the sequence of known polypeptides.

The cytochrome P450 reductase polypeptides provided herein can be used to transfer two electrons from NADPH to a cytochrome P450. Reactions can be performed in vivo, such as in a host cell into which the nucleic acid has been introduced. At least one of the polypeptides will be heterologous to the host. Reactions can also be performed in vitro by contacting with enzyme the appropriate substrate under appropriate conditions.

Also provided herein are nucleic acid molecules encoding a cytochrome P450 polypeptide and a cytochrome P450 reductase polypeptide. For example, provided herein are nucleic acid molecules encoding a cytochrome P450 santalene oxidase polypeptide and a cytochrome P450 reductase polypeptide. In another example, nucleic acid molecules encoding a cytochrome P450 bergamotene synthase polypeptide and a cytochrome P450 reductase polypeptide. Also provided herein are nucleic acid molecules encoding a santalene synthase, cytochrome P450 polypeptide and a cytochrome P450 reductase polypeptide. For example, provided herein are nucleic acid molecules encoding a santalene synthase, cytochrome P450 santalene oxidase polypeptide and a cytochrome P450 reductase polypeptide. In another example, provided herein are nucleic acid molecules encoding a santalene synthase, cytochrome P450 bergamotene oxidase polypeptide and a cytochrome P450 reductase polypeptide. The nucleic acid molecules can be in the same vector or plasmid or on different vectors or plasmids. In such examples, expression of the nucleic acid molecule(s) in a suitable host, for example, a bacterial or yeast cell, results in expression of cytochrome P450 oxidase and cytochrome P450 reductase, or results in expression of santalene synthase, cytochrome P450 oxidase and cytochrome P450 reductase, depending on the included nucleic acid molecules. Such cells can be used to produce the santalene synthases, the cytochrome P450 oxidases and the cytochrome P450 reductases and/or to perform reactions in vivo to produce santalols and bergamotols. For example, santalols and bergamotols can be generated in a host cell from farnesyl diphosphate (FPP), particularly a yeast cell that overproduces the acyclic terpene precursor FPP. In some examples, a nucleic acid molecule encoding a farnesyl diphosphate synthase, such as a *Santalum album* farnesyl diphosphate synthase, can also be expressed in the suitable host, for example, a bacterial or yeast cell, resulting in over-expression of FPP.

1. Cytochrome P450 Reductase Polypeptides

Provided herein are cytochrome P450 reductase polypeptides. Also provided herein are nucleic acid molecules that encode any of the cytochrome P450 reductase polypeptides provided herein. The cytochrome P450 reductase polypeptides provided herein exhibit CPR activity. Typically, the cytochrome P450 reductase polypeptides provided herein the ability to transfer two electrons from NADPH to a cytochrome P450.

For example, provided herein are cytochrome P450 reductase polypeptides that have a sequence of amino acids set forth in SEQ ID NO:12 or 13. Also provided herein are cytochrome P450 reductase polypeptides that exhibit at least 60% amino acid sequence identity to a cytochrome P450 reductase polypeptide having a sequence of amino acids set forth in SEQ ID NO:12 or 13. For example, the cytochrome P450 reductase polypeptides provided herein can exhibit at least at or about or 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% or more amino acid sequence identity to a cytochrome P450 reductase polypeptide set forth in SEQ ID NO:12 or 13, provided the cytochrome P450 reductase polypeptides exhibit cytochrome P450 reductase activity (i.e. transfer two electrons from NADPH to a cytochrome P450). Percent identity can be determined by one skilled in the art using standard alignment programs.

Also provided herein are active fragments of cytochrome P450 reductase polypeptides having a sequence of amino acids set forth in SEQ ID NO:12 or 13. For example, provided herein are truncated cytochrome P450 reductase polypeptides having a sequence of amino acids set forth in SEQ ID NO:14 or 15. Such fragments retain one or more properties of a cytochrome P450 reductase polypeptide. Typically, the active fragments exhibit cytochrome P450 reductase activity (i.e. transfer two electrons from NADPH to a cytochrome P450).

Also provided herein are nucleic acid molecules that have a sequence of amino acids set forth in SEQ ID NO:10 or 11, or degenerates thereof, that encode a cytochrome P450 reductase polypeptide having a sequence of amino acids set forth in SEQ ID NO:12 or 13, respectively. Also provided herein are nucleic acid molecules encoding a cytochrome P450 reductase polypeptide having at least 85% sequence identity to a sequence of nucleotides set forth in SEQ ID NO:10 or 11. For example, the nucleic acid molecules provided herein can exhibit at least or about at least 85%, 86%, 87%, 88%, 89%, 90%, 91%, 92%, 93%, 95%, 95%, 96%, 97%, 98% or 99% or more sequence identity to a sequence of nucleotides set forth in SEQ ID NO:10 or 11, so long as the encoded cytochrome P450 reductase polypeptide exhibits cytochrome P450 reductase activity (i.e. the ability to transfer two electrons from NADPH to a cytochrome P450). Also provided herein are degenerate sequences of the sequences set forth in SEQ ID NO:10 or 11 encoding a cytochrome P450 reductase polypeptide having a sequence of amino acids set forth in SEQ ID NO:12 or 13, respectively. Percent identity can be determined by one skilled in the art using standard alignment programs.

In some examples, the nucleic acid molecules that encode the cytochrome P450 reductase polypeptides are isolated from the sandalwood tree *Santalum album*. In other examples, the nucleic acid molecules and encoded cytochrome P450 reductase polypeptides are variants of those isolated from the sandalwood tree *Santalum album*.

2. Modified Cytochrome P450 Reductase Polypeptides

Provided herein are modified cytochrome P450 reductase polypeptides. The modifications can be made in any region of a cytochrome P450 reductase polypeptide provided the resulting modified cytochrome P450 reductase polypeptides at least retain cytochrome P450 reductase activity (e.g. the ability to transfer two electrons from NADPH to a cytochrome P450).

The modifications can be a single amino acid modification, such as single amino acid replacements (substitutions), insertions or deletions, or multiple amino acid modifications, such as multiple amino acid replacements, insertions or deletions. In some examples, entire or partial domains or regions, such as any domain or region described herein below, are exchanged with corresponding domains or regions or portions thereof from another cytochrome P450 reductase polypeptide. Exemplary of modifications are amino acid replacements, including single or multiple amino acid replacements. For example, modified cytochrome P450 reductase polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the cytochrome P450 reductase polypeptide not containing the modification.

The modifications described herein can be in any cytochrome P450 reductase polypeptide. For example, the modifications described herein can be in a cytochrome P450 reductase having a sequence of amino acids set forth in any of SEQ ID NOS:12-15 or any variant thereof, including any that have at least 60%, 65%, 70%, 75%, 80%, 85%, 90%, 91%, 92%, 93%, 94%, 95%, 96%, 97%, 98%, or 99% sequence identity to a cytochrome P450 reductase having a sequence of amino acids set forth in any of SEQ ID NOS:12-15.

In particular, modified cytochrome P450 reductase polypeptides provided herein contain amino acid replacements or substitutions, additions or deletions, truncations or combinations thereof with reference to the cytochrome P450 reductase polypeptide having a sequence of amino acids set forth in SEQ ID NO:12. It is within the level of one of skill in the art to make such modifications in cytochrome P450 reductase polypeptides, such as any set forth in SEQ ID NOS:12-15 or any variant thereof. Based on this description, it is within the level of one of skill in the art to generate a cytochrome P450 reductase polypeptide containing any one or more of the described mutations, and test each for cytochrome P450 reductase activity described herein, such as the ability to transfer two electrons from NADPH to cytochrome P450.

Also, in some examples, provided herein are modified active fragments of cytochrome P450 reductase polypeptides that contain any of the modifications provided herein. Such fragments retain on or more properties of a cytochrome P450 reductase, such as the ability to transfer two electrons from NADPH to cytochrome P450. Modifications in a cytochrome P450 reductase polypeptide also can be made to a cytochrome P450 reductase polypeptide that also contains other modifications, including modifications of the primary sequence and modifications not in the primary sequence of the polypeptide. For example, modification described herein can be in a cytochrome P450 reductase polypeptide that is a fusion polypeptide or chimeric polypeptide with different cytochrome P450 reductase polypeptides (e.g. contain one or more domains or regions from another cytochrome P450 reductase s) and also synthetic cytochrome P450 reductase polypeptides prepared recombinantly or synthesized or constructed by other methods known in the art based upon the sequence of known polypeptides.

In some examples, the modifications are amino acid replacements. In further examples, the modified cytochrome P450 reductase polypeptides provided herein contain one or more modifications in a domain. For example, the modifications in a domain or structural domain can be by replacement of corresponding heterologous residues from another cytochrome P450 reductase polypeptide.

To retain cytochrome P450 reductase activity, modifications typically are not made at those positions necessary for cytochrome P450 reductase activity, i.e., in the catalytic center or in conserved residues. For example, generally modifications are not made a position corresponding to Ser485, Cys657, Asp702 and Trp704 with reference to a sequence of amino acids set forth in SEQ ID NO:12.

The modified cytochrome P450 reductase polypeptides provided herein can contain two or more modifications, including amino acid replacements or substitutions, insertions or deletions, truncations or combinations thereof. Generally, multiple modifications provided herein can be combined by one of skill in the art so long as the modified cytochrome P450 reductase polypeptide retains cytochrome P450 reductase activity.

Also provided herein are nucleic acid molecules that encode any of the modified cytochrome P450 reductase polypeptides provided herein. In particular examples, the nucleic acid sequence can be codon optimized, for example, to increase expression levels of the encoded sequence. The particular codon usage is dependent on the host organism in which the modified polypeptide is expressed. One of skill in the art is familiar with optimal codons for expression in bacteria or yeast, including for example *E. coli* or *Saccharomyces cerevisiae*. For example, codon usage information is available from the Codon Usage Database available at, for example, kazusa.or.jp.codon (see, e.g., Richmond (2000) *Genome Biology*, 1:241 for a description of the database). See also, Forsburg (2004) *Yeast*, 10:1045-1047; Brown et al. (1991) *Nucleic Acids Research*, 19:4298; Sharp et al. (1988) *Nucleic Acids Research*, 12:8207-8211; Sharp et al. (1991) *Yeast*, 657-78. In examples herein, nucleic acid sequences provided herein are codon optimized based on codon usage in *Saccharomyces cerevisiae*.

The modified polypeptides and encoding nucleic acid molecules provided herein can be produced by standard recombinant DNA techniques known to one of skill in the art. Any method known in the art to effect mutation of any one or more amino acids in a target protein can be employed. Methods include standard site-directed or random mutagenesis of encoding nucleic acid molecules, or solid phase polypeptide synthesis methods. For example, as described herein, nucleic acid molecules encoding a cytochrome P450 reductase polypeptide can be subjected to mutagenesis, such as random mutagenesis of the encoding nucleic acid, by error-prone PCR, site-directed mutagenesis, overlap PCR, gene shuffling, or other recombinant methods. The nucleic acid encoding the polypeptides then can be introduced into a host cell to be expressed heterologously. Hence, also provided herein are nucleic acid molecules encoding any of the modified polypeptides provided herein. In some examples, the modified cytochrome P450 reductase polypeptides are produced synthetically, such as using solid phase or solutions phase peptide synthesis.

3. Additional Modifications

Provided herein are cytochrome P450 reductase polypeptides that contain additional modifications. For example, modified cytochrome P450 reductase polypeptides include, for example, truncated cytochrome P450 reductase polypeptides, cytochrome P450 reductase polypeptides having altered activities or properties, chimeric cytochrome P450 reductase polypeptides, cytochrome P450 reductase polypeptides containing domain swaps, cytochrome P450 reductase fusion proteins, or cytochrome P450 reductase polypeptides having any modification described elsewhere herein.

a. Truncated Polypeptides

Also provided herein are truncated cytochrome P450 reductase polypeptides. The truncated cytochrome P450 reductase polypeptides can be truncated at the N-terminus or C-terminus, so long as the truncated cytochrome P450 reductase polypeptides retain the catalytic activity of a cytochrome P450 reductase, such as cytochrome P450 reductase activity. Typically, the truncated cytochrome P450 reductase polypeptides exhibit cytochrome P450 reductase activity (i.e., the ability to transfer two electrons from NADPH to cytochrome P450). In some examples, the cytochrome P450 reductase polypeptides are truncated at the C-terminus. In other examples, the cytochrome P450 reductase polypeptides are truncated at the N-terminus.

In some examples, the cytochrome P450 reductase polypeptides are truncated at the N-terminus, C-terminus or both termini of a cytochrome P450 reductase polypeptide provided herein, such as truncation of a sequence of amino acids set forth in any of SEQ ID NOS:12 or 13. In other examples, any of the modified cytochrome P450 reductase polypeptides provided herein are truncated. The modified cytochrome P450 reductase polypeptides can be truncated at their N-terminus, C-terminus, or both termini. For example, any cytochrome P450 reductase polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the N-terminus, provided the cytochrome P450 reductase polypeptide retains cytochrome P450 reductase activity. In other examples, any cytochrome P450 reductase polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the C-terminus, provided the cytochrome P450 reductase polypeptide retains cytochrome P450 reductase activity. In some examples, cytochrome P450 reductases can be truncated by digestion with pancreatic steapsin or trypsin, which releases the N-terminal hydrophobic anchor.

For example, provided herein are truncated cytochrome P450 reductase polypeptides having a sequence of amino acids set forth in SEQ ID NO:14 or 15. Also provided herein are truncated cytochrome P450 reductase polypeptides having a sequence of amino acids having at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a truncated cytochrome P450 reductase having a sequence of amino acids set forth in SEQ ID NO:14 or 15, provided the resulting cytochrome P450 reductase polypeptide at least retains cytochrome P450 reductase activity (i.e., the ability to transfer two electrons from NADPH to cytochrome P450). Also provided herein are nucleic acid molecules having a sequence of nucleotides set forth in SEQ ID NOS:63 or 64 that encode the truncated cytochrome P450 reductase polypeptides having a sequence of amino acids set forth in SEQ ID NO:14 or 15, respectively.

b. Polypeptides with Altered Activities or Properties

The modified cytochrome P450 reductase polypeptides provided herein can also exhibit changes in activities and/or properties. The modified cytochrome P450 reductase polypeptides can exhibit, for example, improved properties, such as increased catalytic activity, increased stability, and/or increased expression in a host cell. In other examples, the modified cytochrome P450 reductase polypeptide exhibits a similar, increased and/or improved activity compared to the unmodified cytochrome P450 reductase polypeptide.

c. Domain Swaps

Provided herein are modified cytochrome P450 reductase polypeptides that are chimeric polypeptides containing a swap (deletion and insertion) by deletion of amino acid residues of one of more domains or regions therein or portions thereof and insertion of a heterologous sequence of amino acids. In some examples, the heterologous sequence is a randomized sequence of amino acids. In other examples, the heterologous sequence is a contiguous sequence of amino acids for the corresponding domain or region or portion thereof from another cytochrome P450 reductase. The heterologous sequence that is replaced or inserted generally includes at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more amino acids. In examples where the heterologous sequence is from a corresponding domain or a portion thereof of another cytochrome P450 reductase, the heterologous sequence generally includes at least 50%, 60%, 70%, 80%, 90%, 95% or more contiguous amino acids of the corresponding domain or region or portion. In such an example, adjacent residues to the heterologous corresponding domain or region or portion thereof also can be included in a modified cytochrome P450 reductase polypeptide provided herein.

In one example of swap mutants provided herein, at least one domain or region or portion thereof of a cytochrome P450 reductase polypeptide is replaced with a contiguous sequence of amino acids for the corresponding domain or region or portions thereof from another cytochrome P450 reductase polypeptide. In some examples, 2, 3, 4, 5, 6, 7, 8, 9, 10 or more domains or regions or portions thereof are replaced with a contiguous sequence of amino acids for the corresponding domain or region or portions thereof from another cytochrome P450 reductase polypeptide.

Any domain or region or portion thereof of a cytochrome P450 reductase polypeptide can be replaced with a heterologous sequence of amino acids, such as heterologous sequence from the corresponding domain or region from another cytochrome P450 reductase. A domain or region can be a structural domain or a functional domain. One of skill in the art is familiar with domains or regions in cytochrome P450 reductases. Functional domains include, for example, the catalytic domain or a portion thereof. A structural domain can include all or a portion of α-helix A; β-strand 1; α-helix B; β-strand 2; α-helix C; β-strand 3; α-helix D; β-strand 4; α-helix E; β-strand 5; α-helix F; β-strand 6; β-strand 7; β-strand 8, β-strand 9; β-strand 10; α-helix G; β-strand 11; β-strand 12; β-strand 12'; α-helix H; α-helix I; α-helix J; α-helix K; α-helix M; β-strand 13; β-strand 14; β-strand 15; α-helix N; β-strand 16; β-strand 16'; β-strand 17; α-helix O; β-strand 18; α-helix P; β-strand 10; α-helix Q; α-helix R; β-strand 20; α-helix S; α-helix T; and β-strand 21. One of skill in the art is familiar with various cytochrome P450s and can identify corresponding domains or regions or portions of amino acids thereof. Typically, the resulting modified cytochrome P450 reductase polypeptides exhibit cytochrome P450 reductase activity.

Any methods known in the art for generating chimeric polypeptides can be used to replace all or a contiguous portion of a domain or a cytochrome P450 reductase with all or a contiguous portion of the corresponding domain of a second cytochrome P450 reductase (see, U.S. Pat. Nos. 5,824,774, 6,072,045, 7,186,891 and 8,106,260, and U.S. Pat. Pub. No. 20110081703). Also, gene shuffling methods can be employed to generate chimeric polypeptides and/or polypeptides with domain or region swaps.

For example, corresponding domains or regions of any two cytochrome P450 reductases can be exchanged using any suitable recombinant method known in the art, or by in vitro synthesis. Exemplary of recombinant methods is a two stage overlapping PCR method, such as described herein. In such methods, primers that introduce mutations at a plurality of codon positions in the nucleic acids encoding the targeted domain or portion thereof in the first cytochrome P450 reductase can be employed; the mutations together form the heterologous region (i.e. the corresponding region from the second cytochrome P450 reductase). Alternatively, for example, randomized amino acids can be used to replace particular domains or regions. It is understood that primer errors, PCR errors and/or other errors in the cloning or recombinant methods can result in errors such that the resulting swapped or replaced region or domain does not exhibit an amino acid sequence that is identical to the corresponding region from the second cytochrome P450 reductase synthase.

In an exemplary PCR-based method, the first stage PCR uses (i) a downstream primer that anneals downstream of the region that is being replaced with a mutagenic primer that includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene, and (ii) an upstream primer that anneals upstream of the region that is being replaced together with an opposite strand mutagenic primer that also includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene. If a replacement in which a domain or region of a first cytochrome P450 reductase gene is replaced with the corresponding domain or region from a second cytochrome P450 reductase is being performed, nucleotides in the mutagenic primers between the flanking regions from the first cytochrome P450 reductase contain codons for the corresponding region of the second cytochrome P450 reductase. In instances where the amino acids in a domain or region are to be randomized, nucleotides of the mutagenic primers between the flanking regions from the first cytochrome P450 reductase contains random nucleotides. An overlapping PCR is then performed to join the two fragments, using the upstream and downstream oligo. The resulting PCR product then can be cloned into any suitable vector for expression of the modified cytochrome P450 reductase.

Further, any of the modified cytochrome P450 reductase polypeptides containing swap mutations herein can contain one or more further amino acid replacements as described herein above.

d. Additional Variants

Cytochrome P450 reductase polypeptides provided herein can be modified by any method known to one of skill in the art for generating protein variants, including, but not limited to, DNA or gene shuffling, error prone PCR, overlap PCR or other recombinant methods. In one example, nucleic acid molecules encoding any cytochrome P450 reductase polypeptide or variant cytochrome P450 reductase polypeptide provided herein can be modified by gene shuffling. Gene shuffling involves one or more cycles of random fragmentation and reassembly of at least two nucleotide sequences, followed by screening to select nucleotide sequences encoding polypeptides with desired properties. The recombination can be performed in vitro (see Stemmer et al. (1994) *Proc Natl Acad Sci USA* 91:10747-10751; Stemmer et al. (1994) *Nature* 370:389-391; Cramieri et al. (1998) *Nature* 391:288-291; U.S. Pat. Nos. 5,605,793, 5,811,238, 5,830,721, 5,834,252 and 5,837,458) or in vivo (see, International Pat. Pub. No. WO199707205). The nucleic acid molecules encoding the polypeptides then can be introduced into a host cell to be expressed heterologously and tested for their cytochrome P450 reductase activity by any method described in section G below.

e. Fusion or Chimeric Proteins

Nucleic acid molecules provided herein include fusion or chimeric nucleic acid molecules that contain a cytochrome P450 polypeptide and a cytochrome P450 reductase polypeptide. For example, provided herein are nucleic acid molecules encoding a fusion polypeptide that is capable of catalyzing the formation of a santalol or bergamotol, such as an α-santalol, β-santalol, epi-β-santalol or Z-α-trans-bergamotol, from santalenes or bergamotene that contains any cytochrome P450 polypeptide and any cytochrome P450 reductase polypeptide provided herein. For example, provided herein are nucleic acid molecules encoding a fusion polypeptide that contains a cytochrome P450 polypeptide set forth in any of SEQ ID NOS:6-9 and a cytochrome P450 reductase polypeptide set forth in any of SEQ ID NOS:12-15. Also provided herein are fusion polypeptides containing a cytochrome P450 polypeptide set forth in any of SEQ ID NOS:6-9 and a cytochrome P450 reductase polypeptide set forth in any of SEQ ID NOS:12-15. The fusion polypeptides can be linked directly or via a linker.

Nucleic acid molecules provided herein include fusion or chimeric nucleic acid molecules that contain a santalene synthase, cytochrome P450 polypeptide and a cytochrome P450 reductase. For example, provided herein are nucleic acid molecules encoding a fusion polypeptide that contains a santalene synthase set forth in any of SEQ ID NOS:17, 52 or 53, a cytochrome P450 santalene oxidase polypeptide set forth in SEQ ID NO:7 and a cytochrome P450 reductase set forth in any of SEQ ID NOS:12-15. Also provided herein are fusion polypeptides containing a santalene synthase set forth in any of SEQ ID NOS: 17, 52 or 53, a cytochrome P450 santalene oxidase polypeptide set forth in SEQ ID NO:7 and a cytochrome P450 reductase set forth in any of SEQ ID NOS:12-15. In another example, provided herein are nucleic acid molecules encoding a fusion polypeptide that contains a santalene synthase set forth in any of SEQ ID NOS:17, 52 or 53, a cytochrome P450 bergamotene oxidase polypeptide set forth in any of SEQ ID NOS:6, 8 or 9 and a cytochrome P450 reductase set forth in any of SEQ ID NOS:12-15. Also provided herein are fusion polypeptides containing a santalene synthase set forth in any of SEQ ID NOS: 17, 52 or 53, a cytochrome P450 bergamotene oxidase polypeptide set forth in any of SEQ ID NOS:6, 8 or 9 and a cytochrome P450 reductase set forth in any of SEQ ID NOS:12-15. The fusion polypeptides can be linked directly or via a linker.

In another example, provided herein is a nucleic acid molecule that encodes a santalene synthase, a cytochrome P450 and/or a cytochrome P450 reductase, such that, when expressed in a host cell, a bacterial or yeast host cell, a santalene synthase, a cytochrome P450 and/or a cytochrome P450 reductase are expressed. In one another example, provided herein is a nucleic acid molecule that encodes a santalene synthase, a cytochrome P450 santalene oxidase and a cytochrome P450 reductase. In another example, provided herein is a nucleic acid molecule that encodes a santalene synthase, a cytochrome P450 bergamotene oxidase and a cytochrome P450 reductase. Further, when the host cell is capable of producing FPP, the encoded polypeptides catalyze the production of santalols and/or bergamotols.

Other examples of fusion proteins include, but are not limited to, fusions of a signal sequence, a tag such as for localization, e.g. a his$_6$ tag or a myc tag, or a tag for purification, for example, a GST fusion, GFP fusion or CBP fusion, and a sequence for directing protein secretion and/or membrane association.

E. Methods for Producing Modified Cytochrome P450 and Cytochrome P450 Reductase Polypeptides and Encoding Nucleic Acid Molecules Provided are methods for producing modified cytochrome P450 and cytochrome P450 reductase polypeptides, including santalene oxidase and bergamotene oxidase polypeptides. The methods can be used to generate cytochrome P450s and cytochrome P450 reductases with desired properties, including, but not limited to, increased catalytic activity, increased selectivity, increased substrate specificity, increased substrate binding, increased stability, increased expression in a host cell, altered product distribution and/or altered substrate specificity. Modified cytochrome P450s and cytochrome P450 reductases can be produced using any method known in the art and, optionally, screened for the desired properties. In particular examples, modified cytochrome P450s and cytochrome P450 reductases with desired properties are generated by mutation in accord with the methods exemplified herein. Thus, provided herein are modified cytochrome P450s and cytochrome P450 reductases and nucleic acid molecules encoding the modified cytochrome P450s and cytochrome P450 reductases that are produced using the methods described herein.

Exemplary of the methods provided herein are those in which modified cytochrome P450s and cytochrome P450 reductases are produced by replacing one or more endogenous domains or regions of a first cytochrome P450 or cytochrome P450 reductase with the corresponding domain(s) or regions(s) from a second cytochrome P450 or cytochrome P450 reductase (i.e. heterologous domains or regions). In further examples, two or more endogenous domains or regions of a first cytochrome P450 or cytochrome P450 reductase are replaced with the corresponding heterologous domain(s) or regions(s) from two or more other cytochrome P450s or cytochrome P450 reductases, such as a second, third, fourth, fifth, sixth, seventh, eighth, ninth, or tenth cytochrome P450s or cytochrome P450 reductases. Thus, the resulting modified cytochrome P450 or cytochrome P450 reductase can include heterologous domains or regions from 1, 2, 3, 4, 5, 6, 7, 8, 9 or more different cytochrome P450s or cytochrome P450 reductases. In further examples, the methods also or instead include replacing one or more domains or regions of a first cytochrome P450 or cytochrome P450 reductase synthase with randomized amino acid residues.

Any cytochrome P450 or cytochrome P450 reductase can be used in the methods provided herein. The first cytochrome P450 or cytochrome P450 reductase (i.e. the cytochrome P450 or cytochrome P450 reductase to be modified) can be of the same or different class as the second (or third, fourth, fifth, etc.) cytochrome P450 or cytochrome P450 reductase (i.e. the cytochrome P450(s) or cytochrome P450 reductase(s) from which the heterologous domain(s) or region(s) is derived).

In practicing the methods provided herein, all or a contiguous portion of an endogenous domain of a first cytochrome P450 or cytochrome P450 reductase can be replaced with all or a contiguous portion of the corresponding heterologous domain from a second cytochrome P450 or cytochrome P450 reductase. For example, 3, 4, 5, 6, 7, 8, 9, 10 or more contiguous amino acids from a domain or region in a first cytochrome P450 or cytochrome P450 reductase can be replaced with 3, 4, 5, 6, 7, 8, 9, 10 or more contiguous amino acids from the corresponding region from a second cytochrome P450 or cytochrome P450 reductase. In some examples, one or more amino acid residues adjacent to the endogenous domain of the first cytochrome P450 or cytochrome P450 reductase also are replaced, and/or one or more amino acid residues adjacent to the heterologous domain also are used in the replacement. Further, the methods provided herein also include methods in which all or a contiguous portion of a first domain and all or a contiguous portion of a second adjacent domain are replaced with the corresponding domains (or portions thereof) from another cytochrome P450 or cytochrome P450 reductase.

Domains or regions that can be replaced include functional domains or structural domains. Exemplary domains or regions that can be replaced in a cytochrome P450 using the methods described herein include, but are not limited to, structural domains or regions corresponding to helix A, β strand 1-1, β strand 1-2, helix B, β strand 1-5, helix B', helix C, helix C', helix D, β strand 3-1, helix E, helix F, helix G, helix H, β strand 5-1, β strand 5-2, helix I, helix J, helix J', helix K, β strand 1-4, β strand 2-1, β strand 2-2, β strand 1-3, helix K', helix K", Heme domain, helix L, β strand 3-3, β strand 4-1, β strand 4-2 and β strand 3-2. Any one or more of these domains or regions, or a portion thereof, can be replaced with a corresponding domain from another cytochrome P450 using the methods provided herein. These domains are regions can be identified in any cytochrome P450 using methods well known in the art, such as, for example, by alignment using methods known to those of skill in the art (see, e.g., FIG. 5A-5B). Such methods typically maximize matches, and include methods such as using manual alignments and by using the numerous alignment programs available (for example, BLASTP) and others known to those of skill in the art. By aligning the sequences of the cytochrome P450 set forth in SEQ ID NO:50, and any other cytochrome P450, any of the domains or regions recited above can be identified in any cytochrome P450.

Exemplary domains or regions that can be replaced in a cytochrome P450 reductase using the methods described herein include, but are not limited to, structural domains or regions corresponding to α-helix A; β-strand 1; α-helix B; β-strand 2; α-helix C; β-strand 3; α-helix D; β-strand 4; α-helix E; β-strand 5; α-helix F; β-strand 6; β-strand 7; β-strand 8, β-strand 9; β-strand 10; α-helix G; β-strand 11; β-strand 12; β-strand 12'; α-helix H; α-helix I; α-helix J; α-helix K; α-helix M; β-strand 13; β-strand 14; β-strand 15; α-helix N; β-strand 16; β-strand 16'; β-strand 17; α-helix O; β-strand 18; α-helix P; β-strand 10; α-helix Q; α-helix R; β-strand 20; α-helix S; α-helix T; and β-strand 21. These domains are regions can be identified in any cytochrome P450 reductase using methods well known in the art, such as, for example, by alignment using methods known to those of skill in the art (see, e.g., FIGS. 3A-3C). Such methods typically maximize matches, and include methods such as using manual alignments and by using the numerous alignment programs available (for example, BLASTP) and others known to those of skill in the art. By aligning the sequences of the cytochrome P450 reductase set forth in SEQ ID NO:12, and any other cytochrome P450 reductase, any of the domains or regions recited above can be identified in any cytochrome P450 reductase.

In the methods provided herein, all or a contiguous portion of an endogenous domain of a first cytochrome P450 or cytochrome P450 reductase can be replaced with all or a contiguous portion of the corresponding heterologous domain from a second cytochrome P450 or cytochrome P450 reductase using an suitable recombinant method known in the art as discussed above in Sections C.4.c. and D.3.c.

F. Expression of Cytochrome P450 and Cytochrome P450 Reductase Polypeptides and Encoding Nucleic Acid Molecules Cytochrome P450 and cytochrome P450 reductase polypeptides and active fragments thereof, including cytochrome P450 santalene oxidase and cytochrome P450 bergamotene oxidase polypeptides, can be obtained by methods well known in the art for recombinant protein generation and expression. Such cytochrome P450 santalene oxidase polypeptides can be used to produce santalols from santalenes in a host cell from which the cytochrome P450 santalene oxidase is expressed or in vitro following purification of the cytochrome P450 santalene oxidase polypeptide. Such cytochrome P450 bergamotene oxidase polypeptides can be used to produce bergamotols from bergamotenes in a host cell from which the cytochrome P450 bergamotene oxidase is expressed or in vitro following purification of the cytochrome P450 bergamotene oxidase polypeptide. Such cytochrome P450 santalene oxidase and cytochrome P450 bergamotene oxidase polypeptides can be used to produce santalols or bergamotols from a suitable acyclic pyrophosphate precursor, such as FPP, in a host cell in which a santalene synthase and the cytochrome P450 are expressed. Any method known to those of skill in the art for identification of nucleic acids that encode desired genes can be used to obtain the nucleic acid encoding a cytochrome P450, such as a cytochrome P450 santalene oxidase or cytochrome P450 bergamotene oxidase, or cytochrome P450 reductase. For example, nucleic acid encoding unmodified or wild type cytochrome P450 polypeptides or cytochrome P450 reductase polypeptides can be obtained using well known methods from a plant source, such as *Santalum album*. Modified cytochrome P450 polypeptides or cytochrome P450 reductase polypeptides then can be engineered using any method known in the art for introducing mutations into unmodified or wild type cytochrome P450 polypeptides or cytochrome P450 reductase polypeptides, including any method described herein, such as random mutagenesis of the encoding nucleic acid by error-prone PCR, site-directed mutagenesis, overlap PCR, or other recombinant methods. The nucleic acids encoding the polypeptides then can be introduced into a host cell to be expressed heterologously.

In some examples, the cytochrome P450 polypeptides or cytochrome P450 reductase polypeptides provided herein, including cytochrome P450 santalene oxidase and cytochrome P450 bergamotene oxidase polypeptides, are produced synthetically, such as using sold phase or solution phase peptide synthesis.

1. Isolation of Nucleic Acid Encoding *Santalum album* Cytochrome P450 and Cytochrome P450 Reductase Polypeptides Nucleic acids encoding cytochrome P450s or cytochrome P450 reductases, such as cytochrome P450 santalene oxidase and cytochrome P450 bergamotene oxidase, can be cloned or isolated using any available methods known in the art for cloning and isolating nucleic acid molecules. Such methods include PCR amplification of nucleic acids and screening of libraries, including nucleic acid hybridization screening. In some examples, methods for amplification of nucleic acids can be used to isolate nucleic acid molecules encoding a cytochrome P450 or cytochrome P450 reductase polypeptide, including for example, polymerase chain reaction (PCR) methods. A nucleic acid containing material can be used as a starting material from which a cytochrome P450 or cytochrome P450 reductase-encoding nucleic acid molecule can be isolated. For example, DNA and mRNA preparations from *Santalum* species, including but not limited to *Santalum album* can be used to obtain cytochrome P450 or cytochrome P450 reductase genes. Nucleic acid libraries also can be used as a source of starting material. Primers can be designed to amplify a cytochrome P450 or cytochrome P450 reductase-encoding molecule, such as a cytochrome P450 santalene oxidase, cytochrome P450 bergamotene oxidase or cytochrome P450 reductase-encoding molecule. For example, primers can be designed based on known nucleic acid sequences encoding a cytochrome P450 such as those set forth in SEQ ID NOS:22-25. In another example, primers can be designed based on known nucleic acid sequences encoding a cytochrome P450 reductase such as those set forth in SEQ ID NOS:40-41. Nucleic acid molecules generated by amplification can be sequenced and confirmed to encode a cytochrome P450 or cytochrome P450 reductase polypeptide. The nucleic acid molecules provided herein can be used to identify related nucleic acid molecules in other species.

Additional nucleotide sequences can be joined to a cytochrome P450 or cytochrome P450 reductase-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to a cytochrome P450 or cytochrome P450 reductase-encoding nucleic acid molecule. Still further, nucleic acid encoding other moieties or domains also can be included so that the resulting synthase is a fusion protein. For example, nucleic acids encoding other enzymes, such as FPP synthase or santalene synthase, or protein purification tags, such as His or Flag tags.

2. Generation of Modified Nucleic Acid

Nucleic acid encoding a cytochrome P450 or cytochrome P450 reductase, such as a modified cytochrome P450 santalene oxidase polypeptides, modified cytochrome P450 bergamotene oxidase polypeptides or modified cytochrome P450 reductase polypeptides, can be prepared or generated using any method known in the art to effect mutation. Methods for modification include standard rational and/or random mutagenesis of encoding nucleic acid molecules (using e.g., error prone PCR, random site-directed saturation mutagenesis, DNA shuffling or rational site-directed mutagenesis, such as, for example, mutagenesis kits (e.g. QuikChange available from Stratagene)). In addition, routine recombinant DNA techniques can be used to generate nucleic acids encoding polypeptides that contain heterologous amino acid. For example, nucleic acid encoding chimeric polypeptides or polypeptides containing heterologous amino acid sequence, can be generated using a two-step PCR method, such as described above, and/or using restriction enzymes and cloning methodologies for routine subcloning of the desired chimeric polypeptide components.

Once generated, the nucleic acid molecules can be expressed in cells to generate modified cytochrome P450 or cytochrome P450 reductase polypeptides using any method known in the art. The modified cytochrome P450 or cytochrome P450 reductase polypeptides, such as modified cytochrome P450 santalene oxidase polypeptides, modified cytochrome P450 bergamotene oxidase polypeptides or modified cytochrome P450 reductase polypeptides, then can be assessed by screening for a desired property or activity, for example, for the ability to produce a terpenoid from a terpene substrate. In particular examples, modified cytochrome P450 or cytochrome P450 reductase polypeptides with desired properties are generated by mutation and screened for a property in accord with the examples exemplified herein. Typically, in instances where a modified cytochrome P450 santalene oxidase polypeptide is generated, the modified cytochrome P450 santalene oxidase polypeptides produce a santalol from a santalene. Typically, in instances where a modified cytochrome P450 bergamotene oxidase polypeptide is generated, the modified cytochrome P450 bergamotene oxidase polypeptides produce a bergamotol from a bergamotene.

3. Vectors and Cells

For recombinant expression of one or more of the cytochrome P450 or cytochrome P450 reductase polypeptides provided herein, including cytochrome P450 santalene oxidase, cytochrome P450 bergamotene oxidase or cytochrome P450 reductase polypeptides, the nucleic acid containing all or a portion of the nucleotide sequence encoding the synthase can be inserted into an appropriate expression vector, i.e., a vector that contains the necessary elements for the transcription and translation of the inserted protein coding sequence. Depending upon the expression system used, the necessary transcriptional and translational signals also can be supplied by the native promoter for a cytochrome P450 or cytochrome P450 reductase gene, and/or their flanking regions. Thus, also provided herein are vectors that contain nucleic acid encoding any cytochrome P450 or cytochrome P450 reductase polypeptide provided herein. Exemplary vectors include but are not limited to pESC-LEU, pESC-LEU2d, and pYEDP60.

Cells, including prokaryotic and eukaryotic cells, containing the vector also are provided. Also provided are host cells containing nucleic acid molecules encoding cytochrome P450 polypeptides provided herein, including cytochrome P450 santalene oxidases, cytochrome P450 bergamotene oxidases and cytochrome P450 reductases. Such cells and host cells include bacterial cells, yeast cells, fungal cells, Archea, plant cells, insect cells and animal cells. In particular examples, the cells or host cells are yeast cells, such as *Saccharomyces cerevisiae* or *Pichia pastoris* cells. In particular examples, the cells or host cells are *Saccharomyces cerevisiae* cells that express an acyclic pyrophosphate terpene precursor, such as farnesyl diphosphate (FPP). In some examples, the cells or host cells containing a cytochrome P450 provided herein can be modified to produce more FPP than an unmodified cell.

The cells are used to produce a cytochrome P450 or cytochrome P450 reductase polypeptide, such as cytochrome P450 santalene oxidase, cytochrome P450 bergamotene oxidase or cytochrome P450 reductase polypeptides, by growing the above-described cells under conditions whereby the encoded cytochrome P450 or cytochrome P450 reductase is expressed by the cell. In some examples, the cytochrome P450 polypeptide, such as cytochrome P450 santalene oxidase, cytochrome P450 bergamotene oxidase or cytochrome P450 reductase polypeptide, are heterologous to the cell. In some instances, the expressed cytochrome P450 and/or cytochrome P450 reductases are purified. In other instances, the expressed cytochrome P450s and cytochrome P450 reductases, convert one or more santalenes or bergamotenes to one or more santalols or bergamotols in the host cell. In some examples, a santalene synthase, a cytochrome P450 santalene oxidase and a cytochrome P450 reductase are expressed thereby converting the acyclic pyrophosphate terpene precursor FPP to santalol. In other examples, a santalene synthase, a cytochrome P450 bergamotene oxidase and a cytochrome P450 reductase are expressed thereby converting the acyclic pyrophosphate terpene precursor FPP to bergamotol.

Any method known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding a cytochrome P450 or cytochrome P450 reductase polypeptide or modified cytochrome P450 or cytochrome P450 reductase polypeptide, or domains, derivatives, fragments or homologs thereof, can be regulated by a second nucleic acid sequence so that the genes or fragments thereof are expressed in a host transformed with the recombinant DNA molecule(s). For example, expression of the proteins can be controlled by any promoter/enhancer known in the art. In one embodiment, the promoter is not native to the genes for a cytochrome P450 or cytochrome P450 reductase protein. Promoters that can be used include but are not limited to prokaryotic, yeast, mammalian and plant promoters. The type of promoter depends upon the expression system used, described in more detail below.

In one embodiment, a vector is used that contains a promoter operably linked to nucleic acids encoding a cytochrome P450 or cytochrome P450 reductase polypeptide or modified cytochrome P450 or cytochrome P450 reductase polypeptide, or a domain, fragment, derivative or homolog, thereof, one or more origins of replication, and optionally, one or more selectable markers (e.g., an antibiotic resistance gene). Vectors and systems for expression of cytochrome P450 or cytochrome P450 reductase polypeptides are described.

4. Expression Systems

Cytochrome P450 or cytochrome P450 reductase polypeptides, including cytochrome P450 santalene oxidase, cytochrome P450 bergamotene oxidase or cytochrome P450 reductase polypeptides (modified and unmodified) can be produced by any methods known in the art for protein production including in vitro and in vivo methods such as, for example, the introduction of nucleic acid molecules encoding the cytochrome P450 or cytochrome P450 reductase (e.g. cytochrome P450 santalene oxidase, cytochrome P450 bergamotene oxidase or cytochrome P450 reductase) into a host cell or host plant for in vivo production or expression from nucleic acid molecules encoding the cytochrome P450 or cytochrome P405 reductases (e.g. cytochrome P450 santalene oxidase, cytochrome P450 bergamotene oxidase or cytochrome P450 reductase) in vitro. Cytochrome P450 or cytochrome P450 reductase polypeptides such as cytochrome P450 santalene oxidase, cytochrome P450 bergamotene oxidase or cytochrome P450 reductase and modified cytochrome P450 santalene oxidase, cytochrome P450 bergamotene oxidase or cytochrome P450 reductase polypeptides can be expressed in any organism suitable to produce the required amounts and forms of a synthase polypeptide. Expression hosts include prokaryotic and eukaryotic organisms such as *E. coli*, yeast, plants, insect cells, mammalian cells, including human cell lines and transgenic animals. Expression hosts can differ in their protein production levels as well as the types of post-translational modifications that are present on the expressed proteins. The choice of expression host can be made based on these and other factors, such as regulatory and safety considerations, production costs and the need and methods for purification.

Expression in eukaryotic hosts can include expression in yeasts such as those from the *Saccharomyces* genus (e.g. *Saccharomyces cerevisiae*) and *Pichia* genus (e.g. *Pichia pastoris*), insect cells such as *Drosophila* cells and lepidopteran cells, plants and plant cells such as citrus, tobacco, corn, rice, algae, and *lemna*. Eukaryotic cells for expression also include mammalian cells lines such as Chinese hamster ovary (CHO) cells or baby hamster kidney (BHK) cells. Eukaryotic expression hosts also include production in transgenic animals, for example, including production in serum, milk and eggs.

Many expression vectors are available and known to those of skill in the art for the expression of a cytochrome P450 or cytochrome P450 reductase, such as cytochrome P450 santalene oxidase, cytochrome P450 bergamotene oxidase or cytochrome P450 reductase. Exemplary of expression vectors are those encoding a santalene synthase and a FPP synthase, including the vectors described in Example 7. The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells.

Cytochrome P450 or cytochrome P450 reductase polypeptides, including cytochrome P450 santalene oxidase, cytochrome P450 bergamotene oxidase or cytochrome P450 reductase polypeptides and modified cytochrome P450 santalene oxidase, cytochrome P450 bergamotene oxidase or cytochrome P450 reductase polypeptides, also can be used or expressed as protein fusions. For example, a fusion can be generated to add additional functionality to a polypeptide. Examples of fusion proteins include, but are not limited to, fusions of a signal sequence, a tag such as for localization, e.g. a his$_6$ tag or a myc tag, or a tag for purification, for example, a GST fusion, GFP fusion or CBP fusion, and a sequence for directing protein secretion and/or membrane association.

Methods of production of cytochrome P450 and cytochrome P450 reductase polypeptides, including cytochrome P450 santalene oxidase, cytochrome P450 bergamotene oxidase or cytochrome P450 reductase polypeptides, can include co-expression of an acyclic pyrophosphate terpene precursor, such as FPP, in the host cell. In some instances, the host cell naturally expresses FPP. Such a cell can be modified to express greater quantities of FPP (see e.g. U.S. Pat. Nos. 6,531,303, 6,689,593, 7,838,279 and 7,842,497). In other instances, a host cell that does not naturally produce FPP is modified genetically to produce FPP.

a. Prokaryotic Cells

Prokaryotes, especially *E. coli*, provide a system for producing large amounts of the cytochrome P450 and cytochrome P450 reductase polypeptides provided herein. Transformation of *E. coli* is a simple and rapid technique well known to those of skill in the art. Exemplary expression vectors for transformation of *E. coli* cells, include, for example, the pGEM expression vectors, the pQE expression vectors, and the pET expression vectors (see, U.S. Pat. No. 4,952,496; available from Novagen, Madison, Wis.; see, also literature published by Novagen describing the system). Such plasmids include pET 11a, which contains the T7lac promoter, T7 terminator, the inducible *E. coli* lac operator, and the lac repressor gene; pET 12a-c, which contains the T7 promoter, T7 terminator, and the *E. coli* ompT secretion signal; pET 15b and pET19b (Novagen, Madison, Wis.), which contain a His-Tag™ leader sequence for use in purification with a His column and a thrombin cleavage site that permits cleavage following purification over the column, the T7-lac promoter region and the T7 terminator; pACYC-Duet (Novagen, Madison, Wis.; SEQ ID NO:45).

Expression vectors for *E. coli* can contain inducible promoters that are useful for inducing high levels of protein expression and for expressing proteins that exhibit some toxicity to the host cells. Exemplary prokaryotic promoters include, for example, the β-lactamase promoter (Jay et al., (1981) *Proc. Natl. Acad. Sci. USA* 78:5543) and the tac promoter (DeBoer et al., (1983) *Proc. Natl. Acad. Sci. USA* 80:21-25); see also "Useful Proteins from Recombinant Bacteria": in Scientific American 242:79-94 (1980)). Examples of inducible promoters include the lac promoter, the tip promoter, the hybrid tac promoter, the T7 and SP6 RNA promoters and the temperature regulated $\lambda P_L$ promoter.

Cytochrome P450s and cytochrome P450 reductases, including cytochrome P450 santalene oxidase polypeptides, cytochrome P450 bergamotene oxidase polypeptides and cytochrome P450 reductase polypeptides, can be expressed in the cytoplasmic environment of *E. coli*. The cytoplasm is a reducing environment and for some molecules, this can result in the formation of insoluble inclusion bodies. Reducing agents such as dithiothreitol and β-mercaptoethanol and denaturants (e.g., such as guanidine-HCl and urea) can be used to resolubilize the proteins. An alternative approach is the expression of cytochrome P450s and cytochrome P450 reductases in the periplasmic space of bacteria which provides an oxidizing environment and chaperonin-like and disulfide isomerases leading to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility. Typically, temperatures between 25° C. and 37° C. are used. Mutations also can be used to increase solubility of expressed proteins. Typically, bacteria produce aglycosylated proteins.

b. Yeast Cells

Yeast systems, such as, but not limited to, those from the *Saccharomyces* genus (e.g. *Saccharomyces cerevisiae*), *Schizosaccharomyces pombe, Yarrowia lipolytica,*

*Kluyveromyces lactis*, and *Pichia pastoris* can be used to express the cytochrome P450s and cytochrome P450 reductases, such as cytochrome P450 santalene oxidase polypeptides, cytochrome P450 bergamotene oxidase polypeptides and cytochrome P450 reductase polypeptides and modified cytochrome P450 santalene oxidase polypeptides, cytochrome P450 bergamotene oxidase polypeptides and cytochrome P450 reductase polypeptides, provided herein. Yeast expression systems also can be used to produce terpenes whose reactions are catalyzed by the synthases. Yeast can be transformed with episomal replicating vectors or by stable chromosomal integration by homologous recombination. In some examples, inducible promoters are used to regulate gene expression. Exemplary promoter sequences for expression of cytochrome P450 and cytochrome P450 reductase polypeptides in yeast include, among others, promoters for metallothionine, 3-phosphoglycerate kinase (Hitzeman et al. (1980) *J. Biol. Chem.* 255:2073), or other glycolytic enzymes (Hess et al. (1968) *J. Adv. Enzyme Reg.* 7:149; and Holland et al. (1978) *Biochem.* 17:4900), such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other suitable vectors and promoters for use in yeast expression are further described in Hitzeman, EPA-73,657 or in Fleer et al. (1991) *Gene,* 107:285-195; and van den Berg et al. (1990) *Bio/Technology,* 8:135-139. Another alternative includes, but is not limited to, the glucose-repressible ADH2 promoter described by Russell et al. (*J. Biol. Chem.* 258:2674, 1982) and Beier et al. (*Nature* 300:724, 1982), or a modified ADH1 promoter. Shuttle vectors replicable in yeast and *E. coli* can be constructed by, for example, inserting DNA sequences from pBR322 for selection and replication in *E. coli* (Amp$^r$ gene and origin of replication) into the above-described yeast vectors.

Yeast expression vectors can include a selectable marker such as LEU2, TRP1, HIS3, and URA3 for selection and maintenance of the transformed DNA. Exemplary vectors include pESC-Leu, pESC-Leu2D, pESC-His and pYEDP60. Proteins expressed in yeast are often soluble and co-expression with chaperonins, such as Bip and protein disulfide isomerase, can improve expression levels and solubility. Additionally, proteins expressed in yeast can be directed for secretion using secretion signal peptide fusions such as the yeast mating type alpha-factor secretion signal from *Saccharomyces cerevisiae* and fusions with yeast cell surface proteins such as the Aga2p mating adhesion receptor or the *Arxula adeninivorans* glucoamylase. A protease cleavage site (e.g., the Kex-2 protease) can be engineered to remove the fused sequences from the polypeptides as they exit the secretion pathway.

Yeast naturally express the required proteins, including FPP synthase (ERG20; which can produce FPP) for the mevalonate-dependent isoprenoid biosynthetic pathway. Thus, expression of the cytochrome P450s and cytochrome P450 reductases, including cytochrome P450 santalene oxidase polypeptides, cytochrome P450 bergamotene oxidase polypeptides and cytochrome P450 reductase polypeptides provided herein, in yeast cells can result in the production of sesquiterpenes, such as santalenes and bergamotenes from FPP, and santalols and bergamotols. Exemplary yeast cells for the expression of cytochrome P450s and cytochrome P450 reductases, including cytochrome P450 santalene oxidase polypeptides, cytochrome P450 bergamotene oxidase polypeptides and cytochrome P450 reductase polypeptides, include yeast modified to express increased levels of FPP. For example, yeast cells can be modified to produce less squalene synthase or less active squalene synthase (e.g. erg9 mutants; see e.g. U.S. Pat. Nos. 6,531,303 and 6,689,593). This results in accumulation of FPP in the host cell at higher levels compared to wild type yeast cells, which in turn can result in increased yields of sesquiterpenes and sesquiterpenoids (e.g. santalenes, bergamotenes, santalols and bergamotols). In another example, yeast cells can be modified to produce more FPP synthase by introduction of a FPP synthase gene, such as SaFPPS from *Santalum album* (SEQ ID NO:18). In some examples, the native FPP gene in such yeast can be deleted. Other modifications that enable increased production of FPP in yeast include, for example, but are not limited to, modifications that increase production of acetyl CoA, inactivate genes that encode enzymes that use FPP and GPP as substrate and overexpress HMG-CoA reductases, as described in U.S. Pat. No. 7,842,497. Exemplary modified yeast cells include, but are not limited to, YPH499 (MATa, ura3-52, lys2-801, ade2-101, trp1-Δ63, his3-Δ200, leu2-Δ1), WAT11 (MATa, ade2-1, his3-11,-15; leu2-3,-112, ura3-1, canR, cyr+; containing chromosomally integrated *Arabidopsis* NADPH-dependent P450 reductase ATR1; see Pompon et al. (1995) *Toxicol Lett* 82-83:815-822; Ro et al. (2005) *Proc Natl Acad Sci USA* 102:8060-8065); and BY4741 (MATa, his3Δ1, leu2Δ0, met15Δ0, ura3Δ0; ATCC #201388), modified *Saccharomyces cerevisiae* strains CALI5-1 (ura3, leu2, his3, trp1, Δ erg9::HIS3, HMG2cat/TRP1::rDNA, dpp1, sue), ALX7-95 (ura3, his3, trp1, Δerg9::HIS3, HMG2cat/TRP1::rDNA, dpp1 sue), ALX11-30 (ura3, trp1, erg9$^{def}$25, HMG2cat/TRP1::rDNA, dpp1, sue), which are known and described in one or more of U.S. Pat. Nos. 6,531,303, 6,689,593, 7,838,279, 7,842,497, and U.S. Pat. publication Nos. 20040249219 and 20110189717.

c. Plants and Plant Cells

Transgenic plant cells and plants can be used for the expression of cytochrome P450s and cytochrome P450 reductases, including cytochrome P450 santalene oxidase polypeptides, cytochrome P450 bergamotene oxidase polypeptides and cytochrome P450 reductase polypeptides provided herein. Expression constructs are typically transferred to plants using direct DNA transfer such as microprojectile bombardment and PEG-mediated transfer into protoplasts, and with *agrobacterium*-mediated transformation. Expression vectors can include promoter and enhancer sequences, transcriptional termination elements, and translational control elements. Expression vectors and transformation techniques are usually divided between dicot hosts, such as *Arabidopsis* and tobacco, and monocot hosts, such as corn and rice. Examples of plant promoters used for expression include the cauliflower mosaic virus promoter, the nopaline synthase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce proteins (see, for example, Mayfield et al. (2003) *Proc Natl Acad Sci USA* 100:438-442). Transformed plants include, for example, plants selected from the genera *Nicotiana, Solanum, Sorghum, Arabidopsis, Medicago* (alfalfa), *Gossypium* (cotton) and *Brassica* (rape). In some examples, the plant belongs to the species of *Nicotiana tabacum*, and is transformed with vectors that overexpress a cytochrome P450 and/or a cytochrome P450 reductase, such as described in U.S. Pat. Pub. No. 20090123984 and U.S. Pat. No. 7,906,710.

d. Insects and Insect Cells

Insects and insect cells, particularly a baculovirus expression system, can be used for expressing cytochrome P450s and cytochrome P450 reductases, including cytochrome P450 santalene oxidase polypeptides, cytochrome P450 bergamotene oxidase polypeptides and cytochrome P450 reductase polypeptides provided herein (see, for example, Muneta et al. (2003) *J. Vet. Med. Sci.* 65(2):219-223). Insect cells and insect larvae, including expression in the haemolymph, express high levels of protein and are capable of most of the post-translational modifications used by higher eukaryotes. Baculoviruses have a restrictive host range which improves the safety and reduces regulatory concerns of eukaryotic expression. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda* (see, e.g., Mizutani and Ohta (1998) *Plant Physiology* 116:357-367), *Pseudaletia unipuncta* (A7S) and *Danaus plexippus* (DpN1). For high level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schnieder 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

e. Mammalian Expression

Mammalian expression systems can be used to express cytochrome P450s and cytochrome P450 reductases, including cytochrome P450 santalene oxidase polypeptides, cytochrome P450 bergamotene oxidase polypeptides and cytochrome P450 reductase polypeptides provided herein and also can be used to produce terpenes whose reactions are catalyzed by the synthases. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, and the long terminal repeat of Rous sarcoma virus (RSV). These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha-fetoprotein, alpha 1-antitrypsin, beta-globin, myelin basic protein, myosin light chain-2 and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase and thymidine kinase. Fusion with cell surface signaling molecules such as TCR-ζ and Fc$_\epsilon$RI-γ can direct expression of the proteins in an active state on the cell surface.

Many cell lines are available for mammalian expression including mouse, rat human, monkey, and chicken and hamster cells. Exemplary cell lines include, but are not limited to, BHK (i.e. BHK-21 cells), 293-F, CHO, CHO Express (CHOX; Excellgene), Balb/3T3, HeLa, MT2, mouse NS0 (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells. Cell lines also are available adapted to serum-free media which facilitates purification of secreted proteins from the cell culture media. One such example is the serum free EBNA-1 cell line (Pham et al. (2003) *Biotechnol. Bioeng.* 84:332-42).

f. Exemplary Host Cells

Exemplary host cells for expression of a cytochrome p450 polypeptide provided herein, such as a cytochrome P450 santalene oxidase, cytochrome P450 bergamotene oxidase or cytochrome P450 reductase, include prokaryotic and eukaryotic cells. Typically, the host cell produces an acyclic pyrophosphate terpene precursor. For example, the host cell produces farnesyl diphosphate. In some examples, the host cell can be a cell line that produces FPP as part of the mevalonate-dependent isoprenoid biosynthetic pathway (e.g. fungi, including yeast cells, and animal cells) or the mevalonate-independent isoprenoid biosynthetic pathway (e.g. bacteria and higher plants). In some examples, the host cell produces farnesyl diphosphate natively. In other examples, the host cell is modified to produce more farnesyl diphosphate compared to an unmodified cell. Exemplary host cells include bacteria, yeast, insect, plant and mammalian cells. In particular examples, the host cell is a yeast cell. For example, the yeast cell is a *Saccharomyces* genus cell, such as a *Saccharomyces cerevisiae* cell. In another example, the yeast cell is a *Pichia* genus cell, such as a *Pichia pastoris* cell. In other particular examples, the host cell is an *Escherichia coli* cell.

In particular examples, the host cell has been modified to overproduce FPP. Exemplary of such cells are modified yeast cells. For example, yeast cells that have been modified to produce less squalene synthase or less active squalene synthase (e.g. erg9 mutants; see e.g. U.S. Pat. Nos. 6,531,303 and 6,689,593) are useful in the methods provided herein to produce labdenediol diphosphate. Reduced squalene synthase activity results in accumulation of FPP in the host cell at higher levels compared to wild type yeast cells. Exemplary modified yeast cells include, but are not limited to, modified *Saccharomyces cerevisiae* strains YPH499 (MATa, ura3-52, lys2-801, ade2-101, trp1-Δ63, his3-Δ200, leu2-Δ1), WAT11 (MATa, ade2-1, his3-11,-15; leu2-3,-112, ura3-1, canR, cyr+; containing chromosomally integrated *Arabidopsis* NADPH-dependent P450 reductase ATR1; see Pompon et al. (1995) *Toxicol Lett* 82-83:815-822; Ro et al. (2005) *Proc Natl Acad Sci USA* 102:8060-8065); and BY4741 (MATa, his3Δ1, leu2Δ0, met15Δ0, ura3Δ0; ATCC #201388). The use of such host cells for expression of a cytochrome P450 polypeptide provided herein allows for increased yields of the precursor FPP and thus allows for increased yields of santalenes and bergamotenes.

Provided herein are host cells containing any cytochrome P450 polypeptide or catalytically active fragment thereof provided herein. Provided herein are host cells containing a cytochrome P450 polypeptide or a catalytically active fragment thereof. In some examples, the host cell contains a cytochrome P450 polypeptide or catalytically active fragment thereof has a sequence of nucleotides set forth in any of SEQ ID NOS:1-5 and 67-72. In other examples, the host cell contains a cytochrome P450 polypeptide or catalytically active fragment thereof has a sequence of nucleic acids that has at least 60%, 65%, 70%, 75%, 80%, 85%, 90%, 91%, 92%, 93%, 94%, 95%, 96%, 97%, 98%, or 99% percent sequence identity to a sequence of nucleotides set forth in any of SEQ ID NOS:1-5 and 67-72. In other examples, the host cell contains nucleic acid encoding a cytochrome P450 polypeptide or catalytically active fragment thereof that has a sequence of amino acids set forth in any of SEQ ID NOS:6-9, 50 and 73-78. In yet other examples, the host cell contains nucleic acid encoding a cytochrome P450 polypeptide or catalytically active fragment thereof that has at least 60%, 65%, 70%, 75%, 80%, 85%, 90%, 91%, 92%, 93%, 94%, 95%, 96%, 97%, 98%, or 99% percent sequence identity to a sequence of amino acids set forth in any of SEQ ID NOS:6-9, 50 and 73-78.

Provided herein are host cells containing a cytochrome P450 santalene oxidase or a catalytically active fragment thereof. In some examples, the host cell contains a cytochrome P450 santalene oxidase or catalytically active fragment thereof has a sequence of nucleotides set forth in any of SEQ ID NOS:3, 68, 69, 70 or 71. In other examples, the host cell contains a cytochrome P450 santalene oxidase or catalytically active fragment thereof has a sequence of nucleic acids that has at least 60%, 65%, 70%, 75%, 80%, 85%, 90%, 91%, 92%, 93%, 94%, 95%, 96%, 97%, 98%, or 99% percent sequence identity to a sequence of nucleotides set forth in any of SEQ ID NOS:3, 68, 69, 70 or 71. In other examples, the host cell contains nucleic acid encoding a cytochrome P450 santalene oxidase or catalytically active fragment thereof that has a sequence of amino acids set forth in any of SEQ ID NOS:7, 74, 75, 76 or 77. In yet other examples, the host cell contains nucleic acid encoding a cytochrome P450 santalene oxidase or catalytically active fragment thereof that has at least 60%, 65%, 70%, 75%, 80%, 85%, 90%, 91%, 92%, 93%, 94%, 95%, 96%, 97%, 98%, or 99% percent sequence identity to a sequence of amino acids set forth in any of SEQ ID NOS:7, 74, 75, 76 or 77.

Provided herein are host cells containing a cytochrome P450 bergamotene oxidase or a catalytically active fragment thereof. In some examples, the host cell contains a cytochrome P450 bergamotene oxidase or catalytically active fragment thereof has a sequence of nucleotides set forth in any of SEQ ID NOS:2, 4, 5 or 67. In other examples, the host cell contains a cytochrome P450 bergamotene oxidase or catalytically active fragment thereof has a sequence of nucleic acids that has at least 60%, 65%, 70%, 75%, 80%, 85%, 90%, 91%, 92%, 93%, 94%, 95%, 96%, 97%, 98%, or 99% percent sequence identity to a sequence of nucleotides set forth in any of SEQ ID NOS:2, 4, 5 or 67. In other examples, the host cell contains nucleic acid encoding a cytochrome P450 bergamotene oxidase or catalytically active fragment thereof that has a sequence of amino acids set forth in any of SEQ ID NOS:6, 8, 9 or 73. In yet other examples, the host cell contains nucleic acid encoding a cytochrome P450 bergamotene oxidase or catalytically active fragment thereof that has at least 60%, 65%, 70%, 75%, 80%, 85%, 90%, 91%, 92%, 93%, 94%, 95%, 96%, 97%, 98%, or 99% percent sequence identity to a sequence of amino acids set forth in any of SEQ ID NOS:6, 8, 9 or 73.

In some examples, any of the host cells provided herein containing a cytochrome P450 or catalytically active fragment thereof can further contain a terpene synthase. Provided herein are host cells containing a cytochrome P450 or catalytically active fragment thereof and a terpene synthase. In such examples, the terpene synthase can be a santalene synthase. For example, the terpene synthase is a santalene synthase having a sequence of amino acids set forth in any of SEQ ID NOS:17, 52 or 53, or a santalene synthase having at least 80%, 85%, 86%, 87%, 88%, 89%, 90%, 91%, 92%, 93%, 94%, 95%, 96%, 97%, 98%, 99% sequence identity to a sequence of amino acids set forth in any of SEQ ID NOS:17, 52 or 53, or a nucleic acid molecule encoding a santalene synthase. The encoding nucleic acid molecule has a sequence of nucleotides set forth in any of SEQ ID NOS:16, 59 or 60, or a nucleic acid molecule encoding a santalene synthase. The nucleic acid molecule has at least 80%, 85%, 86%, 87%, 88%, 89%, 90%, 91%, 92%, 93%, 94%, 95%, 96%, 97%, 98%, 99% percent identity to a sequence of nucleotides set forth in any of SEQ ID NOS:16, 59 or 60.

Provided herein are host cells containing a cytochrome P450 or catalytically active fragment thereof and a santalene synthase having a sequence of amino acids set forth in any of SEQ ID NOS:17, 52 or 53, or a santalene synthase having at least 80%, 85%, 86%, 87%, 88%, 89%, 90%, 91%, 92%, 93%, 94%, 95%, 96%, 97%, 98%, 99% sequence identity to a sequence of amino acids set forth in any of SEQ ID NOS:17, 52 or 53, or a nucleic acid molecule encoding a santalene synthase. The nucleic acid molecule has a sequence of nucleotides set forth in any of SEQ ID NOS:16, 59 or 60, or a nucleic acid molecule encoding a santalene synthase. The nucleic acid molecule has at least 80%, 85%, 86%, 87%, 88%, 89%, 90%, 91%, 92%, 93%, 94%, 95%, 96%, 97%, 98%, 99% percent identity to a sequence of nucleotides set forth in any of SEQ ID NOS:16, 59 or 60. In such examples, the cytochrome P450 or catalytically active fragment thereof is a cytochrome P450 polypeptide or catalytically active fragment thereof has a sequence of nucleotides set forth in any of SEQ ID NOS:1-5 and 67-72, or a cytochrome P450 polypeptide or catalytically active fragment thereof has a sequence of nucleic acids that has at least 60%, 65%, 70%, 75%, 80%, 85%, 90%, 91%, 92%, 93%, 94%, 95%, 96%, 97%, 98%, or 99% percent sequence identity to a sequence of nucleotides set forth in any of SEQ ID NOS:1-5 and 67-72, or a nucleic acid molecule encoding a cytochrome P450 polypeptide or catalytically active fragment thereof that has a sequence of amino acids set forth in any of SEQ ID NOS:6-9, 50 and 73-78, or a nucleic acid molecule encoding a cytochrome P450 polypeptide or catalytically active fragment thereof that has at least 60%, 65%, 70%, 75%, 80%, 85%, 90%, 91%, 92%, 93%, 94%, 95%, 96%, 97%, 98%, or 99% percent sequence identity to a sequence of amino acids set forth in any of SEQ ID NOS:6-9, 50 and 73-78.

In one example, provided herein is a host cell that contains a cytochrome P450 polypeptide or catalytically active fragment thereof and a santalene synthase. In another example, provided herein is a host cell that contains a cytochrome P450 santalene oxidase or catalytically active fragment thereof and a santalene synthase. In yet another example, provided herein is a host cell that contains a cytochrome P450 bergamotene oxidase or catalytically active fragment thereof and a santalene synthase. Also provided herein are host cells containing a cytochrome P450 or catalytically active fragment thereof and a terpene synthase that further contain a cytochrome P450 reductase or catalytically active fragment thereof. In such examples, the terpene synthase can be a santalene synthase. For example, the terpene synthase is a santalene synthase having a sequence of amino acids set forth in any of SEQ ID NOS:17, 52 or 53, or a santalene synthase having at least 80%, 85%, 86%, 87%, 88%, 89%, 90%, 91%, 92%, 93%, 94%, 95%, 96%, 97%, 98%, 99% sequence identity to a sequence of amino acids set forth in any of SEQ ID NOS:17, 52 or 53, or a nucleic acid molecule encoding a santalene synthase. The nucleic acid molecule has a sequence of nucleotides set forth in any of SEQ ID NOS:16, 59 or 60, or a nucleic acid molecule encoding a santalene synthase. The nucleic acid molecule has at least 80%, 85%, 86%, 87%, 88%, 89%, 90%, 91%, 92%, 93%, 94%, 95%, 96%, 97%, 98%, 99% percent identity to a sequence of nucleotides set forth in any of SEQ ID NOS:16, 59 or 60. In such examples, the cytochrome P450 reductase or catalytically active fragment thereof is a cytochrome P450 reductase or catalytically active fragment thereof has a sequence of nucleotides set forth in any of SEQ ID NOS:10 or 11, or a cytochrome P450 reductase or catalytically active fragment thereof has a sequence of nucleic acids that has at least 60%, 65%, 70%, 75%, 80%, 85%, 90%, 91%, 92%, 93%, 94%, 95%, 96%, 97%, 98%, or 99% percent sequence identity to a sequence of nucleotides set forth in any of SEQ ID NOS:10 or 11, or a nucleic acid molecule encoding a cytochrome P450 reductase or catalytically active fragment thereof that has a sequence of amino acids set forth in any of SEQ ID NOS:12-15 or a nucleic acid molecule encoding a cytochrome P450 reductase or catalytically active fragment thereof that has at least 60%, 65%, 70%, 75%, 80%, 85%, 90%, 91%, 92%, 93%, 94%, 95%, 96%, 97%, 98%, or 99% percent sequence identity to a sequence of amino acids set forth in any of SEQ ID NOS:12-15. In such examples, the cytochrome P450 or catalytically active fragment thereof is a cytochrome P450 polypeptide or catalytically active fragment thereof has a sequence of nucleotides set forth in any of SEQ ID NOS:1-5 and 67-72, or a cytochrome P450 polypeptide or catalytically active fragment thereof has a sequence of nucleic acids that has at least 60%, 65%, 70%, 75%, 80%, 85%, 90%, 91%, 92%, 93%, 94%, 95%, 96%, 97%, 98%, or 99% percent sequence identity to a sequence of nucleotides set forth in any of SEQ ID NOS:1-5 and 67-72, or a nucleic acid molecule encoding a cytochrome P450 polypeptide or catalytically active fragment thereof that has a sequence of amino acids set forth in any of SEQ ID NOS:6-9, 50 and 73-78, or a nucleic acid molecule encoding a cytochrome P450 polypeptide or catalytically active fragment thereof that has at least 60%, 65%, 70%, 75%, 80%, 85%, 90%, 91%, 92%, 93%, 94%, 95%, 96%, 97%, 98%, or 99% percent sequence identity to a sequence of amino acids set forth in any of SEQ ID NOS:6-9, 50 and 73-78.

In one example, provided herein is a host cell containing a cytochrome P450 polypeptide or catalytically active fragment thereof, a santalene synthase and a cytochrome P450 reductase or catalytically active fragment thereof. In another example, provided herein is a host cell containing a cytochrome P450 santalene oxidase or catalytically active fragment thereof, a santalene synthase and a cytochrome P450 reductase or catalytically active fragment thereof. In yet another example, provided herein is a host cell containing a cytochrome P450 bergamotene oxidase or catalytically active fragment thereof, a santalene synthase and a cytochrome P450 reductase or catalytically active fragment thereof.

Provided herein are host cells containing a cytochrome P450 reductase or a catalytically active fragment thereof. In some examples, the host cell contains a cytochrome P450 reductase or catalytically active fragment thereof has a sequence of nucleotides set forth in any of SEQ ID NOS:10 or 11. In other examples, the host cell contains a cytochrome P450 reductase or catalytically active fragment thereof has a sequence of nucleic acids that has at least 60%, 65%, 70%, 75%, 80%, 85%, 90%, 91%, 92%, 93%, 94%, 95%, 96%, 97%, 98%, or 99% percent sequence identity to a sequence of nucleotides set forth in any of SEQ ID NOS:10 or 11. In other examples, the host cell contains nucleic acid encoding a cytochrome P450 reductase or catalytically active fragment thereof that has a sequence of amino acids set forth in any of SEQ ID NOS:12-15. In yet other examples, the host cell contains nucleic acid encoding a cytochrome P450 reductase or catalytically active fragment thereof that has at least 60%, 65%, 70%, 75%, 80%, 85%, 90%, 91%, 92%, 93%, 94%, 95%, 96%, 97%, 98%, or 99% percent sequence identity to a sequence of amino acids set forth in any of SEQ ID NOS:12-15.

In some examples, the host cell containing a cytochrome P450 reductase or catalytically active fragment thereof further contains a cytochrome P450 or catalytically active fragment thereof. For example, provided herein are host cells containing a cytochrome P450 reductase or a catalytically active fragment thereof and a cytochrome P450 or catalytically active fragment thereof. In such examples, the cytochrome P450 or catalytically active fragment thereof is a cytochrome P450 polypeptide or catalytically active fragment thereof has a sequence of nucleotides set forth in any of SEQ ID NOS:1-5 and 67-72, or a cytochrome P450 polypeptide or catalytically active fragment thereof has a sequence of nucleic acids that has at least 60%, 65%, 70%, 75%, 80%, 85%, 90%, 91%, 92%, 93%, 94%, 95%, 96%, 97%, 98%, or 99% percent sequence identity to a sequence of nucleotides set forth in any of SEQ ID NOS:1-5 and 67-72, or a nucleic acid molecule encoding a cytochrome P450 polypeptide or catalytically active fragment thereof that has a sequence of amino acids set forth in any of SEQ ID NOS:6-9, 50 and 73-78, or a nucleic acid molecule encoding a cytochrome P450 polypeptide or catalytically active fragment thereof that has at least 60%, 65%, 70%, 75%, 80%, 85%, 90%, 91%, 92%, 93%, 94%, 95%, 96%, 97%, 98%, or 99% percent sequence identity to a sequence of amino acids set forth in any of SEQ ID NOS:6-9, 50 and 73-78.

In one example, provided herein is a host cell containing a cytochrome P450 polypeptide or catalytically active fragment thereof and a cytochrome P450 reductase or catalytically active fragment thereof. In another example, provided herein is a host cell containing a cytochrome P450 santalene oxidase or catalytically active fragment thereof and a cytochrome P450 reductase or catalytically active fragment thereof. In yet another example, provided herein is a host cell containing a cytochrome P450 bergamotene oxidase or catalytically active fragment thereof and a cytochrome P450 reductase or catalytically active fragment thereof.

5. Purification

Methods for purification of cytochrome P450s and cytochrome P450 reductases, such as cytochrome P450 santalene oxidase polypeptides, cytochrome P450 bergamotene oxidase polypeptides and cytochrome P450 reductase polypeptides, from host cells depend on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary the proteins can be extracted and further purified using standard methods in the art.

Cytochrome P450s and cytochrome P450 reductases, including cytochrome P450 santalene oxidase polypeptides, cytochrome P450 bergamotene oxidase polypeptides and cytochrome P450 reductase polypeptides, can be purified using standard protein purification techniques known in the art including but not limited to, SDS-PAGE, size fraction and size exclusion chromatography, ammonium sulfate precipitation, chelate chromatography and ionic exchange chromatography. Expression constructs also can be engineered to add an affinity tag such as a myc epitope, GST fusion or $His_6$ and affinity purified with myc antibody, glutathione resin, and Ni-resin, respectively, to a protein. Purity can be assessed by any method known in the art including gel electrophoresis and staining and spectrophotometric techniques.

6. Fusion Proteins

Fusion proteins containing a cytochrome P450s and cytochrome P450 reductases, including cytochrome P450 santalene oxidase polypeptides, cytochrome P450 bergamotene oxidase polypeptides and cytochrome P450 reductase polypeptides, and one or more other polypeptides also are provided. Linkage of a cytochrome P450 or cytochrome P450 reductase polypeptide with another polypeptide can be effected directly or indirectly via a linker. In one example, linkage can be by chemical linkage, such as via heterobifunctional agents or thiol linkages or other such linkages. Fusion also can be effected by recombinant means. Fusion of a cytochrome P450 or cytochrome P450 reductase, such as a cytochrome P450 santalene oxidase polypeptide, cytochrome P450 bergamotene oxidase polypeptide and cytochrome P450 reductase polypeptide, to another polypeptide can be to the N- or C-terminus of the cytochrome P450 santalene oxidase polypeptide, cytochrome P450 bergamotene oxidase polypeptide and cytochrome P450 reductase polypeptide.

A fusion protein can be produced by standard recombinant techniques. For example, DNA fragments coding for the different polypeptide sequences can be ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel et al. (eds.) Current Protocols in Molecular Biology, John Wiley & Sons, 1992). Moreover, many expression vectors are commercially available that already encode a fusion moiety (e.g., a GST polypeptide). A cytochrome P450 santalene oxidase polypeptide-encoding nucleic acid can be cloned into such an expression vector such that the fusion moiety is linked in-frame to the cytochrome P450 santalene oxidase protein. A cytochrome P450 bergamotene oxidase polypeptide-encoding nucleic acid can be cloned into such an expression vector such that the fusion moiety is linked in-frame to the cytochrome P450 bergamotene oxidase protein. In some examples, a cytochrome P450 polypeptide-encoding nucleic acid can be cloned into such an expression vector such that the cytochrome P450 is linked in frame to a santalene synthase polypeptide-encoding nucleic acid. For example, a cytochrome P450 santalene oxidase or bergamotene oxidase polypeptide-encoding nucleic acid can be cloned into such an expression vector such that the cytochrome P450 santalene oxidase or bergamotene oxidase is linked in frame to a santalene synthase polypeptide-encoding nucleic acid. The cytochrome P450 and santalene synthases can be linked directly, without a linker, or alternatively, linked indirectly in-frame with a linker.

G. Methods for Producing Terpenoids and Methods For Detecting Such Products and The Activity of the Cytochrome P450 and Cytochrome P450 Reductase Polypeptides The cytochrome P450 polypeptides provided herein can be used to, and assessed for their ability to, produce terpenoids, including monoterpenoids, sesquiterpenoids and diterpenoids, from any suitable terpene substrate, including monoterpenes, sesquiterpenes and diterpenes. Typically, the cytochrome P450 santalene oxidases provided herein produce santalols from santalenes and the cytochrome P450 bergamotene oxidases provided herein produce bergamotols from bergamotenes. Any method known to one of skill in the art can be used to produce terpenoids catalyzed by the cytochrome P450 polypeptides provided herein. The ability of the cytochrome P450 polypeptides provided herein to catalyze the formation of terpenoids from terpene substrates can be assessed using these methods. Terpenoid products analyzed by GC-MS and can be identified based on matches of the MS fragmentation patterns with entries in the NIST and Wiley libraries (for example, as described in Example 6 below).

The cytochrome P450 reductase polypeptides provided herein can be used to, and assessed for their ability to, transfer two electrons from NADPH to any suitable electron receptor, including cytochrome P450s, cytochrome c, heme oxygenases, cytochrome $b_5$ and squalene epoxidases.

Other activities and properties of the cytochrome P450 and cytochrome P450 reductase polypeptides, such as the cytochrome P450 santalene oxidases, cytochrome P450 bergamotene oxidases and cytochrome P450 reductases provided herein, also can be assessed using methods and assays well known in the art. In addition to assessing the activity of the cytochrome P450 and cytochrome P450 reductase polypeptides and their ability to catalyze the formation of terpenoids, the kinetics of the reaction, increased substrate specificity, altered substrate utilization and/or altered product distribution (as compared to another cytochrome P450 and cytochrome P450 reductase polypeptide) can be assessed using methods well known in the art. For example, the amount and type of terpenoids produced from santalenes or bergamotenes by the santalene oxidase and bergamotene oxidase polypeptides provided herein can be assessed by gas chromatography methods (e.g. GC-MS), such as those described in Example 6, and compared to the MS fragmentation patterns with entries in the NIST and Wiley libraries (see Example 6). Products can also be identified by comparison with compounds of authentic sandalwood oil.

Provided below are methods for the production of santalols, including (Z)-α-santalol, (E)-α-santalol, (Z)-β-santalol, (E)-β-santalol, (Z)-epi-β-santalol and (E)-epi-β-santalol, and (E)-α-trans-bergamotol and (Z)-α-trans-bergamotol, where production of the santalols and bergamotols is catalyzed by the cytochrome P450 and cytochrome P450 reductase polypeptides provided herein. Also provided herein are methods for assessing the activity of the cytochrome P450 and cytochrome P450 reductase polypeptides provided herein.

1. Synthesis of Santalols and Bergamotols

The cytochrome P450 santalene oxidase and cytochrome P450 bergamotene oxidase polypeptides provided herein can be used to catalyze the formation of santalols and bergamotols from the terpene substrates santalenes and bergamotenes. In some examples, the cytochrome P450 santalene oxidases are expressed in cells that produce or overexpress a santalene synthase and FPP, such that santalols are produced as described elsewhere herein. In other examples, the cytochrome P450 bergamotene oxidases are expressed in cells that produce of overexpress a santalene synthase, such that bergamotols are produced as described elsewhere herein. In other examples, the cytochrome P450 santalene oxidase and cytochrome P450 bergamotene oxidase polypeptides provided herein are expressed and purified form any suitable host cells, such as any described in Section E. The purified cytochrome P450 santalene oxidase and cytochrome P450 bergamotene oxidase polypeptides are then combined in vitro with santalenes and bergamotenes to produce santalols and bergamotols.

a. Oxidation of Santalenes and Bergamotenes

In some examples, the cytochrome P450 santalene oxidase polypeptides provided herein are overexpressed and purified as described in Section E above. The cytochrome P450 santalene oxidase is then incubated with one or more terpene substrates, including α-santalene, β-santalene, epi-β-santalene and/or α-trans-bergamotene, and one or more of α-santalol, β-santalol and epi-β-santalol, and α-trans-bergamotol, such as (E)-α-santalol, (Z)-α-santalol, (E)-β-santalol, (Z)-β-santalol, (E)-epi-β-santalol, (Z)-epi-β-santalol, (Z)-α-trans-bergamotol and (E)-α-trans-bergamotol, are produced. Alternatively, the cytochrome P450 santalene oxidase polypeptides provided herein expressed in host cells that also produce terpene substrates, including α-santalene, β-santalene, epi-β-santalene and/or α-trans-bergamotene, resulting in the production of one or more of α-santalol, β-santalol and epi-β-santalol, and α-trans-bergamotol, such as (E)-α-santalol, (Z)-α-santalol, (E)-β-santalol, (Z)-β-santalol, (E)-epi-β-santalol, (Z)-epi-β-santalol, (Z)-α-trans-bergamotol and (E)-α-trans-bergamotol. Production of santalols and bergamotols and quantification of the amount of product are then determined using any method provided herein, such as gas chromatography-mass spectroscopy (e.g. GC-MS), gas chromatography-flame ionization detection (GC-FID) and liquid chromatography-mass spectroscopy (LC-MS). Mass spectrometry patterns can be compared to the MS fragmentation patterns with entries in the NIST and Wiley libraries, such as described in Example 6, or by comparison with known terpenoids in sandalwood oil.

In other examples, the cytochrome P450 bergamotene oxidase polypeptides provided herein are overexpressed and purified as described in Section E above. The cytochrome P450 bergamotene oxidase is then incubated with one or more terpene substrates, including α-santalene, β-santalene, epi-β-santalene and/or α-trans-bergamotene, and one or more of (E)-α-trans-bergamotol or (Z)-α-trans-bergamotol is produced. In some examples, small amounts of α-santalol, β-santalol and/or epi-β-santalol are also produced. Alternatively, the cytochrome P450 bergamotene oxidase polypeptides provided herein expressed in host cells that also produce terpene substrates, including α-santalene, β-santalene, epi-β-santalene and/or α-trans-bergamotene, resulting in the production of (E)-α-trans-bergamotol or (Z)-α-trans-bergamotol. In some examples, small amounts of α-santalol, β-santalol and/or epi-β-santalol are also produced. Production of bergamotols and quantification of the amount of product are then determined using any method provided herein, such as gas chromatography-mass spectroscopy (e.g. GC-MS), gas chromatography-flame ionization detection (GC-FID) and liquid chromatography-mass spectroscopy (LC-MS). Mass spectrometry patterns can be compared to the MS fragmentation patterns with entries in the NIST and Wiley libraries, such as described in Example 6, or by comparison with known terpenoids in sandalwood oil.

b. Conversion of Acyclic Pyrophosphate Terpene Precursors

In some examples, terpenoids can be generated biosynthetically from acyclic pyrophosphate terpene precursors, such as geranyl pyrophosphate, farnesyl pyrophosphate and geranylgeranyl pyrophosphate, by expression of a cytochrome P450 monooxygenase in a host cell that produces the acyclic pyrophosphate terpene precursor and a terpene synthase. Suitable host cells are described in Section E above. In one example, santalols and bergamotols are generated biosynthetically by expression of a cytochrome P450 santalene oxidase in a host cell that produces FPP and santalene synthase (see Example 10). In another example, bergamotols are generated biosynthetically by expression of a cytochrome P450 bergamotene oxidase in a host cell that produces FPP and santalene synthase (see Example 10). Production of santalols and bergamotols and quantification of the amount of products are then determined using any method provided herein, such as gas chromatography-mass spectroscopy (e.g. GC-MS), gas chromatography-flame ionization detection (GC-FID) and liquid chromatography-mass spectroscopy (LC-MS). Mass spectrometry patterns can be compared to the MS fragmentation patterns with entries in the NIST and Wiley libraries, such as described in Example 6, or by comparison with known terpenoids in sandalwood oil.

In another example, terpenoids can be generated from acyclic pyrophosphate terpene precursors by 1) incubating an acyclic pyrophosphate terpene precursor with a terpene synthase and 2) incubating the reaction products with a cytochrome P450 monooxygenase. In some examples, the reaction products of the acyclic pyrophosphate terpene precursor with the terpene synthase are isolated. In other examples, the cytochrome P450 monooxygenase is added directly to the first reaction mixture without previous purification. The two steps can be performed simultaneously or sequentially. Terpenoids produced by the reaction can be identified and quantified using any method provided herein, such as gas chromatography-mass spectroscopy (e.g. GC-MS), gas chromatography-flame ionization detection (GC-FID) and liquid chromatography-mass spectroscopy (LC-MS). Mass spectrometry patterns can be compared to the MS fragmentation patterns with entries in the NIST and Wiley libraries, such as described in Example 6, or by comparison with known terpenoids in sandalwood oil.

2. Methods for Production a. Exemplary Cells

Santalols and bergamotols can be produced by expressing a cytochrome P450 synthase polypeptide and/or a cytochrome P450 reductase polypeptide provided herein in a cell line that produces FPP as part of the mevalonate-dependent isoprenoid biosynthetic pathway (e.g. fungi, including yeast cells, and animal cells) or the mevalonate-independent isoprenoid biosynthetic pathway (e.g. bacteria and higher plants). In particular examples, santalols are produced by expressing a cytochrome P450 santalene oxidase polypeptide provided herein and a santalene synthase polypeptide in a cell line that has been modified to overproduce FPP. In other examples, bergamotols are produced by expressing a cytochrome P450 bergamotene oxidase polypeptide provided herein and a santalene synthase polypeptide in a cell line that has been modified to overproduce FPP. Exemplary of such cells are modified yeast cells. For example, yeast cells that have been modified to produce less squalene synthase or less active squalene synthase (e.g. erg9 mutants; see e.g. U.S. Pat. Nos. 6,531,303 and 6,689,593) are useful in the methods provided herein to produce labdenediol diphosphate. Reduced squalene synthase activity results in accumulation of FPP in the host cell at higher levels compared to wild type yeast cells, thus allowing for increased yields of santalenes and bergamotenes. Exemplary modified yeast cells include, but are not limited to, modified *Saccharomyces cerevisiae* strains YPH499 (MATa, ura3-52, lys2-801, ade2-101, trp1-Δ63, his3-Δ200, leu2-Δ1), WAT11 (MATa, ade2-1, his3-11,-15; leu2-3,-112, ura3-1, canR, cyr+; containing chromosomally integrated *Arabidopsis* NADPH-dependent P450 reductase ATR1; see Pompon et al. (1995) *Toxicol Lett* 82-83:815-822; Ro et al. (2005) *Proc Natl Acad Sci USA* 102:8060-8065); and BY4741 (MATa, his3Δ1, leu2Δ0, met15Δ0, ura3Δ0; ATCC #201388).

b. Culture of Cells

In exemplary methods, a cytochrome P450 provided herein is expressed in a host cell line that has been modified to overexpress farnesyl diphosphate and a santalene synthase, whereby upon expression of the cytochrome P450, farnesyl diphosphate is converted to santalols and bergamotols. In other exemplary methods, a cytochrome P450 provided herein and a santalene synthase are expressed in a host cell line that has been modified to overexpress farnesyl diphosphate whereby upon expression of both proteins, farnesyl diphosphate is converted to santalols or bergamotols. The cytochrome P450 and santalene synthase can be expressed separately, or together, as a fusion protein described elsewhere herein. cytochrome P450 and santalene synthase can be expressed simultaneously or sequentially. The host cell is cultured using any suitable method well known in the art. In some examples, such as for high throughput screening of cell expressing various cytochrome P450s, the cells expressing the cytochrome P450 are cultured in individual wells of a 96-well plate. In other examples where the host cell is yeast, the cell expressing the cytochrome P450 polypeptides, santalene synthase and FPP is cultured using fermentation methods such as those described below.

A variety of fermentation methodologies can be used for the production of santalols and bergamotols from yeast cells expressing the cytochrome P450 polypeptides provided herein. For example, large scale production can be effected by either batch or continuous fermentation. A classical batch fermentation is a closed system where the composition of the medium is set at the beginning of the fermentation and not subject to artificial alterations during the fermentation. Thus, at the beginning of the fermentation the medium is inoculated with the desired microorganism or microorganisms and fermentation is permitted to occur without further addition of nutrients. Typically, the concentration of the carbon source in a batch fermentation is limited, and factors such as pH and oxygen concentration are controlled. In batch systems the metabolite and biomass compositions of the system change constantly up to the time the fermentation is stopped. Within batch cultures cells typically modulate through a static lag phase to a high growth log phase and finally to a stationary phase where growth rate is diminished or halted. If untreated, cells in the stationary phase will eventually die.

A variation on the standard batch system is the Fed-Batch system, which is similar to a typical batch system with the exception that nutrients are added as the fermentation progresses. Fed-Batch systems are useful when catabolite repression tends to inhibit the metabolism of the cells and where it is desirable to have limited amounts of substrate in the medium. Also, the ability to feed nutrients will often result in higher cell densities in Fed-Batch fermentation processes compared to Batch fermentation processes. Factors such as pH, dissolved oxygen, nutrient concentrations, and the partial pressure of waste gases such as CO are generally measured and controlled in Fed-Batch fermentations.

Production of the santalols or bergamotols also can be accomplished with continuous fermentation. Continuous fermentation is an open system where a defined fermentation medium is added continuously to a bioreactor and an equal amount of conditioned medium is removed simultaneously for processing. This system generally maintains the cultures at a constant high density where cells are primarily in their log phase of growth. Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems aim to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art.

Following cell culture, the cell culture medium then can be harvested to obtain the produced santalols and bergamotols.

c. Isolation and Assays for Detection and Identification

The santalols and bergamotols produced using the methods above with the cytochrome P450 polypeptides provided herein can be isolated and assessed by any method known in the art. In one example, the cell culture medium is extracted with an organic solvent to partition any terpenes or terpenoids produced into the organic layer. Production of santalols and/or bergamotols can be assessed and/or the santalols and/or bergamotols isolated from other products using any method known in the art, such as, for example, gas chromatography or column chromatography. For example, the organic layer can be analyzed by GC-MS.

The quantity of santalols and/or bergamotols produced can be determined by any known standard chromatographic technique useful for separating and analyzing organic compounds. For example, santalol and/or bergamotol production can be assayed by any known chromatographic technique useful for the detection and quantification of hydrocarbons, such as santalol and/or bergamotol and other terpenoids, including, but not limited to, gas chromatography mass spectrometry (GC-MS), gas chromatography using a flame ionization detector (GC-FID), capillary GC-MS, high performance liquid chromatography (HPLC) and column chromatography. Typically, these techniques are carried out in the presence of known internal standards which are used to quantify the amount of the terpenoid produced. For example, terpenoids, including sesquiterpenoids, such as santalol and/or bergamotol, can be identified by comparison of retention times and mass spectra to those of authentic standards in gas chromatography with mass spectrometry detection. Typical standards include, but are not limited to, santalols and/or bergamotols. In other examples, quantification can be achieved by gas chromatography with flame ionization detection based upon calibration curves with known amounts of authentic standards and normalization to the peak area of an internal standard. These chromatographic techniques allow for the identification of any terpene present in the organic layer, including, for example, other terpenoids produced by the cytochrome P450s.

In some examples, kinetics of santalol and/or bergamotol production can be determined by synthase assays in which radioactive isoprenoid substrates, such as $^3$H FPP or $^{14}$C FPP, are used with varying concentrations of synthase. The products are extracted into an organic layer and radioactivity is measured using a liquid scintillation counter. Kinetic constants are determined from direct fits of the Michaelis-Menton equation to the data.

3. Production of Sandalwood Oil

The cytochrome P450 santalene oxidase and cytochrome P450 bergamotene oxidase polypeptides provided herein can be used to produce sandalwood oil. For example, the cytochrome P450 santalene oxidases can be expressed in cells that produce or overexpress a santalene synthase, such that santalols and bergamotol, including α-santalol, β-santalol and epi-β-santalol, and Z-α-trans-bergamotol, are produced as described elsewhere herein. The terpenoid products can be compared to those found in authentic sandalwood oil from *S. album* by GC-MS analysis, for example, as described in Example 8.

4. Assays for Detecting Enzymatic Activity of Cytochrome P450 and Cytochrome P450 Reductase Polypeptides a. Methods for Determining the Activity of Cytochrome P450 Polypeptides One of skill in the art is familiar with methods and assays to detect the enzymatic activity of cytochrome P450 polypeptides. Cytochrome P450 polypeptides can be expressed in yeast or purified from microsomal membrane fractions. Cytochrome P450 monooxygenase activity can be determined in vitro by incubation of a cytochrome P450 polypeptide with various monoterpene, sesquiterpene and diterpene substrates, as described in Example 11. Reaction products, including ratios of the products, can be determined by any method known to one of skill in the art, including GC-MS, GC-FID, LC-MS, comparison to known standards, and proton and carbon nuclear magnetic resonance (NMR). Alternatively, activity can be determined in vivo by addition of terpene substrates to yeast cultures of the cytochrome P450s and identifying products as described above. Total P450 content in microsomes can be quantified by CO differential absorption spectroscopy (see Guengerich et al. (2009) *Nat Protoc* 4:1245-1251 and Example 8).

Enzyme kinetics can be determined in vitro in the presence of NADPH and CPR. In such assays, CPR is included in limited amounts, e.g., 0.1 U, for determination of enzyme activity and 5 milliunits for determination relative activities and kinetic parameters. Assays can be performed over a range of substrate concentrations and product formation can be determined by GC-MS. Add terpene directly to yeast cultures b. Methods for Determining the Activity of Cytochrome P450 Reductase Polypeptides One of skill in the art is familiar with methods and assays to detect the enzymatic activity of cytochrome P450 reductase polypeptides. In one example, CPR activity can be determined using an assay that detects for C4H (cinnamate 4-hydroxylase) activity, for example, as described in Ro et al. (2001) *Plant Physiology* 126:317-329. C4H is a heme-thiolate protein that catalyzes the formation of p-coumarate from cinnamic acid. This assay can be used in vivo by expression of the cytochrome P450 reductase in yeast cells in the presence of C4H (see also, Ro et al. (2002) *Plant Physiology* 130:1837-1851). C4H activity is determined by detection of p-coumaric acid formation by HPLC (Mizutani et al. (1993) *Plant Cell Physiology* 34:481-488).

In order to assess CPR activity in vitro, CPRs can be purified from yeast microsomal fractions, such as described in Pompon et al. ((1996) *Methods Enzymol* 272:51-64) and Example 8 below. Total P450 content in microsomes can be quantified by CO differential absorption spectroscopy (Omura and Sato (1964) *J Biol Chem* 239:2370-2378; Mizutani and Ohta (1998) *Plant Physiology* 116:357-367). FAD and FMN content can be determined as described in Faeder and Siegel (1973) *Anal Biochem* 53:332-336. CPR activity in vitro can be assessed by a variety of assays known to one of skill in the art. For example, activity can be determined using the C4H assay described above. In another example, activity is determined by measuring reduction of an artificial electron receptor, such as cytochrome c or oxidized ferricyanide (Xia et al. (2011) *J Biol Chem* 286:16246-16260; Hamdane et al. (2009) *J Biol Chem* 284:11374-11384; Shen et al. (1989) *J Biol Chem* 264:7584-7589). Formation of reduced cytochrome c is measured using a spectrophotometer and calculating the rate of reduction from $A_{550}$ change using an extinction coefficient ($\Sigma$=21 mM$^{-1}$ cm$^{-1}$) (Imai (1976) *J Biochem* 80:267-276). Another assay that be used to detect CPR is the ethoxycoumarin O-de-ethylase activity reporter assay in P450 2B4 reconstituted systems (Louerat-Orieu et al (1998) *Eur J Biochem* 258:1040-1049).

The subcellular membrane localization site, e.g., whether the CPR is located in the ER or the chloroplast, of a cytochrome P450 reductase polypeptide can be determined by expressing CPR with GFP-fused to its C-terminus in *Arabidopsis* under the control of cauliflower mosaic virus 35S promoter (see, Ro et al. (2002) *Plant Physiology* 130:1837-1851). Independently transformed T1 and T2 seedlings are then screened for the presence of GFP by fluorescence microscopy and confocal microscopy (see Ro et al. (2002) *Plant Physiology* 130:1837-1851) or by immunoblot analysis of microsomal proteins of seedlings. The functionality of the CPR in the GFP-CPR fusions can be verified using the C4H assay.

G. Examples

The following examples are included for illustrative purposes only and are not intended to limit the scope of the invention.

EXAMPLE 1

Cloning and Sequencing of *Santalum album* cDNA

In this example, RNA was extracted from wood samples of Sandalwood (*Santalum album*) trees and cDNA was generated and sequenced.

A. Isolation and Extraction of *S. album* RNA

Several 25 mm holes were drilled into the lower stems of mature *Santalum album* trees growing on land managed by the Forest Products Commission of Western Australia. Wood samples from the heartwood-sapwood transition zone were collected and frozen immediately in liquid nitrogen. RNA was extracted from 10 g tissue using a protocol modified from Kolosova et al., (2004) *BioTechniques* 36:821-824. After precipitation with LiCl, RNA was stored at −80° C. until cDNA synthesis.

B. Generation of *S. album* cDNA Library

*S. album* xylem total RNA (1.4 μg) was reverse transcribed with SuperScript III reverse transcriptase (Invitrogen) at 42° C. for 1 hour using the SMART-Creator kit with the pDNR-LIB vector (Clontech; SEQ ID NO:20). The ligation mixture was transformed by electroporation into 25 μL of phage resistant electrocompetent *E. coli* cells and Sanger sequenced at the Genome Sciences Centre, Vancouver, Canada.

C. 454 Pyr Sequencing and Sanger Sequencing

Two cDNA libraries from *Santalum album* cores were prepared and sequenced with Sanger technologies generating 11,520 paired end sequences. One plate of 454 Titanium sequencing was done on both libraries and generated 902,111 reads. Assembly was effected using the 454 and Sanger sequences with Newbler assembler v2.6 (454 Life Sciences, Roche Diagnostics) with default parameters. This generated 31,461 contigs (isotigs).

EXAMPLE 2

Identification of Nucleic Acid Encoding *S. album* Cytochrome P450 Polypeptides

Cytochrome P450 encoding genes were identified by comparing the assembled sequences (from Example 1) against a set of known plant P450 encoding genes from the CYP76 families of P450 proteins using a BLASTx search (blast.ncbi.nlm.nih.gov; Altschul et al. (1990) *J Mol Biol* 215:403-410).

Table 4 below provides a summary of 7 isotigs identified in the BLASTx search (blast.ncbi.nlm.nih.gov; Altschul et al. (1990) *J Mol Biol* 215:403-410), including the isotig, lowest E-value, the gene ID of the match in the P450 database, the CYP450 family and the number of reads. The E-value (Expect Value) describes the number of matches expected to occur randomly with a given score. In general, the smaller E-value, the more likely the match is significant.

TABLE 4

Summary of CYP450 transcripts

| # | Query | Lowest E-value with match in P450 data base | Identity to Gene ID of the match in the P450 database CrCYP76B6 (CAC80883) | CYP450 Family | Number of reads |
|---|---|---|---|---|---|
| 1 | isotig05182 | 8.34E−142 | 71% | SaCYP76 | 910 |
| 2 | isotig05183 | 2.68E−145 | 71% | SaCYP76 | 763 |
| 3 | isotig05184 | 1.61E−78 | 52% | SaCYP76 | 470 |
| 4 | isotig06871 | 1.23E−126 | 83% | SaCYP76 | 110 |
| 5 | isotig06872 | 9.19E−156 | 83% | SaCYP76 | 118 |
| 6 | isotig14788 | 1.53E−93 | 86% | SaCYP76 | 11 |
| 7 | isotig29133 | 1.49E−52 | 60% | SaCYP76 | 1 |

Transcripts from this family were the most abundant in the EST database and cluster into four different groups.

Group 1 is represented by 3 isotigs (numbers 1-3 in Table 4) with a total of 2,143 reads including 1,107 unique sequences generating a final assembled sequence of 1917 base pairs (bp) with an open reading frame (ORF) of 1530 bp. Group 2 is represented by 2 isotigs (numbers 4-5 in Table 4), had 228 reads with 140 unique reads generating an assembled sequence of 1776 bp and an ORF of 1530 bp. Group 3 (number 6 in Table 7) was represented by 11 reads generating a partial sequence of 1200 bp. Group 4 (number 7 in Table 7) is a singleton of 277 bp with several stop codons along the sequence.

EXAMPLE 3

Isolation of Cytochrome P450 Encoding cDNA

Group 1 and Group 2 cDNA molecules (numbers 1-5 in the table above) of the CYP76 family identified in Example 2, were selected for cDNA isolation.

A. Cloning of Members of the CYP76 Family

Full-length cDNA molecules were amplified by polymerase chain reaction (PCR) with Phusion Hot Start II DNA Polymerase (Thermo Scientific) of *S. album* cDNA (set forth in SEQ ID NO:1) prepared as described in Example 1 using gene specific primers designed according to the ORF of Group 1 and Group 2 (set forth in Table 5 below). PCR conditions were as follows:

98° C. for 3 min;

2 cycles of: 98° C. for 10 sec, Tm −2° C. for 20 sec, 72° C. for 30 sec;

30 cycles of: 98° C. for 10 sec, Tm for 20 sec, 72° C. for 30 sec;

Final extension at 72° C. for 7 min with a Tm of 55° C. for Isogroup 1 and a Tm of 52° C. for Isogroup 2. The PCR products were gel purified and cloned into the pJET1.2 vector (Fermentas, SEQ ID NO:21) according to the manufacturer's instructions. *E. coli* α-Select chemically competent cells (Bioline) were used for cloning and plasmid propagation. All constructs were verified by DNA sequencing.

TABLE 5

Primers for amplification of cytochrome P450 cDNA

| Primer | Sequence | SEQ ID NO |
|---|---|---|
| Isogroup 1 Forward | ATGGACTTCTTAAGTTTTATCCTGTTTG | 22 |
| Isogroup 1 Reverse | TTACCCCCGGATCGGGACAG | 23 |
| Isogroup 2 Forward | ATGGACTTCTTAAGTTGTATCCTG | 24 |
| Isogroup 2 Reverse | TTACCCCCGGATTGGGACAG | 25 |

Amplification with primers for Isogroup 1 resulted in a single unique cDNA clone designated SaCYP76F38v1 (Sa-CYP76-G5) Amplification with primers from Isogroup 2 resulted in 3 different cDNA clones, designated: SaCYP76F39v1 (SaCYP76-G10), SaCYP76F37v1 (Sa-CYP76-G11) and SaCYP76F38v2 (SaCYP76-G12). A second amplification with primers from Isogroup 2 resulted in 6 additional different cDNA clones, designated SaCYP76F37v2 (SaCYP76-G14), SaCYP76F39v2 (Sa-CYP76-G15), SaCYP76F40 (SaCYP76-G16), SaCYP76F41 (SaCYP76-G17), SaCYP76F42 (SaCYP76-

G13) and SaCYP76F43 (SaCYP76-G18). The SEQ ID NOS of the sequences of the nucleic acids and the encoded amino acids are set forth in Table 6 below. The translated amino acid sequences encoded by the 10 isolated cDNA molecules share between 93% and 99% identity (see Table 7 below) and between 1.0 and 6.6% divergence. Pair distances were prepared with ClustalW (slow/accurate, Gonnet weight matrix) (ebi.ac.uk/clustalw; European Bioinformatics Institute).

TABLE 6

Cytochrome P450 Polypeptides

| Cytochrome P450 | Nucleic acid SEQ ID NO | Amino acid SEQ ID NO |
|---|---|---|
| SaCYP76F38v1 (SaCYP76-G5) | 2 | 6 |
| SaCYP76F39v1 (SaCYP76-G10) | 3 | 7 |
| SaCYP76F37v1 (SaCYP76-G11) | 4 | 8 |
| SaCYP76F38v2 (SaCYP76-G12) | 5 | 9 |
| SaCYP76F37v2 (SaCYP76-G14) | 67 | 73 |
| SaCYP76F39v2 (SaCYP76-G15) | 68 | 74 |
| SaCYP76F40 (SaCYP76-G16) | 69 | 75 |
| SaCYP76F41 (SaCYP76-G17) | 70 | 76 |
| SaCYP76F42 (SaCYP76-G13) | 71 | 77 |
| SaCYP76F43 (SaCYP76-G18) | 72 | 78 |

TABLE 7

Percent amino acid identity for cytochrome P450s from the CYP76 family

| | SaCYP76 | | | | | | | | | |
|---|---|---|---|---|---|---|---|---|---|---|
| | F38v1 | F39v1 | F37v1 | F38v2 | F37v2 | F39v2 | F40 | F41 | F42 | F43 |
| SaCYP76F38v1 | 100 | 94 | 97 | 99 | 98 | 93 | 94 | 96 | 95 | 96 |
| SaCYP76F39v1 | | 100 | 95 | 94 | 95 | 99 | 98 | 96 | 95 | 95 |
| SaCYP76F37v1 | | | 100 | 98 | 99 | 95 | 94 | 95 | 94 | 95 |
| SaCYP76F38v2 | | | | 100 | 99 | 94 | 94 | 96 | 95 | 95 |
| SaCYP76F37v2 | | | | | 100 | 95 | 93 | 95 | 94 | 95 |
| SaCYP76F39v2 | | | | | | 100 | 98 | 95 | 94 | 95 |
| SaCYP76F40 | | | | | | | 100 | 97 | 96 | 95 |
| SaCYP76F41 | | | | | | | | 100 | 97 | 94 |
| SaCYP76F42 | | | | | | | | | 100 | 96 |
| SaCYP76F43 | | | | | | | | | | 100 |

EXAMPLE 4

Sequence and Phylogenetic Analysis of SaCYP76 Proteins

A BLASTx search of the deduced amino acid sequences against the GenBank non-redundant protein database (blast.ncbi.nlm.nih.gov; Altschul et al. (1990) *J Mol Biol* 215:403-410) identified a putative cytochrome P450 from *Vitis vinifera* (GenBank Accession No. XP_002281735; SEQ ID NO:26) that has 62% to 64% sequence identity to the *S. album* CYPs and a CYP76B6 geraniol hydroxylase from *Catharanthus roseus* (GenBank Accession No. CAC80883; Collu et al. (2001) *FEBS Lett* 308:215-220; SEQ ID NO:27) that has 54% to 55% sequence identity to the *S. album* CYPs. Protein alignment of the full length protein sequences was made with ClustalW (ebi.ac.uk/clustalw; European Bioinformatics Institute).

Figure 4:
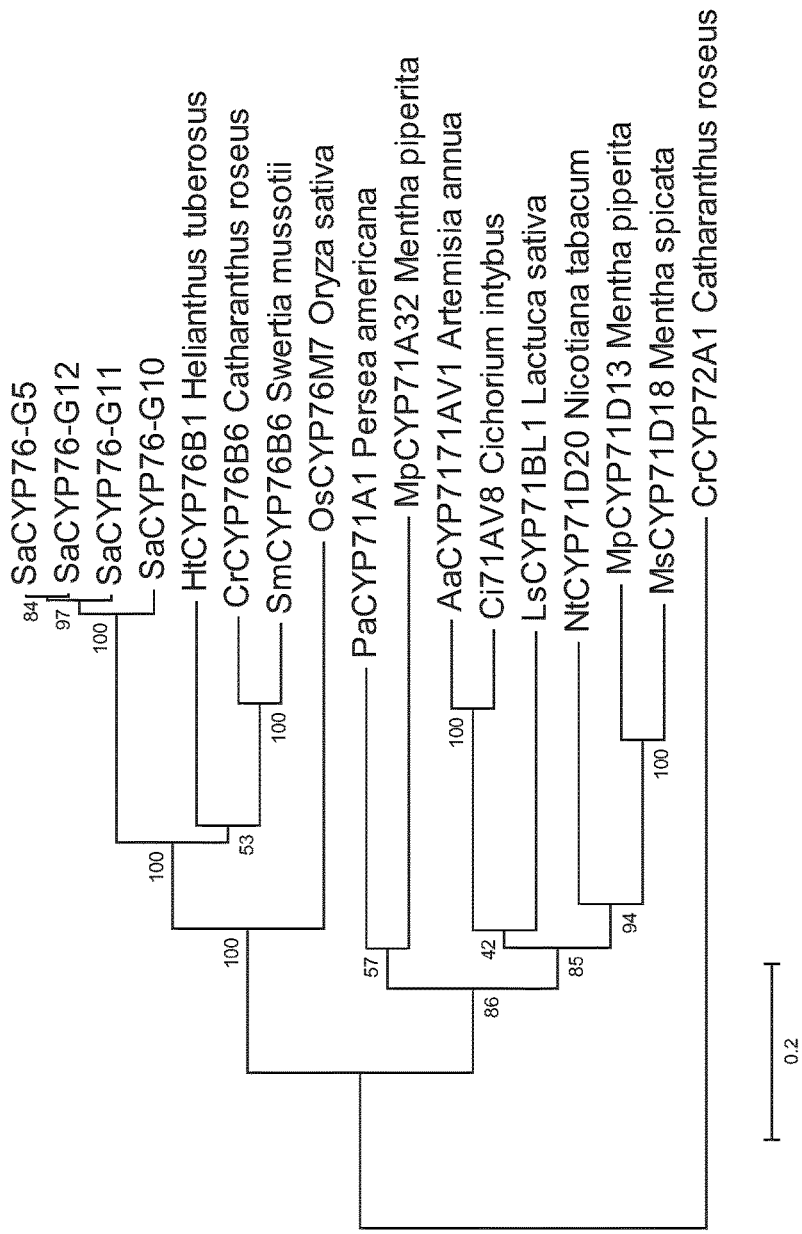
FIG. 4 depicts the neighbor joining phylogeny of the predicted protein sequences of SaCYP76F38v1 (SaCYP76-G5), SaCYP76F39v1 (SaCYP76-G10), SaCYP76F37v1 (SaCYP76-G11) and SaCYP76F38v2 (SaCYP76-G12) and cytochrome P450 enzymes for terpenoid metabolism, as described in Example 4.

Phylogenetic trees were constructed with MEGA version 4 (Centre for Evolutionary Medicine and Informatics; Tamura et al., 2007 *Mol Biol Evol* 24:1596-1599) employing the neighbor joining (NJ) method with default parameters. Bootstrap (500 replications) confidence values over 50% are displayed at branch points. The neighbor-joining phylogeny of the predicted protein sequences of the initial four *S. album* CYP clones SaCYP76F38v1 (SaCYP76-G5), SaCYP76F39v1 (SaCYP76-G10), SaCYP76F37v1 (SaCYP76-G11) SaCYP76F38v2 (SaCYP76-G12) and cytochrome P450 enzymes for terpenoid metabolism in other species is set forth in FIG. 4. The SaCYP76 genes, which form a separate cluster in this phylogeny, are most closely related to the CYP76B cluster that includes geraniol/nerol hydroxylases from different species. Accession numbers of the amino acid sequences included in the phylogeny in FIG. 4, in addition to the *S. album* CYP76 P450 clones SaCYP76F38v1 (SaCYP76-G5), SaCYP76F39v1 (SaCYP76-G10), SaCYP76F37v1 (SaCYP76-G11) SaCYP76F38v2 (SaCYP76-G12) provided herein, included: *Helianthus tuberosus* CYP76B1 (CAA71178; SEQ ID NO:28); *Catharanthus roseus* CYP76B6 (CAC80883; SEQ ID NO:27); *Swertia mussotii* CYP76B6 (ACZ48680; SEQ ID NO:29); *Persea americana* CYP71A1 (P24465; SEQ ID NO:30); *Mentha x piperita* CYP71A32 (Q947B7; SEQ ID NO:31); *Artemisia annua* CYP71AV1 (ABB82944; SEQ ID NO:32); *Cichorium intybus* CYP71AV8 (ADM86719; SEQ ID NO:33); *Lactuca sativa* CYP71BL1 (AEI59780; SEQ ID NO:34); *Nicotiana tabacum* CYP71D20 (Q94FM7; SEQ ID NO:35); *Mentha x piperita* CYP71D13 (Q9XHE7; SEQ ID NO:36); *Mentha spicata* CYP71D18 (Q6WKZ1; SEQ ID NO:37); *Catharanthus roseus* CYP72A1 (Q05047; SEQ ID NO:38); and *Oryza sativa* CYP76M7 (AK105913; SEQ ID NO:39).

Figure 10:
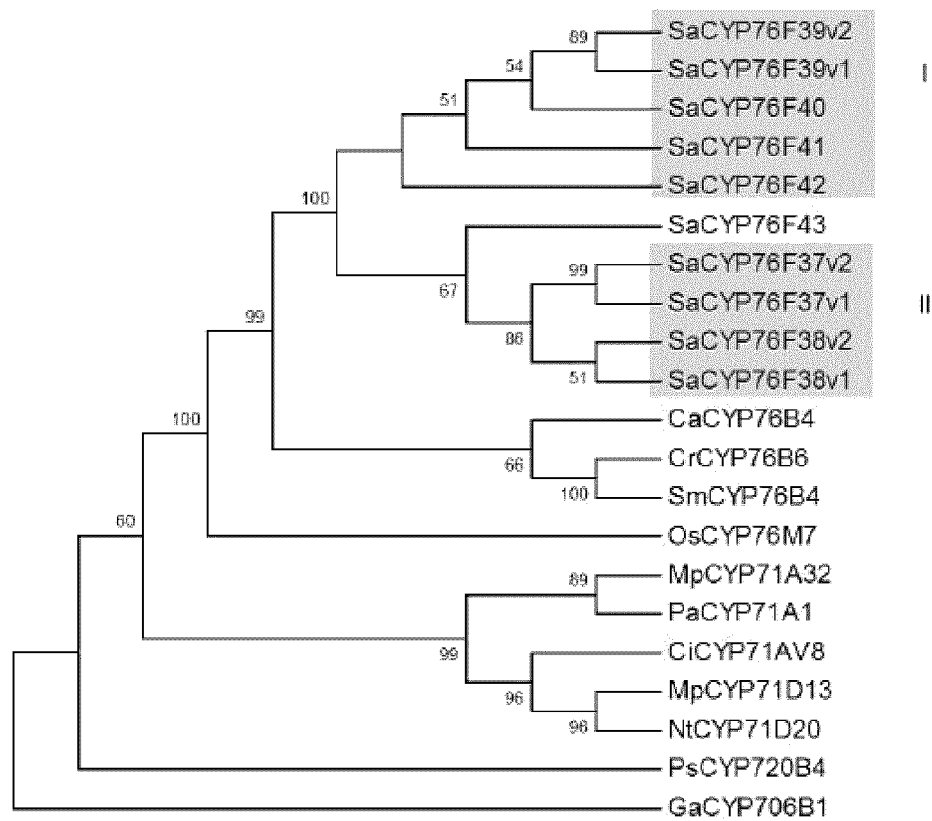
FIG. 10 depicts the neighbor-joining phylogeny of the protein sequences of the *S. album* CYP76Fs and related terpene-modifying cytochrome P450, as described in Example 4. The highlighted CYP76Fs indicated those in clade I (marked with I) and clade II (marked with II).

A second neighbor joining phylogenetic tree was constructed with all 10 *S. album* CYP76F proteins and related terpene-modifying cytochrome P450s members of the CYP71 clan, using *Picea sitchensis* PsCYP720B4 (ADR78276; SEQ ID NO:79) as an outgroup. The phylogenetic tree is set forth in FIG. 10. The *S. album* CYP76F proteins fell into two separate clades and were closest to the CYP76B cluster of other species. Clade I santalene/bergamotene oxidases included SaCYP76F39v1 (SaCYP76-G10), SaCYP76F39v2 (SaCYP76-G15), SaCYP76F40 (SaCYP76-G16), SaCYP76F41 (SaCYP76-G17) and SaCYP76F42 (SaCYP76-G13). Clade II bergamotene oxidases included SaCYP76F37v1 (SaCYP76-G11), SaCYP76F37v2 (SaCYP76-G14), SaCYP76F38v1 (SaCYP76-G5) and SaCYP76F38v2 (SaCYP76-G12). Accession numbers of the amino acid sequences for other terpene-modifying CYPs included in the phylogenetic tree in FIG. 10, in addition to the *S. album* CYP76 P450 clones, include CaCYP76B4 *Camptotheca acuminate* putative geraniol-10- hydroxylase (AES93118; SEQ ID NO:80); CrCYP76B6 *Catharanthus roseus* geraniol 10-hydroxylase (Q8VWZ7; SEQ ID NO:81); SmCYP76B4 *Swertia mussotii* geraniol 10-hydroxylase (D1MI46; SEQ ID NO:82); OsCYP76M7 *Oryza sativa entcassadiene* C11a-hydroxylase (NP_001047185; SEQ ID NO:83); MpCYP71A32 *Mentha x piperita* menthofuran synthase (Q947B7; SEQ ID NO:84); PaCYP71A1 *Persea americana* (P24465; SEQ ID NO:85); CiCYP71AV8 *Cichoriium intybus* valencene oxidase (ADM86719; SEQ ID NO:86); MpCYP71D13 *Mentha x gracilis* (−)-limonene-3-hydroxylase (AY281027; SEQ ID NO:87); NtCYP71D20 *Nicotiana tabacum* 5-epi-aristocholene-1,3-dihydroxylase (AF368376; SEQ ID NO:88); and GaCYP706B1 *Gossypium arboretum* (+)-delta-cadinene-8-hydroxylase (AAK60517; SEQ ID NO:89).

EXAMPLE 5

Cytochrome P450 Reductase

Cytochrome P450 reductase encoding genes were identified by comparing the assembled sequences with a set of known plant cytochrome P450 reductases from *Arabidopsis* (CAB58575.1 (SEQ ID NO:58) and CAB58576.1 (SEQ ID NO:46)). Full length cDNA genes SaCPR1 and SaCPR2 were amplified by polymerase chain reaction (PCR) with Phusion Hot Start II DNA Polymerase (Thermo Scientific) of *S. album* cDNA prepared as described in Example 1 with gene specific primers designed according to the ORF of the cytochrome P450 reductase (set forth in Table 8).

TABLE 8

Primers for PCR of cytochrome P450 reductase genes

| Primer | Sequence | Tm | SEQ ID NO |
|---|---|---|---|
| SaCPR1 Forward | ATG AGT TCG AGC TCG GAG CTA TG | 57 | 40 |
| SaCPR1 Reverse | TCA CCA CAC ATC CCG TAA ATA CCT TC | 57 | 41 |
| SaCPR2 Forward | ATG CAA TTG AGC TCC GTC AAG | 58 | 61 |
| SaCPR2 Reverse | TCA CCA CAC ATC CCG TAA ATA CCT TCC | 58 | 62 |

PCR conditions were as follows:
 98° C. for 3 min;
 2 cycles of: 98° C. for 10 sec, Tm −2° C. for 20 sec, 72° C. for 30 sec;
 30 cycles of: 98° C. for 10 sec, Tm for 20 sec, 72° C. for 30 sec;
 Final extension at 72° C. for 7 min
The PCR products were gel purified and cloned directly into the pET28b(+) vector (SEQ ID NO:51) or first cloned into pJET vector and then subcloned into expression vectors. *E. coli* α-Select chemically competent cells (Bioline) were used for cloning and plasmid propagation. All constructs were verified by DNA sequencing. PCR amplification resulted in two *S. album* cytochrome P450 reductase (CPR) clones designated CPR1 and CPR2, having nucleic acid sequences set forth in SEQ ID NOS:10 and 11, respectively, encoding the proteins set forth in SEQ ID NO:12 and 13.

The two CPR nucleic acid sequences share 70% sequence identity and the two CPR proteins share 82% sequence identity.

The web-based BlastX program (Altschul et al., (1990) *J. Mol. Biol.* 215:403-410) was then used to compare the sequence of the identified with sequences in the GenBank database. The CPR sequences share 79% sequence homology with the *Vitis vinifera* predicted cytochrome P450 reductase-like protein (Genbank Accession No. XP_002270732; SEQ ID NO:42), 78% sequence homology with the *Gossypium hirsutum* cytochrome P450 reductase (Genbank Accession No. ACN54324; SEQ ID NO:43) and 75% sequence homology with the *Artemisia annua* cytochrome P450 reductase (Genbank Accession No. ABI98819; SEQ ID NO:44).

Truncated CPRs were generated containing amino acids 44-692 of SEQ ID NO:12 (truncated protein sequence set forth in SEQ ID NO:14; nucleic acid sequence set forth in SEQ ID NO:63) and amino acids 61-704 of SEQ ID NO:13 (truncated protein sequence set forth in SEQ ID NO:15; nucleic acid sequence set forth in SEQ ID NO:64).

Activity of recombinant SaCPR was assayed using the Cytochrome C Reductase (NADPH) assay kit (Sigma).

EXAMPLE 6

Gas Chromatography-Mass Spectrometry Analysis

Gas chromatography-mass spectrometry (GC-MS) analysis was used to analyze the oxidation products of the *S. album* cytochrome P450s and *S. album* oil.
A. SGE Solgel-Wax Capillary Column
 GC-MS analysis was performed on a Agilent 6890A/5973N GC-MS system containing a SGE Solgel-Wax capillary column (30 m×0.25 mm ID×0.25 µm thickness) in SIM-scan mode (scan: m/z 40-400; SIM: m/z 93, 94, 119, 136, 122, 202 and 204 [dwell time 50]. Volumes of 2 µL samples were injected in pulsed splitless mode at 250° C. with a column flow of 1 mL/min helium and 50 psi pulse pressure for 0.5 min with the following program: 40° C. for 2 min, ramp of 8° C. per min to 100° C., 15° C. per min to 250° C., hold 5 min.

Alternatively, the following program was also used to analyze the products of *S. album* SaCYP76F39v1 (SaCYP76-G10) and *S. album* oil: volumes of 2 µL samples were injected in pulsed splitless mode at 250° C. with a column flow of 0.8 mL/min helium and 10 psi pulse pressure for 0.05 min with the following program: 40° C. for 3 min, 10° C. per min to 100° C., 2° C. per min to 250° C., hold 10 min.

Product identification was based on best match of the MS fragmentation patterns with entries in the NIST and Wiley libraries (Wiley Registry® 9th Edition/NIST 2011; Fred W. McLafferty, John Wiley & Sons, Inc.) and by comparison with compounds of authentic *S. album* oil and Kovats index values.
B. HP5 and DB-Wax Fused Silica Column
 GC-MS analysis was performed on a Agilent 7890A/5975C GC-MS system operating in electron ionization selected ion monitoring (SIM)-scan mode. Samples were analyzed on an HP5 (non-polar; 30 m×0.25 mm ID×0.25 µm thickness) and a DB-Wax fused silica column (polar; 30 m×0.25 mm ID×0.25 µm thickness). In both cases, the injector was operated in pulsed splitless mode at with the injector temperature maintained at 250° C. Helium gas was used as the carrier gas with a flow rate of 0.8 mL/min and pulsed pressure set at 25 psi for 0.5 min. Scan range: m/z 40-500; SIM: m/z 93, 94, 105, 107, 119, 122 and 202 [dwell time 50 msec].

The oven program for the HP5 column was:

40° C. for 3 min, ramp of 10° C. per min to 130° C., 2° C. per min to 180° C., 50° C. per min to 300° C., hold 300° C. for 10 min.

The oven program for the DB-wax column was:

40° C. for 3 min, ramp of 10° C. per min to 130° C., 2° C. per min to 200° C., 50° C. per min to 250° C., hold 250° C. for 15 min.

Chemstation software was used for data acquisition and processing. Compounds were identified by comparison of mass spectral with authentic samples and the NIST/EPA/NIH mass spectral library v2.0 and by comparison of retention indices with those appearing in Valder et al. (2003) *J Essent Oil Res* 15:178-186 and Sciarrone et al. (2011) *J Chromatogr A* 1218:5374.

EXAMPLE 7

Expression in Bacteria and Yeast

The *S. album* FPP synthase, santalene synthase, cytochrome P450 SaCYP76F38v1 (SaCYP76-G5) and cytochrome P450 reductase genes were cloned into a pCDF-Duet (Novagen) and pACYC-Duet (Novagen) bacterial expression vectors. Genes encoding the full length *S. album* cytochrome CYP76F P450s, cytochrome P450 reductase, santalene synthase and farnesyl diphosphate synthase were cloned into various yeast expression vectors to allow expression in the *Saccharomyces cerevisiae* yeast strain BY4741 (MATa his3Δ1 leu2Δ0 met15Δ0 ura3Δ0; ATCC #201388).

A. Bacterial Expression Vectors

Genes encoding FPP synthase (SEQ ID NO:18) and santalene synthase (SEQ ID NO:16), previously characterized from *S. album* (see, International PCT application No. WO2011000026 and Jones et al. (2011)*J Biol Chem* 286: 17445-17454), were cloned into the bacterial expression vector pCDF-Duet (Novagen, SEQ ID NO:65) generating pCDF-Duet:SaFPPS:SaSSy. Genes encoding SaCPR (SEQ ID NO:11) and SaCYP76F38v1 (SaCYP76-G5) gene (SEQ ID NO:2) were cloned into the bacterial expression vector pACYC-Duet (Novagen, SEQ ID NO:45) generating pACYC-Duet:SaCPR:SaCYP76F38v1. These expression vectors are dual expression vectors that allow co-expression of two target genes via two multiple cloning sites.

pCDF-Duet:SaFPPS:SaSSy, which has a streptomycin selectable marker, was transformed into chemically competent C41 (DE3) *E. coli* cells (Avidis). These cells were grown up and rendered chemically competent again using calcium chloride, and transformed with the pACYC-Duet:SaCPR:SaCYP76F38v1, which has a chloramphenicol selectable marker. Both antibiotics were used to select for colonies containing both duet vectors. These colonies were grown overnight in a rich media (terrific broth) at 16° C. and protein expression was initiated through the addition of IPTG. Cytochrome P450 protein expression was supplemented with 5-amino-levulinic acid to aid in porphyrin synthesis, and evidenced by a reddening of the cell pellet.

B. Generation of Yeast Expression Vectors

1. *S. album* Cytochrome P450s

The *S. album* CYP76F full length cDNAs identified in Table 6 above were sub-cloned into the yeast expression vector pYeDP60 (Cullin and Pompon (1988) Gene 65:203-217; Pompon et al. (1996) *Methods Enzymol* 272:51-64; Abecassis et al. (2003) *Methods Mol Biol* 231:165-173) following the uracil-excision (USER) cloning technique of Hamann and Moller (2007) *Protein Expr Purif*56:121-127. The pYeDP60 vector contains a URA marker. The resulting constructs are set forth in Table 9 below.

2. *S. album* Santalene Synthase and Farnesyl Diphosphate Synthase

Santalene synthase encoding cDNA (SaSSY, SEQ ID NO:16) and farnesyl diphosphate synthase encoding cDNA (SaFPPS, SEQ ID NO:18) were cloned into the NotI-Bgl II and BamHI-XhoI sites, respectively, of the galactose inducible expression vectors pESC-LEU (Stratagene, SEQ ID NO:47) or pESC-LEU2d (see, Ro et al. (2008) *BMC Biotechnology* 8:83) by in-Fusion Cloning (Clontech) following the manufacturer's instructions. Additional vectors were generated containing only the SaSSy gene (SEQ ID NO:16). The pESC-LEU and pESC-LEU2d vectors contain a LEU marker and the pESC-LEU2d vector is a high copy number vector containing a deletion in the Leu2 promoter. The resulting constructs are set forth in Table 9 below.

3. Cytochrome P450 Reductase

Cytochrome P450 reductase encoding cDNA (SaCPR, SEQ ID NO:11), identified in Example 3, was cloned into the EcoRi-NotI sites of pESC-HIS vector (Stratagene, SEQ ID NO:49) by in-Fusion Cloning (Clontech) following the manufacturer's instructions. The resulting constructs are summarized in Table 9 below.

TABLE 9

Yeast expression vectors

| Construct ID | Marker | Description (MCS = multiple cloning site) |
| --- | --- | --- |
| pESC-LEU:SaG1:SaG2 | -LEU | MCS1 contains *S. album* Santalene Synthase (SaSSY) |
| | | MCS2 contains *S. album* FPPS (SaFPPS) |
| pESC-LEU2d:SaG1:SaG2 | -LEU | MCS1 contains *S. album* Santalene Synthase (SaSSY) |
| | | MCS2 contains *S. album* FPPS (SaFPPS) |
| pESC-LEU:SaSSY | -LEU | MCS1 contains *S. album* Santalene Synthase (SaSSY) |
| pESC-LEU2d:SaSSY | -LEU | MCS1 contains *S. album* Santalene Synthase (SaSSY) |
| pESC-His:SaCPR | -HIS | MCS1 contains *S. album* cytochrome P450 reductase (SaCPR) |
| pYEDP60:F38v1 | -URA | pYEDP60 contains *S. album* SaCYP76F38v1 (SaCYP76-G5) |
| pYEDP60:F39v1 | -URA | pYEDP60 contains *S. album* SaCYP76F39v1 (SaCYP76-G10) |

TABLE 9-continued

Yeast expression vectors

| Construct ID | Marker | Description (MCS = multiple cloning site) |
|---|---|---|
| pYEDP60:F37v1 | -URA | pYEDP60 contains S. album SaCYP76F37v1 (SaCYP76-G11) |
| pYEDP60:F38v2 | -URA | pYEDP60 contains S. album SaCYP76F38v2 (SaCYP76-G12) |
| pYEDP60:F37v2 | -URA | pYEDP60 contains S. album SaCYP76F37v2 (SaCYP76-G14) |
| pYEDP60:F39v2 | -URA | pYEDP60 contains S. album SaCYP76F39v2 (SaCYP76-G15) |
| pYEDP60:F40 | -URA | pYEDP60 contains S. album SaCYP76F40 (SaCYP76-G16) |
| pYEDP60:F41 | -URA | pYEDP60 contains S. album SaCYP76F41 (SaCYP76-G17) |
| pYEDP60:F42 | -URA | pYEDP60 contains S. album SaCYP76F42 (SaCYP76-G13) |
| pYEDP60:F43 | -URA | pYEDP60 contains S. album SaCYP76F43 (SaCYP76-G18) |

C. Yeast Transformation and Expression

All constructs were transformed into the *Saccharomyces cerevisiae* yeast strain BY4741 (MATa his3Δ1 leu2Δ0 met15Δ0 ura3Δ0; ATCC #201388) using the LiCl method as described in Gietz et al. (1992) *Nucleic Acids Res* 20:1425. Transformed yeast were selected on plates with appropriate synthetic drop-out selection medium and grown at 30° C. for 48 hours.

1. Expression of Santalene Synthase

Production of santalenes and bergamotene was evaluated using constructs encoding the *S. album* santalene synthase. Yeast cells expressing the high copy number construct pESC-LEU2d:SaSSY produced about twice the amount of santalenes and bergamotene as determined by GC-MS (as described in Example 6A) compared to yeast cells expressing the pESC-LEU:SaSSY construct. No differences were observed between the cells expressing the santalene synthase in the presence or absence of farnesyl diphosphate synthase, indicating that FPP produced by yeast enzymes was accessible for *S. album* santalene synthase to produce santalenes and bergamotene. The high copy number construct pESC-LEU2d:SaSSY was used for further experiments.

2. Expression of Santalene Synthase and Cytochrome P450 Reductase

The pESC-LEU2d:SaSSY construct encoding santalene synthase and the pESC-His:SaCPR construct encoding *S. album* cytochrome P450 reductase (SaCPR) were co-transformed into the yeast strain BY4741. SaCPR was included to supply electrons from NADPH to the CYP450.

EXAMPLE 8

Microsome Preparation

In order to purify the *S. album* cytochrome P450 enzymes for use in in vitro assays, microsomes were prepared. Microsomes contain fragmented endoplasmic reticulum (ER) which contains cytochrome P450. Thus, purification of microsomes results in concentrated and isolated cytochrome P450. CO spectra of recombinant P450s encoded by the *S. album* CYP76F P450s was measured according to Guengerich et al. (2009) *Nat Protoc* 4:1245-1251.

Microsome membranes were prepared from 250 mL yeast cultures according to Pompom et al. (1996) *Methods Enzymol* 2(71):51-64. In brief, a 5 mL overnight culture was used to inoculate 50 mL of SD-selective media starting at an OD600 of 0.2 and grown at 30° C., 170 rpm for 24 hours. A volume of 200 mL YPDE medium (1% yeast extract, 2% bacto-peptone, 5% ethanol, 2% dextrose) was inoculated with the 50 mL culture and incubated for another 24 hours at 30° C., 170 rpm. Cells were collected by centrifugation for 10 min at 1,000×g and induced with 2% galactose in 250 mL YP medium at 30° C., 170 rpm for 12-16 hours. For microsome isolation, yeast cells were pelleted by centrifugation at 2,000×g for 10 min, washed once with 5 mL TEK (50 mM Tris-HCl pH 7.5, 1 mM EDTA, 100 mM KCl) and resuspended in TES2 buffer (50 mM Tris-HCl pH 7.5, 1 mM EDTA, 600 mM Sorbitol, 5 mM DTT and 0.25 mM PMSF). All subsequent steps were performed at 4° C. Yeast cell walls were disrupted mechanically using acid-washed glass beads (425-600 μm, Sigma) and vigorous manual shaking for 3×30 sec. The cell homogenate was centrifuged at 10,000×g for 15 min followed by ultracentrifugation of the supernatant at 100,000×g for 1 hour to collect membranes. Microsomes were resuspended and homogenized in a buffer containing 50 mM Tris-HCl buffer pH 7.5, 1 mM EDTA and 30% (v/v) glycerol, and used directly for enzyme assays or stored at −80° C.

Figure 18:
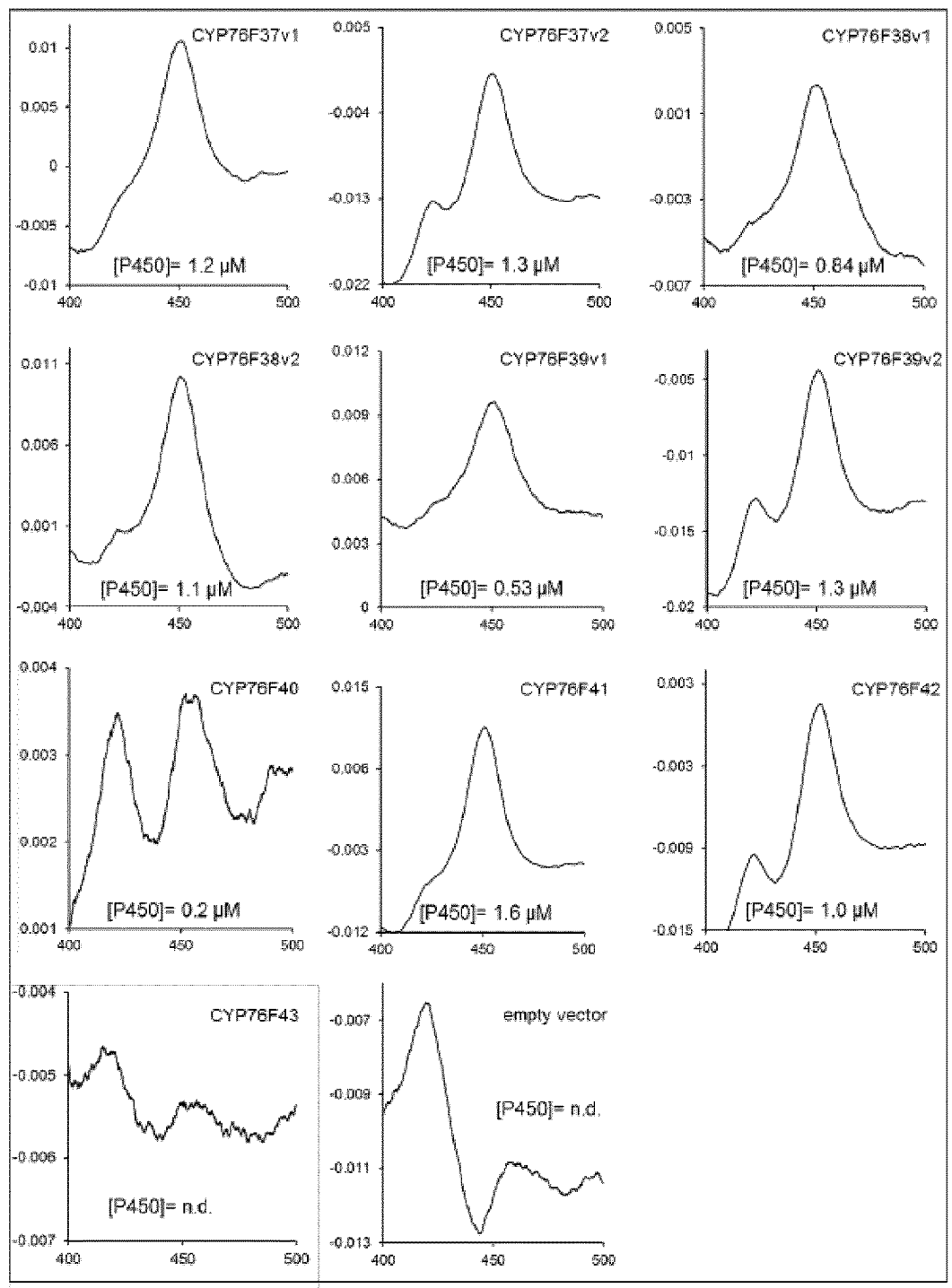
FIG. 18 depicts the reduced CO-difference spectra of isolated microsomes containing *S. album* CYP76F proteins. CO-difference spectra of microsomal fractions from *S. cerevisiae* harboring a cytochrome P450 or an empty vector are shown. Concentration of SaCYP76F proteins are given based on an extinction coefficient of 91,000 $M^{-1}$ $cm^{-1}$.
Figures 19A, 19B, 19C, 19D:
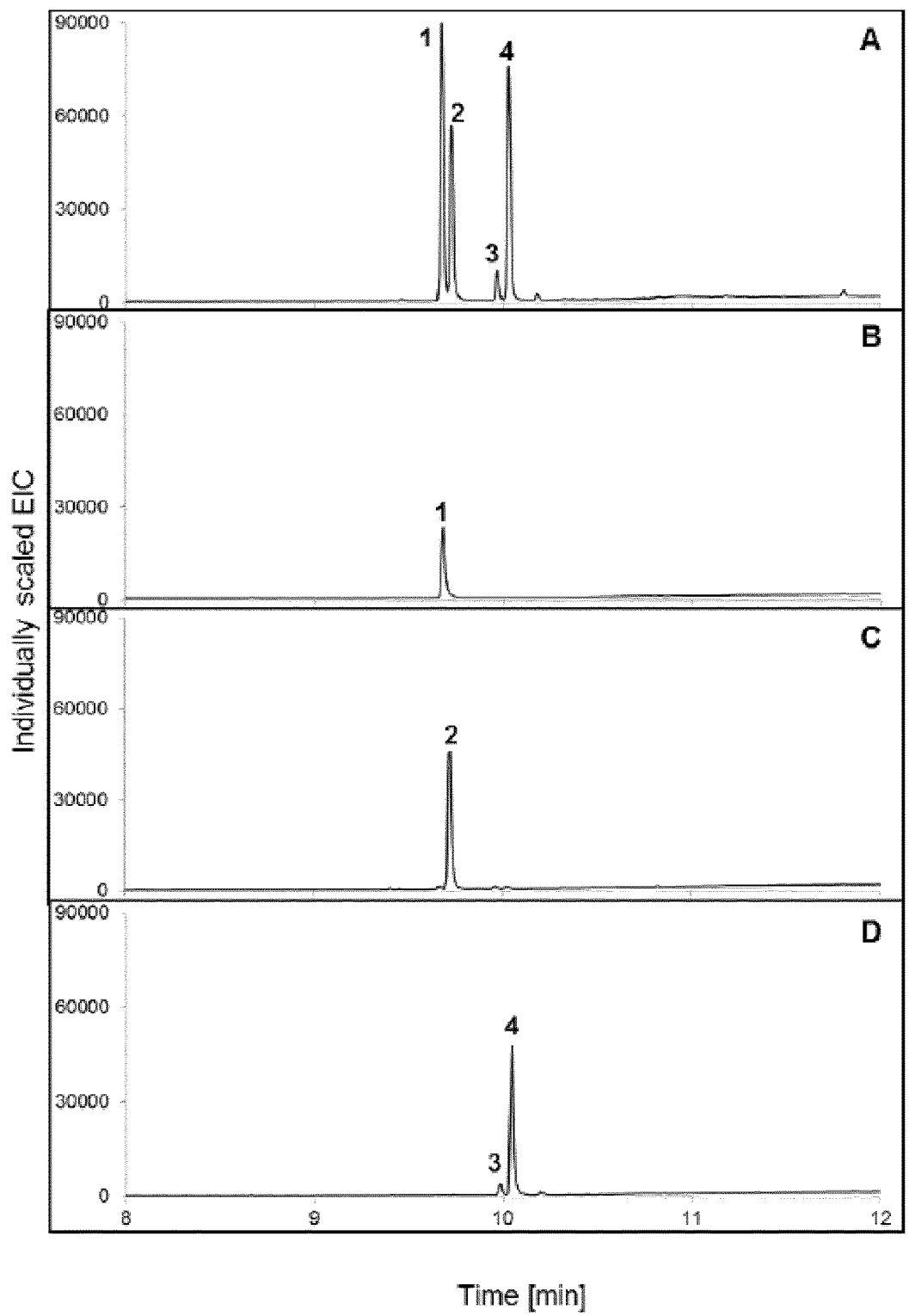
FIGS. 19A-19D depict the GC-MS analysis (extracted ion chromatograms) of a sesquiterpene mixture produced with a recombinant yeast strain expressing SaSSy (FIG. 19A) and fractions separated by TLC (FIGS. 19B-19D). The sesquiterpene mixture and fractions were prepared as described in Example 9. The peaks correspond to: α-santalene, peak 1; α-exo-bergamotene, peak 2; epi-β-santalene, peak 3; and β-santalene, peak 4.

Microsome preparations for all ten *S. album* CYP76Fs except SaCYP76F43 (SaCYP76-G18) displayed characteristic P450 CO difference spectra (see FIG. 18). The P450 content of the microsomal preparations ranged from 0.2 to 1.6 μM. Microsome preparations were screened for P450 activity as described in Example 11 below.

EXAMPLE 9

Generation and Isolation of Sesquiterpene Olefins

The sesquiterpene olefins α-santalene, β-santalene, epi-β-santalene and α-trans-bergamotene are not commercially available but can be produced by expression of *S. album* santalene synthase (SaSSY; SEQ ID NO:16) in yeast as described in Jones et al. (2011) *J Biol Chem* 286:17445-17454.

A sesquiterpene oil containing α-santalene, β-santalene, epi-β-santalene and α-trans-bergamotene was produced in an industrial scale fermentation. The mixture was separated using silver nitrate impregnated TLC plates according to Daramwar et al. (*Analyst* 137:4564-4570 (2012)). Fractions were scraped from the TLC plates and the sesquiterpenes were eluted with pentane followed by GC-MS analysis for purity. The extracted ion chromatograms are shown in FIGS. 19A-19D for the oil containing α-santalene, β-santalene, epi-β-santalene and α-trans-bergamotene (FIG. 19A), α-santalene (peak 1, FIG. 19B), α-trans-bergamotene (peak 2, FIG. 19C) and epi-β-santalene and β-santalene (peaks 3 and 4, FIG. 19D). The isolated sesquiterpenes were used in in vitro assays in Example 11 below.

EXAMPLE 10

Functional Characterization of S. album Cytochrome P450 Activity in S. cerevisiae The S. cerevisiae yeast host strain containing active santalene synthase and cytochrome P450 reductase described in Example 7.C.2. was used to express the S. album cytochrome CYP76F P450s identified in Example 2 above. Activity was assessed by measurement of in vivo formation of oxidation products as described in Section A below. Each S. album CYP76F in a pYeDP60 vector was transformed individually into the yeast host cell expressing santalene synthase and CPR. A control strain was generated that contained the empty pYeDP60 vector.

A. In Vivo P450 Assays in Yeast

For in vivo assays, yeast were grown overnight at 30° C. in 5 mL of 2% dextrose and minimal selective media. The next day, a 50 mL culture was initiated at a starting OD600 of 0.2 and grown at 30° C. with shaking at 170 rpm until the culture reached an OD600 of 0.6-0.8. Protein expression was initiated by transfer into minimal selective media with 2% galactose and grown for about 14-16 hours. Yeast cells were harvested by centrifugation at 1,000×g for 10 min and washed once with 5 mL sterile ddH₂O. Cells were extracted twice with 2 mL hexane:ethyl acetate (85:15) using about 250 μL acid-washed glass beads (425-600 μm, Sigma) and vortexing for 1 min. Pooled extracts were transferred to a clean test-tube containing anhydrous Na₂SO₄ and evaporated under a gentle stream of N₂ gas to about 200 μL. The samples were transferred to a GC glass vial for GC-MS analysis (as described in Example 6) or stored at −80° C.

B. Clade I Santalum album P450s

Clade I S. album P450s SaCYP76F39v1 (SaCYP76-G10), SaCYP76F39v2 (SaCYP76-G15), SaCYP76F40 (SaCYP76-G16), SaCYP76F41 (SaCYP76-G17) and SaCYP76F42 (SaCYP76-G13) were assayed for their activity in vivo with GC-MS analysis as described in Example 6A or 6B.

1. SaCYP76F39v1 (SaCYP76-G10) with GC-MS Analysis as Described in Example 6A

Figures 8A, 8B, 8C:
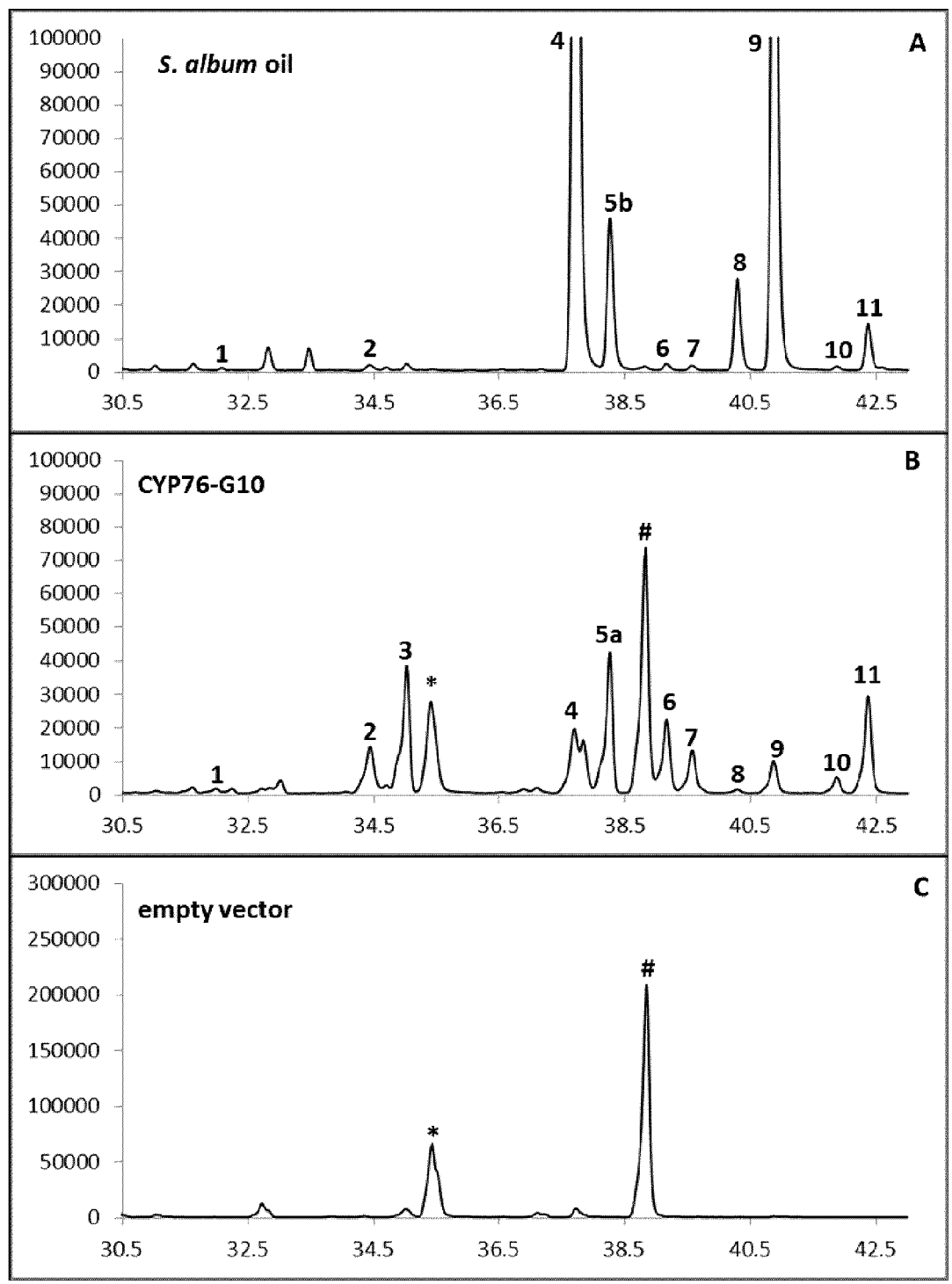
FIGS. 8A-8C depict the GC-MS chromatogram of *S. album* native oil (FIG. 8A) and of products extracted from in vivo assays with SaCYP76F39v1 (SaCYP76-G10) (FIG. 8B) and empty vector (FIG. 8C) as described in Example 10. The peaks are identified in Table 11.

Co-expression of santalene synthase and SaCYP76F39v1 (SaCYP76-G10) resulted in the detection of 11 product peaks identified as α-, β- and epi-β-santalol and α-trans-bergamotol (see FIGS. 8A-8B and Table 11 below). Nine (9) of the 11 products were also detected in the S. album oil, albeit in different ratios, as shown in FIGS. 8A and 8B. The products were identified based on matches of the MS fragmentation patterns with entries in the NIST and Wiley libraries (Wiley Registry® 9th Edition/NIST 2011; Fred W. McLafferty, John Wiley & Sons, Inc.) and by comparison with compounds of authentic S. album oil and Kovats index values (See FIG. 8A and Table 11). The main components of S. album oil are α-santalol, Z-α-trans-bergamotol, E-cis,epi-β-santalol and trans-β-santalol whereas the main products from SaCYP76F39v1 (SaCYP76-G10) are cis-α-santalol, α-santalol and trans-β-santalol. These differences can be due to different physiological conditions, such as pH, under which the SaSSy and SaP450 enzymes are active in the yeast cells and in the trees, or they can be due to changes in the ratios of products over time. The products monitored in yeast were formed and accumulated over a period of hours, while oil extracted from trees is potentially the product of years of accumulation. Farnesol (labeled #), which is produced by yeast independent of the expression of santalene synthase, and dodecanoic acid (labeled *), which is extracted from yeast, were also observed (see FIGS. 8B and 8C).

TABLE 11

Terpenoids identified in in vivo assay with SaCYP76F39v1 (SaCYP76-G10) and S. album oil

| Peak | Retention Time | Retention Index[1] | Products detected from SaCYP76F39v1 | Compounds detected in S. album oil |
|---|---|---|---|---|
| 1 | 32.23 | 2169 | unknown isomer of α-trans-bergamotol | traces |
| 2 | 35.2 | 2214 | unknown | Yes |
| 3 | 35.8 | 2228 | unknown isomer of α-santalol | No |
| 4 | 38.5 | 2294 | cis-α-santalol | Yes |
| 5a | 39.1 | 2308 | unknown isomer of α-santalol | No |
| 5b | 39.1 | 2308 | α-trans-bergamotol | Yes |
| 6 | 40.0 | 2331 | unknown isomer of α-santalol | Yes |
| 7 | 40.4 | 2341 | unknown isomer of α-trans-bergamotol | Yes |
| 8 | 41.1 | 2359 | Epi-β-santalol | Yes |
| 9 | 41.7 | 2374 | β-santalol | Yes |
| 10 | 42.7 | 2399 | unknown isomer of β-santalol | Yes |
| 11 | 43.2 | 2412 | unknown isomer of β-santalol | Yes |

[1]Linear retention indices (LRI) measured on a SGE Solgel-Wax column

* Dodecanoic acid, extracted from yeast; # Farnesol, product of yeast.

2. SaCYP76F39v1 (SaCYP76-G10) with GC-MS Analysis as Described in Example 6B

Figures 11A, 11B:
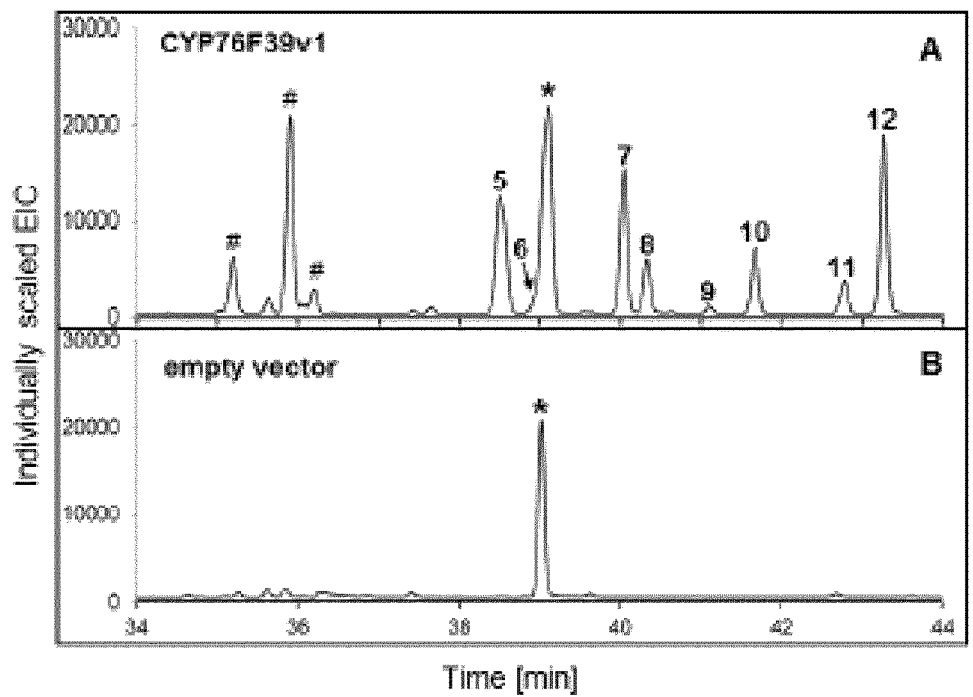
FIGS. 11A-11B depict the GC-MS analysis (extracted ion chromatograms) of products formed in vivo in yeast cells expressing SaSSY, SaCPR2 and SaCYP76F39v1 (SaCYP76-G10) (FIG. 11A) and empty vector (FIG. 11B). The peaks are identified in Table 12. Peaks marked with the symbol (*) correspond to farnesol which is also produced in yeast cells without SaCYP76F. Peaks in FIG. 11A marked with the symbol (#) represent yeast in vivo modifications of santalols (see FIGS. 12A and 12B).

Co-expression of santalene synthase and SaCYP76F39v1 (SaCYP76-G10) resulted in the detection of eight products identified as (Z)- and (E)-α-santalol (peaks 5 and 7), (Z)- and (E)-β-santalol (peaks 6 and 8), (Z)- and (E)-epi-β-santalol (peaks 9 and 11) and (Z)- and (E)-α-trans-bergamotol (peaks 10 and 12) (see FIG. 11A). Table 12 below sets forth the peak number, compound and linear retention indices for the DBwax column and the HP5 column. Product identification was based on best match of the MS fragmentation patterns with entries in the NIST and Wiley libraries (Wiley Registry® 9th Edition/NIST 2011; Fred W. McLafferty, John Wiley & Sons, Inc.) and by comparison with compounds of authentic S. album oil and Kovats index values. As shown in the figure, the product peak for (Z)-α-trans-bergamotol overlapped with a peak corresponding to (E,E)-farnesol, which was produced in yeast independent of SaCYP76F39v1 (SaCYP76-G10) (see FIG. 11B).

Figures 12A, 12B:
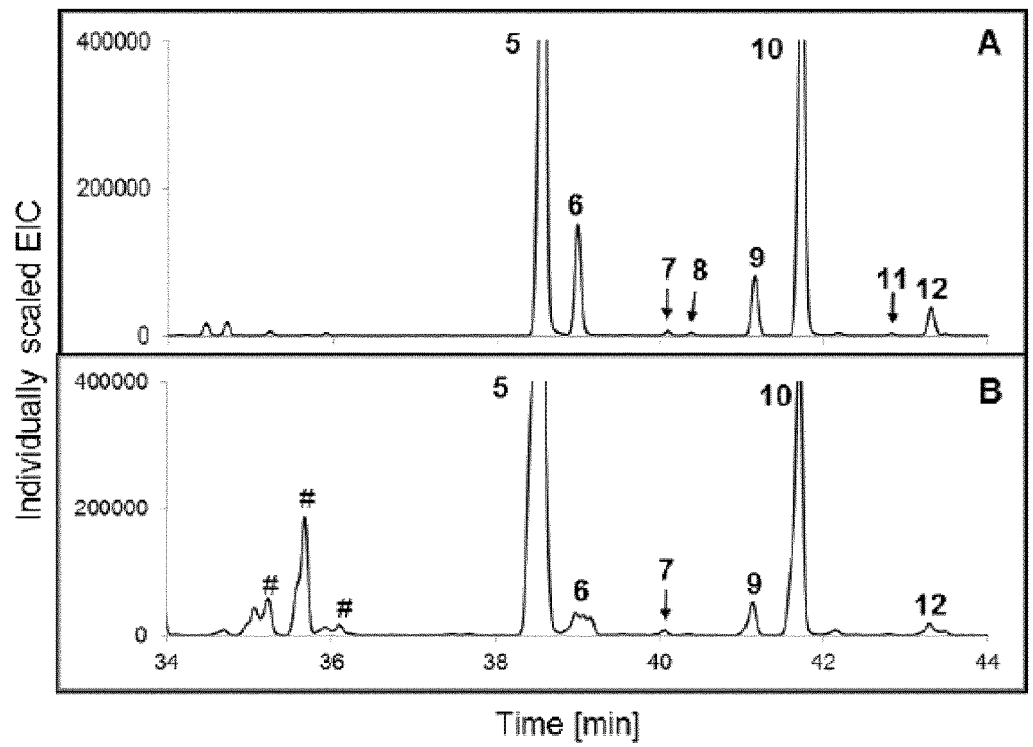
FIGS. 12A-12B depict the GC-MS analysis (extracted ion chromatograms) of sesquiterpenols of natural sandalwood oil sample before (FIG. 12A) and after (FIG. 12B) overnight incubation with yeast cells, which do not contain a SaCYP76F gene. Peaks in FIG. 12B marked with the symbol (#) represent yeast in vivo modifications of santalols independent of SaCYP76F. The peaks are identified in Table 12.

A fraction of the sesquiterpenols produced were modified to unidentified compounds (identified with hash tags (#) in FIG. 11A). When untransformed yeast cells were incubated with authentic sandalwood oil, the same unknown compounds were identified implying that these unidentified compounds are not direct products of SaCYP76F39v1 (SaCYP76-G10) but are produced by an endogenous activity of yeast converting sandalwood sesquiterpenols (see FIGS. 12A-12B).

TABLE 12

Retention indices of sesquiterpenes and sesquiterpenols

| Peak | Compound | LRI[1] DBwax | LRI[2] HP5 |
|---|---|---|---|
| 1 | α-santalene | 1579 | 1423 |
| 2 | α-trans-bergamotene | 1592 | 1437 |
| 3 | epi-β-santalene | 1637 | 1450 |
| 4 | β-santalene | 1652 | 1463 |
| 5 | (Z)-α-santalol | 2343 | 1676 |
| 6 | (Z)-α-trans-bergamotol | 2353 | 1692 |
| 7 | (E)-α-santalol | 2382 | 1697 |
| 8 | (E)-α-trans-bergamotol | 2389 | 1711 |
| 9 | (Z)-epi-β-santalol | 2409 | 1703 |
| 10 | (Z)-β-santalol | 2423 | 1717 |
| 11 | (E)-epi-β-santalol (tentative) | 2452 | 1726 |
| 12 | (E)-β-santalol | 2465 | 1738 |

[1]Linear retention indices (LRI) measured on a DBwax column.
[2]Linear retention indices (LRI) measured on a HP5 column.

3. SaCYP76F39v2 (SaCYP76-G15), SaCYP76F40 (SaCYP76-G16), SaCYP76F41 (SaCYP76-G17) and SaCYP76F42 (SaCYP76-G13)

SaCYP76F39v2 (SaCYP76-G15), SaCYP76F40 (SaCYP76-G16), SaCYP76F41 (SaCYP76-G17) and SaCYP76F42 (SaCYP76-G13) were assayed for their ability to oxidize sesquiterpenes using the in vivo assay described above with GC-MS analysis described in Example 6B. Co-expression of santalene synthase and SaCYP76F39v2 (SaCYP76-G15), SaCYP76F40 (SaCYP76-G16), SaCYP76F41 (SaCYP76-G17) or SaCYP76F42 (SaCYP76-G13) gave product profiles with nearly identical ratios to those observed for SaCYP76F39v1 (SaCYP76-G10) (see Table 12 and FIGS. 13A-13D).

C. Clade II *Santalum album* P450s

Clade II *S. album* P450s SaCYP76F37v1 (SaCYP76-G11), SaCYP76F38v2 (SaCYP76-G12), SaCYP76F37v2 (SaCYP76-G14) and SaCYP76F38v1 (SaCYP76-G5) were assayed for their activity in vivo with GC-MS analysis as described in Example 6A or 6B.

Figures 6A, 6B, 6C, 6D:
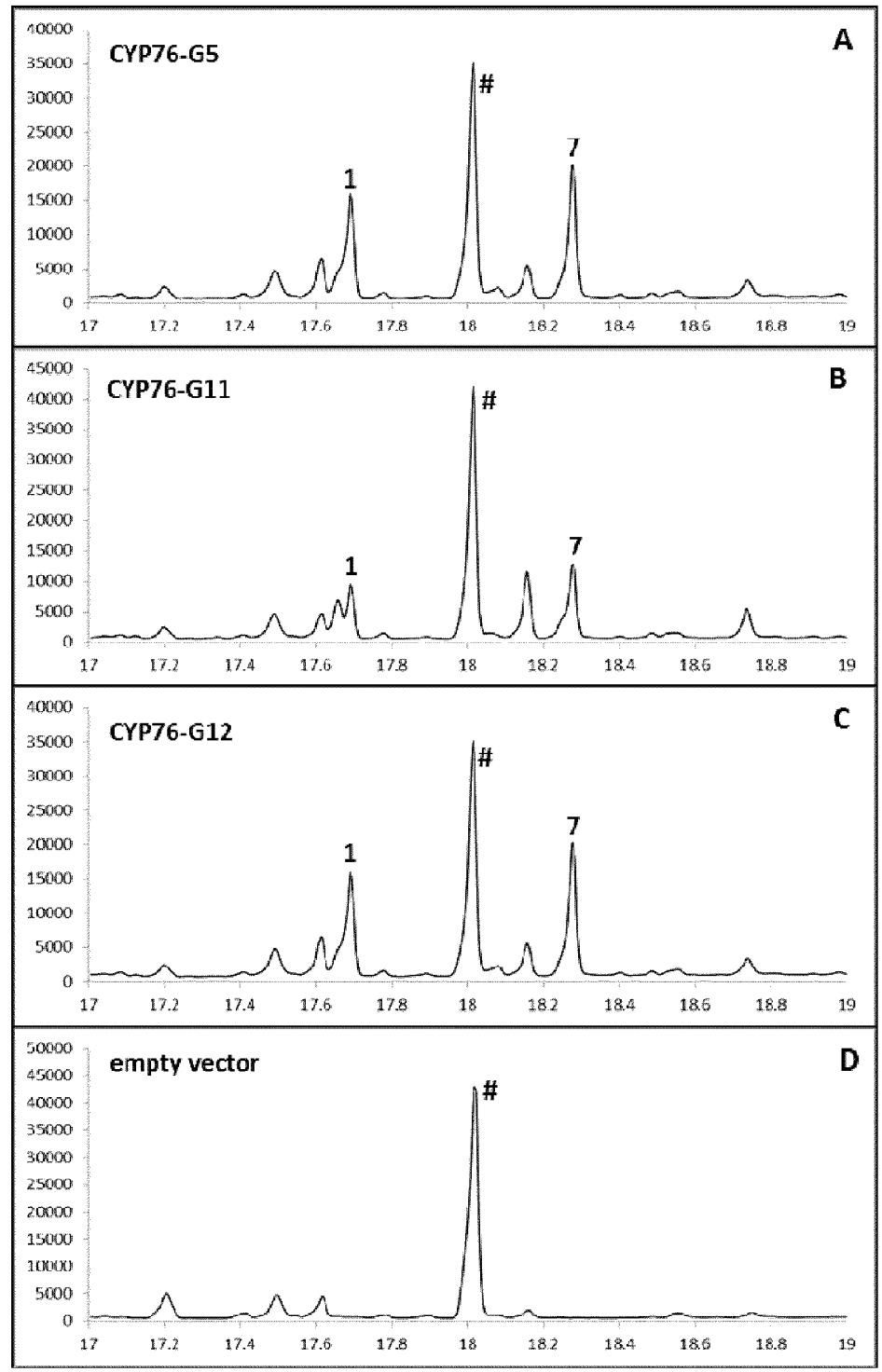
FIGS. 6A-6D depict the GC-MS chromatogram of products extracted from in vivo assays with SaCYP76F38v1 (SaCYP76-G5) (FIG. 6A), SaCYP76F37v1 (SaCYP76-G11) (FIG. 6B), SaCYP76F38v2 (SaCYP76-G12) (FIG. 6C) and empty vector (FIG. 6D) as described in Example 10. The peaks are identified in Table 13.
Figure 7:
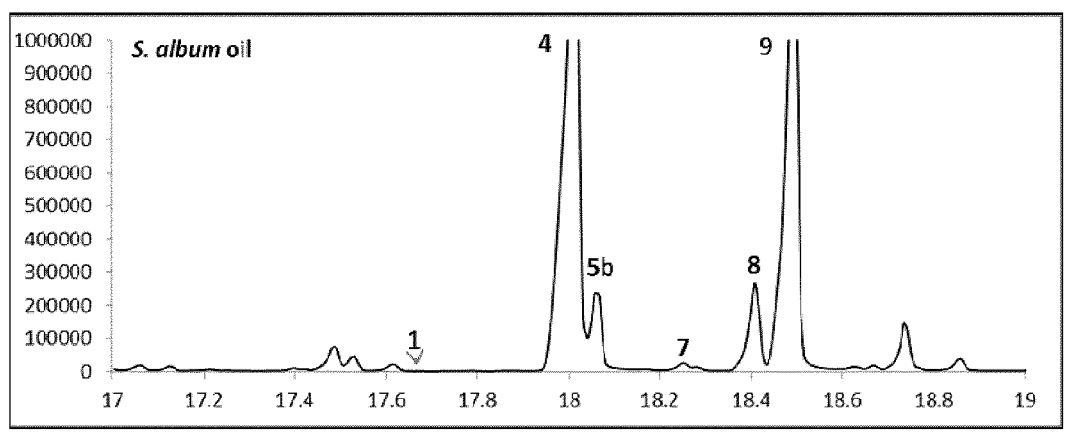
FIG. 7 depicts the total ion chromatogram of *S. album* oil extract. The peaks are identified in Table 13.

1. SaCYP76F38v1 (SaCYP76-G5), SaCYP76F37v1 (SaCYP76-G11) and SaCYP76F38v2 (SaCYP76-G12) with GC-MS Analysis as Described in Example 6A Co-expression of santalene synthase with SaCYP76F38v1 (SaCYP76-G5), SaCYP76F37v1 (SaCYP76-G11) or SaCYP76F38v2 (SaCYP76-G12) in the recombinant yeast system resulted in virtually identical products (see FIGS. 6A, 6B and 6C and Table 13 below). The products were identified based on matches of the MS fragmentation patterns with entries in the NIST and Wiley libraries (Wiley Registry® 9th Edition/NIST 2011; Fred W. McLafferty, John Wiley & Sons, Inc.) and by comparison with compounds of authentic *S. album* oil (See FIG. 7 and Table 13). Peaks 1 and 7, which were observed for SaCYP76F38v1 (SaCYP76-G5), SaCYP76F37v1 (SaCYP76-G11) and SaCYP76F38v2 (SaCYP76-G12), correspond to α-trans-bergamotol, possibly representing different isomers. Peaks 1 and 7 were also observed for *S. album* oil (see FIG. 7 and Table 13). A third peak (labeled #) with a retention time of approximately 18 minutes was identified as farnesol, which is produced by yeast independent of the expression of santalene synthase and SaCYP76, as observed by its expression in the control cells containing an empty vector (FIG. 6D).

TABLE 13

Terpenoids identified in in vivo assay with SaCYP76-F38v1, -F37v1, -F38v2 and *S. album* oil

| Peak | Retention Time | Products detected from CYP76-F38v1, -F37v1, -F38v2 | Compounds detected in *S. album* oil |
|---|---|---|---|
| 1 | 17.64 | unknown isomer of α-trans-bergamotol | traces |
| 4 | 18.00 | cis-α-santalol | Yes |
| 5b | 18.05 | α-trans-bergamotol | Yes |
| 7 | 18.15 | unknown isomer of α-trans-bergamotol | Yes |
| 8 | 18.40 | Epi-β-santalol | Yes |
| 9 | 18.50 | β-santalol | Yes |

[1]Linear retention indices (LRI) measured on a SGE Solgel-Wax column

Farnesol, product of yeast.

2. SaCYP76F38v1 (SaCYP76-G5), SaCYP76F37v1 (SaCYP76-G11) or SaCYP76F38v2 (SaCYP76-G12) or SaCYP76F37v2 (SaCYP76-G14)

SaCYP76F38v1 (SaCYP76-G5), SaCYP76F37v1 (SaCYP76-G11) or SaCYP76F38v2 (SaCYP76-G12) or SaCYP76F37v2 (SaCYP76-G14) were assayed for their ability to oxidize sesquiterpenes using the in vivo assay described above with GC-MS analysis described in Example 6B. Co-expression of santalene synthase with SaCYP76F38v1 (SaCYP76-G5), SaCYP76F37v1 (SaCYP76-G11) or SaCYP76F38v2 (SaCYP76-G12) or SaCYP76F37v2 (SaCYP76-G14) in the recombinant yeast system resulted in mostly E-α-trans-bergamotene (peak 8 in Table 12) with only traces of (E)-α-santalol and (E)-β-santalol (peaks 7 and 12 in Table 12) (see Table 12 and FIGS. 14A-14D)

D. SaCYP76F43 (SaCYP76-G18)

SaCYP76F43 (SaCYP76-G18) was assayed for its ability to oxidize sesquiterpenes using the in vivo assay described above with GC-MS analysis described in Example 6B. No activity was observed after co-expression of santalene synthase with SaCYP76F43 (SaCYP76-G18) (see FIG. 14E).

E. SaCPR1 and SaCPR2

To test if SaCPR1 and SaCPR2, which are 70% identical at the protein level, could affect changes in the product profiles, both CPRs were tested as indicated in Example 6B with representative class I and class II SaCYP76Fs SaCYP76F39v1 and SaCYP76F38v1. No differences were observed in the products and relative abundances as compared to those described in Sections B.2. and C.2. above.

EXAMPLE 11

In Vitro Enzymatic Assays

Yeast microsomes containing a *S. album* cytochrome P450 and a cytochrome P450 reductase, generated in Example 8, were assayed for their ability to oxidize santalenes and bergamotene using either A) a coupled enzyme assay with the in vitro reaction products of SaSSy and FPP; B) an isolated mixture of santalenes and bergamotene as the substrate; or C) individual santalenes or bergamotene as the substrate.

A. Oxidation of Santalenes and Bergamotene Using a Coupled Enzyme Assay

Coupled enzyme assays with *S. album* santalene synthase (SaSSy) expressed in bacteria (Jones et al. (2011) *J Biol Chem* 286:17445-17454) were initiated with 50 μg of His$_6$-tag purified SaSSy and 70 μM farnesyl pyrophosphate (FPP) in TPS buffer (25 mM HEPES pH 7.5, 5 mM MgCl$_2$, 1 mM DTT) in a volume of 450 μL. The assays were incubated for 30 min at 30° C. followed by the addition of 50 μL of the microsome preparation containing a *S. album* cytochrome P450 and a cytochrome P450 reductase and 0.8 mM NADPH. The reaction was incubated for an additional 1 hour at 30° C. and was stopped by extraction with 500 μL hexane/ethyl acetate (85:15). The organic layer was concentrated under a gentle stream of $N_2$ gas to about 100 μL and analyzed by GC-MS analysis (as described in 6A above) or was stored at −80° C.

1. SaCYP76F38v1 (SaCYP76-G5)

The coupled enzyme assay was performed in vitro with SaCYP76F38v1 (SaCYP76-G5) and compared to the in vivo results to verify the utility of the assay. GC-MS analysis of the reaction products from the coupled assay showed the same two peaks identified in the in vivo assay in Example 8. In both assays, SaCYP76F38v1 (SaCYP76-G5) catalyzed the hydroxylation of bergamotene into Z-α-trans-bergamotol but did not catalyze the oxidation of any santalenes.

B. Oxidation of a Mixture of Santalenes and Bergamotene

*S. album* P450s were assayed for their sesquiterpene oxidase activities using a mixture of santalenes and bergamotene as the substrate.

1. Assays

Two different in vitro assays were used to screen the *S. album* CYP76Fs for sesquiterpene oxidase activity.

a. In Vitro Assay 1

Assays were performed in 400 μL reaction volumes containing 150 μL potassium phosphate buffer 100 mM (pH 7.5), 20 μL 20 mM NADPH, 1 μL of 25 mM santalene/bergamotene mixture [containing α-santalene, epi-β-santalene, β-santalene, α-bergamotene] and 80 pmol of the microsomes preparation (prepared as described in Example 8). The reactions were incubated at 30° C. for 1 hour and stopped by adding 500 μL hexane:ethyl acetate (85:15) followed by vortexing for 30 seconds. The organic layer was concentrated under a gentle stream of $N_2$ gas to about 100 μL and analyzed by GC-MS analysis (as described in Example 6A above) or was stored at −80° C.

b. In Vitro Assay 2

Assays were performed in 400 μL reaction volumes containing 50 mM potassium phosphate pH 7.5, 0.8 mM NADPH and 40 μM of substrate. Enzyme reactions were initiated by adding 50 μL of the microsomes preparation (prepared in Example 8), incubated at 30° C. for 2 hours with shaking and stopped by adding 500 μL hexane. The organic layer was transferred to a new GC vial and concentrated under a gentle stream of $N_2$ gas to about 100 μL and analyzed by GC-MS analysis (as described in Example 6B above).

2. Clade I *Santalum album* P450s

Microsomes containing clade I *S. album* P450s SaCYP76F39v1 (SaCYP76-G10), SaCYP76F39v2 (SaCYP76-G15), SaCYP76F40 (SaCYP76-G16), SaCYP76F41 (SaCYP76-G17) and SaCYP76F42 (SaCYP76-G13) were assayed for their sesquiterpene oxidize activity using the assays set forth above using a mixture of santalenes and bergamotene as the substrate.

a. SaCYP76F39v1 (SaCYP76-G10)

The in vitro sesquiterpene oxidase activity Clade I *S. album* P450 SaCYP76F39v1 (SaCYP76-G10) was assessed using both assays described above.

i. Initial Experiment Using In Vitro Assay 1

Figures 9A, 9B:
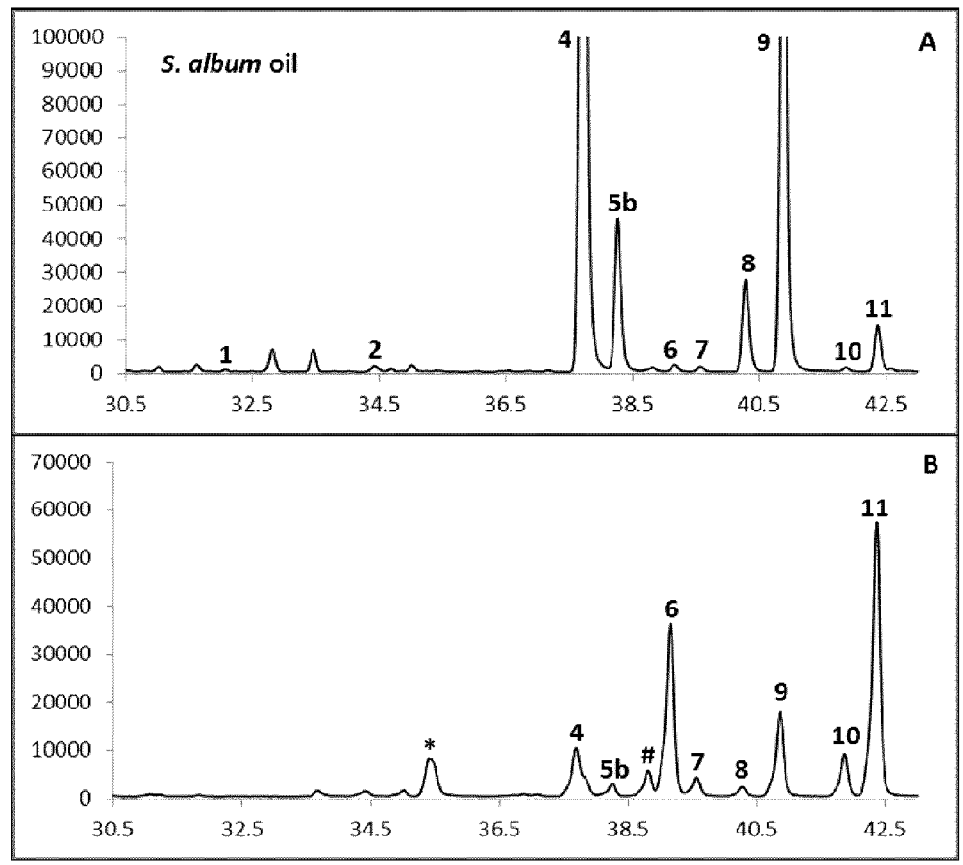
FIGS. 9A-9B depict the GC-MS chromatogram of *S. album* native oil (FIG. 9A) and of products extracted from in vitro assays with SaCYP76F39v1 (SaCYP76-G10) (FIG. 9B) as described in Example 11. The peaks are identified in Table 11.

Microsomes containing SaCYP76F39v1 (SaCYP76-G10) were assayed for their activity using the assay described in Section B.1.a. above. GC-MS analysis revealed eight different product peaks that were identified as santalols (see FIG. 9B, peaks correspond to those in Table 11 above).

Product identification was based on best match of the MS fragmentation patterns with entries in the NIST and Wiley libraries (Wiley Registry® $9^{th}$ Edition/NIST 2011; Fred W. McLafferty, John Wiley & Sons, Inc.) and by comparison with compounds of authentic *S. album* oil (FIG. 9A) and Kovats index values.

ii. Assay Using In Vitro Assay 2

Microsomes containing SaCYP76F39v1 (SaCYP76-G10) were assayed for their activity using the assay described in Section B.1.b above. GC-MS analysis of the reaction products revealed that SaCYP76F39v1 (SaCYP76-G10) catalyzed the hydroxylation of α-santalene, β-santalene, epi-β-santalene and α-trans-bergamotene, leading to 8 different compounds identified as (Z)- and (E)-α-santalol, (Z)- and (E)-β-santalol, (Z)- and (E)-epi-β-santalol and (Z)- and (E)-α-trans-bergamotol (see FIG. 15A and Table 12). The product profile was compared to an authentic sandalwood oil sample (see Table 12 and FIG. 15B), which showed identical retention times and mass spectra for all 8 compounds but in different ratios. SaCYP76F39v1 (SaCYP76-G10) produced (E)-α-santalol and (Z)-α-santalol in a ratio of approximately 5:1, and (E)-β-santalol and (Z)-β-santalol in a ratio of approximately 4:1. The main products formed with SaCYP76F39v1 (SaCYP76-G10) were (E)-α-santalol and (E)-β-santalol while the main compounds of sandalwood oil are (Z)-α-santalol and (Z)-β-santalol. No product was formed in the absence of NADPH or with microsomes from yeast carrying an empty vector (see FIG. 15C).

b. SaCYP76F39v2 (SaCYP76-G15), SaCYP76F40 (SaCYP76-G16), SaCYP76F41 (SaCYP76-G17) and SaCYP76F42 (SaCYP76-G13)

Microsomes containing SaCYP76F39v2 (SaCYP76-G15), SaCYP76F40 (SaCYP76-G16), SaCYP76F41 (SaCYP76-G17) and SaCYP76F42 (SaCYP76-G13) were assayed for their activity using the assay described in Section B.1.b above. GC-MS analysis of the reaction products revealed that SaCYP76F39v2 (SaCYP76-G15), SaCYP76F40 (SaCYP76-G16), SaCYP76F41 (SaCYP76-G17) and SaCYP76F42 (SaCYP76-G13) gave product profiles similar to those observed for SaCYP76F39v1 (SaCYP76-G10) (see Table 12 and FIGS. 16A-16D). The major products observed for SaCYP76F40 (SaCYP76-G16) and SaCYP76F42 (SaCYP76-G13) were (E)-α-trans-bergamotol (or (E)-α-exo-bergamotol) and (E)-β-santalol.

3. Clade II *S. album* P450s

Microsomes containing clade II *S. album* P450s SaCYP76F37v1 (SaCYP76-G11), SaCYP76F38v2 (SaCYP76-G12), SaCYP76F37v2 (SaCYP76-G14) and SaCYP76F38v1 (SaCYP76-G5) were assayed for their sesquiterpene oxidize activity using the assays set forth above using a mixture of santalenes and bergamotene as the substrate.

a. SaCYP76F37v1 (SaCYP76-G11) and SaCYP76F38v2 (SaCYP76-G12)

Microsomes containing SaCYP76F37v1 (SaCYP76-G11) and SaCYP76F38v2 (SaCYP76-G12) were assayed for their activity using the assay described in Section B.1.a. above. GC-MS analysis of the reaction products revealed one product peak that was absent in the control reaction (microsomes containing only vector control). The product peak was identified as Z-α-trans-bergamotol based on best match of its MS fragmentation pattern with entries in the NIST and Wiley libraries (Wiley Registry® $9^{th}$ Edition/NIST 2011; Fred W. McLafferty, John Wiley & Sons, Inc.) and by comparison with compounds of authentic *S. album* oil.

b. SaCYP76F37v1 (SaCYP76-G11), SaCYP76F38v2 (SaCYP76-G12), SaCYP76F37v2 (SaCYP76-G14) and SaCYP76F38v1 (SaCYP76-G5)

Microsomes containing SaCYP76F37v1 (SaCYP76-G11), SaCYP76F38v2 (SaCYP76-G12), SaCYP76F37v2 (SaCYP76-G14) and SaCYP76F38v1 (SaCYP76-G5) were assayed for their activity using the assay described in Section B1b. above. GC-MS analysis of the reaction products revealed that SaCYP76F37v1 (SaCYP76-G11), SaCYP76F38v2 (SaCYP76-G12), SaCYP76F37v2 (SaCYP76-G14) and SaCYP76F38v1 (SaCYP76-G5) produced three compounds, which were identified as (E)-α-trans-bergamotol (or (E)-α-exo-bergamotol) as the major product, and (E)-α-santalol and (E)-β-santalol as minor products (see Table 12 and FIGS. 17A-17D).

4. SaCYP76F43 (SaCYP76-G18)

Microsomes containing SaCYP76F43 (SaCYP76-G18) were assayed for their activity using the assay described in Section B.1.b above using a mixture of santalenes and bergamotene as the substrate. No activity was observed (see FIG. 17E) possibly due to low expression in yeast as evidenced by the corresponding CO difference spectrum (see FIG. 18).

C. Oxidation of Individual Sesquiterpenes

Microsome preparations containing candidate P450 were assayed for their capacity to oxidize individual sesquiterpenes. The sesquiterpenes were isolated as described in Example 9 above. Three fractions containing mainly α-santalene, α-trans-bergamotene, or epi-β-santalene and β-santalene were used as individual substrates in assays containing clade I P450 SaCYP76F39v1 (SaCYP76-G10) or clade II P450 SaCYP76F37v1 (SaCYP76-G11). The assays were performed as described in Section B.1.b. above and products were identified by comparison to authentic standards (see Table 12 and FIG. 20G).

Figures 20A, 20B, 20C, 20D, 20E, 20F, 20G:
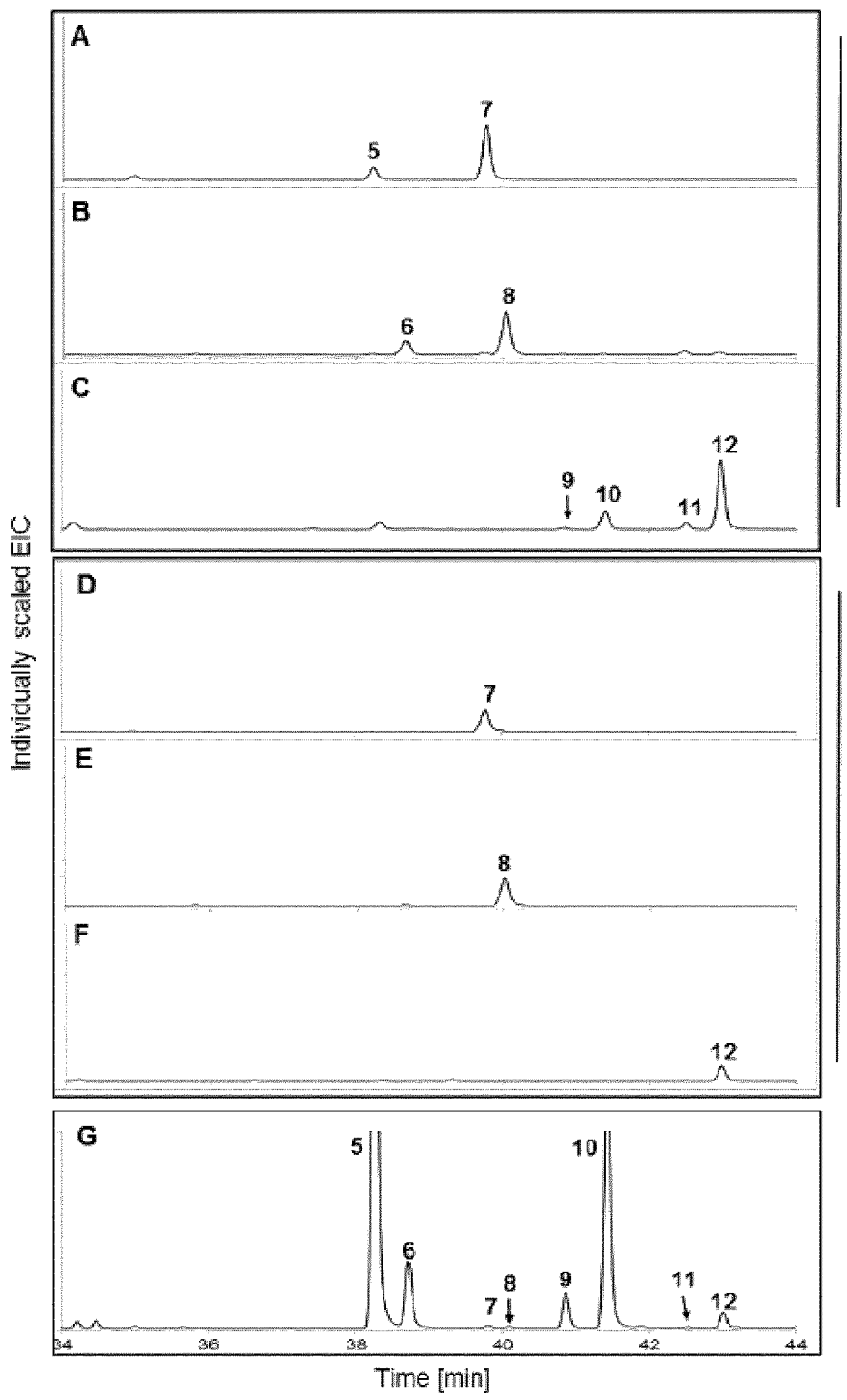
FIGS. 20A-20G depict the GC-MS analysis (extracted ion chromatograms) of products formed in vitro with SaCYP76F39v1 (SaCYP76-G10) or SaCYP76F37v1 (SaCYP76-G11) using partially purified substrates.

Reaction of SaCYP76F39v1 (SaCYP76-G10) with α-santalene produced (Z)- and (E)-α-santalol while only (E)-α-santalol was produced with SaCYP76F37v1 (SaCYP76-G11) (see FIG. 20A versus FIG. 20D). With α-trans-bergamotene, SaCYP76F39v1 (SaCYP76-G10) produced (Z)- and (E)-α-trans-bergamotol while only (E)-α-trans-bergamotol formation was observed for SaCYP76F37v1 (SaCYP76-G11) (see FIG. 20B versus FIG. 20E). SaCYP76F39v1 (SaCYP76-G10) gave four products (Z)- and (E)-epi-β-santalol and (Z)- and (E)-β-santalol in assays with epi-β-santalene and β-santalene whereas only (E)-β-santalol was detected in assays with SaCYP76F37v1 (SaCYP76-G11) (see FIG. 20C versus FIG. 20F). These results confirm the activities observed with microsome in vitro assays with the mixture of santalenes and bergamotene (Section B above).

SUMMARY OF RESULTS FROM EXAMPLES 10 and 11

Clade I *S. album* P450 Santalene/Bergamotene Oxidases

Clade I *S. album* P450s SaCYP76F39v1 (SaCYP76-G10), SaCYP76F39v2 (SaCYP76-G15), SaCYP76F40 (SaCYP76-G16), SaCYP76F41 (SaCYP76-G17) and SaCYP76F42 (SaCYP76-G13) catalyzed the oxidation of santalenes and bergamotene producing the (Z) and (E) stereoisomers of α-, β- and epi-β-santalols and bergamotols. The P450 ratios of (Z) and (E) stereoisomers of α- and β-santalol were approximately 1:5 and 1:4, respectively. Thus SaCYP76F39v1 (SaCYP76-G10), SaCYP76F39v2 (SaCYP76-G15), SaCYP76F40 (SaCYP76-G16), SaCYP76F41 (SaCYP76-G17) and SaCYP76F42 (SaCYP76-G13) were identified as a santalene/bergamotene oxidases.

Clade II *S. album* P450 Bergamotene Oxidases

Clade II *S. album* P450s SaCYP76F37v1 (SaCYP76-G11), SaCYP76F38v2 (SaCYP76-G12), SaCYP76F37v2 (SaCYP76-G14) and SaCYP76F38v1 (SaCYP76-G5) primarily catalyzed the oxidation of bergamotene into bergamotol, with (E)-α-trans-bergamotol as the major product and minor amounts of (E)-α-santalol and (E)-β-santalol observed. SaCYP76F37v1 (SaCYP76-G11), SaCYP76F38v2 (SaCYP76-G12), SaCYP76F37v2 (SaCYP76-G14) and SaCYP76F38v1 were identified as bergamotene oxidases.

EXAMPLE 12

Kinetic Properties

To test the kinetics of the clade I and clade II SaCYP76F enzymes, kinetic assays were performed with SaCYP76F37v1 (SaCYP76-G11) and SaCYP76F39v1 (SaCYP76-G10) with α-santalene or β-santalene as the substrate. Assays were performed in 400 μL reaction volumes containing 50 mM potassium phosphate pH 7.5, 0.8 mM NADPH and substrate concentrations of 12 to 138 μM of α-santalene or β-santalene. Enzyme reactions were initiated by adding either 17 pmol of SaCYP7639v1 or 35 pmol of SaCYP7637v1, incubated at 30° C. for 20 minutes with shaking and stopped by adding 500 μL hexane. The organic layer was transferred to a new GC vial and concentrated under a gentle stream of $N_2$ gas to about 100 μL and analyzed by GC-MS analysis (as described in Example 6B above). Kinetic data were evaluated using tools described in Hernandez and Ruiz ((1998) *Bioinformatics*. 14:227-228).

The apparent $K_m$ values, $k_{cat}$ values and $k_{cat}/K_m$ values for SaCYP76F39v1 (SaCYP76-G10) and SaCYP76F37v1 (SaCYP76-G11) with α-santalene and β-santalene are set forth in Table 14 below.

TABLE 14

Kinetic constants for SaCYP76F39v1 and SaCYP76F37v1

| | α-santalene | | |
|---|---|---|---|
| P450 | $K_m$ (μM) | $k_{cat}$ ($s^{-1}$) | $k_{cat}/K_m$ ($s^{-1} M^{-1}$) |
| SaCYP76F39v1 (SaCYP76-G10) | 25.92 ± 0.11 | 1.12 | $4.3 \times 10^4$ |
| SaCYP76F37v1 (SaCYP76-G11) | 133 ± 0.41 | 0.2 | $1.5 \times 10^3$ |

| | β-santalene | | |
|---|---|---|---|
| P450 | $K_m$ (μM) | $k_{cat}$ | $k_{cat}/K_m$ |
| SaCYP76F39v1 (SaCYP76-G10) | 34.82 ± 0.41 | 1.17 | $3.3 \times 10^4$ |
| SaCYP76F37v1 (SaCYP76-G11) | 157 ± 0.17 | 0.13 | $8.1 \times 10^2$ |

EXAMPLE 13

Substrate Specificity

A. Substrate Specificity of Clade I and Clade II SaCYP76F Enzymes

To test the range of substrates used by the clade I and clade II SaCYP76F enzymes, yeast microsomes containing SaCYP76F37v1 (SaCYP76-G11) and SaCYP76F39v1 (SaCYP76-G10) were assayed for their ability to convert various sesquiterpenes, including the substrates α-santalene and β-santalene and 7 additional sesquiterpenes which resemble santalenes in the acyclic isoprenyl side chain, including α-curcumene, zingiberine, β-bisabolene, β-sesquiphellandrene, α-bisabolol, trans-β-farnesene and trans-nerolidol. Each substrate was tested using the in vitro assay described in Example 11.B.1.b above.

The results are shown in Table 15 below, which sets forth the substrates, including their structures, and the relative activities which represent the rate of product formation relative to product formation by SaCYP76F39v1 (SaCYP76-G10) with β-santalene. As shown in the table, SaCYP76F39v1 (SaCYP76-G10) and SaCYP76F37v1 (SaCYP76-G11) exhibited narrow substrate selectivity, with both preferring santalenes, including α-santalene or β-santalene, as substrates. SaCYP76F39v1 (SaCYP76-G10) efficiently converted only the two santalenes and had low activity with α-bisabolol. SaCYP76F39v1 (SaCYP76-G10) did not use α-curcumene, zingiberene, β-bisabolene, β-sesquiphellandrene, trans-β-farnesene or trans-nerolidol as a substrate. Similarly, SaCYP76F37v1 (SaCYP76-G11) was selectively active with the two santalenes and trans-nerolidol.

TABLE 15

Relative activities of SaCYP76F39v1 and SaCYP76F37v1 with various sesquiterpene substrates.

| Substrate | | SaCYP76F39v1 (SaCYP76-G10) [%]* | SaCYP76F37v1 (SaCYP76-G11) [%]* |
|---|---|---|---|
| α-santalene | 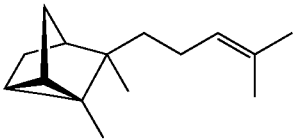 | 99.8 | 17.3 |
| β-santalene | 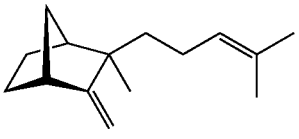 | 100 | 17.7 |
| α-curcumene | 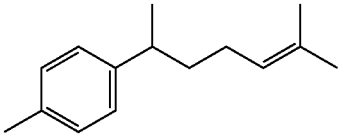 | 0 | 0 |
| zingiberene | 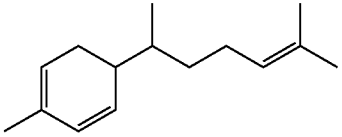 | 0 | 0 |
| β-bisabolene | 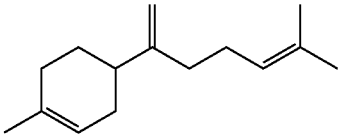 | 0 | 0 |
| β-sesquiphellandrene | 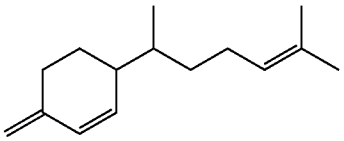 | 0 | 0 |
| α-bisabolol | 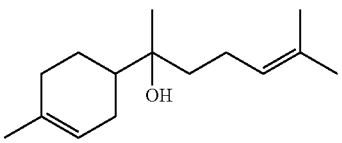 [SMILES: CC(C)=CCCC(C)(O)C1CC=C(C)CC1] | 9.4 | 0 |

TABLE 15-continued

Relative activities of SaCYP76F39v1 and SaCYP76F37v1 with various sesquiterpene substrates.

| Substrate | | SaCYP76F39v1 (SaCYP76-G10) [%]* | SaCYP76F37v1 (SaCYP76-G11) [%]* |
|---|---|---|---|
| trans-farnesene | | 0 | 0 |
| trans-nerolidol | | 0 | 11.3 |

*Relative activities represent rate of product formation relative to product formation by SaCYP76F39v1 eith β-santalene.

B. Oxidation of Various Mono- and Sesquiterpenes Substrates

Yeast microsomes containing S. album cytochrome P450 SaCYP76F38v1 (SaCYP76-G5) and cytochrome P450 reductase were directly assayed for their capacity to oxidize different mono- and sesquiterpene substrates, including linalool, geraniol, nerol, nerolidol and bisabolol. The reaction mixtures contained 50 mM potassium phosphate, 0.8 mM NADPH and 60 to 80 µM of the terpene substrate in a total volume of 350 µL. Enzyme reactions were started by adding 50 µL of the microsome preparation, incubated at 30° C. for 1 hour with shaking and stopped by extraction with 500 µL of hexane/ethyl acetate (85:15). The organic layer was concentrated under a gentle stream of $N_2$ gas to about 100 µL and analyzed by GC-MS analysis as described in Example 6. Results were compared to vector control. The reaction products were identified based on matches of the MS fragmentation patterns with entries in the NIST and Wiley libraries (Wiley Registry® $9^{th}$ Edition/NIST 2011; Fred W. McLafferty, John Wiley & Sons, Inc.).

1. SaCYP76F38v1 (SaCYP76-G5)

Reaction of SaCYP76F38v1 (SaCYP76-G5) with linalool resulted in two products: Peak 1, retention time of at approximately 17.5 minutes and Peak 2, retention time of approximately 18.5 minutes. Linalool had a retention time of approximately 10.5. The best matches for the MS fragmentation patterns of Peaks 1 and 2 correspond to 3,8-dimethyl-1,7-octadien-6-ol and 8-hydroxylinalool, respectively. Reaction of SaCYP76F38v1 (SaCYP76-G5) with geraniol resulted in one product with a retention time of approximately 21 minutes. Geraniol had a retention time of approximately 14 minutes. The best match for this peak's MS fragmentation pattern corresponds to trans,trans-2,6-dimethyl-2,6-octadiene-1,8 diol. Reaction of SaCYP76F38v1 (SaCYP76-G5) with nerol resulted in one product with a retention time of approximately 20.8 minutes, whereas nerol had a retention time of approximately 13.4 minutes. The best match for this peak's MS fragmentation pattern corresponds to 2,6-dimethyl-2,6-octadiene-1,8 diol. Reaction of SaCYP76F38v1 (SaCYP76-G5) with nerolidol resulted in two products, with retention times of approximately 21.3 and 22.3 minutes, whereas nerolidol had a retention time of approximately 16.1 minute. Reaction of SaCYP76F38v1 (SaCYP76-G5) with bisabolol resulted in one product having a retention time of approximately 25.2 with bisabolol having a retention time of approximately 17.6. The MS fragmentation patterns of products formed by reaction of SaCYP76F38v1 (SaCYP76-G5) with nerolidol and bisabolol did not match with known substances in the MS fragmentation pattern databases.

2. SaCYP76F39v1 (SaCYP76-G10)

CYP76-G10 also catalyzed the hydroxylation of linalool, nerol and bisabolol in vitro. In each case, product formation was the same as that catalyzed by CYP76-G5 described above.

Since modifications will be apparent to those of skill in this art, it is intended that this invention be limited only by the scope of the appended claims.

We claim:

1. A host cell, comprising a nucleic acid molecule encoding a cytochrome P450 reductase or a catalytically active portion thereof, wherein:
   (a) the encoded cytochrome P450 reductase or catalytically active portion thereof exhibits at least 95% sequence identity to a cytochrome P450 reductase polypeptide set forth in SEQ ID NO: 13 or a corresponding catalytically active portion thereof;
   (b) the encoded cytochrome P450 reductase polypeptide or catalytically active fragment thereof catalyzes the transfer of two electrons from NADPH to an electron acceptor; and
   (c) the nucleic acid molecule is heterologous to the host cell.

2. The host cell of claim 1, wherein the encoded cytochrome P450 reductase polypeptide or catalytically active fragment thereof exhibits at least 96% amino acid sequence identity to a sequence of amino acids set forth in SEQ ID NO: 13.

3. The host cell of claim 1, wherein the encoded cytochrome P450 reductase polypeptide or catalytically active portion thereof is a *Santalum* P450 reductase polypeptide.

4. The host cell of claim 1, wherein the encoded cytochrome P450 reductase polypeptide or catalytically active portion thereof is a *Santalum album* P450 reductase polypeptide.

5. The host cell of claim 1, wherein the encoded cytochrome P450 reductase polypeptide or catalytically active fragment thereof comprises a sequence of amino acids that has at least 99% sequence identity to a cytochrome P450 reductase polypeptide set forth in SEQ ID NO: 13.

6. The host cell of claim 1, wherein the encoded cytochrome P450 reductase polypeptide or catalytically active fragment thereof comprises a sequence of amino acids set forth in SEQ ID NO: 13.

7. The host cell of claim 1, wherein the encoded cytochrome P450 reductase polypeptide or catalytically active portion thereof is a catalytically active fragment comprising a sequence of amino acids set forth in SEQ ID NO: 15, or a sequence that exhibits at least 95% amino acid sequence identity to a sequence of amino acids set forth in SEQ ID NO: 15.

8. The host cell of claim 1, wherein the electron acceptor is a cytochrome P450, heme oxygenase, cytochrome $b_5$ or squalene epoxidase.

9. The host cell of claim 1, comprising a nucleic acid molecule encoding a cytochrome P450 oxidase polypeptide or a catalytically active portion thereof, wherein:
   (a) the encoded cytochrome P450 oxidase polypeptide or catalytically active portion thereof exhibits at least 95% sequence identity to SEQ ID NO: 50 or a corresponding catalytically active portion thereof;
   (b) the encoded cytochrome P450 oxidase or catalytically active fragment thereof catalyzes the hydroxylation or monooxygenation of santalene and/or bergamotene; and
   (c) the nucleic acid molecule is heterologous to the host cell.

10. The host cell of claim 9, wherein the encoded full-length cytochrome P450 oxidase polypeptide exhibits at least 99% sequence identity to SEQ ID NO: 50.

11. The host cell of claim 1, comprising a nucleic acid molecule encoding a cytochrome P450 oxidase polypeptide or a catalytically active portion thereof, wherein:
  (a) the encoded cytochrome P450 oxidase polypeptide or catalytically active fragment thereof comprises the sequence of amino acids set forth in SEQ ID NO: 7; or
  (b) the encoded cytochrome P450 oxidase polypeptide or catalytically active fragment thereof comprises a sequence of amino acids that exhibits at least 95% sequence identity to a cytochrome P450 oxidase polypeptide set forth in SEQ ID NO: 7; and
  (c) the encoded cytochrome P450 oxidase polypeptide or catalytically active fragment thereof catalyzes the hydroxylation or monooxygenation of santalene and/or bergamotene.

12. The host cell of claim 11, wherein the encoded cytochrome P450 oxidase polypeptide or catalytically active fragment thereof exhibits at least 99% amino acid sequence identity to a sequence of amino acids set forth in SEQ ID NO: 7.

13. The host cell of claim 11, wherein the cytochrome P450 oxidase polypeptide or catalytically active fragment thereof comprises the sequence of amino acids set forth in SEQ ID NO: 7.

14. The host cell of claim 1, comprising:
  (a) a nucleic acid molecule encoding a cytochrome P450 oxidase polypeptide or a catalytically active portion thereof, wherein:
    (i) the encoded cytochrome P450 oxidase polypeptide or catalytically active portion thereof exhibits at least 95% sequence identity to SEQ ID NO:7;
    (ii) the encoded cytochrome P450 oxidase polypeptide or catalytically active fragment thereof catalyzes the hydroxylation or monooxygenation of santalene and/or bergamotene; and
    (iii) the nucleic acid molecule is heterologous to the host cell;
  (b) a nucleic acid molecule encoding a cytochrome P450 reductase or catalytically active portion thereof, wherein:
    (i) the nucleic acid molecule is heterologous to the host cell; and
    (ii) the encoded cytochrome P450 reductase or catalytically active portion thereof comprises the sequence of amino acids set forth in SEQ ID NO: 13, or a sequence of amino acids that has at least 95% sequence identity to a cytochrome P450 reductase polypeptide set forth in SEQ ID NO: 13; and
  (c) a nucleic acid molecule encoding a santalene synthase, wherein:
    (i) the nucleic acid molecule is heterologous to the host cell; and
    (ii) the encoded santalene synthase comprises the sequence of amino acids set forth in any of SEQ ID NO: 17 or a sequence of amino acids that is at least 95% identical to any of SEQ ID NO: 17 or a catalytically active fragment thereof.

15. A host cell, comprising:
  (a) a nucleic acid molecule encoding a cytochrome P450 oxidase polypeptide or a catalytically active portion thereof, wherein:
    (i) the encoded cytochrome P450 oxidase polypeptide or catalytically active portion thereof exhibits at least 95% sequence identity to SEQ ID NO: 7;
    (ii) the encoded cytochrome P450 oxidase polypeptide or catalytically active fragment thereof catalyzes the hydroxylation or monooxygenation of santalene and/or bergamotene;
  (b) a nucleic acid molecule encoding a cytochrome P450 reductase or catalytically active portion thereof, wherein the encoded cytochrome P450 reductase or catalytically active portion thereof comprises the sequence of amino acids set forth in SEQ ID NO: 13, or a sequence of amino acids that has at least 95% sequence identity to a cytochrome P450 reductase polypeptide set forth in SEQ ID NO: 13; and
  (c) a nucleic acid molecule encoding a santalene synthase, wherein the encoded santalene synthase comprises the sequence of amino acids set forth in any of SEQ ID NO: 17 or a sequence of amino acids that is at least 95% identical to any of SEQ ID NO: 17 or a catalytically active fragment thereof, wherein:
    at least one of the nucleic acid molecules set forth in (a) or (b) is heterologous to the host cell.

16. The host cell of claim 11 or 15, wherein the encoded cytochrome P450 oxidase polypeptide or catalytically active portion thereof comprises the sequence of amino acids set forth in SEQ ID NO:7, or a sequence of amino acids that exhibits at least 96% sequence identity to a cytochrome P450 oxidase polypeptide set forth in SEQ ID NO: 7.

17. The host cell of claim 1 or 15, that is a prokaryotic cell or an eukaryotic cell.

18. The host cell of claim 1 of 15, that produces farnesyl diphosphate natively or is modified to produce more farnesyl diphosphate compared to an unmodified cell.

19. An isolated nucleic acid molecule encoding a cytochrome P450 reductase or a catalytically active portion thereof, wherein:
  (a) the nucleic acid molecule is cDNA;
  (b) the encoded cytochrome P450 reductase or catalytically active portion thereof exhibits at least 95% sequence identity to a cytochrome P450 reductase polypeptide set forth in SEQ ID NO: 13; and
  (c) the encoded cytochrome P450 reductase polypeptide or catalytically active fragment thereof catalyzes the transfer of two electrons from NADPH to an electron acceptor.

20. The nucleic acid molecule of claim 19, wherein the encoded cytochrome P450 reductase polypeptide or catalytically active fragment thereof exhibits at least 96% amino acid sequence identity to a sequence of amino acids set forth in SEQ ID NO: 13.

21. The nucleic acid molecule of claim 19, wherein the encoded cytochrome P450 reductase polypeptide or catalytically active fragment thereof comprises a sequence of amino acids set forth in SEQ ID NO: 13.

22. The nucleic acid molecule of claim 19, wherein the encoded cytochrome P450 reductase polypeptide is a catalytically active fragment comprising a sequence of amino acids set forth in SEQ ID NO: 15, or a sequence that exhibits at least 95% amino acid sequence identity to a sequence of amino acids set forth in SEQ ID NO: 15.

23. The nucleic acid molecule of claim 19, wherein the electron acceptor is a cytochrome P450, heme oxygenase, cytochrome $b_5$ or squalene epoxidase.

24. A modified cytochrome P450 reductase polypeptide or catalytically active portion thereof encoded by the nucleic acid molecule of claim 19; wherein the modified cytochrome P450 polypeptide is at least 95% identical to SEQ ID NO: 13, provided that the modified cytochrome P450 reductase sequence is not SEQ ID NO: 13.

25. A vector, comprising the nucleic acid molecule of claim 19.

26. A host cell, comprising the vector of claim 25.

27. A method for producing a cytochrome P450 reductase polypeptide or a catalytically active fragment thereof, comprising:
   (a) culturing the cells of claim 1 or 15 under conditions suitable for expression of the cytochrome P450 reductase polypeptide; and
   (b) optionally isolating the cytochrome P450 reductase polypeptide.

28. A method for producing a santalol, bergamotol and/or mixtures thereof, comprising:
   (a) culturing a host cell of claim 15 under conditions suitable for the formation of a santalol, bergamotol and/or mixtures thereof; wherein the host cell of claim 15 expresses the nucleic acid molecules of part (a), (b) and (c); and
   (b) optionally isolating the santalol, bergamotol and/or mixtures thereof.

* * * * *

SEQUENCE LISTING

<160> NUMBER OF SEQ ID NOS: 89

<210> SEQ ID NO 1
<211> LENGTH: 1530
<212> TYPE: DNA
<213> ORGANISM: Santalum album
<220> FEATURE:
<223> OTHER INFORMATION: CYP76 ORF

<400> SEQUENCE: 1

```
atggacttct taagttttat cctgtttgtt ttattcgcgt gggcacttgt tcgggctctc       60
cctacacttt ctagaggttc caaagcagcc ggcgggaggc ttccgccggg gccagtcccg      120
ttgccggtgg taggaaacct attaaaactc gggagcaaac cacacaagtc gctggcggag      180
ctggccaaat cctacggtcc tataatgtgt ctcaaactag gtcacataat cacaattgtc      240
```

```
atctcaactc ctaccgtcgc caaagaggtt ctccaaaaac aagacgtcgc cttctgtaac      300
cgaaccatcc ctgacgccgt tcgagcccac agacacgacc tccactccat ggtttggtta      360
ccggtttcga cccgttggcg gacccttcga aagataagca actcccacat cttcagtagc      420
caaaggctcg atgaaaacca ccacctccgg cggcggaagc tcgacgagct ccttgccagg      480
gtggcggaga gcagcctggt cggggcagtg gtggatatag gcgcggtggc tttcttgacg      540
agtctaaact tgctatccaa caccgtgttt tcgaaggatt tggtcgaacc aggattgggg      600
gctgtgcagg agatggagga ggtggtgtgg gggatcacgg aggaggccgg gaggcccaat      660
ttggtggatt attttccggt gctgcgaagg ctcgatccgc aaaggacacg ccgtcggatg      720
atgggttatt tcgggaaaat gttcgaggtt ttcggggata tcattgacga gcggcttgaa      780
tggagaaagc aacaaagtga tggtgattcc ccagctgcta caactaatga tgtgttggac      840
gttcttctga atattattga agacgctgaa atcgaagaaa agcctaatag aactgatgtc      900
gaacacctca tactggacct atttgtggcg gggagtgata cgacttccag caccgtcgaa      960
tgggcgatga cagaactcct ccggaaaccg gagactctgg agagagcccg gtcggagctc     1020
catgagacca tcggcccaaa aaacctggtc caagaggccg acttgccccg gctcccctac     1080
ttacaggccg tggtgaaaga aactttccgg ctccaccctc cggtgccgct cctactcccc     1140
cgcactgcgg agaaggacgc cgaactctgc ggcttcacgg tccccgcagg ggctcaaatc     1200
atggtgaacg cgtgggcgat cgggagagat cccgggacat ggggaggacc ggagtcattc     1260
ttgccggaga gattcttggg gtcggatgtg gacgtgaagg ggaggagttt cgagctgatt     1320
ccgttcggcg gagggaggag gatttgcccc ggattacctc tggcgataag gatggtgcat     1380
ttgatgttag gatcactgat ccatgggttc cggtggaagg tgtttgacga tggaatgggg     1440
tcgccggaga ctgcgatgga catggatgag aagtttggca tcactttaca gaaggcgaag     1500
tcgttgtgcg ctgtcccgat ccgggggtaa                                      1530
```

<210> SEQ ID NO 2
<211> LENGTH: 1530
<212> TYPE: DNA
<213> ORGANISM: Santalum album
<220> FEATURE:
<223> OTHER INFORMATION: CYP76F38v1 (CYP76-G5)

<400> SEQUENCE: 2

```
atggacttct taagttttat cctgtttgtt ttattcgcgt gggcacttgt tcgggctctc       60
cctacacttt ctagaggttc caaagcagcc ggcgggaggc ttccgccggg gccagtcccg      120
ttgccggtgg tgggaaacct attaaaactc gggagcaaac cacacaagtc gctggcggag      180
ctggccaaat cctacggtcc tataatgtgt ctcaaactag gtcacataat cacaattgtc      240
atctcaactc ctaccgtcgc caaagaggtt ctccaaaaac aagacgtcgc cttctgtaac      300
cgaaccatcc ctgacgccgt tcgagcccac agacacgacc tccactccat ggtttggtta      360
ccggtttcga cccgttggcg gacccttcga aagataagca actcccacat cttcagtagc      420
caaaggctcg atgaaaacca ccacctccgg cggcggaagc tcgacgagct ccttgccagg      480
gtggcggaga gcagcctggt cggggcagtg gtggatatag gcgcggtggc tttcttgacg      540
agtctaaact tgctatccaa caccgtgttt tcgaaggatt tggtcgaacc aggattgggg      600
gctgtgcagg agatggagga ggtggtgtgg gggatcacgg aggaggccgg gaggcccaat      660
ttggtggatt attttccggt gctgcgaagg ctcgatccgc aggggacacg ccgtcggatg      720
```

```
atgggttatt tcgggaaaat gttcgaggtt ttcggggata tcattgacga gcggcttgaa      780
ttgagaaagc aacaaagtga tggtgattcc ccagctgcta caactaatga tgtgttggac      840
gttcttctga atattattga agacgctgaa attgaagaaa agcctaatag aactgatgtc      900
gaacacttca tagtggacct atttgtggcg gggagtgata cgacttccag caccgtcgaa      960
tgggcgatga cagaactcct ccgtaaaccg gagactctgg agagagcccg gtcggagctc     1020
catgagacca tcggccctaa aaacctggtc caagaggccg acatgccccg gctcccctac     1080
ttacaggccg tggtgaaaga aactttccgg ctccaccctc cggtgccgct cctactcccc     1140
cgcactgcgg agaaggacgc cgaactctgc ggcttcacgg tccccgcagg ggctcaaatc     1200
atggtgaacg cgtgggcgat cgggagagat cccgggacat ggaggacccc ggagtcattc     1260
ttgccggaga gattcttggg gtcggatgtg gacgtgaagg ggaggagttt cgagctgatt     1320
ccgttcggcg gaggggaggag gatttgcccc ggattacctc tggcgataag gatggtgcat     1380
ttgatgttag gatcactgat ccatggggttc cggtggaagg tgtttgacga tggaatgggg     1440
tcgccggaga ctgcgatgga catggatgag aagtttggca tcactttaca gaaggcgaag     1500
tcgttgtgcg ctgtcccgat ccgggggtaa                                      1530
```

<210> SEQ ID NO 3
<211> LENGTH: 1530
<212> TYPE: DNA
<213> ORGANISM: Santalum album
<220> FEATURE:
<223> OTHER INFORMATION: CYP76F39v1 (CYP76-G10)

<400> SEQUENCE: 3

```
atggacttct taagttgtat cctgtttgtt ttattcgcgt gggcacttgt tcgggctctc       60
cctacacttt ctagaggttc caaagctgcc agcgggaggc ttccgccggg gccagtcccg      120
tggccggtgg tgggaaacct gttaaaactc gggaacaaac cacacaagtc attggcggag      180
ctggccaaat cctacggccc cataatgtgt ctcaaacttg gtcacatgac acaattgtc       240 atctcaactc ctaccgtagc caaagaggtt cttcaaaaac aagacgttgc cttctctaac      300
cgaaccactc ctgacgccgt tcgagcccac ggacacgacc tctactccat ggcttggtta      360
ccggtttcca cccgttggcg gaccctgcgg aagataagca attcccacat cttcactagc      420
caaaggctcg atgaaaacca ccacctccgg cggcggaagc tcgacgagct ccttgccaga      480
gtggcggaga gcagcctggt cggggcagtg gtggatatgg gcgcggtagc tttcttgacg      540
agtctaaact tgctatccaa caccgtgtttt tcgaaggatt tggtcgaacc aggattgggg      600
gctgtgcagg agacgaagga ggtggtgtgg gggatgatgg aggaggccgg aaggcccaat      660
ttggtggatt atttcccggt gctgcggagg ctcgatccgc aggggattcg ccgtcggatg      720
acgggttatt tcgggaaaat gttggaagtt ttcggggata tcattgacga gcggcttgaa      780
tggagaaagc aacaaagtga tggtgattcc ccagctggta caactaatga tgtgttggac      840
gttcttctga atattattga agacgctgaa atcgaagaaa agcctaatag aactratgtc      900
gaacacttct tactggacct atttgcggcg gggagtgata cgacttcgag caccgtcgaa      960
tgggcgatga cggaactcct ccgcaaaccg gagactctgg agagagcccg gtcggagctc     1020
catgagacca tcggcccaga aaacctggtc caagaggccg acttgccccg gcttccctac     1080
ttacaggccg tggtgaagga aactttccag ctccaccctc cggtgccgct gctactcccc     1140
cgcactgcgg agaaggacgc cgaactctgc ggcttcacgg tccccgcagg ggcccaaatc     1200
atggtgaacg cgtgggcgat cgggagagat cccgggacat ggaggacccc agagtcattc     1260
```

```
ttgccggaga gattcttggg gtcggatgtg gacgtgaagg ggaggagttt cgagctgatt    1320
ccgttcggcg gagggaggag gatttgcccc ggattaccgc tggcgataag gatggtgcat    1380
ttgatgttag gatcgctgat ccatgggttt cggtggaagg tggatgacga tggaatgggt    1440
tcgccggaga ccgccatgga catggatgaa aagttcggca ttactttaca gaaggcgaag    1500
cccttgtgcg ctgtcccaat ccgggggtaa                                    1530
```

<210> SEQ ID NO 4
<211> LENGTH: 1530
<212> TYPE: DNA
<213> ORGANISM: Santalum album
<220> FEATURE:
<223> OTHER INFORMATION: CYP76F37v1 (CYP76-G11)

<400> SEQUENCE: 4

```
atggacttct taagttgtat cctgtctgtt ttattcgcgt gggcacttgt tcgggctctc     60
cctacacttt ctagaggttc caaagcagcc ggcgggaggc ttccgccggg gccagtcccg    120
ttgccggtgg tgggaaacct gttaaaactc gggagcaaac cacacaagtc gctggcggag    180
ctggccaaat cctacggtcc tataatgtgt ctcaaactag gtcacataat cacaattgtc    240
atctcaactc ctaccgtcgc caaagaggtt ctccaaaaac aagacgtcgc cttctgtaac    300
cgaaccatcc ctgacgccgt tcgagcccac agacacgacc tccactccat ggtttggtta    360
ccggtttcga cccgttggcg gaccctgcgg aagataagca actcccacat cttcagtagc    420
caaaggctcg atgaaaacca ccacctccgg cggcggaagc tcgacgagct ccttaccagg    480
gtggcggaga gcagcctggt cggggcagtg gtggatatag gcgcggtggc tttcttgacg    540
agtctaaact tgctatccaa caccgtgttt tcgaaggatt tggtcgaacc aggattgggg    600
gctgtgcagg agatggagga ggtggtgtgg gggatcacgg aggaggccgg gaggcccaat    660
ttggtggatt attttccggt gctgcgaagg ctcgatccgc aggggacacg ccgtcggatg    720
atgggttatt tcgggaaaat gttcgaggtt ttcggggata tcattgacga gcggcttgaa    780
tggagaaagc aacaaagtga tggtgattcc ccagctggta caactaatga tgtgttggac    840
gttcttctga atattattga agacgctgaa atcgaagaaa agcctaatag aactgatgtc    900
gaacacttct tactggacct atttgcggcg gggagtgata cgacttcgag caccgtcgaa    960
tgggcgatga cggaactcct ccgcaaaccg gagactctgg agagagcccg gtcggagctc   1020
catgagacca tcggcccaga aaacctggtc aagaggccga cttgccccg cttccctac    1080 ttacaggccg tggtgaagga aactttcagg ctccacccctc cggtgccgct gctactcccc   1140
cgcactgcgg agaaggacgc cgaactctgc ggcttcacgg tccccgcagg ggcccaaatc   1200
atggtgaacg cgtgggcgat cgggagagat cccgggacat gggaggaccc agagtcattc   1260
ttgccggaga gattcttggg gtcggatgtg gacgtgaagg ggaggagttt cgagctgatt   1320
ccgttcggcg gagggaggag gatttgcccc ggattaccgc tggcgataag gatggtgcat   1380
ttgatgttag gatcgctgat ccatgggttt cggtggaagg tggatgacga tggaatgggt   1440
tcgccggaga ccgccatgga catggatgaa aagttcggca ttactttaca gaaggcgaag   1500
cccttgtgcg ctgtcccaat ccgggggtaa                                   1530
```

<210> SEQ ID NO 5
<211> LENGTH: 1530
<212> TYPE: DNA
<213> ORGANISM: Santalum album
<220> FEATURE:

-continued

<223> OTHER INFORMATION: CYP76F38v2 (CYP76-G12)

<400> SEQUENCE: 5

```
atggacttct taagttgtat cctgtttgtt ttattcgcgt gggcacttgt tcgggctctc      60
cctacacttt ctagaggttc caaagcagcc ggcgggaggc ttccgccggg gccagtcccg     120
ttgccggtgg tggaaaacct gttaaaactc gggagcaaac cacacaagtc gctggcggag     180
ctggccaaat cctacggtcc tataatgtgt ctcaaactag gtcacataat cacaattgtc     240
atctcaactc ctaccgtcgc caaagaggtt ctccaaaaac aagacgtcgc cttctgtaac     300
cgaaccatcc ctgacgccgt tcgagcccac agacacgacc tccactccat ggtttggtta     360
ccggtttcga cccgttggcg gacccttcga agataagca actcccacat cttcagtagc     420
caaaggctcg atgaaaacca ccacctccgg cggcggaagc tcgacgagct ccttaccagg     480
gtggcggaga gcagcctggt cggggcagtg gtggatatag gcgcggtggc tttcttgacg     540
agtctaaact tgctatccaa caccgtgttt tcgaaggatt tggtcgaacc aggattgggg     600
gctgtgcagg agatggagga ggtggtgtgg gggatcacgg aggaggccgg gaggcccaat     660
ttggtggatt atttccggt gctgcgaagg ctcgatccgc aggggacacg ccgtcggatg     720
atgggttatt tcgggaaaat gttcgaggtt tcggggata tcattgacga gcggcttgaa     780
ttgagaaagc aacaaagtga tggtgattcc ccagctgcta caactaatga tgtgttggac     840
gttcttctga atattattga agacgctgaa attgaagaaa agcctaatag aactgatgtc     900
gaacacttca tagtggacct atttgtggcg gggagtgata cgacttccag caccgtcgaa     960
tgggcgatga cggaactcct ccgtaaaccg gagactctgg agagagcccg gtcggagctc    1020
catgagacca tcggccctaa aaacctggtc caagaggccg acatgccccg gctcccctac    1080
ttacaggccg tggtgaagga aacttttcagg ctccacccttc cggtgccgct gctactcccc    1140
cgcactgcgg agaaggacgc cgaactctgc ggcttcacgg tccccgcagg ggcccaaatc    1200
atggtgaacg cgtgggcgat cgggagagat cccgggacat ggaggaccc agagtcattc    1260
ttgccggaga gattcttggg gtcggatgtg gacgtgaagg ggaggagttt cgagctgatt    1320
ccgttcggcg aggggaggag gatttgcccc ggattaccgc tggcgataag gatggtgcat    1380
ttgatgttag gatcgctgat ccatgggttt cggtggaagg tggatgacga tggaatgggt    1440
tcgccggaga ccgccatgga catggatgaa aagttcggca ttactttaca gaaggcgaag    1500
cccttgtgcg ctgtcccaat ccgggggtaa                                     1530
```

<210> SEQ ID NO 6
<211> LENGTH: 509
<212> TYPE: PRT
<213> ORGANISM: Santalum album
<220> FEATURE:
<223> OTHER INFORMATION: CYP76F38v1 (CYP76-G5)

<400> SEQUENCE: 6

```
Met Asp Phe Leu Ser Phe Ile Leu Phe Val Leu Phe Ala Trp Ala Leu
 1               5                  10                  15

Val Arg Ala Leu Pro Thr Leu Ser Arg Gly Ser Lys Ala Ala Gly Gly
             20                  25                  30

Arg Leu Pro Pro Gly Pro Val Pro Leu Pro Val Val Gly Asn Leu Leu
         35                  40                  45

Lys Leu Gly Ser Lys Pro His Lys Ser Leu Ala Glu Leu Ala Lys Ser
     50                  55                  60

Tyr Gly Pro Ile Met Cys Leu Lys Leu Gly His Ile Ile Thr Ile Val
```

```
                65                  70                  75                  80
Ile Ser Thr Pro Thr Val Ala Lys Glu Val Leu Gln Lys Gln Asp Val
                        85                  90                  95

Ala Phe Cys Asn Arg Thr Ile Pro Asp Ala Val Arg Ala His Arg His
                    100                 105                 110

Asp Leu His Ser Met Val Trp Leu Pro Val Ser Thr Arg Trp Arg Thr
                115                 120                 125

Leu Arg Lys Ile Ser Asn Ser His Ile Phe Ser Gln Arg Leu Asp
            130                 135                 140

Glu Asn His His Leu Arg Arg Lys Leu Asp Glu Leu Leu Ala Arg
145                 150                 155                 160

Val Ala Glu Ser Ser Leu Val Gly Ala Val Val Asp Ile Gly Ala Val
                165                 170                 175

Ala Phe Leu Thr Ser Leu Asn Leu Leu Ser Asn Thr Val Phe Ser Lys
                180                 185                 190

Asp Leu Val Glu Pro Gly Leu Gly Ala Val Gln Glu Met Glu Glu Val
                195                 200                 205

Val Trp Gly Ile Thr Glu Glu Ala Gly Arg Pro Asn Leu Val Asp Tyr
            210                 215                 220

Phe Pro Val Leu Arg Arg Leu Asp Pro Gln Gly Thr Arg Arg Arg Met
225                 230                 235                 240

Met Gly Tyr Phe Gly Lys Met Phe Glu Val Phe Gly Asp Ile Ile Asp
                245                 250                 255

Glu Arg Leu Glu Leu Arg Lys Gln Gln Ser Asp Gly Asp Ser Pro Ala
                260                 265                 270

Ala Thr Thr Asn Asp Val Leu Asp Val Leu Leu Asn Ile Ile Glu Asp
            275                 280                 285

Ala Glu Ile Glu Glu Lys Pro Asn Arg Thr Asp Val Glu His Phe Ile
            290                 295                 300

Val Asp Leu Phe Val Ala Gly Ser Asp Thr Thr Ser Ser Thr Val Glu
305                 310                 315                 320

Trp Ala Met Thr Glu Leu Leu Arg Lys Pro Glu Thr Leu Glu Arg Ala
                325                 330                 335

Arg Ser Glu Leu His Glu Thr Ile Gly Pro Lys Asn Leu Val Gln Glu
                340                 345                 350

Ala Asp Met Pro Arg Leu Pro Tyr Leu Gln Ala Val Val Lys Glu Thr
                355                 360                 365

Phe Arg Leu His Pro Pro Val Pro Leu Leu Pro Arg Thr Ala Glu
            370                 375                 380

Lys Asp Ala Glu Leu Cys Gly Phe Thr Val Pro Ala Gly Ala Gln Ile
385                 390                 395                 400

Met Val Asn Ala Trp Ala Ile Gly Arg Asp Pro Gly Thr Trp Glu Asp
                405                 410                 415

Pro Glu Ser Phe Leu Pro Glu Arg Phe Leu Gly Ser Asp Val Asp Val
                420                 425                 430

Lys Gly Arg Ser Phe Glu Leu Ile Pro Phe Gly Gly Arg Arg Ile
            435                 440                 445

Cys Pro Gly Leu Pro Leu Ala Ile Arg Met Val His Leu Met Leu Gly
                450                 455                 460

Ser Leu Ile His Gly Phe Arg Trp Lys Val Phe Asp Asp Gly Met Gly
465                 470                 475                 480

Ser Pro Glu Thr Ala Met Asp Met Asp Glu Lys Phe Gly Ile Thr Leu
                485                 490                 495
```

-continued

Gln Lys Ala Lys Ser Leu Cys Ala Val Pro Ile Arg Gly
500                    505

<210> SEQ ID NO 7
<211> LENGTH: 509
<212> TYPE: PRT
<213> ORGANISM: Santalum album
<220> FEATURE:
<223> OTHER INFORMATION: CYP76F39v1 (CYP76-G10)

<400> SEQUENCE: 7

Met Asp Phe Leu Ser Cys Ile Leu Phe Val Leu Phe Ala Trp Ala Leu
1               5                   10                  15

Val Arg Ala Leu Pro Thr Leu Ser Arg Gly Ser Lys Ala Ala Ser Gly
            20                  25                  30

Arg Leu Pro Pro Gly Pro Val Pro Trp Pro Val Gly Asn Leu Leu
        35                  40                  45

Lys Leu Gly Asn Lys Pro His Lys Ser Leu Ala Glu Leu Ala Lys Ser
    50                  55                  60

Tyr Gly Pro Ile Met Cys Leu Lys Leu Gly His Met Thr Thr Ile Val
65                  70                  75                  80

Ile Ser Thr Pro Thr Val Ala Lys Glu Val Leu Gln Lys Gln Asp Val
                85                  90                  95

Ala Phe Ser Asn Arg Thr Thr Pro Asp Ala Val Arg Ala His Gly His
            100                 105                 110

Asp Leu Tyr Ser Met Ala Trp Leu Pro Val Ser Thr Arg Trp Arg Thr
        115                 120                 125

Leu Arg Lys Ile Ser Asn Ser His Ile Phe Thr Ser Gln Arg Leu Asp
    130                 135                 140

Glu Asn His His Leu Arg Arg Arg Lys Leu Asp Glu Leu Leu Ala Arg
145                 150                 155                 160

Val Ala Glu Ser Ser Leu Val Gly Ala Val Asp Met Gly Ala Val
                165                 170                 175

Ala Phe Leu Thr Ser Leu Asn Leu Leu Ser Asn Thr Val Phe Ser Lys
            180                 185                 190

Asp Leu Val Glu Pro Gly Leu Gly Ala Val Gln Glu Thr Lys Glu Val
        195                 200                 205

Val Trp Gly Met Met Glu Glu Ala Gly Arg Pro Asn Leu Val Asp Tyr
    210                 215                 220

Phe Pro Val Leu Arg Arg Leu Asp Pro Gln Gly Ile Arg Arg Met
225                 230                 235                 240

Thr Gly Tyr Phe Gly Lys Met Leu Glu Val Phe Gly Asp Ile Ile Asp
                245                 250                 255

Glu Arg Leu Glu Trp Arg Lys Gln Gln Ser Asp Gly Asp Ser Pro Ala
            260                 265                 270

Gly Thr Thr Asn Asp Val Leu Asp Val Leu Asn Ile Ile Glu Asp
        275                 280                 285

Ala Glu Ile Glu Glu Lys Pro Asn Arg Thr Asp Val Glu His Phe Leu
    290                 295                 300

Leu Asp Leu Phe Ala Ala Gly Ser Asp Thr Thr Ser Ser Thr Val Glu
305                 310                 315                 320

Trp Ala Met Thr Glu Leu Leu Arg Lys Pro Glu Thr Leu Glu Arg Ala
                325                 330                 335

Arg Ser Glu Leu His Glu Thr Ile Gly Pro Glu Asn Leu Val Gln Glu
            340                 345                 350

-continued

Ala Asp Leu Pro Arg Leu Pro Tyr Leu Gln Ala Val Val Lys Glu Thr
            355                 360                 365

Phe Arg Leu His Pro Val Pro Leu Leu Pro Arg Thr Ala Glu
    370                 375                 380

Lys Asp Ala Glu Leu Cys Gly Phe Thr Val Pro Ala Gly Ala Gln Ile
385                 390                 395                 400

Met Val Asn Ala Trp Ala Ile Gly Arg Asp Pro Gly Thr Trp Glu Asp
                405                 410                 415

Pro Glu Ser Phe Leu Pro Glu Arg Phe Leu Gly Ser Asp Val Asp Val
            420                 425                 430

Lys Gly Arg Ser Phe Glu Leu Ile Pro Phe Gly Gly Arg Arg Ile
            435                 440                 445

Cys Pro Gly Leu Pro Leu Ala Ile Arg Met Val His Leu Met Leu Gly
            450                 455                 460

Ser Leu Ile His Gly Phe Arg Trp Lys Val Asp Asp Asp Gly Met Gly
465                 470                 475                 480

Ser Pro Glu Thr Ala Met Asp Met Asp Glu Lys Phe Gly Ile Thr Leu
                485                 490                 495

Gln Lys Ala Lys Pro Leu Cys Ala Val Pro Ile Arg Gly
            500                 505

<210> SEQ ID NO 8
<211> LENGTH: 509
<212> TYPE: PRT
<213> ORGANISM: Santalum album
<220> FEATURE:
<223> OTHER INFORMATION: CYP76F37v1 (CYP76-G11)

<400> SEQUENCE: 8

Met Asp Phe Leu Ser Cys Ile Leu Ser Val Leu Phe Ala Trp Ala Leu
1               5                   10                  15

Val Arg Ala Leu Pro Thr Leu Ser Arg Gly Ser Lys Ala Ala Gly Gly
            20                  25                  30

Arg Leu Pro Pro Gly Pro Val Pro Leu Pro Val Val Gly Asn Leu Leu
            35                  40                  45

Lys Leu Gly Ser Lys Pro His Lys Ser Leu Ala Glu Leu Ala Lys Ser
50                  55                  60

Tyr Gly Pro Ile Met Cys Leu Lys Leu Gly His Ile Ile Thr Ile Val
65                  70                  75                  80

Ile Ser Thr Pro Thr Val Ala Lys Glu Val Leu Gln Lys Gln Asp Val
                85                  90                  95

Ala Phe Cys Asn Arg Thr Ile Pro Asp Ala Val Arg Ala His Arg His
            100                 105                 110

Asp Leu His Ser Met Val Trp Leu Pro Val Ser Thr Arg Trp Arg Thr
            115                 120                 125

Leu Arg Lys Ile Ser Asn Ser His Ile Phe Ser Ser Gln Arg Leu Asp
    130                 135                 140

Glu Asn His His Leu Arg Arg Arg Lys Leu Asp Glu Leu Leu Thr Arg
145                 150                 155                 160

Val Ala Glu Ser Ser Leu Val Gly Ala Val Asp Ile Gly Ala Val
                165                 170                 175

Ala Phe Leu Thr Ser Leu Asn Leu Leu Ser Asn Thr Val Phe Ser Lys
            180                 185                 190

Asp Leu Val Glu Pro Gly Leu Gly Ala Val Gln Glu Met Glu Glu Val
            195                 200                 205

```
Val Trp Gly Ile Thr Glu Ala Gly Arg Pro Asn Leu Val Asp Tyr
    210                 215                 220

Phe Pro Val Leu Arg Arg Leu Asp Pro Gln Gly Thr Arg Arg Met
225                 230                 235                 240

Met Gly Tyr Phe Gly Lys Met Phe Glu Val Phe Gly Asp Ile Ile Asp
                245                 250                 255

Glu Arg Leu Glu Trp Arg Lys Gln Gln Ser Asp Gly Asp Ser Pro Ala
            260                 265                 270

Gly Thr Thr Asn Asp Val Leu Asp Val Leu Leu Asn Ile Ile Glu Asp
        275                 280                 285

Ala Glu Ile Glu Glu Lys Pro Asn Arg Thr Asp Val Glu His Phe Leu
    290                 295                 300

Leu Asp Leu Phe Ala Ala Gly Ser Asp Thr Thr Ser Ser Thr Val Glu
305                 310                 315                 320

Trp Ala Met Thr Glu Leu Leu Arg Lys Pro Glu Thr Leu Glu Arg Ala
                325                 330                 335

Arg Ser Glu Leu His Glu Thr Ile Gly Pro Glu Asn Leu Val Gln Glu
            340                 345                 350

Ala Asp Leu Pro Arg Leu Pro Tyr Leu Gln Ala Val Val Lys Glu Thr
        355                 360                 365

Phe Arg Leu His Pro Pro Val Pro Leu Leu Pro Arg Thr Ala Glu
    370                 375                 380

Lys Asp Ala Glu Leu Cys Gly Phe Thr Val Pro Ala Gly Ala Gln Ile
385                 390                 395                 400

Met Val Asn Ala Trp Ala Ile Gly Arg Asp Pro Gly Thr Trp Glu Asp
                405                 410                 415

Pro Glu Ser Phe Leu Pro Glu Arg Phe Leu Gly Ser Asp Val Asp Val
            420                 425                 430

Lys Gly Arg Ser Phe Glu Leu Ile Pro Phe Gly Gly Arg Arg Ile
        435                 440                 445

Cys Pro Gly Leu Pro Leu Ala Ile Arg Met Val His Leu Met Leu Gly
    450                 455                 460

Ser Leu Ile His Gly Phe Arg Trp Lys Val Asp Asp Gly Met Gly
465                 470                 475                 480

Ser Pro Glu Thr Ala Met Asp Met Asp Glu Lys Phe Gly Ile Thr Leu
                485                 490                 495

Gln Lys Ala Lys Pro Leu Cys Ala Val Pro Ile Arg Gly
            500                 505

<210> SEQ ID NO 9
<211> LENGTH: 509
<212> TYPE: PRT
<213> ORGANISM: Santalum album
<220> FEATURE:
<223> OTHER INFORMATION: CYP76F38v2 (CYP76-G12)

<400> SEQUENCE: 9

Met Asp Phe Leu Ser Cys Ile Leu Phe Val Leu Phe Ala Trp Ala Leu
1               5                   10                  15

Val Arg Ala Leu Pro Thr Leu Ser Arg Gly Ser Lys Ala Ala Gly Gly
                20                  25                  30

Arg Leu Pro Pro Gly Pro Val Pro Leu Pro Val Val Gly Asn Leu Leu
            35                  40                  45

Lys Leu Gly Ser Lys Pro His Lys Ser Leu Ala Glu Leu Ala Lys Ser
        50                  55                  60
```

```
Tyr Gly Pro Ile Met Cys Leu Lys Leu Gly His Ile Ile Thr Ile Val
 65                  70                  75                  80

Ile Ser Thr Pro Thr Val Ala Lys Glu Val Leu Gln Lys Gln Asp Val
                 85                  90                  95

Ala Phe Cys Asn Arg Thr Ile Pro Asp Ala Val Arg Ala His Arg His
            100                 105                 110

Asp Leu His Ser Met Val Trp Leu Pro Val Ser Thr Arg Trp Arg Thr
        115                 120                 125

Leu Arg Lys Ile Ser Asn Ser His Ile Phe Ser Ser Gln Arg Leu Asp
    130                 135                 140

Glu Asn His His Leu Arg Arg Arg Lys Leu Asp Glu Leu Leu Thr Arg
145                 150                 155                 160

Val Ala Glu Ser Ser Leu Val Gly Ala Val Asp Ile Gly Ala Val
                165                 170                 175

Ala Phe Leu Thr Ser Leu Asn Leu Leu Ser Asn Thr Val Phe Ser Lys
            180                 185                 190

Asp Leu Val Glu Pro Gly Leu Gly Ala Val Gln Met Glu Glu Val
        195                 200                 205

Val Trp Gly Ile Thr Glu Glu Ala Gly Arg Pro Asn Leu Val Asp Tyr
    210                 215                 220

Phe Pro Val Leu Arg Arg Leu Asp Pro Gln Gly Thr Arg Arg Arg Met
225                 230                 235                 240

Met Gly Tyr Phe Gly Lys Met Phe Glu Val Phe Gly Asp Ile Ile Asp
                245                 250                 255

Glu Arg Leu Glu Leu Arg Lys Gln Gln Ser Asp Gly Asp Ser Pro Ala
            260                 265                 270

Ala Thr Thr Asn Asp Val Leu Asp Val Leu Leu Asn Ile Ile Glu Asp
        275                 280                 285

Ala Glu Ile Glu Glu Lys Pro Asn Arg Thr Asp Val Glu His Phe Ile
    290                 295                 300

Val Asp Leu Phe Val Ala Gly Ser Asp Thr Thr Ser Ser Thr Val Glu
305                 310                 315                 320

Trp Ala Met Thr Glu Leu Leu Arg Lys Pro Glu Thr Leu Glu Arg Ala
                325                 330                 335

Arg Ser Glu Leu His Glu Thr Ile Gly Pro Lys Asn Leu Val Gln Glu
            340                 345                 350

Ala Asp Met Pro Arg Leu Pro Tyr Leu Gln Ala Val Val Lys Glu Thr
        355                 360                 365

Phe Arg Leu His Pro Pro Val Pro Leu Leu Leu Pro Arg Thr Ala Glu
    370                 375                 380

Lys Asp Ala Glu Leu Cys Gly Phe Thr Val Pro Ala Gly Ala Gln Ile
385                 390                 395                 400

Met Val Asn Ala Trp Ala Ile Gly Arg Asp Pro Gly Thr Trp Glu Asp
                405                 410                 415

Pro Glu Ser Phe Leu Pro Glu Arg Phe Leu Gly Ser Asp Val Asp Val
            420                 425                 430

Lys Gly Arg Ser Phe Glu Leu Ile Pro Phe Gly Gly Gly Arg Arg Ile
        435                 440                 445

Cys Pro Gly Leu Pro Leu Ala Ile Arg Met Val His Leu Met Leu Gly
    450                 455                 460

Ser Leu Ile His Gly Phe Arg Trp Lys Val Asp Asp Asp Gly Met Gly
465                 470                 475                 480
```

Ser Pro Glu Thr Ala Met Asp Met Asp Glu Lys Phe Gly Ile Thr Leu
                485                 490                 495

Gln Lys Ala Lys Pro Leu Cys Ala Val Pro Ile Arg Gly
        500                 505

<210> SEQ ID NO 10
<211> LENGTH: 2079
<212> TYPE: DNA
<213> ORGANISM: Santalum album
<220> FEATURE:
<223> OTHER INFORMATION: CPR1

<400> SEQUENCE: 10

| | | | | |
|---|---|---|---|---|
| atgagttcga | gctcggagct | atggaaatcg | atcggctcgg | cgctgggggt gtctccaccg | 60 |
| ccggcatggg | ccgaggagtg | ggcggcggtg | atcgtcacca | cgtccgcggc gctgatcgta | 120 |
| ggtttcgtga | tgttcatgtg | gcggagatcg | ggcgagaagt | ccaaggaatt gaggcctgtg | 180 |
| gtggcgctga | aggcggcgcc | gatcgaggcg | gaggaggacg | atggcgaggt tgactcgggg | 240 |
| aagactaagg | tcactgtgtt | cttcggtacg | cagactggca | ctgccgaagg gttcgctaag | 300 |
| gctttggcag | aagagatcaa | ggcaagatat | gaaaagcag | tcgtcaaagt ggttgacctg | 360 |
| gatgattatg | ctgcagatga | tgatcaatat | ggagaaaaat | tgaaaaatga cgcgctgaca | 420 |
| tttttcatgg | tggccactta | tggtgatgga | gaaccaaccg | ataatgctgc aagattttac | 480 |
| aaatggttta | ctgaggagaa | agaaagggaa | gcttggttac | agcagctgac ttatggcatt | 540 |
| tttggtctgg | gaaatcgtca | atatgaacat | tttaataaga | tagcaaaggt gcttgatgaa | 600 |
| cagcttactg | aacaaggtgc | aaagcgtctc | attcaggttg | gtttaggtga tgatgatcag | 660 |
| tgcatcgagg | atgattttc | tgcttggcgt | gaactactgt | ggccagagtt agatcaatta | 720 |
| ctccggggtg | atgatggtgc | gaattctgtg | tctactccct | atacagctgc tgttcctgaa | 780 |
| taccgagtgg | tgatccatga | tcctactatc | acttcatctg | aggataaatc cttagccacg | 840 |
| gccaatgggg | ctgctttatt | tgacattcac | catccatgca | gagttaaggt tgctgttcaa | 900 |
| agagagcttc | acaaagctga | ctctgaccgc | tcttgcatac | atttggagtt tgatatatca | 960 |
| ggcacgggtc | ttatgtatga | aacgggagac | catgtggtg | tttacgctga aaattgtgtt | 1020 |
| gagactgttg | aagaagcagg | aaagctgttg | ggccaacctt | tagatttgct cttttctgtt | 1080 |
| cacactgaca | aggatgatgg | tacatctctt | gagagctcat | tgcccctcc ttttcctggt | 1140 |
| ccttgcactc | ttcgcactgc | actgtttcaa | tatgcagatc | tattgaaccc tcctaggaag | 1200 |
| gctgctttag | ttgccctggc | agctcatgca | gttgaaccat | ctgaggcaga cagacttaaa | 1260 |
| tttttgtcat | cacctcaggg | aaaggatgag | tatgcgaaat | gggttgttgg cagtcaaaga | 1320 |
| agcctccttg | aggtgatggc | tgagttcccg | tcaataaaag | ttccccttgg tgtgtttttt | 1380 |
| gccgctgtgg | cccccgcct | acagcctcgc | tactattcaa | tctcatcatc gcctaggttc | 1440 |
| tcctctgacc | gggttcatgt | aacctgcgct | ttagtttatg | ccctagtcc aacaggcaga | 1500 |
| attcacagag | gggtgtgttc | cacctggatg | aagaatgcag | ttcctctaga gaaagccgt | 1560 |
| gagtgtagct | gggctcctat | atttattagg | acatctaatt | ttaagctacc agctaatcct | 1620 |
| tctacccag | ttatcatggt | cggccctggt | actggcttgg | ctccgtttag aggattccta | 1680 |
| caggaaagga | tggccttgtt | agaaggcagt | gctcaacttg | gtcctgcttt acttttcttt | 1740 |
| ggatgtagaa | atcgaaggat | ggattttatt | tacgaggatg | aactcaacaa tttcgtcgaa | 1800 |
| caaggtgtga | tatcagagtt | gattgttgca | ttctcgaggg | acgggccaac caaggagtac | 1860 |
| gttcagcata | agatgatgga | taaagctgca | tatatatgga | gtctaatctc tcagggggct | 1920 |

| | |
|---|---|
| tatctttatg tctgtggtga tgcaaagggg atggctagag atgttcatcg aactttgcat | 1980 |
| actcttgttc aacaacagga gagcgtggac tcatcaaaag cagagtcaat agtgaagaag | 2040 |
| cttcagatgg atggacgata tctaagagat gtttggtaa | 2079 |

<210> SEQ ID NO 11
<211> LENGTH: 2115
<212> TYPE: DNA
<213> ORGANISM: Santalum album
<220> FEATURE:
<223> OTHER INFORMATION: CPR2

<400> SEQUENCE: 11

| | |
|---|---|
| atgcaattga gctccgtcaa gctaatccct ttggatctca tgacggctat tttcaacggc | 60 |
| ggtgggagcc ccgccggctc cggggaggcc ctgtcgatgc tgctggagaa tcggaggtg | 120 |
| gtggtggcgc tcacgacgtc gctcgcggtg ctcatcgggt gcgtgttcgc gtacctgtgg | 180 |
| cggttctcga gctcccagaa ggcggtggcg gcggctaagg gcgtagaggt tgcgaggaag | 240 |
| ccggtgatcg ggaaggaatc ggaggcggcg gaggtggatg acggaaagaa gaaggtgacc | 300 |
| atcttcttcg gacgcagac tggaacagcc gaagggttcg ccaaggcgct ggttgaggag | 360 |
| gcaaaagcac gctatgagaa ggccattttt aaattggttg atttggatga ttatgctgcc | 420 |
| gaggatgatg aatatgagga gaagttgaaa aagagaaat cgctttatt cttttagcc | 480 |
| acatatggag atggtgagcc tactgacaat gcagcgaggt tctataaatg gtttactgag | 540 |
| gaaaatgaaa gtgagagtg gctccaaaag cttcagttcg gagtgtttgg ccttggcaac | 600 |
| aggcaatacg agcatttcaa caaggttgca aaggttgtgg atgagattct tgctgagcaa | 660 |
| ggtgggaagc gcctggttcc agtgggtctt ggagatgatg atcaatgcat tgaagatgac | 720 |
| ttcactgcat ggcgtgaatt agtgtggccc gagttggata aattgctcct agatgaggat | 780 |
| gatgcaactg tttctacccc ttatactgct tctgtacctg aataccgggt tgtatttcat | 840 |
| gattctcctg atgattatct gcagaagaac tctagtaatg caaatggtca ttcgatgcat | 900 |
| gatgctcagc atccatgcag ggctaatgtt gctgtgagga gggagcttca ttcgcccttta | 960 |
| tctgatcgtt cttgcactca tctagaattt gacattgctg aactggact tgcgtatgaa | 1020 |
| acagggggacc atgttggtgt gtgctgtgag aatttacctg aagttgtgga agaggctgaa | 1080 |
| agggtactgg gtttgtcacc aggcatctac ttttccatcc atgctgataa agaggatggc | 1140 |
| acaccacttg gaagttcctt gccaccactt tttccaccat gtactttaag aactgcacta | 1200 |
| actcaacatg ctgatcttct aagttttcct aaaaaggctg cgttgcttgc tttagcagct | 1260 |
| catgcttctg atccaagtga agcggatagg ttgaaatatc ttgcatctcc tgcaggaaag | 1320 |
| gatgaatatg cacagtgggt tgttgcaagt cagagaagcc ttctagaagt aatggctgaa | 1380 |
| ttcccttcgg cgaagccccc acttggagtt ttgtttgctg cagttgctcc acgattgcag | 1440 |
| ccacgattct attcgatctc atcctctcca aagattgcac catctaggat acatgttact | 1500 |
| tgcgcattag tatatgataa aacaccaact gggcgaattc acaagggagt gtgctcaact | 1560 |
| tggatgaaga atgcgatgcc ccgggaagaa agccacgatt gcagctgggc tcccattttt | 1620 |
| gttaggcaat ctaatttcaa gctcccttca aatacatcgg tgcctgtcat catgattggt | 1680 |
| cctggcacgg ggttggctcc tttcagggc tttctacagg aaagattagc actgaaagaa | 1740 |
| gctggagttg aactgggacc tgcaatatta ttctttgggt gcaggaaccg taaaatggat | 1800 |
| tacatttatg aggatgagtt ggcacacttt gttgaagccg gtgcgctctc tgagttgatc | 1860 |

-continued

```
gtggctttct cacgggaagg accagccaaa cagtatgtcc agcataagat gatggaaaag    1920
gcctcagaaa tctggaacat gatttccgat ggaggttatg tatatgtatg tggtgatgcc    1980
aaaggcatgg ccaaagatgt ccaccgggcg ctccatacaa ttgttcacga acagggatct    2040
ctagacaatt ccaagacaga gagcatggtg aagaatctcc aaatgaatgg aaggtattta    2100
cgggatgtgt ggtga                                                     2115

<210> SEQ ID NO 12
<211> LENGTH: 692
<212> TYPE: PRT
<213> ORGANISM: Santalum album
<220> FEATURE:
<223> OTHER INFORMATION: CPR1

<400> SEQUENCE: 12
```

Met Ser Ser Ser Ser Glu Leu Trp Lys Ser Ile Gly Ser Ala Leu Gly
 1               5                  10                  15

Val Ser Pro Pro Ala Trp Ala Glu Glu Trp Ala Ala Val Ile Val
             20                  25                  30

Thr Thr Ser Ala Ala Leu Ile Val Gly Phe Val Met Phe Met Trp Arg
         35                  40                  45

Arg Ser Gly Glu Lys Ser Lys Glu Leu Arg Pro Val Val Ala Leu Lys
     50                  55                  60

Ala Ala Pro Ile Glu Ala Glu Asp Asp Gly Glu Val Asp Ser Gly
 65                  70                  75                  80

Lys Thr Lys Val Thr Val Phe Phe Gly Thr Gln Thr Gly Thr Ala Glu
                 85                  90                  95

Gly Phe Ala Lys Ala Leu Ala Glu Glu Ile Lys Ala Arg Tyr Glu Lys
            100                 105                 110

Ala Val Val Lys Val Val Asp Leu Asp Asp Tyr Ala Ala Asp Asp
        115                 120                 125

Gln Tyr Gly Glu Lys Leu Lys Asn Glu Thr Leu Thr Phe Phe Met Val
    130                 135                 140

Ala Thr Tyr Gly Asp Gly Glu Pro Thr Asp Asn Ala Ala Arg Phe Tyr
145                 150                 155                 160

Lys Trp Phe Thr Glu Glu Lys Glu Arg Glu Ala Trp Leu Gln Gln Leu
                165                 170                 175

Thr Tyr Gly Ile Phe Gly Leu Gly Asn Arg Gln Tyr Glu His Phe Asn
            180                 185                 190

Lys Ile Ala Lys Val Leu Asp Glu Gln Leu Thr Glu Gln Gly Ala Lys
        195                 200                 205

Arg Leu Ile Gln Val Gly Leu Gly Asp Asp Asp Gln Cys Ile Glu Asp
    210                 215                 220

Asp Phe Ser Ala Trp Arg Glu Leu Leu Trp Pro Glu Leu Asp Gln Leu
225                 230                 235                 240

Leu Arg Gly Asp Asp Gly Ala Asn Ser Val Ser Thr Pro Tyr Thr Ala
                245                 250                 255

Ala Val Pro Glu Tyr Arg Val Val Ile His Asp Pro Thr Ile Thr Ser
            260                 265                 270

Ser Glu Asp Lys Ser Leu Ala Thr Ala Asn Gly Ala Ala Leu Phe Asp
        275                 280                 285

Ile His His Pro Cys Arg Val Lys Val Ala Val Gln Arg Glu Leu His
    290                 295                 300

Lys Ala Asp Ser Asp Arg Ser Cys Ile His Leu Glu Phe Asp Ile Ser
305                 310                 315                 320

-continued

```
Gly Thr Gly Leu Met Tyr Glu Thr Gly Asp His Val Gly Val Tyr Ala
            325                 330                 335

Glu Asn Cys Val Glu Thr Val Glu Glu Ala Gly Lys Leu Leu Gly Gln
        340                 345                 350

Pro Leu Asp Leu Leu Phe Ser Val His Thr Lys Asp Asp Gly Thr
    355                 360                 365

Ser Leu Glu Ser Ser Leu Pro Pro Phe Pro Gly Pro Cys Thr Leu
370                 375                 380

Arg Thr Ala Leu Phe Gln Tyr Ala Asp Leu Leu Asn Pro Arg Lys
385                 390                 395                 400

Ala Ala Leu Val Ala Leu Ala Ala His Ala Val Glu Pro Ser Glu Ala
                405                 410                 415

Asp Arg Leu Lys Phe Leu Ser Ser Pro Gln Gly Lys Asp Glu Tyr Ala
            420                 425                 430

Lys Trp Val Val Gly Ser Gln Arg Ser Leu Leu Glu Val Met Ala Glu
                435                 440                 445

Phe Pro Ser Ile Lys Val Pro Leu Gly Val Phe Phe Ala Ala Val Ala
    450                 455                 460

Pro Arg Leu Gln Pro Arg Tyr Tyr Ser Ile Ser Ser Ser Pro Arg Phe
465                 470                 475                 480

Ser Ser Asp Arg Val His Val Thr Cys Ala Leu Val Tyr Gly Pro Ser
                485                 490                 495

Pro Thr Gly Arg Ile His Arg Gly Val Cys Ser Thr Trp Met Lys Asn
            500                 505                 510

Ala Val Pro Leu Glu Glu Ser Arg Glu Cys Ser Trp Ala Pro Ile Phe
        515                 520                 525

Ile Arg Thr Ser Asn Phe Lys Leu Pro Ala Asn Pro Ser Thr Pro Val
    530                 535                 540

Ile Met Val Gly Pro Gly Thr Gly Leu Ala Pro Phe Arg Gly Phe Leu
545                 550                 555                 560

Gln Glu Arg Met Ala Leu Leu Glu Gly Ser Ala Gln Leu Gly Pro Ala
                565                 570                 575

Leu Leu Phe Phe Gly Cys Arg Asn Arg Arg Met Asp Phe Ile Tyr Glu
            580                 585                 590

Asp Glu Leu Asn Asn Phe Val Glu Gln Gly Val Ile Ser Glu Leu Ile
        595                 600                 605

Val Ala Phe Ser Arg Asp Gly Pro Thr Lys Glu Tyr Val Gln His Lys
    610                 615                 620

Met Met Asp Lys Ala Ala Tyr Ile Trp Ser Leu Ile Ser Gln Gly Ala
625                 630                 635                 640

Tyr Leu Tyr Val Cys Gly Asp Ala Lys Gly Met Ala Arg Asp Val His
                645                 650                 655

Arg Thr Leu His Thr Leu Val Gln Gln Glu Ser Val Asp Ser Ser
            660                 665                 670

Lys Ala Glu Ser Ile Val Lys Lys Leu Gln Met Asp Gly Arg Tyr Leu
        675                 680                 685

Arg Asp Val Trp
    690

<210> SEQ ID NO 13
<211> LENGTH: 704
<212> TYPE: PRT
<213> ORGANISM: Santalum album
<220> FEATURE:
```

<223> OTHER INFORMATION: CPR2

<400> SEQUENCE: 13

```
Met Gln Leu Ser Ser Val Lys Leu Ile Pro Leu Asp Leu Met Thr Ala
1               5                   10                  15

Ile Phe Asn Gly Gly Gly Ser Pro Ala Gly Ser Gly Glu Ala Leu Ser
            20                  25                  30

Met Leu Leu Glu Asn Arg Glu Val Val Ala Leu Thr Thr Ser Leu
        35                  40                  45

Ala Val Leu Ile Gly Cys Val Phe Ala Tyr Leu Trp Arg Phe Ser Ser
    50                  55                  60

Ser Gln Lys Ala Val Ala Ala Lys Gly Val Glu Val Ala Arg Lys
65                  70                  75                  80

Pro Val Ile Gly Lys Glu Ser Glu Ala Ala Glu Val Asp Asp Gly Lys
                85                  90                  95

Lys Lys Val Thr Ile Phe Phe Gly Thr Gln Thr Gly Thr Ala Glu Gly
            100                 105                 110

Phe Ala Lys Ala Leu Val Glu Glu Ala Lys Ala Arg Tyr Glu Lys Ala
        115                 120                 125

Ile Phe Lys Leu Val Asp Leu Asp Asp Tyr Ala Ala Glu Asp Glu
    130                 135                 140

Tyr Glu Glu Lys Leu Lys Lys Glu Lys Phe Ala Leu Phe Phe Leu Ala
145                 150                 155                 160

Thr Tyr Gly Asp Gly Glu Pro Thr Asp Asn Ala Ala Arg Phe Tyr Lys
                165                 170                 175

Trp Phe Thr Glu Glu Asn Glu Ser Gly Glu Trp Leu Gln Lys Leu Gln
            180                 185                 190

Phe Gly Val Phe Gly Leu Gly Asn Arg Gln Tyr Glu His Phe Asn Lys
        195                 200                 205

Val Ala Lys Val Val Asp Glu Ile Leu Ala Glu Gln Gly Gly Lys Arg
    210                 215                 220

Leu Val Pro Val Gly Leu Gly Asp Asp Asp Gln Cys Ile Glu Asp Asp
225                 230                 235                 240

Phe Thr Ala Trp Arg Glu Leu Val Trp Pro Glu Leu Asp Lys Leu Leu
                245                 250                 255

Leu Asp Glu Asp Asp Ala Thr Val Ser Thr Pro Tyr Thr Ala Ser Val
            260                 265                 270

Pro Glu Tyr Arg Val Val Phe His Asp Ser Pro Asp Asp Tyr Leu Gln
        275                 280                 285

Lys Asn Ser Ser Asn Ala Asn Gly His Ser Met His Asp Ala Gln His
    290                 295                 300

Pro Cys Arg Ala Asn Val Ala Val Arg Arg Glu Leu His Ser Pro Leu
305                 310                 315                 320

Ser Asp Arg Ser Cys Thr His Leu Glu Phe Asp Ile Ala Gly Thr Gly
                325                 330                 335

Leu Ala Tyr Glu Thr Gly Asp His Val Gly Val Cys Cys Glu Asn Leu
            340                 345                 350

Pro Glu Val Val Glu Glu Ala Glu Arg Val Leu Gly Leu Ser Pro Gly
        355                 360                 365

Ile Tyr Phe Ser Ile His Ala Asp Lys Glu Asp Gly Thr Pro Leu Gly
    370                 375                 380

Ser Ser Leu Pro Pro Leu Phe Pro Pro Cys Thr Leu Arg Thr Ala Leu
385                 390                 395                 400
```

Thr Gln His Ala Asp Leu Leu Ser Phe Pro Lys Lys Ala Ala Leu Leu
            405                 410                 415

Ala Leu Ala Ala His Ala Ser Asp Pro Ser Glu Ala Asp Arg Leu Lys
            420                 425                 430

Tyr Leu Ala Ser Pro Ala Gly Lys Asp Glu Tyr Ala Gln Trp Val Val
            435                 440                 445

Ala Ser Gln Arg Ser Leu Leu Glu Val Met Ala Glu Phe Pro Ser Ala
450                 455                 460

Lys Pro Pro Leu Gly Val Leu Phe Ala Ala Val Ala Pro Arg Leu Gln
465                 470                 475                 480

Pro Arg Phe Tyr Ser Ile Ser Ser Ser Pro Lys Ile Ala Pro Ser Arg
                485                 490                 495

Ile His Val Thr Cys Ala Leu Val Tyr Asp Lys Thr Pro Thr Gly Arg
            500                 505                 510

Ile His Lys Gly Val Cys Ser Thr Trp Met Lys Asn Ala Met Pro Arg
            515                 520                 525

Glu Glu Ser His Asp Cys Ser Trp Ala Pro Ile Phe Val Arg Gln Ser
530                 535                 540

Asn Phe Lys Leu Pro Ser Asn Thr Ser Val Pro Val Ile Met Ile Gly
545                 550                 555                 560

Pro Gly Thr Gly Leu Ala Pro Phe Arg Gly Phe Leu Gln Glu Arg Leu
                565                 570                 575

Ala Leu Lys Glu Ala Gly Val Glu Leu Gly Pro Ala Ile Leu Phe Phe
            580                 585                 590

Gly Cys Arg Asn Arg Lys Met Asp Tyr Ile Tyr Glu Asp Glu Leu Ala
            595                 600                 605

His Phe Val Glu Ala Gly Ala Leu Ser Glu Leu Ile Val Ala Phe Ser
610                 615                 620

Arg Glu Gly Pro Ala Lys Gln Tyr Val Gln His Lys Met Met Glu Lys
625                 630                 635                 640

Ala Ser Glu Ile Trp Asn Met Ile Ser Asp Gly Gly Tyr Val Tyr Val
                645                 650                 655

Cys Gly Asp Ala Lys Gly Met Ala Lys Asp Val His Arg Ala Leu His
            660                 665                 670

Thr Ile Val His Glu Gln Gly Ser Leu Asp Asn Ser Lys Thr Glu Ser
            675                 680                 685

Met Val Lys Asn Leu Gln Met Asn Gly Arg Tyr Leu Arg Asp Val Trp
690                 695                 700

<210> SEQ ID NO 14
<211> LENGTH: 649
<212> TYPE: PRT
<213> ORGANISM: Santalum album
<220> FEATURE:
<223> OTHER INFORMATION: CPR1 truncated

<400> SEQUENCE: 14

Met Phe Met Trp Arg Arg Ser Gly Glu Lys Ser Lys Glu Leu Arg Pro
1               5                   10                  15

Val Val Ala Leu Lys Ala Ala Pro Ile Glu Ala Glu Glu Asp Asp Gly
            20                  25                  30

Glu Val Asp Ser Gly Lys Thr Lys Val Thr Val Phe Phe Gly Thr Gln
        35                  40                  45

Thr Gly Thr Ala Glu Gly Phe Ala Lys Ala Leu Ala Glu Glu Ile Lys
    50                  55                  60

Ala Arg Tyr Glu Lys Ala Val Val Lys Val Val Asp Leu Asp Asp Tyr
65                  70                  75                  80

Ala Ala Asp Asp Asp Gln Tyr Gly Glu Lys Leu Lys Asn Glu Thr Leu
            85                  90                  95

Thr Phe Phe Met Val Ala Thr Tyr Gly Asp Gly Glu Pro Thr Asp Asn
                100                 105                 110

Ala Ala Arg Phe Tyr Lys Trp Phe Thr Glu Glu Lys Glu Arg Glu Ala
                115                 120                 125

Trp Leu Gln Gln Leu Thr Tyr Gly Ile Phe Gly Leu Gly Asn Arg Gln
130                 135                 140

Tyr Glu His Phe Asn Lys Ile Ala Lys Val Leu Asp Glu Gln Leu Thr
145                 150                 155                 160

Glu Gln Gly Ala Lys Arg Leu Ile Gln Val Gly Leu Gly Asp Asp Asp
                165                 170                 175

Gln Cys Ile Glu Asp Asp Phe Ser Ala Trp Arg Glu Leu Leu Trp Pro
                180                 185                 190

Glu Leu Asp Gln Leu Leu Arg Gly Asp Asp Gly Ala Asn Ser Val Ser
                195                 200                 205

Thr Pro Tyr Thr Ala Ala Val Pro Glu Tyr Arg Val Val Ile His Asp
210                 215                 220

Pro Thr Ile Thr Ser Ser Glu Asp Lys Ser Leu Ala Thr Ala Asn Gly
225                 230                 235                 240

Ala Ala Leu Phe Asp Ile His His Pro Cys Arg Val Lys Val Ala Val
                245                 250                 255

Gln Arg Glu Leu His Lys Ala Asp Ser Asp Arg Ser Cys Ile His Leu
                260                 265                 270

Glu Phe Asp Ile Ser Gly Thr Gly Leu Met Tyr Glu Thr Gly Asp His
                275                 280                 285

Val Gly Val Tyr Ala Glu Asn Cys Val Glu Thr Val Glu Glu Ala Gly
                290                 295                 300

Lys Leu Leu Gly Gln Pro Leu Asp Leu Leu Phe Ser Val His Thr Asp
305                 310                 315                 320

Lys Asp Asp Gly Thr Ser Leu Glu Ser Ser Leu Pro Pro Phe Pro
                325                 330                 335

Gly Pro Cys Thr Leu Arg Thr Ala Leu Phe Gln Tyr Ala Asp Leu Leu
                340                 345                 350

Asn Pro Pro Arg Lys Ala Ala Leu Val Ala Leu Ala Ala His Ala Val
                355                 360                 365

Glu Pro Ser Glu Ala Asp Arg Leu Lys Phe Leu Ser Ser Pro Gln Gly
                370                 375                 380

Lys Asp Glu Tyr Ala Lys Trp Val Val Gly Ser Gln Arg Ser Leu Leu
385                 390                 395                 400

Glu Val Met Ala Glu Phe Pro Ser Ile Lys Val Pro Leu Gly Val Phe
                405                 410                 415

Phe Ala Ala Val Ala Pro Arg Leu Gln Pro Arg Tyr Tyr Ser Ile Ser
                420                 425                 430

Ser Ser Pro Arg Phe Ser Ser Asp Arg Val His Val Thr Cys Ala Leu
                435                 440                 445

Val Tyr Gly Pro Ser Pro Thr Gly Arg Ile His Arg Gly Val Cys Ser
                450                 455                 460

Thr Trp Met Lys Asn Ala Val Pro Leu Glu Glu Ser Arg Glu Cys Ser
465                 470                 475                 480

Trp Ala Pro Ile Phe Ile Arg Thr Ser Asn Phe Lys Leu Pro Ala Asn

```
                485                 490                 495
Pro Ser Thr Pro Val Ile Met Val Gly Pro Gly Thr Gly Leu Ala Pro
                500                 505                 510

Phe Arg Gly Phe Leu Gln Glu Arg Met Ala Leu Leu Glu Gly Gly Ala
                515                 520                 525

Gln Leu Gly Pro Ala Leu Leu Phe Phe Gly Cys Arg Asn Arg Arg Met
        530                 535                 540

Asp Phe Ile Tyr Glu Asp Glu Leu Asn Asn Phe Val Glu Gln Gly Val
545                 550                 555                 560

Ile Ser Glu Leu Ile Val Ala Phe Ser Arg Asp Gly Pro Thr Lys Glu
                565                 570                 575

Tyr Val Gln His Lys Met Met Asp Lys Ala Ala Tyr Ile Trp Ser Leu
                580                 585                 590

Ile Ser Gln Gly Ala Tyr Leu Tyr Val Cys Gly Asp Ala Lys Gly Met
                595                 600                 605

Ala Arg Asp Val His Arg Thr Leu His Thr Leu Val Gln Gln Gln Glu
        610                 615                 620

Ser Val Asp Ser Ser Lys Ala Glu Ser Ile Val Lys Lys Leu Gln Met
625                 630                 635                 640

Asp Gly Arg Tyr Leu Arg Asp Val Trp
                645
```

```
<210> SEQ ID NO 15
<211> LENGTH: 645
<212> TYPE: PRT
<213> ORGANISM: Santalum album
<220> FEATURE:
<223> OTHER INFORMATION: CPR2 truncated

<400> SEQUENCE: 15

Met Arg Phe Ser Ser Ser Gln Lys Ala Val Ala Ala Ala Lys Gly Val
 1               5                  10                  15

Glu Val Ala Arg Lys Pro Val Ile Gly Lys Ser Glu Ala Ala Glu
                20                  25                  30

Val Asp Asp Gly Lys Lys Lys Val Thr Ile Phe Phe Gly Thr Gln Thr
        35                  40                  45

Gly Thr Ala Glu Gly Phe Ala Lys Ala Leu Val Glu Glu Ala Lys Ala
    50                  55                  60

Arg Tyr Glu Lys Ala Ile Phe Lys Leu Val Asp Leu Asp Asp Tyr Ala
65                  70                  75                  80

Ala Glu Asp Asp Glu Tyr Glu Glu Lys Leu Lys Lys Glu Lys Phe Ala
                85                  90                  95

Leu Phe Phe Leu Ala Thr Tyr Gly Asp Gly Glu Pro Thr Asp Asn Ala
                100                 105                 110

Ala Arg Phe Tyr Lys Trp Phe Thr Glu Glu Asn Glu Ser Gly Glu Trp
        115                 120                 125

Leu Gln Lys Leu Gln Phe Gly Val Phe Gly Leu Gly Asn Arg Gln Tyr
    130                 135                 140

Glu His Phe Asn Lys Val Ala Lys Val Val Asp Glu Ile Leu Ala Glu
145                 150                 155                 160

Gln Gly Gly Lys Arg Leu Val Pro Val Gly Leu Gly Asp Asp Asp Gln
                165                 170                 175

Cys Ile Glu Asp Asp Phe Thr Ala Trp Arg Glu Leu Val Trp Pro Glu
                180                 185                 190

Leu Asp Lys Leu Leu Leu Asp Glu Asp Asp Ala Thr Val Ser Thr Pro
```

```
            195                 200                 205
Tyr Thr Ala Ser Val Pro Glu Tyr Arg Val Val Phe His Asp Ser Pro
210                 215                 220

Asp Asp Tyr Leu Gln Lys Asn Ser Ser Asn Ala Asn Gly His Ser Met
225                 230                 235                 240

His Asp Ala Gln His Pro Cys Arg Ala Asn Val Ala Val Arg Arg Glu
                245                 250                 255

Leu His Ser Pro Leu Ser Asp Arg Ser Cys Thr His Leu Glu Phe Asp
                260                 265                 270

Ile Ala Gly Thr Gly Leu Ala Tyr Glu Thr Gly Asp His Val Gly Val
                275                 280                 285

Cys Cys Glu Asn Leu Pro Glu Val Val Glu Ala Glu Arg Val Leu
290                 295                 300

Gly Leu Ser Pro Gly Ile Tyr Phe Ser Ile His Ala Asp Lys Glu Asp
305                 310                 315                 320

Gly Thr Pro Leu Gly Ser Ser Leu Pro Leu Phe Pro Pro Cys Thr
                325                 330                 335

Leu Arg Thr Ala Leu Thr Gln His Ala Asp Leu Leu Ser Phe Pro Lys
                340                 345                 350

Lys Ala Ala Leu Leu Ala Leu Ala Ala His Ala Ser Asp Pro Ser Glu
                355                 360                 365

Ala Asp Arg Leu Lys Tyr Leu Ala Ser Pro Ala Gly Lys Asp Glu Tyr
370                 375                 380

Ala Gln Trp Val Val Ala Ser Gln Arg Ser Leu Leu Glu Val Met Ala
385                 390                 395                 400

Glu Phe Pro Ser Ala Lys Pro Pro Leu Gly Val Leu Phe Ala Ala Val
                405                 410                 415

Ala Pro Arg Leu Gln Pro Arg Phe Tyr Ser Ile Ser Ser Pro Lys
                420                 425                 430

Ile Ala Pro Ser Arg Ile His Val Thr Cys Ala Leu Val Tyr Asp Lys
                435                 440                 445

Thr Pro Thr Gly Arg Ile His Lys Gly Val Cys Ser Thr Trp Met Lys
450                 455                 460

Asn Ala Met Pro Arg Glu Glu Ser His Asp Cys Ser Trp Ala Pro Ile
465                 470                 475                 480

Phe Val Arg Gln Ser Asn Phe Lys Leu Pro Ser Asn Thr Ser Val Pro
                485                 490                 495

Val Ile Met Ile Gly Pro Gly Thr Gly Leu Ala Pro Phe Arg Gly Phe
                500                 505                 510

Leu Gln Glu Arg Leu Ala Leu Lys Glu Ala Gly Val Glu Leu Gly Pro
                515                 520                 525

Ala Ile Leu Phe Phe Gly Cys Arg Asn Arg Lys Met Asp Tyr Ile Tyr
                530                 535                 540

Glu Asp Glu Leu Ala His Phe Val Glu Ala Gly Ala Leu Ser Glu Leu
545                 550                 555                 560

Ile Val Ala Phe Ser Arg Glu Gly Pro Ala Lys Gln Tyr Val Gln His
                565                 570                 575

Lys Met Met Glu Lys Ala Ser Glu Ile Trp Asn Met Ile Ser Asp Gly
                580                 585                 590

Gly Tyr Val Tyr Val Cys Gly Asp Ala Lys Gly Met Ala Lys Asp Val
                595                 600                 605

His Arg Ala Leu His Thr Ile Val His Glu Gln Gly Ser Leu Asp Asn
610                 615                 620
```

Ser Lys Thr Glu Ser Met Val Lys Asn Leu Gln Met Asn Gly Arg Tyr
625                 630                 635                 640

Leu Arg Asp Val Trp
            645

<210> SEQ ID NO 16
<211> LENGTH: 1710
<212> TYPE: DNA
<213> ORGANISM: Santalum album
<220> FEATURE:
<223> OTHER INFORMATION: Santalene synthase (SaSSY)

<400> SEQUENCE: 16

```
atggattctt ccaccgccac cgccatgaca gctccattca ttgatcctac tgatcatgtg      60
aatctcaaaa ctgatacgga tgcctcagag aatcgaagga tgggaaatta taaacccagc     120
atttggaatt atgattttt acaatcactt gcaactcatc acaatattgt ggaagagagg     180
catctaaagc tagctgagaa gctgaagggc caagtgaagt ttatgtttgg ggcaccaatg     240
gagccgttag caaagctgga gcttgtggat gtggttcaaa ggcttgggct aaaccaccta     300
tttgagacag agatcaagga agcgctgttt agtatttaca aggatgggag caatggatgg     360
tggtttggcc accttcatgc gacatctctc cgatttaggc tgctacgaca gtgtgggctt     420
tttattcccc aagatgtgtt taaaacgttc aaaacaaga ctggggaatt tgatatgaaa     480
ctttgtgaca cgtaaaagg gctgctgagc ttatatgaag cttcatactt gggatggaag     540
ggtgaaaaca tcctagatga agccaaggcc ttcaccacca agtgcttgaa aagtgcatgg     600
gaaaatatat ccgaaaagtg gttagccaaa agagtgaagc atgcattggc tttgcctttg     660
cattggagag tccctcgaat cgaagctaga tggttcattg aggcatatga gcaagaagcg     720
aatatgaacc aacactact caaactcgca aaattagact ttaatatggt gcaatcaatt     780
catcagaaag agattgggga attagcaagg tggtgggtga ctactggctt ggataagtta     840
gcctttgcca ggaataattt actgcagagc tatatgtgga gctgcgcgat tgcttccgac     900
ccgaagttca aacttgctag agaaactatt gtcgaaatcg aagtgtact cacagttgtt     960
gacgatggat atgacgtcta tggttcaatc gacgaacttg atctctacac aagctccgtt    1020
gaaaggtgga gctgtgtgga aattgacaag ttgccaaaca cgttaaaatt aatttttatg    1080
tctatgttca caagaccaa tgaggttggc cttcgagtcc agcatgagcg aggctacaat    1140
agcatcccta ctttatcaa agcgtgggtt gaacagtgta atcatacca gaaagaagca    1200
agatggttcc acgggggaca cacgcctcca ttggaagaat atagcttgaa tggacttgtt    1260
tccataggat ccctctctt gttaatcacg ggctacgtgg caatcgctga aacgaggct    1320
gcactggata aagtgcaccc ccttcctgat cttctgcact actcctccct ccttagtcgc    1380
ctcatcaatg atataggaac gtctccggat gagatggcaa gaggcgataa tctgaagtca    1440
atccattgtt acatgaacga aactgggcgt tccgaggaag ttgctcgtga gcacataaag    1500
ggagtaatcg aggagaattg gaaaatactg aatcagtgct gctttgatca atctcagttt    1560
caggagcctt ttataacctt caatttgaac tctgttcgag gtctcatttt cttctatgaa    1620
tttgggatg gctttgggt gacgatagc tggacaaagg ttgatatgaa gtccgtttg    1680
atcgacccta ttcctctcgg cgaggagtag                                      1710
```

<210> SEQ ID NO 17
<211> LENGTH: 569
<212> TYPE: PRT

<213> ORGANISM: Santalum album
<220> FEATURE:
<223> OTHER INFORMATION: Santalene synthase (SaSSY)

<400> SEQUENCE: 17

```
Met Asp Ser Ser Thr Ala Thr Ala Met Thr Ala Pro Phe Ile Asp Pro
 1               5                  10                  15

Thr Asp His Val Asn Leu Lys Thr Asp Thr Asp Ala Ser Glu Asn Arg
            20                  25                  30

Arg Met Gly Asn Tyr Lys Pro Ser Ile Trp Asn Tyr Asp Phe Leu Gln
        35                  40                  45

Ser Leu Ala Thr His His Asn Ile Val Glu Glu Arg His Leu Lys Leu
50                  55                  60

Ala Glu Lys Leu Lys Gly Gln Val Lys Phe Met Phe Gly Ala Pro Met
65                  70                  75                  80

Glu Pro Leu Ala Lys Leu Glu Leu Val Asp Val Val Gln Arg Leu Gly
                85                  90                  95

Leu Asn His Leu Phe Glu Thr Glu Ile Lys Glu Ala Leu Phe Ser Ile
            100                 105                 110

Tyr Lys Asp Gly Ser Asn Gly Trp Trp Phe Gly His Leu His Ala Thr
        115                 120                 125

Ser Leu Arg Phe Arg Leu Leu Arg Gln Cys Gly Leu Phe Ile Pro Gln
130                 135                 140

Asp Val Phe Lys Thr Phe Gln Asn Lys Thr Gly Glu Phe Asp Met Lys
145                 150                 155                 160

Leu Cys Asp Asn Val Lys Gly Leu Leu Ser Leu Tyr Glu Ala Ser Tyr
                165                 170                 175

Leu Gly Trp Lys Gly Glu Asn Ile Leu Asp Glu Ala Lys Ala Phe Thr
            180                 185                 190

Thr Lys Cys Leu Lys Ser Ala Trp Glu Asn Ile Ser Glu Lys Trp Leu
        195                 200                 205

Ala Lys Arg Val Lys His Ala Leu Ala Leu Pro Leu His Trp Arg Val
210                 215                 220

Pro Arg Ile Glu Ala Arg Trp Phe Ile Glu Ala Tyr Glu Gln Glu Ala
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
            260                 265                 270

Val Thr Thr Gly Leu Asp Lys Leu Ala Phe Ala Arg Asn Asn Leu Leu
        275                 280                 285

Gln Ser Tyr Met Trp Ser Cys Ala Ile Ala Ser Asp Pro Lys Phe Lys
290                 295                 300

Leu Ala Arg Glu Thr Ile Val Glu Ile Gly Ser Val Leu Thr Val Val
305                 310                 315                 320

Asp Asp Gly Tyr Asp Val Tyr Gly Ser Ile Asp Glu Leu Asp Leu Tyr
                325                 330                 335

Thr Ser Ser Val Glu Arg Trp Ser Cys Val Glu Ile Asp Lys Leu Pro
            340                 345                 350

Asn Thr Leu Lys Leu Ile Phe Met Ser Met Phe Asn Lys Thr Asn Glu
        355                 360                 365

Val Gly Leu Arg Val Gln His Glu Arg Gly Tyr Asn Ser Ile Pro Thr
370                 375                 380

Phe Ile Lys Ala Trp Val Glu Gln Cys Lys Ser Tyr Gln Lys Glu Ala
```

```
                385                 390                 395                 400
Arg Trp Phe His Gly Gly His Thr Pro Pro Leu Glu Glu Tyr Ser Leu
                    405                 410                 415
Asn Gly Leu Val Ser Ile Gly Phe Pro Leu Leu Ile Thr Gly Tyr
                420                 425                 430
Val Ala Ile Ala Glu Asn Glu Ala Leu Asp Lys Val His Pro Leu
            435                 440                 445
Pro Asp Leu Leu His Tyr Ser Ser Leu Leu Ser Arg Leu Ile Asn Asp
    450                 455                 460
Ile Gly Thr Ser Pro Asp Glu Met Ala Arg Gly Asp Asn Leu Lys Ser
465                 470                 475                 480
Ile His Cys Tyr Met Asn Glu Thr Gly Ala Ser Glu Glu Val Ala Arg
                485                 490                 495
Glu His Ile Lys Gly Val Ile Glu Glu Asn Trp Lys Ile Leu Asn Gln
                500                 505                 510
Cys Cys Phe Asp Gln Ser Gln Phe Gln Glu Pro Phe Ile Thr Phe Asn
            515                 520                 525
Leu Asn Ser Val Arg Gly Ser His Phe Phe Tyr Glu Phe Gly Asp Gly
        530                 535                 540
Phe Gly Val Thr Asp Ser Trp Thr Lys Val Asp Met Lys Ser Val Leu
545                 550                 555                 560
Ile Asp Pro Ile Pro Leu Gly Glu Glu
                565

<210> SEQ ID NO 18
<211> LENGTH: 1029
<212> TYPE: DNA
<213> ORGANISM: Santalum album
<220> FEATURE:
<223> OTHER INFORMATION: Farnesyl diphosphate synthase (SaFPPS)

<400> SEQUENCE: 18
atgggcgatc ggaaaaccaa atttctcgag gcctactctg tcttgaaatc ggagctcctc      60
cgggaccctg ctttcaattt tacagacgct ccccgtcaat gggtcgaccg gatgctggac     120
tacaatgtgc ctggagggaa actgaatcga gggctctcag tgattgacag ctatgagttg     180
ctgaaagaag gaaagagct aactgatgat gaaatatttc ttgcatctgc actcggttgg     240
tgcattgaat ggcttcaagc atattttctt gttctcgatg atattatgga tggctctcat     300
acacgccgag gtcagccttg ttggttcagg ttgcctgagg ttggtctgat gctgtaaat      360 gatggcataa tgcttcgcaa ccacatccca agaattctca agaagcactt caaaataag      420 ccttattatg tggaactgtt ggatttattt aatgaggtcg agttccaaac aacttcagga     480
cagatgatag atttgataac cacgcttgaa gggcagaaag atcttcaaa gtattcaatg      540 cctattcacc atcgcattgt tcagtataaa actgcttatt actcctttta ccttccggtt     600
gcttgtgcac tgcttatgtc aggtgagaat ctggacagcc acactgaagt ggagaaaatc    660
cttgttgaaa tgggaaccta ttttcaagta caggatgatt acctggactg ctttggtcat    720
cctgatgtca ttggaaagat tggaacagat attgaagatt ttaagtgttc ttggttggtt    780
gtaaaagcgt tggaactttc aacgaggaa cagaagaaat tattatatga aactatggg      840 aaagccgatg aagccagcgt tgcaaaagta aaggcacttt ataaggaact tgaccttgag    900
ggtgcatttg tggagtacga gaatgctagt tatgagaaga taatcagctc aattgaggtg    960
cagccaagca aagcagtaca agcagtgctg aaatcctttt tggcgaagat atacaagcgg    1020
```
cagaaagtag                                                                   1029

<210> SEQ ID NO 19
<211> LENGTH: 342
<212> TYPE: PRT
<213> ORGANISM: Santalum album
<220> FEATURE:
<223> OTHER INFORMATION: Farnesyl diphosphate synthase (SaFPPS)

<400> SEQUENCE: 19

```
Met Gly Asp Arg Lys Thr Lys Phe Leu Glu Ala Tyr Ser Val Leu Lys
  1               5                  10                  15

Ser Glu Leu Leu Arg Asp Pro Ala Phe Asn Phe Thr Asp Ala Ser Arg
             20                  25                  30

Gln Trp Val Asp Arg Met Leu Asp Tyr Asn Val Pro Gly Gly Lys Leu
         35                  40                  45

Asn Arg Gly Leu Ser Val Ile Asp Ser Tyr Glu Leu Leu Lys Glu Gly
     50                  55                  60

Lys Glu Leu Thr Asp Asp Glu Ile Phe Leu Ala Ser Ala Leu Gly Trp
 65                  70                  75                  80

Cys Ile Glu Trp Leu Gln Ala Tyr Phe Leu Val Leu Asp Asp Ile Met
                 85                  90                  95

Asp Gly Ser His Thr Arg Arg Gly Gln Pro Cys Trp Phe Arg Leu Pro
            100                 105                 110

Glu Val Gly Leu Ile Ala Val Asn Asp Gly Ile Met Leu Arg Asn His
        115                 120                 125

Ile Pro Arg Ile Leu Lys Lys His Phe Lys Asn Lys Pro Tyr Tyr Val
    130                 135                 140

Glu Leu Leu Asp Leu Phe Asn Glu Val Glu Phe Gln Thr Thr Ser Gly
145                 150                 155                 160

Gln Met Ile Asp Leu Ile Thr Thr Leu Glu Gly Gln Lys Asp Leu Ser
                165                 170                 175

Lys Tyr Ser Met Pro Ile His His Arg Ile Val Gln Tyr Lys Thr Ala
            180                 185                 190

Tyr Tyr Ser Phe Tyr Leu Pro Val Ala Cys Ala Leu Leu Met Ser Gly
        195                 200                 205

Glu Asn Leu Asp Ser His Thr Glu Val Glu Lys Ile Leu Val Glu Met
    210                 215                 220

Gly Thr Tyr Phe Gln Val Gln Asp Asp Tyr Leu Asp Cys Phe Gly His
225                 230                 235                 240

Pro Asp Val Ile Gly Lys Ile Gly Thr Asp Ile Glu Asp Phe Lys Cys
                245                 250                 255

Ser Trp Leu Val Val Lys Ala Leu Glu Leu Ser Asn Glu Glu Gln Lys
            260                 265                 270

Lys Leu Leu Tyr Glu Asn Tyr Gly Lys Ala Asp Glu Ala Ser Val Ala
        275                 280                 285

Lys Val Lys Ala Leu Tyr Lys Glu Leu Asp Leu Glu Gly Ala Phe Val
    290                 295                 300

Glu Tyr Glu Asn Ala Ser Tyr Glu Lys Ile Ile Ser Ser Ile Glu Val
305                 310                 315                 320

Gln Pro Ser Lys Ala Val Gln Ala Val Leu Lys Ser Phe Leu Ala Lys
                325                 330                 335

Ile Tyr Lys Arg Gln Lys
            340
```

<210> SEQ ID NO 20
<211> LENGTH: 4160
<212> TYPE: DNA
<213> ORGANISM: Artificial Sequence
<220> FEATURE:
<223> OTHER INFORMATION: pDNR-LIB vector

<400> SEQUENCE: 20

| | | | | | |
|---|---|---|---|---|---|
| gcggccgcat | aacttcgtat | agcatacatt | atacgaagtt | atcagtcgac | ggtaccggac | 60 |
| atatgcccgg | gaattcggcc | attacggcct | gcaggatccg | aaaaaacctc | ccacacctcc | 120 |
| ccctgaacct | gaaacataaa | atgaatgcaa | ttgttgttgt | taacttgttt | attgcagctt | 180 |
| ataatggtta | caaataaagc | aatagcatca | caaatttcac | aaataaagca | tttttttcac | 240 |
| tgcattctag | ttgtggtttg | tccaaactca | tcaatgtatc | ttatcatgtc | tggatccggc | 300 |
| cgcctcggcc | ctcgagaagc | tttctagacc | attcgtttgg | cgcgcgggcc | cagtaggtaa | 360 |
| gtgaacatgg | tcatagctgt | ttccctagga | gatcctggta | tgactagtgc | ttggattctc | 420 |
| accaataaaa | aacgcccggc | ggcaaccgag | cgttctgaac | aaatccagat | ggagttctga | 480 |
| ggtcattact | ggatctatca | acaggagtcc | aagcgagctc | gatatcaaat | tacgccccgc | 540 |
| cctgccactc | atcgcagtac | tgttgtaatt | cattaagcat | tctgccgaca | tggaagccat | 600 |
| cacaaacggc | atgatgaacc | tgaatcgcca | gcggcatcag | caccttgtcg | ccttgcgtat | 660 |
| aatatttgcc | catggtgaaa | acggggggcga | agaagttgtc | catattggcc | acgtttaaat | 720 |
| caaaactggt | gaaactcacc | cagggattgg | ctgagacgaa | aaacatattc | tcaataaacc | 780 |
| ctttagggaa | ataggccagg | ttttcaccgt | aacacgccac | atcttgcgaa | tatatgtgta | 840 |
| gaaactgccg | gaaatcgtcg | tggtattcac | tccagagcga | tgaaaacgtt | tcagtttgct | 900 |
| catggaaaac | ggtgtaacaa | gggtgaacac | tatcccatat | caccagctca | ccgtctttca | 960 |
| ttgccatacg | aaattccgga | tgagcattca | tcaggcgggc | aagaatgtga | ataaaggccg | 1020 |
| gataaaactt | gtgcttattt | ttctttacgg | tctttaaaaa | ggccgtaata | tccagctgaa | 1080 |
| cggtctggtt | ataggtacat | tgagcaactg | actgaaatgc | ctcaaaatgt | tctttacgat | 1140 |
| gccattggga | tatatcaacg | gtggtatatc | cagtgatttt | tttctccatt | ttagcttcct | 1200 |
| tagctcctga | aagatccata | acttcgtata | gcatacatta | tacgaagtta | tgcggccgcg | 1260 |
| acgtcaatgc | caataggata | tcggcatttt | cttttgcgtt | tttatttgtt | aactgttaat | 1320 |
| tgtccttgtt | caaggatgct | gtctttgaca | acagatgttt | cttgcctttg | atgttcagc | 1380 |
| aggaagctag | gcgcaaacgt | tgattgtttg | tctgcgtaga | atcctctgtt | tgtcatatag | 1440 |
| cttgtaatca | cgacattgtt | tcctttcgct | tgaggtacag | cgaagtgtga | gtaagtaaag | 1500 |
| gttacatcgt | taggatcaag | atccattttt | aacacaaggc | cagttttgtt | cagcggcttg | 1560 |
| tatgggccag | ttaagaatt | agaaacataa | ccaagcatgt | aaatatcgtt | agacgtaatg | 1620 |
| ccgtcaatcg | tcattttga | tccgcgggag | tcagtgaaca | ggtaccattt | gccgttcatt | 1680 |
| ttaaagacgt | tcgcgcgttc | aatttcatct | gttactgtgt | tagatgcaat | cagcggtttc | 1740 |
| atcactttt | tcagtgtgta | atcatcgttt | agctcaatca | taccgagagc | gccgtttgct | 1800 |
| aactcagccg | tgcgttttt | atcgctttgc | agaagttttt | gactttcttg | acggaagaat | 1860 |
| gatgtgcttt | tgccatagta | tgctttgtta | aataaagatt | cttcgccttg | gtagccatct | 1920 |
| tcagttccag | tgtttgcttc | aaatactaag | tatttgtggc | ctttatcttc | tacgtagtga | 1980 |
| ggatctctca | gcgtatggtt | gtcgcctgag | ctgtagttgc | cttcatcgat | gaactgctgt | 2040 |
| acattttgat | acgttttcc | gtcaccgtca | aagattgatt | tataatcctc | tacaccgttg | 2100 |

| | |
|---|---|
| atgttcaaag agctgtctga tgctgatacg ttaacttgtg cagttgtcag tgtttgtttg | 2160 |
| ccgtaatgtt taccggagaa atcagtgtag aataaacgga ttttttccgtc agatgtaaat | 2220 |
| gtggctgaac ctgaccattc ttgtgtttgg tcttttagga tagaatcatt tgcatcgaat | 2280 |
| ttgtcgctgt ctttaaagac gcggccagcg ttttccagc tgtcaataga agtttcgccg | 2340 |
| acttttgat agaacatgta aatcgatgtg tcatccgcat ttttaggatc tccggctaat | 2400 |
| gcaaagacga tgtggtagcc gtgatagttt gcgacagtgc cgtcagcgtt ttgtaatggc | 2460 |
| cagctgtccc aaacgtccag gccttttgca gaagagatat ttttaattgt ggacgaatcg | 2520 |
| aactcaggaa cttgattttt tcattttttt gctgttcagg gatttgcagc atatcatggc | 2580 |
| gtgtaatatg ggaaatgccg tatgtttcct tatatggctt ttggttcgtt tctttcgcaa | 2640 |
| acgcttgagt tgcgcctcct gccagcagtg cggtagtaaa ggttaatact gttgcttgtt | 2700 |
| ttgcaaactt tttgatgttc atcgttcatg tctcctttt tatgtactgt gttagcggtc | 2760 |
| tgcttcttcc agccctcctg tttgaagatg gcaagttagt tacgcacaat aaaaaaagac | 2820 |
| ctaaaatatg taagggtga cgccaaagta tacactttgc cctttacaca ttttaggtct | 2880 |
| tgcctgcttt atcagtaaca aacccgcgcg atttactttt cgacctcatt ctattagact | 2940 |
| ctcgtttgga ttgcaactgg tctattttcc tcttttgttt gatagaaaat cataaaagga | 3000 |
| tttgcagact acgggcctaa agaactaaaa aatctatctg tttcttttca ttctctgtat | 3060 |
| tttttatagt ttctgttgca tgggcataaa gttgccttt taatcacaat tcagaaaata | 3120 |
| tcataatatc tcatttcact aaataatagt gaacggcagg tatatgtggc gcgcctaagc | 3180 |
| attggtaact gtcagaccaa gtttactcat atatacttta gattgattta aaacttcatt | 3240 |
| tttaatttaa aaggatctag gtgaagatcc ttttttgataa tctcatgacc aaaatcccctt | 3300 |
| aacgtgagtt ttcgttccac tgagcgtcag accccgtaga aaagatcaaa ggatcttctt | 3360 |
| gagatccttt ttttctgcgc gtaatctgct gcttgcaaac aaaaaaacca ccgctaccag | 3420 |
| cggtggtttg tttgccggat caagagctac caactctttt tccgaaggta actggcttca | 3480 |
| gcagagcgca gataccaaat actgttcttc tagtgtagcc gtagttaggc caccacttca | 3540 |
| agaactctgt agcaccgcct acatacccg ctctgctaat cctgttacca gtggctgctg | 3600 |
| ccagtggcga taagtcgtgt cttaccgggt tggactcaag acgatagtta ccggataagg | 3660 |
| cgcagcggtc gggctgaacg gggggttcgt gcacacagcc cagcttggag cgaacgacct | 3720 |
| acaccgaact gagatacccta cagcgtgagc tatgagaaag cgccacgctt cccgaaggga | 3780 |
| gaaaggcgga caggtatccg gtaagcggca gggtcggaac aggagagcgc acgagggagc | 3840 |
| ttccagggg aaacgcctgg tatctttata gtcctgtcgg gtttcgccac ctctgacttg | 3900 |
| agcgtcgatt tttgtgatgc tcgtcagggg ggcggagcct atggaaaaac gccagcaacg | 3960 |
| cggcctttt acggttcctg gccttttgct ggccttttgc tcacatgttc tttcctgcgt | 4020 |
| tatcccctga ttctgtggat aaccgtatta ccgccttacg cgtgtaaaac gacggccagt | 4080 |
| agatctgtaa tacgactcac tatagggcgc tagctcgccg cagccgaacg accgagcgca | 4140 |
| gcgagtcagt gagcgaggaa | 4160 |

<210> SEQ ID NO 21
<211> LENGTH: 2974
<212> TYPE: DNA
<213> ORGANISM: Artificial Sequence
<220> FEATURE:
<223> OTHER INFORMATION: pJET1.2 vector

<400> SEQUENCE: 21

```
gcccctgcag ccgaattata ttattttttgc caaataattt ttaacaaaag ctctgaagtc      60
ttcttcattt aaattcttag atgatacttc atctggaaaa ttgtcccaat tagtagcatc     120
acgctgtgag taagttctaa accattttttt tattgttgta ttatctctaa tcttactact    180
cgatgagttt tcggtattat ctctattttt aacttggagc aggttccatt cattgttttt     240
ttcatcatag tgaataaaat caactgcttt aacacttgtg cctgaacacc atatccatcc     300
ggcgtaatac gactcactat agggagagcg gccgccagat cttccggatg gctcgagttt    360
ttcagcaaga tatctttcta gaagatctcc tacaatattc tcagctgcca tggaaaatcg    420
atgttcttct tttattctct caagattttc aggctgtata ttaaaactta tattaagaac    480
tatgctaacc acctcatcag gaaccgttgt aggtggcgtg ggttttcttg caatcgact     540 ctcatgaaaa ctacgagcta aatattcaat atgttcctct tgaccaactt tattctgcat    600 ttttttttgaa cgaggtttag agcaagcttc aggaaactga dacaggaatt ttattaaaaa   660
tttaaatttt gaagaaagtt cagggttaat agcatccatt ttttgctttg caagttcctc    720
agcattctta acaaaagacg tctcttttga catgtttaaa gtttaaaccct cctgtgtgaa    780 attgttatcc gctcacaatt ccacacatta tacgagccgg aagcataaag tgtaaagcct    840
ggggtgccta atgagtgagc taactcacat taattgcgtt gcgctcactg ccaattgctt    900
tccagtcggg aaacctgtcg tgccagctgc attaatgaat cggccaacgc gcggggagag    960
gcggtttgcg tattgggcgc tcttccgctt cctcgctcac tgactcgctg cgctcggtcg   1020
ttcggctgcg cgagcggta tcagctcact caaaggcggt aatacggtta tccacagaat   1080
caggggataa cgcaggaaag aacatgtgag caaaaggcca gcaaaaggcc aggaaccgta   1140
aaaaggccgc gttgctggcg ttttttccata ggctccgccc ccctgacgag catcacaaaa   1200
atcgacgctc aagtcagagg tggcgaaacc cgacaggact ataaagatac caggcgtttc   1260 ccccctggaag ctccctcgtg cgctctcctg ttccgaccct gccgcttacc ggatacctgt   1320
ccgcctttct cccttcggga agcgtggcgc tttctcatag ctcacgctgt aggtatctca   1380
gttcggtgta ggtcgttcgc tccaagctgg gctgtgtgca cgaaccccccc gttcagcccg   1440 accgctgcgc cttatccggt aactatcgtc ttgagtccaa cccggtaaga cacgacttat   1500
cgccactggc agcagccact ggtaacagga ttagcagagc gaggtatgta ggcggtgcta   1560
cagagttctt gaagtggtgg cctaactacg gctacactag aaggacagta tttggtatct   1620
gcgctctgct gaagccagtt accttcggaa aaagagttgg tagctcttga tccggcaaac   1680
aaaccaccgc tggtagcggt ggtttttttg tttgcaagca gcagattacg cgcagaaaaa   1740
aaggatctca agaagatcct ttgatctttt ctacggggtc tgacgctcag tggaacgaaa   1800
actcacgtta agggattttg gtcatgagat tatcaaaaag gatcttcacc tagatccttt   1860
taaattaaaa atgaagtttt aaatcaatct aaagtatata tgagtaaact tggtctgaca   1920
gttaccaatg cttaatcagt gaggcaccta tctcagcgat ctgtctatttt cgttcatcca   1980 tagttgcctg actccccgtc gtgtagataa ctacgatacg ggagggctta ccatctggcc   2040
ccagtgctgc aatgataccg cgagacccac gctcaccggc tccagattta tcagcaataa   2100
accagccagc cggaagggcc gagcgcagaa gtggtcctgc aactttatcc gcctccatcc   2160
agtctattaa ttgttgccgg gaagctagag taagtagttc gccagttaat agtttgcgca   2220
acgttgttgc cattgctaca ggcatcgtgg tgtcacgctc gtcgtttggt atggcttcat   2280
tcagctccgg ttcccaacga tcaaggcgag ttacatgatc ccccatgttg tgcaaaaaag   2340
```

-continued

```
cggttagctc cttcggtcct ccgatcgttg tcagaagtaa gttggccgca gtgttatcac    2400
tcatggttat ggcagcactg cataattctc ttactgtcat gccatccgta agatgctttt    2460
ctgtgactgg tgagtactca accaagtcat tctgagaata gtgtatgcgg cgaccgagtt    2520
gctcttgccc ggcgtcaata cgggataata ccgcgccaca tagcagaact ttaaaagtgc    2580
tcatcattgg aaaacgttct tcggggcgaa aactctcaag gatcttaccg ctgttgagat    2640
ccagttcgat gtaacccact cgtgcaccca actgatcttc agcatctttt actttcacca    2700
gcgtttctgg gtgagcaaaa acaggaaggc aaaatgccgc aaaaaaggga ataagggcga    2760
cacggaaatg ttgaatactc atactcttcc tttttcaata ttattgaagc atttatcagg    2820
gttattgtct catgagcgga tacatatttg aatgtattta gaaaaataaa caaataggggg   2880 ttccgcgcac atttccccga aaagtgccac ctgacgtcta agaaaccatt attatcatga    2940
cattaaccta taaaaatagg cgtatcacga ggcc                                2974
```

<210> SEQ ID NO 22
<211> LENGTH: 28
<212> TYPE: DNA
<213> ORGANISM: Artificial Sequence
<220> FEATURE:
<223> OTHER INFORMATION: Group 1 Forward Primer

<400> SEQUENCE: 22

```
atggacttct taagttttat cctgtttg                                       28
```

<210> SEQ ID NO 23
<211> LENGTH: 20
<212> TYPE: DNA
<213> ORGANISM: Artificial Sequence
<220> FEATURE:
<223> OTHER INFORMATION: Group 1 Reverse Primer

<400> SEQUENCE: 23

```
ttaccccegg atcgggacag                                                20
```

<210> SEQ ID NO 24
<211> LENGTH: 24
<212> TYPE: DNA
<213> ORGANISM: Artificial Sequence
<220> FEATURE:
<223> OTHER INFORMATION: Group 2 Forward Primer

<400> SEQUENCE: 24

```
atggacttct taagttgtat cctg                                           24
```

<210> SEQ ID NO 25
<211> LENGTH: 20
<212> TYPE: DNA
<213> ORGANISM: Artificial Sequence
<220> FEATURE:
<223> OTHER INFORMATION: Group 2 Reverse Primer

<400> SEQUENCE: 25

```
ttaccccegg attgggacag                                                20
```

<210> SEQ ID NO 26
<211> LENGTH: 499
<212> TYPE: PRT
<213> ORGANISM: Vitis vinifera
<220> FEATURE:
<223> OTHER INFORMATION: putative cytochrome P450
<300> PUBLICATION INFORMATION:
<308> DATABASE ACCESSION NUMBER: XP_002281735

<309> DATABASE ENTRY DATE: 2011-12-07

<400> SEQUENCE: 26

```
Met Glu Leu Leu Ser Cys Leu Leu Cys Phe Leu Ala Ala Trp Thr Ser
1               5                   10                  15

Ile Tyr Ile Met Phe Ser Ala Arg Arg Gly Arg Lys His Ala Ala His
            20                  25                  30

Lys Leu Pro Pro Gly Pro Val Pro Leu Pro Ile Ile Gly Ser Leu Leu
        35                  40                  45

Asn Leu Gly Asn Arg Pro His Glu Ser Leu Ala Asn Leu Ala Lys Thr
50                  55                  60

Tyr Gly Pro Ile Met Thr Leu Lys Leu Gly Tyr Val Thr Thr Ile Val
65                  70                  75                  80

Ile Ser Ser Ala Pro Met Ala Lys Glu Val Leu Gln Lys Gln Asp Leu
                85                  90                  95

Ser Phe Cys Asn Arg Ser Ile Pro Asp Ala Ile Arg Ala Ala Lys His
            100                 105                 110

Asn Gln Leu Ser Met Ala Trp Leu Pro Val Ser Thr Thr Trp Arg Ala
        115                 120                 125

Leu Arg Arg Thr Cys Asn Ser His Leu Phe Thr Pro Gln Lys Leu Asp
    130                 135                 140

Ser Asn Thr His Leu Arg His Gln Lys Val Gln Glu Leu Leu Ala Asn
145                 150                 155                 160

Val Glu Gln Ser Cys Gln Ala Gly Gly Pro Val Asp Ile Gly Gln Glu
                165                 170                 175

Ala Phe Arg Thr Ser Leu Asn Leu Leu Ser Asn Thr Ile Phe Ser Val
            180                 185                 190

Asp Leu Val Asp Pro Ile Ser Glu Thr Ala Gln Glu Phe Lys Glu Leu
        195                 200                 205

Val Arg Gly Val Met Glu Glu Ala Gly Lys Pro Asn Leu Val Asp Tyr
    210                 215                 220

Phe Pro Val Leu Arg Arg Ile Asp Pro Gln Ser Ile Arg Arg Arg Leu
225                 230                 235                 240

Thr Ile Tyr Phe Gly Arg Met Ile Glu Ile Phe Asp Arg Met Ile Lys
                245                 250                 255

Gln Arg Leu Gln Leu Arg Lys Asn Gln Gly Ser Ile Ala Ser Ser Asp
            260                 265                 270

Val Leu Asp Val Leu Leu Asn Ile Ser Glu Asp Asn Ser Ser Glu Ile
        275                 280                 285

Glu Arg Ser His Met Glu His Leu Leu Leu Asp Leu Phe Ala Ala Gly
    290                 295                 300

Thr Asp Thr Thr Ser Ser Thr Leu Glu Trp Ala Met Ala Glu Leu Leu
305                 310                 315                 320

His Asn Pro Glu Thr Leu Leu Lys Ala Arg Met Glu Leu Leu Gln Thr
                325                 330                 335

Ile Gly Gln Asp Lys Gln Val Lys Glu Ser Asp Ile Ser Arg Leu Pro
            340                 345                 350

Tyr Leu Gln Ala Val Val Lys Glu Thr Phe Arg Leu His Pro Ala Val
        355                 360                 365

Pro Phe Leu Leu Pro Arg Arg Val Glu Gly Asp Ala Asp Ile Asp Gly
    370                 375                 380

Phe Ala Val Pro Lys Asn Ala Gln Val Leu Val Asn Ala Trp Ala Ile
385                 390                 395                 400
```

```
Gly Arg Asp Pro Asn Thr Trp Glu Asn Pro Asn Ser Phe Val Pro Glu
                405                 410                 415

Arg Phe Leu Gly Leu Asp Met Asp Val Lys Gly Gln Asn Phe Glu Leu
            420                 425                 430

Ile Pro Phe Gly Ala Gly Arg Arg Ile Cys Pro Gly Leu Pro Leu Ala
        435                 440                 445

Ile Arg Met Val His Leu Met Leu Ala Ser Leu Ile His Ser Tyr Asp
    450                 455                 460

Trp Lys Leu Glu Asp Gly Val Thr Pro Glu Asn Met Asn Met Glu Glu
465                 470                 475                 480

Arg Tyr Gly Ile Ser Leu Gln Lys Ala Gln Pro Leu Gln Ala Leu Pro
                485                 490                 495

Val Arg Val

<210> SEQ ID NO 27
<211> LENGTH: 493
<212> TYPE: PRT
<213> ORGANISM: Catharanthus roseus
<220> FEATURE:
<223> OTHER INFORMATION: CYP76B6 geraniol hydroxylase
<300> PUBLICATION INFORMATION:
<308> DATABASE ACCESSION NUMBER: CAC80883
<309> DATABASE ENTRY DATE: 2001-11-22

<400> SEQUENCE: 27

Met Asp Tyr Leu Thr Ile Ile Leu Thr Leu Leu Phe Ala Leu Thr Leu
 1               5                  10                  15

Tyr Glu Ala Phe Ser Tyr Leu Ser Arg Arg Thr Lys Asn Leu Pro Pro
            20                  25                  30

Gly Pro Ser Pro Leu Pro Phe Ile Gly Ser Leu His Leu Leu Gly Asp
        35                  40                  45

Gln Pro His Lys Ser Leu Ala Lys Leu Ser Lys Lys His Gly Pro Ile
    50                  55                  60

Met Ser Leu Lys Leu Gly Gln Ile Thr Thr Ile Val Ile Ser Ser Ser
65                  70                  75                  80

Thr Met Ala Lys Glu Val Leu Gln Lys Gln Asp Leu Ala Phe Ser Ser
                85                  90                  95

Arg Ser Val Pro Asn Ala Leu His Ala His Asn Gln Phe Lys Phe Ser
            100                 105                 110

Val Val Trp Leu Pro Val Ala Ser Arg Trp Arg Ser Leu Arg Lys Val
        115                 120                 125

Leu Asn Ser Asn Ile Phe Ser Gly Asn Arg Leu Asp Ala Asn Gln His
    130                 135                 140

Leu Arg Thr Arg Lys Val Gln Glu Leu Ile Ala Tyr Cys Arg Lys Asn
145                 150                 155                 160

Ser Gln Ser Gly Glu Ala Val Asp Val Gly Arg Ala Ala Phe Arg Thr
                165                 170                 175

Ser Leu Asn Leu Leu Ser Asn Leu Ile Phe Ser Lys Asp Leu Thr Asp
            180                 185                 190

Pro Tyr Ser Asp Ser Ala Lys Glu Phe Lys Asp Leu Val Trp Asn Ile
        195                 200                 205

Met Val Glu Ala Gly Lys Pro Asn Leu Val Asp Phe Phe Pro Leu Leu
    210                 215                 220

Glu Lys Val Asp Pro Gln Gly Ile Arg His Arg Met Thr Ile His Phe
225                 230                 235                 240

Gly Glu Val Leu Lys Leu Phe Gly Gly Leu Val Asn Glu Arg Leu Glu
```

```
                    245                 250                 255
Gln Arg Arg Ser Lys Gly Glu Lys Asn Asp Val Leu Asp Val Leu Leu
            260                 265                 270

Thr Thr Ser Gln Glu Ser Pro Glu Glu Ile Asp Arg Thr His Ile Glu
            275                 280                 285

Arg Met Cys Leu Asp Leu Phe Val Ala Gly Thr Asp Thr Thr Ser Ser
    290                 295                 300

Thr Leu Glu Trp Ala Met Ser Glu Met Leu Lys Asn Pro Asp Lys Met
305                 310                 315                 320

Lys Lys Thr Gln Asp Glu Leu Ala Gln Val Ile Gly Arg Gly Lys Thr
                325                 330                 335

Ile Glu Glu Ser Asp Ile Asn Arg Leu Pro Tyr Leu Arg Cys Val Met
            340                 345                 350

Lys Glu Thr Leu Arg Ile His Pro Pro Val Pro Phe Leu Ile Pro Arg
            355                 360                 365

Lys Val Glu Gln Ser Val Glu Val Cys Gly Tyr Asn Val Pro Lys Gly
    370                 375                 380

Ser Gln Val Leu Val Asn Ala Trp Ala Ile Gly Arg Asp Glu Thr Val
385                 390                 395                 400

Trp Asp Asp Ala Leu Ala Phe Lys Pro Glu Arg Phe Met Glu Ser Glu
                405                 410                 415

Leu Asp Ile Arg Gly Arg Asp Phe Glu Leu Ile Pro Phe Gly Ala Gly
            420                 425                 430

Arg Arg Ile Cys Pro Gly Leu Pro Leu Ala Leu Arg Thr Val Pro Leu
            435                 440                 445

Met Leu Gly Ser Leu Leu Asn Ser Phe Asn Trp Lys Leu Glu Gly Gly
    450                 455                 460

Met Ala Pro Lys Asp Leu Asp Met Glu Glu Lys Phe Gly Ile Thr Leu
465                 470                 475                 480

Gln Lys Ala His Pro Leu Arg Ala Val Pro Ser Thr Leu
                485                 490
```

<210> SEQ ID NO 28
<211> LENGTH: 477
<212> TYPE: PRT
<213> ORGANISM: Helianthus tuberosus
<220> FEATURE:
<223> OTHER INFORMATION: CYP76B1 7-ethoxycoumarin O-deethylase
<300> PUBLICATION INFORMATION:
<308> DATABASE ACCESSION NUMBER: CAA71178
<309> DATABASE ENTRY DATE: 1997-12-12

<400> SEQUENCE: 28

```
His Glu Trp Val Leu Gly Val Gly Lys Pro Lys Asn Leu Pro Pro Gly
1               5                   10                  15

Pro Thr Arg Leu Pro Ile Ile Gly Asn Leu His Leu Leu Gly Ala Leu
            20                  25                  30

Pro His Gln Ser Leu Ala Lys Leu Ala Lys Ile His Gly Pro Ile Met
        35                  40                  45

Ser Leu Gln Leu Gly Gln Ile Thr Thr Leu Val Ile Ser Ser Ala Thr
    50                  55                  60

Ala Ala Glu Glu Val Leu Lys Lys Gln Asp Leu Ala Phe Ser Thr Arg
65                  70                  75                  80

Asn Val Pro Asp Ala Val Arg Ala Tyr Asn His Glu Arg His Ser Ile
                85                  90                  95

Ser Phe Leu His Val Cys Thr Glu Trp Arg Thr Leu Arg Arg Ile Val
```

```
                100             105             110
Ser Ser Asn Ile Phe Ser Asn Ser Ser Leu Glu Ala Lys Gln His Leu
            115                 120             125
Arg Ser Lys Lys Val Glu Glu Leu Ile Ala Tyr Cys Arg Lys Ala Ala
            130                 135             140
Leu Ser Asn Glu Asn Val His Ile Gly Arg Ala Ala Phe Arg Thr Ser
145                 150                 155             160
Leu Asn Leu Leu Ser Asn Thr Ile Phe Ser Lys Asp Leu Thr Asp Pro
                165                 170             175
Tyr Glu Asp Ser Ala Ser Gly Lys Glu Phe Arg Glu Val Ile Thr Asn
            180                 185             190
Ile Met Val Asp Ser Ala Lys Thr Asn Leu Val Asp Val Phe Pro Val
            195                 200             205
Leu Lys Arg Ile Asp Pro Gln Gly Ile Lys Arg Gly Met Ala Arg His
            210                 215             220
Phe Ser Lys Val Leu Gly Ile Phe Asp Gln Leu Ile Glu Glu Arg Met
225                 230                 235             240
Arg Thr Gly Arg Phe Glu Gln Gly Asp Val Leu Asp Val Cys Leu Lys
                245                 250             255
Met Met Gln Asp Asn Pro Asn Glu Phe Asn His Thr Asn Ile Lys Ala
            260                 265             270
Leu Phe Leu Asp Leu Phe Val Ala Gly Thr Asp Thr Thr Ser Ile Thr
            275                 280             285
Ile Glu Trp Ala Met Thr Glu Leu Leu Arg Lys Pro His Ile Met Ser
290                 295                 300
Lys Ala Lys Glu Glu Leu Glu Lys Val Ile Gly Lys Gly Ser Ile Val
305                 310                 315             320
Lys Glu Asp Asp Val Leu Arg Leu Pro Tyr Leu Ser Cys Ile Val Lys
                325                 330             335
Glu Val Leu Arg Leu His Pro Pro Ser Pro Leu Leu Leu Pro Arg Lys
            340                 345             350
Val Val Thr Gln Val Glu Leu Ser Gly Tyr Thr Ile Pro Ala Gly Thr
            355                 360             365
Leu Val Phe Val Asn Ala Trp Ala Ile Gly Arg Asp Pro Thr Val Trp
            370                 375             380
Asp Asp Ser Leu Glu Phe Lys Pro Gln Arg Phe Leu Glu Ser Arg Leu
385                 390                 395             400
Asp Val Arg Gly His Asp Phe Asp Leu Ile Pro Phe Gly Ala Gly Arg
                405                 410             415
Arg Ile Cys Pro Gly Ile Pro Leu Ala Thr Arg Met Val Pro Ile Met
            420                 425             430
Leu Gly Ser Leu Leu Asn Asn Phe Asp Trp Lys Ile Asp Thr Lys Val
            435                 440             445
Pro Tyr Asp Val Leu Asp Met Thr Glu Lys Asn Gly Thr Thr Ile Ser
450                 455                 460
Lys Ala Lys Pro Leu Cys Val Val Pro Ile Pro Leu Asn
465                 470                 475

<210> SEQ ID NO 29
<211> LENGTH: 495
<212> TYPE: PRT
<213> ORGANISM: Swertia mussotii
<220> FEATURE:
<223> OTHER INFORMATION: CYP76B6 geraniol 10-hydroxylase
<300> PUBLICATION INFORMATION:
```

<308> DATABASE ACCESSION NUMBER: ACZ48680
<309> DATABASE ENTRY DATE: 2010-09-02

<400> SEQUENCE: 29

```
Met Asp Phe Asp Phe Leu Thr Ile Ala Ile Gly Phe Leu Phe Thr Ile
1               5                   10                  15

Thr Leu Tyr Gln Ala Leu Asn Phe Phe Ser Arg Lys Ser Lys Asn Leu
            20                  25                  30

Pro Pro Gly Pro Ser Pro Leu Pro Leu Ile Gly Asn Leu His Leu Leu
        35                  40                  45

Gly Asp Gln Pro His Lys Ser Leu Ala Lys Leu Ala Lys Lys His Gly
50                  55                  60

Pro Ile Met Gly Leu Gln Leu Gly Gln Val Thr Thr Ile Val Val Thr
65                  70                  75                  80

Ser Ser Gly Met Ala Lys Glu Val Leu Gln Lys Gln Asp Leu Ala Phe
                85                  90                  95

Ser Ser Arg Ser Ile Pro Asn Ala Ile His Ala His Asp Gln Tyr Lys
            100                 105                 110

Tyr Ser Val Ile Trp Leu Pro Val Ala Ser Arg Trp Arg Gly Leu Arg
        115                 120                 125

Lys Ala Leu Asn Ser Asn Met Phe Ser Gly Asn Arg Leu Asp Ala Asn
130                 135                 140

Gln His Leu Arg Ser Arg Lys Val Gln Glu Leu Ile Ala Tyr Cys Arg
145                 150                 155                 160

Lys Ser Ser Gln Thr Gly Asp Ala Ile Asp Val Gly Arg Ala Ala Phe
                165                 170                 175

Arg Thr Ser Leu Asn Leu Leu Ser Asn Thr Met Phe Ser Lys Asp Leu
            180                 185                 190

Thr Asp Pro Tyr Ser Asp Ser Ala Lys Glu Phe Lys Asp Leu Val Trp
        195                 200                 205

Asn Val Met Val Glu Ala Gly Lys Pro Asn Leu Val Asp Tyr Phe Pro
210                 215                 220

Leu Leu Asp Lys Val Asp Pro Gln Gly Ile Arg Lys Arg Met Thr Ile
225                 230                 235                 240

His Phe Gly Lys Ile Leu Glu Leu Phe Gly Gly Leu Ile Asp Glu Arg
                245                 250                 255

Leu Gln Gln Lys Lys Ala Lys Gly Val Asn Asp Asp Val Leu Asp Val
            260                 265                 270

Leu Leu Thr Thr Ser Glu Glu Ser Pro Glu Glu Ile Asp Arg Thr His
        275                 280                 285

Ile Gln Arg Met Cys Leu Asp Leu Phe Val Ala Gly Thr Asp Thr Thr
290                 295                 300

Ser Ser Thr Leu Glu Trp Ala Met Ser Glu Met Leu Lys Asn Pro Glu
305                 310                 315                 320

Lys Met Lys Ala Ala Gln Ala Glu Leu Ala Gln Val Ile Gly Lys Gly
                325                 330                 335

Lys Ala Val Glu Glu Ala Asp Leu Ala Arg Leu Pro Tyr Leu Arg Cys
            340                 345                 350

Ala Ile Lys Glu Thr Leu Arg Ile His Pro Pro Val Pro Leu Leu Ile
        355                 360                 365

Pro Arg Arg Thr Glu Gln Glu Val Glu Val Cys Gly Tyr Thr Val Pro
370                 375                 380

Lys Asn Ser Gln Val Leu Val Asn Val Trp Ala Ile Ser Arg Asp Asp
385                 390                 395                 400
```

```
Ala Ile Trp Lys Asp Pro Leu Ser Phe Lys Pro Glu Arg Phe Leu Glu
            405                 410                 415

Ser Glu Leu Glu Met Arg Gly Lys Asp Phe Glu Leu Ile Pro Phe Gly
            420                 425                 430

Ala Gly Arg Arg Ile Cys Pro Gly Leu Pro Leu Ala Val Arg Met Val
            435                 440                 445

Pro Val Met Leu Gly Ser Leu Leu Asn Ser Phe Asp Trp Lys Leu Glu
450                 455                 460

Gly Gly Ile Ala Pro Lys Asp Leu Asp Met Glu Glu Lys Phe Gly Ile
465                 470                 475                 480

Thr Leu Gln Lys Ala His Pro Leu Arg Ala Val Ala Thr Pro Leu
            485                 490                 495

<210> SEQ ID NO 30
<211> LENGTH: 502
<212> TYPE: PRT
<213> ORGANISM: Persea americana
<220> FEATURE:
<223> OTHER INFORMATION: CYP71A1 cytochrome P450
<300> PUBLICATION INFORMATION:
<308> DATABASE ACCESSION NUMBER: P24465
<309> DATABASE ENTRY DATE: 2010-11-02

<400> SEQUENCE: 30

Met Ala Ile Leu Val Ser Leu Leu Phe Leu Ala Ile Ala Leu Thr Phe
1               5                   10                  15

Phe Leu Leu Lys Leu Asn Glu Lys Arg Glu Lys Lys Pro Asn Leu Pro
            20                  25                  30

Pro Ser Pro Pro Asn Leu Pro Ile Ile Gly Asn Leu His Gln Leu Gly
            35                  40                  45

Asn Leu Pro His Arg Ser Leu Arg Ser Leu Ala Asn Glu Leu Gly Pro
50                  55                  60

Leu Ile Leu Leu His Leu Gly His Ile Pro Thr Leu Ile Val Ser Thr
65                  70                  75                  80

Ala Glu Ile Ala Glu Glu Ile Leu Lys Thr His Asp Leu Ile Phe Ala
            85                  90                  95

Ser Arg Pro Ser Thr Thr Ala Ala Arg Arg Ile Phe Tyr Asp Cys Thr
            100                 105                 110

Asp Val Ala Phe Ser Pro Tyr Gly Glu Tyr Trp Arg Gln Val Arg Lys
            115                 120                 125

Ile Cys Val Leu Glu Leu Leu Ser Ile Lys Arg Val Asn Ser Tyr Arg
            130                 135                 140

Ser Ile Arg Glu Glu Glu Val Gly Leu Met Met Glu Arg Ile Ser Gln
145                 150                 155                 160

Ser Cys Ser Thr Gly Glu Ala Val Asn Leu Ser Glu Leu Leu Leu Leu
            165                 170                 175

Leu Ser Ser Gly Thr Ile Thr Arg Val Ala Phe Gly Lys Lys Tyr Glu
            180                 185                 190

Gly Glu Glu Glu Arg Lys Asn Lys Phe Ala Asp Leu Ala Thr Glu Leu
            195                 200                 205

Thr Thr Leu Met Gly Ala Phe Phe Val Gly Asp Tyr Phe Pro Ser Phe
210                 215                 220

Ala Trp Val Asp Val Leu Thr Gly Met Asp Ala Arg Leu Lys Arg Asn
225                 230                 235                 240

His Gly Glu Leu Asp Ala Phe Val Asp His Val Ile Asp Asp His Leu
            245                 250                 255
```

Leu Ser Arg Lys Ala Asn Gly Ser Asp Gly Val Glu Gln Lys Asp Leu
            260                 265                 270

Val Asp Val Leu Leu His Leu Gln Lys Asp Ser Ser Leu Gly Val His
        275                 280                 285

Leu Asn Arg Asn Asn Leu Lys Ala Val Ile Leu Asp Met Phe Ser Gly
290                 295                 300

Gly Thr Asp Thr Thr Ala Val Thr Leu Glu Trp Ala Met Ala Glu Leu
305                 310                 315                 320

Ile Lys His Pro Asp Val Met Glu Lys Ala Gln Gln Glu Val Arg Arg
                325                 330                 335

Val Val Gly Lys Lys Ala Lys Val Glu Glu Asp Leu His Gln Leu
            340                 345                 350

His Tyr Leu Lys Leu Ile Ile Lys Glu Thr Leu Arg Leu His Pro Val
        355                 360                 365

Ala Pro Leu Leu Val Pro Arg Glu Ser Thr Arg Asp Val Val Ile Arg
    370                 375                 380

Gly Tyr His Ile Pro Ala Lys Thr Arg Val Phe Ile Asn Ala Trp Ala
385                 390                 395                 400

Ile Gly Arg Asp Pro Lys Ser Trp Glu Asn Ala Glu Glu Phe Leu Pro
                405                 410                 415

Glu Arg Phe Val Asn Asn Ser Val Asp Phe Lys Gly Gln Asp Phe Gln
            420                 425                 430

Leu Ile Pro Phe Gly Ala Gly Arg Arg Gly Cys Pro Gly Ile Ala Phe
        435                 440                 445

Gly Ile Ser Ser Val Glu Ile Ser Leu Ala Asn Leu Leu Tyr Trp Phe
    450                 455                 460

Asn Trp Glu Leu Pro Gly Asp Leu Thr Lys Glu Asp Leu Asp Met Ser
465                 470                 475                 480

Glu Ala Val Gly Ile Thr Val His Met Lys Phe Pro Leu Gln Leu Val
                485                 490                 495

Ala Lys Arg His Leu Ser
            500

<210> SEQ ID NO 31
<211> LENGTH: 493
<212> TYPE: PRT
<213> ORGANISM: Mentha x piperita
<220> FEATURE:
<223> OTHER INFORMATION: CYP71A32 (+)-pulegone 9-hydroxylase
<300> PUBLICATION INFORMATION:
<308> DATABASE ACCESSION NUMBER: Q947B7
<309> DATABASE ENTRY DATE: 2012-09-05

<400> SEQUENCE: 31

Met Ala Ala Leu Leu Val Phe Phe Ser Val Ser Leu Ile Leu Leu Ala
 1               5                  10                  15

Val Leu Phe His Lys Arg Lys Ser Ser Leu Ser Ser Arg Lys Arg Pro
            20                  25                  30

Pro Pro Ser Pro Leu Arg Leu Pro Val Ile Gly His Phe His Leu Ile
        35                  40                  45

Gly Ala Leu Ser His Arg Ser Phe Thr Ser Leu Ser Lys Arg Tyr Gly
    50                  55                  60

Glu Val Met Leu Leu His Phe Gly Ser Ala Pro Val Leu Val Ala Ser
65                  70                  75                  80

Ser Ala Ala Ala Ala Arg Glu Ile Met Lys Asn Gln Asp Val Ile Phe
                85                  90                  95

```
Ala Ser Arg Pro Arg Leu Ser Ile Phe Asp Arg Leu Met Tyr Ser Gly
            100                 105                 110

Lys Gly Val Ala Phe Ala Pro Tyr Gly Glu His Trp Arg Asn Ala Arg
        115                 120                 125

Ser Met Cys Met Leu Gln Leu Leu Ser Ala Lys Arg Val Gln Ser Phe
    130                 135                 140

Gly Gly Ile Arg Glu Glu Thr Ser Ala Met Ile Glu Lys Ile Arg
145                 150                 155                 160

Arg Ser Lys Pro Thr Thr Val Val Asn Leu Ser Glu Met Phe Met Ala
                165                 170                 175

Leu Thr Asn Gly Val Ile His Arg Ala Val Leu Gly Arg Lys Gly Asp
            180                 185                 190

Gly Gly Asp Asp Phe Asn Arg Ile Leu Ile Lys Val Ile Lys Leu Leu
        195                 200                 205

Gly Ser Phe Asn Val Gly Asp Tyr Val Pro Trp Leu Ser Trp Ile Asn
    210                 215                 220

Arg Ile Asn Gly Val Asp Ala Glu Val Glu Lys Val Gly Thr Lys Leu
225                 230                 235                 240

Asp Gly Ser Met Glu Gly Ile Leu Arg Lys Tyr Arg Arg Lys Lys Val
                245                 250                 255

Gly Asp Asp Glu Thr Asn Phe Val Asp Thr Leu Leu Gln Phe Gln Arg
            260                 265                 270

Glu Ser Lys Asp Thr Asp Pro Val Glu Asp Val Ile Lys Ala Leu
        275                 280                 285

Ile Phe Asp Met Val Ser Ala Gly Thr Asp Thr Thr Phe Ala Ala Leu
    290                 295                 300

Glu Trp Thr Met Ala Glu Leu Ile Lys Asn Pro Arg Thr Leu Lys Thr
305                 310                 315                 320

Leu Gln Asn Glu Val Arg Glu Val Ser Arg Asn Lys Gly Gly Ile Thr
                325                 330                 335

Glu Asp Asp Val Asp Lys Met Pro Tyr Leu Lys Ala Val Ser Lys Glu
            340                 345                 350

Ile Leu Arg Leu His Pro Pro Phe Ala Ile Leu Pro Arg Glu Leu
        355                 360                 365

Thr Gln Asp Ala Asn Met Leu Gly Tyr Asp Ile Pro Arg Gly Thr Val
    370                 375                 380

Val Leu Val Asn Asn Trp Ala Ile Ser Arg Asp Pro Ser Leu Trp Glu
385                 390                 395                 400

Asn Pro Glu Glu Phe Arg Pro Glu Arg Phe Leu Glu Thr Ser Ile Asp
                405                 410                 415

Tyr Lys Gly Leu His Phe Glu Met Leu Pro Phe Gly Ser Gly Arg Arg
            420                 425                 430

Gly Cys Pro Gly Ser Thr Phe Ala Met Ala Leu Tyr Glu Leu Ala Leu
        435                 440                 445

Ser Lys Leu Val Asn Glu Phe Asp Phe Arg Leu Gly Asn Gly Asp Arg
    450                 455                 460

Ala Glu Asp Leu Asp Met Thr Glu Ala Pro Gly Phe Val Val His Lys
465                 470                 475                 480

Lys Ser Pro Leu Leu Val Leu Ala Thr Pro Arg Gln Ser
                485                 490

<210> SEQ ID NO 32
<211> LENGTH: 495
```

```
<212> TYPE: PRT
<213> ORGANISM: Artemisia annua
<220> FEATURE:
<223> OTHER INFORMATION: CYP71AV1 amorpha-4,11-diene C-12 oxidase
<300> PUBLICATION INFORMATION:
<308> DATABASE ACCESSION NUMBER: ABB82944
<309> DATABASE ENTRY DATE: 2006-04-13

<400> SEQUENCE: 32

Met Lys Ser Ile Leu Lys Ala Met Ala Leu Ser Leu Thr Thr Ser Ile
 1               5                  10                  15

Ala Leu Ala Thr Ile Leu Leu Phe Val Tyr Lys Phe Ala Thr Arg Ser
             20                  25                  30

Lys Ser Thr Lys Lys Ser Leu Pro Glu Pro Trp Arg Leu Pro Ile Ile
         35                  40                  45

Gly His Met His His Leu Ile Gly Thr Thr Pro His Arg Gly Val Arg
     50                  55                  60

Asp Leu Ala Arg Lys Tyr Gly Ser Leu Met His Leu Gln Leu Gly Glu
65                  70                  75                  80

Val Pro Thr Ile Val Ser Ser Pro Lys Trp Ala Lys Glu Ile Leu
                 85                  90                  95

Thr Thr Tyr Asp Ile Thr Phe Ala Asn Arg Pro Glu Thr Leu Thr Gly
             100                 105                 110

Glu Ile Val Leu Tyr His Asn Thr Asp Val Val Leu Ala Pro Tyr Gly
         115                 120                 125

Glu Tyr Trp Arg Gln Leu Arg Lys Ile Cys Thr Leu Glu Leu Leu Ser
130                 135                 140

Val Lys Lys Val Lys Ser Phe Gln Ser Leu Arg Glu Glu Glu Cys Trp
145                 150                 155                 160

Asn Leu Val Gln Glu Ile Lys Ala Ser Gly Ser Gly Arg Pro Val Asn
                 165                 170                 175

Leu Ser Glu Asn Val Phe Lys Leu Ile Ala Thr Ile Leu Ser Arg Ala
             180                 185                 190

Ala Phe Gly Lys Gly Ile Lys Asp Gln Lys Glu Leu Thr Glu Ile Val
         195                 200                 205

Lys Glu Ile Leu Arg Gln Thr Gly Gly Phe Asp Val Ala Asp Ile Phe
210                 215                 220

Pro Ser Lys Lys Phe Leu His His Leu Ser Gly Lys Arg Ala Arg Leu
225                 230                 235                 240

Thr Ser Leu Arg Lys Lys Ile Asp Asn Leu Ile Asp Asn Leu Val Ala
                 245                 250                 255

Glu His Thr Val Asn Thr Ser Ser Lys Thr Asn Glu Thr Leu Leu Asp
             260                 265                 270

Val Leu Leu Arg Leu Lys Asp Ser Ala Glu Phe Pro Leu Thr Ser Asp
         275                 280                 285

Asn Ile Lys Ala Ile Ile Leu Asp Met Phe Gly Ala Gly Thr Asp Thr
290                 295                 300

Ser Ser Ser Thr Ile Glu Trp Ala Ile Ser Glu Leu Ile Lys Cys Pro
305                 310                 315                 320

Lys Ala Met Glu Lys Val Gln Ala Glu Leu Arg Lys Ala Leu Asn Gly
                 325                 330                 335

Lys Glu Lys Ile His Glu Glu Asp Ile Gln Glu Leu Ser Tyr Leu Asn
             340                 345                 350

Met Val Ile Lys Glu Thr Leu Arg Leu His Pro Pro Leu Pro Leu Val
         355                 360                 365
```

```
Leu Pro Arg Glu Cys Arg Gln Pro Val Asn Leu Ala Gly Tyr Asn Ile
    370                 375                 380

Pro Asn Lys Thr Lys Leu Ile Val Asn Val Phe Ala Ile Asn Arg Asp
385                 390                 395                 400

Pro Glu Tyr Trp Lys Asp Ala Glu Ala Phe Ile Pro Glu Arg Phe Glu
                405                 410                 415

Asn Ser Ser Ala Thr Val Met Gly Ala Glu Tyr Glu Tyr Leu Pro Phe
                420                 425                 430

Gly Ala Gly Arg Arg Met Cys Pro Gly Ala Ala Leu Gly Leu Ala Asn
            435                 440                 445

Val Gln Leu Pro Leu Ala Asn Ile Leu Tyr His Phe Asn Trp Lys Leu
450                 455                 460

Pro Asn Gly Val Ser Tyr Asp Gln Ile Asp Met Thr Glu Ser Ser Gly
465                 470                 475                 480

Ala Thr Met Gln Arg Lys Thr Glu Leu Leu Leu Val Pro Ser Phe
                485                 490                 495

<210> SEQ ID NO 33
<211> LENGTH: 496
<212> TYPE: PRT
<213> ORGANISM: Cichorium intybus
<220> FEATURE:
<223> OTHER INFORMATION: CYP71AV8 valencene oxidase
<300> PUBLICATION INFORMATION:
<308> DATABASE ACCESSION NUMBER: ADM86719
<309> DATABASE ENTRY DATE: 2011-01-24

<400> SEQUENCE: 33

Met Glu Ile Ser Ile Pro Thr Thr Leu Gly Leu Ala Val Ile Ile Phe
1               5                   10                  15

Ile Ile Phe Lys Leu Leu Thr Arg Thr Thr Ser Lys Lys Asn Leu Leu
                20                  25                  30

Pro Glu Pro Trp Arg Leu Pro Ile Ile Gly His Met His His Leu Ile
            35                  40                  45

Gly Thr Met Pro His Arg Gly Val Met Glu Leu Ala Arg Lys His Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
                100                 105                 110

Thr Asp Ile Val Leu Ala Pro Tyr Gly Glu Tyr Trp Arg Gln Leu Arg
            115                 120                 125

Lys Leu Cys Thr Leu Glu Leu Leu Ser Asn Lys Val Lys Ser Phe
130                 135                 140

Gln Ser Leu Arg Glu Glu Glu Cys Trp Asn Leu Val Lys Asp Ile Arg
145                 150                 155                 160

Ser Thr Gly Gln Gly Ser Pro Ile Asn Leu Ser Glu Asn Ile Phe Lys
                165                 170                 175

Met Ile Ala Thr Ile Leu Ser Arg Ala Ala Phe Gly Lys Gly Ile Lys
            180                 185                 190

Asp Gln Met Lys Phe Thr Glu Leu Val Lys Glu Ile Leu Arg Leu Thr
        195                 200                 205

Gly Gly Phe Asp Val Ala Asp Ile Phe Pro Ser Lys Lys Leu Leu His
    210                 215                 220
```

His Leu Ser Gly Lys Arg Ala Lys Leu Thr Asn Ile His Asn Lys Leu
225                 230                 235                 240

Asp Asn Leu Ile Asn Asn Ile Ile Ala Glu His Pro Gly Asn Arg Thr
            245                 250                 255

Ser Ser Ser Gln Glu Thr Leu Leu Asp Val Leu Leu Arg Leu Lys Glu
        260                 265                 270

Ser Ala Glu Phe Pro Leu Thr Ala Asp Asn Val Lys Ala Val Ile Leu
    275                 280                 285

Asp Met Phe Gly Ala Gly Thr Asp Thr Ser Ser Ala Thr Ile Glu Trp
290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
            325                 330                 335

Asp Leu Gln Glu Leu Asn Tyr Leu Lys Leu Val Ile Lys Glu Thr Leu
        340                 345                 350

Arg Leu His Pro Pro Leu Pro Leu Val Met Pro Arg Glu Cys Arg Glu
    355                 360                 365

Pro Cys Val Leu Gly Gly Tyr Asp Ile Pro Ser Lys Thr Lys Leu Ile
370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Thr Val Met
            405                 410                 415

Gly Ser Glu Tyr Glu Tyr Leu Pro Phe Gly Ala Gly Arg Arg Met Cys
        420                 425                 430

Pro Gly Ala Ala Leu Gly Leu Ala Asn Val Glu Leu Pro Leu Ala His
    435                 440                 445

Ile Leu Tyr Tyr Phe Asn Trp Lys Leu Pro Asn Gly Lys Thr Phe Glu
450                 455                 460

Asp Leu Asp Met Thr Glu Ser Phe Gly Ala Thr Val Gln Arg Lys Thr
465                 470                 475                 480

Glu Leu Leu Leu Val Pro Thr Asp Phe Gln Thr Leu Thr Ala Ser Thr
            485                 490                 495

```
<210> SEQ ID NO 34
<211> LENGTH: 490
<212> TYPE: PRT
<213> ORGANISM: Lactuca sativa
<220> FEATURE:
<223> OTHER INFORMATION: CYP71BL1 costunolide synthase
<300> PUBLICATION INFORMATION:
<308> DATABASE ACCESSION NUMBER: AEI59780
<309> DATABASE ENTRY DATE: 2011-06-26

<400> SEQUENCE: 34
```

Met Glu Pro Leu Thr Ile Val Ser Leu Ala Val Ala Ser Phe Leu Leu
1               5                   10                  15

Phe Ala Phe Trp Ala Leu Ser Pro Lys Thr Ser Lys Asn Leu Pro Pro
            20                  25                  30

Gly Pro Pro Lys Leu Pro Ile Ile Gly Asn Ile His Gln Leu Lys Ser
        35                  40                  45

Pro Thr Pro His Arg Val Leu Arg Asn Leu Ala Lys Lys Tyr Gly Pro
    50                  55                  60

Ile Met His Leu Gln Leu Gly Gln Val Ser Thr Val Val Ser Thr
65                  70                  75                  80

-continued

```
Pro Arg Leu Ala Arg Glu Ile Met Lys Thr Asn Asp Ile Ser Phe Ala
                85                  90                  95
Asp Arg Pro Thr Thr Thr Ser Gln Ile Phe Phe Tyr Lys Ala Gln
            100                 105                 110
Asp Ile Gly Trp Ala Pro Tyr Gly Glu Tyr Trp Arg Gln Met Lys Lys
            115                 120                 125
Ile Cys Thr Leu Glu Leu Leu Ser Ala Lys Lys Val Arg Ser Phe Ser
            130                 135                 140
Ser Ile Arg Glu Glu Glu Leu Arg Arg Ile Ser Lys Val Leu Glu Ser
145                 150                 155                 160
Lys Ala Gly Thr Pro Val Asn Phe Thr Glu Met Thr Val Glu Met Val
                165                 170                 175
Asn Asn Val Ile Cys Lys Ala Thr Leu Gly Asp Ser Cys Lys Asp Gln
                180                 185                 190
Ala Thr Leu Ile Glu Val Leu Tyr Asp Val Leu Lys Thr Leu Ser Ala
                195                 200                 205
Phe Asn Leu Ala Ser Tyr Tyr Pro Gly Leu Gln Phe Leu Asn Val Ile
            210                 215                 220
Leu Gly Lys Lys Ala Lys Trp Leu Lys Met Gln Lys Gln Leu Asp Asp
225                 230                 235                 240
Ile Leu Glu Asp Val Leu Lys Glu His Arg Ser Lys Gly Arg Asn Lys
                245                 250                 255
Ser Asp Gln Glu Asp Leu Val Asp Val Leu Leu Arg Val Lys Asp Thr
            260                 265                 270
Gly Gly Leu Asp Phe Thr Val Thr Asp Glu His Val Lys Ala Val Val
            275                 280                 285
Leu Asp Met Leu Thr Ala Gly Thr Asp Thr Ser Ser Ala Thr Leu Glu
290                 295                 300
Trp Ala Met Thr Glu Leu Met Arg Asn Pro His Met Met Lys Arg Ala
305                 310                 315                 320
Gln Glu Glu Val Arg Ser Val Val Lys Gly Asp Thr Ile Thr Glu Thr
                325                 330                 335
Asp Leu Gln Ser Leu His Tyr Leu Lys Leu Ile Val Lys Glu Thr Leu
            340                 345                 350
Arg Leu His Ala Pro Thr Pro Leu Leu Val Pro Arg Glu Cys Arg Gln
            355                 360                 365
Ala Cys Asn Val Asp Gly Tyr Asp Ile Pro Ala Lys Thr Lys Ile Leu
            370                 375                 380
Val Asn Ala Trp Ala Cys Gly Thr Asp Pro Asp Ser Trp Lys Asp Ala
385                 390                 395                 400
Glu Ser Phe Ile Pro Glu Arg Phe Glu Asn Cys Pro Ile Asn Tyr Met
                405                 410                 415
Gly Ala Asp Phe Glu Phe Ile Pro Phe Gly Ala Gly Arg Arg Ile Cys
            420                 425                 430
Pro Gly Leu Thr Phe Gly Leu Ser Met Val Glu Tyr Pro Leu Ala Asn
            435                 440                 445
Phe Leu Tyr His Phe Asp Trp Lys Leu Pro Asn Gly Leu Lys Pro His
            450                 455                 460
Glu Leu Asp Ile Thr Glu Ile Thr Gly Ile Ser Thr Ser Leu Lys His
465                 470                 475                 480
Gln Leu Lys Ile Val Pro Ile Leu Lys Ser
                485                 490
```

```
<210> SEQ ID NO 35
<211> LENGTH: 504
<212> TYPE: PRT
<213> ORGANISM: Nicotiana tabacum
<220> FEATURE:
<223> OTHER INFORMATION: CYP71D20 5-epiaristolochene 1,3-dihydroxylase
<300> PUBLICATION INFORMATION:
<308> DATABASE ACCESSION NUMBER: Q94FM7
<309> DATABASE ENTRY DATE: 2012-04-18

<400> SEQUENCE: 35
```

| Met | Gln | Phe | Phe | Ser | Leu | Val | Ser | Ile | Phe | Leu | Phe | Leu | Ser | Phe | Leu |
|---|---|---|---|---|---|---|---|---|---|---|---|---|---|---|---|
| 1 | | | | 5 | | | | | 10 | | | | | 15 | |

| Phe | Leu | Leu | Arg | Lys | Trp | Lys | Asn | Ser | Asn | Ser | Gln | Ser | Lys | Lys | Leu |
| | | | 20 | | | | | 25 | | | | | 30 | | |

| Pro | Pro | Gly | Pro | Trp | Lys | Ile | Pro | Ile | Leu | Gly | Ser | Met | Leu | His | Met |
| | | | 35 | | | | | 40 | | | | | 45 | | |

| Ile | Gly | Gly | Glu | Pro | His | His | Val | Leu | Arg | Asp | Leu | Ala | Lys | Lys | Tyr |
| | | 50 | | | | | 55 | | | | | 60 | | | |

| Gly | Pro | Leu | Met | His | Leu | Gln | Leu | Gly | Glu | Ile | Ser | Ala | Val | Val | Val |
| 65 | | | | | 70 | | | | | 75 | | | | | 80 |

| Thr | Ser | Arg | Asp | Met | Ala | Lys | Glu | Val | Leu | Lys | Thr | His | Asp | Val | Val |
| | | | | 85 | | | | | 90 | | | | | 95 | |

| Phe | Ala | Ser | Arg | Pro | Lys | Ile | Val | Ala | Met | Asp | Ile | Ile | Cys | Tyr | Asn |
| | | | 100 | | | | | 105 | | | | | 110 | | |

| Gln | Ser | Asp | Ile | Ala | Phe | Ser | Pro | Tyr | Gly | Asp | His | Trp | Arg | Gln | Met |
| | | | 115 | | | | | 120 | | | | | 125 | | |

| Arg | Lys | Ile | Cys | Val | Met | Glu | Leu | Leu | Asn | Ala | Lys | Asn | Val | Arg | Ser |
| | | 130 | | | | | 135 | | | | | 140 | | | |

| Phe | Ser | Ser | Ile | Arg | Arg | Asp | Glu | Val | Val | Arg | Leu | Ile | Asp | Ser | Ile |
| 145 | | | | | 150 | | | | | 155 | | | | | 160 |

| Arg | Ser | Asp | Ser | Ser | Gly | Glu | Leu | Val | Asn | Phe | Thr | Gln | Arg | Ile |
| | | | | 165 | | | | | 170 | | | | | 175 |

| Ile | Trp | Phe | Ala | Ser | Ser | Met | Thr | Cys | Arg | Ser | Ala | Phe | Gly | Gln | Val |
| | | | 180 | | | | | 185 | | | | | 190 | | |

| Leu | Lys | Gly | Gln | Asp | Ile | Phe | Ala | Lys | Lys | Ile | Arg | Glu | Val | Ile | Gly |
| | | | 195 | | | | | 200 | | | | | 205 | | |

| Leu | Ala | Glu | Gly | Phe | Asp | Val | Val | Asp | Ile | Phe | Pro | Thr | Tyr | Lys | Phe |
| | | 210 | | | | | 215 | | | | | 220 | | | |

| Leu | His | Val | Leu | Ser | Gly | Met | Lys | Arg | Lys | Leu | Leu | Asn | Ala | His | Leu |
| 225 | | | | | 230 | | | | | 235 | | | | | 240 |

| Lys | Val | Asp | Ala | Ile | Val | Glu | Asp | Val | Ile | Asn | Glu | His | Lys | Lys | Asn |
| | | | | 245 | | | | | 250 | | | | | 255 | |

| Leu | Ala | Ala | Gly | Lys | Ser | Asn | Gly | Ala | Leu | Gly | Gly | Glu | Asp | Leu | Ile |
| | | | 260 | | | | | 265 | | | | | 270 | | |

| Asp | Val | Leu | Leu | Arg | Leu | Met | Asn | Asp | Thr | Ser | Leu | Gln | Phe | Pro | Ile |
| | | | 275 | | | | | 280 | | | | | 285 | | |

| Thr | Asn | Asp | Asn | Ile | Lys | Ala | Val | Ile | Val | Asp | Met | Phe | Ala | Ala | Gly |
| | | 290 | | | | | 295 | | | | | 300 | | | |

| Thr | Glu | Thr | Ser | Ser | Thr | Thr | Thr | Val | Trp | Ala | Met | Ala | Glu | Met | Met |
| 305 | | | | | 310 | | | | | 315 | | | | | 320 |

| Lys | Asn | Pro | Ser | Val | Phe | Thr | Lys | Ala | Gln | Ala | Glu | Val | Arg | Glu | Ala |
| | | | | 325 | | | | | 330 | | | | | 335 | |

| Phe | Arg | Asp | Lys | Val | Ser | Phe | Asp | Glu | Asn | Asp | Val | Glu | Glu | Leu | Lys |
| | | | 340 | | | | | 345 | | | | | 350 | | |

| Tyr | Leu | Lys | Leu | Val | Ile | Lys | Glu | Thr | Leu | Arg | Leu | His | Pro | Pro | Ser |

-continued

```
                355                 360                 365
Pro Leu Leu Val Pro Arg Glu Cys Arg Glu Asp Thr Asp Ile Asn Gly
            370                 375                 380

Tyr Thr Ile Pro Ala Lys Thr Lys Val Met Val Asn Val Trp Ala Leu
385                 390                 395                 400

Gly Arg Asp Pro Lys Tyr Trp Asp Asp Ala Glu Ser Phe Lys Pro Glu
                405                 410                 415

Arg Phe Glu Gln Cys Ser Val Asp Phe Phe Gly Asn Asn Phe Glu Phe
            420                 425                 430

Leu Pro Phe Gly Gly Gly Arg Arg Ile Cys Pro Gly Met Ser Phe Gly
        435                 440                 445

Leu Ala Asn Leu Tyr Leu Pro Leu Ala Gln Leu Leu Tyr His Phe Asp
    450                 455                 460

Trp Lys Leu Pro Thr Gly Ile Met Pro Arg Asp Leu Asp Leu Thr Glu
465                 470                 475                 480

Leu Ser Gly Ile Thr Ile Ala Arg Lys Gly Gly Leu Tyr Leu Asn Ala
                485                 490                 495

Thr Pro Tyr Gln Pro Ser Arg Glu
            500

<210> SEQ ID NO 36
<211> LENGTH: 500
<212> TYPE: PRT
<213> ORGANISM: Mentha x piperita
<220> FEATURE:
<223> OTHER INFORMATION: CYP71D13 (-)-(4S)-Limonene-3-hydroxylase
<300> PUBLICATION INFORMATION:
<308> DATABASE ACCESSION NUMBER: Q9XHE7
<309> DATABASE ENTRY DATE: 2006-11-28

<400> SEQUENCE: 36

Met Glu Leu Gln Ile Ser Ser Ala Ile Ile Ile Leu Val Val Thr Tyr
1               5                   10                  15

Thr Ile Ser Leu Leu Ile Ile Lys Gln Trp Arg Lys Pro Lys Pro Gln
            20                  25                  30

Glu Asn Leu Pro Pro Gly Pro Pro Lys Leu Pro Leu Ile Gly His Leu
        35                  40                  45

His Leu Leu Trp Gly Lys Leu Pro Gln His Ala Leu Ala Ser Val Ala
    50                  55                  60

Lys Gln Tyr Gly Pro Val Ala His Val Gln Leu Gly Glu Val Phe Ser
65                  70                  75                  80

Val Val Leu Ser Ser Arg Glu Ala Thr Lys Glu Ala Met Lys Leu Val
                85                  90                  95

Asp Pro Ala Cys Ala Asp Arg Phe Glu Ser Ile Gly Thr Lys Ile Met
            100                 105                 110

Trp Tyr Asp Asn Asp Asp Ile Ile Phe Ser Pro Tyr Ser Val His Trp
        115                 120                 125

Arg Gln Met Arg Lys Ile Cys Val Ser Glu Leu Leu Ser Ala Arg Asn
    130                 135                 140

Val Arg Ser Phe Gly Phe Ile Arg Gln Asp Glu Val Ser Arg Leu Leu
145                 150                 155                 160

Gly His Leu Arg Ser Ser Ala Ala Ala Gly Glu Ala Val Asp Leu Thr
                165                 170                 175

Glu Arg Ile Ala Thr Leu Thr Cys Ser Ile Ile Cys Arg Ala Ala Phe
            180                 185                 190

Gly Ser Val Ile Arg Asp His Glu Glu Leu Val Glu Leu Val Lys Asp
```

```
                195                 200                 205
Ala Leu Ser Met Ala Ser Gly Phe Glu Leu Ala Asp Met Phe Pro Ser
    210                 215                 220

Ser Lys Leu Leu Asn Leu Leu Cys Trp Asn Lys Ser Lys Leu Trp Arg
225                 230                 235                 240

Met Arg Arg Arg Val Asp Ala Ile Leu Glu Ala Ile Val Glu Glu His
                245                 250                 255

Lys Leu Lys Lys Ser Gly Glu Phe Gly Gly Glu Asp Ile Ile Asp Val
            260                 265                 270

Leu Phe Arg Met Gln Lys Asp Ser Gln Ile Lys Val Pro Ile Thr Thr
        275                 280                 285

Asn Ala Ile Lys Ala Phe Ile Phe Asp Thr Phe Ser Ala Gly Thr Glu
    290                 295                 300

Thr Ser Ser Thr Thr Thr Leu Trp Val Met Ala Glu Leu Met Arg Asn
305                 310                 315                 320

Pro Glu Val Met Ala Lys Ala Gln Ala Glu Val Arg Ala Ala Leu Lys
                325                 330                 335

Gly Lys Thr Asp Trp Asp Val Asp Val Gln Glu Leu Lys Tyr Met
            340                 345                 350

Lys Ser Val Val Lys Glu Thr Met Arg Met His Pro Pro Ile Pro Leu
        355                 360                 365

Ile Pro Arg Ser Cys Arg Glu Glu Cys Glu Val Asn Gly Tyr Thr Ile
    370                 375                 380

Pro Asn Lys Ala Arg Ile Met Ile Asn Val Trp Ser Met Gly Arg Asn
385                 390                 395                 400

Pro Leu Tyr Trp Glu Lys Pro Glu Thr Phe Trp Pro Glu Arg Phe Asp
                405                 410                 415

Gln Val Ser Arg Asp Phe Met Gly Asn Asp Phe Glu Phe Ile Pro Phe
            420                 425                 430

Gly Ala Gly Arg Arg Ile Cys Pro Gly Leu Asn Phe Gly Leu Ala Asn
        435                 440                 445

Val Glu Val Pro Leu Ala Gln Leu Leu Tyr His Phe Asp Trp Lys Leu
    450                 455                 460

Ala Glu Gly Met Asn Pro Ser Asp Met Asp Met Ser Glu Ala Glu Gly
465                 470                 475                 480

Leu Thr Gly Ile Arg Lys Asn Asn Leu Leu Val Pro Thr Pro Tyr
                485                 490                 495

Asp Pro Ser Ser
        500

<210> SEQ ID NO 37
<211> LENGTH: 496
<212> TYPE: PRT
<213> ORGANISM: Mentha spicata
<220> FEATURE:
<223> OTHER INFORMATION: CYP71D18 (-)-(4S)-Limonene-6-hydroxylase
<300> PUBLICATION INFORMATION:
<308> DATABASE ACCESSION NUMBER: Q6WKZ1
<309> DATABASE ENTRY DATE: 2012-04-18

<400> SEQUENCE: 37

Met Glu Leu Asp Leu Leu Ser Ala Ile Ile Leu Val Ala Thr Tyr
1               5                   10                  15

Ile Val Ser Leu Leu Ile Asn Gln Trp Arg Lys Ser Lys Ser Gln Gln
            20                  25                  30

Asn Leu Pro Pro Ser Pro Pro Lys Leu Pro Val Ile Gly His Leu His
```

```
            35                  40                  45
Phe Leu Trp Gly Gly Leu Pro Gln His Val Phe Arg Ser Ile Ala Gln
 50                  55                  60

Lys Tyr Gly Pro Val Ala His Val Gln Leu Gly Glu Val Tyr Ser Val
 65                  70                  75                  80

Val Leu Ser Ser Ala Glu Ala Ala Lys Gln Ala Met Lys Val Leu Asp
                 85                  90                  95

Pro Asn Phe Ala Asp Arg Phe Asp Gly Ile Gly Ser Arg Thr Met Trp
            100                 105                 110

Tyr Asp Lys Asp Asp Ile Ile Phe Ser Pro Tyr Asn Asp His Trp Arg
            115                 120                 125

Gln Met Arg Arg Ile Cys Val Thr Glu Leu Leu Ser Pro Lys Asn Val
            130                 135                 140

Arg Ser Phe Gly Tyr Ile Arg Gln Glu Ile Glu Arg Leu Ile Arg
145                 150                 155                 160

Leu Leu Gly Ser Ser Gly Gly Ala Pro Val Asp Val Thr Glu Glu Val
                165                 170                 175

Ser Lys Met Ser Cys Val Val Cys Arg Ala Ala Phe Gly Ser Val
                180                 185                 190

Leu Lys Asp Gln Gly Ser Leu Ala Glu Leu Val Lys Glu Ser Leu Ala
            195                 200                 205

Leu Ala Ser Gly Phe Glu Leu Ala Asp Leu Tyr Pro Ser Ser Trp Leu
            210                 215                 220

Leu Asn Leu Leu Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
                245                 250                 255

Lys Ser Gly Glu Phe Gly Gly Glu Asp Ile Val Asp Val Leu Phe Arg
                260                 265                 270

Met Gln Lys Gly Ser Asp Ile Lys Ile Pro Ile Thr Ser Asn Cys Ile
            275                 280                 285

Lys Gly Phe Ile Phe Asp Thr Phe Ser Ala Gly Ala Glu Thr Ser Ser
            290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
                340                 345                 350

Leu Lys Glu Thr Leu Arg Leu His Pro Pro Phe Pro Leu Ile Pro Arg
            355                 360                 365

Gln Ser Arg Glu Glu Cys Glu Val Asn Gly Tyr Thr Ile Pro Ala Lys
            370                 375                 380

Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Glu Val Ser
                405                 410                 415

Arg Asp Phe Met Gly Asn Asp Phe Glu Phe Ile Pro Phe Gly Ala Gly
                420                 425                 430

Arg Arg Ile Cys Pro Gly Leu His Phe Gly Leu Ala Asn Val Glu Ile
            435                 440                 445

Pro Leu Ala Gln Leu Leu Tyr His Phe Asp Trp Lys Leu Pro Gln Gly
            450                 455                 460
```

```
Met Thr Asp Ala Asp Leu Asp Met Thr Glu Thr Pro Gly Leu Ser Gly
465                 470                 475                 480

Pro Lys Lys Lys Asn Val Cys Leu Val Pro Thr Leu Tyr Lys Ser Pro
            485                 490                 495

<210> SEQ ID NO 38
<211> LENGTH: 524
<212> TYPE: PRT
<213> ORGANISM: Catharanthus roseus
<220> FEATURE:
<223> OTHER INFORMATION: CYP72A1 Secologanin synthase
<300> PUBLICATION INFORMATION:
<308> DATABASE ACCESSION NUMBER: Q05047
<309> DATABASE ENTRY DATE: 2012-09-05

<400> SEQUENCE: 38

Met Glu Met Asp Met Asp Thr Ile Arg Lys Ala Ile Ala Ala Thr Ile
1               5                   10                  15

Phe Ala Leu Val Met Ala Trp Ala Trp Arg Val Leu Asp Trp Ala Trp
            20                  25                  30

Phe Thr Pro Lys Arg Ile Glu Lys Arg Leu Arg Gln Gln Gly Phe Arg
        35                  40                  45

Gly Asn Pro Tyr Arg Phe Leu Val Gly Asp Val Lys Glu Ser Gly Lys
50                  55                  60

Met His Gln Glu Ala Leu Ser Lys Pro Met Glu Phe Asn Asn Asp Ile
65                  70                  75                  80

Val Pro Arg Leu Met Pro His Ile Asn His Thr Ile Asn Thr Tyr Gly
                85                  90                  95

Arg Asn Ser Phe Thr Trp Met Gly Arg Ile Pro Arg Ile His Val Met
            100                 105                 110

Glu Pro Glu Leu Ile Lys Glu Val Leu Thr His Ser Ser Lys Tyr Gln
        115                 120                 125

Lys Asn Phe Asp Val His Asn Pro Leu Val Lys Phe Leu Leu Thr Gly
130                 135                 140

Val Gly Ser Phe Glu Gly Ala Lys Trp Ser Lys His Arg Arg Ile Ile
145                 150                 155                 160

Ser Pro Ala Phe Thr Leu Glu Lys Leu Lys Ser Met Leu Pro Ala Phe
                165                 170                 175

Ala Ile Cys Tyr His Asp Met Leu Thr Lys Trp Glu Lys Ile Ala Glu
            180                 185                 190

Lys Gln Gly Ser His Glu Val Asp Ile Phe Pro Thr Phe Asp Val Leu
        195                 200                 205

Thr Ser Asp Val Ile Ser Lys Val Ala Phe Gly Ser Thr Tyr Glu Glu
210                 215                 220

Gly Gly Lys Ile Phe Arg Leu Leu Lys Glu Leu Met Asp Leu Thr Ile
225                 230                 235                 240

Asp Cys Met Arg Asp Val Tyr Ile Pro Gly Trp Ser Tyr Leu Pro Thr
                245                 250                 255

Lys Arg Asn Lys Arg Met Lys Glu Ile Asn Lys Glu Ile Thr Asp Met
            260                 265                 270

Leu Arg Phe Ile Ile Asn Lys Arg Met Lys Ala Leu Lys Ala Gly Glu
        275                 280                 285

Pro Gly Glu Asp Asp Leu Leu Gly Val Leu Leu Glu Ser Asn Ile Gln
290                 295                 300

Glu Ile Gln Lys Gln Gly Asn Lys Lys Asp Gly Gly Met Ser Ile Asn
305                 310                 315                 320
```

```
Asp Val Ile Glu Glu Cys Lys Leu Phe Tyr Phe Ala Gly Gln Glu Thr
                325                 330                 335

Thr Gly Val Leu Leu Thr Trp Thr Thr Ile Leu Leu Ser Lys His Pro
            340                 345                 350

Glu Trp Gln Glu Arg Ala Arg Glu Glu Val Leu Gln Ala Phe Gly Lys
        355                 360                 365

Asn Lys Pro Glu Phe Glu Arg Leu Asn His Leu Lys Tyr Val Ser Met
    370                 375                 380

Ile Leu Tyr Glu Val Leu Arg Leu Tyr Pro Pro Val Ile Asp Leu Thr
385                 390                 395                 400

Lys Ile Val His Lys Asp Thr Lys Leu Gly Ser Tyr Thr Ile Pro Ala
                405                 410                 415

Gly Thr Gln Val Met Leu Pro Thr Val Met Leu His Arg Glu Lys Ser
            420                 425                 430

Ile Trp Gly Glu Asp Ala Met Glu Phe Asn Pro Met Arg Phe Val Asp
        435                 440                 445

Gly Val Ala Asn Ala Thr Lys Asn Asn Val Thr Tyr Leu Pro Phe Ser
    450                 455                 460

Trp Gly Pro Arg Val Cys Leu Gly Gln Asn Phe Ala Leu Leu Gln Ala
465                 470                 475                 480

Lys Leu Gly Leu Ala Met Ile Leu Gln Arg Phe Lys Phe Asp Val Ala
                485                 490                 495

Pro Ser Tyr Val His Ala Pro Phe Thr Ile Leu Thr Val Gln Pro Gln
            500                 505                 510

Phe Gly Ser His Val Ile Tyr Lys Lys Leu Glu Ser
        515                 520

<210> SEQ ID NO 39
<211> LENGTH: 499
<212> TYPE: PRT
<213> ORGANISM: Oryza sativa
<220> FEATURE:
<223> OTHER INFORMATION: CYP76M7 cytochrome P450
<300> PUBLICATION INFORMATION:
<308> DATABASE ACCESSION NUMBER: BAG97435
<309> DATABASE ENTRY DATE: 2008-12-04

<400> SEQUENCE: 39

Met Glu Asn Ser Gln Val Trp Leu Leu Trp Gly Ala Leu Ser Val Ala
 1               5                  10                  15

Val Leu Phe Tyr Leu Ser Thr Leu Arg Arg Arg Tyr Ala Gly Gly Lys
                20                  25                  30

Pro Leu Pro Pro Gly Pro Thr Pro Leu Pro Leu Ile Gly Asn Leu His
            35                  40                  45

Leu Ala Gly Gly Thr Phe His His Lys Leu Arg Asp Leu Ala Arg Val
    50                  55                  60

His Gly Pro Val Met Thr Leu Lys Leu Gly Leu Ala Thr Asn Val Val
65                  70                  75                  80

Ile Ser Ser Arg Glu Ala Ala Ile Glu Ala Tyr Thr Lys Tyr Asp Arg
                85                  90                  95

His Leu Ala Ala Arg Ala Thr Pro Asp Thr Phe Arg Ala Cys Gly Phe
            100                 105                 110

Ala Asp Arg Ser Met Val Phe Ile Pro Ser Ser Asp Pro Gln Trp Lys
        115                 120                 125

Ala Leu Arg Gly Ile Gln Gly Ser His Val Phe Thr Pro Arg Gly Leu
    130                 135                 140
```

Ala Ala Val Arg Pro Ile Arg Glu Arg Lys Val Gly Asp Leu Ile Ala
145                 150                 155                 160

Tyr Leu Arg Ala His Ala Gly Glu Glu Val Leu Leu Gly Gln Ala Met
            165                 170                 175

Tyr Thr Gly Leu Leu Asn Leu Val Ser Phe Ser Tyr Phe Ser Ile Asp
            180                 185                 190

Ile Val Asp Met Gly Ser Gln Met Ala Arg Asp Leu Arg Glu Val Val
            195                 200                 205

Asp Asp Ile Ile Ser Val Val Gly Lys Pro Asn Ile Ser Asp Phe Tyr
210                 215                 220

Pro Phe Leu Arg Pro Leu Asp Leu Gln Gly Leu Arg Arg Trp Thr Thr
225                 230                 235                 240

Lys Arg Phe Asn Arg Val Phe Ser Ile Met Gly Asp Ile Ile Asp Arg
                245                 250                 255

Arg Leu Ala His Ile Arg Asp Gly Lys Pro Arg His Asp Asp Phe Leu
            260                 265                 270

Asp Ser Leu Leu Glu Leu Met Ala Thr Gly Lys Met Glu Arg Val Asn
        275                 280                 285

Val Val Asn Met Leu Phe Glu Ala Phe Val Ala Gly Val Asp Thr Met
290                 295                 300

Ala Leu Thr Leu Glu Trp Val Met Ala Glu Leu Leu His Asn Pro Ala
305                 310                 315                 320

Ile Met Ala Arg Val Arg Ala Glu Leu Ser Asp Val Leu Gly Gly Lys
                325                 330                 335

Glu Ala Val Glu Glu Ala Asp Ala Ala Arg Leu Pro Tyr Leu Gln Ala
            340                 345                 350

Val Leu Lys Glu Ala Met Arg Leu His Pro Val Gly Ala Leu Leu Leu
            355                 360                 365

Pro His Phe Ala Ala Glu Asp Gly Val Glu Ile Gly Gly Tyr Ala Val
    370                 375                 380

Pro Arg Gly Ser Thr Val Leu Phe Asn Ala Trp Ala Ile Met Arg Asp
385                 390                 395                 400

Pro Ala Ala Trp Glu Arg Pro Asp Glu Phe Val Pro Glu Arg Phe Leu
                405                 410                 415

Gly Arg Ser Pro Pro Leu Asp Phe Arg Gly Lys Asp Val Glu Phe Met
                420                 425                 430

Pro Phe Gly Ser Gly Arg Arg Leu Cys Pro Gly Leu Pro Leu Ala Glu
        435                 440                 445

Arg Val Val Pro Phe Ile Leu Ala Ser Met Leu His Thr Phe Glu Trp
    450                 455                 460

Lys Leu Pro Gly Gly Met Thr Ala Glu Asp Val Asp Val Ser Glu Lys
465                 470                 475                 480

Phe Lys Ser Ala Asn Val Leu Ala Val Pro Leu Lys Ala Val Pro Val
                485                 490                 495

Leu Ile Lys

<210> SEQ ID NO 40
<211> LENGTH: 23
<212> TYPE: DNA
<213> ORGANISM: Artificial Sequence
<220> FEATURE:
<223> OTHER INFORMATION: SaCPR1 Forward Primer

<400> SEQUENCE: 40

```
atgagttcga gctcggagct atg                                              23
```

<210> SEQ ID NO 41
<211> LENGTH: 26
<212> TYPE: DNA
<213> ORGANISM: Artificial Sequence
<220> FEATURE:
<223> OTHER INFORMATION: SaCPR1 Reverse Primer

<400> SEQUENCE: 41

```
tcaccacaca tcccgtaaat accttc                                           26
```

<210> SEQ ID NO 42
<211> LENGTH: 705
<212> TYPE: PRT
<213> ORGANISM: Vitis vinifera
<220> FEATURE:
<223> OTHER INFORMATION: Predicted cytochrome P450 reductase-like protein
<300> PUBLICATION INFORMATION:
<308> DATABASE ACCESSION NUMBER: XP_002270732
<309> DATABASE ENTRY DATE: 2011-12-07

<400> SEQUENCE: 42

Met Gln Ser Ser Ser Val Lys Val Ser Pro Phe Asp Leu Met Ser Ala
 1               5                  10                  15

Ile Ile Lys Gly Ser Met Asp Gln Ser Asn Val Ser Ser Glu Ser Gly
            20                  25                  30

Gly Ala Ala Met Val Leu Glu Asn Arg Glu Phe Ile Met Ile Leu
        35                  40                  45

Thr Thr Ser Ile Ala Val Leu Ile Gly Cys Val Val Val Leu Ile Trp
 50                  55                  60

Arg Arg Ser Gly Gln Lys Gln Ser Lys Thr Pro Glu Pro Lys Pro
 65                  70                  75                  80

Leu Ile Val Lys Asp Leu Glu Val Glu Val Asp Asp Gly Lys Gln Lys
                85                  90                  95

Val Thr Ile Phe Phe Gly Thr Gln Thr Gly Thr Ala Glu Gly Phe Ala
            100                 105                 110

Lys Ala Leu Ala Glu Glu Ala Lys Ala Arg Tyr Glu Lys Ala Ile Phe
        115                 120                 125

Lys Val Val Asp Leu Asp Asp Tyr Ala Gly Asp Asp Glu Tyr Glu
    130                 135                 140

Glu Lys Leu Lys Lys Glu Thr Leu Ala Phe Phe Leu Ala Thr Tyr
145                 150                 155                 160

Gly Asp Gly Glu Pro Thr Asp Asn Ala Ala Arg Phe Tyr Lys Trp Phe
                165                 170                 175

Ala Glu Gly Lys Glu Arg Gly Glu Trp Leu Gln Asn Leu Lys Tyr Gly
            180                 185                 190

Val Phe Gly Leu Gly Asn Arg Gln Tyr Glu His Phe Asn Lys Val Ala
        195                 200                 205

Lys Val Val Asp Asp Ile Ile Thr Glu Gln Gly Gly Lys Arg Ile Val
    210                 215                 220

Pro Val Gly Leu Gly Asp Asp Gln Cys Ile Glu Asp Asp Phe Ala
225                 230                 235                 240

Ala Trp Arg Glu Leu Leu Trp Pro Glu Leu Asp Gln Leu Leu Arg Asp
                245                 250                 255

Glu Asp Asp Ala Thr Thr Val Ser Thr Pro Tyr Thr Ala Val Leu
            260                 265                 270

-continued

```
Glu Tyr Arg Val Val Phe His Asp Pro Glu Gly Ala Ser Leu Gln Asp
        275                 280                 285

Lys Ser Trp Gly Ser Ala Asn Gly His Thr Val His Asp Ala Gln His
290                 295                 300

Pro Cys Arg Ala Asn Val Ala Val Arg Lys Glu Leu His Thr Pro Ala
305                 310                 315                 320

Ser Asp Arg Ser Cys Thr His Leu Glu Phe Asp Ile Ser Gly Thr Gly
                325                 330                 335

Leu Thr Tyr Glu Thr Gly Asp His Val Gly Val Tyr Cys Glu Asn Leu
            340                 345                 350

Pro Glu Thr Val Glu Glu Ala Glu Arg Leu Leu Gly Phe Ser Pro Asp
        355                 360                 365

Val Tyr Phe Ser Ile His Thr Glu Arg Glu Asp Gly Thr Pro Leu Ser
    370                 375                 380

Gly Ser Ser Leu Ser Pro Pro Phe Pro Pro Cys Thr Leu Arg Thr Ala
385                 390                 395                 400

Leu Thr Arg Tyr Ala Asp Val Leu Ser Ser Pro Lys Lys Ser Ala Leu
                405                 410                 415

Val Ala Leu Ala Ala His Ala Ser Asp Pro Ser Glu Ala Asp Arg Leu
            420                 425                 430

Lys Tyr Leu Ala Ser Pro Ser Gly Lys Asp Glu Tyr Ala Gln Trp Val
        435                 440                 445

Val Ala Ser Gln Arg Ser Leu Leu Glu Ile Met Ala Glu Phe Pro Ser
    450                 455                 460

Ala Lys Pro Pro Leu Gly Val Phe Phe Ala Ala Val Ala Pro Arg Leu
465                 470                 475                 480

Gln Pro Arg Tyr Tyr Ser Ile Ser Ser Ser Pro Lys Met Val Pro Ser
                485                 490                 495

Arg Ile His Val Thr Cys Ala Leu Val Cys Asp Lys Met Pro Thr Gly
            500                 505                 510

Arg Ile His Lys Gly Ile Cys Ser Thr Trp Met Lys Tyr Ala Val Pro
        515                 520                 525

Leu Glu Glu Ser Gln Asp Cys Ser Trp Ala Pro Ile Phe Val Arg Gln
    530                 535                 540

Ser Asn Phe Lys Leu Pro Ala Asp Thr Ser Val Pro Ile Ile Met Ile
545                 550                 555                 560

Gly Pro Gly Thr Gly Leu Ala Pro Phe Arg Gly Phe Leu Gln Glu Arg
                565                 570                 575

Phe Ala Leu Lys Glu Ala Gly Ala Glu Leu Gly Ser Ser Ile Leu Phe
            580                 585                 590

Phe Gly Cys Arg Asn Arg Lys Met Asp Tyr Ile Tyr Glu Asp Glu Leu
        595                 600                 605

Asn Gly Phe Val Glu Ser Gly Ala Leu Ser Glu Leu Ile Val Ala Phe
    610                 615                 620

Ser Arg Glu Gly Pro Thr Lys Gln Tyr Val Gln His Lys Met Met Glu
625                 630                 635                 640

Lys Ala Ser Asp Ile Trp Asn Val Ile Ser Gln Gly Gly Tyr Ile Tyr
                645                 650                 655

Val Cys Gly Asp Ala Lys Gly Met Ala Arg Asp Val His Arg Thr Leu
            660                 665                 670

His Thr Ile Leu Gln Glu Gln Gly Ser Leu Asp Ser Ser Lys Ala Glu
        675                 680                 685

Ser Met Val Lys Asn Leu Gln Met Thr Gly Arg Tyr Leu Arg Asp Val
```

```
                    690                 695                 700

Trp
705

<210> SEQ ID NO 43
<211> LENGTH: 710
<212> TYPE: PRT
<213> ORGANISM: Gossypium hirsutum
<220> FEATURE:
<223> OTHER INFORMATION: cytochrome P450 reductase
<300> PUBLICATION INFORMATION:
<308> DATABASE ACCESSION NUMBER: ACN54324
<309> DATABASE ENTRY DATE: 2009-12-31

<400> SEQUENCE: 43

Met Asp Ser Ser Ser Ser Ser Ser Gly Pro Ser Pro Leu Asp
 1               5                  10                  15

Leu Met Ser Ala Leu Val Lys Ala Lys Met Asp Pro Ser Asn Ala Ser
                20                  25                  30

Ser Asp Ser Ala Ala Gln Val Thr Thr Val Leu Phe Glu Asn Arg Glu
            35                  40                  45

Phe Val Met Ile Leu Thr Thr Ser Ile Ala Val Leu Ile Gly Cys Val
    50                  55                  60

Val Ile Leu Ile Trp Arg Arg Ser Ala Ser Gln Lys Pro Lys Gln Ile
65                  70                  75                  80

Gln Leu Pro Leu Lys Pro Ser Ile Ile Lys Glu Pro Glu Leu Glu Val
                85                  90                  95

Asp Asp Gly Lys Lys Lys Val Thr Ile Leu Phe Gly Thr Gln Thr Gly
            100                 105                 110

Thr Ala Glu Gly Phe Ala Lys Ala Leu Val Glu Glu Ala Lys Ala Arg
        115                 120                 125

Tyr Glu Lys Ala Thr Phe Asn Ile Val Asp Leu Asp Asp Tyr Ala Ala
130                 135                 140

Asp Asp Glu Glu Tyr Glu Glu Lys Met Lys Lys Asp Asn Leu Ala Phe
145                 150                 155                 160

Phe Phe Leu Ala Thr Tyr Gly Asp Gly Glu Pro Thr Asp Asn Ala Ala
                165                 170                 175

Arg Phe Tyr Lys Trp Phe Thr Glu Gly Lys Glu Arg Gly Glu Trp Leu
            180                 185                 190

Gln Asn Met Lys Tyr Gly Ile Phe Gly Leu Gly Asn Lys Gln Tyr Glu
        195                 200                 205

His Phe Asn Lys Val Ala Lys Val Val Asp Glu Leu Leu Thr Glu Gln
210                 215                 220

Gly Ala Lys Arg Ile Val Pro Leu Gly Leu Gly Asp Asp Gln Cys
225                 230                 235                 240

Ile Glu Asp Asp Phe Thr Ala Trp Arg Glu Leu Val Trp Pro Glu Leu
                245                 250                 255

Asp Gln Leu Leu Arg Asp Glu Asp Ala Thr Val Ser Thr Pro Tyr
            260                 265                 270

Thr Ala Ala Val Leu Glu Tyr Arg Val Val Phe Tyr Asp Pro Ala Asp
        275                 280                 285

Ala Pro Leu Glu Asp Lys Asn Trp Ser Asn Ala Asn Gly His Ala Thr
                295                 300

Tyr Asp Ala Gln His Pro Cys Arg Ser Asn Val Ala Val Arg Lys Glu
305                 310                 315                 320

Leu His Ala Pro Glu Ser Asp Arg Ser Cys Thr His Leu Glu Phe Asp
```

325                 330                 335
Ile Ala Gly Thr Gly Leu Ser Tyr Glu Thr Gly Asp His Val Gly Val
            340                 345                 350
Tyr Cys Glu Asn Leu Asp Glu Val Asp Glu Ala Leu Ser Leu Leu
            355                 360                 365
Gly Leu Ser Pro Asp Thr Tyr Phe Ser Val His Thr Asp Lys Glu Asp
        370                 375                 380
Gly Thr Pro Leu Gly Gly Ser Ser Leu Pro Ser Ser Phe Pro Pro Cys
385                 390                 395                 400
Thr Leu Arg Thr Ala Leu Ala Arg Tyr Ala Asp Leu Leu Ser Ser Pro
                405                 410                 415
Lys Lys Ala Ala Leu Leu Ala Leu Ala Ala His Ala Ser Asp Pro Thr
            420                 425                 430
Glu Ala Asp Arg Leu Arg His Leu Ala Ser Pro Ala Gly Lys Asp Glu
            435                 440                 445
Tyr Ala Gln Trp Ile Val Ala Asn Gln Arg Ser Leu Leu Glu Val Met
        450                 455                 460
Ala Glu Phe Pro Ser Ala Lys Pro Pro Leu Gly Val Phe Phe Ala Ala
465                 470                 475                 480
Val Ala Pro Arg Leu Gln Pro Arg Tyr Tyr Ser Ile Ser Ser Ser Pro
                485                 490                 495
Arg Leu Ala Pro Ser Arg Ile His Val Thr Cys Ala Leu Val Tyr Glu
            500                 505                 510
Lys Thr Pro Thr Gly Arg Ile His Lys Gly Val Cys Ser Thr Trp Met
            515                 520                 525
Lys Asn Ala Val Ser Ser Gly Lys Ser Asp Asp Cys Gly Trp Ala Pro
        530                 535                 540
Ile Phe Val Arg Gln Ser Asn Phe Lys Leu Pro Ser Asp Thr Lys Val
545                 550                 555                 560
Pro Ile Ile Met Ile Gly Pro Gly Thr Gly Leu Ala Pro Phe Arg Gly
                565                 570                 575
Phe Leu Gln Glu Arg Leu Ala Leu Lys Glu Ala Gly Ala Glu Leu Gly
            580                 585                 590
Pro Ser Val Leu Phe Phe Gly Cys Arg Asn Arg Lys Met Asp Phe Ile
            595                 600                 605
Tyr Glu Asp Glu Leu Asn Asn Phe Val Asn Ser Gly Ala Leu Ser Glu
        610                 615                 620
Leu Val Val Ala Phe Ser Arg Glu Gly Pro Thr Lys Glu Tyr Val Gln
625                 630                 635                 640
His Lys Met Met Glu Lys Ala Lys Asp Ile Trp Asp Met Ile Ser Gln
                645                 650                 655
Gly Gly Tyr Leu Tyr Val Cys Gly Asp Ala Lys Gly Met Ala Arg Asp
            660                 665                 670
Val His Arg Ala Leu His Thr Ile Phe Gln Glu Gln Gly Ser Leu Asp
            675                 680                 685
Ser Ser Lys Ala Glu Ser Met Val Lys Asn Leu Gln Met Ser Gly Arg
        690                 695                 700
Tyr Leu Arg Asp Val Trp
705                 710

<210> SEQ ID NO 44
<211> LENGTH: 704
<212> TYPE: PRT
<213> ORGANISM: Artemisia annua

```
<220> FEATURE:
<223> OTHER INFORMATION: cytochrome P450 reductase
<300> PUBLICATION INFORMATION:
<308> DATABASE ACCESSION NUMBER: ABI98819
<309> DATABASE ENTRY DATE: 2009-09-15

<400> SEQUENCE: 44

Met Gln Ser Thr Thr Ser Val Lys Leu Ser Pro Phe Asp Leu Met Thr
 1               5                  10                  15

Ala Leu Leu Asn Gly Lys Val Ser Phe Asp Thr Ser Asn Thr Ser Asp
            20                  25                  30

Thr Asn Ile Pro Leu Ala Val Phe Met Glu Asn Arg Glu Leu Leu Met
        35                  40                  45

Ile Leu Thr Thr Ser Val Ala Val Leu Ile Gly Cys Val Val Val Leu
    50                  55                  60

Val Trp Arg Arg Ser Ser Ala Ala Lys Lys Ala Ala Glu Ser Pro
65                  70                  75                  80

Val Ile Val Val Pro Lys Lys Val Thr Glu Asp Glu Val Asp Asp Gly
                85                  90                  95

Arg Lys Lys Val Thr Val Phe Phe Gly Thr Gln Thr Gly Thr Ala Glu
            100                 105                 110

Gly Phe Ala Lys Ala Leu Val Glu Glu Ala Lys Ala Arg Tyr Glu Lys
        115                 120                 125

Ala Val Phe Lys Val Ile Asp Leu Asp Asp Tyr Ala Ala Glu Asp Asp
    130                 135                 140

Glu Tyr Glu Glu Lys Leu Lys Lys Glu Ser Leu Ala Phe Phe Phe Leu
145                 150                 155                 160

Ala Thr Tyr Gly Asp Gly Glu Pro Thr Asp Asn Ala Ala Arg Phe Tyr
                165                 170                 175

Lys Trp Phe Thr Glu Gly Glu Glu Lys Gly Glu Trp Leu Asp Lys Leu
            180                 185                 190

Gln Tyr Ala Val Phe Gly Leu Gly Asn Arg Gln Tyr Glu His Phe Asn
        195                 200                 205

Lys Ile Ala Lys Val Val Asp Glu Lys Leu Val Glu Gln Gly Ala Lys
    210                 215                 220

Arg Leu Val Pro Val Gly Met Gly Asp Asp Asp Gln Cys Ile Glu Asp
225                 230                 235                 240

Asp Phe Thr Ala Trp Lys Glu Leu Val Trp Pro Glu Leu Asp Gln Leu
                245                 250                 255

Leu Arg Asp Glu Asp Asp Thr Ser Val Ala Thr Pro Tyr Thr Ala Ala
            260                 265                 270

Val Ala Glu Tyr Arg Val Val Phe His Asp Lys Pro Glu Thr Tyr Asp
        275                 280                 285

Gln Asp Gln Leu Thr Asn Gly His Ala Val His Asp Ala Gln His Pro
    290                 295                 300

Cys Arg Ser Asn Val Ala Val Lys Lys Glu Leu His Ser Pro Leu Ser
305                 310                 315                 320

Asp Arg Ser Cys Thr His Leu Glu Phe Asp Ile Ser Asn Thr Gly Leu
                325                 330                 335

Ser Tyr Glu Thr Gly Asp His Val Gly Val Tyr Val Gly Asn Leu Ser
            340                 345                 350

Glu Val Val Asp Glu Ala Glu Lys Leu Ile Gly Leu Pro Pro His Thr
        355                 360                 365

Tyr Phe Ser Val His Ala Asp Asn Glu Asp Gly Thr Pro Leu Gly Gly
    370                 375                 380
```

```
Ala Ser Leu Pro Pro Pro Phe Pro Pro Cys Thr Leu Arg Lys Ala Leu
385                 390                 395                 400

Ala Ser Tyr Ala Asp Val Leu Ser Ser Pro Lys Lys Ser Ala Leu Leu
            405                 410                 415

Ala Leu Ala Ala His Ala Thr Asp Ser Thr Glu Ala Asp Arg Leu Lys
        420                 425                 430

Phe Leu Ala Ser Pro Ala Gly Lys Asp Glu Tyr Ala Gln Trp Ile Val
    435                 440                 445

Ala Ser His Arg Ser Leu Leu Glu Val Met Glu Ala Phe Pro Ser Ala
450                 455                 460

Lys Pro Pro Leu Gly Val Phe Phe Ala Ser Val Ala Pro Arg Leu Gln
465                 470                 475                 480

Pro Arg Tyr Tyr Ser Ile Ser Ser Ser Pro Arg Phe Ala Pro Asn Arg
            485                 490                 495

Ile His Val Thr Cys Ala Leu Val Tyr Glu Gln Thr Pro Ser Gly Arg
        500                 505                 510

Val His Lys Gly Val Cys Ser Thr Trp Met Lys Asn Ala Val Pro Met
    515                 520                 525

Thr Glu Ser Gln Asp Cys Ser Trp Ala Pro Ile Tyr Val Arg Thr Ser
530                 535                 540

Asn Phe Arg Leu Pro Ser Asp Pro Lys Val Pro Val Ile Met Ile Gly
545                 550                 555                 560

Pro Gly Thr Gly Leu Ala Pro Phe Arg Gly Phe Leu Gln Glu Arg Leu
            565                 570                 575

Ala Gln Lys Glu Ala Gly Thr Glu Leu Gly Thr Ala Ile Leu Phe Phe
        580                 585                 590

Gly Cys Arg Asn Arg Lys Val Asp Phe Ile Tyr Glu Asp Glu Leu Asn
    595                 600                 605

Asn Phe Val Glu Thr Gly Ala Leu Ser Glu Leu Val Thr Ala Phe Ser
610                 615                 620

Arg Glu Gly Ala Thr Lys Glu Tyr Val Gln His Lys Met Thr Gln Lys
625                 630                 635                 640

Ala Ser Asp Ile Trp Asn Leu Leu Ser Glu Gly Ala Tyr Leu Tyr Val
            645                 650                 655

Cys Gly Asp Ala Lys Gly Met Ala Lys Asp Val His Arg Thr Leu His
        660                 665                 670

Thr Ile Val Gln Glu Gln Gly Ser Leu Asp Ser Ser Lys Ala Glu Leu
    675                 680                 685

Tyr Val Lys Asn Leu Gln Met Ala Gly Arg Tyr Leu Arg Asp Val Trp
690                 695                 700
```

<210> SEQ ID NO 45
<211> LENGTH: 4008
<212> TYPE: DNA
<213> ORGANISM: Artificial Sequence
<220> FEATURE:
<223> OTHER INFORMATION: pACYC-Duet vector

<400> SEQUENCE: 45

```
ggggaattgt gagcggataa caattcccct gtagaaataa ttttgtttaa ctttaataag     60
gagatatacc atgggcagca gccatcacca tcatcaccac agccaggatc cgaattcgag    120
ctcggcgcgc ctgcaggtcg acaagcttgc ggccgcataa tgcttaagtc gaacagaaag    180
taatcgtatt gtacacggcc gcataatcga aattaatacg actcactata ggggaattgt    240
```

```
gagcggataa caattcccca tcttagtata ttagttaagt ataagaagga gatatacata    300
tggcagatct caattggata tcggccggcc acgcgatcgc tgacgtcggt accctcgagt    360
ctggtaaaga aaccgctgct gcgaaatttg aacgccagca catggactcg tctactagcg    420
cagcttaatt aacctaggct gctgccaccg ctgagcaata actagcataa ccccttgggg    480
cctctaaacg ggtcttgagg ggttttttgc tgaaacctca ggcatttgag aagcacacgg    540
tcacactgct tccggtagtc aataaaccgg taaaccagca atagacataa gcggctattt    600
aacgaccctg ccctgaaccg acgaccgggt cgaatttgct ttcgaatttc tgccattcat    660
ccgcttatta tcacttattc aggcgtagca ccaggcgttt aagggcacca ataactgcct    720 taaaaaatt acgccccgcc ctgccactca tcgcagtact gttgtaattc attaagcatt    780
ctgccgacat ggaagccatc acagacggca tgatgaacct gaatcgccag cggcatcagc    840
accttgtcgc cttgcgtata atatttgccc atagtgaaaa cggggcgaa aagttgtcc    900 atattggcca cgtttaaatc aaaactggtg aaactcaccc agggattggc tgagacgaaa    960
aacatattct caataaaccc tttagggaaa taggccaggt tttcaccgta acacgccaca   1020
tcttgcgaat atatgtgtag aaactgccgg aaatcgtcgt ggtattcact ccagagcgat   1080
gaaaacgttt cagtttgctc atggaaaacg gtgtaacaag ggtgaacact atcccatatc   1140
accagctcac cgtctttcat tgccatacgg aactccggat gagcattcat caggcgggca   1200
agaatgtgaa taaaggccgg ataaaacttg tgcttatttt tctttacggt ctttaaaaag   1260
gccgtaatat ccagctgaac ggtctggtta taggtacatt gagcaactga ctgaaatgcc   1320
tcaaaatgtt ctttacgatg ccattgggat atatcaacgg tggtatatcc agtgatttt   1380 ttctccattt tagcttcctt agctcctgaa aatctcgata actcaaaaaa tacgcccggt   1440
agtgatctta tttcattatg gtgaaagttg gaacctctta cgtgccgatc aacgtctcat   1500
tttcgccaaa agttggccca gggcttcccg gtatcaacag ggacaccagg atttatttat   1560
tctgcgaagt gatcttccgt cacaggtatt tattcggcgc aaagtgcgtc gggtgatgct   1620
gccaacttac tgatttagtg tatgatggtg ttttttgaggt gctccagtgg cttctgtttc   1680
tatcagctgt ccctcctgtt cagctactga cggggtggtg cgtaacggca aaagcaccgc   1740
cggacatcag cgctagcgga gtgtatactg gcttactatg ttggcactga tgagggtgtc   1800
agtgaagtgc ttcatgtggc aggagaaaaa aggctgcacc ggtgcgtcag cagaatatgt   1860
gatacaggat atattccgct tcctcgctca ctgactcgct acgctcggtc gttcgactgc   1920
ggcgagcgga aatggcttac gaacggggcg gagatttcct ggaagatgcc aggaagatac   1980
ttaacaggga agtgagaggg ccgcggcaaa gccgttttc cataggctcc gccccctga   2040 caagcatcac gaaatctgac gctcaaatca gtggtggcga aacccgacag gactataaag   2100
ataccaggcg tttccctgg cggctccctc gtgcgctctc ctgttcctgc ctttcggttt   2160
accggtgtca ttccgctgtt atggccgcgt ttgtctcatt ccacgcctga cactcagttc   2220
cgggtaggca gttcgctcca agctggactg tatgcacgaa ccccccgttc agtccgaccg   2280
ctgcgcctta tccggtaact atcgtcttga gtccaacccg gaaagacatg caaaagcacc   2340
actggcagca gccactggta attgatttag aggagttagt cttgaagtca tgcgccggtt   2400
aaggctaaac tgaaaggaca gtttttggtg actgcgctcc tccaagccag ttacctcggt   2460
tcaaagagtt ggtagctcag agaaccttcg aaaaaccgcc ctgcaaggcg gttttttcgt   2520
tttcagagca agagattacg cgcagaccaa aacgatctca agaagatcat cttattaatc   2580
agataaaata tttctagatt tcagtgcaat ttatctcttc aaatgtagca cctgaagtca   2640
```

```
gccccatacg atataagttg taattctcat gttagtcatg ccccgcgccc accggaagga    2700
gctgactggg ttgaaggctc tcaagggcat cggtcgagat cccggtgcct aatgagtgag    2760
ctaacttaca ttaattgcgt tgcgctcact gcccgctttc cagtcgggaa acctgtcgtg    2820
ccagctgcat taatgaatcg gccaacgcgc ggggagaggc ggtttgcgta ttgggcgcca    2880
gggtggtttt tcttttcacc agtgagacgg gcaacagctg attgcccttc accgcctggc    2940
cctgagagag ttgcagcaag cggtccacgc tggtttgccc cagcaggcga aaatcctgtt    3000
tgatggtggt taacggcggg atataacatg agctgtcttc ggtatcgtcg tatcccacta    3060
ccgagatgtc cgcaccaacg cgcagcccgg actcggtaat ggcgcgcatt gcgcccagcg    3120
ccatctgatc gttggcaacc agcatcgcag tgggaacgat gccctcattc agcatttgca    3180
tggtttgttg aaaaccggac atggcactcc agtcgcctcc ccgttccgct atcggctgaa    3240
tttgattgcg agtgagatat ttatgccagc cagccagacg cagacgcgcc gagacagaac    3300
ttaatgggcc cgctaacagc gcgatttgct ggtgacccaa tgcgaccaga tgctccacgc    3360
ccagtcgcgt accgtcttca tgggagaaaa taatactgtt gatgggtgtc tggtcagaga    3420
catcaagaaa taacgccgga acattagtgc aggcagcttc cacagcaatg gcatcctggt    3480
catccagcgg atagttaatg atcagcccac tgacgcgttg cgcgagaaga ttgtgcaccg    3540
ccgctttaca ggcttcgacg ccgcttcgtt ctaccatcga caccaccacg ctggcaccca    3600
gttgatcggc gcgagattta atcgccgcga caatttgcga cggcgcgtgc agggccagac    3660
tggaggtggc aacgccaatc agcaacgact gtttgcccgc cagttgttgt gccacgcggt    3720
tgggaatgta attcagctcc gccatcgccg cttccacttt ttcccgcgtt ttcgcagaaa    3780
cgtggctggc ctggttcacc acgcgggaaa cggtctgata agagacaccg gcatactctg    3840
cgacatcgta taacgttact ggtttcacat tcaccaccct gaattgactc tcttccgggc    3900
gctatcatgc cataccgcga aaggttttgc gccattcgat ggtgtccggg atctcgacgc    3960
tctcccttat gcgactcctg cattaggaaa ttaatacgac tcactata            4008

<210> SEQ ID NO 46
<211> LENGTH: 712
<212> TYPE: PRT
<213> ORGANISM: Arabidopsis thaliana
<220> FEATURE:
<223> OTHER INFORMATION: NADPH cytochrome P450 reductase

<400> SEQUENCE: 46

Met Ser Ser Ser Ser Ser Ser Thr Ser Met Ile Asp Leu Met Ala
 1               5                  10                  15

Ala Ile Ile Lys Gly Glu Pro Val Ile Val Ser Asp Pro Ala Asn Ala
                20                  25                  30

Ser Ala Tyr Glu Ser Val Ala Ala Glu Leu Ser Ser Met Leu Ile Glu
            35                  40                  45

Asn Arg Gln Phe Ala Met Ile Val Thr Thr Ser Ile Ala Val Leu Ile
        50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
```

```
            115                 120                 125
Ala Arg Tyr Glu Lys Thr Arg Phe Lys Ile Val Asp Leu Asp Asp Tyr
130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
                180                 185                 190

Trp Leu Lys Asn Leu Lys Tyr Gly Val Phe Gly Leu Gly Asn Arg Gln
                195                 200                 205

Tyr Glu His Phe Asn Lys Val Ala Lys Val Val Asp Asp Ile Leu Val
210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Gly Asp Thr Ala Val Ala Thr
                260                 265                 270

Pro Tyr Thr Ala Ala Val Leu Glu Tyr Arg Val Ser Ile His Asp Ser
                275                 280                 285

Glu Asp Ala Lys Phe Asn Asp Ile Thr Leu Ala Asn Gly Asn Gly Tyr
290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Met Lys Leu Gly Asp His Val
                340                 345                 350

Gly Val Leu Cys Asp Asn Leu Ser Glu Thr Val Asp Glu Ala Leu Arg
                355                 360                 365

Leu Leu Asp Met Ser Pro Asp Thr Tyr Phe Ser Leu His Ala Glu Lys
                370                 375                 380

Glu Asp Gly Thr Pro Ile Ser Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
                420                 425                 430

Thr Glu Ala Glu Arg Leu Lys His Leu Ala Ser Pro Ala Gly Lys Asp
                435                 440                 445

Glu Tyr Ser Lys Trp Val Val Glu Ser Gln Arg Ser Leu Leu Glu Val
                450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
                500                 505                 510

Glu Lys Met Pro Thr Gly Arg Ile His Lys Gly Val Cys Ser Thr Trp
                515                 520                 525

Met Lys Asn Ala Val Pro Tyr Glu Lys Ser Glu Lys Leu Phe Leu Gly
530                 535                 540
```

Arg Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
            565                 570                 575

Arg Gly Phe Leu Gln Glu Arg Leu Ala Leu Val Glu Ser Gly Val Glu
        580                 585                 590

Leu Gly Pro Ser Val Leu Phe Phe Gly Cys Arg Asn Arg Arg Met Asp
        595                 600                 605

Phe Ile Tyr Glu Glu Leu Gln Arg Phe Val Glu Ser Gly Ala Leu
610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
            645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
        690                 695                 700

Gly Arg Tyr Leu Arg Asp Val Trp
705                 710

<210> SEQ ID NO 47
<211> LENGTH: 7745
<212> TYPE: DNA
<213> ORGANISM: Artificial Sequence
<220> FEATURE:
<223> OTHER INFORMATION: pESC-LEU vector

<400> SEQUENCE: 47

```
tcgcgcgttt cggtgatgac ggtgaaaacc tctgacacat gcagctcccg gagacggtca      60
cagcttgtct gtaagcggat gccggagcag acaagcccgt cagggcgcgt cagcgggtg      120 ttggcgggtg tcgggctggc ttaactatgc ggcatcaga gcagattgta ctgagagtgc      180
accatatcga ctacgtcgta aggccgtttc tgacagagta aaattcttga gggaactttc      240
accattatgg gaaatgcttc aagaaggtat tgacttaaac tccatcaaat ggtcaggtca      300
ttgagtgttt tttatttgtt gtattttttt tttttagag aaaatcctcc aatatcaaat      360
taggaatcgt agtttcatga ttttctgtta cacctaactt tttgtgtggt gccctcctcc      420
ttgtcaatat taatgttaaa gtgcaattct ttttccttat cacgttgagc cattagtatc      480
aatttgctta cctgtattcc tttactatcc tcctttttct ccttcttgat aaatgtatgt      540
agattgcgta tatagtttcg tctaccctat gaacatattc catttgtaa tttcgtgtcg      600 tttctattat gaatttcatt tataaagttt atgtacaaat atcataaaaa aagagaatct      660
ttttaagcaa ggatttttctt aacttcttcg gcgacagcat caccgacttc ggtggtactg      720
ttggaaccac ctaaatcacc agttctgata cctgcatcca aaccttttt aactgcatct      780 tcaatggcct taccttcttc aggcaagttc aatgacaatt tcaacatcat tgcagcagac      840
aagatagtgg cgatagggtc aaccttattc tttggcaaat ctggagcaga accgtggcat      900
ggttcgtaca aaccaaatgc ggtgttcttg tctggcaaag aggccaagga cgcagatggc      960
aacaaaccca aggaacctgg gataacggag gcttcatcgg agatgatatc accaaacatg      1020
ttgctggtga ttataatacc atttaggtgg gttgggttct taactaggat catggcggca      1080
```

```
gaatcaatca attgatgttg aaccttcaat gtagggaatt cgttcttgat ggtttcctcc   1140
acagtttttc tccataatct tgaagaggcc aaaagattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttctttacgg attttttagta aaccttgttc aggtctaaca   1500
ctaccggtac cccatttagg accacccaca gcacctaaca aaacggcatc agccttcttg   1560
gaggcttcca gcgcctcatc tggaagtgga acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa acgacgatc    1740 ttcttagggg cagacattag aatggtatat ccttgaaata tatatatata tattgctgaa   1800
atgtaaaagg taagaaaagt tagaaagtaa gacgattgct aaccacctat tggaaaaaac   1860
aataggtcct taaataatat tgtcaacttc aagtattgtg atgcaagcat ttagtcatga   1920
acgcttctct attctatatg aaaagccggt tccggcgctc tcacctttcc ttttttctccc  1980 aatttttcag ttgaaaaagg tatatgcgtc aggcgacctc tgaaattaac aaaaaatttc   2040
cagtcatcga atttgattct gtgcgatagc gcccctgtgt gttctcgtta tgttgaggaa   2100
aaaaataatg gttgctaaga gattcgaact cttgcatctt acgatacctg agtattccca   2160
cagttaactg cggtcaagat atttcttgaa tcaggcgcct tagaccgctc ggccaaacaa   2220
ccaattactt gttgagaaat agagtataat tatcctataa atataacgtt tttgaacaca   2280
catgaacaag gaagtacagg acaattgatt ttgaagagaa tgtggatttt gatgtaattg   2340
ttgggattcc atttttaata aggcaataat attaggtatg tagatatact agaagttctc   2400
ctcgaccgtc gatatgcggt gtgaaatacc gcacagatgc gtaaggagaa aataccgcat   2460
caggaaattg taaacgttaa tattttgtta aaattcgcgt taaattttg ttaaatcagc    2520 tcattttta accaataggc cgaaatcggc aaaatccctt ataaatcaaa agaatagacc    2580
gagatagggt tgagtgttgt tccagtttgg aacaagagtc cactattaaa gaacgtggac   2640
tccaacgtca aagggcgaaa aaccgtctat cagggcgatg gcccactacg tgaaccatca   2700
ccctaatcaa gttttttggg gtcgaggtgc cgtaaagcac taaatcggaa ccctaaaggg   2760
agcccccgat ttagagcttg acggggaaag ccggcgaacg tggcgagaaa ggaagggaag   2820
aaagcgaaag gagcgggcgc tagggcgctg gcaagtgtag cggtcacgct gcgcgtaacc   2880
accacacccg ccgcgcttaa tgcgccgcta cagggcgcgt ccattcgcca ttcaggctgc   2940
gcaactgttg ggaagggcga tcggtgcggg cctcttcgct attacgccag ctgaattgga   3000
gcgacctcat gctatacctg agaaagcaac ctgacctaca ggaaagagtt actcaagaat   3060
aagaattttc gttttaaaac ctaagagtca ctttaaaatt tgtatacact tattttttt    3120 ataacttatt taataataaa aatcataaat cataagaaat tcgcttattt agaagtgtca   3180
acaacgtatc taccaacgat ttgacccttt tccatctttt cgtaaatttc tggcaaggta   3240
gacaagccga caaccttgat tggagacttg accaaacctc tggcgaagaa ttgttaatta   3300
agagctcaga tcttatcgtc gtcatccttg taatccatcg atactagtgc ggccgccctt   3360
tagtgagggt tgaattcgaa ttttcaaaaa ttcttacttt ttttttggat ggacgcaaag   3420
```

```
aagtttaata atcatattac atggcattac caccatatac atatccatat acatatccat    3480
atctaatctt acttatatgt tgtggaaatg taaagagccc cattatctta gcctaaaaaa    3540
accttctctt tggaactttc agtaatacgc ttaactgctc attgctatat tgaagtacgg    3600
attagaagcc gccgagcggg tgacagccct ccgaaggaag actctcctcc gtgcgtcctc    3660
gtcttcaccg gtcgcgttcc tgaaacgcag atgtgcctcg cgccgcactg ctccgaacaa    3720
taaagattct acaatactag cttttatggt tatgaagagg aaaaattggc agtaacctgg    3780
ccccacaaac cttcaaatga acgaatcaaa ttaacaacca taggatgata atgcgattag    3840
tttttttagcc ttatttctgg ggtaattaat cagcgaagcg atgattttg atctattaac    3900
agatatataa atgcaaaaac tgcataacca cttttaactaa tactttcaac attttcggtt    3960
tgtattactt cttattcaaa tgtaataaaa gtatcaacaa aaaattgtta atatacctct    4020
atactttaac gtcaaggaga aaaaaccccg gatccgtaat acgactcact atagggcccg    4080
ggcgtcgaca tggaacagaa gttgatttcc gaagaagacc tcgagtaagc ttggtaccgc    4140
ggctagctaa gatccgctct aaccgaaaag gaaggagtta gacaacctga agtctaggtc    4200
cctatttatt tttttatagt tatgttagta ttaagaacgt tatttatatt tcaaattttt    4260
cttttttttc tgtacagacg cgtgtacgca tgtaacatta tactgaaaac cttgcttgag    4320
aaggttttgg gacgctcgaa gatccagctg cattaatgaa tcggccaacg cgcggggaga    4380
ggcggtttgc gtattgggcg ctcttccgct tcctcgctca ctgactcgct gcgctcggtc    4440
gttcggctgc ggcgagcggt atcagctcac tcaaaggcgg taatacggtt atccacagaa    4500
tcagggggata acgcaggaaa gaacatgtga gcaaaaggcc agcaaaaggc caggaaccgt    4560
aaaaaggccg cgttgctggc gttttttccat aggctccgcc cccctgacga gcatcacaaa    4620
aatcgacgct caagtcagag gtggcgaaac ccgacaggac tataaagata ccaggcgttt    4680
ccccctggaa gctccctcgt gcgctctcct gttccgaccc tgccgcttac cggatacctg    4740
tccgcctttc tcccttcggg aagcgtggcg ctttctcata gctcacgctg taggtatctc    4800
agttcggtgt aggtcgttcg ctccaagctg ggctgtgtgc acgaaccccc cgttcagccc    4860
gaccgctgcg ccttatccgg taactatcgt cttgagtcca acccggtaag acacgactta    4920
tcgccactgg cagcagccac tggtaacagg attagcagag cgaggtatgt aggcggtgct    4980
acagagttct tgaagtggtg gcctaactac ggctacacta aaggacagt atttggtatc    5040
tgcgctctgc tgaagccagt taccttcgga aaaagagttg gtagctcttg atccggcaaa    5100
caaaccaccg ctggtagcgg tggttttttt gtttgcaagc agcagattac gcgcagaaaa    5160
aaaggatctc aagaagatcc tttgatcttt tctacggggt ctgacgctca gtggaacgaa    5220
aactcacgtt aagggatttt ggtcatgaga ttatcaaaaa ggatcttcac ctagatcctt    5280
ttaaattaaa aatgaagttt taaatcaatc taaagtatat atgagtaaac ttggtctgac    5340
agttaccaat gcttaatcag tgaggcacct atctcagcga tctgtctatt tcgttcatcc    5400
atagttgcct gactccccgt cgtgtagata actacgatac gggagggctt accatctggc    5460
cccagtgctg caatgatacc gcgagaccca cgctcaccgg ctccagattt atcagcaata    5520
aaccagccag ccggaagggc cgagcgcaga agtggtcctg caactttatc cgcctccatc    5580
cagtctatta attgttgccg ggaagctaga gtaagtagtt cgccagttaa tagtttgcgc    5640
aacgttgttg ccattgctac aggcatcgtg gtgtcacgct cgtcgtttgg tatggcttca    5700
ttcagctccg gttcccaacg atcaaggcga gttacatgat ccccccatgtt gtgcaaaaaa    5760
gcggttagct ccttcggtcc tccgatcgtt gtcagaagta agttggccgc agtgttatca    5820
```

```
ctcatggtta tggcagcact gcataattct cttactgtca tgccatccgt aagatgcttt    5880
tctgtgactg gtgagtactc aaccaagtca ttctgagaat agtgtatgcg gcgaccgagt    5940
tgctcttgcc cggcgtcaat acgggataat accgcgccac atagcagaac tttaaaagtg    6000
ctcatcattg gaaaacgttc ttcggggcga aaactctcaa ggatcttacc gctgttgaga    6060
tccagttcga tgtaacccac tcgtgcaccc aactgatctt cagcatcttt actttcacc    6120 agcgtttctg ggtgagcaaa aacaggaagg caaaatgccg caaaaaaggg aataagggcg    6180
acacggaaat gttgaatact catactcttc cttttcaat attattgaag catttatcag     6240
ggttattgtc tcatgagcgg atacatattt gaatgtattt agaaaaataa acaaataggg    6300
gttccgcgca catttccccg aaaagtgcca cctgaacgaa gcatctgtgc ttcattttgt    6360
agaacaaaaa tgcaacgcga gagcgctaat ttttcaaaca aagaatctga gctgcatttt    6420
tacagaacag aaatgcaacg cgaaagcgct attttaccaa cgaagaatct gtgcttcatt    6480
tttgtaaaac aaaaatgcaa cgcgagagcg ctaattttc aaacaaagaa tctgagctgc     6540 attttacag aacagaaatg caacgcgaga gcgctatttt accaacaaag aatctatact    6600
tcttttttgt tctacaaaaa tgcatcccga gagcgctatt tttctaacaa agcatcttag    6660 attactttt ttctccttg tgcgctctat aatgcagtct cttgataact ttttgcactg      6720
taggtccgtt aaggttagaa gaaggctact ttggtgtcta ttttctcttc cataaaaaaa    6780
gcctgactcc acttcccgcg tttactgatt actagcgaag ctgcgggtgc attttttcaa    6840
gataaaggca tccccgatta tattctatac cgatgtggat tgcgcatact tgtgaacag     6900 aaagtgatag cgttgatgat tcttcattgg tcagaaaatt atgaacggtt tcttctattt    6960
tgtctctata tactacgtat aggaaatgtt tacattttcg tattgttttc gattcactct    7020
atgaatagtt cttactacaa ttttttgtc taaagagtaa tactagagat aaacataaaa    7080
aatgtagagg tcgagtttag atgcaagttc aaggagcgaa aggtggatgg gtaggttata    7140
tagggatata gcacagagat atatagcaaa gagatacttt tgagcaatgt tgtgtggaagc    7200 ggtattcgca atattttagt agctcgttac agtccggtgc gttttgtt ttttgaaagt       7260 gcgtcttcag agcgcttttg gttttcaaaa gcgctctgaa gttcctatac tttctagaga    7320
ataggaactt cggaatagga acttcaaagc gtttccgaaa acgagcgctt ccgaaaatgc    7380
aacgcgagct gcgcacatac agctcactgt tcacgtcgca cctatatctg cgtgttgcct    7440
gtatatatat atacatgaga agaacggcat agtgcgtgtt tatgcttaaa tgcgtactta    7500
tatgcgtcta tttatgtagg atgaaaggta gtctagtacc tcctgtgata ttatcccatt    7560
ccatgcgggg tatcgtatgc ttccttcagc actaccctt agctgttcta tatgctgcca    7620
ctcctcaatt ggattagtct catccttcaa tgctatcatt tcctttgata ttggatcata    7680
ctaagaaacc attattatca tgacattaac ctataaaaat aggcgtatca cgaggccctt    7740
tcgtc                                                                 7745
```

<210> SEQ ID NO 48

<400> SEQUENCE: 48

000

<210> SEQ ID NO 49
<211> LENGTH: 6705
<212> TYPE: DNA
<213> ORGANISM: Artificial Sequence
<220> FEATURE:
<223> OTHER INFORMATION: pESC-HIS vector

<400> SEQUENCE: 49

```
tcgcgcgttt cggtgatgac ggtgaaaacc tctgacacat gcagctcccg gagacggtca      60
cagcttgtct gtaagcggat gccgggagca gacaagcccg tcagggcgcg tcagcggdtg     120
ttggcgggtg tcgggctgg  cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tcttttttcta    300
ttactcttgg cctcctctag tacactctat atttttttat gcctcggtaa tgattttcat     360
ttttttttt  ccctagcgg  atgactcttt tttttctta  gcgattggca ttatcacata     420
atgaattata cattatataa agtaatgtga tttcttcgaa gaatatacta aaaaatgagc     480
aggcaagata acgaaggca  aagatgacag agcagaaagc cctagtaaag cgtattacaa     540
atgaaaccaa gattcagatt gcgatctctt taaagggtgg tcccctagcg atagagcact     600
cgatcttccc agaaaaagag gcagaagcag tagcagaaca ggccacacaa tcgcaagtga     660
ttaacgtcca cacaggtata gggtttctgg accatatgat acatgctctg gccaagcatt     720
ccggctggtc gctaatcgtt gagtgcattg gtgacttaca catagacgac catcacacca     780
ctgaagactg cgggattgct ctcggtcaag cttttaaaga ggccctaggg gccgtgcgtg     840
gagtaaaaag gtttggatca ggatttgcgc ctttggatga ggcactttcc agagcggtgg     900
tagatctttc gaacaggccg tacgcagttg tcgaacttgg tttgcaaagg agaaagtag     960
gagatctctc ttgcgagatg atcccgcatt ttcttgaaag ctttgcagag gctagcagaa    1020
ttaccctcca cgttgattgt ctgcgaggca agaatgatca tcaccgtagt gagagtgcgt    1080
tcaaggctct tgcggttgcc ataagagaag ccacctcgcc caatggtacc aacgatgttc    1140
cctccaccaa aggtgttctt atgtagtgac accgattatt taaagctgca gcatacgata    1200
tatatacatg tgtatatatg tatacctatg aatgtcagta agtatgtata cgaacagtat    1260
gatactgaag atgacaaggt aatgcatcat tctatacgtg tcattctgaa cgaggcgcgc    1320
tttccttttt tcttttttgct ttttcttttt ttttctcttg aactcgacgg atctatgcgg    1380
tgtgaaatac cgcacagatg cgtaaggaga aataccgcca tcaggaaatt gtaaacgtta    1440
atattttgtt aaaattcgcg ttaaattttt gttaaatcag ctcatttttt aaccaatagg    1500
ccgaaatcgg caaaatccct tataaatcaa agaatagac  cgagataggg ttgagtgttg    1560
ttccagtttg gaacaagagt ccactattaa agaacgtgga ctccaacgtc aaagggcgaa    1620
aaaccgtcta tcagggcgat ggcccactac gtgaaccatc accctaatca gttttttgg    1680
ggtcgaggtg ccgtaaagca ctaaatcgga accctaaagg agcccccga  tttagagctt    1740
gacggggaaa gccggcgaac gtggcgagaa aggaagggaa gaaagcgaaa ggagcgggcg    1800
ctagggcgct ggcaagtgta gcggtcacgc tgcgcgtaac caccacccc  gccgcgctta    1860
atgcgccgct acagggcgcg tccattcgcc attcaggctg cgcaactgtt gggaagggcg    1920
atcggtgcgg gcctcttcgc tattacgcca gctgaattgg agcgacctca tgctataccT    1980
gagaaagcaa cctgacctac aggaaagagt tactcaagaa taagaattt  cgttttaaaa    2040
cctaagagtc actttaaaat ttgtatacac ttattttttt tataacttat ttaataataa    2100
aaatcataaa tcataagaaa ttcgcttatt tagaagtgtc aacaacgtat ctaccaacga    2160
tttgacccctt ttccatcttt tcgtaaattt ctggcaaggt agacaagccg acaaccttga    2220
```

```
ttggagactt gaccaaacct ctggcgaaga attgttaatt aagagctcag atcttatcgt    2280
cgtcatcctt gtaatccatc gatactagtg cggccgccct ttagtgaggg ttgaattcga    2340
attttcaaaa attcttactt ttttttttgga tggacgcaaa gaagtttaat aatcatatta    2400
catggcatta ccaccatata catatccata tacatatcca tatctaatct tacttatatg    2460
ttgtggaaat gtaaagagcc ccattatctt agcctaaaaa aaccttctct ttggaacttt    2520
cagtaatacg cttaactgct cattgctata ttgaagtacg gattagaagc cgccgagcgg    2580
gtgacagccc tccgaaggaa gactctcctc cgtgcgtcct cgtcttcacc ggtcgcgttc    2640
ctgaaacgca gatgtgcctc gcgccgcact gctccgaaca ataaagattc tacaatacta    2700
gcttttatgg ttatgaagag gaaaaattgg cagtaacctg gccccacaaa ccttcaaatg    2760
aacgaatcaa attaacaacc ataggatgat aatgcgatta gttttttagc cttatttctg    2820
gggtaattaa tcagcgaagc gatgattttt gatctattaa cagatatata aatgcaaaaa    2880
ctgcataacc actttaacta atactttcaa cattttcggt ttgtattact tcttattcaa    2940
atgtaataaa agtatcaaca aaaaattgtt aatatacctc tatactttaa cgtcaaggag    3000
aaaaaacccc ggatccgtaa tacgactcac tatagggccc gggcgtcgac atggaacaga    3060
agttgatttc cgaagaagac ctcgagtaag cttggtaccg cggctagcta agatccgctc    3120
taaccgaaaa ggaaggagtt agacaacctg aagtctaggt ccctatttat tttttttatag    3180 ttatgttagt attaagaacg ttatttatat ttcaaatttt tctttttttt ctgtacagac    3240
gcgtgtacgc atgtaacatt atactgaaaa ccttgcttga aaggttttg ggacgctcga    3300 agatccagct gcattaatga atcggccaac gcgcggggag aggcggtttg cgtattgggc    3360
gctcttccgc ttcctcgctc actgactcgc tgcgctcggt cgttcggctg cggcgagcgg    3420
tatcagctca ctcaaaggcg gtaatacggt tatccacaga atcaggggat aacgcaggaa    3480
agaacatgtg agcaaaaggc cagcaaaagg ccaggaaccg taaaaaggcc gcgttgctgg    3540
cgttttccca taggctccgc cccctgacg agcatcacaa aaatcgacgc tcaagtcaga    3600
ggtggcgaaa cccgacagga ctataaagat accaggcgtt tcccctgga agctccctcg    3660 tgcgctctcc tgttccgacc ctgccgctta ccggatacct gtccgccttt ctcccttcgg    3720
gaagcgtggc gctttctcat agctcacgct gtaggtatct cagttcggtg taggtcgttc    3780
gctccaagct gggctgtgtg cacgaacccc ccgttcagcc cgaccgctgc gccttatccg    3840
gtaactatcg tcttgagtcc aacccggtaa gacacgactt atcgccactg gcagcagcca    3900
ctggtaacag gattagcaga gcgaggtatg taggcggtgc tacagagttc ttgaagtggt    3960
ggcctaacta cggctacact agaaggacag tatttggtat ctgcgctctg ctgaagccag    4020
ttaccttcgg aaaaagagtt ggtagctctt gatccggcaa acaaaccacc gctggtagcg    4080
gtggtttttt tgtttgcaag cagcagatta cgcgcagaaa aaaggatctc aagaagatc    4140 ctttgatctt ttctacgggg tctgacgctc agtggaacga aaactcacgt taagggattt    4200
tggtcatgag attatcaaaa aggatcttca cctagatcct ttaaattaa aaatgaagtt    4260 ttaaatcaat ctaaagtata tatgagtaaa cttggtctga cagttaccaa tgcttaatca    4320
gtgaggcacc tatctcagcg atctgtctat ttcgttcatc catagttgcc tgactccccg    4380
tcgtgtagat aactacgata cgggagggct taccatctgg ccccagtgct gcaatgatac    4440
cgcgagaccc acgctcaccg gctccagatt tatcagcaat aaaccagcca gccgaaggg    4500 ccgagcgcag aagtggtcct gcaactttat ccgcctccat ccagtctatt aattgttgcc    4560
gggaagctag agtaagtagt tcgccagtta atagtttgcg caacgttgtt gccattgcta    4620
```

```
caggcatcgt ggtgtcacgc tcgtcgtttg gtatggcttc attcagctcc ggttcccaac    4680
gatcaaggcg agttacatga tcccccatgt tgtgcaaaaa agcggttagc tccttcggtc    4740
ctccgatcgt tgtcagaagt aagttggccg cagtgttatc actcatggtt atggcagcac    4800
tgcataattc tcttactgtc atgccatccg taagatgctt ttctgtgact ggtgagtact    4860
caaccaagtc attctgagaa tagtgtatgc ggcgaccgag ttgctcttgc ccggcgtcaa    4920
tacgggataa taccgcgcca catagcagaa ctttaaaagt gctcatcatt ggaaaacgtt    4980
cttcggggcg aaaactctca aggatcttac cgctgttgag atccagttcg atgtaaccca    5040
ctcgtgcacc caactgatct tcagcatctt ttactttcac cagcgtttct gggtgagcaa    5100
aaacaggaag gcaaaatgcc gcaaaaaagg gaataagggc gacacggaaa tgttgaatac    5160
tcatactctt cctttttcaa tattattgaa gcatttatca gggttattgt ctcatgagcg    5220
gatacatatt tgaatgtatt tagaaaaata acaaatagg ggttccgcgc acatttcccc     5280
gaaaagtgcc acctgaacga agcatctgtg cttcattttg tagaacaaaa atgcaacgcg    5340
agagcgctaa ttttcaaac aaagaatctg agctgcattt ttacagaaca gaaatgcaac     5400
gcgaaagcgc tattttacca cgaagaatc tgtgcttcat ttttgtaaaa caaaatgca     5460
acgcgagagc gctaattttt caaacaaaga atctgagctg cattttttaca gaacagaaat    5520
gcaacgcgag agcgctattt taccaacaaa gaatctatac ttctttttttg ttctacaaaa    5580
atgcatcccg agagcgctat ttttctaaca aagcatctta gattactttt tttctccttt    5640
gtgcgctcta taatgcagtc tcttgataac tttttgcact gtaggtccgt taaggttaga    5700
agaaggctac tttggtgtct atttttctctt ccataaaaaa agcctgactc cacttcccgc    5760
gtttactgat tactagcgaa gctgcgggtg cattttttca agataaaggc atccccgatt    5820
atattctata ccgatgtgga ttgcgcatac tttgtgaaca gaaagtgata gcgttgatga    5880
ttcttcattg gtcagaaaat tatgaacggt tccttctatt ttgtctctat atactacgta    5940
taggaaatgt ttacattttc gtattgtttt cgattcactc tatgaatagt tcttactaca    6000
attttttgt ctaaagagta atactagaga taaacataaa aaatgtagag gtcgagttta     6060
gatgcaagtt caaggagcga aaggtggatg ggtaggttat atagggatat agcacagaga    6120
tatatagcaa agagatactt ttgagcaatg tttgtggaag cggtattcgc aatattttag    6180
tagctcgtta cagtccggtg cgttttggt ttttgaaag tgcgtcttca gagcgctttt      6240
ggttttcaaa agcgctctga agttcctata ctttctagag aataggaact tcggaatagg    6300
aacttcaaag cgtttccgaa aacgagcgct tccgaaaatg caacgcgagc tgcgcacata    6360
cagctcactg ttcacgtcgc acctatatct gcgtgttgcc tgtatatata tatacatgag    6420
aagaacggca tagtgcgtgt ttatgcttaa atgcgtactt atatgcgtct atttatgtag    6480
gatgaaaggt agtctagtac ctcctgtgat attatcccat tccatgcggg gtatcgtatg    6540
cttccttcag cactaccctt tagctgttct atatgctgcc actcctcaat tggattagtc    6600
tcatccttca atgctatcat ttcctttgat attggatcat ctaagaaacc attattatca    6660
tgacattaac ctataaaaat aggcgtatca cgaggcccctt tcgtc                   6705
```

<210> SEQ ID NO 50
<211> LENGTH: 509
<212> TYPE: PRT
<213> ORGANISM: Santalum album
<220> FEATURE:
<223> OTHER INFORMATION: CYP76 ORF

<400> SEQUENCE: 50

```
Met Asp Phe Leu Ser Phe Ile Leu Phe Val Leu Phe Ala Trp Ala Leu
 1               5                  10                  15
Val Arg Ala Leu Pro Thr Leu Ser Arg Gly Ser Lys Ala Ala Gly Gly
            20                  25                  30
Arg Leu Pro Pro Gly Pro Val Pro Leu Pro Val Val Gly Asn Leu Leu
        35                  40                  45
Lys Leu Gly Ser Lys Pro His Lys Ser Leu Ala Glu Leu Ala Lys Ser
 50                  55                  60
Tyr Gly Pro Ile Met Cys Leu Lys Leu Gly His Ile Ile Thr Ile Val
 65                  70                  75                  80
Ile Ser Thr Pro Thr Val Ala Lys Glu Val Leu Gln Lys Gln Asp Val
                85                  90                  95
Ala Phe Cys Asn Arg Thr Ile Pro Asp Ala Val Arg Ala His Arg His
            100                 105                 110
Asp Leu His Ser Met Val Trp Leu Pro Val Ser Thr Arg Trp Arg Thr
        115                 120                 125
Leu Arg Lys Ile Ser Asn Ser His Ile Phe Ser Ser Gln Arg Leu Asp
130                 135                 140
Glu Asn His His Leu Arg Arg Lys Leu Asp Glu Leu Leu Ala Arg
145                 150                 155                 160
Val Ala Glu Ser Ser Leu Val Gly Ala Val Asp Ile Gly Ala Val
                165                 170                 175
Ala Phe Leu Thr Ser Leu Asn Leu Leu Ser Asn Thr Val Phe Ser Lys
            180                 185                 190
Asp Leu Val Glu Pro Gly Leu Gly Ala Val Gln Glu Met Glu Glu Val
        195                 200                 205
Val Trp Gly Ile Thr Glu Glu Ala Gly Arg Pro Asn Leu Val Asp Tyr
210                 215                 220
Phe Pro Val Leu Arg Arg Leu Asp Pro Gln Arg Thr Arg Arg Arg Met
225                 230                 235                 240
Met Gly Tyr Phe Gly Lys Met Phe Glu Val Phe Gly Asp Ile Ile Asp
                245                 250                 255
Glu Arg Leu Glu Trp Arg Lys Gln Gln Ser Asp Gly Asp Ser Pro Ala
            260                 265                 270
Ala Thr Thr Asn Asp Val Leu Asp Val Leu Leu Asn Ile Ile Glu Asp
        275                 280                 285
Ala Glu Ile Glu Glu Lys Pro Asn Arg Thr Asp Val Glu His Leu Ile
290                 295                 300
Leu Asp Leu Phe Val Ala Gly Ser Asp Thr Thr Ser Ser Thr Val Glu
305                 310                 315                 320
Trp Ala Met Thr Glu Leu Leu Arg Lys Pro Glu Thr Leu Glu Arg Ala
                325                 330                 335
Arg Ser Glu Leu His Glu Thr Ile Gly Pro Lys Asn Leu Val Gln Glu
            340                 345                 350
Ala Asp Leu Pro Arg Leu Pro Tyr Leu Gln Ala Val Val Lys Glu Thr
        355                 360                 365
Phe Arg Leu His Pro Pro Val Pro Leu Leu Pro Arg Thr Ala Glu
370                 375                 380
Lys Asp Ala Glu Leu Cys Gly Phe Thr Val Pro Ala Gly Ala Gln Ile
385                 390                 395                 400
Met Val Asn Ala Trp Ala Ile Gly Arg Asp Pro Gly Thr Trp Glu Asp
                405                 410                 415
```

```
Pro Glu Ser Phe Leu Pro Glu Arg Phe Leu Gly Ser Asp Val Asp Val
            420                 425                 430

Lys Gly Arg Ser Phe Glu Leu Ile Pro Phe Gly Gly Arg Arg Ile
        435                 440                 445

Cys Pro Gly Leu Pro Leu Ala Ile Arg Met Val His Leu Met Leu Gly
    450                 455                 460

Ser Leu Ile His Gly Phe Arg Trp Lys Val Phe Asp Asp Gly Met Gly
465                 470                 475                 480

Ser Pro Glu Thr Ala Met Asp Met Asp Glu Lys Phe Gly Ile Thr Leu
                485                 490                 495

Gln Lys Ala Lys Ser Leu Cys Ala Val Pro Ile Arg Gly
            500                 505

<210> SEQ ID NO 51
<211> LENGTH: 5368
<212> TYPE: DNA
<213> ORGANISM: Artificial Sequence
<220> FEATURE:
<223> OTHER INFORMATION: pET28(+) vector

<400> SEQUENCE: 51
```

| | | | | | |
|---|---|---|---|---|---|
| atccggatat | agttcctcct | ttcagcaaaa | aacccctcaa | gacccgttta | gaggccccaa | 60 |
| ggggttatgc | tagttattgc | tcagcggtgg | cagcagccaa | ctcagcttcc | tttcgggctt | 120 |
| tgttagcagc | cggatctcag | tggtggtggt | ggtggtgctc | gagtgcggcc | gcaagcttgt | 180 |
| cgacggagct | cgaattcgga | tcccgaccca | tttgctgtcc | accagtcatg | ctagccatat | 240 |
| ggctgccgcg | cggcaccagg | ccgctgctgt | gatgatgatg | atgatggctg | ctgcccatgg | 300 |
| tatatctcct | tcttaaagtt | aaacaaaatt | atttctagag | gggaattgtt | atccgctcac | 360 |
| aattccccta | tagtgagtcg | tattaatttc | gcgggatcga | gatctcgatc | ctctacgccg | 420 |
| gacgcatcgt | ggccggcatc | accgcgcca | caggtgcggt | tgctggcgcc | tatatcgccg | 480 |
| acatcaccga | tggggaagat | cgggctcgcc | acttcgggct | catgagcgct | tgtttcggcg | 540 |
| tgggtatggt | ggcaggcccc | gtggccgggg | gactgttggg | cgccatctcc | ttgcatgcac | 600 |
| cattccttgc | ggcggcggtg | ctcaacggcc | tcaacctact | actgggctgc | ttcctaatgc | 660 |
| aggagtcgca | taagggagag | cgtcgagatc | ccggacacca | tcgaatggcg | caaaaccttt | 720 |
| cgcggtatgg | catgatagcg | cccggaagag | agtcaattca | gggtggtgaa | tgtgaaacca | 780 |
| gtaacgttat | acgatgtcgc | agagtatgcc | ggtgtctctt | atcagaccgt | ttcccgcgtg | 840 |
| gtgaaccagg | ccagccacgt | ttctgcgaaa | acgcgggaaa | aagtggaagc | ggcgatggcg | 900 |
| gagctgaatt | acattcccaa | ccgcgtggca | caacaactgg | cgggcaaaca | gtcgttgctg | 960 |
| attggcgttg | ccacctccag | tctggccctg | cacgcgccgt | cgcaaattgt | cgcggcgatt | 1020 |
| aaatctcgcg | ccgatcaact | gggtgccagc | gtggtggtgt | cgatggtaga | acgaagcggc | 1080 |
| gtcgaagcct | gtaaagcggc | ggtgcacaat | cttctcgcgc | aacgcgtcag | tgggctgatc | 1140 |
| attaactatc | cgctggatga | ccaggatgcc | attgctgtgg | aagctgcctg | cactaatgtt | 1200 |
| ccggcgttat | ttcttgatgt | ctctgaccag | acacccatca | acagtattat | tttctcccat | 1260 |
| gaagacggta | cgcgactggg | cgtggagcat | ctggtcgcat | tgggtcacca | gcaaatcgcg | 1320 |
| ctgttagcgg | cccattaag | ttctgtctcg | gcgcgtctgc | gtctggctgg | ctggcataaa | 1380 |
| tatctcactc | gcaatcaaat | tcagccgata | gcggaacggg | aaggcgactg | gagtgccatg | 1440 |
| tccggttttc | aacaaaccat | gcaaatgctg | aatgagggca | tcgttcccac | tgcgatgctg | 1500 |

```
gttgccaacg atcagatggc gctgggcgca atgcgcgcca ttaccgagtc cgggctgcgc   1560
gttggtgcgg atatctcggt agtgggatac gacgataccg aagacagctc atgttatatc   1620
ccgccgttaa ccaccatcaa acaggatttt cgcctgctgg ggcaaaccag cgtggaccgc   1680
ttgctgcaac tctctcaggg ccaggcggtg aagggcaatc agctgttgcc cgtctcactg   1740
gtgaaaagaa aaaccaccct ggcgcccaat acgcaaaccg cctctccccg cgcgttggcc   1800
gattcattaa tgcagctggc acgacaggtt tcccgactgg aaagcgggca gtgagcgcaa   1860
cgcaattaat gtaagttagc tcactcatta ggcaccggga tctcgaccga tgcccttgag   1920
agccttcaac ccagtcagct ccttccggtg ggcgcggggc atgactatcg tcgccgcact   1980
tatgactgtc ttctttatca tgcaactcgt aggacaggtg ccggcagcgc tctgggtcat   2040
tttcggcgag gaccgctttc gctggagcgc gacgatgatc ggcctgtcgc ttgcggtatt   2100
cggaatcttg cacgccctcg ctcaagcctt cgtcactggt cccgccacca aacgtttcgg   2160
cgagaagcag gccattatcg ccggcatggc ggccccacgg gtgcgcatga tcgtgctcct   2220
gtcgttgagg acccggctag gctggcgggg ttgccttact ggttagcaga atgaatcacc   2280
gatacgcgag cgaacgtgaa gcgactgctg ctgcaaaacg tctgcgacct gagcaacaac   2340
atgaatggtc ttcggtttcc gtgtttcgta aagtctggaa acgcggaagt cagcgccctg   2400
caccattatg ttccggatct gcatcgcagg atgctgctgg ctaccctgtg aacacctac    2460 atctgtatta cgaagcgct ggcattgacc ctgagtgatt tttctctggt cccgccgcat    2520
ccataccgcc agttgtttac cctcacaacg ttccagtaac cgggcatgtt catcatcagt   2580
aacccgtatc gtgagcatcc tctctcgttt catcggtatc attaccccca tgaacagaaa   2640 tccccccttac acggaggcat cagtgaccaa acaggaaaaa accgccctta acatggcccg   2700
ctttatcaga agccagacat taacgcttct ggagaaactc aacgagctgg acgcggatga   2760
acaggcagac atctgtgaat cgcttcacga ccacgctgat gagctttacc gcagctgcct   2820
cgcgcgtttc ggtgatgacg gtgaaaacct ctgacacatg cagctcccgg agacggtcac   2880
agcttgtctg taagcggatg ccgggagcag acaagcccgt cagggcgcgt cagcgggtgt   2940
tggcgggtgt cggggcgcag ccatgaccca gtcacgtagc gatagcggag tgtatactgg   3000
cttaactatg cggcatcaga gcagattgta ctgagagtgc accatatatg cggtgtgaaa   3060
taccgcacag atgcgtaagg agaaaatacc gcatcaggcg ctcttccgct tcctcgctca   3120
ctgactcgct gcgctcggtc gttcggctgc ggcgagcggt atcagctcac tcaaaggcgg   3180
taatacggtt atccacagaa tcaggggata acgcaggaaa gaacatgtga gcaaaaggcc   3240
agcaaaaggc caggaaccgt aaaaaggccg cgttgctggc gtttttccat aggctccgcc   3300
cccctgacga gcatcacaaa aatcgacgct caagtcagag gtggcgaaac ccgacaggac   3360
tataaagata ccaggcgttt ccccctggaa gctccctcgt gcgctctcct gttccgaccc   3420
tgccgcttac cggatacctg tccgcctttc tcccttcggg aagcgtggcg ctttctcata   3480
gctcacgctg taggtatctc agttcggtgt aggtcgttcg ctccaagctg ggctgtgtgc   3540
acgaaccccc cgttcagccc gaccgctgcg ccttatccgg taactatcgt cttgagtcca   3600
acccggtaag acacgactta tcgccactgg cagcagccac tggtaacagg attagcagag   3660
cgaggtatgt aggcggtgct acagagttct tgaagtggtg gcctaactac ggctacacta   3720
gaaggacagt atttggtatc tgcgctctgc tgaagccagt taccttcgga aaaagagttg   3780
gtagctcttg atccggcaaa caaaccaccg ctggtagcgg tggttttttt gtttgcaagc   3840
agcagattac gcgcagaaaa aaaggatctc aagaagatcc tttgatcttt tctacggggt   3900
```

```
ctgacgctca gtggaacgaa aactcacgtt aagggatttt ggtcatgaac aataaaactg   3960
tctgcttaca taaacagtaa tacaaggggt gttatgagcc atattcaacg ggaaacgtct   4020
tgctctaggc cgcgattaaa ttccaacatg gatgctgatt tatatgggta taaatgggct   4080
cgcgataatg tcgggcaatc aggtgcgaca atctatcgat tgtatgggaa gcccgatgcg   4140
ccagagttgt ttctgaaaca tggcaaaggt agcgttgcca atgatgttac agatgagatg   4200
gtcagactaa actggctgac ggaatttatg cctcttccga ccatcaagca ttttatccgt   4260
actcctgatg atgcatggtt actcaccact gcgatccccg ggaaaacagc attccaggta   4320
ttagaagaat atcctgattc aggtgaaaat attgttgatg cgctggcagt gttcctgcgc   4380
cggttgcatt cgattcctgt ttgtaattgt ccttttaaca gcgatcgcgt atttcgtctc   4440
gctcaggcgc aatcacgaat gaataacggt ttggttgatg cgagtgattt tgatgacgag   4500
cgtaatggct ggcctgttga acaagtctgg aaagaaatgc ataaactttt gccattctca   4560
ccggattcag tcgtcactca tggtgatttc tcacttgata accttatttt tgacgagggg   4620
aaattaatag gttgtattga tgttggacga gtcggaatcg cagaccgata ccaggatctt   4680
gccatccctat ggaactgcct cggtgagttt tctccttcat tacagaaacg cttttttcaa   4740
aaatatggta ttgataatcc tgatatgaat aaattgcagt tcatttgat gctcgatgag   4800
ttttctaag aattaattca tgagcggata catatttgaa tgtatttaga aaataaaca   4860
aataggggtt ccgcgcacat ttccccgaaa agtgccacct gaaattgtaa acgttaatat   4920
tttgttaaaa ttcgcgttaa attttttgtta aatcagctca ttttttaacc aataggccga   4980
aatcggcaaa atcccttata atcaaaaga atagaccgag ataggggttga gtgttgttcc   5040
agtttggaac aagagtccac tattaaagaa cgtggactcc aacgtcaaag gcgaaaaac   5100
cgtctatcag ggcgatggcc cactacgtga accatcaccc taatcaagtt ttttggggtc   5160
gaggtgccgt aaagcactaa atcggaaccc taaaggagc ccccgattta gagcttgacg   5220
gggaaagccg gcgaacgtgg cgagaaagga agggaagaaa gcgaaaggag cgggcgctag   5280
ggcgctggca agtgtagcgg tcacgctgcg cgtaaccacc acaccgccg cgcttaatgc   5340
gccgctacag ggcgcgtccc attcgcca                                      5368
```

<210> SEQ ID NO 52
<211> LENGTH: 569
<212> TYPE: PRT
<213> ORGANISM: Santalum austrocaledonicum
<220> FEATURE:
<223> OTHER INFORMATION: santalene synthase (SauSSy)
<300> PUBLICATION INFORMATION:
<308> DATABASE ACCESSION NUMBER: ADO87001
<309> DATABASE ENTRY DATE: 2011-05-17

<400> SEQUENCE: 52

```
Met Asp Ser Ser Thr Ala Thr Ala Met Thr Ala Pro Phe Ile Asp Pro
1               5                   10                  15

Thr Asp His Val Asn Leu Lys Thr Asp Thr Asp Ala Ser Glu Asn Arg
            20                  25                  30

Arg Met Gly Asn Tyr Lys Pro Ser Ile Trp Asn Tyr Asp Phe Leu Gln
        35                  40                  45

Ser Leu Ala Thr His His Asn Ile Val Glu Glu Arg His Leu Lys Leu
    50                  55                  60

Ala Glu Lys Leu Lys Gly Gln Val Lys Phe Met Phe Gly Ala Pro Met
65                  70                  75                  80
```

-continued

```
Glu Pro Leu Ala Lys Leu Glu Leu Val Asp Val Val Gln Arg Leu Gly
                 85                  90                  95
Leu Asn His Arg Phe Glu Thr Glu Ile Lys Glu Ala Leu Phe Ser Ile
            100                 105                 110
Tyr Lys Asp Glu Ser Asn Gly Trp Trp Phe Gly His Leu His Ala Thr
        115                 120                 125
Ser Leu Arg Phe Arg Leu Leu Arg Gln Cys Gly Leu Phe Ile Pro Gln
    130                 135                 140
Asp Val Phe Lys Thr Phe Gln Asn Lys Thr Gly Glu Phe Asp Met Lys
145                 150                 155                 160
Leu Cys Asp Asn Val Lys Gly Leu Leu Ser Leu Tyr Glu Ala Ser Tyr
                165                 170                 175
Leu Gly Trp Lys Gly Glu Asn Ile Leu Asp Glu Ala Lys Ala Phe Ala
            180                 185                 190
Thr Lys Tyr Leu Lys Ser Ala Trp Glu Asn Ile Ser Glu Lys Trp Leu
        195                 200                 205
Ala Lys Arg Val Lys His Ala Leu Ala Leu Pro Leu His Trp Arg Val
    210                 215                 220
Pro Arg Ile Glu Ala Arg Trp Phe Ile Glu Ala Tyr Glu Gln Glu Ala
225                 230                 235                 240
Asn Met Asn Pro Thr Leu Leu Lys Leu Ala Lys Leu Asp Phe Asn Met
                245                 250                 255
Val Gln Ser Ile His Gln Lys Glu Ile Gly Glu Leu Ala Arg Trp Trp
            260                 265                 270
Val Thr Thr Gly Leu Asp Lys Leu Ala Phe Ala Arg Asn Asn Leu Leu
        275                 280                 285
Gln Ser Tyr Met Trp Ser Cys Ala Ile Ala Ser Asp Pro Lys Phe Lys
    290                 295                 300
Leu Ala Arg Glu Thr Ile Val Glu Ile Gly Ser Val Leu Thr Val Val
305                 310                 315                 320
Asp Asp Ala Tyr Asp Val Tyr Gly Ser Met Asp Glu Leu Asp Leu Tyr
                325                 330                 335
Thr Ser Ser Val Glu Arg Trp Ser Cys Val Glu Ile Asp Lys Leu Pro
            340                 345                 350
Asn Thr Leu Lys Leu Ile Phe Met Ser Met Phe Asn Lys Thr Asn Glu
        355                 360                 365
Val Gly Leu Arg Val Gln His Glu Arg Gly Tyr Asn Ser Ile Pro Thr
    370                 375                 380
Phe Ile Lys Ala Trp Val Gln Gln Cys Lys Ser Tyr Gln Lys Glu Ala
385                 390                 395                 400
Arg Trp Phe His Gly Gly His Thr Pro Pro Leu Glu Glu Tyr Ser Leu
                405                 410                 415
Asn Gly Leu Val Ser Ile Gly Phe Pro Leu Leu Leu Ile Thr Gly Tyr
            420                 425                 430
Val Ala Ile Ala Glu Asn Glu Ala Ala Leu Asp Lys Val His Pro Leu
        435                 440                 445
Pro Asp Leu Leu His Tyr Ser Ser Leu Leu Ser Arg Leu Ile Asn Asp
    450                 455                 460
Ile Gly Thr Ser Pro Asp Glu Met Ala Arg Gly Asp Asn Leu Lys Ser
465                 470                 475                 480
Ile His Cys Tyr Met Asn Gly Thr Gly Ala Ser Glu Glu Val Ala Arg
                485                 490                 495
Glu His Ile Lys Gly Val Ile Glu Glu Asn Trp Lys Ile Leu Asn Gln
```

-continued

```
                500              505                510
Cys Cys Phe Asp Gln Ser Gln Phe Gln Glu Pro Phe Ile Thr Phe Asn
            515                 520                 525

Leu Asn Ser Val Arg Gly Ser His Phe Phe Tyr Glu Phe Gly Asp Gly
            530                 535                 540

Phe Gly Val Thr Asp Ser Trp Thr Lys Val Asp Met Lys Ser Val Leu
545                 550                 555                 560

Ile Asp Pro Ile Pro Leu Gly Glu Glu
                565

<210> SEQ ID NO 53
<211> LENGTH: 569
<212> TYPE: PRT
<213> ORGANISM: Santalum spicatum
<220> FEATURE:
<223> OTHER INFORMATION: santalene synthase (SspiSSy)
<300> PUBLICATION INFORMATION:
<308> DATABASE ACCESSION NUMBER: ADO87002
<309> DATABASE ENTRY DATE: 2011-05-17

<400> SEQUENCE: 53

Met Asp Ser Ser Thr Ala Thr Thr Ala Pro Phe Ile Asp His
1               5                   10                  15

Thr Asp His Val Asn Leu Lys Ile Asp Asn Asp Ser Ser Glu Ser Arg
                20                  25                  30

Arg Met Gly Asn Tyr Lys Pro Ser Ile Trp Asn Tyr Asp Phe Leu Gln
            35                  40                  45

Ser Leu Ala Ile His His Asn Ile Val Glu Lys His Leu Lys Leu
50                  55                  60

Ala Glu Lys Leu Lys Gly Gln Val Met Ser Met Phe Gly Ala Pro Met
65                  70                  75                  80

Glu Pro Leu Ala Lys Leu Glu Leu Val Asp Val Val Gln Arg Leu Gly
                85                  90                  95

Leu Asn His Gln Phe Glu Thr Glu Ile Lys Glu Ala Leu Phe Ser Val
            100                 105                 110

Tyr Lys Asp Gly Ser Asn Gly Trp Trp Phe Gly His Leu His Ala Thr
        115                 120                 125

Ser Leu Arg Phe Arg Leu Leu Arg Gln Cys Gly Leu Phe Ile Pro Gln
    130                 135                 140

Asp Val Phe Lys Thr Phe Gln Ser Lys Thr Asp Glu Phe Asp Met Lys
145                 150                 155                 160

Leu Cys Asp Asn Ile Lys Gly Leu Leu Ser Leu Tyr Glu Ala Ser Phe
                165                 170                 175

Leu Gly Trp Lys Gly Glu Asn Ile Leu Asp Glu Ala Lys Ala Phe Ala
            180                 185                 190

Thr Lys Tyr Leu Lys Asn Ala Trp Glu Asn Ile Ser Gln Lys Trp Leu
        195                 200                 205

Ala Lys Arg Val Lys His Ala Leu Ala Leu Pro Leu His Trp Arg Val
    210                 215                 220

Pro Arg Ile Glu Ala Arg Trp Phe Ile Glu Ala Tyr Glu Gln Glu Glu
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
            260                 265                 270

Val Thr Thr Gly Leu Asp Lys Leu Ala Phe Ala Arg Asn Asn Leu Leu
```

```
              275                 280                 285
Gln Ser Tyr Met Trp Ser Cys Ala Ile Ala Ser Asp Pro Lys Phe Lys
290                 295                 300

Leu Ala Arg Glu Thr Ile Val Glu Ile Gly Ser Val Leu Thr Val Val
305                 310                 315                 320

Asp Asp Ala Tyr Asp Val Tyr Gly Ser Met Asp Glu Leu Asp His Tyr
                325                 330                 335

Thr Tyr Ser Val Glu Arg Trp Ser Cys Val Glu Ile Asp Lys Leu Pro
            340                 345                 350

Asn Thr Leu Lys Leu Ile Phe Met Ser Met Phe Asn Lys Thr Asn Glu
        355                 360                 365

Val Gly Leu Arg Val Gln His Glu Arg Gly Tyr Asn Gly Ile Pro Thr
370                 375                 380

Phe Ile Lys Ala Trp Val Glu Gln Cys Lys Ala Tyr Gln Lys Glu Ala
385                 390                 395                 400

Arg Trp Tyr His Gly His Thr Pro Pro Leu Glu Glu Tyr Ser Leu
                405                 410                 415

Asn Gly Leu Val Ser Ile Gly Phe Pro Leu Leu Ile Thr Gly Tyr
            420                 425                 430

Ile Ala Ile Ala Glu Asn Glu Ala Ala Leu Asp Lys Val His Pro Leu
        435                 440                 445

Pro Asp Leu Leu His Tyr Ser Ser Leu Leu Ser Arg Leu Ile Asn Asp
450                 455                 460

Met Gly Thr Ser Pro Asp Glu Met Ala Arg Gly Asp Asn Leu Lys Ser
465                 470                 475                 480

Ile His Cys Tyr Met Asn Glu Thr Gly Ala Ser Glu Glu Val Ala Arg
                485                 490                 495

Glu His Ile Lys Gly Ile Glu Glu Asn Trp Lys Ile Leu Asn Gln
            500                 505                 510

Cys Cys Phe Asp Gln Ser Gln Phe Gln Glu Pro Phe Ile Thr Phe Asn
        515                 520                 525

Leu Asn Ser Val Arg Gly Ser His Phe Phe Tyr Glu Phe Gly Asp Gly
530                 535                 540

Phe Gly Val Thr Asp Ser Trp Thr Lys Val Asp Met Lys Ser Val Leu
545                 550                 555                 560

Ile Asp Pro Ile Pro Leu Gly Glu Glu
                565

<210> SEQ ID NO 54
<211> LENGTH: 4
<212> TYPE: PRT
<213> ORGANISM: Artificial Sequence
<220> FEATURE:
<223> OTHER INFORMATION: ExxR motif
<220> FEATURE:
<221> NAME/KEY: VARIANT
<222> LOCATION: (2)...(3)
<223> OTHER INFORMATION: Xaa = any amino acid

<400> SEQUENCE: 54

Glu Xaa Xaa Arg
 1

<210> SEQ ID NO 55
<211> LENGTH: 8
<212> TYPE: PRT
<213> ORGANISM: Artificial Sequence
<220> FEATURE:
```

```
<223> OTHER INFORMATION: motif
<220> FEATURE:
<221> NAME/KEY: VARIANT
<222> LOCATION: 1
<223> OTHER INFORMATION: Xaa = Pro or Ile
<220> FEATURE:
<221> NAME/KEY: VARIANT
<222> LOCATION: 5, 7
<223> OTHER INFORMATION: Xaa = any amino acid
<220> FEATURE:
<221> NAME/KEY: VARIANT
<222> LOCATION: 6
<223> OTHER INFORMATION: Xaa = Pro or Gly

<400> SEQUENCE: 55

Xaa Pro Gly Pro Xaa Xaa Xaa Pro
 1               5

<210> SEQ ID NO 56
<211> LENGTH: 7
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 4
<223> OTHER INFORMATION: Xaa = any amino acid
<220> FEATURE:
<221> NAME/KEY: VARIANT
<222> LOCATION: 7
<223> OTHER INFORMATION: Xaa = Gly or Ala

<400> SEQUENCE: 56

Gly Arg Arg Xaa Cys Pro Xaa
 1               5

<210> SEQ ID NO 57
<211> LENGTH: 6
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 1
<223> OTHER INFORMATION: Xaa = Ala or Gly
<220> FEATURE:
<221> NAME/KEY: VARIANT
<222> LOCATION: 3
<223> OTHER INFORMATION: Xaa = any amino acid
<220> FEATURE:
<221> NAME/KEY: VARIANT
<222> LOCATION: 4
<223> OTHER INFORMATION: Xaa = Asp or Glu
<220> FEATURE:
<221> NAME/KEY: VARIANT
<222> LOCATION: 6
<223> OTHER INFORMATION: Xaa = Thr or Ser

<400> SEQUENCE: 57

Xaa Gly Xaa Xaa Thr Xaa
 1               5

<210> SEQ ID NO 58
<211> LENGTH: 692
<212> TYPE: PRT
<213> ORGANISM: Arabidopsis thaliana
<220> FEATURE:
<223> OTHER INFORMATION: NADPH cytochrome P450 reductase
<300> PUBLICATION INFORMATION:
<308> DATABASE ACCESSION NUMBER: CAB58575.1
<309> DATABASE ENTRY DATE: 1999-10-19
```

<400> SEQUENCE: 58

```
Met Thr Ser Ala Leu Tyr Ala Ser Asp Leu Phe Lys Gln Leu Lys Ser
 1               5                  10                  15

Ile Met Gly Thr Asp Ser Leu Ser Asp Val Val Leu Val Ile Ala
            20                  25                  30

Thr Thr Ser Leu Ala Leu Val Ala Gly Phe Val Val Leu Leu Trp Lys
        35                  40                  45

Lys Thr Thr Ala Asp Arg Ser Gly Glu Leu Lys Pro Leu Met Ile Pro
 50                  55                  60

Lys Ser Leu Met Ala Lys Asp Glu Asp Asp Leu Asp Leu Gly Ser
 65              70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
130                 135                 140

Val Ala Thr Tyr Gly Asp Gly Glu Pro Thr Asp Asn Ala Ala Arg Phe
145                 150                 155                 160

Ser Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Asp Gln Ser Ile Glu
210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350

Ser Leu Asp Leu Val Phe Ser Ile His Ala Asp Lys Glu Asp Gly Ser
        355                 360                 365

Pro Leu Glu Ser Ala Val Pro Pro Phe Pro Gly Pro Cys Thr Leu
370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
```

```
                    405                 410                 415
Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
        435                 440                 445

Phe Pro Ser Ala Lys Pro Pro Leu Gly Val Phe Phe Ala Ala Ile Ala
    450                 455                 460

Pro Arg Leu Gln Pro Arg Tyr Tyr Ser Ile Ser Ser Cys Gln Asp Trp
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
    530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
    610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690

<210> SEQ ID NO 59
<211> LENGTH: 1713
<212> TYPE: DNA
<213> ORGANISM: Santalum austrocaledonicum
<220> FEATURE:
<223> OTHER INFORMATION: santalene synthase
<300> PUBLICATION INFORMATION:
<308> DATABASE ACCESSION NUMBER: HQ343277
<309> DATABASE ENTRY DATE: 2011-05-17

<400> SEQUENCE: 59
atggattctt ccaccgccac cgccatgaca gctccattca ttgatcctac tgatcatgtg      60
aatctcaaaa ctgatactga tgcctcagag aatcgaagga tggggaatta taaacccagc    120
atttggaatt atgatttttt acaatcactt gcaactcatc acaatattgt ggaagagagg    180
catctaaagc tagctgagaa gctgaagggc caagtgaagt ttatgtttgg ggcaccaatg    240
gagccgttag caaagctgga gcttgtggat gtggttcaaa ggctcgggct aaaccaccga    300
```

```
tttgagacag agatcaagga agcgctattt agtatttata aggacgagag caatggatgg      360
tggtttggcc accttcatgc gacatctctc cgatttaggc tgctacgaca gtgtgggctt      420
tttatccccc aggatgtgtt taaaacgttc caaaacaaaa ctggtgaatt tgatatgaaa      480
ctgtgtgaca acgtaaaagg gctgctgagc ttatatgaag cttcatactt gggatggaag      540
ggtgaaaaca tcctagatga agccaaggcc ttcgccacca agtacttgaa aagtgcatgg      600
gaaaatatat ctgaaaagtg gttagccaaa agagtgaagc atgcattggc tttacctttg      660
cattggagag tccctcgaat cgaagctaga tggttcattg aggcatatga gcaagaagcg      720
aatatgaacc caacactact caaactcgca aaattagact ttaatatggt gcaatcaatt      780
catcagaaag agattgggga attagcaagg tggtgggtga ctactggctt ggataagtta      840
gcctttgcta ggaataattt actgcaaagc tatatgtgga gctgcgcgat tgcttccgac      900
ccgaagttca aacttgctag agaaactatt gtcgaaatcg gaagtgtact cacagttgtt      960
gatgatgcat atgacgtcta tggttcaatg gacgaacttg atctctacac aagctccgtt     1020
gaaaggtgga gctgtgtaga aattgacaag ttgccaaaca cgttaaaatt gattttttatg    1080 tctatgttta ataagaccaa tgaggttggc cttcgagtcc agcatgagcg aggctacaat     1140
agcatcccta cttttatcaa agcgtgggtt caacagtgta atcatacca gaaagaagca      1200 agatggttcc acgggggaca cacgcctccg ttggaagaat atagcttgaa tggacttgtt     1260
tccataggat tccctctctt gttgatcacc ggctacgtgg caatcgctga gaacgaggct     1320
gcactggata aagtgcaccc ccttcctgat cttctgcact actcctcccct ccttagtcgc    1380 ctcatcaatg atataggaac gtctccggat gagatggcaa gaggcgataa tctgaagtca     1440
atccattgtt acatgaacgg aactgggggct tccgaggaag ttgctcgtga gcacataaag    1500
ggagtaatcg aggagaattg gaaaatactg aatcagtgct gctttgatca atctcagttt     1560
caggagcctt ttataacctt caatttgaac tctgttcgag ggtctcattt cttctatgaa     1620
tttggggatg gctttgggggt gacggatagc tggacaaagg ttgatatgaa gtccgttttg    1680
attgacccta ttcctctcgg cgaggagtag taa                                  1713
```

<210> SEQ ID NO 60
<211> LENGTH: 1713
<212> TYPE: DNA
<213> ORGANISM: Santalum spicatum
<220> FEATURE:
<223> OTHER INFORMATION: santalene synthase
<300> PUBLICATION INFORMATION:
<308> DATABASE ACCESSION NUMBER: HQ343278
<309> DATABASE ENTRY DATE: 2011-05-17

<400> SEQUENCE: 60

```
atggattctt ccaccgccac cgccacgaca gctccattta ttgatcatac tgatcatgtg       60
aatcttaaaa ttgataatga ttcctccgag agtcgaagga tgggcaatta taaacccagt      120
atttggaatt atgattttct gcaatcactt gcaatccatc acaatattgt ggaagagaag      180
catctaaagc tagctgagaa gctgaagggc caagtgatgt ctatgtttgg ggcaccaatg      240
gagccgttag caaagctgga gcttgtggat gtggttcaaa ggcttgggct aaaccaccaa      300
tttgagacag agatcaagga agcccctattt agtgtttaca aggatgggag caatggatgg      360
tggtttggcc accttcatgc aacatctctt cgatttaggc tactacgaca gtgtgggctt      420
tttatccccc aggatgtgtt taaaacgttc cagagcaaaa ctgatgaatt tgatatgaaa      480
ctgtgtgaca acataaaagg gttgttgagc ttgtatgaag cttcattcct ggggtggaag      540
```

```
ggtgaaaaca tcctagatga agccaaggcc ttcgccacca agtacttgaa aaatgcatgg      600
gaaaatatat cccaaaagtg gctagccaaa agagtgaagc atgcactggc tttgcctctg      660
cactggagag tccctcgaat cgaggctaga tggttcattg aggcatatga gcaagaagag      720
aacatgaacc caacactact caaacttgca aaattagact ttaacatggt gcaatcaatt      780
catcagaaag agattgggga attagcaagg tggtgggtga ctactggctt ggataagtta      840
gcctttgcta ggaataattt actgcaaagc tatatgtgga gctgcgcgat tgcttccgac      900
ccaaagttca aacttgctag agaaactatt gtcgaaatcg aagtgtact cacagttgtg       960 gacgatgcat atgatgtcta tggttcaatg gatgaacttg atcactacac atactccgtt     1020
gaaaggtgga gctgtgtaga aattgacaag ctgccaaaca cgttaaaatt gattttatg      1080 tctatgttca acaagaccaa tgaggttggc cttcgagtcc agcatgagcg aggctacaac     1140
ggcatcccta cttttatcaa agcatgggtt gaacagtgta agcatacca gaaagaggca      1200 agatggtacc atgggggaca cacgcctcca ttggaggaat atagcttgaa tggacttgtt     1260
tccataggat tccctctctt gttgatcacc ggctacatcg caatcgctga gaacgaggct     1320
gcactggata agtgcacccc cttcctgat cttctgcact actcctccct ccttagtcgc      1380
ctcatcaatg acatgggaac gtctccggac gagatggcaa gaggtgacaa tctgaagtca     1440
atccactgtt acatgaacga aactggggct tctgaggaag ttgctcgtga gcacataaaa     1500
ggaataatcg aggagaattg gaaaatactg aatcagtgct gctttgatca atctcagttt     1560
caggagcctt ttataacctt caatttgaac tctgttcgag ggtctcattt cttctatgaa     1620
tttggggatg gctttgggt gacagatagc tggacaaagg ttgatatgaa gtctgttttg      1680
atcgacccta ttcctctcgg cgaggagtag taa                                  1713

<210> SEQ ID NO 61
<211> LENGTH: 21
<212> TYPE: DNA
<213> ORGANISM: Artificial Sequence
<220> FEATURE:
<223> OTHER INFORMATION: SaCPR2 forward primer

<400> SEQUENCE: 61
atgcaattga gctccgtcaa g                                                21

<210> SEQ ID NO 62
<211> LENGTH: 27
<212> TYPE: DNA
<213> ORGANISM: Artificial Sequence
<220> FEATURE:
<223> OTHER INFORMATION: SaCPR2 reverse primer

<400> SEQUENCE: 62
tcaccacaca tcccgtaaat accttcc                                          27

<210> SEQ ID NO 63
<211> LENGTH: 1950
<212> TYPE: DNA
<213> ORGANISM: Santalum album
<220> FEATURE:
<223> OTHER INFORMATION: CPR1 truncated

<400> SEQUENCE: 63
atgttcatgt ggcggagatc gggcgagaag tccaaggaat tgaggcctgt ggtggcgctg       60
aaggcggcgc cgatcgaggc ggaggaggac gatggcgagg ttgactcggg gaagactaag      120
gtcactgtgt tcttcggtac gcagactggc actgccgaag ggttcgctaa ggctttggca      180
```

```
gaagagatca aggcaagata tgaaaaagca gtcgtcaaag tggttgacct ggatgattat      240
gctgcagatg atgatcaata tggagaaaaa ttgaaaaatg agacgctgac atttttcatg      300
gtggccactt atggtgatgg agaaccaacc gataatgctg caagatttta caaatggttt      360
actgaggaga agaaaggga agcttggtta cagcagctga cttatggcat ttttggtctg       420
ggaaatcgtc aatatgaaca ttttaataag atagcaaagg tgcttgatga acagcttact      480
gaacaaggtg caaagcgtct cattcaggtt ggtttaggtg atgatgatca gtgcatcgag      540
gatgattttt ctgcttggcg tgaactactg tggccagagt tagatcaatt actccggggt      600
gatgatggtc gaattctgt gtctactccc tatacagctg ctgttcctga ataccgagtg       660
gtgatccatg atcctactat cacttcatct gaggataaat ccttagccac ggccaatggg      720
gctgctttat ttgacattca ccatccatgc agagttaagg ttgctgttca agagagctt       780 cacaaagctg actctgaccg ctcttgcata catttggagt ttgatatatc aggcacgggt      840
cttatgtatg aaacgggaga ccatgtgggt gtttacgctg aaaattgtgt tgagactgtt      900
gaagaagcag gaaagctgtt gggccaacct ttagatttgc tcttttctgt tcacactgac      960
aaggatgatg gtacatctct tgagagctca ttgcccccctc ctttttcctgg tccttgcact   1020 cttcgcactg cactgtttca atatgcagat ctattgaacc ctcctaggaa ggctgcttta    1080
gttgccctgg cagctcatgc agttgaacca tctgaggcag acagacttaa attttttgtca    1140 tcacctcagg gaaaggatga gtatgcgaaa tgggttgttg gcagtcaaag aagcctcctt    1200
gaggtgatgg ctgagttccc gtcaataaaa gttccccttg gtgtgttttt tgccgctgtg    1260
gccccccgcc tacagcctcg ctactattca atctcatcat cgcctaggtt ctcctctgac    1320
cgggttcatg taacctgcgc tttagtttat ggccctagtc caacaggcag aattcacaga    1380
ggggtgtgtt ccacctggat gaagaatgca gttcctctag aagaaagccg tgagtgtagc    1440
tgggctccta tatttattag gacatctaat tttaagctac cagctaatcc ttctacccca    1500
gttatcatgg tcggccctgg tactggcttg gcaccgtttta gaggattcct acaggaaagg    1560
atggccctgt tagaaggcgg tgctcaactt ggtcctgctt acttttctt tggatgtaga    1620 aatcgaagga tggattttat ttacgaggat gaactcaaca atttcgtcga acaaggtgtg    1680
atatcagagt tgattgttgc attctcgagg gacgggccaa ccaaggagta cgttcagcat    1740
aagatgatgg ataaagctgc atatatatgg agtctaatct ctcagggggc ttatcttta    1800 gtctgtggtg atgcaaaggg gatggctaga gatgttcatc gaactttgca tactcttgtt    1860
caacaacagg agagcgtgga ctcatcaaaa gcagagtcaa tagtgaagaa gcttcagatg    1920
gatggacgat atctaagaga tgtttggtaa                                       1950
```

<210> SEQ ID NO 64
<211> LENGTH: 1938
<212> TYPE: DNA
<213> ORGANISM: Santalum album
<220> FEATURE:
<223> OTHER INFORMATION: CPR2 truncated

<400> SEQUENCE: 64

```
atgcggttct cgagctccca gaaggcggtg gcggcggcta agggcgtaga ggttgcgagg       60
aagccggtga tcgggaagga atcggaggcg gcggaggtgg atgacggaaa gaagaaggtg      120
accatcttct cgggacgca gactggaaca gccgaagggt cgccaaggc gctggttgag       180 gaggcaaaag cacgctatga gaaggccatt tttaaattgg ttgatttgga tgattatgct      240
```

```
gccgaggatg atgaatatga ggagaagttg aaaaaagaga aattcgcttt attcttttta      300
gccacatatg gagatggtga gcctactgac aatgcagcga ggttctataa atggtttact      360
gaggaaaatg aaagtggaga gtggctccaa agcttcagt tcggagtgtt tggccttggc       420
aataggcaat acgagcattt caacaaggtt gcaaaggttg tggatgagat tcttgctgag      480
caaggtggga agcgcctggt tccagtgggt cttggagatg atgatcaatg cattgaagat      540
gacttcactg catggcgtga attagtgtgg cccgagttgg ataaattgct cctagatgag      600
gatgatgcaa ctgtttctac ccctttatact gcttctgtac cggaataccg ggttgtattt      660
catgattctc ctgatgatta tctgcagaag aactctagta atgcaaatgg tcattcgatg      720
catgatgctc agcatccatg cagggctaat gttgctgtga ggagggagct tcattcgcct      780
ttatctgatc gttcttgcac tcatctagaa tttgacattg ctggaactgg acttgcgtat      840
gaaacagggg accatgttgg tgtgtgctgt gagaatttac ctgaagttgt ggaagaggct      900
gaaagggtac tgggttttgtc accaggcatc tactttttcca tccatgctga taaagaggat       960
ggcacaccac ttgaagttc cttgccacca cttttttccac catgtacttt aagaactgca     1020
ctaactcaac atgctgatct tctaagtttt cctaaaaagg ctgcgttgct tgctttagca     1080
gctcatgctt ctgatccaag tgaagcggat aggttgaaat atcttgcatc tcctgcagga     1140
aaggatgaat atgcacagtg ggttgttgca agtcagagaa gccttctaga agtaatggct     1200
gaattcccct cggcgaagcc cccacttgga gttttgtttg ctgcagttgc tccacgattg     1260
cagccacgat tctattcgat ctcatcctct ccaaagattg caccatctag gatacatgtt     1320
acttgcgcat tagtatatga taaaacacca actgggcgaa ttcacaaggg agtgtgctca     1380
acttggatga agaatgcgat gccccgggaa gaaagccacg attgcagctg ggctcccatt     1440
tttgttaggc aatctaattt caagctccct tcaaatacat cggtgcctgt catcatgatt     1500
ggtcctggca cggggttggc tcctttcagg ggctttctac aggaaagatt agcactgaaa     1560
gaagctggag ttgaactggg acctgcaata ttattctttg ggtgcaggaa ccgtaaaatg     1620
gattacattt atgaggatga gttggcacac tttgttgaag ccggtgcgct ctctgagttg     1680
atcgtggctt tctcacggga aggaccagcc aaacagtatg tccagcataa gatgatggaa     1740
aaggcctcag aaatctggaa catgatttcc gatggaggtt atgtatatgt atgtggtgat     1800
gccaaaggca tggccaaaga tgtccaccgg gcgctccata caattgttca cgaacaggga     1860
tctctagaca attccaagac agagagcatg gtgaagaatc tccaaatgaa tggaaggtat     1920
ttacgggatg tgtggtga                                                     1938
```

<210> SEQ ID NO 65
<211> LENGTH: 3781
<212> TYPE: DNA
<213> ORGANISM: Artificial Sequence
<220> FEATURE:
<223> OTHER INFORMATION: pCDF-Duet vector

<400> SEQUENCE: 65

```
ggggaattgt gagcggataa caattcccct gtagaaataa ttttgtttaa ctttaataag       60
gagatatacc atgggcagca gccatcacca tcatcaccac agccaggatc cgaattcgag      120
ctcggcgcgc ctgcaggtcg acaagcttgc ggccgcataa tgcttaagtc gaacagaaag      180
taatcgtatt gtacacggcc gcataatcga attaatacg actcactata gggaattgt        240 gagcggataa caattcccca tcttagtata ttagttaagt ataagaagga gatatacata      300
tggcagatct caattggata tcggccggcc acgcgatcgc tgacgtcggt accctcgagt     360
```

```
ctggtaaaga aaccgctgct gcgaaatttg aacgccagca catggactcg tctactagcg    420
cagcttaatt aacctaggct gctgccaccg ctgagcaata actagcataa ccccttgggg    480
cctctaaacg ggtcttgagg ggttttttgc tgaaacctca ggcatttgag aagcacacgg    540
tcacactgct tccggtagtc aataaaccgg taaaccagca atagacataa gcggctattt    600
aacgaccctg ccctgaaccg acgaccgggt catcgtggcc ggatcttgcg gcccctcggc    660
ttgaacgaat tgttagacat tatttgccga ctaccttggt gatctcgcct ttcacgtagt    720
ggacaaattc ttccaactga tctgcgcgcg aggccaagcg atcttcttct tgtccaagat    780
aagcctgtct agcttcaagt atgacgggct gatactgggc cggcaggcgc tccattgccc    840
agtcggcagc gacatccttc ggcgcgattt tgccggttac tgcgctgtac caaatgcggg    900
acaacgtaag cactacattt cgctcatcgc cagcccagtc gggcggcgag ttccatagcg    960
ttaaggtttc atttagcgcc tcaaatagat cctgttcagg aaccggatca aagagttcct   1020
ccgccgctgg acctaccaag gcaacgctat gttctcttgc ttttgtcagc aagatagcca   1080
gatcaatgtc gatcgtggct ggctcgaaga tacctgcaag aatgtcattg cgctgccatt   1140
ctccaaattg cagttcgcgc ttagctggat aacgccacgg aatgatgtcg tcgtgcacaa   1200
caatggtgac ttctacagcg cggagaatct cgctctctcc aggggaagcc gaagtttcca   1260
aaaggtcgtt gatcaaagct cgccgcgttg tttcatcaag ccttacggtc accgtaacca   1320
gcaaatcaat atcactgtgt ggcttcaggc cgccatccac tgcggagccg tacaaatgta   1380
cggccagcaa cgtcggttcg agatggcgct cgatgacgcc aactacctct gatagttgag   1440
tcgatacttc ggcgatcacc gcttccctca tactcttcct tttcaatat tattgaagca   1500
tttatcaggg ttattgtctc atgagcggat acatatttga atgtatttag aaaaataaac   1560
aaatagctag ctcactcggt cgctacgctc cgggcgtgag actgcggcgg cgctgcgga   1620
cacatacaaa gttacccaca gattccgtgg ataagcaggg gactaacatg tgaggcaaaa   1680
cagcagggcc gcgccggtgg cgttttttcca taggctccgc cctcctgcca gagttcacat   1740
aaacagacgc ttttccggtg catctgtggg agccgtgagg ctcaaccatg aatctgacag   1800
tacgggcgaa acccgacagg acttaaagat ccccaccgtt tccggcgggt cgctccctct   1860
tgcgctctcc tgttccgacc ctgccgttta ccggatacct gttccgcctt tctcccttac   1920
gggaagtgtg gcgctttctc atagctcaca cactggtatc tcggctcggt gtaggtcgtt   1980
cgctccaagc tgggctgtaa gcaagaactc cccgttcagc ccgactgctg cgccttatcc   2040
ggtaactgtt cacttgagtc caacccggaa aagcacggta aaacgccact ggcagcagcc   2100
attggtaact gggagttcgc agaggatttg tttagctaaa cacgcggttg ctcttgaagt   2160
gtgcgccaaa gtccggctac actggaagga cagatttggt tgctgtgctc tgcgaaagcc   2220
agttaccacg gttaagcagt tccccaactg acttaacctt cgatcaaacc acctccccag   2280
gtggtttttt cgtttacagg gcaaaagatt acgcgcagaa aaaaggatc tcaagaagat   2340
cctttgatct tttctactga accgctctag atttcagtgc aatttatctc ttcaaatgta   2400
gcacctgaag tcagccccat acgatataag ttgtaattct catgttagtc atgccccgcg   2460
cccaccggaa ggagctgact gggttgaagg ctctcaaggg catcggtcga tcccggtg   2520
cctaatgagt gagctaactt acattaattg cgttgcgctc actgcccgct tccagtcgg   2580
gaaacctgtc gtgccagctg cattaatgaa tcggccaacg cgcggggaga ggcggtttgc   2640
gtattgggcg ccagggtggt ttttcttttc accagtgaga cgggcaacag ctgattgccc   2700
```

-continued

```
ttcaccgcct ggccctgaga gagttgcagc aagcggtcca cgctggtttg ccccagcagg    2760
cgaaaatcct gtttgatggt ggttaacggc gggatataac atgagctgtc ttcggtatcg    2820
tcgtatccca ctaccgagat gtccgcacca acgcgcagcc cggactcggt aatggcgcgc    2880
attgcgccca cgccatctg atcgttggca accagcatcg cagtgggaac gatgccctca     2940
ttcagcattt gcatggtttg ttgaaaaccg gacatggcac tccagtcgcc ttcccgttcc    3000
gctatcggct gaatttgatt gcagtgaga tatttatgcc agccagccag acgcagacgc     3060
gccgagacag aacttaatgg gcccgctaac agcgcgattt gctggtgacc caatgcgacc    3120
agatgctcca cgcccagtcg cgtaccgtct tcatgggaga aaataatact gttgatgggt    3180
gtctggtcag agacatcaag aaataacgcc ggaacattag tgcaggcagc ttccacagca    3240
atggcatcct ggtcatccag cggatagtta atgatcagcc cactgacgcg ttgcgcgaga    3300
agattgtgca ccgccgcttt acaggcttcg acgccgcttc gttctaccat cgacaccacc    3360
acgctggcac ccagttgatc ggcgcgagat ttaatcgccg cgacaatttg cgacggcgcg    3420
tgcagggcca gactggaggt ggcaacgcca atcagcaacg actgtttgcc cgccagttgt    3480
tgtgccacgc ggttgggaat gtaattcagc tccgccatcg ccgcttccac ttttttcccgc   3540 gttttcgcag aaacgtggct ggcctggttc accacgcggg aaacggtctg ataagagaca    3600
ccggcatact ctgcgacatc gtataacgtt actggtttca cattcaccac cctgaattga    3660
ctctcttccg ggcgctatca tgccataccg cgaaaggttt tgcgccattc gatggtgtcc    3720
gggatctcga cgctctcccct tatgcgactc ctgcattagg aaattaatac gactcactat   3780
a                                                                    3781
```

<210> SEQ ID NO 66
<211> LENGTH: 471
<212> TYPE: PRT
<213> ORGANISM: Bacillus megaterium
<220> FEATURE:
<223> OTHER INFORMATION: cytochrome P450BM-3

<400> SEQUENCE: 66

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Arg Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
```

```
                165                 170                 175
Met Val Arg Ala Leu Asp Glu Ala Met Asn Lys Leu Gln Arg Ala Asn
            180                 185                 190

Pro Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg
465                 470

<210> SEQ ID NO 67
<211> LENGTH: 1530
<212> TYPE: DNA
<213> ORGANISM: Santalum album
<220> FEATURE:
<223> OTHER INFORMATION: SaCYP76F37v2 (CYP76-G14)

<400> SEQUENCE: 67
atggacttct taagttgtat cctgtttgtt ttattcgcgt gggcacttgt tcgggctctc      60
cctacacttt ctagaggttc caaagcagcc ggcgggaggc ttccgccggg gccagtcccg     120
ttgccggtgg tgggaaacct gttaaaactc gggagcaaac cacacaagtc gctggcggag     180
ctggccaaat cctacggtcc tataatgtgt ctcaaactag gtcacataat cacaattgtc     240
atctcaactc ctaccgtcgc caagagggtt ctccaaaaac aagacgtcgc cttctgtaac     300
```

| | |
|---|---|
| cgaaccatcc ctgacgccgt tcgagcccac agacacgacc tccactccat ggtttggtta | 360 |
| ccggtttcga cccgttggcg gacccttcga aagataagca actcccacat cttcagtagc | 420 |
| caaaggctcg atgaaaacca ccacctccgg cggcggaagc tcgacgagct ccttaccagg | 480 |
| gtggcggaga gcagcctggt cggggcagtg gtggatatag gcgcggtggc tttcttgacg | 540 |
| agtctaaact tgctatccaa caccgtgttt tcgaaggatt tggtcgaacc aggattgggg | 600 |
| gctgtgcagg agatggagga ggtggtgtgg gggatcacgg aggaggccgg gaggcccaat | 660 |
| ttggtggatt attttccggt gctgcgaagg ctcgatccgc aggggacacg ccgtcggatg | 720 |
| atgggttatt tcgggaaaat gttcgaggtt tcggggata tcattgacga gcggcttgaa | 780 |
| ttgagaaagc aacaaagtga tggtgattcc ccagctgcta caactaatga tgtgttggac | 840 |
| gttcttctga atattattga agacgctgaa attgaagaaa agcctaatag aactgatgtc | 900 |
| gaacacttct tactggacct atttgcggcg gggagtgata cgacttcgag caccgtcgaa | 960 |
| tgggcgatga cggaactcct ccgcaaaccg gagactctgg agagagcccg gtcggagctc | 1020 |
| catgagacca tcgcccaga aaacctggtc caagaggccg acttgccccg gcttccctac | 1080 |
| ttacaggccg tggtgaagga actttcagg ctccacctc cggtgccgct gctactcccc | 1140 |
| cgcactgcgg agaaggacgc cgaactctgc ggcttcacgg tccccgcagg ggcccaaatc | 1200 |
| atggtgaacg cgtgggcgat cgggagagat cccgggacat gggaggaccc agagtcattc | 1260 |
| ttgccggaga gattcttggg gtcggatgtg acgtgaagg ggaggagttt cgagctgatt | 1320 |
| ccgttcggcg gagggaggag gatttgcccc ggattaccgc tggcgataag gatggtgcat | 1380 |
| ttgatgttag gatcgctgat ccatgggttt cggtggaagg tggatgacga tggaatgggt | 1440 |
| tcgccggaga ccgccatgga catggatgaa aagttcggca ttactttaca gaaggcgaag | 1500 |
| cccttgtgcg ctgtcccaat ccgggggtaa | 1530 |

<210> SEQ ID NO 68
<211> LENGTH: 1530
<212> TYPE: DNA
<213> ORGANISM: Santalum album
<220> FEATURE:
<223> OTHER INFORMATION: SaCYP76F39v2 (CYP76-G15)

<400> SEQUENCE: 68

| | |
|---|---|
| atggacttct taagttgtat cctgtctgtt ttgttcgcgt gggcgctggt tcgagctctc | 60 |
| cgtaaacttt ctagaggttc caaagctgcc agcgggaggc ttccgccggg gccagtcccg | 120 |
| tggccggtgg tgggaaacct gttaaaactc gggaacaaac cacacaagtc attggcggag | 180 |
| ctggccaaat cctacggccc cataatgtgt ctcaaacttg gtcacatgac cacaattgtc | 240 |
| atctcaactc ctaccgtagc caagagggtt cttcaaaaac aagacgttgc cttctctaac | 300 |
| cgaaccatcc ccgacgccgt tcgagcctat ggacacgacc tctactccat ggcttggtta | 360 |
| ccggtttcca cccgttggcg gaccctgcgc aagataagca attcccacat cttcactagc | 420 |
| caaaggctcg atgaaaacca ccacctccgg cggcggaagc tcgacgagct ccttgccaga | 480 |
| gtggcggaga gcagcctggt cggggcagtg gtggatatgg gcgcggtagc tttcttgacg | 540 |
| agtctaaact tgctatccaa caccgtgttt tcgaaggatt tggtcgaacc aggattgggg | 600 |
| gctgtgcagg agacgaagga ggtggtgtgg ggatgatgg aggaggccgg aagcccaat | 660 |
| ttggtggatt attttcccggt gctgcggagg ctcgatccgc aggggattcg ccgtcggatg | 720 |
| acgggttatt tcgggaaaat gttggaagtt tcggggata tcattgacga gcggcttgaa | 780 |
| tggagaaagc aacaaagtga tggtgattcc ccagctggta caactaatga tgtgttggac | 840 |

```
gttcttctga atattattga agacgctgaa atcgaagaaa agcctaatag aactgatgtc      900
gaacacttct tactggacct atttgcggcg gggagtgata cgacttcgag caccgtcgaa      960
tgggcgatga cggaactcct ccgcaaaccg agactctgg agagagcccg gtcggagctc     1020
catgagacca tcgcccaga aaacctggtc caagaggccg acttgccccg gcttccctac     1080
ttacaggccg tggtgaagga aactttcagg ctccaccctc cggtgccgct gctactcccc     1140
cgcactgcgg agaaggacgc cgaactctgc ggcttcacgg tccccgcagg ggcccaaatc     1200
atggtgaacg cgtgggcgat cgggagagat cccgggacat gggaggaccc agagtcattc     1260
ttgccggaga gattcttggg gtcggatgtg acgtgaagg ggaggagttt cgagctgatt     1320
ccgttcggcg gagggaggag gatttgcccc ggattaccgc tggcgataag gatggtgcat     1380
ttgatgttag gatcgctgat ccatgggttt cggtggaagg tggatgacga tggaatgggt     1440
tcgccggaga ccgccatgga catggatgaa aagttcggca ttactttaca gaaggcgaag     1500
cccttgtgcg ctgtcccaat ccgggggtaa                                     1530
```

<210> SEQ ID NO 69
<211> LENGTH: 1530
<212> TYPE: DNA
<213> ORGANISM: Santalum album
<220> FEATURE:
<223> OTHER INFORMATION: SaCYP76F40 (CYP76-G16)

<400> SEQUENCE: 69

```
atggacttct taagttgtat cctgtctgtt ttgttcgcgt gggcgctggt tcgagctctc       60
cgtaaacttt ctagaggttc caaagctgcc agcgggaggc ttccgccggg gccagtcccg      120
tggccggtgg tgggaaacct gttaaaactc gggaacaaac cacacaagtc attggcggag      180
ctggccaaat cctacggccc cataatgtgt ctcaaacttg gtcacatgac acaattgtc      240
atctcaactc ctaccgtagc caagagagtt cttcaaaaac aagacgttgc cttctctaac      300
cgaaccactc ctgacgccgt tcgagcccac ggacacgacc tctactccat ggcttggtta      360
ccggtttcca cccgttggcg gaccctgcga agataagca attcccacat cttcactagc      420
caaaggctcg atgaaaacca ccacctccgg cggcggaagc tcgacgagct ccttgccaga      480
gtggcggaga gcagcctggt cggggcagtg gtggatatgg gcgcggtagc tttcttgacg      540
agtctaaact tgctatccaa caccgtgttt tcgaaggatt tggtcgaacc aggattgggg      600
gctgtgcagg agacgaagga ggtggtgtgg gggatgatgg aggaggccgg aaggcccaat      660
ttggtggatt atttcccggt gctgcggagg ctcgatccgc aggggattcg ccgtcggatg      720
acgggttatt tcgggaaaat gttggaagtt ttcgggata tcattgacga gcggcttgaa      780
tggagaaagc aacaaagtga tggtgattcc ccagctggta caactaatga tgtgttggac      840
gttcttctga atattattga agacgctgaa attgaagaaa agcctaatag aactgatgtc      900
gaacacttca tagtggacct atttgtgcg gggagtgata cgacttccag caccgtcgaa      960
tgggcgatga cggaactcct ccgtaaaccg agactctgg agagagcccg gtcggagctc     1020
catgagacca tcggccctaa aaacctggtc caagaggccg acatgccccg gctcccctac     1080
ttacaggccg tggtgaaaga aactttccgg ctccaccctc cggtgccgct cctactcccc     1140
cgcactgcgg agaaggacgc cgaactctgc ggcttcacgg tccccgcagg ggcccaaatc     1200
atggtgaacg cgtgggcgat cgggagagat cccgggacat gggaggaccc ggagtcattc     1260
ttgccggaga gattcttggg gtcggatgtg acgtgaagg ggaggagttt cgagctgatt     1320
```

```
ccttcggcg agggaggag gatttgcccc ggattacctc tggcgataag gatggtgcat     1380
ttgatgttag gatcactgat ccatgggttc cggtggaagg tggctgacga tggaatgggg     1440
tcgccggaga ctgcgatgga catggatgag aagtttggca tcactttaca gaaggcgaag     1500
tcgttgtgcg ctgtcccaat ccggggtaa                                         1530

<210> SEQ ID NO 70
<211> LENGTH: 1530
<212> TYPE: DNA
<213> ORGANISM: Santalum album
<220> FEATURE:
<223> OTHER INFORMATION: SaCYP76F41 (CYP76-G17)

<400> SEQUENCE: 70
atggacttct taagttgtat cctgtttgtt ttgttcgcat gggcgctggt tcatgctctc       60
cgtacacttt ctagaggttc caaagctgcc agcggggaggc ttccgccggg gccagtcccg      120
tggccggtgg tgggaaacct gttaaaactc gggaacaaac cacacaagtc attggcggag      180
ctggccaaat cctacggccc cataatgtgt ctcaaacttg gtcacatgac acaattgtc       240 atctcaactc ctaccgtagc caaagaggtt cttcaaaaac aagacgttgc cttctctaac      300
cgaaccactc ctgacgccgt tcgagcccac ggacacgacc tctactccat ggcttggtta      360
ccggtttcca cccgttggcg gaccctgcgg aagataagca attcccacat cttcactagc      420
caaaggctcg atgaaaacca ccacctccgg cggcggaagc tcgacgagct ccttgccaga      480
gtggcggaga gcagcctggt cggggcagtg gtggatatgg gcgcggtagc tttcttgacg      540
agtctaaact tgctatccaa caccgtgttt tcgaaggatt tggtcgaacc aggattgggg      600
gctgtgcagg agatggagga ggtggtgtgg gggatcacgg aggaggccgg gaggcccaat      660
ttggtggatt atttccggt gctgcgaagg ctcgatccgc aggggacacg ccgtcggatg      720
atgggttatt tcgggaaaat gttcgaggtt ttcggggata tcattgacga gcggcttgaa      780
ttgagaaagc aacaaagtga tggtgattcc ccagctgcta caactaatga tgtgttggac      840
gttcttctga atattattga agacgctgaa attgaagaaa agcctaatag aactgatgtc      900
gaacacttca tagtggacct atttgtggcg gggagtgata cgacttccag caccgtcgaa      960
tgggcgatga cggaactcct ccgtaaaccg gagactctgg agagagcccg gtcggagctc     1020
catgagacca tcgccctaa aaacctggtc caagaggccg acatgccccg gctcccctac     1080
ttacaggccg tggtgaaaga aactttccgg ctccaccctc cggtgccgct cctactcccc     1140
cgcactgcgg agaaggacgc cgaactctgc ggcttcacgg tccccgcagg ggcccaaatc     1200
atggtgaacg cgtgggcgat cgggagagat cccgggacat gggaggaccc ggagtcattc     1260
ttgccggaga gattcttggg gtcggatgtg gacgtgaagg ggaggagttt cgagctgatt     1320 ccttcggcg agggaggag gatttgcccc ggattacctc tggcgataag gatggtgcat     1380
ttgatgttag gatcactgat ccatgggttc cggtggaagg tggctgacga tggaatgggg     1440
tcgccggaga ctgcgatgga catggatgag aagtttggca tcactttaca gaaggcgaag     1500
tcgttgtgcg ctgtcccaat ccggggtaa                                         1530

<210> SEQ ID NO 71
<211> LENGTH: 1530
<212> TYPE: DNA
<213> ORGANISM: Santalum album
<220> FEATURE:
<223> OTHER INFORMATION: SaCYP76F42 (CYP76-G13)

<400> SEQUENCE: 71
```

```
atggacttct taagttgtat cctgtctgtt ttgttcgcat gggcgctggt tcgagctctc      60
cgtacacttt ctagaggttc caaagctgcc ggcgggaggc ttccgccggg gccagtcccg     120
ttgccggtgg tgggaaacct gttaaaactc gggaacaaac cacacaagtc attggcggcg     180
ctggccaaat cctacgatcc catcatgtgt ctcaaacttg gtcacatgac acaattgtc      240 atctcaagtc ctaccgtagc caaagaggtt cttcaaaaac aagacgtcgc cttctgtaac     300
cgaaccaccc ctgacgccgt tcgagcccac ggacacgacc tctactccat ggcttggtta     360
ccggtttcca cccgttggcg gaccctgcga aagataagca actcccacat cttcactagc     420
caaaggctcg atgaaaacca ccacctccgg cggcagaagc tcgacgagct ccttgccagg     480
gtggcagaga gcagcctggt cggggcagcg gtggatatag gcgcggtagc tttcgtgacg     540
agtctaaact tgctatccaa cacagtgttt tcgaaggatt tggtcgaacc aggattgggg     600
gctgtgcagg agatgaagga ggtggtgtgg ggaatcatgg aggaagccgg gaggcccaat     660
ttggtggatt atttcccggt gctgcggagg ctcgatccgc aggggatacg ccgtcggatg     720
atgggttatt tcgggaaaat gttcgaggtt ttcggggata tcattgacga gcggcttgaa     780
ttgagaaagc aacaaagtga tggtgattcc ccagctgcta caactaatga tgtgttggac     840
gttcttctga atattattga agacgctgaa attgaagaaa agcctaatag aactgatgtc     900
gaacacttca tagtggacct atttgtggcg gggagtgata cgacttccag caccgtcgaa     960
tgggcgatga cggaactcct ccgtaaaccg gagactctgg agagagcccg gtcggagctc    1020
catgagacca tcggccctaa aaacctggtc caagaggccg acatgccccg gctcccctac    1080
ttacaggccg tggtgaaaga actttccgg ctccaccctc cggtgccgct cctactcccc    1140
cgcactgcgg agaaggacgc cgaactctgc ggcttcacgg tccccgcagg ggcccaaatc    1200
atggtgaacg cgtgggcgat cgggagagat cccgggacat gggaggaccc ggagtcattc    1260
ttgccggaga gattcttggg gtcggatgtg gacgtgaagg ggaggagttt cgagctgatt    1320
cctttcggcg gagggaggag gatttgcccc ggattacctc tggcgataag gatggtgcat    1380
ttgatgttag gatcactgat ccatgggttc cggtggaagg tggctgacga tggaatgggg    1440
tcgccggaga ctgcgatgga catggatgag aagtttggca tcactttaca gaaggcgaag    1500
tcgttgtgcg ctgtcccaat ccgggggtaa                                     1530
```

<210> SEQ ID NO 72
<211> LENGTH: 1530
<212> TYPE: DNA
<213> ORGANISM: Santalum album
<220> FEATURE:
<223> OTHER INFORMATION: SaCYP76F43 (CYP76-G18)

<400> SEQUENCE: 72

```
atggacttct taagttgtat cctgtttgtt ttattcgcgt gggcacttgt tcgggctctc      60
cctacacttt ctagaggttc caaagcagcc ggcgggaggc ttccgccggg gccagtcccg     120
ttgccggtgg tgggaaacct attaaaactc gggagcaaac cacacaagtc gctggcggag     180
ctggccaaat cctacggtcc tataatgtgt ctcaaactag gtcacataat cacaattgtc     240
atctcaactc ctaccgtcgc caaagaggtt ctccaaaaac aagacgtcgc cttctgtaac     300
cgaaccatcc ctgacgccgt tcgagcccac agacacgacc tctactccat ggcttggtta     360
ccggtttcca cccgttggcg gaccctgcga aagataagca actcccacat cttcactagc     420
caaaggctcg atgaaaacca ccacctccgg cggcagaagc tcgacgagct ccttgccagg     480
```

```
gtggcagaga gcagcctggt cggggcagcg gtggatatag gcgcggtagc tttcgtgacg    540
agtctaaact tgctatccaa cacagtgttt tcgaaggatt tggtcgaacc aggattgggg    600
gctgtgcagg agatgaagga ggtggtgtgg ggaatcatgg aggaagccgg gaggcccaat    660
ttggtggatt atttcccggt gctgcggagg ctcgatccgc aggggatacg ccgtcggatg    720
acgggtaatt tcgggaaaat gttggaggtt ttcggggata tcattgacga gcggcttgaa    780
tggagaaagc aacaaagtga tggtgattcc ccagctggta caactaatga tgtgttggac    840
gttcttctga atattcttga agacgctgaa atcgaagaaa agcctaatag aactgatgtc    900
gaacacctct tactggacct atttgtggcg gggagtgata cgacttccag caccgtcgaa    960
tgggcgatga ctgaactcct ccggaaaccg gagactctgg agagagcccg gtcggagctc   1020
catgagacca tcggccctaa aaacctggtc caagaggccg acatgccccg gctcccctac   1080
ttacaggccg tggtgaaaga aactttccgg ctccaccctc cggtgccgct cctactcccc   1140
cgcactgcgg agaaggacgc cgaactctgc ggcttcacgg tccccgcagg ggctcaaatc   1200
atggtgaacg cgtgggcgat cgggagagat cccgggacat ggaggacccc ggagtcattc   1260
ttgccggaga gattcttggg gtcggatgtg gacgtgaagg ggaggagttt cgagctgatt   1320
ccgttcggcg gaggggaggag gatttgcccc ggattacctc tggcgataag gatggtgcat   1380
ttgatgttag gatcactgat ccatgggttc cggtggaagg tgtttgacga tggaatgggg   1440
tcgccggaga ctgcgatgga catggatgag aagtttggca tcactttaca gaaggcgaag   1500
tcgttgtgcg ctgtcccaat ccggggggtaa                                   1530
```

<210> SEQ ID NO 73
<211> LENGTH: 509
<212> TYPE: PRT
<213> ORGANISM: Santalum album
<220> FEATURE:
<223> OTHER INFORMATION: SaCYP76F37v2 (CYP76-G14)

<400> SEQUENCE: 73

```
Met Asp Phe Leu Ser Cys Ile Leu Phe Val Leu Phe Ala Trp Ala Leu
 1               5                  10                  15

Val Arg Ala Leu Pro Thr Leu Ser Arg Gly Ser Lys Ala Ala Gly Gly
            20                  25                  30

Arg Leu Pro Pro Gly Pro Val Pro Leu Pro Val Val Gly Asn Leu Leu
        35                  40                  45

Lys Leu Gly Ser Lys Pro His Lys Ser Leu Ala Glu Leu Ala Lys Ser
    50                  55                  60

Tyr Gly Pro Ile Met Cys Leu Lys Leu Gly His Ile Ile Thr Ile Val
65                  70                  75                  80

Ile Ser Thr Pro Thr Val Ala Lys Glu Val Leu Gln Lys Gln Asp Val
                85                  90                  95

Ala Phe Cys Asn Arg Thr Ile Pro Asp Ala Val Arg Ala His Arg His
            100                 105                 110

Asp Leu His Ser Met Val Trp Leu Pro Val Ser Thr Arg Trp Arg Thr
        115                 120                 125

Leu Arg Lys Ile Ser Asn Ser His Ile Phe Ser Gln Arg Leu Asp
    130                 135                 140

Glu Asn His His Leu Arg Arg Arg Lys Leu Asp Glu Leu Leu Thr Arg
145                 150                 155                 160

Val Ala Glu Ser Ser Leu Val Gly Ala Val Val Asp Ile Gly Ala Val
                165                 170                 175
```

```
Ala Phe Leu Thr Ser Leu Asn Leu Leu Ser Asn Thr Val Phe Ser Lys
            180                 185                 190

Asp Leu Val Glu Pro Gly Leu Gly Ala Val Gln Glu Met Glu Glu Val
        195                 200                 205

Val Trp Gly Ile Thr Glu Glu Ala Gly Arg Pro Asn Leu Val Asp Tyr
    210                 215                 220

Phe Pro Val Leu Arg Arg Leu Asp Pro Gln Gly Thr Arg Arg Arg Met
225                 230                 235                 240

Met Gly Tyr Phe Gly Lys Met Phe Glu Val Phe Gly Asp Ile Ile Asp
                245                 250                 255

Glu Arg Leu Glu Leu Arg Lys Gln Gln Ser Asp Gly Asp Ser Pro Ala
            260                 265                 270

Ala Thr Thr Asn Asp Val Leu Asp Val Leu Leu Asn Ile Ile Glu Asp
        275                 280                 285

Ala Glu Ile Glu Glu Lys Pro Asn Arg Thr Asp Val Glu His Phe Leu
    290                 295                 300

Leu Asp Leu Phe Ala Ala Gly Ser Asp Thr Thr Ser Ser Thr Val Glu
305                 310                 315                 320

Trp Ala Met Thr Glu Leu Leu Arg Lys Pro Glu Thr Leu Glu Arg Ala
                325                 330                 335

Arg Ser Glu Leu His Glu Thr Ile Gly Pro Glu Asn Leu Val Gln Glu
            340                 345                 350

Ala Asp Leu Pro Arg Leu Pro Tyr Leu Gln Ala Val Val Lys Glu Thr
        355                 360                 365

Phe Arg Leu His Pro Val Pro Leu Leu Pro Arg Thr Ala Glu
    370                 375                 380

Lys Asp Ala Glu Leu Cys Gly Phe Thr Val Pro Ala Gly Ala Gln Ile
385                 390                 395                 400

Met Val Asn Ala Trp Ala Ile Gly Arg Asp Pro Gly Thr Trp Glu Asp
                405                 410                 415

Pro Glu Ser Phe Leu Pro Glu Arg Phe Leu Gly Ser Asp Val Asp Val
            420                 425                 430

Lys Gly Arg Ser Phe Glu Leu Ile Pro Phe Gly Gly Arg Arg Ile
        435                 440                 445

Cys Pro Gly Leu Pro Leu Ala Ile Arg Met Val His Leu Met Leu Gly
    450                 455                 460

Ser Leu Ile His Gly Phe Arg Trp Lys Val Asp Asp Asp Gly Met Gly
465                 470                 475                 480

Ser Pro Glu Thr Ala Met Asp Met Asp Glu Lys Phe Gly Ile Thr Leu
                485                 490                 495

Gln Lys Ala Lys Pro Leu Cys Ala Val Pro Ile Arg Gly
            500                 505

<210> SEQ ID NO 74
<211> LENGTH: 509
<212> TYPE: PRT
<213> ORGANISM: Santalum album
<220> FEATURE:
<223> OTHER INFORMATION: SaCYP76F39v2 (CYP76-G15)

<400> SEQUENCE: 74

Met Asp Phe Leu Ser Cys Ile Leu Ser Val Leu Phe Ala Trp Ala Leu
1               5                   10                  15

Val Arg Ala Leu Arg Lys Leu Ser Arg Gly Ser Lys Ala Ala Ser Gly
            20                  25                  30
```

```
Arg Leu Pro Pro Gly Pro Val Pro Trp Pro Val Val Gly Asn Leu Leu
         35                  40                  45
Lys Leu Gly Asn Lys Pro His Lys Ser Leu Ala Glu Leu Ala Lys Ser
 50                  55                  60
Tyr Gly Pro Ile Met Cys Leu Lys Leu Gly His Met Thr Thr Ile Val
 65                  70                  75                  80
Ile Ser Thr Pro Thr Val Ala Lys Glu Val Leu Gln Lys Gln Asp Val
                 85                  90                  95
Ala Phe Ser Asn Arg Thr Ile Pro Asp Ala Val Arg Ala Tyr Gly His
                100                 105                 110
Asp Leu Tyr Ser Met Ala Trp Leu Pro Val Ser Thr Arg Trp Arg Thr
            115                 120                 125
Leu Arg Lys Ile Ser Asn Ser His Ile Phe Thr Ser Gln Arg Leu Asp
130                 135                 140
Glu Asn His His Leu Arg Arg Lys Leu Asp Glu Leu Leu Ala Arg
145                 150                 155                 160
Val Ala Glu Ser Ser Leu Val Gly Ala Val Val Asp Met Gly Ala Val
                165                 170                 175
Ala Phe Leu Thr Ser Leu Asn Leu Leu Ser Asn Thr Val Phe Ser Lys
            180                 185                 190
Asp Leu Val Glu Pro Gly Leu Gly Ala Val Gln Glu Thr Lys Glu Val
        195                 200                 205
Val Trp Gly Met Met Glu Glu Ala Gly Arg Pro Asn Leu Val Asp Tyr
210                 215                 220
Phe Pro Val Leu Arg Arg Leu Asp Pro Gln Gly Ile Arg Arg Arg Met
225                 230                 235                 240
Thr Gly Tyr Phe Gly Lys Met Leu Glu Val Phe Gly Asp Ile Ile Asp
                245                 250                 255
Glu Arg Leu Glu Trp Arg Lys Gln Gln Ser Asp Gly Asp Ser Pro Ala
            260                 265                 270
Gly Thr Thr Asn Asp Val Leu Asp Val Leu Leu Asn Ile Ile Glu Asp
        275                 280                 285
Ala Glu Ile Glu Glu Lys Pro Asn Arg Thr Asp Val Glu His Phe Leu
290                 295                 300
Leu Asp Leu Phe Ala Ala Gly Ser Asp Thr Thr Ser Ser Thr Val Glu
305                 310                 315                 320
Trp Ala Met Thr Glu Leu Leu Arg Lys Pro Glu Thr Leu Glu Arg Ala
                325                 330                 335
Arg Ser Glu Leu His Glu Thr Ile Gly Pro Glu Asn Leu Val Gln Glu
            340                 345                 350
Ala Asp Leu Pro Arg Leu Pro Tyr Leu Gln Ala Val Val Lys Glu Thr
        355                 360                 365
Phe Arg Leu His Pro Pro Val Pro Leu Leu Leu Pro Arg Thr Ala Glu
370                 375                 380
Lys Asp Ala Glu Leu Cys Gly Phe Thr Val Pro Ala Gly Ala Gln Ile
385                 390                 395                 400
Met Val Asn Ala Trp Ala Ile Gly Arg Asp Pro Gly Thr Trp Glu Asp
                405                 410                 415
Pro Glu Ser Phe Leu Pro Glu Arg Phe Leu Gly Ser Asp Val Asp Val
            420                 425                 430
Lys Gly Arg Ser Phe Glu Leu Ile Pro Phe Gly Gly Gly Arg Arg Ile
        435                 440                 445
Cys Pro Gly Leu Pro Leu Ala Ile Arg Met Val His Leu Met Leu Gly
```

```
                450                 455                 460
Ser Leu Ile His Gly Phe Arg Trp Lys Val Asp Asp Gly Met Gly
465                 470                 475                 480

Ser Pro Glu Thr Ala Met Asp Met Asp Glu Lys Phe Gly Ile Thr Leu
                485                 490                 495

Gln Lys Ala Lys Pro Leu Cys Ala Val Pro Ile Arg Gly
                500                 505

<210> SEQ ID NO 75
<211> LENGTH: 509
<212> TYPE: PRT
<213> ORGANISM: Santalum album
<220> FEATURE:
<223> OTHER INFORMATION: SaCYP76F40 (CYP76-G16)

<400> SEQUENCE: 75

Met Asp Phe Leu Ser Cys Ile Leu Ser Val Leu Phe Ala Trp Ala Leu
1               5                   10                  15

Val Arg Ala Leu Arg Lys Leu Ser Arg Gly Ser Lys Ala Ala Ser Gly
            20                  25                  30

Arg Leu Pro Pro Gly Pro Val Pro Trp Pro Val Val Gly Asn Leu Leu
        35                  40                  45

Lys Leu Gly Asn Lys Pro His Lys Ser Leu Ala Glu Leu Ala Lys Ser
50                  55                  60

Tyr Gly Pro Ile Met Cys Leu Lys Leu Gly His Met Thr Thr Ile Val
65                  70                  75                  80

Ile Ser Thr Pro Thr Val Ala Lys Glu Val Leu Gln Lys Gln Asp Val
            85                  90                  95

Ala Phe Ser Asn Arg Thr Thr Pro Asp Ala Val Arg Ala His Gly His
        100                 105                 110

Asp Leu Tyr Ser Met Ala Trp Leu Pro Val Ser Thr Arg Trp Arg Thr
        115                 120                 125

Leu Arg Lys Ile Ser Asn Ser His Ile Phe Thr Ser Gln Arg Leu Asp
        130                 135                 140

Glu Asn His His Leu Arg Arg Arg Lys Leu Asp Glu Leu Leu Ala Arg
145                 150                 155                 160

Val Ala Glu Ser Ser Leu Val Gly Ala Val Asp Met Gly Ala Val
            165                 170                 175

Ala Phe Leu Thr Ser Leu Asn Leu Leu Ser Asn Thr Val Phe Ser Lys
        180                 185                 190

Asp Leu Val Glu Pro Gly Leu Gly Ala Val Gln Glu Thr Lys Glu Val
        195                 200                 205

Val Trp Gly Met Met Glu Glu Ala Gly Arg Pro Asn Leu Val Asp Tyr
210                 215                 220

Phe Pro Val Leu Arg Arg Leu Asp Pro Gln Gly Ile Arg Arg Arg Met
225                 230                 235                 240

Thr Gly Tyr Phe Gly Lys Met Leu Glu Val Phe Gly Asp Ile Ile Asp
            245                 250                 255

Glu Arg Leu Glu Trp Arg Lys Gln Gln Ser Asp Gly Asp Ser Pro Ala
        260                 265                 270

Gly Thr Thr Asn Asp Val Leu Asp Val Leu Leu Asn Ile Ile Glu Asp
        275                 280                 285

Ala Glu Ile Glu Glu Lys Pro Asn Arg Thr Asp Val Glu His Phe Ile
290                 295                 300

Val Asp Leu Phe Val Ala Gly Ser Asp Thr Thr Ser Ser Thr Val Glu
```

Trp Ala Met Thr Glu Leu Leu Arg Lys Pro Glu Thr Leu Glu Arg Ala
                325                 330                 335

Arg Ser Glu Leu His Glu Thr Ile Gly Pro Lys Asn Leu Val Gln Glu
                340                 345                 350

Ala Asp Met Pro Arg Leu Pro Tyr Leu Gln Ala Val Lys Glu Thr
                355                 360                 365

Phe Arg Leu His Pro Pro Val Pro Leu Leu Pro Arg Thr Ala Glu
    370                 375                 380

Lys Asp Ala Glu Leu Cys Gly Phe Thr Val Pro Ala Gly Ala Gln Ile
385                 390                 395                 400

Met Val Asn Ala Trp Ala Ile Gly Arg Asp Pro Gly Thr Trp Glu Asp
                405                 410                 415

Pro Glu Ser Phe Leu Pro Glu Arg Phe Leu Gly Ser Asp Val Asp Val
                420                 425                 430

Lys Gly Arg Ser Phe Glu Leu Ile Pro Phe Gly Gly Gly Arg Arg Ile
                435                 440                 445

Cys Pro Gly Leu Pro Leu Ala Ile Arg Met Val His Leu Met Leu Gly
                450                 455                 460

Ser Leu Ile His Gly Phe Arg Trp Lys Val Ala Asp Asp Gly Met Gly
465                 470                 475                 480

Ser Pro Glu Thr Ala Met Asp Met Asp Glu Lys Phe Gly Ile Thr Leu
                485                 490                 495

Gln Lys Ala Lys Ser Leu Cys Ala Val Pro Ile Arg Gly
                500                 505

<210> SEQ ID NO 76
<211> LENGTH: 509
<212> TYPE: PRT
<213> ORGANISM: Santalum album
<220> FEATURE:
<223> OTHER INFORMATION: SaCYP76F41 (CYP76-G17)

<400> SEQUENCE: 76

Met Asp Phe Leu Ser Cys Ile Leu Phe Val Leu Phe Ala Trp Ala Leu
1               5                   10                  15

Val His Ala Leu Arg Thr Leu Ser Arg Gly Ser Lys Ala Ala Ser Gly
                20                  25                  30

Arg Leu Pro Pro Gly Pro Val Pro Trp Pro Val Val Gly Asn Leu Leu
                35                  40                  45

Lys Leu Gly Asn Lys Pro His Lys Ser Leu Ala Glu Leu Ala Lys Ser
    50                  55                  60

Tyr Gly Pro Ile Met Cys Leu Lys Leu Gly His Met Thr Thr Ile Val
65                  70                  75                  80

Ile Ser Thr Pro Thr Val Ala Lys Glu Val Leu Gln Lys Gln Asp Val
                85                  90                  95

Ala Phe Ser Asn Arg Thr Thr Pro Asp Ala Val Arg Ala His Gly His
                100                 105                 110

Asp Leu Tyr Ser Met Ala Trp Leu Pro Val Ser Thr Arg Trp Arg Thr
                115                 120                 125

Leu Arg Lys Ile Ser Asn Ser His Ile Phe Thr Ser Gln Arg Leu Asp
                130                 135                 140

Glu Asn His His Leu Arg Arg Arg Lys Leu Asp Glu Leu Leu Ala Arg
145                 150                 155                 160

Val Ala Glu Ser Ser Leu Val Gly Ala Val Val Asp Met Gly Ala Val 165                 170                 175
Ala Phe Leu Thr Ser Leu Asn Leu Leu Ser Asn Thr Val Phe Ser Lys
            180                 185                 190

Asp Leu Val Glu Pro Gly Leu Gly Ala Val Gln Glu Met Glu Glu Val
        195                 200                 205

Val Trp Gly Ile Thr Glu Glu Ala Gly Arg Pro Asn Leu Val Asp Tyr
    210                 215                 220

Phe Pro Val Leu Arg Arg Leu Asp Pro Gln Gly Thr Arg Arg Arg Met
225                 230                 235                 240

Met Gly Tyr Phe Gly Lys Met Phe Glu Val Phe Gly Asp Ile Ile Asp
                245                 250                 255

Glu Arg Leu Glu Leu Arg Lys Gln Gln Ser Asp Gly Asp Ser Pro Ala
            260                 265                 270

Ala Thr Thr Asn Asp Val Leu Asp Val Leu Leu Asn Ile Ile Glu Asp
        275                 280                 285

Ala Glu Ile Glu Glu Lys Pro Asn Arg Thr Asp Val Glu His Phe Ile
    290                 295                 300

Val Asp Leu Phe Val Ala Gly Ser Asp Thr Thr Ser Ser Thr Val Glu
305                 310                 315                 320

Trp Ala Met Thr Glu Leu Leu Arg Lys Pro Glu Thr Leu Glu Arg Ala
                325                 330                 335

Arg Ser Glu Leu His Glu Thr Ile Gly Pro Lys Asn Leu Val Gln Glu
            340                 345                 350

Ala Asp Met Pro Arg Leu Pro Tyr Leu Gln Ala Val Val Lys Glu Thr
        355                 360                 365

Phe Arg Leu His Pro Pro Val Pro Leu Leu Pro Arg Thr Ala Glu
    370                 375                 380

Lys Asp Ala Glu Leu Cys Gly Phe Thr Val Pro Ala Gly Ala Gln Ile
385                 390                 395                 400

Met Val Asn Ala Trp Ala Ile Gly Arg Asp Pro Gly Thr Trp Glu Asp
                405                 410                 415

Pro Glu Ser Phe Leu Pro Glu Arg Phe Leu Gly Ser Asp Val Asp Val
            420                 425                 430

Lys Gly Arg Ser Phe Glu Leu Ile Pro Phe Gly Gly Arg Arg Ile
        435                 440                 445

Cys Pro Gly Leu Pro Leu Ala Ile Arg Met Val His Leu Met Leu Gly
    450                 455                 460

Ser Leu Ile His Gly Phe Arg Trp Lys Val Ala Asp Asp Gly Met Gly
465                 470                 475                 480

Ser Pro Glu Thr Ala Met Asp Met Asp Glu Lys Phe Gly Ile Thr Leu
                485                 490                 495

Gln Lys Ala Lys Ser Leu Cys Ala Val Pro Ile Arg Gly
            500                 505

<210> SEQ ID NO 77
<211> LENGTH: 509
<212> TYPE: PRT
<213> ORGANISM: Santalum album
<220> FEATURE:
<223> OTHER INFORMATION: SaCYP76F42 (CYP76-G13)

<400> SEQUENCE: 77

Met Asp Phe Leu Ser Cys Ile Leu Ser Val Leu Phe Ala Trp Ala Leu
1               5                   10                  15

Val Arg Ala Leu Arg Thr Leu Ser Arg Gly Ser Lys Ala Ala Gly Gly

```
                    20                  25                  30
Arg Leu Pro Pro Gly Pro Val Pro Leu Pro Val Val Gly Asn Leu Leu
                35                  40                  45

Lys Leu Gly Asn Lys Pro His Lys Ser Leu Ala Ala Leu Ala Lys Ser
 50                  55                  60

Tyr Asp Pro Ile Met Cys Leu Lys Leu Gly His Met Thr Thr Ile Val
 65                  70                  75                  80

Ile Ser Ser Pro Thr Val Ala Lys Glu Val Leu Gln Lys Gln Asp Val
                85                  90                  95

Ala Phe Cys Asn Arg Thr Thr Pro Asp Ala Val Arg Ala His Gly His
                100                 105                 110

Asp Leu Tyr Ser Met Ala Trp Leu Pro Val Ser Thr Arg Trp Arg Thr
                115                 120                 125

Leu Arg Lys Ile Ser Asn Ser His Ile Phe Thr Ser Gln Arg Leu Asp
                130                 135                 140

Glu Asn His His Leu Arg Arg Gln Lys Leu Asp Glu Leu Leu Ala Arg
145                 150                 155                 160

Val Ala Glu Ser Ser Leu Val Gly Ala Ala Val Asp Ile Gly Ala Val
                165                 170                 175

Ala Phe Val Thr Ser Leu Asn Leu Leu Ser Asn Thr Val Phe Ser Lys
                180                 185                 190

Asp Leu Val Glu Pro Gly Leu Gly Ala Val Gln Glu Met Lys Glu Val
                195                 200                 205

Val Trp Gly Ile Met Glu Glu Ala Gly Arg Pro Asn Leu Val Asp Tyr
                210                 215                 220

Phe Pro Val Leu Arg Arg Leu Asp Pro Gln Gly Ile Arg Arg Arg Met
225                 230                 235                 240

Met Gly Tyr Phe Gly Lys Met Phe Glu Val Phe Gly Asp Ile Ile Asp
                245                 250                 255

Glu Arg Leu Glu Leu Arg Lys Gln Gln Ser Asp Gly Asp Ser Pro Ala
                260                 265                 270

Ala Thr Thr Asn Asp Val Leu Asp Val Leu Leu Asn Ile Ile Glu Asp
                275                 280                 285

Ala Glu Ile Glu Glu Lys Pro Asn Arg Thr Asp Val Glu His Phe Ile
                290                 295                 300

Val Asp Leu Phe Val Ala Gly Ser Asp Thr Thr Ser Ser Thr Val Glu
305                 310                 315                 320

Trp Ala Met Thr Glu Leu Leu Arg Lys Pro Glu Thr Leu Glu Arg Ala
                325                 330                 335

Arg Ser Glu Leu His Glu Thr Ile Gly Pro Lys Asn Leu Val Gln Glu
                340                 345                 350

Ala Asp Met Pro Arg Leu Pro Tyr Leu Gln Ala Val Val Lys Glu Thr
                355                 360                 365

Phe Arg Leu His Pro Pro Val Pro Leu Leu Pro Arg Thr Ala Glu
                370                 375                 380

Lys Asp Ala Glu Leu Cys Gly Phe Thr Val Pro Ala Gly Ala Gln Ile
385                 390                 395                 400

Met Val Asn Ala Trp Ala Ile Gly Arg Asp Pro Gly Thr Trp Glu Asp
                405                 410                 415

Pro Glu Ser Phe Leu Pro Glu Arg Phe Leu Gly Ser Asp Val Asp Val
                420                 425                 430

Lys Gly Arg Ser Phe Glu Leu Ile Pro Phe Gly Gly Arg Arg Ile
                435                 440                 445
```

```
Cys Pro Gly Leu Pro Leu Ala Ile Arg Met Val His Leu Met Leu Gly
            450                 455                 460

Ser Leu Ile His Gly Phe Arg Trp Lys Val Ala Asp Asp Gly Met Gly
465                 470                 475                 480

Ser Pro Glu Thr Ala Met Asp Met Asp Glu Lys Phe Gly Ile Thr Leu
                485                 490                 495

Gln Lys Ala Lys Ser Leu Cys Ala Val Pro Ile Arg Gly
            500                 505

<210> SEQ ID NO 78
<211> LENGTH: 509
<212> TYPE: PRT
<213> ORGANISM: Santalum album
<220> FEATURE:
<223> OTHER INFORMATION: SaCYP76F43 (CYP76-G18)

<400> SEQUENCE: 78

Met Asp Phe Leu Ser Cys Ile Leu Phe Val Leu Phe Ala Trp Ala Leu
  1               5                  10                  15

Val Arg Ala Leu Pro Thr Leu Ser Arg Gly Ser Lys Ala Ala Gly Gly
             20                  25                  30

Arg Leu Pro Pro Gly Pro Val Pro Leu Pro Val Val Gly Asn Leu Leu
         35                  40                  45

Lys Leu Gly Ser Lys Pro His Lys Ser Leu Ala Glu Leu Ala Lys Ser
 50                  55                  60

Tyr Gly Pro Ile Met Cys Leu Lys Leu Gly His Ile Ile Thr Ile Val
 65                  70                  75                  80

Ile Ser Thr Pro Thr Val Ala Lys Glu Val Leu Gln Lys Gln Asp Val
                 85                  90                  95

Ala Phe Cys Asn Arg Thr Ile Pro Asp Ala Val Arg Ala His Arg His
            100                 105                 110

Asp Leu Tyr Ser Met Ala Trp Leu Pro Val Ser Thr Arg Trp Arg Thr
        115                 120                 125

Leu Arg Lys Ile Ser Asn Ser His Ile Phe Thr Ser Gln Arg Leu Asp
130                 135                 140

Glu Asn His His Leu Arg Arg Gln Lys Leu Asp Glu Leu Leu Ala Arg
145                 150                 155                 160

Val Ala Glu Ser Ser Leu Val Gly Ala Val Asp Ile Gly Ala Val
                165                 170                 175

Ala Phe Val Thr Ser Leu Asn Leu Leu Ser Asn Thr Val Phe Ser Lys
            180                 185                 190

Asp Leu Val Glu Pro Gly Leu Gly Ala Val Gln Glu Met Lys Glu Val
        195                 200                 205

Val Trp Gly Ile Met Glu Glu Ala Gly Arg Pro Asn Leu Val Asp Tyr
    210                 215                 220

Phe Pro Val Leu Arg Arg Leu Asp Pro Gln Gly Ile Arg Arg Arg Met
225                 230                 235                 240

Thr Gly Asn Phe Gly Lys Met Leu Glu Val Phe Gly Asp Ile Ile Asp
                245                 250                 255

Glu Arg Leu Glu Trp Arg Lys Gln Gln Ser Asp Gly Asp Ser Pro Ala
            260                 265                 270

Gly Thr Thr Asn Asp Val Leu Asp Val Leu Asn Ile Leu Glu Asp
        275                 280                 285

Ala Glu Ile Glu Glu Lys Pro Asn Arg Thr Asp Val Glu His Leu Leu
    290                 295                 300
```

Leu Asp Leu Phe Val Ala Gly Ser Asp Thr Thr Ser Ser Thr Val Glu
305                 310                 315                 320

Trp Ala Met Thr Glu Leu Leu Arg Lys Pro Glu Thr Leu Glu Arg Ala
            325                 330                 335

Arg Ser Glu Leu His Glu Thr Ile Gly Pro Lys Asn Leu Val Gln Glu
        340                 345                 350

Ala Asp Met Pro Arg Leu Pro Tyr Leu Gln Ala Val Val Lys Glu Thr
    355                 360                 365

Phe Arg Leu His Pro Pro Val Pro Leu Leu Pro Arg Thr Ala Glu
370                 375                 380

Lys Asp Ala Glu Leu Cys Gly Phe Thr Val Pro Ala Gly Ala Gln Ile
385                 390                 395                 400

Met Val Asn Ala Trp Ala Ile Gly Arg Asp Pro Gly Thr Trp Glu Asp
                405                 410                 415

Pro Glu Ser Phe Leu Pro Glu Arg Phe Leu Gly Ser Asp Val Asp Val
            420                 425                 430

Lys Gly Arg Ser Phe Glu Leu Ile Pro Phe Gly Gly Arg Arg Ile
        435                 440                 445

Cys Pro Gly Leu Pro Leu Ala Ile Arg Met Val His Leu Met Leu Gly
450                 455                 460

Ser Leu Ile His Gly Phe Arg Trp Lys Val Phe Asp Asp Gly Met Gly
465                 470                 475                 480

Ser Pro Glu Thr Ala Met Asp Met Asp Glu Lys Phe Gly Ile Thr Leu
                485                 490                 495

Gln Lys Ala Lys Ser Leu Cys Ala Val Pro Ile Arg Gly
            500                 505

<210> SEQ ID NO 79
<211> LENGTH: 483
<212> TYPE: PRT
<213> ORGANISM: Artificial Sequence
<220> FEATURE:
<223> OTHER INFORMATION: CYP720B4
<300> PUBLICATION INFORMATION:
<308> DATABASE ACCESSION NUMBER: Genbank ADR78276
<309> DATABASE ENTRY DATE: 2011-12-08

<400> SEQUENCE: 79

Met Ala Pro Met Ala Asp Gln Ile Ser Leu Leu Val Val Phe Thr
1               5                   10                  15

Val Ala Val Ala Leu Leu His Leu Ile His Arg Trp Trp Asn Ile Gln
                20                  25                  30

Arg Gly Pro Lys Met Ser Asn Lys Glu Val His Leu Pro Pro Gly Ser
            35                  40                  45

Thr Gly Trp Pro Leu Ile Gly Glu Thr Phe Ser Tyr Tyr Arg Ser Met
    50                  55                  60

Thr Ser Asn His Pro Arg Lys Phe Ile Asp Asp Arg Glu Lys Arg Tyr
65                  70                  75                  80

Asp Ser Asp Ile Phe Ile Ser His Leu Phe Gly Gly Arg Thr Val Val
                85                  90                  95

Ser Ala Asp Pro Gln Phe Asn Lys Phe Val Leu Gln Asn Glu Gly Arg
            100                 105                 110

Phe Phe Gln Ala Gln Tyr Pro Lys Ala Leu Lys Ala Leu Ile Gly Asn
        115                 120                 125

Tyr Gly Leu Leu Ser Val His Gly Asp Leu Gln Arg Lys Leu His Gly
    130                 135                 140

Ile Ala Val Asn Leu Leu Arg Phe Glu Arg Leu Lys Val Asp Phe Met
145                 150                 155                 160

Glu Glu Ile Gln Asn Leu Val His Ser Thr Leu Asp Arg Trp Ala Asp
            165                 170                 175

Met Lys Glu Ile Ser Leu Gln Asn Glu Cys His Gln Met Val Leu Asn
        180                 185                 190

Leu Met Ala Lys Gln Leu Leu Asp Leu Ser Pro Ser Lys Glu Thr Ser
    195                 200                 205

Asp Ile Cys Glu Leu Phe Val Asp Tyr Thr Asn Ala Val Ile Ala Ile
210                 215                 220

Pro Ile Lys Ile Pro Gly Ser Thr Tyr Ala Lys Gly Leu Lys Ala Arg
225                 230                 235                 240

Glu Leu Leu Ile Lys Lys Ile Ser Glu Met Ile Lys Glu Arg Arg Asn
            245                 250                 255

His Pro Glu Val Val His Asn Asp Leu Leu Thr Lys Leu Val Glu Glu
        260                 265                 270

Gly Leu Ile Ser Asp Glu Ile Ile Cys Asp Phe Ile Leu Phe Leu Leu
    275                 280                 285

Phe Ala Gly His Glu Thr Ser Ser Arg Ala Met Thr Phe Ala Ile Lys
290                 295                 300

Phe Leu Thr Tyr Cys Pro Lys Ala Leu Lys Gln Met Lys Glu Glu His
305                 310                 315                 320

Asp Ala Ile Leu Lys Ser Lys Gly Gly His Lys Leu Asn Trp Asp
            325                 330                 335

Asp Tyr Lys Ser Met Ala Phe Thr Gln Cys Val Ile Asn Glu Thr Leu
        340                 345                 350

Arg Leu Gly Asn Phe Gly Pro Gly Val Phe Arg Glu Ala Lys Glu Asp
    355                 360                 365

Thr Lys Val Lys Asp Cys Leu Ile Pro Lys Gly Trp Val Val Phe Ala
370                 375                 380

Phe Leu Thr Ala Thr His Leu His Glu Lys Phe His Asn Glu Ala Leu
385                 390                 395                 400

Thr Phe Asn Pro Trp Arg Trp Gln Leu Asp Lys Asp Val Pro Asp Asp
            405                 410                 415

Ser Leu Phe Ser Pro Phe Gly Gly Ala Arg Leu Cys Pro Gly Ser
        420                 425                 430

His Leu Ala Lys Leu Glu Leu Ser Leu Phe Leu His Ile Phe Ile Thr
    435                 440                 445

Arg Phe Ser Trp Glu Ala Arg Ala Asp Asp Arg Thr Ser Tyr Phe Pro
450                 455                 460

Leu Pro Tyr Leu Thr Lys Gly Phe Pro Ile Ser Leu His Gly Arg Val
465                 470                 475                 480

Glu Asn Glu

<210> SEQ ID NO 80
<211> LENGTH: 501
<212> TYPE: PRT
<213> ORGANISM: Camptotheca acuminate
<220> FEATURE:
<223> OTHER INFORMATION: CYP76B4 geraniol-10-hydroxylase
<300> PUBLICATION INFORMATION:
<308> DATABASE ACCESSION NUMBER: Genbank AES93118
<309> DATABASE ENTRY DATE: 2011-11-09

<400> SEQUENCE: 80

-continued

```
Met Asp Ile Met Asp Phe Met Ser Phe Phe Ile Met Phe Phe Gly His
1               5                   10                  15

Leu Gln Ile Val Ser Ser Pro Thr Thr Ala Ala Ser Cys Lys Gly Cys
            20                  25                  30

Lys Lys Ala Ser Thr Gly Pro Lys Pro Phe Pro Val Ile Gly Asn Leu
            35                  40                  45

Leu Asp Val Val Gly Asn Gln Pro His Lys Ser Leu Ala Asn Leu Ala
50                      55                  60

Lys Thr His Gly Pro Leu Met Thr Leu Lys Leu Gly Gln Ile Thr Thr
65                      70                  75                  80

Val Val Val Ser Ser Ser Thr Met Ala Lys Gln Ile Leu Gln Asn His
                85                  90                  95

Asp Leu Tyr Phe Ser Asn Arg Tyr Thr Arg Asp Ala Ile Arg Ala Leu
            100                 105                 110

Asn Gln Asp Gln Phe Ser Val Ile Trp Leu Pro Val Val Thr Arg Trp
            115                 120                 125

Arg Asn Leu Arg Lys Ile Leu Asn Leu Tyr Met Leu Ser Thr Glu Arg
            130                 135                 140

Leu Gly Ala Asn Gln Pro Ile Arg Cys Gln Lys Val Glu Glu Leu Ile
145                 150                 155                 160

Ala Tyr Val Arg Gln Ser Cys Gln Ala Ser Val Ser Val Asp Ile Gly
                165                 170                 175

Gln Ala Ala Phe Arg Thr Met Ile Asn Leu Thr Ser Lys Thr Ile Phe
                180                 185                 190

Ser Val Asp Leu Ala Asp Pro Ser Ser Asp Thr Ala Gln Glu Leu Lys
            195                 200                 205

Glu Leu Phe Trp Arg Ile Met Glu Glu Leu Gly Lys Pro Asn Leu Ala
            210                 215                 220

Asp Tyr Phe Pro Val Leu Arg Lys Leu Asp Pro Gln Gly Ile Arg Arg
225                 230                 235                 240

Arg Thr Thr Ile His Phe Ala Lys Val Phe Asp Leu Phe Asp Arg Met
                245                 250                 255

Ile Asp Gln Arg Leu Glu Leu Leu Arg Ser Asp Asp Cys Cys Thr Gly
            260                 265                 270

Asn Asp Leu Leu Asp Ser Leu Leu Asn Ile Ser Gln Asn Asn Ser Asp
            275                 280                 285

Glu Ile Asp Gln Asn Gln Ile Lys Arg Met Leu Met Asp Val Phe Ile
            290                 295                 300

Ala Ala Thr Asp Thr Thr Ser Ser Thr Leu Glu Trp Ala Met Thr Glu
305                 310                 315                 320

Leu Leu Arg Asn Pro Glu Thr Leu Leu Lys Ala Lys Ala Glu Leu Gln
                325                 330                 335

Gln Ile Val Gly Lys Gly Lys Leu Val Glu Glu Leu Asp Ile Ala Arg
                340                 345                 350

Leu Pro Tyr Leu Gln Ala Ile Val Lys Glu Thr Phe Arg Leu His Thr
            355                 360                 365

Thr Val Pro Phe Leu Ile Pro Arg Gln Val Asp Glu Asp Val Glu Val
370                 375                 380

Cys Gly Phe Thr Val Pro Lys Gly Ala Gln Val Leu Val Asn Ala Trp
385                 390                 395                 400

Ala Ile Gly His Asp Pro Ser Ile Trp Pro Lys Pro Asp Ser Phe Met
                405                 410                 415

Pro Glu Arg Phe Leu Glu Ser Glu Val Asp Val Arg Gly Leu Asp Phe
```

```
                        420                 425                 430
Glu Leu Ile Pro Phe Gly Gly Arg Arg Ile Cys Pro Gly Ser Ala
                435                 440                 445

Leu Ala Leu Arg Met Leu His Leu Met Leu Gly Ser Leu Ile Asn Ser
    450                 455                 460

Phe Asp Trp Arg Leu Glu Asp Gly Ile Ala Pro Asn Asp Met Asp Met
465                 470                 475                 480

Glu Glu Lys Phe Gly Leu Ser Leu Gln Lys Ala Arg Pro Leu Leu Phe
                485                 490                 495

Ala Pro Val His Ile
                500

<210> SEQ ID NO 81
<211> LENGTH: 493
<212> TYPE: PRT
<213> ORGANISM: Catharanthus roseus
<220> FEATURE:
<223> OTHER INFORMATION: CYP76B6 geraniol-10-hydroxylase
<300> PUBLICATION INFORMATION:
<308> DATABASE ACCESSION NUMBER: Genbank Q8VWZ7
<309> DATABASE ENTRY DATE: 2013-04-03

<400> SEQUENCE: 81

Met Asp Tyr Leu Thr Ile Ile Leu Thr Leu Leu Phe Ala Leu Thr Leu
1               5                   10                  15

Tyr Glu Ala Phe Ser Tyr Leu Ser Arg Arg Thr Lys Asn Leu Pro Pro
            20                  25                  30

Gly Pro Ser Pro Leu Pro Phe Ile Gly Ser Leu His Leu Leu Gly Asp
        35                  40                  45

Gln Pro His Lys Ser Leu Ala Lys Leu Ser Lys Lys His Gly Pro Ile
    50                  55                  60

Met Ser Leu Lys Leu Gly Gln Ile Thr Thr Ile Val Ile Ser Ser Ser
65                  70                  75                  80

Thr Met Ala Lys Glu Val Leu Gln Lys Gln Asp Leu Ala Phe Ser Ser
                85                  90                  95

Arg Ser Val Pro Asn Ala Leu His Ala His Asn Gln Phe Lys Phe Ser
            100                 105                 110

Val Val Trp Leu Pro Val Ala Ser Arg Trp Arg Ser Leu Arg Lys Val
        115                 120                 125

Leu Asn Ser Asn Ile Phe Ser Gly Asn Arg Leu Asp Ala Asn Gln His
    130                 135                 140

Leu Arg Thr Arg Lys Val Gln Glu Leu Ile Ala Tyr Cys Arg Lys Asn
145                 150                 155                 160

Ser Gln Ser Gly Glu Ala Val Asp Val Gly Arg Ala Ala Phe Arg Thr
                165                 170                 175

Ser Leu Asn Leu Leu Ser Asn Leu Ile Phe Ser Lys Asp Leu Thr Asp
            180                 185                 190

Pro Tyr Ser Asp Ser Ala Lys Glu Phe Lys Asp Leu Val Trp Asn Ile
        195                 200                 205

Met Val Glu Ala Gly Lys Pro Asn Leu Val Asp Phe Phe Pro Leu Leu
    210                 215                 220

Glu Lys Val Asp Pro Gln Gly Ile Arg His Arg Met Thr Ile His Phe
225                 230                 235                 240

Gly Glu Val Leu Lys Leu Phe Gly Gly Leu Val Asn Glu Arg Leu Glu
                245                 250                 255

Gln Arg Arg Ser Lys Gly Glu Lys Asn Asp Val Leu Asp Val Leu Leu
```

```
                    260                 265                 270
Thr Thr Ser Gln Glu Ser Pro Glu Glu Ile Asp Arg Thr His Ile Glu
            275                 280                 285

Arg Met Cys Leu Asp Leu Phe Val Ala Gly Thr Asp Thr Thr Ser Ser
        290                 295                 300

Thr Leu Glu Trp Ala Met Ser Glu Met Leu Lys Asn Pro Asp Lys Met
305                 310                 315                 320

Lys Lys Thr Gln Asp Glu Leu Ala Gln Val Ile Gly Arg Gly Lys Thr
                325                 330                 335

Ile Glu Glu Ser Asp Ile Asn Arg Leu Pro Tyr Leu Arg Cys Val Met
            340                 345                 350

Lys Glu Thr Leu Arg Ile His Pro Pro Val Pro Phe Leu Ile Pro Arg
        355                 360                 365

Lys Val Glu Gln Ser Val Glu Val Cys Gly Tyr Asn Val Pro Lys Gly
    370                 375                 380

Ser Gln Val Leu Val Asn Ala Trp Ala Ile Gly Arg Asp Glu Thr Val
385                 390                 395                 400

Trp Asp Asp Ala Leu Ala Phe Lys Pro Glu Arg Phe Met Glu Ser Glu
                405                 410                 415

Leu Asp Ile Arg Gly Arg Asp Phe Glu Leu Ile Pro Phe Gly Ala Gly
            420                 425                 430

Arg Arg Ile Cys Pro Gly Leu Pro Leu Ala Leu Arg Thr Val Pro Leu
        435                 440                 445

Met Leu Gly Ser Leu Leu Asn Ser Phe Asn Trp Lys Leu Glu Gly Gly
    450                 455                 460

Met Ala Pro Lys Asp Leu Asp Met Glu Glu Lys Phe Gly Ile Thr Leu
465                 470                 475                 480

Gln Lys Ala His Pro Leu Arg Ala Val Pro Ser Thr Leu
                485                 490

<210> SEQ ID NO 82
<211> LENGTH: 495
<212> TYPE: PRT
<213> ORGANISM: Swertia mussotii
<220> FEATURE:
<223> OTHER INFORMATION: CYP76B4 geraniol-10-hydroxylase
<300> PUBLICATION INFORMATION:
<308> DATABASE ACCESSION NUMBER: Genbank D1MI46
<309> DATABASE ENTRY DATE: 2013-04-03

<400> SEQUENCE: 82

Met Asp Phe Asp Phe Leu Thr Ile Ala Ile Gly Phe Leu Phe Thr Ile
1               5                   10                  15

Thr Leu Tyr Gln Ala Leu Asn Phe Phe Ser Arg Lys Ser Lys Asn Leu
            20                  25                  30

Pro Pro Gly Pro Ser Pro Leu Pro Leu Ile Gly Asn Leu His Leu Leu
        35                  40                  45

Gly Asp Gln Pro His Lys Ser Leu Ala Lys Leu Ala Lys Lys His Gly
    50                  55                  60

Pro Ile Met Gly Leu Gln Leu Gly Gln Val Thr Thr Ile Val Val Thr
65                  70                  75                  80

Ser Ser Gly Met Ala Lys Glu Val Leu Gln Lys Gln Asp Leu Ala Phe
                85                  90                  95

Ser Ser Arg Ser Ile Pro Asn Ala Ile His Ala His Asp Gln Tyr Lys
            100                 105                 110

Tyr Ser Val Ile Trp Leu Pro Val Ala Ser Arg Trp Arg Gly Leu Arg
```

```
            115                 120                 125
Lys Ala Leu Asn Ser Asn Met Phe Ser Gly Asn Arg Leu Asp Ala Asn
130                 135                 140

Gln His Leu Arg Ser Arg Lys Val Gln Glu Leu Ile Ala Tyr Cys Arg
145                 150                 155                 160

Lys Ser Ser Gln Thr Gly Asp Ala Ile Asp Val Gly Arg Ala Ala Phe
                165                 170                 175

Arg Thr Ser Leu Asn Leu Leu Ser Asn Thr Met Phe Ser Lys Asp Leu
            180                 185                 190

Thr Asp Pro Tyr Ser Asp Ser Ala Lys Glu Phe Lys Asp Leu Val Trp
        195                 200                 205

Asn Val Met Val Glu Ala Gly Lys Pro Asn Leu Val Asp Tyr Phe Pro
210                 215                 220

Leu Leu Asp Lys Val Asp Pro Gln Gly Ile Arg Lys Arg Met Thr Ile
225                 230                 235                 240

His Phe Gly Lys Ile Leu Glu Leu Phe Gly Gly Leu Ile Asp Glu Arg
                245                 250                 255

Leu Gln Gln Lys Lys Ala Lys Gly Val Asn Asp Asp Val Leu Asp Val
            260                 265                 270

Leu Leu Thr Thr Ser Glu Glu Ser Pro Glu Glu Ile Asp Arg Thr His
        275                 280                 285

Ile Gln Arg Met Cys Leu Asp Leu Phe Val Ala Gly Thr Asp Thr Thr
290                 295                 300

Ser Ser Thr Leu Glu Trp Ala Met Ser Glu Met Leu Lys Asn Pro Glu
305                 310                 315                 320

Lys Met Lys Ala Ala Gln Ala Glu Leu Ala Gln Val Ile Gly Lys Gly
                325                 330                 335

Lys Ala Val Glu Glu Ala Asp Leu Ala Arg Leu Pro Tyr Leu Arg Cys
            340                 345                 350

Ala Ile Lys Glu Thr Leu Arg Ile His Pro Pro Val Pro Leu Leu Ile
        355                 360                 365

Pro Arg Arg Thr Glu Gln Glu Val Glu Val Cys Gly Tyr Thr Val Pro
370                 375                 380

Lys Asn Ser Gln Val Leu Val Asn Val Trp Ala Ile Ser Arg Asp Asp
385                 390                 395                 400

Ala Ile Trp Lys Asp Pro Leu Ser Phe Lys Pro Glu Arg Phe Leu Glu
                405                 410                 415

Ser Glu Leu Glu Met Arg Gly Lys Asp Phe Glu Leu Ile Pro Phe Gly
            420                 425                 430

Ala Gly Arg Arg Ile Cys Pro Gly Leu Pro Leu Ala Val Arg Met Val
        435                 440                 445

Pro Val Met Leu Gly Ser Leu Leu Asn Ser Phe Asp Trp Lys Leu Glu
450                 455                 460

Gly Gly Ile Ala Pro Lys Asp Leu Asp Met Glu Glu Lys Phe Gly Ile
465                 470                 475                 480

Thr Leu Gln Lys Ala His Pro Leu Arg Ala Val Ala Thr Pro Leu
                485                 490                 495

<210> SEQ ID NO 83
<211> LENGTH: 499
<212> TYPE: PRT
<213> ORGANISM: Oryza sativa
<220> FEATURE:
<223> OTHER INFORMATION: CYP76M7 ent-cassadiene C11a-hydroxylase
<300> PUBLICATION INFORMATION:
```

<308> DATABASE ACCESSION NUMBER: NCBI NP_001047185
<309> DATABASE ENTRY DATE: 2010-06-08

<400> SEQUENCE: 83

| | | | | | | | | | | | | | | |
|---|---|---|---|---|---|---|---|---|---|---|---|---|---|---|
| Met | Glu | Asn | Ser | Gln | Val | Trp | Leu | Leu | Trp | Gly | Ala | Leu | Ser | Val | Ala |
| 1 | | | | 5 | | | | | 10 | | | | | 15 | |
| Val | Leu | Phe | Tyr | Leu | Ser | Thr | Leu | Arg | Arg | Tyr | Ala | Gly | Gly | Lys | |
| | | | 20 | | | | | 25 | | | | | 30 | | |
| Pro | Leu | Pro | Pro | Gly | Pro | Thr | Pro | Leu | Pro | Ile | Gly | Asn | Leu | His | |
| | | 35 | | | | 40 | | | | 45 | | | | | |
| Leu | Ala | Gly | Gly | Thr | Phe | His | His | Lys | Leu | Arg | Asp | Leu | Ala | Arg | Val |
| | 50 | | | | | 55 | | | | | 60 | | | | |
| His | Gly | Pro | Val | Met | Thr | Leu | Lys | Leu | Gly | Leu | Ala | Thr | Asn | Val | Val |
| 65 | | | | | 70 | | | | | 75 | | | | | 80 |
| Ile | Ser | Ser | Arg | Glu | Ala | Ala | Ile | Glu | Ala | Tyr | Thr | Lys | Tyr | Asp | Arg |
| | | | | 85 | | | | | 90 | | | | | 95 | |
| His | Leu | Ala | Ala | Arg | Ala | Thr | Pro | Asp | Thr | Phe | Arg | Ala | Cys | Gly | Phe |
| | | | 100 | | | | | 105 | | | | | 110 | | |
| Ala | Asp | Arg | Ser | Met | Val | Phe | Ile | Pro | Ser | Ser | Asp | Pro | Gln | Trp | Lys |
| | | 115 | | | | | 120 | | | | | 125 | | | |
| Ala | Leu | Arg | Gly | Ile | Gln | Gly | Ser | His | Val | Phe | Thr | Pro | Arg | Gly | Leu |
| | 130 | | | | | 135 | | | | | 140 | | | | |
| Ala | Ala | Val | Arg | Pro | Ile | Arg | Glu | Arg | Lys | Val | Gly | Asp | Leu | Ile | Ala |
| 145 | | | | | 150 | | | | | 155 | | | | | 160 |
| Tyr | Leu | Arg | Ala | His | Ala | Gly | Glu | Glu | Val | Leu | Leu | Gly | Gln | Ala | Met |
| | | | | 165 | | | | | 170 | | | | | 175 | |
| Tyr | Thr | Gly | Leu | Leu | Asn | Leu | Val | Ser | Phe | Ser | Tyr | Phe | Ser | Ile | Asp |
| | | | 180 | | | | | 185 | | | | | 190 | | |
| Ile | Val | Asp | Met | Gly | Ser | Gln | Met | Ala | Arg | Asp | Leu | Arg | Glu | Val | Val |
| | | 195 | | | | | 200 | | | | | 205 | | | |
| Asp | Asp | Ile | Ile | Ser | Val | Val | Gly | Lys | Pro | Asn | Ile | Ser | Asp | Phe | Tyr |
| | 210 | | | | | 215 | | | | | 220 | | | | |
| Pro | Phe | Leu | Arg | Pro | Leu | Asp | Leu | Gln | Gly | Leu | Arg | Arg | Trp | Thr | Thr |
| 225 | | | | | 230 | | | | | 235 | | | | | 240 |
| Lys | Arg | Phe | Asn | Arg | Val | Phe | Ser | Ile | Met | Gly | Asp | Ile | Ile | Asp | Arg |
| | | | | 245 | | | | | 250 | | | | | 255 | |
| Arg | Leu | Ala | His | Ile | Arg | Asp | Gly | Lys | Pro | Arg | His | Ala | Asp | Phe | Leu |
| | | | 260 | | | | | 265 | | | | | 270 | | |
| Asp | Ser | Leu | Leu | Glu | Leu | Met | Ala | Thr | Gly | Lys | Met | Glu | Arg | Val | Asn |
| | | 275 | | | | | 280 | | | | | 285 | | | |
| Val | Val | Asn | Met | Leu | Phe | Glu | Ala | Phe | Val | Ala | Gly | Val | Asp | Thr | Met |
| | 290 | | | | | 295 | | | | | 300 | | | | |
| Ala | Leu | Thr | Leu | Glu | Trp | Val | Met | Ala | Glu | Leu | Leu | His | Asn | Pro | Ala |
| 305 | | | | | 310 | | | | | 315 | | | | | 320 |
| Ile | Met | Ala | Arg | Val | Arg | Ala | Glu | Leu | Ser | Asp | Val | Leu | Gly | Gly | Lys |
| | | | | 325 | | | | | 330 | | | | | 335 | |
| Glu | Ala | Val | Glu | Glu | Ala | Asp | Ala | Ala | Arg | Leu | Pro | Tyr | Leu | Gln | Ala |
| | | | 340 | | | | | 345 | | | | | 350 | | |
| Val | Leu | Lys | Glu | Ala | Met | Arg | Leu | His | Pro | Val | Gly | Ala | Leu | Leu | Leu |
| | | 355 | | | | | 360 | | | | | 365 | | | |
| Pro | His | Phe | Ala | Ala | Glu | Asp | Gly | Val | Glu | Ile | Gly | Gly | Tyr | Ala | Val |
| | 370 | | | | | 375 | | | | | 380 | | | | |
| Pro | Arg | Gly | Ser | Thr | Val | Leu | Phe | Asn | Ala | Trp | Ala | Ile | Met | Arg | Asp |
| 385 | | | | | 390 | | | | | 395 | | | | | 400 |

```
Pro Ala Ala Trp Glu Arg Pro Asp Glu Phe Val Pro Glu Arg Phe Leu
                405                 410                 415

Gly Arg Ser Pro Pro Leu Asp Phe Arg Gly Lys Asp Val Glu Phe Met
            420                 425                 430

Pro Phe Gly Ser Gly Arg Arg Leu Cys Pro Gly Leu Pro Leu Ala Glu
        435                 440                 445

Arg Val Val Pro Phe Ile Leu Ala Ser Met Leu His Thr Phe Glu Trp
    450                 455                 460

Lys Leu Pro Gly Gly Met Thr Ala Glu Asp Val Asp Val Ser Glu Lys
465                 470                 475                 480

Phe Lys Ser Ala Asn Val Leu Ala Val Pro Leu Lys Ala Val Pro Val
                485                 490                 495

Leu Ile Lys

<210> SEQ ID NO 84
<211> LENGTH: 493
<212> TYPE: PRT
<213> ORGANISM: Mentha x piperita
<220> FEATURE:
<223> OTHER INFORMATION: CYP71A32 menthofuran synthase
<300> PUBLICATION INFORMATION:
<308> DATABASE ACCESSION NUMBER: Uniprot Q947B7
<309> DATABASE ENTRY DATE: 2013-04-03

<400> SEQUENCE: 84

Met Ala Ala Leu Leu Val Phe Phe Ser Val Ser Leu Ile Leu Leu Ala
 1               5                  10                  15

Val Leu Phe His Lys Arg Lys Ser Ser Leu Ser Ser Arg Lys Arg Pro
                20                  25                  30

Pro Pro Ser Pro Leu Arg Leu Pro Val Ile Gly His Phe His Leu Ile
            35                  40                  45

Gly Ala Leu Ser His Arg Ser Phe Thr Ser Leu Ser Lys Arg Tyr Gly
        50                  55                  60

Glu Val Met Leu Leu His Phe Gly Ser Ala Pro Val Leu Val Ala Ser
65                  70                  75                  80

Ser Ala Ala Ala Arg Glu Ile Met Lys Asn Gln Asp Val Ile Phe
                85                  90                  95

Ala Ser Arg Pro Arg Leu Ser Ile Phe Asp Arg Leu Met Tyr Ser Gly
                100                 105                 110

Lys Gly Val Ala Phe Ala Pro Tyr Gly Glu His Trp Arg Asn Ala Arg
            115                 120                 125

Ser Met Cys Met Leu Gln Leu Leu Ser Ala Lys Arg Val Gln Ser Phe
        130                 135                 140

Gly Gly Ile Arg Glu Glu Thr Ser Ala Met Ile Glu Lys Ile Arg
145                 150                 155                 160

Arg Ser Lys Pro Thr Thr Val Val Asn Leu Ser Glu Met Phe Met Ala
                165                 170                 175

Leu Thr Asn Gly Val Ile His Arg Ala Val Leu Gly Arg Lys Gly Asp
                180                 185                 190

Gly Gly Asp Asp Phe Asn Arg Ile Leu Ile Lys Val Ile Lys Leu Leu
        195                 200                 205

Gly Ser Phe Asn Val Gly Asp Tyr Val Pro Trp Leu Ser Trp Ile Asn
    210                 215                 220

Arg Ile Asn Gly Val Asp Ala Glu Val Glu Lys Val Gly Thr Lys Leu
225                 230                 235                 240
```

```
Asp Gly Ser Met Glu Gly Ile Leu Arg Lys Tyr Arg Arg Lys Lys Val
                245                 250                 255

Gly Asp Asp Glu Thr Asn Phe Val Asp Thr Leu Leu Gln Phe Gln Arg
            260                 265                 270

Glu Ser Lys Asp Thr Asp Pro Val Glu Asp Val Ile Lys Ala Leu
        275                 280                 285

Ile Phe Asp Met Val Ser Ala Gly Thr Asp Thr Thr Phe Ala Ala Leu
    290                 295                 300

Glu Trp Thr Met Ala Glu Leu Ile Lys Asn Pro Arg Thr Leu Lys Thr
305                 310                 315                 320

Leu Gln Asn Glu Val Arg Glu Val Ser Arg Asn Lys Gly Gly Ile Thr
                325                 330                 335

Glu Asp Asp Val Asp Lys Met Pro Tyr Leu Lys Ala Val Ser Lys Glu
            340                 345                 350

Ile Leu Arg Leu His Pro Pro Phe Ala Ile Leu Leu Pro Arg Glu Leu
        355                 360                 365

Thr Gln Asp Ala Asn Met Leu Gly Tyr Asp Ile Pro Arg Gly Thr Val
    370                 375                 380

Val Leu Val Asn Asn Trp Ala Ile Ser Arg Asp Pro Ser Leu Trp Glu
385                 390                 395                 400

Asn Pro Glu Glu Phe Arg Pro Glu Arg Phe Leu Glu Thr Ser Ile Asp
                405                 410                 415

Tyr Lys Gly Leu His Phe Glu Met Leu Pro Phe Gly Ser Gly Arg Arg
            420                 425                 430

Gly Cys Pro Gly Ser Thr Phe Ala Met Ala Leu Tyr Glu Leu Ala Leu
        435                 440                 445

Ser Lys Leu Val Asn Glu Phe Asp Phe Arg Leu Gly Asn Gly Asp Arg
    450                 455                 460

Ala Glu Asp Leu Asp Met Thr Glu Ala Pro Gly Phe Val Val His Lys
465                 470                 475                 480

Lys Ser Pro Leu Leu Val Leu Ala Thr Pro Arg Gln Ser
                485                 490

<210> SEQ ID NO 85
<211> LENGTH: 502
<212> TYPE: PRT
<213> ORGANISM: Persea americana
<220> FEATURE:
<223> OTHER INFORMATION: CYP71A1
<300> PUBLICATION INFORMATION:
<308> DATABASE ACCESSION NUMBER: Uniprot P24465
<309> DATABASE ENTRY DATE: 2013-04-03

<400> SEQUENCE: 85

Met Ala Ile Leu Val Ser Leu Leu Phe Leu Ala Ile Ala Leu Thr Phe
1               5                   10                  15

Phe Leu Leu Lys Leu Asn Glu Lys Arg Glu Lys Lys Pro Asn Leu Pro
                20                  25                  30

Pro Ser Pro Pro Asn Leu Pro Ile Ile Gly Asn Leu His Gln Leu Gly
            35                  40                  45

Asn Leu Pro His Arg Ser Leu Arg Ser Leu Ala Asn Glu Leu Gly Pro
        50                  55                  60

Leu Ile Leu Leu His Leu Gly His Ile Pro Thr Leu Ile Val Ser Thr
65                  70                  75                  80

Ala Glu Ile Ala Glu Glu Ile Leu Lys Thr His Asp Leu Ile Phe Ala
                85                  90                  95
```

```
Ser Arg Pro Ser Thr Thr Ala Ala Arg Arg Ile Phe Tyr Asp Cys Thr
            100                 105                 110
Asp Val Ala Phe Ser Pro Tyr Gly Glu Tyr Trp Arg Gln Val Arg Lys
        115                 120                 125
Ile Cys Val Leu Glu Leu Leu Ser Ile Lys Arg Val Asn Ser Tyr Arg
    130                 135                 140
Ser Ile Arg Glu Glu Glu Val Gly Leu Met Met Glu Arg Ile Ser Gln
145                 150                 155                 160
Ser Cys Ser Thr Gly Glu Ala Val Asn Leu Ser Glu Leu Leu Leu Leu
                165                 170                 175
Leu Ser Ser Gly Thr Ile Thr Arg Val Ala Phe Gly Lys Lys Tyr Glu
            180                 185                 190
Gly Glu Glu Arg Lys Asn Lys Phe Ala Asp Leu Ala Thr Glu Leu
        195                 200                 205
Thr Thr Leu Met Gly Ala Phe Phe Val Gly Asp Tyr Phe Pro Ser Phe
    210                 215                 220
Ala Trp Val Asp Val Leu Thr Gly Met Asp Ala Arg Leu Lys Arg Asn
225                 230                 235                 240
His Gly Glu Leu Asp Ala Phe Val Asp His Val Ile Asp His Leu
                245                 250                 255
Leu Ser Arg Lys Ala Asn Gly Ser Asp Gly Val Glu Gln Lys Asp Leu
            260                 265                 270
Val Asp Val Leu Leu His Leu Gln Lys Asp Ser Ser Leu Gly Val His
        275                 280                 285
Leu Asn Arg Asn Asn Leu Lys Ala Val Ile Leu Asp Met Phe Ser Gly
    290                 295                 300
Gly Thr Asp Thr Thr Ala Val Thr Leu Glu Trp Ala Met Ala Glu Leu
305                 310                 315                 320
Ile Lys His Pro Asp Val Met Glu Lys Ala Gln Gln Glu Val Arg Arg
                325                 330                 335
Val Val Gly Lys Lys Ala Lys Val Glu Glu Asp Leu His Gln Leu
            340                 345                 350
His Tyr Leu Lys Leu Ile Ile Lys Glu Thr Leu Arg Leu His Pro Val
        355                 360                 365
Ala Pro Leu Leu Val Pro Arg Glu Ser Thr Arg Asp Val Val Ile Arg
    370                 375                 380
Gly Tyr His Ile Pro Ala Lys Thr Arg Val Phe Ile Asn Ala Trp Ala
385                 390                 395                 400
Ile Gly Arg Asp Pro Lys Ser Trp Glu Asn Ala Glu Glu Phe Leu Pro
                405                 410                 415
Glu Arg Phe Val Asn Asn Ser Val Asp Phe Lys Gly Gln Asp Phe Gln
            420                 425                 430
Leu Ile Pro Phe Gly Ala Gly Arg Arg Gly Cys Pro Gly Ile Ala Phe
        435                 440                 445
Gly Ile Ser Ser Val Glu Ile Ser Leu Ala Asn Leu Leu Tyr Trp Phe
    450                 455                 460
Asn Trp Glu Leu Pro Gly Asp Leu Thr Lys Glu Asp Leu Asp Met Ser
465                 470                 475                 480
Glu Ala Val Gly Ile Thr Val His Met Lys Phe Pro Leu Gln Leu Val
                485                 490                 495
Ala Lys Arg His Leu Ser
            500
```

<210> SEQ ID NO 86
<211> LENGTH: 496
<212> TYPE: PRT
<213> ORGANISM: Cichoriium intybus
<220> FEATURE:
<223> OTHER INFORMATION: CYP71AV8 valencene oxidase
<300> PUBLICATION INFORMATION:
<308> DATABASE ACCESSION NUMBER: Genbank ADM86719
<309> DATABASE ENTRY DATE: 2011-01-24

<400> SEQUENCE: 86

```
Met Glu Ile Ser Ile Pro Thr Thr Leu Gly Leu Ala Val Ile Ile Phe
 1               5                  10                  15

Ile Ile Phe Lys Leu Leu Thr Arg Thr Thr Ser Lys Lys Asn Leu Leu
            20                  25                  30

Pro Glu Pro Trp Arg Leu Pro Ile Ile Gly His Met His His Leu Ile
        35                  40                  45

Gly Thr Met Pro His Arg Gly Val Met Glu Leu Ala Arg Lys His Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Asn Lys Lys Val Lys Ser Phe
    130                 135                 140

Gln Ser Leu Arg Glu Glu Glu Cys Trp Asn Leu Val Lys Asp Ile Arg
145                 150                 155                 160

Ser Thr Gly Gln Gly Ser Pro Ile Asn Leu Ser Glu Asn Ile Phe Lys
                165                 170                 175

Met Ile Ala Thr Ile Leu Ser Arg Ala Ala Phe Gly Lys Gly Ile Lys
            180                 185                 190

Asp Gln Met Lys Phe Thr Glu Leu Val Lys Glu Ile Leu Arg Leu Thr
        195                 200                 205

Gly Gly Phe Asp Val Ala Asp Ile Phe Pro Ser Lys Lys Leu Leu His
    210                 215                 220

His Leu Ser Gly Lys Arg Ala Lys Leu Thr Asn Ile His Asn Lys Leu
225                 230                 235                 240

Asp Asn Leu Ile Asn Asn Ile Ile Ala Glu His Pro Gly Asn Arg Thr
                245                 250                 255

Ser Ser Ser Gln Glu Thr Leu Leu Asp Val Leu Leu Arg Leu Lys Glu
            260                 265                 270

Ser Ala Glu Phe Pro Leu Thr Ala Asp Asn Val Lys Ala Val Ile Leu
        275                 280                 285

Asp Met Phe Gly Ala Gly Thr Asp Thr Ser Ser Ala Thr Ile Glu Trp
    290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Leu Gln Glu Leu Asn Tyr Leu Lys Leu Val Ile Lys Glu Thr Leu
            340                 345                 350

Arg Leu His Pro Pro Leu Pro Leu Val Met Pro Arg Glu Cys Arg Glu
```

```
                355             360             365
Pro Cys Val Leu Gly Gly Tyr Asp Ile Pro Ser Lys Thr Lys Leu Ile
        370             375             380

Val Asn Val Phe Ala Ile Asn Arg Asp Pro Glu Tyr Trp Lys Asp Ala
385             390             395             400

Glu Thr Phe Met Pro Glu Arg Phe Glu Asn Ser Pro Ile Thr Val Met
            405             410             415

Gly Ser Glu Tyr Glu Tyr Leu Pro Phe Gly Ala Gly Arg Arg Met Cys
        420             425             430

Pro Gly Ala Ala Leu Gly Leu Ala Asn Val Glu Leu Pro Leu Ala His
        435             440             445

Ile Leu Tyr Tyr Phe Asn Trp Lys Leu Pro Asn Gly Lys Thr Phe Glu
        450             455             460

Asp Leu Asp Met Thr Glu Ser Phe Gly Ala Thr Val Gln Arg Lys Thr
465             470             475             480

Glu Leu Leu Leu Val Pro Thr Asp Phe Gln Thr Leu Thr Ala Ser Thr
            485             490             495
```

<210> SEQ ID NO 87
<211> LENGTH: 1732
<212> TYPE: DNA
<213> ORGANISM: Mentha x gracilis
<220> FEATURE:
<223> OTHER INFORMATION: CYP71D13 (-)-limonene-3-hydroxylase
<300> PUBLICATION INFORMATION:
<308> DATABASE ACCESSION NUMBER: Genbank AY281027
<309> DATABASE ENTRY DATE: 2003-11-07

<400> SEQUENCE: 87

```
aataatggag ctccagattt cgtcggcaat tataatcctc gtcgcaacat tcgtcgcatc      60
cctcctaatc aagcaatggc gaaaatcgga atcccaacaa aacctgcccc cgggcccgcc     120
gaagctgccg ctggtcggcc acctccacct cctatggggg aagctgccgc agcacgcgat     180
ggccgacatg gccaagaagt acggccccgt cacccacgtg cagctcggcg aggtcttctc     240
cgtcgtcctt tcgtcgcgag aagcgacgaa agaggcgatg aagctgctcg acccccgcgtg    300 cgcggacagg ttcgagagca tcgggacgag gatcatgtgg tacgacaacg acgacatcat     360
cttcagcccg tacagcgacc actggcgcca gatgcgcaag atatgcgtct ctgagctcct     420
cagtgcccgc aacgtacggt ccttcgggtt catccgtcag gacgagatgt cgcgcctcct     480
ccgccacctc cagtcgtcgg cgggggagac cgtcgacatg acagagagga tagcgacgct     540
tacgtgctcc atcatctgta gggcggcgtt cggggccatc atcaacgatc acgaggagct     600
tgtggagttg gtgaaggact cgctgagcat ggcgtcaggg tttgagcttg ctgacttgtt     660
cccctcctcc aaactcctca acttgctctg ctggaacaag agcaagttgt ggaggatgcg     720
ccgccgcgtc gacaccatcc tcgaggccat cgtggaggag cacaagctca gaagagcgg      780 cgagtttggc ggtgaagaca tcatcgacgt cctcttcaga atgcagaagg acagccagat     840
caaagtcccc atcaccacca atgccatcaa agccttcatc ttcgacacgt tctcagcagg     900
gactgagacc tcgtcgacca ccaccttatg ggtgatggca gagctgatga ggaatccggc     960
agtgatggcg aaggcgcagg cggaggtgag agcggcactg aagggaaga cgagtgtgga   1020 tgtggatgac gtgcaggagc tcaagtacat gaaatcggtg gtgaaggaga caatgaggat   1080 gcacccccccg atcccgttga tcccgagatc atgcagagaa gaatgcgagg ttaacggata   1140
taaaattccg aacaaggcta ggatcatgat caacgtctgg tctatgggaa ggaatcccct   1200
```

-continued

```
ctactgggaa aagccggaga cctttggcc cgaaagattc gaccaagttt cgagggattt    1260
catgggaagc gatttcgagt tcatcccgtt tggagcggga agaagaatct gccccggttt    1320
gaatttcggg ctggccaacg tcgaggttcc attggcacaa cttctttacc acttcgactg    1380
gaaattagcg gaaggaatga agccttcgga tatggacatg tccgaggccg aaggccttac    1440
cggaataaga aagaacaatc ttctactggt tcccacaccc tacaatcctt cctcatgatc    1500
aataatcttt tactccttca aataaagagt gcatatacat atatgtacat gtagctcagg    1560
gttataaata agcaaatatg taacttttcc cttttttgaac tctattatgt aatccaaaac    1620
tagcatgtca tgtatctagg tttcaattca tatgcataat tttgtgcatg tattacccca    1680
gtagtgatgt ggttaatgcc cgagaccttt gtggtaaaaa aaaaaaaaaa aa            1732
```

<210> SEQ ID NO 88
<211> LENGTH: 1515
<212> TYPE: DNA
<213> ORGANISM: Nicotiana tabacum
<220> FEATURE:
<223> OTHER INFORMATION: CYP71D20 5-epi-aristocholene-1,3-dihydroxylase
<300> PUBLICATION INFORMATION:
<308> DATABASE ACCESSION NUMBER: Genbank AF368376
<309> DATABASE ENTRY DATE: 2005-09-20

<400> SEQUENCE: 88

```
atgcaattct tcagcttggt ttccattttc ctattcctat ctttcctatt tctgttgagg      60
aaatggaaga actccaatag ccaaagcaaa aaattgccac caggtccatg gaaaatacca    120
atactaggaa gtatgcttca tatgattggt ggagaaccgc accatgtcct tagagattta    180
gccaaaaaat atggaccact tatgcacctt cagttaggtg aaatttctgc agttgtggtt    240
acttctaggg acatggcaaa agaagtgcta aaaactcatg acgtcgtttt tgcatctagg    300
cctaaaattg tagccatgga cattatctgt tataaccagt ccgacattgc ctttagccct    360
tatggcgacc actggagaca aatgcgtaaa atttgtgtca tggaacttct caatgcaaag    420
aatgttcggt ctttcagctc catcagacgt gatgaagtcg ttcgtctcat tgactctatc    480
cggtcagatt cttcttcagg tgagctagtt aattttacgc agaggatcat ttggtttgca    540
agctccatga cgtgtagatc agcatttggg caagtactca aggggcaaga catatttgcc    600
aaaaagatca gagaagtaat aggattagca gaaggctttg atgtggtaga catcttccct    660
acatacaagt ttcttcatgt tctcagtggg atgaagcgta aacttttgaa tgcccacctt    720
aaggtagacg ccattgttga ggatgtcatc aacgagcaca gaaaaaatct gcagctggc    780 aagagtaatg gcgcattagg aggcgaagat ctaattgatg tcctactgag acttatgaat    840
gacacaagtc ttcaatttcc catcaccaac gacaatatca agctgttatt gttgacatg    900 tttgctgccg aacagaaac ttcatcaaca acaactgtat gggctatggc tgaaatgatg    960
aagaatccaa gtgtattcac caaagctcaa gcagaagtgc gagaagcctt tagggacaaa    1020
gtatcttttg atgaaaatga tgtggaggag ctgaaatact aaagttagt cattaaagaa    1080 actttgagac ttcatccacc gtctccactt ttggtcccaa gagaatgcag ggaagatacg    1140
gatataaacg gctacactat tcctgcgaag accaaagtta tggttaatgt tgggcattg    1200 ggaagagatc caaatattg ggatgacgcg gaaagctttg agccagagag atttgagcaa    1260
tgctctgtgg attttttgg taataatttt gagtttcttc cctttggcgg tggacggaga    1320
atttgtcctg gaatgtcatt tggtttagct aatcttact tgccattggc tcaattactc    1380
tatcactttg actggaaact cccaaccgga atcatgccaa gagacttaga cttgaccgaa    1440
```

```
ttatcgggaa taactattgc tagaaagggt ggcctttact taaatgccac tccttatcaa    1500
ccttctcgag agtaa                                                     1515
```

<210> SEQ ID NO 89
<211> LENGTH: 536
<212> TYPE: PRT
<213> ORGANISM: Gossypium arboretum
<220> FEATURE:
<223> OTHER INFORMATION: CYP706B1 (+)-delta-cadinene-8-hydroxylase
<300> PUBLICATION INFORMATION:
<308> DATABASE ACCESSION NUMBER: Genbank AAK60517
<309> DATABASE ENTRY DATE: 2001-11-01

<400> SEQUENCE: 89

```
Met Leu Gln Ile Ala Phe Ser Ser Tyr Ser Trp Leu Leu Thr Ala Ser
 1               5                  10                  15

Asn Gln Lys Asp Gly Met Leu Phe Pro Val Ala Leu Ser Phe Leu Val
            20                  25                  30

Ala Ile Leu Gly Ile Ser Leu Trp His Val Trp Thr Ile Arg Lys Pro
        35                  40                  45

Lys Lys Asp Ile Ala Pro Leu Pro Pro Gly Pro Arg Gly Leu Pro Ile
    50                  55                  60

Val Gly Tyr Leu Pro Tyr Leu Gly Thr Asp Asn Leu His Leu Val Phe
65                  70                  75                  80

Thr Asp Leu Ala Ala Ala Tyr Gly Pro Ile Tyr Lys Leu Trp Leu Gly
                85                  90                  95

Asn Lys Leu Cys Val Val Ile Ser Ser Ala Pro Leu Ala Lys Glu Val
            100                 105                 110

Val Arg Asp Asn Asp Ile Thr Phe Ser Glu Arg Asp Pro Pro Val Cys
        115                 120                 125

Ala Lys Ile Ile Thr Phe Gly Leu Asn Asp Ile Val Phe Asp Ser Tyr
    130                 135                 140

Ser Ser Pro Asp Trp Arg Met Lys Arg Lys Val Leu Val Arg Glu Met
145                 150                 155                 160

Leu Ser His Ser Ser Ile Lys Ala Cys Tyr Gly Leu Arg Arg Glu Gln
                165                 170                 175

Val Leu Lys Gly Val Gln Asn Val Ala Gln Ser Ala Gly Lys Pro Ile
            180                 185                 190

Asp Phe Gly Glu Thr Ala Phe Leu Thr Ser Ile Asn Ala Met Met Ser
        195                 200                 205

Met Leu Trp Gly Gly Lys Gln Gly Gly Glu Arg Lys Gly Ala Asp Val
    210                 215                 220

Trp Gly Gln Phe Arg Asp Leu Ile Thr Glu Leu Met Val Ile Leu Gly
225                 230                 235                 240

Lys Pro Asn Val Ser Asp Ile Phe Pro Val Leu Ala Arg Phe Asp Ile
                245                 250                 255

Gln Gly Leu Glu Lys Glu Met Thr Lys Ile Val Asn Ser Phe Asp Lys
            260                 265                 270

Leu Phe Asn Ser Met Ile Glu Glu Arg Glu Asn Phe Ser Asn Lys Leu
        275                 280                 285

Ser Lys Glu Asp Gly Asn Thr Glu Thr Lys Asp Phe Leu Gln Leu Leu
    290                 295                 300

Leu Asp Leu Lys Gln Lys Asn Asp Ser Gly Ile Ser Ile Thr Met Asn
305                 310                 315                 320

Gln Val Lys Ala Leu Leu Met Asp Ile Val Val Gly Gly Thr Asp Thr
                325                 330                 335
```

```
Thr Ser Thr Met Met Glu Trp Thr Met Ala Glu Leu Ile Ala Asn Pro
            340             345             350
Glu Ala Met Lys Lys Val Lys Gln Glu Ile Asp Asp Val Val Gly Ser
            355             360             365
Asp Gly Ala Val Asp Glu Thr His Leu Pro Lys Leu Arg Tyr Leu Asp
    370             375             380
Ala Ala Val Lys Glu Thr Phe Arg Leu His Pro Pro Met Pro Leu Leu
385             390             395             400
Val Pro Arg Cys Pro Gly Asp Ser Ser Asn Val Gly Gly Tyr Ser Val
                405             410             415
Pro Lys Gly Thr Arg Val Phe Leu Asn Ile Trp Cys Ile Gln Arg Asp
            420             425             430
Pro Gln Leu Trp Glu Asn Pro Leu Glu Phe Lys Pro Glu Arg Phe Leu
        435             440             445
Thr Asp His Glu Lys Leu Asp Tyr Leu Gly Asn Asp Ser Arg Tyr Met
    450             455             460
Pro Phe Gly Ser Gly Arg Arg Met Cys Ala Gly Val Ser Leu Gly Glu
465             470             475             480
Lys Met Leu Tyr Ser Ser Leu Ala Ala Met Ile His Ala Tyr Asp Trp
            485             490             495
Asn Leu Ala Asp Gly Glu Glu Asn Asp Leu Ile Gly Leu Phe Gly Ile
                500             505             510
Ile Met Lys Lys Lys Lys Pro Leu Ile Leu Val Pro Thr Pro Arg Pro
            515             520             525
Ser Asn Leu Gln His Tyr Met Lys
530             535
```